(12) United States Patent
Lu et al.

(10) Patent No.: US 10,993,967 B2
(45) Date of Patent: May 4, 2021

(54) COMBINATORIAL CANCER IMMUNOTHERAPY

(71) Applicant: Senti Biosciences, Inc., South San Francisco, CA (US)

(72) Inventors: Timothy Kuan-Ta Lu, Cambridge, MA (US); Russell Morrison Gordley, San Francisco, CA (US); Jack Tzu-Chiao Lin, Redwood City, CA (US); Brian Scott Garrison, San Jose, CA (US); Philip Janmin Lee, Alameda, CA (US); Alba Gonzalez-Junca, San Francisco, CA (US); Don-Hong Wang, South San Francisco, CA (US); Daniel Frimannsson, Alameda, CA (US)

(73) Assignee: SENTI BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 16/656,452

(22) Filed: Oct. 17, 2019

(65) Prior Publication Data

US 2020/0171093 A1 Jun. 4, 2020

Related U.S. Application Data

(60) Provisional application No. 62/843,180, filed on May 3, 2019, provisional application No. 62/747,114, filed on Oct. 17, 2018, provisional application No. 62/747,109, filed on Oct. 17, 2018.

(51) Int. Cl.
| | |
|---|---|
| *A61K 35/28* | (2015.01) |
| *A61P 35/00* | (2006.01) |
| *C07K 14/715* | (2006.01) |
| *C12N 5/0775* | (2010.01) |
| *C12N 15/63* | (2006.01) |
| *C07K 16/28* | (2006.01) |
| *C07K 16/30* | (2006.01) |

(52) U.S. Cl.
CPC .............. *A61K 35/28* (2013.01); *A61P 35/00* (2018.01); *C07K 14/7155* (2013.01); *C12N 5/0668* (2013.01); *C12N 15/63* (2013.01); *C07K 16/2878* (2013.01); *C07K 16/30* (2013.01)

(58) Field of Classification Search
CPC ......... A61K 35/28; A61K 35/14; A61P 35/00; C07K 14/7155; C07K 16/2878; C07K 16/30; C12N 5/0668; C12N 15/63; C12N 15/85; C12N 5/10; C12N 15/86
See application file for complete search history.

(56) References Cited

U.S. PATENT DOCUMENTS

| | | | |
|---|---|---|---|
| 4,965,195 A | 10/1990 | Namen et al. | |
| 5,328,988 A | 7/1994 | Namen et al. | |
| 5,486,359 A | 1/1996 | Caplan et al. | |
| 5,536,657 A | 7/1996 | Chua et al. | |
| 5,554,512 A | 9/1996 | Lyman et al. | |
| 5,591,625 A | 1/1997 | Gerson et al. | |
| 5,674,486 A | 10/1997 | Sobol et al. | |
| 5,705,149 A | 1/1998 | Namen et al. | |
| 5,780,268 A | 7/1998 | Coleman et al. | |
| 5,827,735 A | 10/1998 | Young et al. | |
| 5,965,122 A | 10/1999 | Namen et al. | |
| 5,981,724 A | 11/1999 | Armitage et al. | |
| 6,153,182 A | 11/2000 | Lillard, Jr. | |
| 6,156,301 A | 12/2000 | Namen et al. | |
| 6,187,307 B1 | 2/2001 | Cohen | |
| 6,307,024 B1 | 10/2001 | Novak et al. | |
| 6,361,997 B1 | 3/2002 | Huss | |
| 6,392,126 B1 | 5/2002 | Mahajan | |
| 6,632,424 B1 | 10/2003 | Lyman et al. | |
| 6,686,178 B2 | 2/2004 | Novak et al. | |
| 6,929,932 B2 | 8/2005 | Presnell et al. | |
| 7,534,867 B1 | 5/2009 | Hannum et al. | |
| 7,611,699 B2 | 11/2009 | Novak et al. | |
| 7,833,754 B2 | 11/2010 | Felber et al. | |
| 7,993,918 B2 | 8/2011 | Paludan et al. | |
| 7,998,472 B2 | 11/2011 | Huss et al. | |
| 8,071,741 B2 | 12/2011 | Filpula et al. | |
| 8,178,660 B2 | 5/2012 | Weiner et al. | |
| 8,318,483 B2 | 11/2012 | Mistry et al. | |
| 8,367,409 B2 | 2/2013 | Abbot et al. | |
| 8,741,283 B2 | 6/2014 | Filpula et al. | |
| 8,765,462 B2 | 7/2014 | Medin et al. | |
| 9,198,938 B2 | 12/2015 | Abbot et al. | |
| 9,303,080 B2 | 4/2016 | Felber et al. | |
| 9,434,925 B2 | 9/2016 | Nelson | |
| 9,487,800 B2 | 11/2016 | Schonfeld et al. | |
| 9,492,482 B2 | 11/2016 | Beech et al. | |
| 9,725,492 B2 | 8/2017 | Felber et al. | |
| 9,790,261 B2 | 10/2017 | Felber et al. | |
| 10,022,405 B2 | 7/2018 | Medin et al. | |
| 10,046,049 B2 | 8/2018 | Beech et al. | |
| 10,155,024 B2 | 12/2018 | Cho et al. | |
| 10,201,592 B2 | 2/2019 | Wong et al. | |

(Continued)

FOREIGN PATENT DOCUMENTS

| | | | |
|---|---|---|---|
| EP | 1658853 A1 | 5/2006 | |
| KR | 100788930 B1 | 12/2007 | |
| WO | WO-1995/027722 A1 | 10/1995 | |
| WO | WO-1998/017799 A1 | 4/1998 | |
| WO | WO-2005/037218 A2 | 4/2005 | |

(Continued)

OTHER PUBLICATIONS

Aalbers, C. et al., "Preclinical Potency and Biodistribution Studies on an AAV 5 Vector Expressing Human Interferon-[beta] (ART-102) for Local Treatment of Patients with Rheumatoid Arthritis", PLOS One, Jun. 24, 2015, vol. 10, No. 6, pp. 1-17.

(Continued)

*Primary Examiner* — Titilayo Moloye
(74) *Attorney, Agent, or Firm* — Goodwin Procter LLP

(57) ABSTRACT

Provided herein are methods and compositions for dynamically controlling and targeting multiple immunosuppressive mechanisms in cancer. Some aspects provide cells engineered to produce multiple effector molecules, each of which modulates a different immunosuppressive mechanisms of a tumor, as well as methods of using the cells to treat cancer, such as ovarian, breast, or colon cancer.

31 Claims, 120 Drawing Sheets

Specification includes a Sequence Listing.

(56) References Cited

U.S. PATENT DOCUMENTS

| | | |
|---|---|---|
| 2001/0023070 A1 | 9/2001 | Ebner et al. |
| 2003/0003545 A1 | 1/2003 | Ebner et al. |
| 2004/0033217 A1 | 2/2004 | Vanguri et al. |
| 2004/0076622 A1 | 4/2004 | Studeny Matus et al. |
| 2005/0037218 A1 | 2/2005 | Lottes et al. |
| 2005/0037306 A1 | 2/2005 | Nakatsu |
| 2007/0119895 A1 | 5/2007 | Pesch et al. |
| 2007/0149493 A1 | 6/2007 | Ross |
| 2008/0150368 A1 | 6/2008 | Gurcan |
| 2010/0135958 A1 | 6/2010 | Hwu et al. |
| 2012/0051210 A1 | 3/2012 | Komatsu |
| 2014/0011881 A1 | 1/2014 | Shin et al. |
| 2014/0050709 A1 | 2/2014 | Leen et al. |
| 2014/0255363 A1 | 9/2014 | Metelitsa et al. |
| 2015/0035235 A1 | 2/2015 | Tsuda |
| 2015/0123183 A1 | 5/2015 | Kato et al. |
| 2015/0203820 A1 | 7/2015 | Wang et al. |
| 2016/0008435 A1 | 1/2016 | Cho et al. |
| 2016/0026854 A1 | 1/2016 | Hwang et al. |
| 2016/0146819 A1 | 5/2016 | Ince |
| 2016/0220612 A1 | 8/2016 | Mazzolini et al. |
| 2016/0237407 A1* | 8/2016 | Wagner ............. C07K 14/7051 |
| 2017/0044227 A1 | 2/2017 | Schonfeld et al. |
| 2017/0128569 A1 | 5/2017 | Beech et al. |
| 2017/0133175 A1 | 5/2017 | Lin et al. |
| 2017/0133633 A1 | 5/2017 | Wang et al. |
| 2017/0142367 A1 | 5/2017 | Nakano et al. |
| 2017/0239297 A1 | 8/2017 | Gunther et al. |
| 2018/0044392 A1 | 2/2018 | Felber et al. |
| 2018/0071295 A1 | 3/2018 | Kuo et al. |
| 2018/0140686 A1 | 5/2018 | Varadarajan et al. |
| 2018/0160993 A9 | 6/2018 | Lee et al. |
| 2018/0161026 A1 | 6/2018 | Housman et al. |
| 2018/0161038 A1 | 6/2018 | Lorenzo |
| 2018/0162939 A1* | 6/2018 | Ma ..................... C07K 16/2812 |
| 2018/0170390 A1 | 6/2018 | Tatsushiro et al. |
| 2018/0191619 A1 | 7/2018 | Karthikeyan et al. |
| 2018/0213731 A1 | 8/2018 | Wykman et al. |
| 2019/0183977 A1 | 6/2019 | Wong et al. |
| 2020/0171093 A1 | 6/2020 | Lu et al. |

FOREIGN PATENT DOCUMENTS

| | | |
|---|---|---|
| WO | WO-2005/037306 A1 | 4/2005 |
| WO | WO-2007/119895 A1 | 10/2007 |
| WO | WO-2007/149493 A2 | 12/2007 |
| WO | WO-2008/150368 A1 | 12/2008 |
| WO | WO-2012/051210 A2 | 4/2012 |
| WO | WO-2014/011881 A2 | 1/2014 |
| WO | WO-2015/035235 A1 | 3/2015 |
| WO | WO-2015/123183 A1 | 8/2015 |
| WO | WO-2016/026854 A2 | 2/2016 |
| WO | WO-2016/146819 A1 | 9/2016 |
| WO | WO-2017/133175 A1 | 8/2017 |
| WO | WO-2017/133633 A1 | 8/2017 |
| WO | WO-2017/142367 A1 | 8/2017 |
| WO | WO-2017/147383 A1 | 8/2017 |
| WO | WO-2017141181 A1 * | 8/2017 ............. A61K 35/28 |
| WO | WO-2018/033254 A2 | 2/2018 |
| WO | WO-2018/071295 A1 | 4/2018 |
| WO | WO-2018/160993 A1 | 9/2018 |
| WO | WO-2018/161026 A1 | 9/2018 |
| WO | WO-2018/161038 A1 | 9/2018 |
| WO | WO-2018/170390 A1 | 9/2018 |
| WO | WO-2018/191619 A1 | 10/2018 |
| WO | WO-2018/213731 A1 | 11/2018 |
| WO | WO-2020/081869 A1 | 4/2020 |

OTHER PUBLICATIONS

Adams, S. et al., "Immunotherapy for ovarian cancer: what are the targets of the future?", Future Oncol. 2015;11(9):1293-1296. doi: 10.2217/fon.15.44.

Beegle, J. et al., "Preclinical evaluation of mesenchymal stem cells overexpressing VEGF to treat critical limb ischemia", Mol Ther Methods Clin Dev. Aug. 24, 2016;3:16053. doi: 10.1038/mtm.2016. 53. eCollection 2016.

Chen, F. et al., "IL10-transduced mesenchymal stem cells improve the acute graft-versus-host disease protection in a murine model", Blood (2007) 110 (11): 3242. Database Biosis, Biosciences Information Service, XP002781954, Database accession No. PREV200800218514.

Chen, X. et al., "A Tumor-selective Biotherapy With Prolonged Impact on Established Metastases Based on Cytokine Gene-engineered MSCs", Mol Ther. Apr. 2008;16(4):749-56. doi: 10.1038/mt.2008.3. Epub Feb. 5, 2008.

Choi, J.J. et al., "Mesenchymal stem cells overexpressing interleukin-10 attenuate collagen-induced arthritis in mice", Clinical and Experimental Immunology, Aug. 1, 2008, vol. 152, No. 2, pp. 269-276.

Cieri, N. et al., "IL-7 and IL-15 instruct the generation of human memory stem T cells from naive precursors", Blood. Jan. 24, 2013;121(4):573-84. doi: 10.1182/blood-2012-05-431718. Epub Nov. 15, 2012.

Cruz, C. et al., "Adverse Events Following Infusion of T Cells for Adoptive Immunotherapy: A 10 Year Experience", Cytotherapy. Oct. 2010;12(6):743-9. doi: 10.3109/14653241003709686.

Dembinski, J. et al., "Tumor Stroma Engraftment of Gene-Modified Mesenchymal Stem Cells as Anti-Tumor Therapy against Ovarian Cancer", Cytotherapy. Jan. 2013;15(1):20-32. doi: 10.1016/j.jcyt. 2012.10.003.

Deng, P. et al., "Clinical trial perspective for adult and juvenile Huntington's disease using genetically-engineered mesenchymal stem cells",Neural Regen Res. May 2016;11(5):702-5. doi: 10.4103/1673-5374.182682.

Dominici, M. et al., "Minimal criteria for defining multipotent mesenchymal stromal cells. The International Society for Cellular Therapy position statement", Cytotherapy. 2006;8(4):315-7.

Dubinett, S. et al., "Chemokines: Can Effector Cells be Re-directed to the Site of Tumor?", Cancer J. Jul.-Aug. 2010;16(4):325-35. doi: 10.1097/PPO.0b013e3181eb33bc.

Gao, P. et al., Therapeutic potential of human mesenchymal stem cells producing IL-12 in a mouse xenograft model of renal cell carcinoma et al., Cancer Letters 290 (2010) 157-166.

Gilham, D. et al., "CAR—T cells and solid tumors: tuning T cells to challenge an inveterate foe", Trends Mol Med. Jul. 2012;18(7):377-84. doi: 10.1016/j.molmed.2012.04.009. Epub May 19, 2012.

Hamanishi J. et al., "Immune checkpoint inhibition in ovarian cancer", Int Immunol. Jul. 2016;28(7):339-48. doi: 10.1093/intimm/dxw020. Epub Apr. 7, 2016.

Hu, Y.L. et al., "Mesenchymal stem cells: A promising targeted-delivery vehicle in cancer gene therapy", J Control Release, 147 (2), 154-62 Oct. 15, 2010.

Kidd, S. et al., "Direct Evidence of Mesenchymal Stem Cell Tropism for Tumor and Wounding Microenvironments using in Vivo Bioluminescence Imaging", Stem Cells. Oct. 2009;27(10):2614-23. doi: 10.1002/stem.187.

Koneru, M. et al., "A phase I clinical trial of adoptive T cell therapy using IL-12 secreting MUC-16ecto directed chimeric antigen receptors for recurrent ovarian cancer", J Transl Med. Mar. 28, 2015;13:102. doi: 10.1186/s12967-015-0460-x.

Lengyel, E., "Ovarian Cancer Development and Metastasis", Am J Pathol. Sep. 2010;177(3):1053-64. doi: 10.2353/ajpath.2010. 100105. Epub Jul. 22, 2010.

Li, S. et al., "Oncolytic virotherapy for ovarian cancer", Oncolytic Virother. Aug. 2012;1:1-21.

Li, Y.Q. et al., "Tumor Secretion of CCL22 Activates Intratumoral Treg Infiltration and Is Independent Prognostic Predictor of Breast Cancer", PLoS One. Oct. 4, 2013;8(10):e76379. doi: 10.1371/journal. pone.0076379. eCollection 2013.

Ling, X. et al., "Mesenchymal Stem Cells Overexpressing IFN-β Inhibit Breast Cancer Growth and Metastases through Stat3 Signaling in a Syngeneic Tumor Model", Cancer Microenviron. Mar. 19, 2010;3(1):83-95. doi: 10.1007/s12307-010-0041-8.

(56) References Cited

OTHER PUBLICATIONS

Marofi, F. et al., "Mesenchymal Stromal/Stem Cells: A New Era in the Cell-Based Targeted Gene Therapy of Cancer", Front Immunol. Dec. 18, 2017;8:1770. doi: 10.3389/fimmu.2017.01770. eCollection 2017.
Martin, I. et al., "Challenges for mesenchymal stromal cell therapies", Sci Transl Med. Feb. 20, 2019;11(480). pii: eaat2189. doi: 10.1126/scitranslmed.aat2189.
Mirzaei, H. et al., "Application of Mesenchymal Stem Cells in Melanoma: A Potential Therapeutic Strategy for Delivery of Targeted Agents", Current Medicinal Chemistry, Jan. 1, 2016, pp. 455-463.
Mohammadi, M. et al., "Mesenchymal stem cell: a new horizon in cancer gene therapy", Cancer Gene Ther. Sep. 2016;23(9):285-6. doi: 10.1038/cgt.2016.35. Epub Aug. 19, 2016.
Nowakowski, A. et al., "Genetic Engineering of Mesenchymal Stem Cells to Induce Their Migration and Survival", Stem Cells Int. 2016;2016:4956063. doi: 10.1155/2016/4956063. Epub May 3, 2016.
Parker, B. et al., "Antitumour actions of interferons: implications for cancer therapy", Nat Rev Cancer. Mar. 2016;16(3):131-44. doi: 10.1038/nrc.2016.14.
PCT International Search Report and Written Opinion, PCT Application No. PCT/US2018/027492, dated Aug. 10, 2018, 17 pages.
PCT International Search Report, PCT Application No. PCT/US2018/022855, dated Jul. 2, 2018, 4 pages.
Roby, K. et al., "Antitumour actions of interferons: implications for cancer therapy", Carcinogenesis. Apr. 2000;21(4):585-91.
Schukur, L. et al., "Implantable synthetic cytokine converter cells with AND-gate logic treat experimental psoriasis", Sci Transl Med. Dec. 16, 2015;7(318):318ra201. doi: 10.1126/scitranslmed.aac4964.
Sharma, A. et al., "High Throughput Characterization of Adult Stem Cells Engineered for Delivery of Therapeutic Factors for Neuroprotective Strategies", J Vis Exp. Jan. 4, 2015;(95):e52242. doi: 10.3791/52242.
Shi, Yufang, et al., "Tumour-associated mesenchymal stem/stromal cells: emerging therapeutic targets", Nature Reviews, Drug Discovery, Nov. 4, 2016, vol. 16, No. 1, pp. 35-52.
Squillaro, T. et al., "Clinical Trials With Mesenchymal Stem Cells: An Update", Cell Transplant. 2016;25(5):829-48. doi: 10.3727/096368915X689622. Epub Sep. 29, 2015.
Studeny, M. et al., "Mesenchymal Stem Cells: Potential Precursors for Tumor Stroma and Targeted-Delivery Vehicles for Anticancer Agents", J Natl Cancer Inst. Nov. 3, 2004;96(21):1593-603.
Sun, Z. et al., "The roles of mesenchymal stem cells in tumor inflammatory microenvironment", J Hematol Oncol. Feb. 6, 2014;7:14. doi: 10.1186/1756-8722-7-14.
Wang D. et al., "Allogeneic Mesenchymal Stem Cell Transplantation in Severe and Refractory Systemic Lupus Erythematosus: 4 Years of Experience", Cell Transplant. 2013;22(12):2267-77. doi: 10.3727/096368911X582769c.
Wang, H. et al., "Genetically engineered bone marrow-derived mesenchymal stem cells co-expressing IFN-[gamma] and IL-10 inhibit hepatocellular carcinoma by modulating MAPK pathway", Journal of B.U.ON.: official journal of the Balkan Union of Oncology, Nov. 1, 2017, pp. 1517-1524.
Wang, V. et al., "The Transcriptional Specificity of NF-kappa β Dimers is Coded within the kappa βDNA Response Elements", Cell Reports, Oct. 2012, vol. 2, No. 4, pp. 824-839.
Waterman, R. et al., "Mesenchymal Stem Cell 1 (MSC1)—Based Therapy Attenuates Tumor Growth Whereas MSC2-Treatment Promotes Tumor Growth and Metastasis", PLoS One. 2012;7(9):e45590. doi: 10.1371/journal.pone.0045590. Epub Sep. 20, 2012.
Wiedemann, G. et al., "Cancer cell-derived IL-1a induces CCL22 and the recruitment of regulatory T cells", Oncoimmunology. Apr. 25, 2016;5(9):e1175794. eCollection 2016.
Woo, S.R. et al., "The STING pathway and the T cell-inflamed tumor Microenvironment", (2015) Trends Immunol. Apr. 2015;36(4):250-6. doi: 10.1016/j.it.2015.02.003. Epub Mar. 7, 2015.
Xie, C. et al., "Interferon-b gene-modified human bone marrow mesenchymal stem cells attenuate hepatocellular carcinoma through inhibiting AKT/FOXO3a pathway", Br J Cancer. Sep. 3, 2013;109(5):1198-205. doi: 10.1038/bjc.2013.422. Epub Jul. 25, 2013.
Xishan, Z. et al., "Mouse Flk-1+Sca-1-Mesenchymal Stem Cells: Functional Plasticity in Vitro and Immunoregulation in Vivo", Transplantation, Mar. 15, 2014, vol. 97, No. 5, pp. 509-517.
Xu, G. et al., "Bone marrow-derived mesenchymal stem cells co-expressing interleukin-18 and interferon-[beta] exhibit potent antitumor effect against intracranial glioma in rats", Oncology Reports, Aug. 5, 2015, vol. 34, No. 4, pp. 1915-1922.
Zhang, Y. et al., "Gene therapy of ovarian cancer using IL-21-secreting human umbilical cord mesenchymal stem cells in nude mice", J Ovarian Res. Jan. 20, 2014;7:8. doi: 10.1186/1757-2215-7-8.
Zhao, Q. et al., "MSCs derived from iPSCs with a modified protocol are tumor-tropic but have much less potential to promote tumors than bone marrow MSCs", Proc Natl Acad Sci U S A. Jan. 13, 2015;112(2):530-5. doi: 10.1073/pnas.1423008112. Epub Dec. 29, 2014.
Zhao, R. et al., "Mechanisms of and perspectives on the mesenchymal stem cell in immunotherapy", J Lab Clin Med. May 2004;143(5):284-91.
PCT International Search Report and Written Opinion, PCT Application No. PCT/US2019/056824, dated Apr. 23, 2020, 12 pages.
Shoji et al. "Local convection-enhanced delivery of an anti-CD40 agonistic monoclonal antibody induces antitumor effects in mouse glioma models.", Neuro-Oncology 18(8), 1120-1128, 2016.
Reardon et al. "Glioblastoma Eradication Following Immune Checkpoint Blockade in an Orthotopic, Immunocompetent Model." Cancer Immunol Res. Feb. 2016;4(2): 124-35 (Year: 2016).

* cited by examiner

Negative control

Anti-firefly luciferase (MSCs)

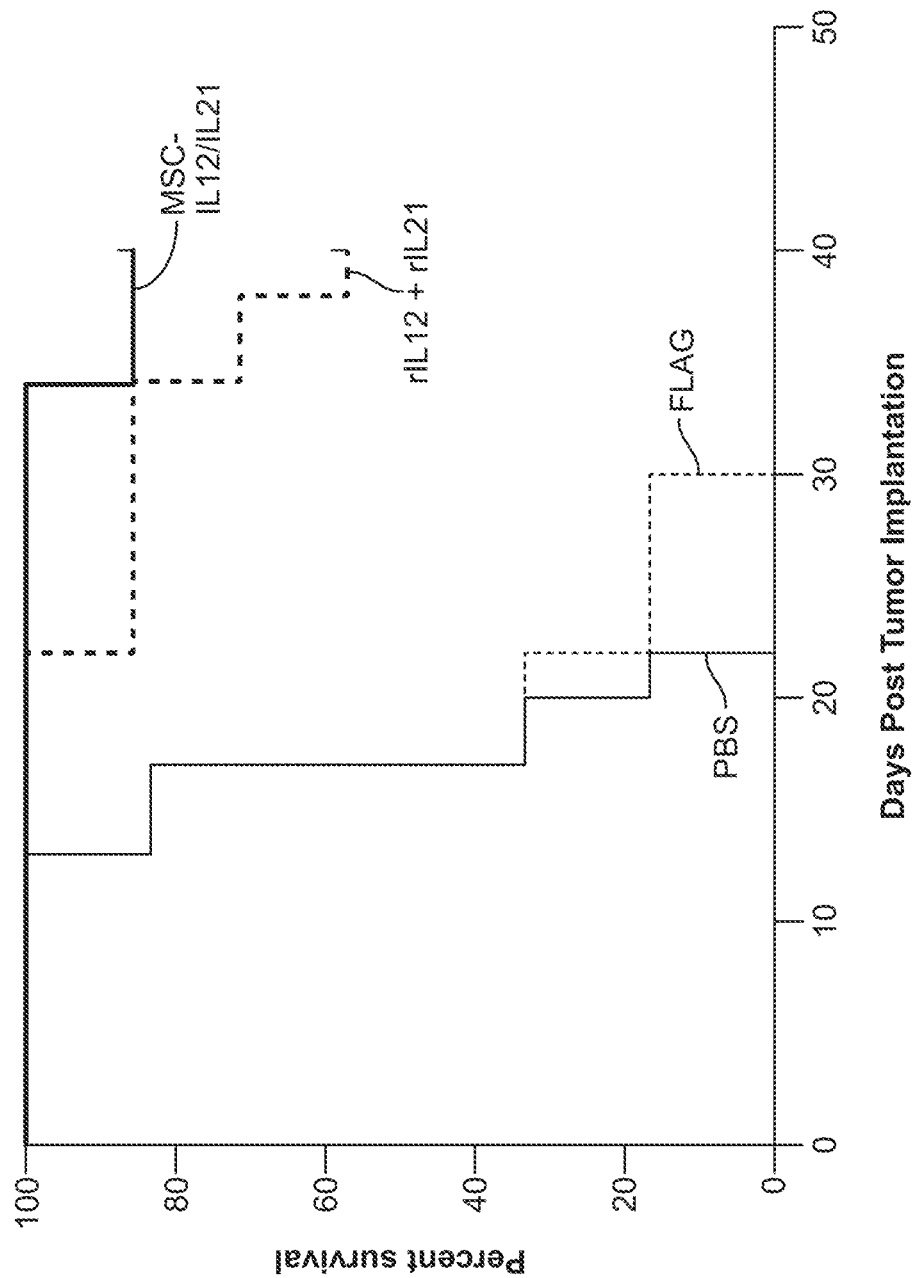

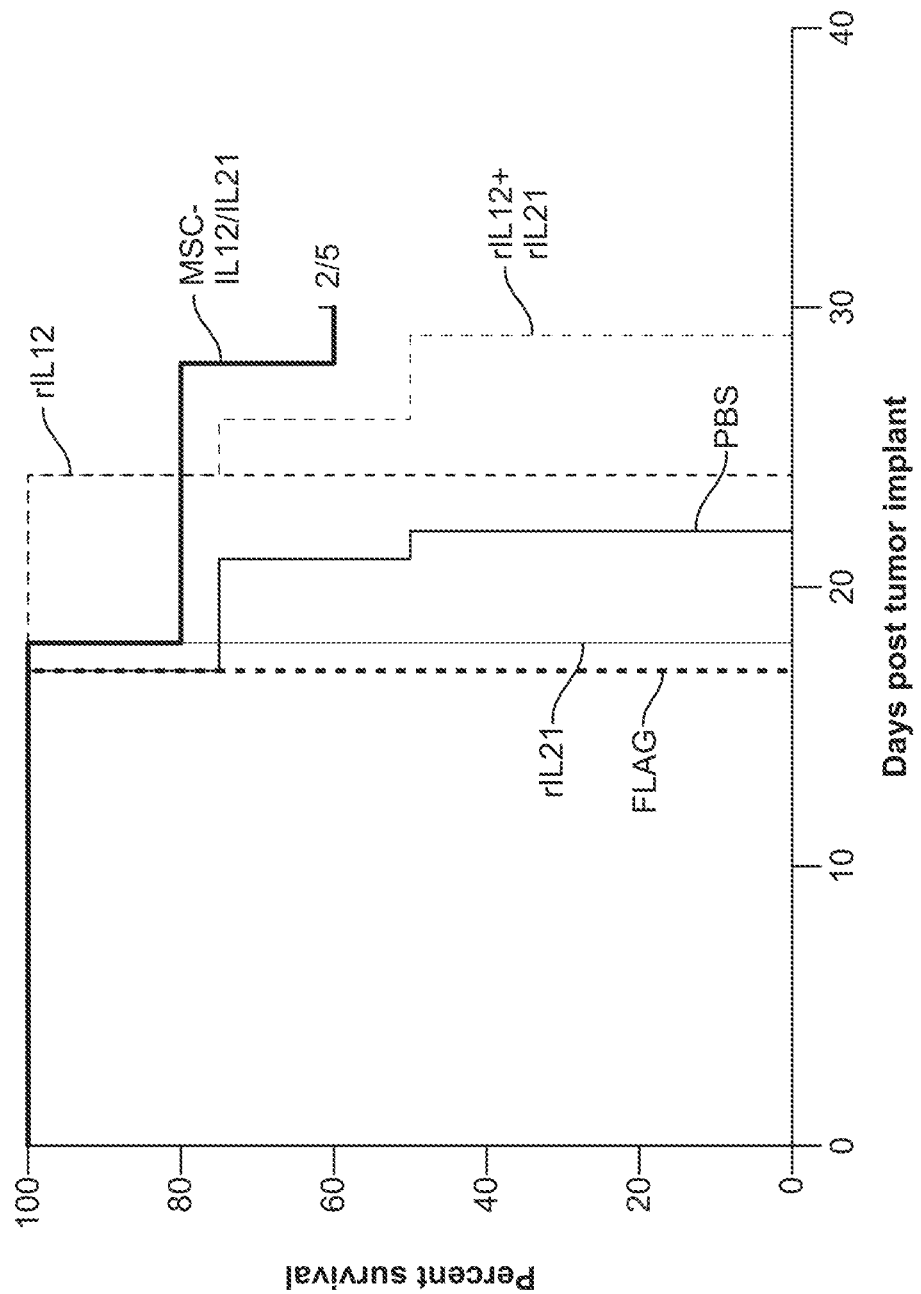

COMBINATORIAL CANCER IMMUNOTHERAPY

CROSS REFERENCE TO RELATED APPLICATIONS

This application claims the benefit of U.S. Provisional Application Nos. 62/747,109 filed on Oct. 17, 2018; 62/747,114 filed on Oct. 17, 2018; and 62/843,180 filed May 3, 2019, each of which is hereby incorporated in its entirety by reference.

SEQUENCE LISTING

The instant application contains a Sequence Listing which has been submitted via EFS-Web and is hereby incorporated herein by reference in its entirety. Said ASCII copy, created on Nov. 26, 2019, is named STB011_SequenceListing.txt, and is 142,504 bytes in size.

BACKGROUND

There are more than 22,000 new cases of ovarian cancer and more than 14,000 deaths each year in the United States (Siegel R L, et al. (2016) CA Cancer J Clin 66(1):7-30), with an estimated annual healthcare burden of greater than $600M (Dizon D M J (2010) Gynecol Oncol 116(3)). Conventional approaches, such as chemotherapy (e.g., carboplatin/cisplatin and/or paclitaxel), are often unable to cure ovarian cancer. Approximately 70% of patients do not achieve remission on first-line chemotherapy, and 40-50% of patients that do have a remission will relapse within three years.

Treatment of other cancers, such as breast cancer and colon cancer, is associated with five-year survival rates of 85% and 65%, respectively. Therapies often include a combination of invasive surgeries and chemotherapies.

SUMMARY

Provided herein, in some embodiments, is a combinatorial cell-based immunotherapy for the targeted treatment of cancer, such as ovarian cancer, breast cancer, colon cancer, lung cancer, and pancreatic cancer. This combinatorial immunotherapy relies on engineered cell circuits that enable multifactorial modulation within and/or near a tumor (a "tumor microenvironment (TME)"). Despite exciting advancements in combinatorial immunotherapy, its efficacy against cancer has been limited due in part to the following challenges. It is difficult to deliver multiple therapies simultaneously to achieve maximal efficacy without triggering significant side effects. It is also difficult in clinical trials to determine the appropriate dosing and timing of multiple systemically-administered and/or locally-injected therapies.

The combinatorial immunotherapy provided herein, however, is tumor-specific and effective yet limits systemic toxicity. This combinatorial immunotherapy delivers to a tumor microenvironment multiple immunomodulatory effector molecules from a single delivery vehicle. The design of the delivery vehicle is optimized to improve overall function in cancer therapy, including, but not limited to, optimization of the promoters, linkers, signal peptides, and order of the multiple immunomodulatory effector molecules.

Advantageously, cell circuits of the present disclosure are engineered in mesenchymal stem cells (MSCs), which are able to selectively home to tumors (including metastases), are able to produce a pro-inflammatory/immunostimulatory secretome and under certain conditions an anti-inflammatory secretome, and are hypoimmunogenic. These characteristics, among others, enable their use for allogenic cell therapies, for example, without significant safety issues, side effects, or rejection.

It has been increasingly recognized that tumors are a complex interplay between the tumor cells and the surrounding stroma, which includes the extracellular matrix, cancer-associated stromal cells (MSCs and fibroblasts), tumor vasculature, and the immune system. The TME suppresses anti-tumor immune responses through multiple mechanisms that target both the innate and adaptive immune system of the patient. For example, tumors can recruit and induce regulatory T cells that suppress the anti-tumor activity of conventional T cells by elaborating specific chemokines such as CCL22. Tumors can also express molecules that inhibit the activity of T cells and NK cells, such as immune checkpoints such as PD-L1. Thus, targeting a single pathway is likely insufficient for achieving robust efficacy against solid tumors.

Non-limiting examples of effector molecules encompassed by the present disclosure include cytokines, antibodies, chemokines, nucleotides, peptides, enzymes, and oncolytic viruses. For example, MSCs may be engineered to express (and typically secrete) at least one, two, three or more of the following effector molecules: IL-12, IL-16, IFN-β, IFN-γ, IL-2, IL-15, IL-7, IL-36γ, IL-18, IL-1β, IL-21, OX40-ligand, CD40L, anti-PD-1 antibodies, anti-PD-L1 antibodies, anti-CTLA-4 antibodies, anti-TGFβ antibodies, anti-TNFR2, MIP1α (CCL3), MIP1β (CCL5), CCL21, CpG oligodeoxynucleotides, and anti-tumor peptides (e.g., anti-microbial peptides having anti-tumor activity, see, e.g., Gaspar, D. et al. *Front Microbiol*. 2013; 4: 294; Chu, H. et al. PLoS One. 2015; 10(5): e0126390, and website: aps.unmc.edu/AP/main.php).

Provided for herein is an engineered cell comprising: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule. In some aspects, the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the cell is a mesenchymal stem cell (MSC). In some aspects, the cell is a stem cell. In some aspects, the cell is an immune cell. In some aspects, the cell is a natural killer (NK) cell. In some aspects, the cell is a NKT cell. In some aspects, the cell is an innate lymphoid cell. In some aspects, the cell is a tumor-infiltrating lymphocyte (TIL). In some aspects, the cell is a mast cell. In some aspects, the cell is a eosinophil. In some aspects, the cell is a basophil. In some aspects, the cell is a monocyte. In some aspects, the cell is a macrophage. In some aspects, the cell is a neutrophil. In some aspects, the cell is a myeloid cell. In some aspects, the cell is a dendritic cell. In some aspects, the cell is a T cell. In some aspects, the cell is a CD8+ T cell. In some aspects, the cell is a CD4+ T cell. In some aspects, the cell is a cytotoxic T lymphocyte (CTL). In some aspects, the cell is a viral-specific T cell. In some aspects, the cell is a gamma-delta T cell. In some aspects, the cell is a T regulatory cell. In some aspects, the cell is a B cell.

In some aspects, the promoter comprises an exogenous promoter polynucleotide sequence. In some aspects, the promoter comprises an endogenous promoter. In some aspects, the promoter is operably linked to the expression cassette such that the polynucleotides are capable of being transcribed as a single polynucleotide comprising the formula S1-E1-L-S2-E2. In some aspects, the linker polynucleotide sequence is operably associated with the translation of the first effector molecule and the second effector molecule as separate polypeptides. In some aspects, the linker polynucleotide sequence encodes a 2A ribosome skipping tag. In some aspects, the 2A ribosome skipping tag is selected from the group consisting of: P2A, T2A, E2A, and F2A. In some aspects, the linker polynucleotide sequence encodes a T2A ribosome skipping tag. In some aspects, the linker polynucleotide sequence encodes an Internal Ribosome Entry Site (IRES). In some aspects, the linker polynucleotide sequence encodes a cleavable polypeptide. In some aspects, the cleavable polypeptide comprises a Furin recognition polypeptide sequence. In some aspects, the linker polynucleotide sequence further encodes a Gly-comprising, Ser-comprising, or Gly-Ser comprising polypeptide sequence, e.g., a Gly-Ser-Gly polypeptide sequence. In some aspects, the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus.

In some aspects, the linker polynucleotide sequence encodes a second promoter, wherein the promoter is operably linked to the expression cassette such that a first polynucleotide comprising the formula S1-E1 is capable of being transcribed, wherein the second promoter is operably linked to the expression cassette such that a second polynucleotide comprising the formula S2-E2 is capable of being transcribed, and wherein the first and the second polynucleotide are separate polynucleotides. In some aspects, the promoter and the second promoter are identical. In some aspects, the promoter and the second promoter are different.

In some aspects, the engineered cell is HLA-typed with reference to a subject in need of therapeutic treatment. In some aspects, the engineered cell is a human cell. In some aspects, the human cell is an isolated cell from a subject, e.g., the subject who will receive the cell. In some aspects, the isolated cell is isolated from a tissue consisting of the group of: bone marrow, adipose tissue, the umbilical cord, fetal liver, muscle, and lung tissue. In some aspects, the engineered cell is a cultured cell.

In some aspects, the engineered MSC comprises a cellular marker phenotype comprising the cellular markers CD105+, CD73+, and CD90+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof. In some aspects, the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−. In some aspects, the cellular marker phenotype is determined or has been determined by flow-cytometry.

In some aspects, the engineered cell comprises a T cell. In some aspects, the engineered cell comprises a NK cell. In some aspects, the engineered cell comprises a NKT cell.

In some aspects, the cellular marker phenotype further comprises a cellular marker comprising a cognate receptor or a cognate receptor ligand for the first effector molecule, the second effector molecule, or the first and second effector molecules expressed in the engineered cells. In some aspects, the receptor is selected from the group consisting of: IL12RB1, IL12RB2, CCL7, and combinations thereof.

In some aspects, the promoter and/or the second promoter comprises a constitutive promoter. In some aspects, the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb. In some aspects, the promoter comprises an SFFV promoter. In some aspects, the promoter and/or the second promoter comprises an inducible promoter. In some aspects, the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof.

In some aspects, the first signal peptide or the second signal peptide comprises a native signal peptide native to the first effector molecule or the second effector molecule, respectively. In some aspects, the first signal peptide or the second signal peptide comprises a non-native signal peptide non-native to the first effector molecule or the second effector molecule, respectively. In some aspects, the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21.

In some aspects, the first signal peptide and the second signal peptide are identical. In some aspects, the polynucleotide sequence encoding the first signal peptide comprises a codon optimized polynucleotide sequence. In some aspects, the first secretion polypeptide is a human IL12 signal peptide.

In some aspects, the polynucleotide sequence encoding the second signal peptide comprises a codon optimized polynucleotide sequence. In some aspects, the second secretion polypeptide is a human IL21 signal peptide.

In some aspects, the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme.

In some aspects, the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme. In some aspects, the therapeutic class of the first effector molecule and the second effector molecule are different.

In some aspects, the first effector molecule and/or the second effector molecule is a modified effector molecule. In some aspects, the first effector molecule and/or the second effector molecule is modified to comprises a cell membrane tethering domain. In some aspects, the cell membrane tethering domain comprises a transmembrane-intracellular domain or a transmembrane domain. In some aspects, the cell membrane tethering domain comprises a cell surface receptor, or a cell membrane-bound portion thereof. In some aspects, the modified effector molecule is a fusion protein that comprises the cell surface receptor, or a cell membrane-bound portion thereof. In some aspects, the modified effector molecule further comprises a linker between the effector molecule and the cell membrane tethering domain. In some aspects, when expressed the modified effector molecule is tethered to a cell membrane of the engineered cell.

In some aspects, the cytokine is selected from the group consisting of: IL12, IL7, IL21, IL18, IL15, Type I interferons, and Interferon-gamma. In some aspects, the IL12 cytokine is an IL12p70 fusion protein. In some aspects, the chemokine is selected from the group consisting of: CCL21a, CXCL10, CXCL11, CXCL13, CXCL10-11 fusion, CCL19, CXCL9, and XCL1. In some aspects, the growth factor is selected from the group consisting of: Flt3L and GM-CSF. In some aspects, the co-activation molecule is selected from the group consisting of: 4-1BBL and CD40L. In some aspects, the tumor microenvironment modifier is selected from the group consisting of: adenosine deaminase, TGFbeta inhibitors, immune checkpoint inhibitors, VEGF inhibitors, and HPGE2. In some aspects, the TGFbeta inhibitors are selected from the group consisting of: an anti-TGFbeta peptide, an anti-TGFbeta antibody, a TGFb-TRAP, and combinations thereof. In some aspects, the immune checkpoint inhibitors comprise anti-PD-1 antibodies. In some aspects, the VEGF inhibitors comprise anti-VEGF antibodies, anti-VEGF peptides, or combinations thereof.

In some aspects, the first effector molecule and the second effector molecule are human-derived effector molecules.

In some aspects, the first effector molecule comprises interleukin 12 (IL12), for example, p35 and p40 as a dimer that is generally referred to in the art as IL-12p70. In some aspects, the first effector molecule comprises an IL12p70 fusion protein. In some aspects, the IL12p70 fusion protein is a human IL12p70 fusion protein. In some aspects, the human IL12p70 fusion protein comprises the sequence shown in SEQ ID NO: 137. In some aspects, the human IL12 comprises the p35 subunit indicated in SEQ ID NO: 137. In some aspects, the human IL12 comprises the p40 subunit indicated in SEQ ID NO: 137.

In some aspects, the second effector molecule comprises CCL21a. In some aspects, the CCL21a is a human CCL21a. In some aspects, the second effector molecule comprises IL7. In some aspects, the IL7 is a human IL7. In some aspects, the second effector molecule comprises IL21. In some aspects, the IL21 is a human IL21.

In some aspects, the expression cassette further comprises an E3 comprising a polynucleotide sequence encoding a third effector molecule. In some aspects, the third effector molecule comprises Flt3L. In some aspects, the third effector molecule comprises anti-PD1. For example, anti-PD1 can be an anti-PD1 antibody. In some aspects, the expression cassette further comprises an E4 comprising a polynucleotide sequence encoding a fourth effector molecule. In some aspects, the fourth effector molecule comprises adenosine deaminase. In some aspects, the third effector molecule comprises adenosine deaminase. In some aspects, the third effector molecule comprises CD40L. In some aspects, the third effector molecule comprises a CXCL10-CXCL11 fusion protein. In some aspects, the third effector molecule comprises XCL1.

In some aspects, the second effector molecule comprises Flt3L. In some aspects, the second effector molecule comprises a CXCL10-CXCL11 fusion protein. In some aspects, the second effector molecule comprises anti-PD1. In some aspects, the second effector molecule comprises CD40L.

In some aspects, the first effector molecule comprises interferon-beta and the second effector molecule comprises Flt3L.

In some aspects, the polynucleotide sequence encoding the first effector molecule comprises a codon optimized polynucleotide sequence. In some aspects, the polynucleotide sequence encoding the second effector molecule comprises a codon optimized polynucleotide sequence.

In some aspects, the engineered cell comprises a polynucleotide sequence encoding the promoter and the expression cassette. In some aspects, the exogenous polynucleotide sequence comprises the sequence shown in SEQ ID NO: 144.

In some aspects, the exogenous polynucleotide sequence is integrated into the genome of the engineered cell. In some aspects, the exogenous polynucleotide sequence comprises one or more viral vector polynucleotide sequences.

In some aspects, the one or more viral vector polynucleotide sequences comprise lentiviral, retroviral, retrotransposon, or adenoviral polynucleotide sequences.

In some aspects, the expression cassette further comprises following E2, an additional exogenous polynucleotide sequence comprising a formula, oriented from 5' to 3', comprising:

$$(L-S-E)_X$$

wherein S comprises a polynucleotide sequence encoding a signal peptide, E comprises a polynucleotide sequence encoding an effector molecule, L comprises a linker polynucleotide sequence, X=1 to 20 wherein the promoter is operably linked to the expression cassette, and wherein for each X the corresponding signal peptide is operably associated with the effector molecule.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising $$S1-E1-L-S2-E2$$

wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is a mesenchymal stem cell (MSC). In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is a mesenchymal stem cell (MSC), wherein the MSC comprises a cellular marker phenotype comprising CD73+, CD90+, CD105+, and CD166+, CD11b−, CD14−, CD19−, CD34−, CD45−, and HLA-DR−. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144. In some aspects, the cellular marker phenotype is determined or has been determined by flow-cytometry.

Also provided for herein is an engineered MSC comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered MSC comprises a cellular marker phenotype comprising CD73+, CD90+, CD105+, and CD166+, CD11b−, CD14−, CD19−, CD34−, CD45−, and HLA-DR−. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144. In some aspects, the cellular marker phenotype is determined or has been determined by flow-cytometry.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell. In some aspects, the human IL12p70 fusion protein comprises the sequence shown in SEQ ID NO: 137.

In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144. In some aspects, the cell is a mesenchymal stem cell (MSC). In some aspects, the cell is a natural killer (NK) cell. In some aspects, the cell is a NKT cell. In some aspects, the cell is an innate lymphoid cell. In some aspects, the cell is a tumor-infiltrating lymphocyte (TIL). In some aspects, the cell is a mast cell. In some aspects, the cell is a eosinophil. In some aspects, the cell is a basophil. In some aspects, the cell is a monocyte. In some aspects, the cell is a macrophage. In some aspects, the cell is a neutrophil. In some aspects, the cell is a myeloid cell. In some aspects, the cell is a dendritic cell. In some aspects, the cell is a T cell. In some aspects, the cell is a CD8+ T cell. In some aspects, the cell is a CD4+ T cell. In some aspects, the cell is a cytotoxic T lymphocyte (CTL). In some aspects, the cell is a viral-specific T cell. In some aspects, the cell is a gamma-delta T cell. In some aspects, the cell is a T regulatory cell. In some aspects, the cell is a B cell. In some aspects, the cell is a human cell.

In some aspects, the engineered cell is HLA-typed with reference to a subject in need of therapeutic treatment. In some aspects, the engineered cell is a human cell. In some aspects, the human cell is an isolated cell from a subject, e.g., the subject who will receive the cell. In some aspects, the isolated cell is isolated from a tissue consisting of the group of: bone marrow, adipose tissue, the umbilical cord, fetal liver, muscle, and lung tissue. In some aspects, the engineered cell is a cultured cell.

In some aspects, the engineered MSC comprises a cellular marker phenotype comprising the cellular markers CD105+, CD73+, and CD90+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof. In some aspects, the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−. In some aspects, the cellular marker phenotype is determined or has been determined by flow-cytometry.

In some aspects, the engineered cell comprises a T cell. In some aspects, the T cell is a CD8+ T cell, a CD4+ T cell, a cytotoxic T lymphocyte (CTL), a viral-specific T cell, a gamma-delta T cell, or a T regulatory cell. In some aspects, the engineered cell comprises a NK cell. In some aspects, the engineered cell comprises a NKT cell. In some aspects, the engineered cell comprises a monocyte cell. In some aspects, the engineered cell comprises a macrophage. In some aspects, the engineered cell comprises a TIL.

In some aspects, the exogenous polynucleotide sequence is integrated into the genome of the engineered cell. In some aspects, the exogenous polynucleotide sequence comprises one or more viral vector polynucleotide sequences. In some aspects, the one or more viral vector polynucleotide sequences comprise lentiviral, retroviral, retrotransposon, or adenoviral polynucleotide sequences. In some aspects, the one or more viral vector polynucleotide sequences comprise lentiviral polynucleotide sequences.

In some aspects, the cell secretes each effector molecule. In some aspects, the first effector molecule is secreted at a ratio that is 10 fold higher relative to secretion of the second effector molecule.

In some aspects, the cell further comprises an antigen recognizing receptor. In some aspects, the antigen recognizing receptor recognizes an antigen selected from the group consisting of: 5T4, ADAM9, ADGRE2, AFP, AXL, B7-H3, B7-H4, B7-H6, C4.4, CA6, Cadherin 3, Cadherin 6, CCR1, CCR4, CD117, CD123, CD131, CD133, CD138, CD142, CD166, CD25, CD244, CD30, CD300LF, CD33, CD352, CD37, CD38, CD44, CD56, CD66e, CD70, CD71, CD74, CD79b, CD80, CD93, CEA, CEACAM5, Claudin18.2, CLEC12A, cMet, CSPG4, CTLA, DLK1, DLL3, DR5, EGFR, EMB, ENPP3, EpCAM, EphA2, Ephrin A4, ETBR, FGFR2, FGFR3, FRalpha, FRb, FLT3, GAPT, GCC, GD2, GFRa4, gpA33, GPC3, gpNBM, GPRC5, HER2, IL-1RAP, IL-13R, IL-13Ra, IL-13Ra2, IL-8, IL-15, IL1RAP, Integrin aV, KIT, L1CAM, LAMP1, LAT2, Lewis Y, LeY, LILRA2, LILRB2, LIV-1, LRRC, LY6E, MCSP, Mesothelin, MLC1, MS4A3, MUC1, MUC16, MUC1C, MYADM, NaPi2B, Nectin 4, NKG2D, NOTCH3, NY ESO 1, Ovarin, P-cadherin, pan-Erb2, PIEZO1, PRAM1, PSCA, PSMA, PTK7, ROR1, S Aures, SCT, SLAMF7, SLC22A16, SLC17A9, SLITRK6, SPNS3, SSTR2, STEAP1, Survivin, TDGF1, TIM1, TROP2, VSTM1, and WT1.

In some aspects, the antigen recognizing receptor comprises an antigen-binding domain. In some aspects, the antigen-binding domain comprises an antibody, an antigen-binding fragment of an antibody, a F(ab) fragment, a F(ab') fragment, a single chain variable fragment (scFv), or a single-domain antibody (sdAb). In some aspects, the antigen-binding domain comprises a single chain variable fragment (scFv). In some aspects, the scFv comprises a heavy chain variable domain (VH) and a light chain variable domain (VL). In some aspects, the VH and VL are separated by a peptide linker. In some aspects, the scFv comprises the structure VH-L-VL or VL-L-VH, wherein VH is the heavy chain variable domain, L is the peptide linker, and VL is the light chain variable domain.

In some aspects, the antigen recognizing receptor is a chimeric antigen receptor (CAR) or T cell receptor (TCR). In some aspects, the antigen recognizing receptor is a chimeric antigen receptor (CAR). In some aspects, the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain. In some aspects, the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain. In some aspects, the CAR comprises a spacer region between the antigen-binding domain and the transmembrane domain.

Also provided for herein is a population of cells, the population of cells comprising any of the engineered cells described herein. In some aspects, the population of cells is enriched for the engineered cells.

In some aspects, the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules. In some aspects, the first effector molecule is IL12 or an IL12p70 fusion protein. In some aspects, the population of cells enriched for the engineered cells express IL12 receptor β1 or increased levels thereof, IL12 receptor β2 or increased levels thereof, or IL12 receptor β1 and IL12 receptor β2 or increased levels thereof. In some aspects, the second effector molecule is IL21. In some aspects, the second effector molecule is CCL21. In some aspects, the population of cells enriched for the engineered cells express a CCL21 receptor or increased levels thereof. In some aspects, the CCL21 receptor is CCR7.

Also provided for herein is a method of stimulating a cell-mediated immune response to a tumor cell in a subject, the method comprising administering to a subject having a tumor a therapeutically effective dose of any of the engineered cells or the population of cells described herein.

Also provided for herein is a method of stimulating (e.g., inducing) an immune response, the method comprising administering to a subject a therapeutically effective dose of any of the engineered cells or the population of cells described herein.

Also provided for herein is a method of providing anti-tumor immunity in a subject, the method comprising administering to a subject in need thereof a therapeutically effective dose of any of the engineered cells any of the engineered cells or the population of cells described herein.

Also provided for herein is a method of treating a subject having cancer, the method comprising administering to a subject having a tumor a therapeutically effective dose of any of the engineered cells or the population of cells described herein.

Also provided for herein is a method of reducing tumor volume in a subject, the method comprising administering to a subject having a tumor a therapeutically effective dose of any of the engineered cells or the population of cells described herein.

In some aspects, the engineered cell is derived from the subject. In some aspects, the engineered cell is allogeneic with reference to the subject.

In some aspects, the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor. In some aspects, the tumor is an ovarian tumor. In some aspects, the tumor is a tumor located in a peritoneal space.

Also provided for herein is an engineered cell comprising: a) a promoter; and b) an exogenous polynucleotide sequence comprising an expression cassette described in a formula, oriented from 5' to 3', comprising:

$$(L-S-E)_X$$

wherein S comprises a polynucleotide sequence encoding a signal peptide, E comprises a polynucleotide sequence encoding an effector molecule, L comprises a linker polynucleotide sequence, X=2 to 20, wherein the promoter is operably linked to the expression cassette, wherein for the first iteration of the (L-S-E) unit L is absent, and wherein for each X the corresponding signal peptide is operably associated with the effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a population of cells comprising one or more engineered cells, wherein the one or more engineered cells comprise: a) a promoter; and b) an exogenous polynucleotide sequence comprising an expression cassette described in a formula, oriented from 5' to 3', comprising $$S1-E1-L-S2-E2$$

wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a population of cells comprising one or more engineered cells, wherein the one or more engineered cells comprise: a) a promoter; and b) an exogenous polynucleotide sequence comprising an expression cassette described in a formula, oriented from 5' to 3', comprising $$S1-E1-L-S2-E2$$

wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the one or more engineered cells express a cognate receptor or cognate receptor ligand for the first effector molecule, the second effector molecule, or the first and second effector molecules expressed in the engineered cells. In some aspects, the first effector molecule is IL12 or an IL12p70 fusion protein. In some aspects, the second effector molecule is IL21. In some aspects, the second effector molecule is CCL21.

Also provided for herein is a population of cells comprising one or more engineered cells, wherein the one or more engineered cells comprise a construct, wherein the construct comprises: a) an SFFV promoter; and b) an exogenous polynucleotide sequence comprising an expression cassette described in a formula, oriented from 5' to 3', comprising $$S1-E1-L-S2-E2$$

wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a population of cells comprising one or more engineered cells, wherein the one or more engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is a method of producing a population of cells enriched for one or more receptors or receptor ligands, comprising culturing one or more cells under conditions where the one or more cells are contacted with a first effector molecule, a second effector molecule, or a first and a second effector molecule, wherein the contacted cells express one or more cognate receptors or cognate receptor ligands for the first effector molecule, the second effector molecule, or the first and second effector molecules, and wherein the first effector molecule, the second effector molecule, or the first and the second effector molecules increase growth, viability, or growth and viability of the contacted cells relative to cells cultured in the absence of the first effector molecule, the second effector molecule, or the first and second effector molecules.

In some aspects, the first effector molecule, the second effector molecule, or the first and second effector molecules are heterologously expressed in one or more cells, and the one or more cells are contacted with the first effector molecule, the second effector molecule, or the first and second effector molecules in an autocrine manner. In some aspects, the first effector molecule, the second effector molecule, or the first and second effector molecules are expressed in one or more additional cells, and the one or more cells are contacted with the first effector molecule, the second effector molecule, or the first and second effector molecules in an paracrine manner. In some aspects, the one or more additional cells are a feeder cells. In some aspects, the one or more cells are cultured in media.

In some aspects, the one or more cells are contacted with the first effector molecule, the second effector molecule, or the first and second effector molecules by addition of a soluble first effector molecule, a soluble second effector molecule, or a soluble first and second effector molecules to the media. In some aspects, the soluble first effector molecule and/or soluble second effector molecule is a recombinant effector molecule.

In some aspects, the one or more cells are cultured under adherent conditions. In some aspects, the one or more cells are adhered onto a surface. In some aspects, the adhered cells are contacted with the first effector molecule, the second effector molecule, or the first and second effector molecules by exposing the one or more cells to first effector molecule, the second effector molecule, or the first and second effector molecules is immobilized on the surface.

In some aspects, the first effector molecule is IL12 or an IL12p70 fusion protein. In some aspects, the population of cells is enriched for IL12 receptor β1 (IL12Rβ1), enriched for IL12 receptor β2 (IL12Rβ2), or enriched for IL12Rβ1 and IL12Rβ2. In some aspects, the population of MSCs comprises a cellular marker phenotype comprising the cellular markers CD105+, CD73+, CD90+, IL12Rβ1+, and IL12Rβ2+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof.

In some aspects, the population of cells comprises a cell selected from the group consisting of: natural killer (NK) cells, NKT cells, innate lymphoid cells, mast cells, eosinophils, basophils, monocytes, macrophages, neutrophils, and dendritic cells, T cells, CD8+ T cells, CD4+ T cells, gamma-delta T cells, and T regulatory cells, and B cells. In some aspects, the population of cells comprises a T cell, a NK cell, a NKT cell, a monocyte, a macrophage, or a myeloid derived cell.

In some aspects, the second effector molecule is IL21. In some aspects, the second effector molecule is CCL21. In some aspects, the population of cells is enriched for CCR7. In some aspects, the population of MSCs comprises a cellular marker phenotype comprising the cellular markers CD105+, CD73+, CD90+, IL12Rβ1+, IL12Rβ2+, and CCR7+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof.

Also provided for herein is a population of cells enriched for one or more receptors or receptor ligands produced by any of the methods described herein.

Also provided for herein is one or more proteins expressed by a polynucleotide sequence, wherein the polynucleotide sequence comprising a promoter and an expression cassette described in a formula, oriented from 5' to 3', comprising

E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule.

Also provided for herein is one or more proteins expressed by a polynucleotide sequence, wherein the polynucleotide sequence comprises an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, the first signal peptide is operably linked to the first effector molecule, and the second signal peptide is operably linked to the second effector molecule.

Also provided for herein is an isolated polynucleotide sequence comprising a promoter and an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule.

Also provided for herein is an isolated polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, the first signal peptide is operably linked to the first effector molecule, and the second signal peptide is operably linked to the second effector molecule.

In some aspects, the promoter comprises an exogenous promoter polynucleotide sequence. In some aspects, the promoter comprises an endogenous promoter. In some aspects, the promoter is operably linked to the expression cassette such that the polynucleotides are capable of being transcribed as a single polynucleotide comprising the formula S1-E1-L-S2-E2.

In some aspects, the linker polynucleotide sequence is operably associated with the translation of the first effector molecule and the second effector molecule as separate polypeptides. In some aspects, the linker polynucleotide sequence encodes a 2A ribosome skipping tag. In some aspects, the 2A ribosome skipping tag is selected from the group consisting of: P2A, T2A, E2A, and F2A. In some aspects, the linker polynucleotide sequence encodes a T2A ribosome skipping tag. In some aspects, the linker polynucleotide sequence encodes an Internal Ribosome Entry Site (IRES).

In some aspects, the linker polynucleotide sequence encodes a cleavable polypeptide. In some aspects, the cleavable polypeptide comprises a Furin recognition polypeptide sequence. In some aspects, the linker polynucleotide sequence further encodes a Gly-comprising, Ser-comprising, or Gly-Ser comprising polypeptide sequence, e.g., a Gly-Ser-Gly polypeptide sequence. In some aspects, the linker polynucleotide sequence encodes a Furin recognition polypeptide sequence, a Gly-Ser-Gly polypeptide sequence, and a T2A ribosome skipping tag in a Furin:Gly-Ser-Gly: T2A orientation from N-terminus to C-terminus.

In some aspects, the linker polynucleotide sequence encodes a second promoter, wherein the promoter is operably linked to the expression cassette such that a first polynucleotide comprising the formula S1-E1 is capable of being transcribed, wherein the second promoter is operably linked to the expression cassette such that a second polynucleotide comprising the formula S2-E2 is capable of being transcribed, and wherein the first and the second polynucleotide are separate polynucleotides. In some aspects, the promoter and the second promoter are identical. In some aspects, the promoter and the second promoter are different.

In some aspects, the promoter and/or the second promoter comprises a constitutive promoter. In some aspects, the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb. In some aspects, the promoter comprises an SFFV promoter. In some aspects, the promoter and/or the second promoter comprises an inducible promoter. In some aspects, the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof.

In some aspects, the first signal peptide or the second signal peptide comprises a native signal peptide native to the first effector molecule or the second effector molecule, respectively. In some aspects, the first signal peptide or the second signal peptide comprises a non-native signal peptide non-native to the first effector molecule or the second effector molecule, respectively. In some aspects, the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21. In some aspects, the first signal peptide and the second signal peptide are identical. In some aspects, the polynucleotide sequence encoding the first signal peptide comprises a codon optimized polynucleotide sequence.

In some aspects, the first secretion polypeptide is a human IL12 signal peptide. In some aspects, the polynucleotide sequence encoding the second signal peptide comprises a codon optimized polynucleotide sequence. In some aspects, the second secretion polypeptide is a human IL21 signal peptide.

In some aspects, the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme. In some aspects, the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme. In some aspects, the therapeutic class of the first effector molecule and the second effector molecule are different. In some aspects, the first effector molecule and/or the second effector molecule is a modified effector molecule.

In some aspects, the first effector molecule and/or the second effector molecule is modified to comprises a cell membrane tethering domain. In some aspects, the cell membrane tethering domain comprises a transmembrane-intracellular domain or a transmembrane domain. In some aspects, the cell membrane tethering domain comprises a cell surface receptor, or a cell membrane-bound portion thereof. In some aspects, the modified effector molecule is a fusion protein that comprises the cell surface receptor, or a cell membrane-bound portion thereof. In some aspects, the modified effector molecule further comprises a linker between the effector molecule and the cell membrane tethering domain. In some aspects, when expressed in a cell, the modified effector molecule is tethered to a cell membrane of the cell.

In some aspects, the cytokine is selected from the group consisting of: IL12, IL7, IL21, IL18, IL15, Type I interferons, and Interferon-gamma. In some aspects, the IL12 cytokine is an IL12p70 fusion protein. In some aspects, the chemokine is selected from the group consisting of: CCL21a, CXCL10, CXCL11, CXCL13, CXCL10-11 fusion, CCL19, CXCL9, and XCL1. In some aspects, the growth factor is selected from the group consisting of: Flt3L and GM-CSF. In some aspects, the co-activation molecule is selected from the group consisting of: 4-1BBL and CD40L. In some aspects, the tumor microenvironment modifier is selected from the group consisting of: adenosine deaminase, TGFbeta inhibitors, immune checkpoint inhibitors, VEGF inhibitors, and HPGE2. In some aspects, the TGFbeta inhibitors are selected from the group consisting of: an anti-TGFbeta peptide, an anti-TGFbeta antibody, a TGFb-TRAP, and combinations thereof. In some aspects, the immune checkpoint inhibitors comprise anti-PD-1 antibodies. In some aspects, the VEGF inhibitors comprise anti-VEGF antibodies, anti-VEGF peptides, or combinations thereof.

In some aspects, the first effector molecule and the second effector molecule are human-derived effector molecules.

In some aspects, the first effector molecule comprises IL12. In some aspects, the first effector molecule comprises an IL12p70 fusion protein. In some aspects, the IL12p70 fusion protein is a human IL12p70 fusion protein.

In some aspects, the second effector molecule comprises CCL21a. In some aspects, the CCL21a is a human CCL21a.

In some aspects, the second effector molecule comprises IL7. In some aspects, the IL7 is a human IL7. In some aspects, the second effector molecule comprises IL21. In some aspects, the IL21 is a human IL21.

In some aspects, the expression cassette further comprises an E3 comprising a polynucleotide sequence encoding a third effector molecule. In some aspects, the third effector molecule comprises Flt3L. In some aspects, the third effector molecule comprises anti-PD1.

In some aspects, the expression cassette further comprises an E4 comprising a polynucleotide sequence encoding a fourth effector molecule. In some aspects, the fourth effector molecule comprises adenosine deaminase.

In some aspects, the third effector molecule comprises adenosine deaminase. In some aspects, the third effector molecule comprises CD40L. In some aspects, the third effector molecule comprises a CXCL10-CXCL11 fusion protein. In some aspects, the third effector molecule comprises XCL1.

In some aspects, the second effector molecule comprises Flt3L. In some aspects, the second effector molecule comprises a CXCL10-CXCL11 fusion protein. In some aspects, the second effector molecule comprises anti-PD1. In some aspects, the second effector molecule comprises CD40L.

In some aspects, the first effector molecule comprises interferon-beta and the second effector molecule comprises Flt3L.

In some aspects, the polynucleotide sequence encoding the first effector molecule comprises a codon optimized polynucleotide sequence. In some aspects, the polynucleotide sequence encoding the second effector molecule comprises a codon optimized polynucleotide sequence.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an exogenous polynucleotide sequence comprising an SFFV promoter and an expression cassette described in a formula, oriented from 5' to 3', comprising

E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an exogenous polynucleotide sequence comprising an SFFV promoter and an expression cassette described in a formula, oriented from 5' to 3', comprising

E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; wherein the SFFV promoter is operably linked to the expression cassette, the first signal peptide is operably linked to the first effector molecule, and the second signal peptide is operably linked to the second effector molecule; wherein the promoter is operably linked to the expression cassette such that the polynucleotides are capable of being transcribed as a single polynucleotide comprising the formula S1-E1-L-S2-E2; and wherein the polynucleotide sequence comprises the polynucleotide sequence shown in SEQ ID NO: 144.

In some aspects, the exogenous polynucleotide sequence is encoded by a nucleic acid selected from the group consisting of: a DNA, a cDNA, an RNA, an mRNA, and a naked plasmid.

Also provided for herein is an expression vector comprising any of the exogenous polynucleotide sequences described herein. In some aspects, the expression vector is a viral vector. In some aspects, the viral vector is a lentiviral vector.

Also provided for herein is a pharmaceutical composition comprising any of the exogenous polynucleotide sequences described herein, and a pharmaceutically acceptable carrier.

Also provided for herein is a pharmaceutical composition comprising any of engineered cells described herein, and a pharmaceutically acceptable carrier.

An isolated cell comprising any of the exogenous polynucleotide sequences described herein, any of the expression vectors described herein, or any of the pharmaceutical compositions described herein.

In some aspects, the isolated cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, an MSC, an induced pluripotent stem cell (iPSC), and an iPSC-derived cell.

In some aspects, the isolated cell is an MSC.

In some aspects, the exogenous polynucleotide sequence is integrated into the genome of the cell. In some aspects, the exogenous polynucleotide sequence comprises one or more viral vector polynucleotide sequences.

In some aspects, the one or more viral vector polynucleotide sequences comprise lentiviral, retroviral, retrotransposon, or adenoviral polynucleotide sequences. In some aspects, the one or more viral vector polynucleotide sequences comprise lentiviral polynucleotide sequences.

In some aspects, the engineered cell is HLA-typed with reference to a subject in need of therapeutic treatment. In some aspects, the engineered cell is a human cell. In some aspects, the human cell is an isolated cell from a subject, e.g., the subject who will receive the cell. In some aspects, the isolated cell is isolated from a tissue consisting of the group of: bone marrow, adipose tissue, the umbilical cord, fetal liver, muscle, and lung tissue. In some aspects, the cell is a cultured cell.

In some aspects, the MSC comprises a cellular marker phenotype comprising the cellular markers CD105+, CD73+, and CD90+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof. In some aspects, the MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−. In some aspects, the cellular marker phenotype is determined or has been determined by flow-cytometry.

In some aspects, the cellular marker phenotype further comprises a cellular marker comprising a cognate receptor or a cognate receptor ligand for the first effector molecule, the second effector molecule, or the first and second effector molecules expressed in the cell. In some aspects, the receptor is selected from the group consisting of: IL12RB1, IL12RB2, CCL7, and combinations thereof.

In some aspects, the cell secretes each effector molecule. In some aspects, the first effector molecule is secreted at a ratio that is 10 fold higher relative to secretion of the second effector molecule.

In some aspects, the cell further comprises an antigen recognizing receptor. In some aspects, the antigen recognizing receptor comprises an antigen-binding domain. In some aspects, the antigen-binding domain comprises an antibody, an antigen-binding fragment of an antibody, a F(ab) fragment, a F(ab') fragment, a single chain variable fragment (scFv), or a single-domain antibody (sdAb). In some aspects, the antigen-binding domain comprises a single chain variable fragment (scFv). In some aspects, the scFv comprises a heavy chain variable domain (VH) and a light chain variable domain (VL). In some aspects, the VH and VL are separated by a peptide linker. In some aspects, the scFv comprises the structure VH-L-VL or VL-L-VH, wherein VH is the heavy chain variable domain, L is the peptide linker, and VL is the light chain variable domain.

In some aspects, the antigen recognizing receptor is a chimeric antigen receptor (CAR) or T cell receptor (TCR). In some aspects, the antigen recognizing receptor is a chimeric antigen receptor (CAR). In some aspects, the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain. In some aspects, the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain. In some aspects, the CAR comprises a spacer region between the antigen-binding domain and the transmembrane domain.

Also provided for herein is a virus comprising any of the exogenous polynucleotide sequences described herein or any of the expression vectors described herein. In some aspects, the virus is selected from the group consisting of: a lentivirus, a retrovirus, a retrotransposon, and an adenovirus. In some aspects, the virus is a lentivirus.

Also provided for herein is a method of reducing tumor volume in a subject, the method comprising delivering to a subject having a tumor a composition comprising cells engineered to produce multiple effector molecules that modulate tumor-mediated immunosuppressive mechanisms, in an effective amount to reduce the volume of the tumor, wherein the engineered cells comprise: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of reducing tumor volume in a subject, the method comprising delivering to a subject having a tumor a composition comprising cells engineered to produce IL12 and IL21, in an effective amount to reduce the volume of the tumor, wherein the engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of stimulating (e.g., inducing) an immune response, the method comprising delivering to a subject a composition comprising cells engineered to produce multiple effector molecules that modulate tumor-mediated immunosuppressive mechanisms, in an effective amount to induce an immune response, wherein the engineered cells comprise: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of stimulating (e.g., inducing) an immune response in a subject, the method comprising delivering to a subject a composition comprising cells engineered to produce IL12 and IL21, in an effective amount to induce an immune response, wherein the engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

In some aspects, the method further comprises administering a checkpoint inhibitor. In some aspects, the checkpoint inhibitor is an anti-PD-1 antibody, anti-PD-1L antibody or an anti-CTLA-4 antibody. In some aspects, the method further comprises administering an anti-CD40 antibody.

In some aspects, the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor. In some aspects, the tumor is an ovarian tumor. In some aspects, the tumor is a tumor located in a peritoneal space.

In some aspects, the administering comprises systemic administration, intraperitoneal administration, or intratumoral administration.

In some aspects, the volume of the tumor is reduced by at least 25% relative to a control, optionally wherein the control is an unmodified cell. In some aspects, the volume of the tumor is reduced by at least 50% relative to a control, optionally wherein the control is an unmodified cell. In some aspects, the volume of the tumor is reduced by at least 75% relative to a control, optionally wherein the control is an unmodified cell.

Also provided for herein is a method of reducing tumor volume in a subject, the method comprising delivering to a subject having a tumor a composition capable of engineering an cell to produce multiple effector molecules that modulate tumor-mediated immunosuppressive mechanisms, in an effective amount to reduce the volume of the tumor, wherein each engineered cell comprises: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is method of reducing tumor volume in a subject, the method comprising delivering to a subject having a tumor a composition capable of engineering a cell to produce IL12 and IL21, in an effective amount to reduce the volume of the tumor, wherein the engineered cell comprises a construct, wherein the construct comprises: a)

an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of stimulating (e.g., inducing) an immune response in a subject, the method comprising delivering to a subject a composition capable of engineering an cell to produce multiple effector molecules that modulate tumor-mediated immunosuppressive mechanisms, in an effective amount to induce an immune response, wherein the engineered cell comprises: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is method of stimulating (e.g., inducing) an immune response in a subject, the method comprising delivering to a subject a composition capable of engineering a cell to produce IL12 and IL21, in an effective amount to induce an immune response, wherein the engineered cell comprises a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

In some aspects, the composition comprises a delivery system selected from the group consisting of: a viral system, a transposon system, and a nuclease genomic editing system. In some aspects, the viral system is selected from the group consisting of: a lentivirus, a retrovirus, a retrotransposon, and an adenovirus. In some aspects, the nuclease genomic editing system is selected from the group consisting of: a zinc-finger system, a TALEN system, and a CRISPR system.

In some aspects, the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.

In some aspects, the administering comprises systemic administration, intraperitoneal administration, or intratumoral administration.

BRIEF DESCRIPTION OF THE DRAWINGS

FIG. 2A shows the treatment schematic.

FIG. 2B shows tumor free mice rejecting the tumor implant in contrast to naïve control mice where the tumor became established.

FIG. 7B shows the tumor weight for individual mice in each treatment, and the mean±SEM for each treatment group.

FIG. 9B shows the tumor weight for individual mice in each treatment, and the mean±SEM for each treatment group.

FIG. 10A shows that engineered MSCs expressing GFP do not elicit toxicity. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 10A represents an individual mouse.

FIG. 10B shows the tumor weight for individual mice in each treatment, and the mean±SEM for each treatment group.

FIG. 11B shows the tumor weight for individual mice in each treatment, and the mean±SEM for each treatment group.

FIG. 13B shows the tumor weight for individual mice in each treatment, and the mean±SEM for each treatment group.

FIG. 17A shows the tumor volume of the individual group. Each line of FIG. 17A represents an individual mouse.

FIG. 17B shows body weight represented as mean±SEM (top left), tumor volume represented as mean±SEM (bottom left), and survival rate (right).

FIG. 18B shows the tumor weight for individual mice in each treatment, and the mean±SEM for each treatment group.

FIG. 18C is a representative graph of the infiltrating immune population within the tumor microenvironment for individual mice in each treatment, and the mean±SEM for each treatment group.

FIG. 18D shows the percentage of regulatory T cells (Treg) in the total CD3 population for individual mice in each treatment, and the mean±SEM for each treatment group. There was a significant decrease in the numbers of Tregs in the tumor microenvironment treated with engineered MSC-IL2 and CCL21a.

FIG. 18E correlates the percentage of immune infiltration with tumor weight. Samples with high lymphocytes (CD3+) were found to correlate with low tumor weight, while samples with high myeloid (CD11b+) infiltration were correlated with higher tumor burden.

FIG. 21B shows the immune profile of three (3) mice in the day 18 group to better characterize the tumor microenvironment.

FIG. 22B shows the tumor weight for individual mice in each treatment group, and the mean±SEM for each treatment group.

FIG. 23A shows a significant increase in infiltrating CD3 and CD8 cytotoxic T population in the combo group compared to the group dosed with naïve MSC.

FIG. 23B shows a significant reduction in granulocytic myeloid-derived suppressor cells (gMDSCs) and macrophage population in the combo group compared to group treated with Naïve MSC.

FIG. 24A shows that samples with more CD3+ and CD8+ T cells (top left and top center graph) correlate strongly with a decrease in tumor weight. These figures also show that samples with fewer CD11b myeloid cells, including macrophage, dendritic cells, and MDSC, display lower tumor burden (lower center and lower right graph).

FIG. 24B shows that samples with fewer CD11b myeloid cells, including macrophage, dendritic cells, and MDSC, display lower tumor burden (upper row).

FIG. 25A shows that all three lots of MSC-IL12+MSC-CCL21a can reduce tumor burden in both subcutaneous and intraperitoneal model (first 5 graphs are from the SC model and last 3 are from the IP model). Tumors from all mice were collected on day 11. Each line of FIG. 25A represents an individual mouse.

each TL number represents one lot). FIG. 25B shows the average tumor weight from each group, and the mean±SEM for each treatment group.

FIG. 26B shows the tumor weight for individual mice in each treatment, and the mean for each treatment group. MSC-IL12+MSC-CCL21a shows best efficacy compared to mice injected with naïve MSC. Treatment efficacy was also observed in the group treated with MSC-IFNb+MSC-CCL21a.

FIG. 27A are graphs that show immune profiles of each group treated with indicated engineered MSC. A consistent decrease in macrophage population was observed after treating with MSC-IL12+MSC-CCL21a. A general trend of increased infiltration in CD3+ population and decreased infiltration in CD11b+ population was also observed when compared to group treated with MSC-IL12+MSC-CCL21a against naïve MSC.

FIG. 27B are graphs that show immune profiles of each group treated with indicated engineered MSC. A general trend of increased infiltration in CD3+ population and decreased infiltration in CD11b+ population was also observed when compared to group treated with MSC-IL12+MSC-CCL21a against naïve MSC.

FIG. 28A shows the correlation of immune infiltration with tumor weight.

FIG. 28B shows the correlation of immune infiltration with tumor weight. Samples with low macrophage and dendritic cells have lower tumor burden (top center and top right).

FIG. 29 shows graphs combining the in vivo data from the colorectal cancer models above (FIG. 22A and FIG. 26A). The combined CT26 data from FIG. 22A and FIG. 26A capture three groups: Tumor only (PBS), treated with naïve MSC, and treated with MSC-IL12+MSC-CCL21a.

FIG. 37A shows homing in a CT26 tumor model (images shown).

FIG. 37B shows homing in a CT26 tumor model for individual mice in each treatment, and the mean±SEM for each treatment group (quantification summary of images shown in FIG. 37A).

FIG. 37C shows quantitative real time PCR for individual mice in each treatment, and the mean±SEM for each treatment group.

FIG. 37D shows fluorescence microscopy against firefly luciferase.

FIG. 37E shows homing in a B16F10 tumor model for individual mice in each treatment, and the mean±SEM for each treatment group (quantification summary of images).

FIG. 40A shows the mean tumor burden as assessed by BLI for PBS treated (circle), MSC-Flag-Myc ("Naïve MSC" square), and IL12p70/CCL21a expressing MSCs (triangle).

FIG. 40B shows the tumor burden in individual mice as assessed by BLI for PBS treated, MSC-Flag-Myc ("Naïve MSC"), and IL12p70/CCL21a expressing MSCs (left, middle, and right panels, respectively). Each line of FIG. 40B represents an individual mouse.

FIG. 52B demonstrates the BLI luciferase measurements of individual mice.

FIG. 53B shows survival curves of the treatment groups.

FIG. 57A shows naïve untreated mice.

FIG. 57B shows mice that previously received the treatment of IL12-expressing MSCs alone.

FIG. 57C shows mice that previously received the combination treatment of IL12-expressing MSCs and IL21-expressing MSCs.

FIG. 58A shows summarized BLI assessment of efficacy normalized day 17 vs day 7 for individual mice in each treatment, and the mean±SEM for each treatment group.

FIG. 58B shows BLI measurements over time for individual mice.

FIG. 58C shows BLI measurements over time for individual mice.

FIG. 58D shows survival curves of the treatment groups.

FIG. 59A shows summarized BLI assessment of efficacy normalized day 17 vs day 7 for individual mice in each treatment, and the mean±SEM for each treatment group.

FIG. 59B shows BLI measurements over time for individual mice.

FIG. 59C shows BLI measurements over time for individual mice.

FIG. 59D shows BLI measurements over time for individual mice for multiple administrations of higher doses.

FIG. 59E shows survival curves of the treatment groups.

FIG. 60A shows summarized BLI assessment of efficacy normalized day 18 vs day 9 for individual mice in each treatment, and the mean±SEM for each treatment group.

FIG. 60B shows BLI measurements over time for individual mice.

FIG. 60C shows survival curves of the treatment groups.

FIG. 61A shows summarized luciferase quantification.

FIG. 61B shows representative images of luciferase signal in organs.

FIG. 63A shows survival curves of MSC-IL12 vs rIL12.

FIG. 63B shows survival curves of MSC-IL21 vs rIL21.

FIG. 63C shows efficacy of mice either treated with MSCs engineered to produce cytokines or treated with recombinant cytokine therapy in a CT26 model. FIG. 63C shows survival curves of MSC-IL12/IL21 vs rIL12+rIL21.

FIG. 63D shows BLI assessments of tumor burden for mice either treated with MSCs engineered to produce cytokines or treated with recombinant cytokine therapy.

FIG. 63E shows BLI assessments of tumor burden for mice either treated with MSCs engineered to produce cytokines or treated with recombinant cytokine therapy.

FIG. 64A shows tumor weight assessments of tumor burden for individual mice in each treatment, and the mean±SEM for each treatment group, for mice either treated with MSCs engineered to produce cytokines or treated with recombinant cytokine therapy FIG. 64B shows efficacy of mice either treated with MSCs engineered to produce cytokines or treated with recombinant cytokine therapy in a B16F10 model. FIG. 64B shows survival curves of treatment groups.

Figure 65A:
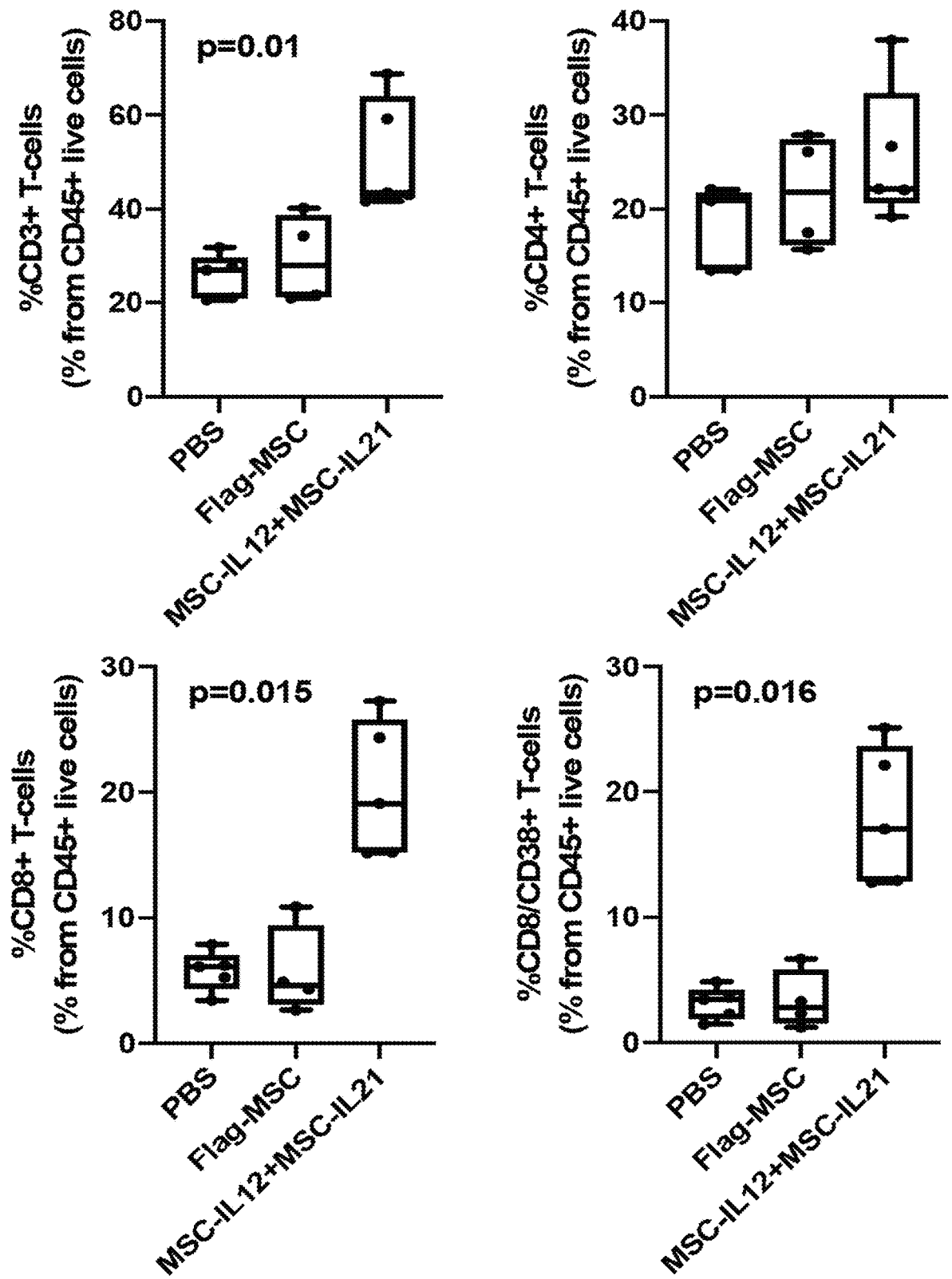

FIG. 65A shows the immune profile of mice following treatment with MSCs producing both IL12 and IL21 in a CT26 IP tumor model. Results shown are multicolor flow cytometry analysis used to characterize immune infiltrates in response to treatment. FIG. 65A shows T-cell subsets and activation markers (CD3, CD4, CD8, CD8/CD38+) for individual mice in each treatment, and the mean±SEM for each treatment group.

Figure 65B:
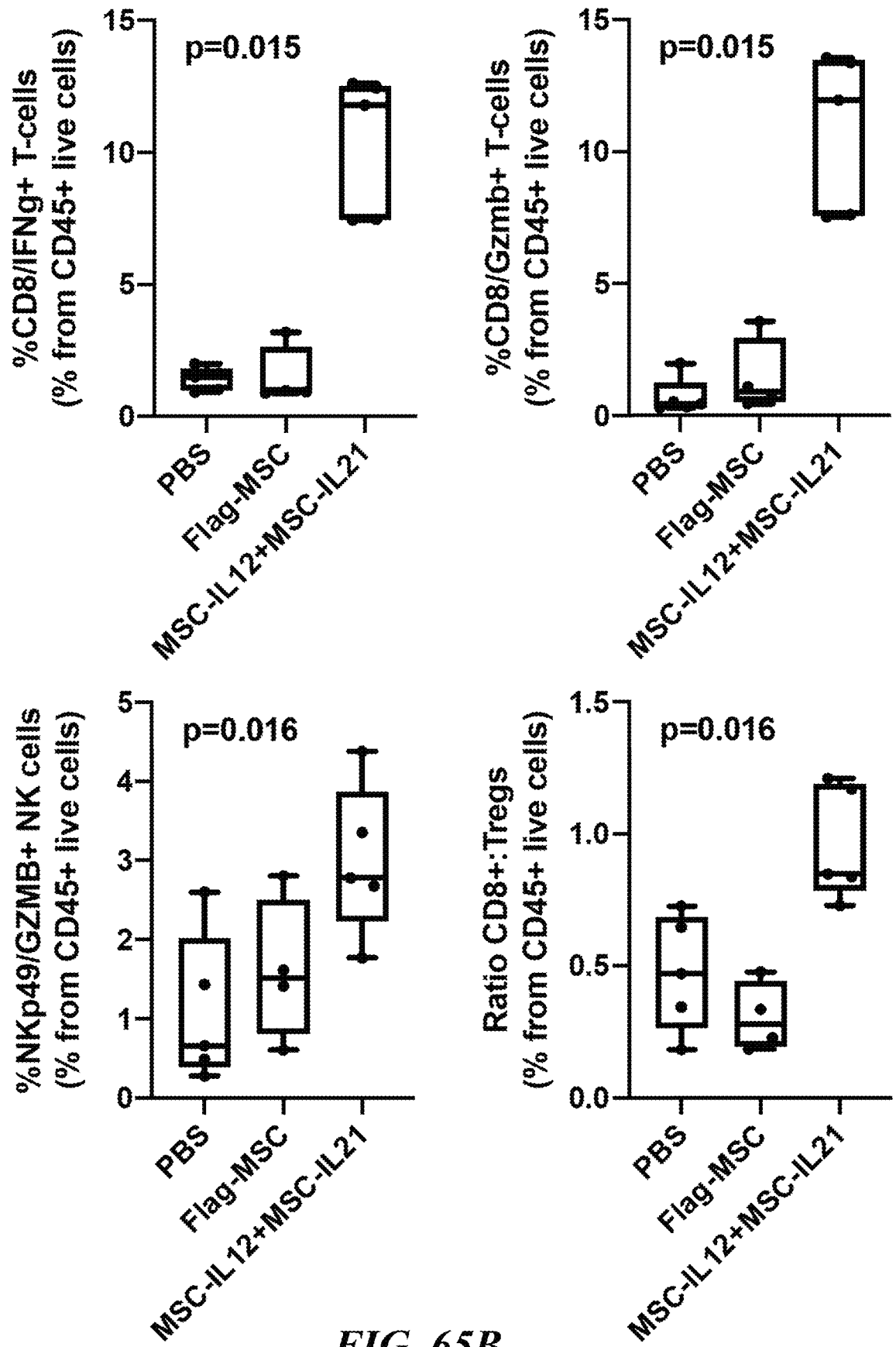

FIG. 65B shows the immune profile of mice following treatment with MSCs producing both IL12 and IL21 in a CT26 IP tumor model. Results shown are multicolor flow cytometry analysis used to characterize immune infiltrates in response to treatment. FIG. 65B shows T-cell subsets and activation markers (CD8/IFNg+, CD8/Gzmb+, NK/Gzmb+ and ratio CD8:Tregs-FoxP3) for individual mice in each treatment, and the mean±SEM for each treatment group.

Figure 65C:
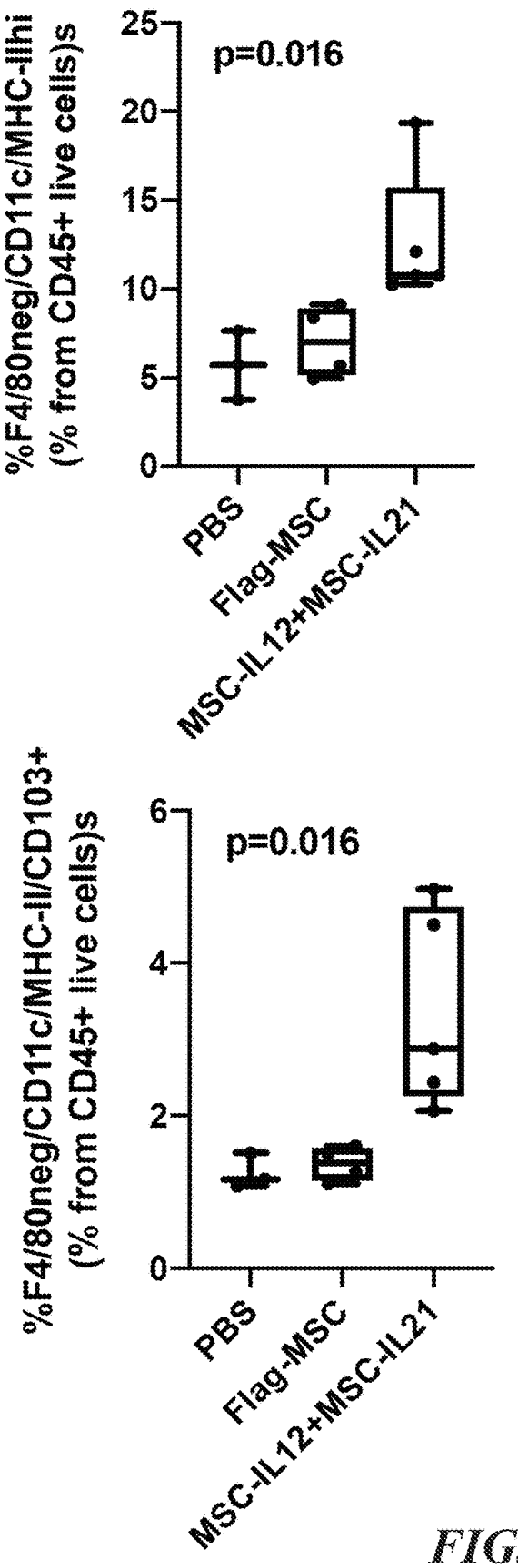
Figure 65C:
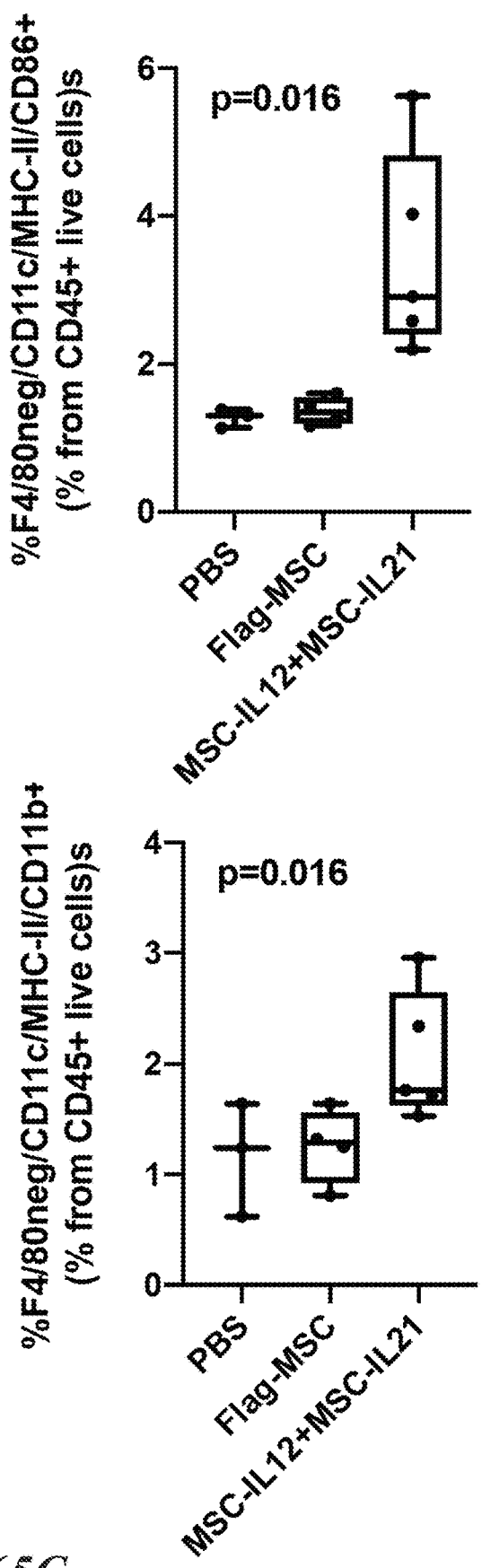

FIG. 65C shows the immune profile of mice following treatment with MSCs producing both IL12 and IL21 in a CT26 IP tumor model. Results shown are multicolor flow cytometry analysis used to characterize immune infiltrates in response to treatment. FIG. 65C shows the immune profile of antigen-presenting cells such as dendritic cells for individual mice in each treatment, and the mean±SEM for each treatment group.

DETAILED DESCRIPTION

Mesenchymal stem cells (MSCs) (also referred to as mesenchymal stromal cells, multipotent stromal cells, marrow stromal cells, or multipotent mesenchymal stromal cells) are a subset of non-hematopoietic adult stem cells that originate from the mesoderm. They possess self-renewal ability and multilineage differentiation into not only mesoderm lineages, such as chondrocytes, osteocytes and adipocytes, but also ectodermic cells and endodermic cells. MSCs, free of both ethical concerns and teratoma formation, are the major stem cell type used for cell therapy for treatment of both immune diseases and non-immune diseases. They can be easily isolated from the bone marrow, adipose tissue, the umbilical cord, fetal liver, muscle, and lung and can be successfully expanded in vitro. MSCs can be defined by cell surface marker phenotype including a cellular marker phenotype comprising CD105+, CD73+, CD90+, CD45−, CD34−, CD14−; a cellular marker phenotype comprising CD105+, CD73+, CD90+, CD11b−, CD79α−; or a cellular marker phenotype comprising CD105+, CD73+, CD90+, CD19−, HLA class II−, as discussed in greater detail in Dominici, et al. (Cytotherapy. 2006; 8(4):315-7), incorporated by reference for all purposes. Further, when MSCs are delivered exogenously and systemically to humans and animals, they tend to home to (migrate directly to) damaged tissue sites with inflammation, including tumor microenvironments and metastatic regions. The inflammation-directed MSC homing involves several important cell trafficking-related molecules, including chemokines, adhesion molecules, and matrix metalloproteinases (MMPs).

Provided herein are methods of engineering cells, such as MSCs, to produce effector molecules that modulate different tumor-mediated immunosuppressive mechanisms. These MSCs are referred to herein as "engineered MSCs." These MSCs, which typically contain engineered nucleic acid, do not occur in nature. In some embodiments, the MSCs are engineered to include a nucleic acid comprising a promoter operably linked to a nucleotide sequence encoding an effector molecule, for example, one that stimulates an immune response.

Also provided herein are methods of engineering cells such as immune cells, including, but not limited to natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell, to produce effector molecules. These cells, including both MSCs and immune cells, are referred to herein as "engineered cells." These cells, which typically contain engineered nucleic acid, do not occur in nature. In some embodiments, the cells are engineered to include a nucleic acid comprising a promoter operably linked to a nucleotide sequence encoding an effector molecule, for example, one that stimulates an immune response.

An "effector molecule," refers to a molecule (e.g., a nucleic acid such as DNA or RNA, or a protein (polypeptide) or peptide) that binds to another molecule and modulates the biological activity of that molecule to which it binds. For example, an effector molecule may act as a ligand to increase or decrease enzymatic activity, gene expression, or cell signaling. Thus, in some embodiments, an effector molecule modulates (activates or inhibits) different immunomodulatory mechanisms. By directly binding to and modulating a molecule, an effector molecule may also indirectly modulate a second, downstream molecule. In some embodiments, an effector molecule is a secreted molecule, while in other embodiments, an effector molecule is bound to the cell surface or remains intracellular. For example, effector molecules include intracellular transcription factors, microRNA, and shRNAs that modify the internal cell state to, for example, enhance immunomodulatory activity, homing properties, or persistence of the cell. Non-limiting examples of effector molecules include cytokines, chemokines, enzymes that modulate metabolite levels, antibodies or decoy molecules that modulate cytokines, homing molecules, and/or integrins.

The term "modulate" encompasses maintenance of a biological activity, inhibition (partial or complete) of a biological activity, and stimulation/activation (partial or complete) of a biological activity. The term also encompasses decreasing or increasing (e.g., enhancing) a biological activity. Two different effector molecules are considered to "modulate different tumor-mediated immunosuppressive mechanisms" when one effector molecule modulates a tumor-mediated immunosuppressive mechanism (e.g., stimulates T cell signaling) that is different from the tumor-mediated immunosuppressive mechanism modulated by the other effector molecule (e.g., stimulates antigen presentation and/or processing).

Modulation by an effector molecule may be direct or indirect. Direct modulation occurs when an effector molecule binds to another molecule and modulates activity of that molecule. Indirect modulation occurs when an effector molecule binds to another molecule, modulates activity of that molecule, and as a result of that modulation, the activity of yet another molecule (to which the effector molecule is not bound) is modulated.

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in an increase in an immunostimulatory and/or anti-tumor immune response by at least 20%, at least 30%, at least 40%, at least 50%, at least 60%, at least 70%, at least 80%, at least 90%, at least 100%. In some embodiments, modulation of a tumor-mediated immunosuppressive mechanism results in an increase in an immunostimulatory and/or anti-tumor immune response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "an increase" in an immunostimulatory and/or anti-tumor immune response, for example, systemically or in a tumor microenvironment, is relative to the immunostimulatory and/or anti-tumor immune response that would otherwise occur, in the absence of the effector molecule(s).

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in an increase in an immunostimulatory and/or anti-tumor immune response by at least 3 fold, at least 5 fold, at least 10 fold, at least 20 fold, at least 50 fold, or at least 100 fold. In some embodiments, modulation of a tumor-mediated immunosuppressive mechanism results in an increase in an immunostimulatory and/or anti-tumor immune response by 2-10, 2-20, 2-30, 2-40, 2-50, 2-60, 2-70, 2-80, 2-90, or 2-100 fold.

Non-limiting examples of immunostimulatory and/or anti-tumor immune mechanisms include T cell signaling, activity and/or recruitment, antigen presentation and/or processing, natural killer cell-mediated cytotoxic signaling, activity and/or recruitment, dendritic cell differentiation and/or maturation, immune cell recruitment, pro-inflammatory macrophage signaling, activity and/or recruitment, stroma degradation, immunostimulatory metabolite production, stimulator of interferon genes (STING) signaling (which increases the secretion of IFN and Th1 polarization, promoting an anti-tumor immune response), and/or Type I interferon signaling. An effector molecule may stimulate at least one (one or more) of the foregoing immunostimulatory mechanisms, thus resulting in an increase in an immunostimulatory response. Changes in the foregoing immunostimulatory and/or anti-tumor immune mechanisms may be assessed, for example, using in vitro assays for T cell proliferation or cytotoxicity, in vitro antigen presentation assays, expression assays (e.g., of particular markers), and/or cell secretion assays (e.g., of cytokines).

In some embodiments, modulation of a tumor-mediated immunosuppressive mechanism by at least one effector molecule results in a decrease in an immunosuppressive response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in a decrease in an immunosuppressive response by at least 20%, at least 30%, at least 40%, at least 50%, at least 60%, at least 70%, at least 80%, at least 90%, at least 100%. In some embodiments, modulation of a tumor-mediated immunosuppressive mechanism results in a decrease in an immunosuppressive response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "a decrease" in an immunosuppressive response, for example, systemically or in a tumor microenvironment, is relative to the immunosuppressive response that would otherwise occur, in the absence of the effector molecule(s).

In some embodiments, modulation of a tumor-mediated immunosuppressive mechanism by at least one effector molecule results in a decrease in an immunosuppressive response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in a decrease in an immunosuppressive response by at least 3 fold, at least 5 fold, at least 10 fold, at least 20 fold, at least 50 fold, or at least 100 fold. In some embodiments, modulation of a tumor-mediated immunosuppressive mechanism results in a decrease in an immunosuppressive response by 2-10, 2-20, 2-30, 2-40, 2-50, 2-60, 2-70, 2-80, 2-90, or 2-100 fold.

Non-limiting examples of immunosuppressive mechanisms include negative costimulatory signaling, pro-apoptotic signaling of cytotoxic cells (e.g., T cells and/or NK cells), T regulatory (Treg) cell signaling, tumor checkpoint molecule production/maintenance, myeloid-derived suppressor cell signaling, activity and/or recruitment, immunosuppressive factor/metabolite production, and/or vascular endothelial growth factor signaling. An effector molecule may inhibit at least one (one or more) of the foregoing immunosuppressive mechanisms, thus resulting in a decrease in an immunosuppressive response. Changes in the foregoing immunosuppressive mechanisms may be assessed, for example, by assaying for an increase in T cell proliferation and/or an increase in IFNγ production (negative co-stimulatory signaling, $T_{reg}$ cell signaling and/or MDSC); Annexin V/PI flow staining (pro-apoptotic signaling); flow staining for expression, e.g., PDL1 expression (tumor checkpoint molecule production/maintenance); ELISA, LUMINEX®, RNA via qPCR, enzymatic assays, e.g., IDO tryptophan catabolism (immunosuppressive factor/metabolite production); and phosphorylation of PI3K, Akt, p38 (VEGF signaling).

In some embodiments, cells, such as MSCs, are engineered to express membrane-tethered anti-CD3 and/or anti-CD28 agonist extracellular domains.

In some embodiments, cells, such as MSCs, are engineered to produce at least two (e.g., 2, 3, 4, 5, 6, 7, 8, 9, 10 or more) effector molecules, each of which modulates a different tumor-mediated immunosuppressive mechanism. In other embodiments, cells are engineered to produce at least one effector molecule that is not natively produced by the cells. Such an effector molecule may, for example, complement the function of effector molecules natively produced by the cells In some embodiments, effector molecules function additively: the effect of two effector molecules, for example, may be equal to the sum of the effect of the two effector molecules functioning separately. In other embodiments, effector molecules function synergistically: the effect of two effector molecules, for example, may be greater than the combined function of the two effector molecules. The present disclosure also encompasses additivity and synergy between an effector molecule(s) and the immune cell (e.g., MSC) from which they are produced.

Effector molecules that modulate tumor-mediated immunosuppressive mechanisms and/or modify tumor microenvironments may be, for example, secreted factors (e.g., cytokines, chemokines, antibodies, and/or decoy receptors that modulate extracellular mechanisms involved in the immune system), inhibitors (e.g., antibodies, antibody fragments, ligand TRAP and/or small blocking peptides), intracellular factors that control cell state (e.g., microRNAs and/or transcription factors that modulate the state of cells to enhance pro-inflammatory properties), factors packaged into exosomes (e.g., microRNAs, cytosolic factors, and/or extracellular factors), surface displayed factors (e.g., checkpoint inhibitors, TRAIL), and and/or metabolic genes (e.g., enzymes that produce/modulate or degrade metabolites or amino acids).

In some embodiments, effector molecules may be selected from the following non-limiting classes of molecules: cytokines, antibodies, chemokines, nucleotides, peptides, and enzymes. Non-limiting examples of the foregoing classes of effector molecules are listed in Table 1 and specific sequences encoding exemplary effector molecules are listed in Table 6. Effector molecules can be human, such as those listed in Table 1 or Table 6 or human equivalents of murine effector molecules listed in Table 1 or Table 6. Effector molecules can be human-derived, such as the endogenous human effector molecule or an effector molecule modified and/or optimized for function, e.g., codon optimized to improve expression, modified to improve stability, or modified at its signal sequence (see below). Various programs and algorithms for optimizing function are known to those skilled in the art and can be selected based on the improvement desired, such as codon optimization for a specific species (e.g., human, mouse, bacteria, etc.).

TABLE 1

Exemplary Effector Molecules

| Effector name | Category | Function |
| --- | --- | --- |
| anti-CD40 or CD40 Ligand | Agonist antibody | Stimulates B-cells and antigen presenting cells. |
| Flt3L | Ligand agonist | Stimulates myeloid cells and antigen presenting cells |
| CXCL10-11 fusion | Chemokine | Attracts T-cells |
| TGFb blocking peptides | Antagonist peptides | Inhibit TGFb pathway, TME modifier |
| Adenosine deaminase (ADA) | TME modifier | Degradation of suppressive adenosine in the TME |
| Kyneurinase | TME modifier | Degradation of kyneurine |
| HPGE2 | TME modifier | Degradation of PGE2 |
| CXCL13 | Chemokine | Attracts B-cells |
| anti PD-1/PD-L1 | Agonist antibody | Remove checkpoint |
| anti-CTLA-4 | Agonist antibody | Remove checkpoint |
| anti-VEGF | Antagonist antibody | Neutralizes an immunosuppressive/angiogenesis factor |
| anti-TNFa | Antagonist antibody | Neutralizes cytokine/pro-tumor factor |
| anti-IL-10 | Antagonist antibody | Neutralizes immunosuppressive cytokine |
| anti-SDF1/CXCL12 | Antagonist antibody | Neutralizes pro-tumor chemokine |
| (TβRII)2 trap | Capture trap | Neutralizes an immunosuppressive cytokine |
| CCL21 | Chemokine | Attracts leukocytes/NK |
| CCL1 | Chemokine | Attracts leukocytes/NK |
| CCL17 | Chemokine | Attracts leukocytes/NK |
| CCL19 | Chemokine | Attracts leukocytes/NK |
| CCL21 | Chemokine | Attracts leukocytes/NK |
| CCL20 | Chemokine | Attracts leukocytes/NK |
| CCL21a | Chemokine | Attracts leukocytes/NK |
| MIP1b (CCL5) | Chemokine | Attracts leukocytes/NK |
| CXCL10 | Chemokine | Attracts leukocytes/NK |
| CXCL11 | Chemokine | Attracts leukocytes/NK |
| CCL2 | Chemokine | Attracts monocytes |
| MIP-1alpha (CCL3) | Chemokine | Attracts leukocytes/NK |
| XCL1 | Chemokine | Attracts leukocytes/NK |
| IFNbeta | Cytokine | T cell response, tumor cell killing |
| IFNgamma | Cytokine | T cell response, tumor cell killing |
| IL-12 | Cytokine | T cells, NK cells |
| IL-1beta | Cytokine | T cells, NK cells |
| IL-15 | Cytokine | Stimulates T-cells and NK |
| IL-2 | Cytokine | Stimulates T-cells and NK |
| IL-21 | Cytokine | Stimulates T-cells |
| IL-24 | Cytokine | Stimulates T-cells |
| IL36-gamma | Cytokine | Stimulates T-cells |
| IL-7 | Cytokine | Stimulates T-cells |
| IL-22 | Cytokine | Stimulates T-cells |
| IL-18 | Cytokine | Stimulates T-cells |
| Granzymes/Perforin | Enzyme | Direct tumor cell killing |
| OX86 (anti-OX40) | ligand | Stimulates T-cells |
| anti-TGFbeta | Neutralizing antibody | Neutralizes an Immunosuppressive cytokine |
| TRAIL | Receptor/ligand | Direct tumor cell killing |
| FASL (CD49L) | Receptor/ligand | Direct tumor cell killing |
| OX40-L | Receptor/Ligand | Stimulates T-cells |
| cGAS | secreted molecule | Stimulates antigen-presenting cells |
| 41BBL | secreted molecule | Co-activation of T-cells |
| CD40L | secreted molecule | Stimulates T-cells |
| GM-CSF | secreted molecule | Growth factor for monocytes |
| STING | secreted molecule | Stimulates antigen-presenting cells |
| HAC-V 'microbody'_PD1 | Antagonist antibody | inhibits checkpoint |
| yCD | Pro-drug | Converts to cytotoxic molecule upon activation |
| CpG/Nucleotides | Nucleotides | STING agonist |

In some embodiments, cells, such as MSCs, comprise an engineered nucleic acid that comprises a promoter operably linked to a nucleotide sequence encoding an effector molecule. In some embodiments, an engineered nucleic acid comprises a promoter operably linked to a nucleotide sequence encoding at least 2 effector molecules. For example, the engineered nucleic acid may comprise a promoter operably linked to a nucleotide sequence encoding at least 3, at least 4, at least 5, at least 6, at least 7, at least 8, at least 8, at least 9, or at least 10 effector molecules. In some embodiments, an engineered nucleic acid comprises a promoter operably linked to a nucleotide sequence encoding 1, 2, 3, 4, 5, 6, 7, 8, 9, 10, or more effector molecules.

Engineered cells, such as engineered MSCs, in some embodiments, are engineered to include at least two engineered nucleic acids, each comprising a promoter operably linked to a nucleotide sequence encoding at least one (e.g., 1, 2 or 3) effector molecule. For example, the cells may be engineered to comprise at least 2, at least 3, at least 4, at least 5, at least 6, at least 7, at least 8, at least 8, at least 9, or at least 10, engineered nucleic acids, each comprising a promoter operably linked to a nucleotide sequence encoding at least one (e.g., 1, 2 or 3) effector molecule. In some embodiments, the cells are engineered to comprise 2, 3, 4, 5, 6, 7, 8, 9, 10, or more engineered nucleic acids, each comprising a promoter operably linked to a nucleotide sequence encoding at least one (e.g., 1, 2 or 3) effector molecule.

An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. The term "engineered nucleic acids" includes recombinant nucleic acids and synthetic nucleic acids. A "recombinant nucleic acid" refers to a molecule that is constructed by joining nucleic acid molecules and, in some embodiments, can replicate in a live cell. A "synthetic nucleic acid" refers to a molecule that is amplified or chemically, or by other means, synthesized. Synthetic nucleic acids include those that are chemically modified, or otherwise modified, but can base pair with naturally-occurring nucleic acid molecules. Recombinant nucleic acids and synthetic nucleic acids also include those molecules that result from the replication of either of the foregoing. Engineered nucleic acid of the present disclosure may be encoded by a single molecule (e.g., included in the same plasmid or other vector) or by multiple different molecules (e.g., multiple different independently-replicating molecules).

Engineered nucleic acid of the present disclosure may be produced using standard molecular biology methods (see, e.g., Green and Sambrook, Molecular Cloning, A Laboratory Manual, 2012, Cold Spring Harbor Press). In some embodiments, engineered nucleic acid constructs are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 'Y extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. In some embodiments, engineered nucleic acid constructs are produced using IN-FUSION® cloning (Clontech).

A "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous." In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see, e.g., U.S. Pat. Nos. 4,683,202 and 5,928,906).

Promoters of an engineered nucleic acid may be "inducible promoters," which refer to promoters that are characterized by regulating (e.g., initiating or activating) transcriptional activity when in the presence of, influenced by or contacted by a signal. The signal may be endogenous or a normally exogenous condition (e.g., light), compound (e.g., chemical or non-chemical compound) or protein (e.g., cytokine) that contacts an inducible promoter in such a way as to be active in regulating transcriptional activity from the inducible promoter. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

A promoter is "responsive to" or "modulated by" a local tumor state (e.g., inflammation or hypoxia) or signal if in the presence of that state or signal, transcription from the promoter is activated, deactivated, increased, or decreased. In some embodiments, the promoter comprises a response element. A "response element" is a short sequence of DNA within a promoter region that binds specific molecules (e.g., transcription factors) that modulate (regulate) gene expression from the promoter. Response elements that may be used in accordance with the present disclosure include, without limitation, a phloretin-adjustable control element (PEACE), a zinc-finger DNA-binding domain (DBD), an interferon-gamma-activated sequence (GAS) (Decker, T. et al. *J Interferon Cytokine Res.* 1997 March; 17(3):121-34, incorporated herein by reference), an interferon-stimulated response element (ISRE) (Han, K. J. et al. *J Biol Chem.* 2004 Apr. 9; 279(15):15652-61, incorporated herein by reference), a NF-kappaB response element (Wang, V. et al. Cell Reports. 2012; 2(4): 824-839, incorporated herein by reference), and a STAT3 response element (Zhang, D. et al. *J of Biol Chem.* 1996; 271: 9503-9509, incorporated herein by reference). Other response elements are encompassed herein. Response elements can also contain tandem repeats (e.g., consecutive repeats of the same nucleotide sequence encoding the response element) to generally increase sensitivity of the response element to its cognate binding molecule. Tandem repeats can be labeled 2×, 3×, 4×, 5×, etc. to denote the number of repeats present.

Non-limiting examples of responsive promoters (also referred to as "inducible promoters") (e.g., TGF-beta responsive promoters) are listed in Table 2, which shows the design of the promoter and transcription factor, as well as the effect of the inducer molecule towards the transcription factor (TF) and transgene transcription (T) is shown (B, binding; D, dissociation; n.d., not determined) (A, activation; DA, deactivation; DR, derepression) (see Horner, M. & Weber, W. *FEBS Letters* 586 (2012) 20784-2096m, and references cited therein). Other non-limiting examples of inducible promoters include those presented in Table 3.

TABLE 2

Examples of Responsive Promoters.

| System | Promoter and operator | Transcription factor (TF) | Inducer molecule | Response to inducer TF | T |
|---|---|---|---|---|---|
| *Transcriptional activator-responsive promoters* | | | | | |
| AIR | PAIR (OalcA-PhCMVmin) | AlcR | Acetaldehyde | n.d. | A |
| ART | PART (OARG-PhCMVmin) | ArgR-VP16 | l-Arginine | B | A |
| BIT | PBIT3 (OBirA3-PhCMVmin) | BIT (BirA-VP16) | Biotin | B | A |
| Cumate - activator | PCR5 (OCuO6-PhCMVmin) | cTA (CymR-VP16) | Cumate | D | DA |
| Cumate - reverse activator | PCR5 (OCuO6-PhCMVmin) | rcTA (rCymR-VP16) | Cumate | B | A |
| E-OFF | PETR (OETR-PhCMVmin) | ET (E-VP16) | Erythromycin | D | DA |
| NICE-OFF | PNIC (ONIC-PhCMVmin) | NT (HdnoR-VP16) | 6-Hydroxy-nicotine | D | DA |
| PEACE | PTtgR1 (OTtgR-PhCMVmin) | TtgA1 (TtgR-VP16) | Phloretin | D | DA |
| PIP-OFF | PPIR (OPIR-Phsp70min) | PIT (PIP-VP16) | Pristinamycin I | D | DA |
| QuoRex | PSCA (OscbR-PhCMVmin)PSPA (OpapRI-PhCMVmin) | SCA (ScbR-VP16) | SCB1 | D | DA |
| Redox | PROP (OROP-PhCMVmin) | REDOX (REX-VP16) | NADH | D | DA |
| TET-OFF | PhCMV*-1 (OtetO7-PhCMVmin) | tTA (TetR-VP16) | Tetracycline | D | DA |
| TET-ON | PhCMV*-1 (OtetO7-PhCMVmin) | rtTA (rTetR-VP16) | Doxycycline | B | A |
| TIGR | PCTA (OrheO-PhCMVmin) | CTA (RheA-VP16) | Heat | D | DA |
| TraR | O7x(tra box)-PhCMVmin | p65-TraR | 3-Oxo-C8-HSL | B | A |
| VAC-OFF | P1VanO2 (OVanO2-PhCMVmin) | VanA1 (VanR-VP16) | Vanillic acid | D | DA |
| *Transcriptional repressor-responsive promoters* | | | | | |
| Cumate - repressor | PCuO (PCMV5-OCuO) | CymR | Cumate | D | DR |
| E-ON | PETRON8 (PSV40-OETR8) | E-KRAB | Erythromycin | D | DR |
| NICE-ON | PNIC (PSV40-ONIC8) | NS (HdnoR-KRAB) | 6-Hydroxy-nicotine | D | DR |
| PIP-ON | PPIRON (PSV40-OPIR3) | PIT3 (PIP-KRAB) | Pristinamycin I | D | DR |
| Q-ON | PSCAON8 (PSV40-OscbR8) | SCS (ScbR-KRAB) | SCB1 | D | DR |
| TET-ON<comma>repressor-based | OtetO-PHPRT | tTS-H4 (TetR-HDAC4) | Doxycycline | D | DR |
| T-REX | PTetO (PhCMV-OtetO2) | TetR | Tetracycline | D | DR |
| UREX | PUREX8 (PSV40-OhucO8) | mUTS (KRAB-HucR) | Uric acid | D | DR |
| VAC-ON | PVanON8 (PhCMV-OVanO8) | VanA4 (VanR-KRAB) | Vanillic acid | D | DR |
| *Hybrid promoters* | | | | | |
| QuoRexPIP-ON(NOT IF gate) | OscbR8-OPIR3-PhCMVmin | SCAPIT3 | SCB1Pristinamycin I | DD | DADR |
| QuoRexE-ON(NOT IF gate) | OscbR8-OETR8-PhCMVmin | SCAE-KRAB | SCB1Erythromycin | DD | DADR |
| TET-OFFE-ON(NOT IF gate) | OtetO7-OETR8-PhCMVmin | tTAE-KRAB | TetracyclineErythromycin | DD | DADR |
| TET-OFFPIP-ONE-ON | OtetO7-OPIR3-OETR8-PhCMVmin | tTAPIT3E-KRAB | TetracyclinePristinamycin IErythromycin | DDD | DADRDR |

TABLE 3

Exemplary Inducible Promoters

| Name | DNA SEQUENCE | Source |
|---|---|---|
| minimal promoter; minP | AGAGGGTATATAATGGAAGCTCGACTT CCAG (SEQ ID NO: 1) | EU581860.1 (PRomega) |
| NFkB response element protein promoter; 5x NFkB-RE | GGGAATTTCCGGGGACTTTCCGGGAAT TTCCGGGGACTTTCCGGGAATTTCC (SEQ ID NO: 2) | EU581860.1 (Promega) |
| CREB response element protein promoter; 4x CRE | CACCAGACAGTGACGTCAGCTGCCAGA TCCCATGGCCGTCATACTGTGACGTCTT TCAGACACCCCATTGACGTCAATGGGA GAA (SEQ ID NO: 3) | DQ904461.1 (Promega) |
| NFAT response element protein promoter; 3x NFAT binding sites | GGAGGAAAAACTGTTTCATACAGAAGG CGTGGAGGAAAAACTGTTTCATACAGA AGGCGTGGAGGAAAAACTGTTTCATAC AGAAGGCGT (SEQ ID NO: 4) | D.Q904462.1 (Promega) |
| SRF response element protein promoter; 5x SRE | AGGATGTCCATATTAGGACATCTAGGA TGTCCATATTAGGACATCTAGGATGTC CATATTAGGACATCTAGGATGTCCATA TTAGGACATCTAGGATGTCCATATTAG GACATCT (SEQ ID NO: 5) | FJ773212.1 (Promega) |
| SRF response element protein promoter 2; 5x SRF-RE | AGTATGTCCATATTAGGACATCTACCA TGTCCATATTAGGACATCTACTATGTCC ATATTAGGACATCTTGTATGTCCATATT AGGACATCTAAAATGTCCATATTAGGA CATCT (SEQ ID NO: 6) | FJ773213.1 (Promega) |
| AP1 response element protein promoter; 6x AP1-RE | TGAGTCAGTGACTCAGTGAGTCAGTGA CTCAGTGAGTCAGTGACTCAG (SEQ ID NO: 7) | JQ858516.1 (Promega) |
| TCF-LEF response element protein promoter; 8x TCF-LEF-RE | AGATCAAAGGGTTTAAGATCAAAGGGC TTAAGATCAAAGGGTATAAGATCAAAG GGCCTAAGATCAAAGGGACTAAGATCA AAGGGTTTAAGATCAAAGGGCTTAAGA TCAAAGGGCCTA (SEQ ID NO: 8) | JX099537.1 (Promega) |
| SBEx4 | GTCTAGACGTCTAGACGTCTAGACGTC TAGAC (SEQ ID NO: 9) | Addgene Cat No: 16495 |
| SMAD2/3-CAGACA x4 | CAGACACAGACACAGACACAGACA (SEQ ID NO: 10) | Jonk et al. (J Biol Chem. 1998 Aug. 14; 273(33): 21145-52. |
| STAT3 binding site | Ggatccggtactcgagatctgcgatct aagtaagcttggcattccggtactgtt ggtaaagccac (SEQ ID NO: 11) | Addgene Sequencing Result #211335 |

Other non-limiting examples of promoters include the cytomegalovirus (CMV) promoter, the elongation factor 1-alpha (EF1a) promoter, the elongation factor (EFS) promoter, the MND promoter (a synthetic promoter that contains the U3 region of a modified MoMuLV LTR with myeloproliferative sarcoma virus enhancer), the phosphoglycerate kinase (PGK) promoter, the spleen focus-forming virus (SFFV) promoter, the simian virus 40 (SV40) promoter, and the ubiquitin C (UbC) promoter (see Table 4).

TABLE 4

Exemplary Constitutive Promoters

| Name | DNA SEQUENCE |
|---|---|
| CMV | GTTGACATTGATTATTGACTAGTTATTAATAGTAATCAATTACGGGGTCATT AGTTCATAGCCCATATATGGAGTTCCGCGTTACATAACTTACGGTAAATGG CCCGCCTGGCTGACCGCCCAACGACCCCCGCCCATTGACGTCAATAATGAC GTATGTTCCCATAGTAACGCCAATAGGGACTTTCCATTGACGTCAATGGGT GGAGTATTTACGGTAAACTGCCCACTTGGCAGTACATCAAGTGTATCATAT GCCAAGTACGCCCCCTATTGACGTCAATGACGGTAAATGGCCCGCCTGGCA TTATGCCCAGTACATGACCTTATGGGACTTTCCTACTTGGCAGTACATCTAC GTATTAGTCATCGCTATTACCATGGTGATGCGGTTTTGGCAGTACATCAATG GGCGTGGATAGCGGTTTGACTCACGGGGATTTCCAAGTCTCCACCCCATTG ACGTCAATGGGAGTTTGTTTTGGCACCAAAATCAACGGGACTTTCCAAAAT |

TABLE 4-continued

Exemplary Constitutive Promoters

| Name | DNA SEQUENCE |
|---|---|
| | GTCGTAACAACTCCGCCCCATTGACGCAAATGGGCGGTAGGCGTGTACGGT<br>GGGAGGTCTATATAAGCAGAGCTC (SEQ ID NO: 12) |
| EF1a | GGCTCCGGTGCCCGTCAGTGGGCAGAGCGCACATCGCCCACAGTCCCCGA<br>GAAGTTGGGGGGAGGGGTCGGCAATTGAACCGGTGCCTAGAGAAGGTGGC<br>GCGGGGTAAACTGGGAAAGTGATGCCGTGTACTGGCTCCGCCTTTTTCCCG<br>AGGGTGGGGGAGAACCGTATATAAGTGCAGTAGTCGCCGTGAACGTTCTTT<br>TTCGCAACGGGTTTGCCGCCAGAACACAGGTAAGTGCCGTGTGTGGTTCCC<br>GCGGGGCCTGGCCTCTTTACGGGTTATGGCCCTTGCGTGCCTTGAATTACTTC<br>CACCTGGCTGCAGTACGTGATTCTTGATCCCGAGCTTCGGGTTGGAAGTGG<br>GTGGGAGAGTTCGAGGCCTTGCGCTTAAGGAGCCCCTTCGCCTCGTGCTTG<br>AGTTGAGGCCTGGCCTGGGCGCTGGGGCCGCCGCGTGCGAATCTGGTGGC<br>ACCTTCGCGCCTGTCTCGCTGCTTTCGATAAGTCTCTAGCCATTTAAAATTT<br>TTGATGACCTGCTGCGACGCTTTTTTTCTGGCAAGATAGTCTTGTAAATGCG<br>GGCCAAGATCTGCACACTGGTATTTCGGTTTTTGGGGCCGCGGGCGGCGAC<br>GGGGCCCGTGCGTCCCAGCGCACATGTTCGGCGAGGCGGGGCCTGCGAGC<br>GCGACCACCGAGAATCGGACGGGGGTAGTCTCAAGCTGGCCGGCCTGCTC<br>TGGTGCCTGTCCTCGCGCCGCCGTGTATCGCCCCGCCCCGGGCGGCAAGGC<br>TGGCCCGGTCGGCACCAGTTGCGTGAGCGGAAAGATGGCCGCTTCCCGGTC<br>CTGCTGCAGGGAGCTCAAAATGGAGGACGCGGCGCTCGGGAGAGCGGGCG<br>GGTGAGTCACCCACACAAAGGAAAAGGGCCTTTCCGTCCTCAGCCGTCGCT<br>TCATGTGACTCCACGGAGTACCGGGCGCCGTCCAGGCACCTCGATTAGTTC<br>TCGAGCTTTTGGAGTACGTCGTCTTTAGGTTGGGGGGAGGGGTTTTATGCG<br>ATGGAGTTTCCCCACACTGAGTGGGTGGAGACTGAAGTTAGGCCAGCTTGG<br>CACTTGATGTAATTCTCCTTGGAATTTGCCCTTTTTGAGTTTGGATCTTGGT<br>TCATTCTCAAGCCTCAGACAGTGGTTCAAAGTTTTTTTCTTCCATTTCAGGT<br>GTCGTGA (SEQ ID NO: 13) |
| EFS | GGATCTGCGATCGCTCCGGTGCCCGTCAGTGGGCAGAGCGCACATCGCCCA<br>CAGTCCCCGAGAAGTTGGGGGGAGGGGTCGGCAATTGAACCGGTGCCTAG<br>AGAAGGTGGCGCGGGGTAAACTGGGAAAGTGATGTCGTGTACTGGCTCCG<br>CCTTTTTCCCGAGGGTGGGGGAGAACCGTATATAAGTGCAGTAGTCGCCGT<br>GAACGTTCTTTTTCGCAACGGGTTTGCCGCCAGAACACAGCTGAAGCTTCG<br>AGGGGCTCGCATCTCTCCTTCACGCGCCCGCCGCCCTACCTGAGGCCGCCA<br>TCCACGCCGGTTGAGTCGCGTTCTGCCGCCTCCCGCCTGTGGTGCCTCCTGA<br>ACTGCGTCCGCCGTCTAGGTAAGTTTAAAGCTCAGGTCGAGACCGGGCCTT<br>TGTCCGGCGCTCCCTTGGAGCCTACCTAGACTCAGCCGGCTCTCCACGCTTT<br>GCCTGACCCTGCTTGCTCAACTCTACGTCTTTGTTTCGTTTTCTGTTCTGCGC<br>CGTTACAGATCCAAGCTGTGACCGGCGCCTAC (SEQ ID NO: 14) |
| MND | TTTATTTAGTCTCCAGAAAAAGGGGGGAATGAAAGACCCCACCTGTAGGTT<br>TGGCAAGCTAGGATCAAGGTTAGGAACAGAGAGACAGCAGAATATGGGCC<br>AAACAGGATATCTGTGGTAAGCAGTTCCTGCCCCGGCTCAGGGCCAAGAA<br>CAGTTGGAACAGCAGAATATGGGCCAAACAGGATATCTGTGGTAAGCAGT<br>TCCTGCCCCGGCTCAGGGCCAAGAACAGATGGTCCCCAGATGCGGTCCCGC<br>CCTCAGCAGTTTCTAGAGAACCATCAGATGTTTCCAGGGTGCCCCAAGGAC<br>CTGAAATGACCCTGTGCCTTATTTGAACTAACCAATCAGTTCGCTTCTCGCT<br>TCTGTTCGCGCGCTTCTGCTCCCCGAGCTCAATAAAAGAGCCCA (SEQ ID<br>NO: 15) |
| PGK | GGGGTTGGGGTTGCGCCTTTTCCAAGGCAGCCCTGGGTTTGCGCAGGGACG<br>CGGCTGCTCTGGGCGTGGTTCCGGGAAACGCAGCGGCGCCGACCCTGGGT<br>CTCGCACATTCTTCACGTCCGTTCGCAGCGTCACCCGGATCTTCGCCGCTAC<br>CCTTGTGGGCCCCCCGGCGACGCTTCCTGCTCCGCCCCTAAGTCGGGAAGG<br>TTCCTTGCGGTTCGCGGCGTGCCGGACGTGACAAACGGAAGCCGCACGTCT<br>CACTAGTACCCTCGCAGACGGACAGCGCCAGGGAGCAATGGCAGCGCGCC<br>GACCGCGATGGGCTGTGGCCAATAGCGGCTGCTCAGCGGGGCGCGCCGAG<br>AGCAGCGGCCGGGAAGGGGCGGTGCGGGAGGCGGGGTGTGGGGCGGTAG<br>TGTGGGCCCTGTTCCTGCCCGCGCGGTGTTCCGCATTCTGCAAGCCTCCGG<br>AGCGCACGTCGGCAGTCGGCTCCCTCGTTGACCGAATCACCGACCTCTCTC<br>CCCAG (SEQ ID NO: 16) |
| SFFV | GTAACGCCATTTTGCAAGGCATGGAAAAATACCAAACCAAGAATAGAGAA<br>GTTCAGATCAAGGGCGGGTACATGAAAATAGCTAACGTTGGGCCAAACAG<br>GATATCTGCGGTGAGCAGTTTCGGCCCCGGCCCGGGGCAAGAACAGATG<br>GTCACCGCAGTTTCGGCCCCGGCCCGAGGCCAAGAACAGATGGTCCCCAG<br>ATATGGCCCAACCCTCAGCAGTTTCTTAAGACCCATCAGATGTTTCCAGGC<br>TCCCCCAAGGACCTGAAATGACCCTGCGCCTTATTTGAATTAACCAATCAG<br>CCTGCTTCTCGCTTCTGTTCGCGCGCTTCTGCTTCCCGAGCTCTATAAAAGA<br>GCTCACAACCC CTCACTCGGCGCGCCAGTCCTCCGACAGACTGAGTCGCCC<br>GGG (SEQ ID NO: 17) |
| SV40 | CTGTGGAATGTGTGTCAGTTAGGGTGTGGAAAGTCCCCAGGCTCCCCAGCA<br>GGCAGAAGTATGCAAAGCATGCATCTCAATTAGTCAGCAACCAGGTGTGG<br>AAAGTCCCCAGGCTCCCCAGCAGGCAGAAGTATGCAAAGCATGCATCTCA<br>ATTAGTCAGCAACCATAGTCCCGCCCCTAACTCCGCCCATCCCGCCCCTAA |

TABLE 4-continued

Exemplary Constitutive Promoters

| Name | DNA SEQUENCE |
|---|---|
| | CTCCGCCCAGTTCCGCCCATTCTCCGCCCCATGGCTGACTAATTTTTTTTAT<br>TTATGCAGAGGCCGAGGCCGCCTCTGCCTCTGAGCTATTCCAGAAGTAGTG<br>AGGAGGCTTTTTTGGAGGCCTAGGCTTTTGCAAAAAGCT<br>(SEQ ID NO: 18) |
| UbC | GCGCCGGGTTTTGGCGCCTCCCGCGGGCGCCCCCCTCCTCACGGCGAGCGC<br>TGCCACGTCAGACGAAGGGCGCAGGAGCGTTCCTGATCCTTCCGCCCGGAC<br>GCTCAGGACAGCGGCCCGCTGCTCATAAGACTCGGCCTTAGAACCCCAGTA<br>TCAGCAGAAGGACATTTTAGGACGGGACTTGGGTGACTCTAGGGCACTGG<br>TTTTCTTTCCAGAGAGCGGAACAGGCGAGGAAAAGTAGTCCCTTCTCGGCG<br>ATTCTGCGGAGGGATCTCCGTGGGGCGGTGAACGCCGATGATTATATAAG<br>GACGCGCCGGGTGTGGCACAGCTAGTTCCGTCGCAGCCGGGATTTGGGTCG<br>CGGTTCTTGTTTGTGGATCGCTGTGATCGTCACTTGGTGAGTTGCGGGCTGC<br>TGGGCTGGCCGGGGCTTTCGTGGCCGCCGGGCCGCTCGGTGGGACGGAAG<br>CGTGTGGAGAGACCGCCAAGGGCTGTAGTCTGGGTCCGCGAGCAAGGTTG<br>CCCTGAACTGGGGGTTGGGGGGAGCGCACAAAATGGCGGCTGTTCCCGAG<br>TCTTGAATGGAAGACGCTTGTAAGGCGGGCTGTGAGGTCGTTGAAACAAG<br>GTGGGGGGCATGGTGGGCGGCAAGAACCCAAGGTCTTGAGGCCTTCGCTA<br>ATGCGGGAAAGCTCTTATTCGGGTGAGATGGGCTGGGGCACCATCTGGGG<br>ACCCTGACGTGAAGTTTGTCACTGACTGGAGAACTCGGGTTTGTCGTCTGG<br>TTGCGGGGGCGGCAGTTATGCGGTGCCGTTGGGCAGTGCACCCGTACCTTT<br>GGGAGCGCGCGCCTCGTCGTGTCGTGACGTCACCCGTTCTGTTGGCTTATA<br>ATGCAGGGTGGGGCCACCTGCCGGTAGGTGTGCGGTAGGCTTTTCTCCGTC<br>GCAGGACGCAGGGTTCGGGCCTAGGGTAGGCTCTCCTGAATCGACAGGCG<br>CCGGACCTCTGGTGAGGGGAGGGATAAGTGAGGCGTCAGTTTCTTTGGTCG<br>GTTTTATGTACCTATCTTCTTAAGTAGCTGAAGCTCCGGTTTTGAACTATGC<br>GCTCGGGGTTGGCGAGTGTGTTTTGTGAAGTTTTTTAGGCACCTTTTGAAAT<br>GTAATCATTTGGGTCAATATGTAATTTTCAGTGTTAGACTAGTAAAGCTTCT<br>GCAGGTCGACTCTAGAAAATTGTCCGCTAAATTCTGGCCGTTTTTGGCTTTT<br>TTGTTAGAC (SEQ ID NO: 19) |
| hEF1aV1 | GGCTCCGGTGCCCGTCAGTGGGCAGAGCGCACATCGCCCACAGTCCCC<br>GAGAAGTTGGGGGGAGGGGTCGGCAATTGAACCGGTGCCTAGAGAAGG<br>TGGCGCGGGGTAAACTGGGAAAGTGATGTCGTGTACTGGCTCCGCCTTT<br>TTCCCGAGGGTGGGGGAGAACCGTATATAAGTGCAGTAGTCGCCGTGAA<br>CGTTCTTTTTCGCAACGGGTTTGCCGCCAGAACACAGGTAAGTGCCGTGT<br>GTGGTTCCCGCGGGCCTGGCCTCTTTACGGGTTATGGCCCTTGCGTGCC<br>TTGAATTACTTCCACCTGGCTGCAGTACGTGATTCTTGATCCCGAGCTTC<br>GGGTTGGAAGTGGGTGGGAGAGTTCGAGGCCTTGCGCTTAAGGAGCCC<br>CTTCGCCTCGTGCTTGAGTTGAGGCCTGGCCTGGGCGCTGGGGCCGCC<br>GCGTGCGAATCTGGTGGCACCTTCGCGCCTGTCTCGCTGCTTTCGATAA<br>GTCTCTAGCCATTTAAAATTTTTGATGACCTGCTGCGACGCTTTTTTTCTG<br>GCAAGATAGTCTTGTAAATGCGGGCCAAGATCTGCACACTGGTATTTCGG<br>TTTTTGGGGCCGCGGGCGGCGACGGGGCCCGTCGTCCCAGCGCACAT<br>GTTCGGCGAGGCGGGGCCTGCGAGCGCGGCCACCGAGAATCGGACGG<br>GGGTAGTCTCAAGCTGGCCGGCCTGCTCTGGTGCCTGGTCTCGCGCCG<br>CCGTGTATCGCCCCGCCCTGGGCGGCAAGGCTGGCCCGGTCGGCACCA<br>GTTGCGTGAGCGGAAAGATGGCCGCTTCCCGGCCCTGCTGCAGGGAGC<br>TCAAAATGGAGGACGCGGCGCTCGGGAGAGCGGGCGGGTGAGTCACCC<br>ACACAAAGGAAAAGGGCCTTTCCGTCCTCAGCCGTCGCTTCATGTGACTC<br>CACGGAGTACCGGGCGCCGTCCAGGCACCTCGATTAGTTCTCGAGCTTT<br>TGGAGTACGTCGTCTTTAGGTTGGGGGGAGGGGTTTTATGCGATGGAGT<br>TTCCCCACACTGAGTGGGTGGAGACTGAAGTTAGGCCAGCTTGGCACTT<br>GATGTAATTCTCCTTGGAATTTGCCCTTTTTGAGTTTGGATCTTGGTTCATT<br>CTCAAGCCTCAGACAGTGGTTCAAAGTTTTTTTCTTCCATTTCAGGTGTCG<br>TGA (SEQ ID NO: 20) |
| hCAGG | ACTAGTTATTAATAGTAATCAATTACGGGGTCATTAGTTCATAGCCCATAT<br>ATGGAGTTCCGCGTTACATAACTTACGGTAAATGGCCCGCCTGGCTGACC<br>GCCCAACGACCCCCGCCCATTGACGTCAATAATGACGTATGTTCCCATAG<br>TAACGCCAATAGGGACTTTCCATTGACGTCAATGGGTGGAGTATTTACGG<br>TAAACTGCCCACTTGGCAGTACATCAAGTGTATCATATGCCAAGTACGCC<br>CCCTATTGACGTCAATGACGGTAAATGGCCCGCCTGGCATTATGCCCAGT<br>ACATGACCTTATGGGACTTTCCTACTTGGCAGTACATCTACGTATTAGTCA<br>TCGCTATTACCATGGTCGAGGTGAGCCCCACGTTCTGCTTCACTCTCCCC<br>ATCTCCCCCCCCTCCCCACCCCCAATTTTGTATTTATTTATTTTTTAATTAT<br>TTTGTGCAGCGATGGGGGCGGGGGGGGGGGGGGGCGCGCGCCAGGC<br>GGGGCGGGGCGGGGCGAGGGGCGGGGCGGGGCGAGGCGGAGAGGTG<br>CGGCGGCAGCCAATCAGAGCGGCGCGCTCCGAAAGTTTCCTTTTATGGC<br>GAGGCGGCGGCGGCGGCGGCCCTATAAAAAGCGAAGCGCGCGGCGGG<br>CGGGGAGTCGCTGCGACGCTGCCTTCGCCCCGTGCCCCGCTCCGCCGC<br>CGCCTCGCGCCGCCCGCCCCGGCTCTGACTGACCGCGTTACTCCCACA<br>GGTGAGCGGGCGGGACGGCCCTTCTCCTCCGGGCTGTAATTAGCGCTTG<br>GTTTAATGACGGCTTGTTTCTTTTCTGTGGCTGCGTGAAAGCCTTGAGGG<br>GCTCCGGGAGGGCCCTTTGTGCGGGGGGAGCGGCTCGGGGGTGCGT<br>GCGTGTGTGTGCGTGGGGAGCGCCGCGTGCGGCTCCGCGCTGCCCG |

TABLE 4-continued

Exemplary Constitutive Promoters

| Name | DNA SEQUENCE |
|---|---|
| | GCGGCTGTGAGCGCTGCGGGCGCGGCGCGGGGCTTTGTGCGCTCCGCA<br>GTGTGCGCGAGGGGAGCGCGGCCGGGGGCGGTGCCCCGCGGTGCGGG<br>GGGGGCTGCGAGGGGAACAAAGGCTGCGTGCGGGGTGTGTGCGTGGG<br>GGGGTGAGCAGGGGGTGTGGGCGCGTCGGTCGGGCTGCAACCCCCCCT<br>GCACCCCCCTCCCCGAGTTGCTGAGCACGGCCCGGCTTCGGGTGCGGG<br>GCTCCGTACGGGGCGTGGCGCGGGGCTCGCCGTGCCGGGCGGGGGGT<br>GGCGGCAGGTGGGGGTGCCGGGCGGGGCGGGGCCGCCTCGGGCCGG<br>GGAGGGCTCGGGGGAGGGGCGCGGCGGCCCCCGGAGCGCCGGCGGC<br>TGTCGAGGCGCGCGAGCCGCAGCCATTGCCTTTTATGGTAATCGTGCG<br>AGAGGGCGCAGGGACTTCCTTTGTCCCAAATCTGTGCGGAGCCGAAATC<br>TGGGAGGCGCCGCCGCACCCCCTCTAGCGGGCGCGGGGCGAAGCGGT<br>GCGGCGCCGGCAGGAAGGAAATGGGCGGGAGGGCCTTCGTGCGTCG<br>CCGCGCCGCCGTCCCCTTCTCCCTCTCCAGCCTCGGGGCTGTCCGCGG<br>GGGGACGGCTGCCTTCGGGGGGGACGGGGCAGGGCGGGGTTCGGCTT<br>CTGGCGTGTGACCGGCGGCTCTAGAGCCTCTGCTAACCATGTTCATGCC<br>TTCTTCTTTTTCCTACAGCTCCTGGGCAACGTGCTGGTTATTGTGCTGTCT<br>CATCATTTTGGCAAAGAATTC (SEQ ID NO: 21) |
| hEF1aV2 | Gggcagagcgcacatcgcccacagtccccgagaagttgggggagggggtcg<br>gcaattgaaccggtgcctagagaaggtggcgcggggtaaactgggaaagtg<br>atgtcgtgtactggctccgcttttttcccgagggtggggagaaccgtata<br>taagtgcagtagtcgccgtgaacgttcttttcgcaacgggtttgccgcca<br>gaacacag (SEQ ID NO: 22) |
| hACTb | CCACTAGTTCCATGTCCTTATATGGACTCATCTTTGCCTATTGCGACACAC<br>ACTCAATGAACACCTACTACGCGCTGCAAAGAGCCCCGCAGGCCTGAGG<br>TGCCCCCACCTCACCACTCTTCCTATTTTTGTGTAAAAATCCAGCTTCTTG<br>TCACCACCTCCAAGGAGGGGGAGGAGGAGGAAGGCAGGTTCCTCTAGG<br>CTGAGCCGAATGCCCCTCTGTGGTCCCACGCCACTGATCGCTGCATGCC<br>CACCACCTGGGTACACACAGTCTGTGATTCCCGGAGCAGAACGGACCCT<br>GCCCACCCGGTCTTGTGTGCTACTCAGTGGACAGACCCAAGGCAAGAAA<br>GGGTGACAAGGACAGGGTCTTCCCAGGCTGGCTTTGAGTTCCTAGCACC<br>GCCCCGCCCCCAATCCTCTGTGGCACATGGAGTCTTGGTCCCCAGAGTC<br>CCCCAGCGGCCTCCAGATGGTCTGGGAGGGCAGTTCAGCTGTGGCTGC<br>GCATAGCAGACATACAACGGACGGTGGGCCCAGACCCAGGCTGTGTAGA<br>CCCAGCCCCCCGCCCCGCAGTGCCTAGGTCACCCACTAACGCCCCAG<br>GCCTGGTCTTGGCTGGGCGTGACTGTTACCCTCAAAAGCAGGCAGCTCC<br>AGGGTAAAAGGTGCCCTGCCCTGTAGAGCCCACCTTCCTTCCCAGGGCT<br>GCGGCTGGGTAGGTTTGTAGCCTTCATCACGGGCCACCTCCAGCCACTG<br>GACCGCTGGCCCCTGCCCTGTCCTGGGGAGTGTGGTCCTGCGACTTCTA<br>AGTGGCCGCAAGCCACCTGACTCCCCCAACACCACACTCTACCTCTCAA<br>GCCCAGGTCTCTCCCTAGTGACCCACCCAGCACATTTAGCTAGCTGAGC<br>CCCACAGCCAGAGGTCCTCAGGCCCTGCTTTCAGGGCAGTTGCTCTGAA<br>GTCGGCAAGGGGGAGTGACTGCCTGGCCACTCCATGCCCTCCAAGAGCT<br>CCTTCTGCAGGAGCGTACAGAACCCAGGGCCCTGGCACCCGTGCAGACC<br>CTGGCCCACCCCACCTGGGCGCTCAGTGCCCAAGAGATGTCCACACCTA<br>GGATGTCCCGCGGTGGGTGGGGGCCCGAGAGACGGGCAGGCCGGGG<br>GCAGGCCTGGCCATGCGGGGCCGAACCGGGCACTGCCCAGCGTGGGG<br>CGCGGGGGCCACGGCGCGCGCCCCAGCCCCCGGGCCCAGCACCCCA<br>AGGCGGCCAACGCCAAAACTCTCCCTCCTCCTCTTCCTCAATCTCGCTCT<br>CGCTCTTTTTTTTTTTCGCAAAAGGAGGGGAGAGGGGGTAAAAAAATGCT<br>GCACTGTGCGGCGAAGCCGTGAGTGAGCGGCGCGGGGCCAATCAGCG<br>TGCGCCGTTCCGAAAGTTGCCTTTTATGGCTCGAGCGGCCGCGGCGGCG<br>CCCTATAAAACCCAGCGGCGCGACGCGCCACCACCGCCGAGACCGCGT<br>CCGCCCCGCGAGCACAGAGCCTCGCCTTTGCCGATCCGCCGCCCGTCC<br>ACACCCGCCGCCAGgtaagcccggccagccgaccggggcaggcggctcac<br>ggcccggccgcaggcggccgcggcccctttcgcccgtgcagagccgccgtc<br>tgggccgcagcggggggcgcatggggggggaaccggaccgccgtgggggg<br>cgcgggagaagccccctgggcctccggagatgggggacaccccacgccagt<br>tcggaggcgcgaggccgcgctcgggaggcgcgctccggggggtgccgctct<br>cggggcggggcaaccggcggggtctttgtctgagccgggctcttgccaa<br>tggggatcgcagggtgggcgaggcggagcccccgccaggccaggtggggg<br>ctggggcgccattgcgcgtgcgcgctggtccttttgggcgctaactgcgtg<br>cgcgctgggaattggcgctaattgcgcgtgcgcgctgggactcaaggcgc<br>taactgcgcgtgcgttctggggcccggggtgccgcggcctgggctgggc<br>gaaggcgggctcggccggaaggggtggggtcgccgcggctcccgggcgct<br>tgcgcgcacttcctgcccgagccgctggccgcccgagggtgtggccgctg<br>cgtgcgcgcgcgccgaccaggcgctgtttgaacccgggcggaggcggggct<br>ggcgcccggttgggaggggggttggggcctggcttcctgccgcgcgcgcg<br>gggacgcctccgaccagtgtttgccttttatggtaataacgcggccggcc<br>cggcttccttttgtccccaatctgggcgcgcgccggccgcccctggcggcc<br>taaggactaggcgcgccggaagtggccagggcgggggcgacctcggctca<br>cagcgcgcccggctat (SEQ ID NO: 23) |
| heIF4A1 | GTTGATTTCCTTCATCCCTGGCACACGTCCAGGCAGTGTCGAATCCATCT<br>CTGCTACAGGGGAAAACAAATAACATTTGAGTCCAGTGGAGACCGGGAG |

TABLE 4-continued

Exemplary Constitutive Promoters

| Name | DNA SEQUENCE |
|---|---|
| | CAGAAGTAAAGGGAAGTGATAACCCCCAGAGCCCGGAAGCCTCTGGAGG<br>CTGAGACCTCGCCCCCCTTGCGTGATAGGGCCTACGGAGCCACATGACC<br>AAGGCACTGTCGCCTCCGCACGTGTGAGAGTGCAGGGCCCCAAGATGG<br>CTGCCAGGCCTCGAGGCCTGACTCTTCTATGTCACTTCCGTACCGGCGA<br>GAAAGGCGGGCCCTCCAGCCAATGAGGCTGCGGGCGGGCCTTCACCT<br>TGATAGGCACTCGAGTTATCCAATGGTGCCTGCGGGCCGGAGCGACTAG<br>GAACTAACGTCATGCCGAGTTGCTGAGCGCCGGCAGGCGGGGCCGGGG<br>CGGCCAAACCAATGCGATGGCCGGGGCGGAGTCGGGCGCTCTATAAGTT<br>GTCGATAGGCGGGCACTCCGCCCTAGTTTCTAAGGACCATG<br>(SEQ ID NO: 24) |
| hGAPDH | AGTTCCCCAACTTTCCCGCCTCTCAGCCTTTGAAAGAAAGAAAGGGGAGG<br>GGGCAGGCCGCGTGCAGTCGCGAGCGGTGCTGGGCTCCGGCTCCAATT<br>CCCCATCTCAGTCGCTCCCAAAGTCCTTCTGTTTCATCCAAGCGTGTAAG<br>GGTCCCCGTCCTTGACTCCCTAGTGTCCTGCTGCCCACAGTCCAGTCCT<br>GGGAACCAGCACCGATCACCTCCCATCGGGCCAATCTCAGTCCCTTCCC<br>CCCTACGTCGGGGCCCACACGCTCGGTGCGTGCCCAGTTGAACCAGGC<br>GGCTGCGGAAAAAAAAAAGCGGGGAGAAAGTAGGGCCCGGCTACTAGC<br>GGTTTTACGGGCGCACGTAGCTCAGGCCTCAAGACCTTGGGCTGGGACT<br>GGCTGAGCCTGGCGGGAGGCGGGGTCCGAGTCACCGCCTGCCGCCGC<br>GCCCCCGGTTTCTATAAATTGAGCCCGCAGCCTCCCGCTTCGCTCTCTGC<br>TCCTCCTGTTCGACAGTCAGCCGCATCTTCTTTTGCGTCGCCAGgtgaagac<br>gggcggagagaaacccgggaggctagggacggcctgaaggcggcagggcgg<br>gcgcaggccggatgtgttcgcgccgctgcggggtgggcccgggcggcctccg<br>acttgcaggggcgggcggaggacgtgatgcggcgcgggctgggcatggaggc<br>ctggtggggagggaggggaggcgtgggtgtcggccggggccactaggcgc<br>tcactgttctctccctccgcgcagCCGAGCCACATCGCTGAGACAC<br>(SEQ ID NO: 25) |
| hGRP78 | AGTGCGGTTACCAGCGGAAATGCCTCGGGGTCAGAAGTCGCAGGAGAGA<br>TAGACAGCTGCTGAACCAATGGGACCAGCGGATGGGGCGGATGTTATCT<br>ACCATTGGTGAACGTTAGAAACGAATAGCAGCCAATGAATCAGCTGGGG<br>GGGCGGAGCAGTGACGTTTATTGCGGAGGGGGCCGCTTCGAATCGGCG<br>GCGGCCAGCTTGGTGGCCTGGGCCAATGAACGGCCTCCAACGAGCAGG<br>GCCTTCACCAATCGGCGGCCTCCACGACGGGGCTGGGGGAGGGTATAT<br>AAGCCGAGTAGGCGACGGTGAGGTCGACGCCGGCCAAGACAGCACAGA<br>CAGATTGACCTATTGGGTGTTTCGCGAGTGTGAGAGGGAAGCGCCGCG<br>GCCTGTATTTCTAGACCTGCCCTTCGCCTGGTTCGTGGCGCCTTGTGACC<br>CCGGGCCCCTGCCGCCTGCAAGTCGGAAATTGCGCTGTGCTCCTGTGCT<br>ACGGCCTGTGGCTGGACTGCCTGCTGCTGCCCAACTGGCTGGCAC<br>(SEQ ID NO: 26) |
| hGRP94 | TAGTTTCATCACCACCGCCACCCCCCCGCCCCCCCGCCATCTGAAAGGG<br>TTCTAGGGGATTTGCAACCTCTCTCGTGTGTTTCTTCTTTCCGAGAAGCG<br>CCGCCACACGAGAAAGCTGGCCGCGAAAGTCGTGCTGGAATCACTTCCA<br>ACGAAACCCCAGGCATAGATGGGAAAGGGTGAAGAACACGTTGCCATGG<br>CTACCGTTTCCCCGGTCACGGAATAAACGCTCTCTAGGATCCGGAAGTAG<br>TTCCGCCGCGACCTCTCTAAAAGGATGGATGTGTTCTCTGCTTACATTCAT<br>TGGACGTTTTCCCTTAGAGGCCAAGGCCGCCCAGGCAAAGGGGCGGTCC<br>CACGCGTGAGGGGCCCGCGGAGCCATTTGATTGGAGAAAAAGCTGCAAAC<br>CCTGACCAATCGGAAGGAGCCACGCTTCGGGCATCGGTCACCGCACCTG<br>GACAGCTCCGATTGGTGGACTTCCGCCCCCCCTCACGAATCCTCATTGG<br>GTGCCGTGGGTGCGTGGTGCGGCGCGATTGGTGGGTTCATGTTTCCCGT<br>CCCCCGCCCGCGAGAAGTGGGGGTGAAAAGCGGCCCGACCTGCTTGGG<br>GTGTAGTGGGCGGACCGCGCGGCTGGAGGTGTGAGGATCCGAACCCAG<br>GGGTGGGGGGTGGAGGCGGCTCCTGCGATCGAAGGGGACTTGAGACTC<br>ACCGGCCGCACGTC (SEQ ID NO: 27) |
| hHSP70 | GGGCCGCCCACTCCCCCTTCCTCTCAGGGTCCCTGTCCCCTCCAGTGAA<br>TCCCAGAAGACTCTGGAGAGTTCTGAGCAGGGGGCGGCACTCTGGCCTC<br>TGATTGGTCCAAGGAAGGCTGGGGGGCAGGACGGGAGGCGAAAACCCT<br>GGAATATTCCCGACCTGGCAGCCTCATCGAGCTCGGTGATTGGCTCAGA<br>AGGGAAAAGCGGGTCTCCGTGACGACTTATAAAAGCCAGGGGCAAGC<br>GGTCCGGATAACGGCTAGCCTGAGGAGCTGCTGCGACAGTCCACTACCT<br>TTTTCGAGAGTGACTCCCGTTGTCCCAAGGCTTCCCAGAGCGAACCTGTG<br>CGGCTGCAGGCACCGGCGCGTCGAGTTTCCGGCGTCCGGAAGGACCGA<br>GCTCTTCTCGCGGATCCAGTGTTCCGTTTCCAGCCCCCAATCTCAGAGCG<br>GAGCCGACAGAGAGCAGGGAACCC (SEQ ID NO: 28) |
| hKINb | GCCCCACCCCCGTCCGCGTTACAACCGGGAGGCCCGCTGGGTCCTGCA<br>CCGTCACCCTCCTCCCTGTGACCGCCCACCTGATACCCAAACAACTTTCT<br>CGCCCCTCCAGTCCCCAGCTCGCCGAGCGCTTGCGGGGAGCCACCCAG<br>CCTCAGTTTCCCCAGCCCCGGGCGGGGCGAGGGGCGATGACGTCATGC<br>CGGCGCGCGGCATTGTGGGCGGGGCGAGGCGGGGCGCCGGGGGGA<br>GCAACACTGAGACGCCATTTTCGGCGGCGGGAGCGGCGCAGGCGGCCG<br>AGCGGGACTGGCTGGGTCGGCTGGGCTGCTGGTGCGAGGAGCCGCGG |

TABLE 4-continued

Exemplary Constitutive Promoters

| Name | DNA SEQUENCE |
|---|---|
| | GGCTGTGCTCGGCGGCCAAGGGGACAGCGCGTGGGTGGCCGAGGATG<br>CTGCGGGGCGGTAGCTCCGGCGCCCTCGCTGGTGACTGCTGCGCCGT<br>GCCTCACACAGCCGAGGCGGGCTCGGCGCACAGTCGCTGCTCCGCGCT<br>CGCGCCCGGCGGCGCTCCAGGTGCTGACAGCGCGAGAGAGCGCGGCC<br>TCAGGAGCAACAC (SEQ ID NO: 29) |
| hUBIb | TTCCAGAGCTTTCGAGGAAGGTTTCTTCAACTCAAATTCATCCGCCTGATA<br>ATTTTCTTATATTTTCCTAAAGAAGGAAGAGAAGCGCATAGAGGAGAAGG<br>GAAATAATTTTTTAGGAGCCTTTCTTACGGCTATGAGGAATTTGGGGCTCA<br>GTTGAAAAGCCTAAACTGCCTCTCGGGAGGTTGGGCGCGGCGAACTACT<br>TTCAGCGGCGCACGGAGACGGCGTCTACGTGAGGGGTGATAAGTGACG<br>CAACACTCGTTGCATAAATTTGCGCTCCGCCAGCCCGGAGCATTTAGGG<br>GCGGTTGGCTTTGTTGGGTGAGCTTGTTTGTGTCCCTGTGGGTGGACGT<br>GGTTGGTGATTGGCAGGATCCTGGTATCCGCTAACAGgtactggcccacagccgt<br>aaagacctgcggggcgtgagaggggaatgggtgaggtcaagctggaggcttc<br>ttggggttgggtgggccgctgaggggaggggagggcgaggtgacgcgacacccgg<br>cctttctgggagagtgggccttgttgacctaaggggggcgagggcagttggcacg<br>cgcacgcgccgacagaaactaacagacattaaccaacagccattccgtcgcgttt<br>acttgggaggaaggcggaaaagaggtagtttgtgtggcttctggaaaccctaaat<br>ttggaatcccagtatgagaatggtgtcccttcttgtgtttcaatgggattttttac<br>ttcgcgagtcttgtgggtttggttttgttttcagtttgcctaacaccgtgcttag<br>gtttgaggcagattggagttcggtcgggggagtttgaatatccggaacagttagt<br>ggggaaagctgtggacgcttggtaagagagcgctctggattttccgctgttgacg<br>ttgaaaccttgaatgacgaatttcgtattaagtgacttagccttgtaaaattgag<br>gggaggcttgcggaatattaacgtatttaaggcattttgaaggaatagttgctaa<br>ttttgaagaatattaggtgtaaaagcaagaaatacaatgatcctgaggtgacacg<br>cttatgttttacttttaaactagGTCACC (SEQ ID NO: 30) |

In some embodiments, a promoter of the present disclosure is modulated by signals within a tumor microenvironment. A tumor microenvironment is considered to modulate a promoter if, in the presence of the tumor microenvironment, the activity of the promoter is increased or decreased by at least 10%, relative to activity of the promoter in the absence of the tumor microenvironment. In some embodiments, the activity of the promoter is increased or decreased by at least 20%, at least 30%, at least 40%, at least 50%, at least 60%, at least 70%, at least 80%, at least 90%, at least 100%, relative to activity of the promoter in the absence of the tumor microenvironment. For example, the activity of the promoter is increased or decreased by 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%, relative to activity of the promoter in the absence of the tumor microenvironment.

In some embodiments, the activity of the promoter is increased or decreased by at least 2 fold (e.g., 2, 3, 4, 5, 10, 25, 20, 25, 50, or 100 fold), relative to activity of the promoter in the absence of the tumor microenvironment. For example, the activity of the promoter is increased or decreased by at least 3 fold, at least 5 fold, at least 10 fold, at least 20 fold, at least 50 fold, or at least 100 fold, relative to activity of the promoter in the absence of the tumor microenvironment. In some embodiments, the activity of the promoter is increased or decreased by 2-10, 2-20, 2-30, 2-40, 2-50, 2-60, 2-70, 2-80, 2-90, or 2-100 fold, relative to activity of the promoter in the absence of the tumor microenvironment.

In some embodiments, a promoter of the present disclosure is activated under a hypoxic condition. A "hypoxic condition" is a condition where the body or a region of the body is deprived of adequate oxygen supply at the tissue level. Hypoxic conditions can cause inflammation (e.g., the level of inflammatory cytokines increase under hypoxic conditions). In some embodiments, the promoter that is activated under hypoxic condition is operably linked to a nucleotide encoding an effector molecule that decreases the expression of activity of inflammatory cytokines, thus reducing the inflammation caused by the hypoxic condition. In some embodiments, the promoter that is activated under hypoxic conditions comprises a hypoxia responsive element (HRE). A "hypoxia responsive element (HRE)" is a response element that responds to hypoxia-inducible factor (HIF). The HRE, in some embodiments, comprises a consensus motif NCGTG (where N is either A or G).

In some embodiments, engineered cells produce multiple effector molecules. For example, cells may be engineered to produce 2-20 different effector molecules. In some embodiments, Cells engineered to produce 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20 effector molecules. In some embodiments, cells are engineered to produce 1, 2, 3, 4, 5, 6, 7, 8, 9, 10, 11, 12, 13, 14, 15, 16, 17, 18, 19, or 20 effector molecules.

In some embodiments, exogenous sequences can be multicistronic, i.e., more than one separate polypeptide (e.g., multiple effector molecules) can be produced from a single mRNA transcript. Exogenous sequences can be multicistronic through the use of various linkers, e.g., a polynucleotide sequence encoding a first effector molecule can be linked to a nucleotide sequence encoding a second effector molecule, such as in a first gene:linker:second gene 5' to 3' orientation. A linker can encode a 2A ribosome skipping element, such as T2A. Other 2A ribosome skipping elements include, but are not limited to, E2A, P2A, and F2A. 2A ribosome skipping elements allow production of separate polypeptides encoded by the first and second genes are produced during translation. A linker can encode a cleavable linker polypeptide sequence, such as a Furin cleavage site or a TEV cleavage site, wherein following expression the cleavable linker polypeptide is cleaved such that separate polypeptides encoded by the first and second genes are produced. A cleavable linker can include a polypeptide sequence, such as such a flexible linker (e.g., a Gly-Ser-Gly sequence), that further promotes cleavage.

A linker can encode an Internal Ribosome Entry Site (IRES), such that separate polypeptides encoded by the first and second genes are produced during translation. A linker can encode a splice acceptor, such as a viral splice acceptor.

A linker can be a combination of linkers, such as a Furin-2A linker that can produce separate polypeptides through 2A ribosome skipping followed by further cleavage of the Furin site to allow for complete removal of 2A residues. In some embodiments, a combination of linkers can include a Furin sequence, a flexible linker, and 2A linker. Accordingly, in some embodiments, the linker is a Furin-Gly-Ser-Gly-2A fusion polypeptide. In some embodiments, a linker of the present disclosure is a Furin-Gly-Ser-Gly-T2A fusion polypeptide.

In general, a multicistronic system can use any number or combination of linkers, to express any number of genes or portions thereof (e.g., an exogenous sequence can encode a first, a second, and a third effector molecule, each separated by linkers such that separate polypeptides encoded by the first, second, and third effector molecules are produced).

Exogenous sequences can use multiple promoters to express genes from multiple ORFs, i.e., more than one separate mRNA transcript can be produced from the exogenous sequence. For example, a first promoter can be operably linked to a polynucleotide sequence encoding a first effector molecule, and a second promoter can be operably linked to a polynucleotide sequence encoding a second effector molecule.

"Linkers," as used herein can refer to polypeptides that link a first polypeptide sequence and a second polypeptide sequence, the multicistronic linkers described above, or the additional promoters that are operably linked to additional ORFs described above.

Engineered cells, such as MSCs, of the present disclosure typically produce multiple effector molecules, at least two of which modulate different tumor-mediated immunosuppressive mechanisms. In some embodiments, at least one of the effector molecules stimulates an inflammatory pathway in the tumor microenvironment, and at least one of the effector molecules inhibits a negative regulator of inflammation in the tumor microenvironment.

A "tumor microenvironment" is the cellular environment in which a tumor exists, including surrounding blood vessels, immune cells, fibroblasts, bone marrow-derived inflammatory cells, lymphocytes, signaling molecules and the extracellular matrix (ECM) (see, e.g., Pattabiraman, D. R. & Weinberg, R. A. *Nature Reviews Drug Discovery* 13, 497-512 (2014); Balkwill, F. R. et al. *J Cell Sci* 125, 5591-5596, 2012; and Li, H. et al. *J Cell Biochem* 101(4), 805-15, 2007).

In some embodiments, cells are engineered to produce at least one homing molecule. "Homing," refers to active navigation (migration) of a cell to a target site (e.g., a cell, tissue (e.g., tumor), or organ). A "homing molecule" refers to a molecule that directs cells to a target site. In some embodiments, a homing molecule functions to recognize and/or initiate interaction of a cell to a target site. Non-limiting examples of homing molecules include CXCR1, CCR9, CXCR2, CXCR3, CXCR4, CCR2, CCR4, FPR2, VEGFR, IL6R, CXCR1, CSCR7, and PDGFR.

In some embodiments, a homing molecule is a chemokine receptor (cell surface molecule that binds to a chemokine). Chemokines are small cytokines or signaling proteins secreted by cells that can induce directed chemotaxis in cells. Chemokines can be classified into four main subfamilies: CXC, CC, CX3C and XC, all of which exert biological effects by binding selectively to chemokine receptors located on the surface of target cells. In some embodiments, cells are engineered to produce CXCR4, a chemokine receptor which allows cells to home along a chemokine gradient towards a stromal cell-derived factor 1 (also known as SDF1, C—X—C motif chemokine 12, and CXCL12)-expressing cell, tissue, or tumor. Non-limiting examples of chemokine receptors that may be produced by the engineered cells of the present disclosure include: CXC chemokine receptors (e.g., CXCR1, CXCR2, CXCR3, CXCR4, CXCR5, CXCR6, and CXCR7), CC chemokine receptors (CCR1, CCR2, CCR3, CCR4, CCR5, CCR6, CCR7, CCR8, CCR9, CCR10, and CCR11), CX3C chemokine receptors (e.g., CX3CR1, which binds to CX3CL1), and XC chemokine receptors (e.g., XCR1). In some embodiments, a chemokine receptor is a G protein-linked transmembrane receptor, or a member of the tumor necrosis factor (TNF) receptor superfamily (including but not limited to TNFRSF1A, TNFRSF1B). In some embodiments, cells are engineered to produce CXCL8, CXCL9, and/or CXCL10, 11 or a fusion protein that encompass CXCL10 and CXCL11 (promote T-cell recruitment), CCL3 and/or CXCL5, CCL21 (Th1 recruitment and polarization). In some embodiments cells are engineered to produce CXCL13 to promote B-cell recruitment.

In some embodiments, cells are engineered to produce G-protein coupled receptors (GPCRs) that detect N-formylated-containing oligopeptides (including but not limited to FPR2 and FPRL1).

In some embodiments, cells are engineered to produce receptors that detect interleukins (including but not limited to IL6R).

In some embodiments, cells are engineered to produce receptors that detect growth factors secreted from other cells, tissues, or tumors (including but not limited to FGFR, PDGFR, EGFR, and receptors of the VEGF family, including but not limited to VEGF-C and VEGF-D).

In some embodiments, a homing molecule is an integrin. Integrins are transmembrane receptors that facilitate cell-extracellular matrix (ECM) adhesion. Integrins are obligate heterodimers having two subunits: α (alpha) and β (beta). The α subunit of an integrin may be, without limitation: ITGA1, ITGA2, ITGA3, ITGA4, ITGA5, ITGA6, IGTA7, ITGA8, ITGA9, IGTA10, IGTA11, ITGAD, IGTAE, ITGAL, ITGAM, ITGAV, ITGA2B, ITGAX. The β subunit of an integrin may be, without limitation: ITGB1, ITGB2, ITGB3, ITGB4, ITGB5, ITGB6, ITGB7, and ITGB8. Cells of the present disclosure may be engineered to produce any combination of the integrin α and β subunits.

In some embodiments, a homing molecule is a matrix metalloproteinase (MMP). MMPs are enzymes that cleave components of the basement membrane underlying the endothelial cell wall. Non-limiting examples of MMPs include MMP-2, MMP-9, and MMP. In some embodiments, cells are engineered to produce an inhibitor of a molecule (e.g., protein) that inhibits MMPs. For example, cells may be engineered to express an inhibitor (e.g., an RNAi molecule) of membrane type 1 MMP (MT1-MMP) or TIMP metallopeptidase inhibitor 1 (TIMP-1).

In some embodiments, a homing molecule is a ligand that binds to selectin (e.g., hematopoietic cell E-/L-selectin ligand (HCELL), Dykstra et al., Stem Cells. 2016 October; 34(10):2501-2511) on the endothelium of a target tissue, for example.

The term "homing molecule" also encompasses transcription factors that regulate the production of molecules that improve/enhance homing of cells.

In some embodiments, cell homing is increased by locally irradiating a tumor/cancer cells in a subject. Radiological tissue damage aids in cell homing, as well as endogenous T cell homing to that damaged tissue.

Examples of Engineered Cells

Cells (e.g., MSCs) as provided herein are engineered to produce multiple effector molecules, at least two of which modulate different tumor-mediated immunosuppressive mechanisms. In some embodiments, at least one (e.g., 1, 2, 3, 4, 5, or more) effector molecule stimulates at least one immunostimulatory mechanism in the tumor microenvironment, or inhibits at least one immunosuppressive mechanism in the tumor microenvironment. In some embodiments, at least one (e.g., 1, 2, 3, 4, 5, or more) effector molecule inhibits at least one immunosuppressive mechanism in the tumor microenvironment, and at least one effector molecule (e.g., 1, 2, 3, 4, 5, or more) inhibits at least one immunosuppressive mechanism in the tumor microenvironment. In yet other embodiments, at least two (e.g., 2, 3, 4, 5, or more) effector molecules stimulate at least one immunostimulatory mechanism in the tumor microenvironment. In still other embodiments, at least two (e.g., 1, 2, 3, 4, 5, or more) effector molecules inhibit at least one immunosuppressive mechanism in the tumor microenvironment.

In some embodiments, a cell (e.g., MSC) is engineered to produce at least one effector molecule that stimulates T cell signaling, activity and/or recruitment. In some embodiments, a cell (e.g., MSC) is engineered to produce at least one effector molecule that stimulates antigen presentation and/or processing. In some embodiments, a cell (e.g., MSC) is engineered to produce at least one effector molecule that stimulates natural killer cell-mediated cytotoxic signaling, activity and/or recruitment. In some embodiments, a cell (e.g., MSC) is engineered to produce at least one effector molecule that stimulates dendritic cell differentiation and/or maturation. In some embodiments, a cell (e.g., MSC) is engineered to produce at least one effector molecule that stimulates immune cell recruitment. In some embodiments, a cell (e.g., MSC) is engineered to produce at least one effector molecule that stimulates M1 macrophage signaling, activity and/or recruitment. In some embodiments, a cell (e.g., MSC) is engineered to produce at least one effector molecule that stimulates Th1 polarization. In some embodiments, a cell (e.g., MSC) is engineered to produce at least one effector molecule that stimulates stroma degradation. In some embodiments, a cell (e.g., MSC) is engineered to produce at least one effector molecule that stimulates immunostimulatory metabolite production. In some embodiments, a cell (e.g., MSC) is engineered to produce at least one effector molecule that stimulates Type I interferon signaling. In some embodiments, a cell (e.g., MSC) is engineered to produce at least one effector molecule that inhibits negative costimulatory signaling. In some embodiments, a cell (e.g., MSC) is engineered to produce at least one effector molecule that inhibits pro-apoptotic signaling (e.g., via TRAIL) of anti-tumor immune cells. In some embodiments, a cell (e.g., MSC) is engineered to produce at least one effector molecule that inhibits T regulatory ($T_{reg}$) cell signaling, activity and/or recruitment. In some embodiments, a cell (e.g., MSC) is engineered to produce at least one effector molecule that inhibits tumor checkpoint molecules. In some embodiments, a cell (e.g., MSC) is engineered to produce at least one effector molecule that activates stimulator of interferon genes (STING) signaling. In some embodiments, a cell (e.g., MSC) is engineered to produce at least one effector molecule that inhibits myeloid-derived suppressor cell signaling, activity and/or recruitment. In some embodiments, a cell (e.g., MSC) is engineered to produce at least one effector molecule that degrades immunosuppressive factors/metabolites. In some embodiments, a cell (e.g., MSC) is engineered to produce at least one effector molecule that inhibits vascular endothelial growth factor signaling. In some embodiments, a cell (e.g., MSC) is engineered to produce at least one effector molecule that directly kills tumor cells (e.g., granzyme, perforin, oncolytic viruses, cytolytic peptides and enzymes, anti-tumor antibodies, e.g., that trigger ADCC).

In some embodiments, at least one effector molecule: stimulates T cell signaling, activity and/or recruitment, stimulates antigen presentation and/or processing, stimulates natural killer cell-mediated cytotoxic signaling, activity and/or recruitment, stimulates dendritic cell differentiation and/or maturation, stimulates immune cell recruitment, stimulates macrophage signaling, stimulates stroma degradation, stimulates immunostimulatory metabolite production, or stimulates Type I interferon signaling; and at least one effector molecule inhibits negative costimulatory signaling, inhibits pro-apoptotic signaling of anti-tumor immune cells, inhibits T regulatory (Treg) cell signaling, activity and/or recruitment, inhibits tumor checkpoint molecules, activates stimulator of interferon genes (STING) signaling, inhibits myeloid-derived suppressor cell signaling, activity and/or recruitment, degrades immunosuppressive factors/metabolites, inhibits vascular endothelial growth factor signaling, or directly kills tumor cells.

In some embodiments, a cell (e.g., MSC) is engineered to produce at least one effector molecule selected from IL-12, IFN-β, IFN-γ, IL-2, IL-15, IL-7, IL-36γ, IL-18, IL-1β, OX40-ligand, and CD40L; and/or at least one effector molecule selected from anti-PD-1 antibodies, anti-PD-L1 antibodies, anti-CTLA-4 antibodies, and anti-IL-35 antibodies; and/or at least one effector molecule selected from MIP1α (CCL3), MIP1β (CCL5), and CCL21; and/or at least one effector molecule selected from CpG oligodeoxynucleotides; and/or at least one effector molecule selected from microbial peptides.

In some embodiments, a cell (e.g., MSC) is engineered to produce IFN-β and at least one effector molecule selected from cytokines, antibodies, chemokines, nucleotides, peptides, enzymes, and stimulators of interferon genes (STINGs). In some embodiments, a cell (e.g., MSC) is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments, a cell (e.g., MSC) is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments the cytokine is produced as an engineered fusion protein with an antibody, antibody-fragment, or receptor that self-binds to the cytokine to induce cell-specific targeted binding such as with IL-2 fused to an antibody fragment preventing it from binding to Treg cells and preferentially binding to CD8 and NK cells. In some embodiments, a cell (e.g., MSC) is engineered to produce IFN-β and at least one antibody (e.g., anti-PD-1 antibody, anti-PD-L1 antibody, anti-CTLA-4 antibody, anti-VEGF, anti-TGF-β, anti-IL-10, anti-TNF-α, and/or anti-IL-35 antibody). In some embodiments, a cell (e.g., MSC) is engineered to produce IFN-β and at least one chemokine (MIP1α (CCL3), MIP1β (CCL5), and/or CCL21). In some embodiments, a cell (e.g., MSC) is engineered to produce IFN-β and at least one nucleotide (e.g., a CpG oligodeoxynucleotide). In some embodiments, a cell (e.g., MSC) is engineered to produce IFN-β and at least one peptide (e.g., an anti-tumor peptide). In some embodiments, a cell (e.g., MSC) is engineered to produce IFN-β and at least one enzyme. In some embodiments, a cell (e.g., MSC) is engineered to produce IFN-β and at least one STING activator. In some embodiments, a cell (e.g., MSC) is engineered to produce IFN-β and at least one effector with direct anti-tumor activity (e.g., oncolytic virus).

In some embodiments, a cell (e.g., MSC) is engineered to produce IFN-α and MIP1-α. In some embodiments, a cell (e.g., MSC) is engineered to produce IFN-α and MIP1-β. In some embodiments, a cell (e.g., MSC) is engineered to produce IFN-α and CXCL9. In some embodiments, a cell (e.g., MSC) is engineered to produce IFN-α and CXCL10. In some embodiments, a cell (e.g., MSC) is engineered to produce IFN-α and CXCL11. In some embodiments, a cell (e.g., MSC) is engineered to produce IFN-α and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-β and MIP1-α. In some embodiments, a cell (e.g., MSC) is engineered to produce IFN-β and MIP1-β. In some embodiments, a cell (e.g., MSC) is engineered to produce IFN-β and CXCL9. In some embodiments, a cell (e.g., MSC) is engineered to produce IFN-β and CXCL10. In some embodiments, a cell (e.g., MSC) is engineered to produce IFN-β and CXCL11. In some embodiments, a cell (e.g., MSC) is engineered to produce IFN-β and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L. In some embodiments, a cell (e.g., MSC) is engineered to produce IL-12 and MIP1-α.

In some embodiments, a cell (e.g., MSC) is engineered to produce IL-12 and MIP1-β. In some embodiments, a cell (e.g., MSC) is engineered to produce IL-12 and CXCL9. In some embodiments, a cell (e.g., MSC) is engineered to produce IL-12 and CXCL10. In some embodiments, a cell (e.g., MSC) is engineered to produce IL-12 and CXCL11. In some embodiments, a cell (e.g., MSC) is engineered to produce IL-12 and CCL21. In some embodiments, the cell is engineered to further produce IFN-β, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce TNF-related apoptosis-inducing ligand (TRAIL) and MIP1-α. In some embodiments, a cell (e.g., MSC) is engineered to produce TRAIL and MIP1-β. In some embodiments, a cell (e.g., MSC) is engineered to produce TRAIL and CXCL9. In some embodiments, a cell (e.g., MSC) is engineered to produce TRAIL and CXCL10. In some embodiments, a cell (e.g., MSC) is engineered to produce TRAIL and CXCL11. In some embodiments, a cell (e.g., MSC) is engineered to produce TRAIL and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a stimulator of interferon gene (STING) and MIP1-α. In some embodiments, a cell (e.g., MSC) is engineered to produce STING and MIP1-β. In some embodiments, a cell (e.g., MSC) is engineered to produce STING and CXCL9. In some embodiments, a cell (e.g., MSC) is engineered to produce STING and CXCL10. In some embodiments, a cell (e.g., MSC) is engineered to produce STING and CXCL11. In some embodiments, a cell (e.g., MSC) is engineered to produce STING and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CD40L and MIP1-α. In some embodiments, a cell (e.g., MSC) is engineered to produce CD40L and MIP1-β. In some embodiments, a cell (e.g., MSC) is engineered to produce CD40L and CXCL9. In some embodiments, a cell (e.g., MSC) is engineered to produce CD40L and CXCL10. In some embodiments, a cell (e.g., MSC) is engineered to produce CD40L and CXCL11. In some embodiments, a cell (e.g., MSC) is engineered to produce CD40L and CCL21. In some embodiments, the cell is engineered to further produce IL-12, IFN-γ, IL-2, IL-7, IL-15, IL36-γ, IL-18, and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce cytosine deaminase and MIP1-α. In some embodiments, a cell (e.g., MSC) is engineered to produce cytosine deaminase and MIP1-β. In some embodiments, a cell (e.g., MSC) is engineered to produce cytosine deaminase and CXCL9. In some embodiments, a cell (e.g., MSC) is engineered to produce cytosine deaminase and CXCL10. In some embodiments, a cell (e.g., MSC) is engineered to produce cytosine deaminase and CXCL11. In some embodiments, a cell (e.g., MSC) is engineered to produce cytosine deaminase and CCL21. In some embodiments, the cell is engineered to further produce IL-12, IFN-γ, IL-2, IL-7, IL-15, IL36-γ, IL-18, CD40L, and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-α and IL-12. In some embodiments, a cell (e.g., MSC) is engineered to produce IFN-α and IFN-γ. In some embodiments, a cell (e.g., MSC) is engineered to produce IFN-α and IL-2. In some embodiments, a cell (e.g., MSC) is engineered to produce IFN-α and IL-7. In some embodiments, a cell (e.g., MSC) is engineered to produce IFN-α and IL-15. In some embodiments, a cell (e.g., MSC) is engineered to produce IFN-α and IL-36γ. In some embodiments, a cell (e.g., MSC) is engineered to produce IFN-α and IL-18. In some embodiments, a cell (e.g., MSC) is engineered to produce IFN-α and CD40L. In some embodiments, a cell (e.g., MSC) is engineered to produce IFN-α and 41BB-L. In some embodiments, the cell is engineered to further produce MIP1-α, MIP1-β, CXCL9, CXCL10, CXCL11, CXCL10-11 fusion, CXCL13 and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-β and IL-12. In some embodiments, a cell (e.g., MSC) is engineered to produce IFN-β and IFN-γ. In some embodiments, a cell (e.g., MSC) is engineered to produce IFN-β and IL-2. In some embodiments, a cell (e.g., MSC) is engineered to produce IFN-β and IL-7. In some embodiments, a cell (e.g., MSC) is engineered to produce IFN-β and IL-15. In some embodiments, a cell (e.g., MSC) is engineered to produce IFN-β and IL-36γ. In some embodiments, a cell (e.g., MSC) is engineered to produce IFN-β and IL-18. In some embodiments, a cell (e.g., MSC) is engineered to produce IFN-β and CD40L. In some embodiments, a cell (e.g., MSC) is engineered to produce IFN-β and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce TNF-related apoptosis-inducing ligand (TRAIL) and IL-12. In some embodiments, a cell (e.g., MSC) is engineered to produce TRAIL and IFN-γ. In some embodiments, a cell (e.g., MSC) is engineered to produce TRAIL and IL-2. In some embodiments, a cell (e.g., MSC) is engineered to produce TRAIL and IL-7. In some embodiments, a cell (e.g., MSC) is engineered to produce TRAIL and IL-15. In some embodiments, a cell (e.g., MSC) is engineered to produce TRAIL and IL-36γ. In some embodiments, a cell (e.g., MSC) is engineered to produce TRAIL and IL-18. In some embodiments, a cell (e.g., MSC) is engineered to produce TRAIL and CD40L. In some embodiments, a cell (e.g., MSC) is engineered to produce TRAIL and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a stimulator of interferon gene (STING) and IL-12. In some embodiments, a cell (e.g., MSC) is engineered to produce STING and IFN-γ. In some embodiments, a cell (e.g., MSC) is engineered to produce STING and IL-2. In some embodiments, a cell (e.g., MSC) is engineered to produce STING and IL-7. In some embodiments, a cell (e.g., MSC) is engineered to produce STING and IL-15. In some embodiments, a cell (e.g., MSC) is engineered to produce STING and IL-36γ. In some embodiments, a cell (e.g., MSC) is engineered to produce STING and IL-18. In some embodiments, a cell (e.g., MSC) is engineered to produce STING and CD40L. In some embodiments, a cell (e.g., MSC) is engineered to produce STING and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CD40L and IL-12. In some embodiments, a cell (e.g., MSC) is engineered to produce CD40L and IFN-γ. In some embodiments, a cell (e.g., MSC) is engineered to produce CD40L and IL-2. In some embodiments, a cell (e.g., MSC) is engineered to produce CD40L and IL-7. In some embodiments, a cell (e.g., MSC) is engineered to produce CD40L and IL-15. In some embodiments, a cell (e.g., MSC) is engineered to produce CD40L and IL-36γ. In some embodiments, a cell (e.g., MSC) is engineered to produce CD40L and IL-18. In some embodiments, a cell (e.g., MSC) is engineered to produce CD40L and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce cytosine deaminase and IL-12. In some embodiments, a cell (e.g., MSC) is engineered to produce cytosine deaminase and IFN-γ. In some embodiments, a cell (e.g., MSC) is engineered to produce cytosine deaminase and IL-2. In some embodiments, a cell (e.g., MSC) is engineered to produce cytosine deaminase and IL-7. In some embodiments, a cell (e.g., MSC) is engineered to produce cytosine deaminase and IL-15. In some embodiments, a cell (e.g., MSC) is engineered to produce cytosine deaminase and IL-36γ. In some embodiments, a cell (e.g., MSC) is engineered to produce cytosine deaminase and IL-18. In some embodiments, a cell (e.g., MSC) is engineered to produce cytosine deaminase and CD40L. In some embodiments, a cell (e.g., MSC) is engineered to produce cytosine deaminase and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce MIP1-α and IL-12. In some embodiments, a cell (e.g., MSC) is engineered to produce MIP1-α and MIP1-γ. In some embodiments, a cell (e.g., MSC) is engineered to produce MIP1-α and IL-2. In some embodiments, a cell (e.g., MSC) is engineered to produce MIP1-α and IL-7. In some embodiments, a cell (e.g., MSC) is engineered to produce MIP1-α and IL-15. In some embodiments, a cell (e.g., MSC) is engineered to produce MIP1-α and IL-36γ. In some embodiments, a cell (e.g., MSC) is engineered to produce MIP1-α and IL-18. In some embodiments, a cell (e.g., MSC) is engineered to produce MIP1-α and CD40L. In some embodiments, a cell (e.g., MSC) is engineered to produce MIP1-α and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce MIP1-β and IL-12. In some embodiments, a cell (e.g., MSC) is engineered to produce MIP1-β and MIP1-γ. In some embodiments, a cell (e.g., MSC) is engineered to produce MIP1-β and IL-2. In some embodiments, a cell (e.g., MSC) is engineered to produce MIP1-β and IL-7. In some embodiments, a cell (e.g., MSC) is engineered to produce MIP1-β and IL-15. In some embodiments, a cell (e.g., MSC) is engineered to produce MIP1-β and IL-36γ. In some embodiments, a cell (e.g., MSC) is engineered to produce MIP1-β and IL-18. In some embodiments, a cell (e.g., MSC) is engineered to produce MIP1-β and CD40L. In some embodiments, a cell (e.g., MSC) is engineered to produce MIP1-β and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CXCL9 and IL-12. In some embodiments, a cell (e.g., MSC) is engineered to produce CXCL9 and IFN-γ. In some embodiments, a cell (e.g., MSC) is engineered to produce CXCL9 and IL-2. In some embodiments, a cell (e.g., MSC) is engineered to produce CXCL9 and IL-7. In some embodiments, a cell (e.g., MSC) is engineered to produce CXCL9 and IL-15. In some embodiments, a cell (e.g., MSC) is engineered to produce CXCL9 and IL-36γ. In some embodiments, a cell (e.g., MSC) is engineered to produce CXCL9 and IL-18. In some embodiments, a cell (e.g., MSC) is engineered to produce CXCL9 and CD40L. In some embodiments, a cell (e.g., MSC) is engineered to produce CXCL9 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a CXCL10 and IL-12. In some embodiments, a cell (e.g., MSC) is engineered to produce CXCL10 and IFN-γ. In some embodiments, a cell (e.g., MSC) is engineered to produce CXCL10 and IL-2. In some embodiments, a cell (e.g., MSC) is engineered to produce CXCL10 and IL-7. In some embodiments, a cell (e.g., MSC) is engineered to produce CXCL10 and IL-15. In some embodiments, a cell (e.g., MSC) is engineered to produce CXCL10 and IL-36γ. In some embodiments, a cell (e.g., MSC) is engineered to produce CXCL10 and IL-18. In some embodiments, a cell (e.g., MSC) is engineered to produce CXCL10 and CD40L. In some embodiments, a cell (e.g., MSC) is engineered to produce CXCL10 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CXCL11 and IL-12. In some embodiments, a cell (e.g., MSC) is engineered to produce CXCL11 and IFN-γ. In some embodiments, a cell (e.g., MSC) is engineered to produce CXCL11 and IL-2. In some embodiments, a cell (e.g., MSC) is engineered to produce CXCL11 and IL-7. In some embodiments, a cell (e.g., MSC) is engineered to produce CXCL11 and IL-15. In some embodiments, a cell (e.g., MSC) is engineered to produce CXCL11 and IL-36γ. In some embodiments, a cell (e.g., MSC) is engineered to produce CXCL11 and IL-18. In some embodiments, a cell (e.g., MSC) is engineered to produce CXCL11 and CD40L. In some embodiments, a cell (e.g., MSC) is engineered to produce CXCL11 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CCL21 and IL-12. In some embodiments, a cell (e.g., MSC) is engineered to produce CCL21 and IFN-γ. In some embodiments, a cell (e.g., MSC) is engineered to produce CCL21 and IL-2. In some embodiments, a cell (e.g., MSC) is engineered to produce CCL21 and IL-7. In some embodiments, a cell (e.g., MSC) is engineered to produce CCL21 and IL-15. In some embodiments, a cell (e.g., MSC) is engineered to produce CCL21 and IL-36γ. In some embodiments, a cell (e.g., MSC) is engineered to produce CCL21 and IL-18. In some embodiments, a cell (e.g., MSC) is engineered to produce CCL21 and CD40L. In some embodiments, a cell (e.g., MSC) is engineered to produce CCL21 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-α and anti-PD-L1 antibody. In some embodiments, a cell (e.g., MSC) is engineered to produce IFN-α and OX40L. In some embodiments, a cell (e.g., MSC) is engineered to produce IFN-α and anti-CTLA4 antibody. In some embodiments, a cell (e.g., MSC) is engineered to produce IFN-α and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce IFN-β and anti-PD-L1 antibody. In some embodiments, a cell (e.g., MSC) is engineered to produce IFN-β and OX40L. In some embodiments, a cell (e.g., MSC) is engineered to produce IFN-β and anti-CTLA4 antibody. In some embodiments, a cell (e.g., MSC) is engineered to produce IFN-β and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce TRAIL and anti-PD-L1 antibody. In some embodiments, a cell (e.g., MSC) is engineered to produce TRAIL and OX40L. In some embodiments, a cell (e.g., MSC) is engineered to produce TRAIL and anti-CTLA4 antibody. In some embodiments, a cell (e.g., MSC) is engineered to produce TRAIL and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce STING and anti-PD-L1 antibody. In some embodiments, a cell (e.g., MSC) is engineered to produce STING and OX40L. In some embodiments, a cell (e.g., MSC) is engineered to produce STING and anti-CTLA4 antibody. In some embodiments, a cell (e.g., MSC) is engineered to produce STING and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CD40L and anti-PD-L1 antibody. In some embodiments, a cell (e.g., MSC) is engineered to produce CD40L and OX40L. In some embodiments, a cell (e.g., MSC) is engineered to produce CD40L and anti-CTLA4 antibody. In some embodiments, a cell (e.g., MSC) is engineered to produce CD40L and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce cytosine deaminase and anti-PD-L1 antibody. In some embodiments, a cell (e.g., MSC) is engineered to produce cytosine deaminase and OX40L. In some embodiments, a cell (e.g., MSC) is engineered to produce cytosine deaminase and anti-CTLA4 antibody. In some embodiments, a cell (e.g., MSC) is engineered to produce cytosine deaminase and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce MIP1-α and anti-PD-L1 antibody. In some embodiments, a cell (e.g., MSC) is engineered to produce MIP1-α and OX40L. In some embodiments, a cell (e.g., MSC) is engineered to produce MIP1-α and anti-CTLA4 antibody. In some embodiments, a cell (e.g., MSC) is engineered to produce MIP1-α and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce MIP1-β and anti-PD-L1 antibody. In some embodiments, a cell (e.g., MSC) is engineered to produce MIP1-β and OX40L. In some embodiments, a cell (e.g., MSC) is engineered to produce MIP1-β and anti-CTLA4 antibody. In some embodiments, a cell (e.g., MSC) is engineered to produce MIP1-β and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL9 and anti-PD-L1 antibody. In some embodiments, a cell (e.g., MSC) is engineered to produce CXCL9 and OX40L. In some embodiments, a cell (e.g., MSC) is engineered to produce CXCL9 and anti-CTLA4 antibody. In some embodiments, a cell (e.g., MSC) is engineered to produce CXCL9 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL10 and anti-PD-L1 antibody. In some embodiments, a cell (e.g., MSC) is engineered to produce CXCL10 and OX40L. In some embodiments, a cell (e.g., MSC) is engineered to produce CXCL10 and anti-CTLA4 antibody. In some embodiments, a cell (e.g., MSC) is engineered to produce CXCL10 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL11 and anti-PD-L1 antibody. In some embodiments, a cell (e.g., MSC) is engineered to produce CXCL11 and OX40L. In some embodiments, a cell (e.g., MSC) is engineered to produce CXCL11 and anti-CTLA4 antibody. In some embodiments, a cell (e.g., MSC) is engineered to produce CXCL11 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CCL21 and anti-PD-L1 antibody. In some embodiments, a cell (e.g., MSC) is engineered to produce CCL21 and OX40L. In some embodiments, a cell (e.g., MSC) is engineered to produce CCL21 and anti-CTLA4 antibody. In some embodiments, a cell (e.g., MSC) is engineered to produce CCL21 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce IL-12 and anti-PD-L1 antibody. In some embodiments, a cell (e.g., MSC) is engineered to produce IL-12 and OX40L. In some embodiments, a cell (e.g., MSC) is engineered to produce IL-12 and anti-CTLA4 antibody. In some embodiments, a cell (e.g., MSC) is engineered to produce IL-12 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IFN-γ and anti-PD-L1 antibody. In some embodiments, a cell (e.g., MSC) is engineered to produce IFN-γ and OX40L. In some embodiments, a cell (e.g., MSC) is engineered to produce IFN-γ and anti-CTLA4 antibody. In some embodiments, a cell (e.g., MSC) is engineered to produce IFN-γ and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-2 and anti-PD-L1 antibody. In some embodiments, a cell (e.g., MSC) is engineered to produce IL-2 and OX40L. In some embodiments, a cell (e.g., MSC) is engineered to produce IL-2 and anti-CTLA4 antibody. In some embodiments, a cell (e.g., MSC) is engineered to produce IL-2 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-7 and anti-PD-L1 antibody. In some embodiments, a cell (e.g., MSC) is engineered to produce IL-7 and OX40L. In some embodiments, a cell (e.g., MSC) is engineered to produce IL-7 and anti-CTLA4 antibody. In some embodiments, a cell (e.g., MSC) is engineered to produce IL-7 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-15 and anti-PD-L1 antibody. In some embodiments, a cell (e.g., MSC) is engineered to produce IL-15 and OX40L. In some embodiments, a cell (e.g., MSC) is engineered to produce IL-15 and anti-CTLA4 antibody. In some embodiments, a cell (e.g., MSC) is engineered to produce IL-15 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-36-γ and anti-PD-L1 antibody. In some embodiments, a cell (e.g., MSC) is engineered to produce IL-36-γ and OX40L. In some embodiments, a cell (e.g., MSC) is engineered to produce IL-36-γ and anti-CTLA4 antibody. In some embodiments, a cell (e.g., MSC) is engineered to produce IL-36-γ and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-18 and anti-PD-L1 antibody. In some embodiments, a cell (e.g., MSC) is engineered to produce IL-18 and OX40L. In some embodiments, a cell (e.g., MSC) is engineered to produce IL-18 and anti-CTLA4 antibody. In some embodiments, a cell (e.g., MSC) is engineered to produce IL-18 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce CD40L and anti-PD-L1 antibody. In some embodiments, a cell (e.g., MSC) is engineered to produce CD40L and OX40L. In some embodiments, a cell (e.g., MSC) is engineered to produce CD40L and anti-CTLA4 antibody. In some embodiments, a cell (e.g., MSC) is engineered to produce CD40L and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce 41BB-L and anti-PD-L1 antibody. In some embodiments, a cell (e.g., MSC) is engineered to produce 41BB-L and OX40L. In some embodiments, a cell (e.g., MSC) is engineered to produce 41BB-L and anti-CTLA4 antibody. In some embodiments, a cell (e.g., MSC) is engineered to produce 41BB-L and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

Secretion Signals

In general, the one or more effector molecules comprise a secretion signal peptide (also referred to as a signal peptide or signal sequence) at the effector molecule's N-terminus that direct newly synthesized proteins destined for secretion or membrane insertion to the proper protein processing pathways. The secretion signal peptide operably associated with a effector molecule can be a native secretion signal peptide native secretion signal peptide (e.g., the secretion signal peptide generally endogenously associated with the given effector molecule). The secretion signal peptide operably associated with a effector molecule can be a non-native secretion signal peptide native secretion signal peptide. Non-native secretion signal peptides can promote improved expression and function, such as maintained secretion, in particular environments, such as tumor microenvironments. Non-limiting examples of non-native secretion signal peptide are shown in Table 5.

TABLE 5

Exemplary Signal Secretion Peptides

| Name | Source Protein (Uni-SEQUENCE prot) | DNA SEQUENCE |
|---|---|---|
| IL-12 | MCHQQLVI SWFSLVFL ASPLVA (SEQ ID NO: 112) | P29460 | ATGTGTCACCAGCAGCTCGTTATAT CCTGGTTTAGTTTGGTGTTTCTCGC TTCACCCCTGGTGGCA (SEQ ID NO: 31) |
| IL-12 (Codon Optimized) | MCHQQLVI SWFSLVFL ASPLVA (SEQ ID NO: 112) | — | ATGTGCCATCAGCAACTCGTCATCT CCTGGTTCTCCCTTGTGTTCCTCGC TTCCCCTCTGGTCGCC (SEQ ID NO: 32) |
| IL-2 (Optimized) | MQLLSCI ALILALV (SEQ ID NO: 113) | — | ATGCAACTGCTGTCATGTATCGCAC TCATCCTGGCGCTGGTA (SEQ ID NO: 33) |
| IL-2 (Native) | MYRMQLLS CIALSLAL VTNS (SEQ ID NO: 114) | P60568 | ATGTATCGGATGCAACTTTTGAGCT GCATCGCATTGTCTCTGGCGCTGGT GACAAATTCC (SEQ ID NO: 34) |
| Trypsi-nogen-2 | MNLLLILT FVAAAVA (SEQ ID NO: 115) | P07478 | ATGAATCTCTTGCTCATACTTACGT TTGTCGCTGCTGCCGTTGCG (SEQ ID NO: 35) |
| Gaussia Luciferase | MGVKVLFA LICIAVAE A (SEQ ID NO: 116) | — | ATGGGCGTGAAGGTCTTGTTTGCCC TTATCTGCATAGCTGTTGCGGAGGC G (SEQ ID NO: 36) |
| CD5 | MPMGSLQP LATLYLLG MLVASCLG (SEQ ID NO: 117) | P06127 | ATGCCGATGGGGAGCCTTCAACCTT TGGCAACGCTTTATCTTCTGGGGAT GTTGGTTGCTAGTTGCCTTGGG (SEQ ID NO: 37) |

TABLE 5-continued

Exemplary Signal Secretion Peptides

| Name | Source Protein (Uni-prot) SEQUENCE | DNA SEQUENCE |
|---|---|---|
| IgKVII (mouse) | METDTLLL WVLLLWVP GSTGD (SEQ ID NO: 118) | ATGGAAACTGACACGTTGTTGCTGT GGGTATTGCTCTTGTGGGTCCCAGG ATCTACGGGCGAC (SEQ ID NO: 38) |
| IgKVII (human) | MDMRVPAQ P01597 LLGLLLLW LRGARC (SEQ ID NO: 119) | ATGGATATGAGGGTTCCCGCCCAGC TTTTGGGGCTGCTTTTGTTGTGGCT TCGAGGGGCTCGGTGT (SEQ ID NO: 39) |
| VSV-G | MKCLLYLA— FLFIGVNC (SEQ ID NO: 120) | ATGAAGTGTCTGTTGTACCTGGCGT TTCTGTTCATTGGTGTAAACTGT (SEQ ID NO: 40) |
| Prolactin | MNIKGSPW P01236 KGSLLLLL VSNLLLCQ SVAP (SEQ ID NO: 121) | ATGAATATCAAAGGAAGTCCGTGG AAGGGTAGTCTCCTGCTGCTCCTG TATCTAACCTTCTCCTTTGTCAATC CGTGGCACCC (SEQ ID NO: 41) |
| Serum albumin preproprotein | MKWVTFIS P02768 LLFLFSSA YS (SEQ ID NO: 122) | ATGAAATGGGTAACATTCATATCAC TTCTCTTTCTGTTCAGCTCTGCGTA TTCT (SEQ ID NO: 42) |
| Azurocidin preproprotein | MTRLTVLA 20160 LLAGLLAS SRA (SEQ ID NO: 123) | ATGACAAGGCTTACTGTTTTGGCTC TCCTCGCTGGACTCTTGGCTTCCTC CCGAGCA (SEQ ID NO: 43) |
| Osteonectin (BM40) | MRAWIFFL P09486 LCLAGRAL A (SEQ ID NO: 124) | ATGAGGGCTTGGATTTTTTTCTGC TCTGCCTTGCCGGTCGAGCCCTGG CG (SEQ ID NO: 44) |
| CD33 | MPLLLLLP P20138 LLWAGALA (SEQ ID NO: 125) | ATGCCTCTTCTGCTTTTGCTTCCTC TTTTGTGGGCAGGTGCCCTCGCA (SEQ ID NO: 45) |
| IL-6 | MNSFSTSA P05231 FGPVAFSL GLLLVLPA AFPAP (SEQ ID NO: 126) | ATGAACTCTTTCTCAACCTCTGCGT TTGGTCCGGTCGCTTTCTCCCTTGG GCTCCTGCTTGTCTTGCCAGCAGCG TTTCCTGCGCCA (SEQ ID NO: 46) |
| IL-8 | MTSKLAVA P10145 LLAAFLIS AALC (SEQ ID NO: 127) | ATGACAAGTAAACTGGCGGTAGCC TTGCTCGCGGCCTTTTTGATTTCC GCAGCCCTTTGT (SEQ ID NO: 47) |
| CCL2 | MKVSAALL P13500 CLLLIAAT FIPQGLA (SEQ ID NO: 128) | ATGAAGGTAAGTGCAGCGTTGCTTT GCCTTCTCCTCATTGCAGCGACCTT TATTCCTCAAGGGCTGGCC (SEQ ID NO: 48) |
| TIMP2 | MGAAARTL P16035 RLALGLLL LATLLRPA DA (SEQ ID NO: 129) | ATGGGAGCGGCAGCTAGAACACTT CGACTTGCCCTTGGGCTCTTGCTCC TTGCAACCCTCCTTAGACCTGCCGA CGCA (SEQ ID NO: 49) |
| VEGFB | MSPLLRRL P49765 LLAAL LQLAPAQA (SEQ ID NO: 130) | ATGTCACCGTTGTTGCGGAGATTGC TGTTGGCCGCACTTTTGCAACTGGC TCCTGCTCAAGCC (SEQ ID NO: 50) |
| Osteoprotegerin | MNNLLCCA O00300 LVFLDISI KWTTQ (SEQ ID NO: 131) | ATGAATAACCTGCTCTGTTGTGCGC TCGTGTTCCTGGACATTTCTATAAA ATGGACAACGCAA (SEQ ID NO: 51) |
| Serpin E1 | MQMSPALT P05121 CLVLGLAL VFGEGSA (SEQ ID NO: 132) | ATGCAAATGTCTCCTGCCCTTACCT GTCTCGTACTTGGTCTTGCGCTCGT ATTTGGAGAGGGATCAGCC (SEQ ID NO: 52) |
| GROalpha | MARAALSA P09341 APSNPRLL RVALLLLL LV AAGRRAAG (SEQ ID NO: 133) | ATGGCAAGGGCTGCACTCAGTGCTG CCCCGTCTAATCCCAGATTGCTTCG AGTTGCATTGCTTCTTCTGTTGCTG GTTGCAGCTGGTAGGAGAGCAGCGG GT (SEQ ID NO: 53) |
| CXCL12 | MNAKVVVV P48061 LVLVLTAL CLSDG (SEQ ID NO: 134) | ATGAATGCAAAAGTCGTGGTCGTGC TGGTTTTGGTTCTGACGGCGTTGTG TCTTAGTGATGGG (SEQ ID NO: 54) |
| IL-21 (Codon Optimized) | MERIVICL Q9HBE4 MVIFLGT LVHKSSS (SEQ ID NO: 135) | ATGGAACGCATTGTGATCTGCCTGA TGGTCATCTTCCTGGGCACCTTAGT GCACAAGTCGAGCAGC (SEQ ID NO: 55) |

Cell Types

The present disclosure refers to mesenchymal stem cells (MSCs) (e.g., human MSCs) engineered to produce multiple effector molecules. An engineered cell (engineered to produce effector molecules), as provided herein, may also be selected from natural killer (NK) cells, NKT cells, innate lymphoid cells, mast cells, eosinophils, basophils, macrophages, neutrophils, and dendritic cells, T cells (e.g., CD8+ T cells, CD4+ T cells, gamma-delta T cells, and T regulatory cells (CD4$^+$, FOXP3$^+$, CD25$^+$)) and B cells. It should be understood, however, that any reference to MSC engineering can also be applied to other cell types (e.g., cell types of the immune system).

In some embodiments, an engineered cell (e.g., MSC) is from (e.g., obtained from or derived from) bone marrow. In some embodiments, an engineered mesenchymal stem cell is from (e.g., obtained from or derived from) adipose tissue. In some embodiments, an engineered mesenchymal stem cell is from (e.g., obtained from or derived from) an umbilical cord. In some embodiments, engineered mesenchymal stem cell is from a pluripotent stem cell (e.g., an embryonic stem cell or an induced pluripotent stem cell).

Thus, the present disclosure provides a T cell (e.g., CD8+ T cell, CD4+ T cell, gamma-delta T cell, or T regulatory cell (CD4$^+$, FOXP3$^+$, CD25$^+$)) engineered to produce multiple effector molecules, at least two of which modulate different tumor-mediated immunosuppressive mechanisms. In some embodiments, a B cell is engineered to produce multiple effector molecules, at least two of which modulate different tumor-mediated immunosuppressive mechanisms. In some embodiments, a NK cell is engineered to produce multiple effector molecules, at least two of which modulate different tumor-mediated immunosuppressive mechanisms. In some embodiments, a NKT cell is engineered to produce multiple effector molecules, at least two of which modulate different tumor-mediated immunosuppressive mechanisms. In some embodiments, an innate lymphoid cell is engineered to produce multiple effector molecules, at least two of which modulate different tumor-mediated immunosuppressive mechanisms. In some embodiments, a mast cell is engineered to produce multiple effector molecules, at least two of which modulate different tumor-mediated immunosuppressive mechanisms. In some embodiments, an eosinophil is engineered to produce multiple effector molecules, at least two of which modulate different tumor-mediated immunosuppressive mechanisms. In some embodiments, a basophil is engineered to produce multiple effector molecules, at least two of which modulate different tumor-mediated immunosuppressive mechanisms. In some embodiments, a macrophage is engineered to produce multiple effector molecules, at least two of which modulate different tumor-mediated immunosuppressive mechanisms. In some embodiments, a neutrophil is engineered to produce multiple effector molecules, at least two of which modulate different tumor-mediated immunosuppressive mechanisms. In some embodiments, a dendritic cell is engineered to produce multiple effector molecules, at least two of which modulate different tumor-mediated immunosuppressive mechanisms.

In some embodiments, at least one of the effector molecules stimulates an immunostimulatory mechanism in the tumor microenvironment and/or inhibits an immunosuppressive mechanism in the tumor microenvironment.

In some embodiments, at least one of the effector molecules (a) stimulates T cell signaling, activity and/or recruitment, (b) stimulates antigen presentation and/or processing, (c) stimulates natural killer cell-mediated cytotoxic signaling, activity and/or recruitment, (d) stimulates dendritic cell differentiation and/or maturation, (e) stimulates immune cell recruitment, (f) stimulates pro-inflammatory macrophage signaling, activity and/or recruitment or inhibits anti-inflammatory macrophage signaling, activity and/or recruitment, (g) stimulates stroma degradation, (h) stimulates immunostimulatory metabolite production, (i) stimulates Type I interferon signaling, (j) inhibits negative costimulatory signaling, (k) inhibits pro-apoptotic signaling of anti-tumor immune cells, (l) inhibits T regulatory ($T_{reg}$) cell signaling, activity and/or recruitment, (m) inhibits tumor checkpoint molecules, (n) stimulates stimulator of interferon genes (STING) signaling, (o) inhibits myeloid-derived suppressor cell signaling, activity and/or recruitment, (p) degrades immunosuppressive factors/metabolites, (q) inhibits vascular endothelial growth factor signaling, and/or (r) directly kills tumor cells.

Methods

Also provided herein are methods that include culturing the engineered MSCs (or other engineered immune cell) of the present disclosure. Methods of culturing MSCs are known. In some embodiments, MSCs are culture in growth medium (e.g., MSCGM human Mesenchymal Stem Cell Growth BULLETKIT™ Medium (serum containing), THERAPEAK™ MSCGM-CD™ Mesenchymal Stem Cell Chemically Defined Medium (serum free), or RoosterBio xeno-free MSC media). Methods of culturing other cells, such as immune cells, are known to those skilled in the art.

Further provided herein are methods that include delivering, or administering, to a subject (e.g., a human subject) engineered cells as provided herein to produce in vivo at least one effector molecule produced by the cells. In some embodiments, the cells are administered via intravenous, intraperitoneal, intratracheal, subcutaneous, intratumoral, oral, anal, intranasal (e.g., packed in a delivery particle), or arterial (e.g., internal carotid artery) routes. Thus, the cells may be administered systemically or locally (e.g., to a TME).

The engineered cells or polynucleotides described herein can be in a composition containing a pharmaceutically acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Some methods comprise selecting a subject (or patient population) having a tumor (or cancer) and treating that subject with engineered cells.

The engineered cells of the present disclosure may be used, in some instances, to treat cancer, such as ovarian cancer. Other cancers are described herein. For example, the engineered cells may be used to treat bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and/or uterine tumors.

The methods provided herein also include delivering a preparation of engineered cells, such as engineered cells. A preparation, in some embodiments, is a substantially pure preparation, containing, for example, less than 5% (e.g., less than 4%, 3%, 2%, or 1%) of cells other than cells. A preparation may comprise $1\times10^5$ cells/kg to $1\times10^7$ cells/kg, such as engineered cells.

The methods provided herein also include delivering a composition in vivo capable of producing the engineered cells described herein, such as delivering a lentivirus in vivo. Other in vivo delivery mechanisms and systems can also be used, including those known for use in human therapy, such as viral delivery systems (e.g., retroviral or adenoviral systems), transposons (e.g., Sleeping Beauty and PiggyBac transposon systems), integrated using PhiC31 into genomic pseudosites, or using nucleases, such as zinc fingers (ZFs), clustered regularly interspaced short palindromic repeats (CRISPR), or transcription activator-like effector nucleases (TALENs).

TABLE 6

Sequences encoding exemplary effector molecules

IL12 (Human) (SEQ ID NO: 56)

ATGTGCCATCAGCAGCTTGTCATATCTTGGTTTTCACTTGTATTCCTGGCCAGCCCTTTGGTTGCG
ATCTGGGAGCTCAAGAAGGATGTGTACGTTGTAGAGCTGGACTGGTACCCCGATGCTCCCGGTG
AGATGGTCGTTTTGACATGTGACACTCCAGAAGAGGACGGTATTACGTGGACTCTGGACCAGTC
CTCCGAAGTTCTTGGTTCTGGTAAGACTCTGACTATCCAGGTGAAAGAATTTGGGGATGCGGGA
CAATACACATGCCACAAGGGAGGCGAGGTGTTGTCTCATAGTTTGCTGCTTCTCCACAAGAAAG
AGGATGGAATCTGGAGCACCGACATACTCAAGGATCAAAAGGAACCCAAAAATAAGACATTTC
TGCGATGTGAGGCTAAGAACTATAGTGGCCGCTTCACTTGTTGGTGGCTGACTACCATCAGCAC
AGATCTCACGTTTTCAGTAAAAAGTAGTAGAGGTTCAAGTGATCCTCAAGGGGTAACGTGCGGT
GCTGCAACACTGTCTGCTGAACGCGTAAGAGGAGATAATAAGGAGTACGAGTATTCCGTAGAA
TGCCAAGAGGACAGTGCTTGTCCTGCGGCCGAGGAGTCTCTCCCAATAGAAGTGATGGTGGACG
CGGTGCATAAACTGAAATATGAGAACTACACAAGCAGTTTTTTTATAAGAGATATCATCAAGCC
CGATCCGCCGAAGAATTTGCAACTTAAACCGCTTAAAAACTCACGCCAGGTTGAAGTATCCTGG
GAGTATCCGGATACATGGTCAACACCACACAGCTATTTTTCCCTTACCTTCTGTGTGCAGGTCCA
AGGGAAGAGCAAAAGGGAGAAGAAGGACAGGGTATTCACTGATAAAACTTCCGGACGGTCAT
CTGCCGAAAAAACGCTAGTATATCTGTACGGGCGCAGGATAGGTACTATAGTTCTTCTTGGTCT
GAGTGGGCCTCAGTTCCGTGCTCTGGGGGAGGAAGTGGAGGAGGGTCCGGCGGTGGAAGCGGG
GGAGGGAGTCGCAACTTGCCAGTGGCTACACCAGATCCAGGCATGTTTCCATGTCTGCATCATT
CCCAGAATCTCCTGAGAGCGGTGTCAAATATGCTCCAAAAAGCGAGACAAACACTGGAATTTTA
CCCGTGTACCAGTGAGGAGATTGATCACGAGGACATAACCAAGGACAAGACCTCAACTGTAGA
AGCGTGTTTGCCGCTGGAGTTGACTAAGAATGAGTCCTGCCTCAATTCCAGAGAAACTTCATTC
ATTACTAACGGCAGTTGTCTTGCATCCCGGAAAACGTCCTTTATGATGGCCCTTTGCCTTAGTTC
AATTTACGAGGATCTTAAAATGTATCAAGTGGAGTTTAAAACCATGAATGCTAAACTTCTTATG
GACCCCAAACGACAAATTTTTCTGGATCAGAATATGCTTGCCGTGATAGACGAACTCATGCAGG
CGCTTAATTTTAACTCCGAAACAGTTCCACAAAAATCTAGCCTTGAAGAACCTGATTTTTATAAA
ACGAAGATTAAACTGTGTATCCTGCTGCATGCCTTTCGCATCCGAGCTGTCACAATCGATAGGG
TTATGTCCTACCTTAACGCGAGCtaG

IL 12p70 (Human; codon optimized; bold denotes signal
sequence) (SEQ ID NO: 57)

**ATGTGCCATCAGCAACTCGTCATCTCCTGGTTCTCCCTTGTGTTCCTCGCTTCCCCTCTGGTC
GCC**ATTTGGGAACTGAAGAAGGACGTCTACGTGGTCGAGCTGGATTGGTACCCGGACGCCCC
TGGAGAAATGGTCGTGCTGACTTGCGATACGCCAGAAGAGGACGGCATAACCTGGACCCTGG
ATCAGAGCTCCGAGGTGCTCGGAAGCGGAAAGACCCTGACCATTCAAGTCAAGGAGTTCGGC
GACGCGGGCCAGTACACTTGCCACAAGGGTGGCGAAGTGCTGTCCCACTCCCTGCTGCTGCT
GCACAAGAAGAGGATGGAATCTGGTCCACTGACATCCTCAAGGACCAAAAAGAACCGAAGA
ACAAGACCTTCCTCCGCTGCGAAGCCAAGAACTACAGCGGTCGGTTCACCTGTTGGTGGCTG
ACGACAATCTCCACCGACCTGACTTTCTCCGTGAAGTCGTCACGGGGATCAAGCGATCCTCAG
GGCGTGACCTGTGGAGCCGCCACTCTGTCCGCCGAGAGAGTCAGGGGAGCAACAAGGAAT
ATGAGTACTCCGTGGAATGCCAGGAGGACAGCGCCTGCCCTGCCGCGGAAGAGTCCCTGCC
TATCGAGGTCATGGTCGATGCCGTGCATAAGCTGAAATACGAGAACTACACTTCCTCCTTCTTT
ATCCGCGACATCATCAAGCCTGACCCCCCCAAGAACTTGCAGCTGAAGCCACTCAAGAACTCC
CGCCAAGTGGAAGTGTCTTGGGAATATCCAGACACTTGGAGCACCCCGCACTCATACTTCTCG
CTCACTTTCTGTGTGCAAGTCAGGGAAAGTCCAAACGGGAGAAGAAAGACCGGGTGTTCAC
CGACAAAACCTCCGCCACTGTGATTTGTCGGAAGAACGCGTCAATCAGCGTCCGGGCGCAGG
ATAGATACTACTCGTCCTCCTGGAGCGAATGGGCCAGCGTGCCTTGTTCCGGTGGCGGATCA
GGCGGAGGTTCAGGAGGAGGCTCCGGAGGAGGTTCCCGGAACCTCCCTGTGGCAACCCCCG
ACCCTGGAATGTTCCCGTGCCTACACCACTCCCAAAACCTCCTGAGGGCTGTGTCGAACATGT
TGCAGAAGGCCCGCCAGACCCTTGAGTTCTACCCCTGCACCTCGGAAGAAATTGATCACGAG
GACATCACCAAGGACAAGACCTCGACCGTGGAAGCCTGCCTGCCGCTGGAACTGACCAAGAA
CGAATCGTGTCTGAACTCCCGCGAGACAAGCTTTATCACTAACGGCAGCTGCCTGGCGTCGA
GAAAGACCTCATTCATGATGGCGCTCTGTCTTTCCTCGATCTACGAAGATCTGAAGATGTATCA
GGTCGAGTTCAAGACCATGAACGCCAAGCTGCTCATGGACCCGAAGCGGCAGATCTTCCTGG
ACCAGAATATGCTCGCCGTGATTGATGAACTGATGCAGGCCCTGAATTTCAACTCCGAGACTG
TGCCTCAAAAGTCCAGCCTGGAAGAACCGGACTTCTACAAGACCAAGATCAAGCTGTGCATCC
TGTTGCACGCTTTCCGCATTCGAGCCGTGACCATTGACCGCGTGATGTCCTACCTGAACGCCA
GT

IL12 (Mouse) (SEQ ID NO: 58)

ATGTGTCCACAGAAGCTGACAATAAGTTGGTTTGCCATTGTCCTCCTGGTGAGCCCACTCATGGC
AATGTGGGAACTCGAAAAGGATGTCTACGTGGTAGAAGTAGATTGGACTCCAGACGCGCCAGG
GGAGACAGTGAATTTGACATGTGACACACCAGAAGAAGATGACATTACATGGACATCTGACCA
ACGCCATGGCGTAATAGGGAGTGGGAAAAACACTCACGATCACAGTTAAAGAGTTCTTGGATGCT
GGTCAATATACTTGCCATAAAGGCGGCGAGACACTCAGCCACTCACATTTGCTTTTGCATAAAA
AAGAGAATGGCATTTGGAGCACTGAAATACTTAAGAACTTAAGAACAAGACATTTCTCAAGTG
TGAGGCCCCTAATTACAGCGGCAGGTTCACGTGCTCATGGCTGGTCCAGCGCAACATGGACCTC
AAGTTTAACATAAAATCTTCTTCCTCTTCACCTGACTCCAGAGCTGTTACTTGCGGCATGGCTTC
TCTGAGCGCAGAAAAGTAACGTTGGATCAAAGAGACTACGAAAGTACTCTGTTTCTTGTCAA
GAGGATGTTACGTGCCCGACGCCGAAGAAACGCTTCCAATTGAACTCGCGTTGGAAGCTCGCC
AACAAAACAAGTATAAAACTACAGTACAAGCTTCTTTATACGGGATATAATTAAACCCGATCC
CCCCAAGAACTTGCAAATGAAACCACTTAAGAACAGCCAGGTGGAAGTTTCCTGGGAGTATCCA
GACTCATGGAGTACTCCTCACAGCTATTTTTCTCTGAAATTCTTTGTAAGGATACAACGGAAGAA
AGAGAAGATGAAAGAGACCGAGGAGGGTTGTAATCAGAAGGGAGCGTTTCTCGTGGAGAAAAC
GTCTACCGAAGTCCAATGTAAAGGTGGCAATGTGTGCGTCCAAGCTCAGGATAGACTCTATAAT
TCAAGTTGCTCCAAGTGGGCCTGTGTTCCATGCCGCGTTCGGAGCGGGGGAGGTAGCGGAGGAG

TABLE 6-continued

Sequences encoding exemplary effector molecules

```
GTAGTGGGGGTGGGTCAGGAGGAGGGAGTCGAGTTATCCCGGTGTCAGGCCCCGCACGCTGCTT
GAGCCAGAGTCGCAACCTCCTTAAGCAACAAGATGACATGGTGAAAACAGCACGCGAAAAGCT
TAAACACTACTCTTGTACGGCGGAGGATATTGATCACGAGGATATTACCCGAGACCAAACTAGC
ACTTTGAAAACCTGTCTGCCCCTTGAACTTCATAAAAATGAGAGCTGTCTGGCTACACGAGAGA
CGTCAAGTACGACTAGGGGCAGCTGTCTCCCGCCGCAAAAGACAAGCCTCATGATGACGCTCTG
TTTGGGTTCCATTTACGAGGACTTGAAAATGTATCAAACGGATTCCAGGCTATAAATGCGGCG
TTGCAGAACCATAACCATCAACAAATTATACTTGATAAAGGCATGTTGGTGGCGATTGATGAAC
TCATGCAGAGTCTCAATCACAACGGGGAAACGTTGAGACAGAAACCCCCAGTCGGTGAAGCGG
ACCCATATCGAGTAAAAATGAGCTCTGCATTCTGCTTCACGCATTCAGCACTAGAGTTGTTACC
ATCAACCGGGTAATGGGATATCTCTCCAGTGCGtaG
```

IL21 (Human; codon optimized; bold denotes signal sequence)
(SEQ ID NO: 59)

```
ATGGAACGCATTGTGATCTGCCTGATGGTCATCTTCCTGGGCACCTTAGTGCACAAGTCGAG
CAGCCAGGGACAGGACAGGCACATGATTAGAATGCGCCAGCTCATCGATATCGTGGACCAGT
TGAAGAACTACGTGAACGACCTGGTGCCCGAGTTCCTGCCGGCCCCCGAAGATGTGGAAACC
AATTGCGAATGGTCGGCATTTTCCTGCTTTCAAAAGGCACAGCTCAAGTCCGCTAACACCGGG
AACAACGAACGGATCATCAACGTGTCCATCAAAAAGCTGAAGCGGAAGCCTCCCTCCACCAAC
GCCGGACGGAGGCAGAAGCATAGGCTGACTTGCCCGTCATGCGACTCCTACGAGAAGAAGC
CGCCGAAGGAGTTCCTGGAGCGGTTCAAGTCGCTCCTGCAAAAGATGATTCATCAGCACCTG
TCCCTCCCGGACTCATGGGTCTGAGGATTCA
```

IL12p70_T2A_IL21 (Human; codon optimized; bold denotes
signal sequences) (SEQ ID NO: 60)

```
ATGTGCCATCAGCAACTCGTCATCTCCTGGTTCTCCCTTGTGTTCCTCGCTTCCCCTCTGGTC
GCCATTTGGGAACTGAAGAAGGACGTCTACGTGGTCGAGCTGGATTGGTACCCGGACGCCCC
TGGAGAAATGGTCGTGCTGACTTGCGATACGCCAGAAGAGGACGGCATAACCTGGACCCTGG
ATCAGAGCTCCGAGGTGCTCGGAAGCGGAAAGACCCTGACCATTCAAGTCAAGGAGTTCGGC
GACGCGGGCCAGTACACTTGCCACAAGGGTGGCGAAGTGCTGTCCCACTCCCTGCTGCTGCT
GCACAAGAAAGAGGATGGAATCTGGTCCACTGACATCCTCAAGGACCAAAAGAACCGAAGA
ACAAGACCTTCCTCCGCTGCGAAGCCAAGAACTACAGCGGTCGGTTCACCTGTTGGTGGCTG
ACGACAATCTCCACCGACCTGACTTTCTCCGTGAAGTCGTCACGGGGATCAAGCGATCCTCAG
GGCGTGACCTGTGGAGCCGCCACTCTGTCCGCCGAGAGAGTCAGGGGAGACAACAAGGAAT
ATGAGTACTCCGTGGAATGCCAGGAGGACAGCGCCTGCCCTGCCGCGGAAGAGTCCCTGCC
TATCGAGGTCATGGTCGATGCCGTGCATAAGCTGAAATACGAGAACTACACTTCCTCCTTCTTT
ATCCGCGACATCATCAAGCCTGACCCCCCCAAGAACTTGCAGCTGAAGCCACTCAAGAACTCC
CGCCAAGTGGAAGTGTCTTGGGAATATCCAGACACTTGGAGCACCCCGCACTCATACTTCTCG
CTCACTTTCTGTGTGCAAGTGCAGGGAAAGTCCAAACGGGAGAAGAAAGACCGGGTGTTCAC
CGACAAAACCTCCGCCACTGTGATTTGTCGGAAGAACGCGTCAATCAGCGTCCGGGCGCAGG
ATAGATACTACTCGTCCTCCTGGAGCGAATGGGCCAGCGTGCCTTGTTCCGGTGGCGGATCA
GGCGGAGGTTCAGGAGGAGGCTCCGGAGGAGGTTCCCGGAACCTCCCTGTGGCAACCCCCG
ACCCTGGAATGTTCCCGTGCCTACACCACTCCCAAAACCTCCTGAGGGCTGTGTCGAACATGT
TGCAGAAGGCCCGCCAGACCCTTGAGTTCTACCCCTGCACCTCGGAAGAAATTGATCACGAG
GACATCACCAAGGACAAGACCTCGACCGTGGAAGCCTGCCTGCCGCTGGAACTGACCAAGAA
CGAATCGTGTCTGAACTCCCGCGAGACAAGCTTTATCACTAACGGCAGCTGCCTGGCGTCGA
GAAAGACCTCATTCATGATGGCGCTCTGTCTTTCCTCGATCTACGAAGATCTGAAGATGTATCA
GGTCGAGTTCAAGACCATGAACGCCAAGCTGCTCATGGACCCGAAGCGGCAGATCTTCCTGG
ACCAGAATATGCTCGCCGTGATTGATGAACTGATGCAGGCCCTGAATTTCAACTCCGAGACTG
TGCCTCAAAAGTCCAGCCTGGAAGAACCGGACTTCTACAAGACCAAGATCAAGCTGTGCATCC
TGTTGCACGCTTTCCGCATTCGAGCCGTGACCATTGACCGCGTGATGTCCTACCTGAACGCCA
GTAGACGGAAACGCGGAAGCGGAGAGGGCAGAGGCTCGCTGCTTACATGCGGGGACGTGGA
AGAGAACCCCGGTCCGATGGAACGCATTGTGATCTGCCTGATGGTCATCTTCCTGGGCACCT
TAGTGCACAAGTCGAGCAGCCAGGGACAGGACAGGCACATGATTAGAATGCGCCAGCTCAT
CGATATCGTGGACCAGTTGAAGAACTACGTGAACGACCTGGTGCCCGAGTTCCTGCCGGCCC
CCGAAGATGTGGAAACCAATTGCGAATGGTCGGCATTTTCCTGCTTTCAAAAGGCACAGCTCA
AGTCCGCTAACACCGGGAACAACGAACGGATCATCAACGTGTCCATCAAAAAGCTGAAGCGG
AAGCCTCCCTCCACCAACGCCGGACGGAGGCAGAAGCATAGGCTGACTTGCCCGTCATGCGA
CTCCTACGAGAAGAAGCCGCCGAAGGAGTTCCTGGAGCGGTTCAAGTCGCTCCTGCAAAAGA
TGATTCATCAGCACCTGTCCTCCCGGACTCATGGGTCTGAGGATTCA
```

IL-12 2A CCL21a (Human) (SEQ ID NO: 61)

```
ATGTGCCATCAGCAGCTTGTCATATCTTGGTTTTCACTTGTATTCCTGGCCAGCCCTTTGGTTGCG
ATCTGGGAGCTCAAGAAGGATGTGTACGTTGTAGAGCTGGACTGGTACCCCGATGCTCCCGGTG
AGATGGTCGTTTTGACATGTGACACTCCAGAAGAGGACGGTATTACGTGGACTCTGGACCAGTC
CTCCGAAGTTCTTGGTTCTGGTAAGACTCTGACTATCCAGGTGAAAGAATTTGGGGATGCGGGA
CAATACACATGCCACAAGGGAGGCGAGGTGTTGTCTCATAGTTTGCTGCTTCTCCACAAGAAAG
AGGATGGAATCTGGAGCACCGACATACTCAAGGATCAAAAGGAACCCAAAAATAAGACATTTC
TGCGATGTGAGGCTAAGAACTATAGTGGCCGCTTCACTTGTTGGTGGCTGACTACCATCAGCAC
AGATCTCACGTTTTCAGTAAAAAGTAGTAGAGGTTCAAGTGATCCTCAAGGGGTAACGTGCGGT
GCTGCAACACTGTCTGCTGAACGCGTAAGAGGAGATAATAAGGAGTACGAGTATTCCGTAGAA
TGCCAAGAGGACAGTGCTTGTCCTGCGGCCGAGGAGTCTCTCCCAATAGAAGTGATGGTGGACG
CGGTGCATAAACTGAAATATGAGAACTACACAAGCAGTTTTTTTATAAGAGATATCATCAAGCC
CGATCCGCCGAAGAATTTGCAACTTAAACCGCTTAAAAACTCACGCCAGGTTGAAGTATCCTGG
GAGTATCCGGATACATGGTCAACACCACACAGCTATTTTCCCTTACTTCTGTGTGCAGGTCCA
AGGGAAGAGCAAAAGGGAGAAGAAGGACAGGGTATTCACTGATAAAACTTCCGCGACGGTCAT
```

TABLE 6-continued

Sequences encoding exemplary effector molecules

```
CTGCCGAAAAAACGCTAGTATATCTGTACGGGCGCAGGATAGGTACTATAGTTCTTCTTGGTCT
GAGTGGGCCTCAGTTCCGTGCTCTGGGGGAGGAAGTGGAGGAGGGTCCGGCGGTGGAGCGGG
GGAGGGAGTCGCAACTTGCCAGTGGCTACACCAGATCCAGGCATGTTTCCATGTCTGCATCATT
CCCAGAATCTCCTGAGAGCGGTGTCAAATATGCTCCAAAAAGCGAGACAAACACTGGAATTTTA
CCCGTGTACCAGTGAGGAGATTGATCACGAGGACATAACCAAGGACAAGACCTCAACTGTAGA
AGCGTGTTTGCCGCTGGAGTTGACTAAGAATGAGTCCTGCCTCAATTCCAGAGAAACTTCATTC
ATTACTAACGGCAGTTGTCTTGCATCCCGGAAAACGTCCTTTATGATGGCCCTTTGCCTTAGTTC
AATTTACGAGGATCTTAAAATGTATCAAGTGGAGTTTAAAACCATGAATGCTAAACTTCTTATG
GACCCCAAACGACAAATTTTTCTGGATCAGAATATGCTTGCCGTGATAGACGAACTCATGCAGG
CGCTTAATTTTAACTCCGAAACAGTTCCACAAAAATCTAGCCTTGAAGAACCTGATTTTTATAAA
ACGAAGATTAAACTGTGTATCCTGCTGCATGCCTTTCGCATCCGAGCTGTCACAATCGATAGGG
TTATGTCCTACCTTAACGCGAGCCGGCGCAAGAGGGGTTCCGGAGAGGGAAGGGGTAGTCTGCT
CACCTGCGGCGATGTTGAAGAAAATCCTGGTCCCATGGCGCAAAGTCTGGCTCTTTCACTCCTG
ATCCTGGTCTTGGCCTTCGGGATTCCGAGGACCCAAGGAAGTGATGGTGGCGCCCAAGATTGTT
GCCTTAAATACAGCCAGCGGAAAATACCCGCGAAAGTGGTCAGGAGTTATAGAAAACAGGAGC
CTTCCCTGGGTTGTAGTATCCCCGCCATACTTTTCCTCCCGAGAAAACGGAGCCAGGCCGAACT
GTGCGCTGACCCTAAGGAACTTTGGGTGCAACAACTTATGCAACACCTGGATAAGACACCTTCT
CCTCAAAAGCCAGCTCAGGGCTGCCGAAAAGATAGAGGCGCCTCAAAAACCGGAAAAAGGGC
AAAGGTTCTAAAGGATGTAAGCGGACTGAACGCTCTCAAACGCCTAAAGGGCCGtaG
```

IL-12 2A CCL21a (Mouse) (SEQ ID NO: 62)

```
ATGTGTCCACAGAAGCTGACAATAAGTTGGTTTGCCATTGTCCTCCTGGTGAGCCCACTCATGGC
AATGTGGGAACTCGAAAAGGATGTCTACGTGGTAGAAGTAGATTGGACTCCAGACGCGCCAGG
GGAGACAGTGAATTTGACATGTGACACACCAGAAGAAGATGACATTACATGGACATCTGACCA
ACGCCATGGCGTAATAGGGAGTGGGAAAACACTCACGATCACAGTTAAAGAGTTCTTGGATGCT
GGTCAATATACTTGCCATAAAGGCGGCGAGACACTCAGCCACTCACATTTGCTTTTGCATAAAA
AAGAGAATGGCATTTGGAGCACTGAAATACTTAAGAACTTTAAGAACAAGCATTTCTCAAGTG
TGAGGCCCCTAATTACAGCGGCAGGTTCACGTGCTCATGGCTGGTCCAGCGCAACATGGACCTC
AAGTTTAACATAAAATCTTCTTCCTCTTCACCTGACTCCAGAGCTGTTACTTGCGGCATGGCTTC
TCTGAGCGCAGAAAAAGTAACGTTGGATCAAAGAGACTACGAAAAGTACTCTGTTTCTTGTCAA
GAGGATGTTACGTGCCCGACGGCCGAAGAAACGCTTCCAATTGAACTCGCGTTGGAAGCTCGCC
AACAAAACAAGTATGAAAACTACAGTACAAGCTTCTTTATACGGGATATAATTAAACCCGATCC
CCCCAAGAACTTGCAAATGAAACCACTTAAGAACAGCCAGGTGGAAGTTTCCTGGGAGTATCCA
GACTCATGGAGTACTCCTCACAGCTATTTTTCTCTGAAATTCTTTGTAAGGATACAACGGAAGAA
AGAAGAAGATGAAAGAGACCGAGGAGGGTTGTAATCAGAAGGGAGCGTTTCTCGTGGAGAAAAC
GTCTACCGAAGTCCAATGTAAAGGTGGCAATGTGTGCGTCCAAGCTCAGGATAGATACTATAAT
TCAAGTTGCTCCAAGTGGGCCTGTGTTCCATGCCGCGTTCGGAGCGGGGAGGTAGCGGAGGAG
GTAGTGGGGTGGGTCAGGAGGAGGGAGTCGAGTTATCCCGGTGTCAGGCCCCGCACGCTGCTT
GAGCCAGAGTCGCAACCTCCTTAAGCAACAGATGACATGGTGAAACAGCACGCGAAAAGCT
TAAACACTACTCTTGTACGGCGGAGGATATTGATCACGAGGATATTACCCGAGACCAAACTAGC
ACTTTGAAAACCTGTCTGCCCCTTGAACTTCATAAAAATGAGAGCTGTCTGGCTACACGAGAGA
CGTCAAGTACGACTAGGGGCAGCTGTCTCCCGCCGCAAAAGACAAGCCTCATGATGACGCTCTG
TTTGGGTTCCATTTACGAGGACTTGAAAATGTATCAAACGGAGTTCCAGGCTATAAATGCGGCG
TTGCAGAACCATAACCATCAACAAATTATACTTGATAAAGGCATGTTGGTGGCGATTGATGAAC
TCATGCAGAGTCTCAATCACAACGGGGAAACGTTGAGACAGAAACCCCCAGTCGGTGAAGCGG
ACCCATATCGAGTAAAAATGAAGCTCTGCATTCTGCTTCACGCATTCAGCACTAGAGTTGTTACC
ATCAACCGGGTAATGGGATATCTCTCCAGTGCGCGGCGCAAGAGGGTTCCGGAGGGGAAGG
GGTAGTCTGCTCACCTGCGGCGATGTTGAAGAAAATCCTGGTCCCATGGCGCAAATGATGACCC
TTTCCCTGCTGAGTCTTGTCCTCGCGCTCTGCATCCCGTGGACGCAGGGGTCTGATGGGGGGGC
CAAGACTGTTGCCTGAAGTATTCACAAAAAAAGATACCGTACTCTATTGTCAGAGGGTACAGGA
AGCAAGAACCTCCTTGGGTTGCCCTATACCAGCAATTCTTTTCTCCCCACGCAAGCATTCCAA
CCAGAACTGTGTGCGAACCCCGAGGAGGGTTGGGTACAGAACTTGATGCGAAGGCTTGACCAG
CCCCCAGCCCCTGGCAAGCAGTCACCTGGGTGCAGAAAAAACAGAGGTACTTCAAAGAGCGGC
AAGAAAGGCAAAGGGAGTAAAGGATGTAAAAGAACGGAGCAGACCCAGCCTTCACGAGGCtaG
```

CCL21a 2A IL-12 (Mouse) (SEQ ID NO: 63)

```
ATGGCGCAAATGATGACCCTTTCCCTGCTGAGTCTTGTCCTCGCGCTCTGCATCCCGTGGACGCA
GGGGTCTGATGGGGGGGCCAAGACTGTTGCCTGAAGTATTCACAAAAAAAGATACCGTACTCT
ATTGTCAGAGGGTACAGGAAGCAAGAACCCTCCTTGGGTTGCCCTATACCAGCAATTCTTTTCTC
CCCACGCAAGCATTCCAAACCAGAACTGTGTGCGAACCCCGAGGAGGGTTGGGTACAGAACTT
GATGCGAAGGCTTGACCAGCCCCCAGCCCCTGGCAAGCAGTCACCTGGGTGCAGAAAAAACAG
AGGTACTTCAAAGAGCGGCAAGAAAGGCAAAGGGAGTAAAGGATGTAAAAGAACGGAGCAGA
CCCAGCCTTCACGAGGCCGGCGCAAGAGGGGTTCCGGAGAGGGAAGGGGTAGTCTGCTCACCT
GCGGCGATGTTGAAGAAAATCCTGGTCCCATGTGTCCACAGAAGCTGACAATAAGTTGGTTTGC
CATTGTCCTCCTGGTGAGCCCACTCATGGCAATGTGGGAACTCGAAAAGGATGTCTACGTGGTA
GAAGTAGATTGGACTCCAGACGCGCCAGGGGAGACAGTGAATTTGACATGTGACACACCAGAA
GAAGATGACATTACATGGACATCTGACCAACGCCATGGCGTAATAGGGAGTGGGAAAACACTC
ACGATCACAGTTAAAGAGTTCTTGGATGCTGGTCAATATACTTGCCATAAAGGCGGCGAGACAC
TCAGCCACTCACATTTGCTTTTGCATAAAAAAGAGAATGGCATTTGGAGCACTGAAATACTTAA
GAACTTTAAGAACAAGCATTTCTCAAGTGTGAGGCCCCTAATTACAGCGGCAGGTTCACGTGC
TCATGGCTGGTCCAGCGCAACATGGACCTCAAGTTTAACATAAAATCTTCTTCCTCTTCACCTGA
CTCCAGAGCTGTTACTTGCGGCATGGCTTCTCTGAGCGCAGAAAAGTAACGTTGGATCAAAGA
GACTACGAAAGTACTCTGTTTCTTGTCAAGAGGATGTTACGTGCCCGACGGCCGAAGAAACGC
TTCCAATTGAACTCGCGTTGGAAGCTCGCCAACAAAACAAGTATGAAAACTACAGTACAAGCTT
CTTTATACGGGATATAATTAAACCCGATCCCCCCAAGAACTTGCAAATGAAACCACTTAAGAAC
AGCCAGGTGGAAGTTTCCTGGGAGTATCCAGACTCATGGAGTACTCCTCACAGCTATTTTTCTCT
```

TABLE 6-continued

Sequences encoding exemplary effector molecules

```
GAAATTCTTTGTAAGGATACAACGGAAGAAAGAGAAGATGAAAGAGACCGAGGAGGGTTGTAA
TCAGAAGGGAGCGTTTCTCGTGGAGAAAACGTCTACCGAAGTCCAATGTAAAGGTGGCAATGT
GTGCGTCCAAGCTCAGGATAGATACTATAATTCAAGTTGCTCCAAGTGGGCCTGTGTTCCATGC
CGCGTTCGGAGCGGGGGAGGTAGCGGAGGAGGTAGTGGGGGTGGGTCAGGAGGAGGGAGTCG
AGTTATCCCGGTGTCAGGCCCCGCACGCTGCTTGAGCCAGAGTCGCAACCTCCTTAAGACAACA
GATGACATGGTGAAAACAGCACGCGAAAAGCTTAAACACTACTCTTGTACGGCGGAGGATATT
GATCACGAGGATATTACCCGAGACCAAACTAGCACTTTGAAAACCTGTCTGCCCCTTGAACTTC
ATAAAAATGAGAGCTGTCTGGCTACACGAGAGACGTCAAGTACGACTAGGGGCAGCTGTCTCC
CGCCGCAAAAGACAAGCCTCATGATGACGCTCTGTTTGGGTTCCATTTACGAGGACTTGAAAAT
GTATCAAACGGAGTTCCAGGCTATAAATGCGGCGTTGCAGAACCATAACCATCAACAAATTATA
CTTGATAAAGGCATGTTGGTGGCGATTGATGAACTCATGCAGAGTCTCAATCACAACGGGGAAA
CGTTGAGACAGAAACCCCCAGTCGGTGAAGCGGACCCATATCGAGTAAAAATGAAGCTCTGCA
TTCTGCTTCACGCATTCAGCACTAGAGTTGTTACCATCAACCGGGTAATGGGATATCTCTCCAGT
GCGtaG
```

IL7 (Mouse) (SEQ ID NO: 64)

```
ATGTTTCATGTGTCCTTCAGGTACATATTTGGTATCCCACCACTTATATTGGTGCTCTTGCCTGTA
ACCAGCTCTGAATGTCATATAAAAGACAAGGAGGGCAAAGCATACGATCTCGTATTGATGATCT
CAATCGATGAACTTGACAAGATGACAGGGACCGATTCTAATTGTCCAAATAACGAGCCAAACTT
CTTTCGGAAACACGTGTGTGATGATACAAAAGAAGCTGCTTTTCTTAACAGAGCTGCCAGAAAA
CTCAAGCAGTTCCTCAAGATGAATATATCCGAGGAATTTAACGTGCATCTCCTCACAGTATCTCA
GGGAACTCAAACCCTTGTAAACTGCACTTCTAAGGAGGAAGAATGTCAAAGAGCAGAAGAA
AAATGATGCATGTTTTTTGAAACGGCTGTTGAGGGAGATCAAAACATGCTGGAATAAAATCCTC
AAGGGCTCAATTtaG
```

IL15 (Human) (SEQ ID NO: 65)

```
ATGGAAACAGACACATTGCTGCTTTGGGTATTGTTGCTCTGGGTGCCTGGATCAACAGGAAACT
GGGTAAACGTAATTTCAGATCTGAAGAAGATCGAGGACCTTATTCAATCCATGCACATCGATGC
CACTCTCTACACCGAAAGCGACGTTCACCCATCTTGCAAGGTGACCGCTATGAAATGTCAGTTG
TTGGAACTTCAGGTAATTTCTCTGGAGAGCGGCGATGCCTCAATACATGACACCGTTGAAAATC
TTATCATCCTTGCTAATGATTCACTCTCTAGTAATGGGAACGTAACAGAGAGCGGGTGTAAGGA
GTGTGAAGAACTGGAGGAGAAAAACATTAAGGAATTTTTGCAGTCATTCGTCCATATAGTGCAA
ATGTTCATAAACACTTCCAGAAGAAAGCGAGGCTCTGGGGAGGGGCGAGGCTCTCTGCTGACCT
GTGGGGATGTAGAAGAGAATCCAGGTCCCATGGACCGGCTGACCAGCTCATTCCTGCTTCGAT
TGTGCCAGCCTACGTGCTCTCCATCACATGTCCTCCCCCAATGAGCGTCGAGCATGCTGACATCT
GGGTGAAGTCATACTCCTTGTACAGCAGAGAGAGATACATTTGTAATTCCGGATTCAAGCGCAA
GGCCGGCACCTCCTCTCTGACAGAGTGCGTCCTTAACAAAGCAACCAACGTAGCACATTGGACC
ACACCATCCTTGAAGTGCATACGAGAACCTAAATCTTGCGATAAGACTCATACTTGTCCACCTT
GTCCAGCCCCAGAACTGCTTGGCGGACCCTCAGTATTTTTGTTCCCACCAAAGCCAAAAGACAC
ACTCATGATATCCGAACTCCTGAGGTGACCTGTGTCGTTGTAGACGTTTCCCACGAAGATCCTG
AAGTAAAATTCAACTGGTACGTGGATGGGGTCGAAGTCCATAACGCCAAGACTAAACCAAGGG
AGGAACAGTATAACTCTACTTACCGAGTAGTTTCTGTGTTGACCGTGCTGCACCAGGACTGGTT
GAACGGGAAGGAGTACAAATGCAAGGTGAGCAATAAAGCTCTGCCCGCACCAATCGAAAAGAC
AATATCTAAGGCCAAGGGGCAGCCACGAGAGCCCCAGGTATACACACTGCCACCCTCACGCGA
TGAATTGACTAAGAACCAGGTTTCCCTGACCTGTCTTGTAAAAGGTTTCTACCCTTCCGACATAG
CTGTTGAGTGGGAAAGTAACGGGCAGCCAGAGAACAATTACAAGACAACTCCACCCGTTCTTG
ATAGCGATGGATCATTTTTTCTGTATTCCAAACTCACTGTCGATAAAAGTCGCTGGCAGCAAGG
CAATGTTTTTAGCTGCTCAGTCATGCACGAAGCACTGCATAATCACTACACACAAAAAAGTTTG
TCCCTTAGCCCTGGTAAGtaG
```

IL15 (Human) (SEQ ID NO: 66)

```
ATGTACTCAATGCAGTTGGCCTCCTGTGTAACATTGACCTTGGTCCTCTTGGTCAACAGCAATTG
GATCGATGTACGCTACGACTTGGAGAAGATTGAGTCCCTTATACAGAGTATACACATAGATACA
ACCTTGTATACTGACAGTGACTTCCATCCCAGCTGTAAAGTGACTGCAATGAACTGTTTTTTGTT
GGAGTTGCAAGTAATTCTGCATGAATACAGCAACATGACCCTCAATGAAACCGTTAGGAATGTC
CTTTATCTCGCAAATTCTACTCTGAGTAGCAATAAGAATGTTGCCGAAAGCGGCTGCAAGGAGT
GCGAAGAACTGGAGGAAAAAACTTTCACCGAGTTTCTCCAGAGTTTCATCAGAATTGTCCAAAT
GTTCATTAATACAAGTAGTGGTGGTGGGAGCGGGGGTGGAGGCAGTGGAGGTGGGAGCGG
AGGTGGAGGGTCCGGAGGGGGAGCCTTCAAGGCACTACTTGTCCTCCACCCGTATCCATCGAG
CACGCCGATATTCGAGTTAAAAATTATAGTGTTAATAGCAGAGAACGATACGTCTCGCAACTCAG
GGTTTAAGAGAAAGGCCGGAACTTCAACTCTCATAGAATGCGTGATTAATAAGAATACTAACGT
CGCACATTGGACTACTCCCAGTCTCAAGTGCATACGCGATCCATCTCTCGCTCATTACTCACCAG
TACCTACAGTGGTTACTCCTAAGGTGACCTCTCAGCCCGAATCACCATCTCCCAGCGCAAAAGA
GCCTGAGGCCTTTTCTCCTAAATCAGACACTGCTATGACTACAGAAACAGCCATAATGCCAGGA
AGCCGGCTGACACCATCTCAAACTACCAGCGCAGGCACAACTGGGACTGGCTCCCACAAAAGC
TCACGCGCACCAAGTCTCGCCGCAACAATGACATTGGAGCCTACAGCAGCACATCTCTTAGAA
TCACAGAAATTTCTCCCCACAGTAGCAAGATGACCAAGGTGGCAATTAGTACCAGCGTCCTTCT
TGTAGGAGCTGGAGTTGTGATGGCATTTTTGGCATGGTATATCAAAAGCAGGtaG
```

IL15 (Mouse) (SEQ ID NO: 67)

```
ATGAAGATCCTCAAGCCATACATGCGAAACACTAGTATTAGCTGTTACTTGTGTTTTCTGCTGAA
TAGTCATTTTTTGACTGAAGCAGGAATCCATGTATTTATACTCGGTTGTGTGTCTGTAGGTCTGC
CAAAGACTGAGGCTAATTGGATTGACGTGCGCTATGATCTTGAAAAAATAGAGTCCTTGATTCA
ATCAATACACATCGATACCACTCTCTACACCGACAGTGATTTCCATCCTTCCTGCAAGGTAACAG
```

TABLE 6-continued

Sequences encoding exemplary effector molecules

CTATGAATTGCTTCCTCCTGGAGCTCCAAGTCATTCTCCATGAGTACTCCAACATGACTTTGAAC
GAAACTGTAAGAAACGTATTGTATCTGGCTAATAGCACCTTGTCTAGTAACAAAAATGTGGCAG
AGAGCGGCTGCAAAGAATGTGAAGAATTGGAAGAGAAAACATTTACAGAGTTCCTGCAATCCT
TTATTCGCATCGTCCAAATGTTTATCAATACCTCTtaG

IL15 (Mouse) (SEQ ID NO: 68)

ATGTATTCCATGCAACTTGCCAGTTGTGTAACCCTTACTCTCGTCCTGCTCGTTAATTCCGCTGGT
GCTAACTGGATAGATGTTCGATACGATCTGGAAAAGATTGAGTCCCTTATCCAATCCATTCATAT
AGATACCACCCTTTATACTGACAGCGACTTCCATCCTTCTTGCAAGGTGACCGCTATGAATTGTT
TCCTGCTGGAACTCCAAGTTATTCTGCATGAATACTCTAATATGACACTTAACGAGACCGTAAG
AAATGTTCTCTATCTCGCTAATAGTACTTTGAGCTCAAATAAGAACGTGGCCGAGTCTGGGTGT
AAGGAATGCGAAGAGCTGGAAGAAAAGACATTCACCGAGTTTCTCCAGTCTTTCATACGGATTG
TGCAGATGTTTATCAACACATCAGATTACAAAGACGACGATGATAAGtaG

IL18 (Mouse) (SEQ ID NO: 69)

ATGGCAGCCATGTCTGAGGACTCTTGTGTGAACTTTAAAGAAATGATGTTCATAGACAATACAC
TCTACTTTATACCTGAGGAGAATGGAGATTTGGAATCTGACAACTTTGGCAGGCTGCATTGCAC
TACCGCAGTTATCCGAAACATCAACGATCAGGTACTGTTTGTTGATAAAAGACAACCTGTATTC
GAGGACATGACCGACATAGATCAGTCTGCCTCAGAGCCCAGATAGGCTTATCATCTATATGT
ACAAGGACAGCGAAGTACGAGGCCTGGCTGTTACACTCTCAGTCAAAGACTCTAAGATGAGCA
CCCTGTCATGCAAGAACAAAATTATCAGTTTTGAGGAGATGGACCCACCTGAAAACATAGATGA
CATTCAGTCAGACCTCATTTTTTTTCAAAAGCGGGTACCAGGACACAACAAAATGGAATTTGAA
TCATCACTCTACGAAGGACATTTCCTTGCATGCCAGAAAGAGGATGACGCATTCAAATTGATCC
TGAAAAAAAGGACGAAAATGGTGATAAATCAGTCATGTTTACATTGACCAATCTTCACCAAAG
TtaG

IL18 (Mouse) (SEQ ID NO: 70)

ATGGCTGCAATGTCTGAAGATAGCTGTGTCAACTTTAAGGAGATGATGTTCATTGATAATACTTT
GTACTTTATACCTGAAGAAAATGGAGACCTTGAGTCAGACAACTTCGGGAGACTGCACTGCACA
ACTGCCGTTATCCGAAACATAAATGATCAAGTATTGTTCGTGGACAAAAGACAACCAGTCTTTG
AGGATATGACAGACATCGACCAATCCGCATCTGAACCTCAGACTAGGCTGATCATCTATATGTA
CGCCGACTCCGAAGTAAGAGGCCTTGCTGTGACACTTAGTGTTAAGGATAGTAAGATGAGCACA
CTGTCCTGTAAGAATAAGATTATATCTTTTGAAGAGATGGACCCTCCCGAGAACATAGATGACA
TCCAGAGCGACTTGATCTTCTTTCAGAAGCGAGTGCCAGGCCATAACAAGATGGAATTTGAATC
ATCTCTTTATGAAGGCCATTTCCTCGCATGTCAAAAGGAGGACGATGCCTTCAAGCTCATTCTGA
AAAAAAAGACGAGAACGGTGATAAGAGCGTGATGTTCACTCTGACAAATCTGCACCAGTCAta
G

IL18 (Human) (SEQ ID NO: 71)

ATGTATCGCATGCAACTCCTGTCCTGCATTGCTCTGAGCTTGGCTTTGGTAACCAACTCATACTT
CGGGAAACTGGAGAGTAAACTCTCCGTAATCAGGAATCTTAATGACCAAGTATTGTTTATTGAC
CAGGGCAACCGCCCGTTGTTCGAGGATATGACTGATTCTGACTGTCGGGATAACGCTCCGAGAA
CTATCTTTATCATTTCAATGTACAAGGACAGCCAACCGCGGGGTATGGCTGTGACAATCAGTGT
CAAATGTGAGAAGATTTCCACGCTGTCCTGCGAAAACAAGATAATTTCTTTCAAAGAAATGAAC
CCCCCTGACAATATAAAGGATACAAAGAGTGATATCATCTTCTTTCAGAGGTCCGTGCCCGGCC
ACGATAATAAGATGCAATTTGAAAGTTCATCTTATGAGGGGTACTTTTTGGCATGCGAGAAAGA
AAGGGATCTCTTCAAGTTGATCCTGAAGAAGGAGGACGAATTGGGCGACCGCTCCATCATGTTC
ACAGTCCAGAAC GAGGACtaG

IL18 (Human) (SEQ ID NO: 72)

ATGTACCGCATGCAGCTCCTGAGTTGTATTGCCCTTTCCCTCGCTCTCGTTACCAATTCTTACTTC
GGTAAGCTTGCCTCTAAACTCTCTGTTATTAGGAACTTGAACGACCAAGTCCTTTTCATAGACCA
AGGGAACAGACCACTGTTTGAAGATATGACGGATAGCGATTGCCGAGATAATGCCCCTAGGAC
GATTTTTATCATTAGTATGTATGCGGACTCTCAACCGAGGGGATGGCCGTTACTATAAGTGTG
AAATGCGAGAAAATATCAACGCTCAGTTGTGAGAACAAAATCATAAGTTTCAAGGAGATGAAT
CCACCTGATAACATCAAAGACACTAAGTCTGATATTATATTTTTCCAACGAAGTGTTCCGGGAC
ACGATAACAAAATGCAATTTGAGAGCTCCTCATACGAGGGCTACTTCCTCGCGTGTGAGAAAGA
AAGGGATTTGTTTAAGCTTATCCTCAAGAAAGAGGACGAGTTGGGGGATCGGAGCATAATGTTT
ACCGTACAGAATGAGGACtaG

IL21 (Mouse) (SEQ ID NO: 73)

ATGGAGCGGACACTCGTGTGTCTTGTCGTAATTTTTCTCGGGACAGTCGCACACAAGTCCTCACC
CCAGGGTCCTGATCGCCTTCTCATACGCCTCCGACATTTGATCGACATTGTAGAGCAGCTCAAA
ATTTACGAGAATGACCTCGATCCCGAGCTTTTGAGTGCTCCCCAAGACGTTAAGGGTCATTGCG
AGCACGCAGCTTTTGCTTGCTTCCAGAAGGCCAAGTTGAAACCAAGCAACCCTGGTAATAATAA
GACTTTCATCATCGACTTGGTCGCCCAACTCCGAAGGAGGCTGCCTGCCCGGCGCGGAGGAAAA
AAACAAAAGCATATTGCAAAGTGTCCTTCATGTGATTCATACGAAAAGCGGACTCCCAAAGAGT
TCTTGGAAAGGTTGAAATGGCTTCTTCAGAAGATGATTCATCAACATTTGTCAtaG

TABLE 6-continued

Sequences encoding exemplary effector molecules

IFN-beta (Human) (SEQ ID NO: 74)

ATGACCAACAAATGCCTTTTGCAAATTGCCCTGCTTTTGTGTTTTAGCACTACCGCATTGAGCAT
GTCATATAACCTCCTCGGCTTCCTTCAGAGATCATCAAACTTTCAGTGTCAGAAACTGCTTTGGC
AACTTAATGGCAGGCTCGAATATTGTCTGAAAGATCGGATGAATTTCGACATTCCAGAAGAAAT
AAAACAGCTTCAACAATTCCAGAAAGAGGACGCCGCCCTGACTATTTACGAGATGCTCCAGAAT
ATCTTCGCCATTTTCCGGCAGGACAGCTCATCCACGGGGTGGAATGAGACTATTGTAGAAAATC
TTCTGGCTAATGTGTACCATCAAATTAATCACCTCAAAACGGTGCTTGAGGAAAAACTTGAAAA
GGAAGATTTCACACGGGGCAAGTTGATGTCCTCCCTGCACCTTAAACGATACTACGGCAGGATT
CTTCATTACTTGAAGGCTAAGGAGTATAGCCATTGCGCGTGGACAATTGTACGGGTAGAAATAC
TGCGAAACTTTTATTTCATCAACCGGCTCACTGGATACCTTAGAAATtaG

IFN-beta (Mouse) (SEQ ID NO: 75)

ATGAACAATCGGTGGATACTCCACGCCGCATTTCTCCTCTGCTTTAGCACGACGGCCCTGTCCAT
CAACTACAAACAGCTTCAGTTGCAGGAGCGGACTAACATAAGGAAGTGCCAGGAACTGCTGGA
ACAGCTTAATGGTAAAATTAATCTTACATACCGAGCTGACTTCAAAATTCCTATGGAAATGACC
GAGAAGATGCAGAAATCCTACACGGCATTCGCCATCCAGGAAATGCTCCAGAACGTATTTCTCG
TGTTCCGCAATAATTTCTCTTCTACGGGTTGGAACGAAACCATTGTTGTTAGACTGCTTGACGAA
CTGCATCAGCAAACCGTGTTCCTTAAAACCGTGCTTGAGGAGAAGCAGGAGGAGCGCCTGACTT
GGGAGATGTCTAGTACCGCACTTCACTTGAAATCCTACTACTGGCGCGTTCAGCGGTATCTGAA
GCTGATGAAGTATAACTCATACGCCTGGATGGTAGTGCGCGCAGAGATCTTCAGAAACTTTCTT
ATCATCCGGCGACTGACCCGAAACTTTCAGAATtaG

IFN-gamma (Human) (SEQ ID NO: 76)

ATGAAGTACACTAGCTATATATTGGCCTTCCAGCTTTGCATCGTATTGGGTAGCCTCGGATGCTA
TTGCCAAGACCCGTATGTCAAAGAAGCCGAAAATCTCAAAAAGTATTTCAATGCCGGACACTCA
GACGTCGCGGATAACGGTACACTGTTTCTTGGCATCCTGAAAAATTGGAAGGAAGAGAGTGAC
AGAAAAATAATGCAGTCACAAATAGTGTCCTTTTACTTTAAGCTGTTCAAAAATTTCAAGGATG
ACCAAAGTATCCAGAAGAGTGTTGAAACTATCAAAGAGGACATGAATGTGAATTCTTTAACA
GTAATAAGAAGAAGCGCGATGACTTCGAGAAACTCACTAATTACAGCGTAACGGATCTTAACGT
CCAACGCAAGGCAATCCACGAGCTTATACAGGTAATGGCTGAGCTTAGTCCCGCAGCCAAGAC
AGGGAAGAGAAAAAGGTCTCAAATGCTTTTTCGGGGCCGGCGAGCTTCACAAtaG

IFN-gamma (Mouse) (SEQ ID NO: 77)

ATGAACGCTACGCATTGCATCCTCGCACTCCAATTGTTCCTCATGGCTGTGTCAGGGTGTTACTG
TCACGGTACTGTCATAGAAAGCCTCGAATCCCTGAATAACTATTTTAACAGTAGCGGTATAGAT
GTAGAAGAAAAGTCTCTCTTTCTTGACATCTGGAGGAATTGGCAAAAGGATGGAGACATGAAG
ATTCTCCAATCTCAGATTATATCATTTTACTTGAGGCTTTTTGAGGTTCTGAAGGATAACCAGGC
GATCAGCAATAATATCAGCGTAATTGAATCTCACCTTATTACAACATTTTTCTCAAATTCCAAGG
CAAAGAAAGATGCTTTCATGTCTATCGCGAAATTTGAGGTGAACAATCCTCAGGTACAAAGGCA
AGCCTTTAACGAGCTGATTAGAGTTGTACATCAGTTGTTGCCCGAAAGTAGTCTTAGAAAACGC
AAACGGAGCCGATGCtaG

IFN-alpha (Mouse) (SEQ ID NO: 78)

ATGGCAAGGTTGTGCGCTTTTCTCATGGTACTGGCTGTGCTCTCCTATTGGCCTACTTGTTCTCTG
GGATGCGACTTGCCACAGACCCACAATCTGCGGAATAAGAGGGCTCTGACTCTGCTGGTGCAAA
TGAGACGGCTCTCTCCACTTAGCTGTTTGAAAGATAGAAAGGATTTCGGGTTCCCCCAGGAGAA
GGTGGATGCCCAGCAGATCAAGAAGGCACAGGCTATCCCCGTCCTTTCCGAGCTGACCCAGCAA
ATTTTGAACATCTTTACAAGTAAGGATAGTTCAGCTGCATGGAATACCACACTTTTGGATTCTTT
TTGTAACGATCTGCATCAGCAGCTGAACGATCTCCAGGGATGCCTGATGCAGCAAGTCGGCGTG
CAAGAATTTCCACTCACCCAGGAGGACGCTCTGCTCGCAGTGCGAAAGTATTTTCACCGAATTA
CCGTGTACCTCCGGGAGAAAAAGCATTCACCCTGCGCTTGGGAAGTAGTCAGGGCCGAAGTATG
GAGAGCCCTTAGTAGCTCCGCTAATGTACTGGGCCGGTTGCGGGAAGAGAAAtaG

CCL21 (Human) (SEQ ID NO: 79)

ATGGCGCAAAGTCTGGCTCTTTCACTCCTGATCCTGGTCTTGGCCTTCGGGATTCCGAGGACCCA
AGGAAGTGATGGTGCGCCCAAGATTGTTGCCTTAAATACAGCCAGCGGAAAATACCCGCGAA
AGTGGTCAGGAGTTATAGAAAACAGGAGCCTTCCCTGGGTTGTAGTATCCCCGCCATACTTTTC
CTCCCGAGAAAACGGAGCCAGGCCGAACTGTGCGCTGACCCTAAGGAACTTTGGGTGCAACAA
CTTATGCAACACCTGGATAAGACACCTTCTCCTCAAAAGCCAGCTCAGGGCTGCCGAAAAGATA
GAGGCGCCTCAAAAACCGGAAAAAAGGGCAAAGGTTCTAAAGGATGTAAGCGGACTGAACGCT
CTCAAACGCCTAAAGGGCCGtaG

CCL21a (Mouse) (SEQ ID NO: 80)

ATGGCGCAAATGATGACCCTTTCCCTGCTGAGTCTTGTCCTCGCGCTCTGCATCCCGTGGACGCA
GGGGTCTGATGGGGGGGCCAAGACTGTTGCCTGAAGTATTCACAAAAAAAGATACCGTACTCT
ATTGTCAGAGGGTACAGGAAGCAAGAACCCTCCTTGGGTTGCCCTATACCAGCAATTCTTTTCTC
CCCACGCAAGCATTCCAAACCAGAACTGTGTGCGAACCCCGAGGAGGGTTGGGTACAGAACTT
GATGCGAAGGCTTGACCAGCCCCCAGCCCCTGGCAAGCAGTCACCTGGGTGCAGAAAAAACAG
AGGTACTTCAAAGAGCGGCAAGAAAGGCAAAGGGAGTAAAGGATGTAAAAGAACGGAGCAGA
CCCAGCCTTCACGAGGGCtaG

TABLE 6-continued

Sequences encoding exemplary effector molecules

Tail-less CCL21 (Human) (SEQ ID NO: 81)

ATGGCGCAAAGTCTGGCTCTTTCACTCCTGATCCTGGTCTTGGCCTTCGGGATTCCGAGGACCCA
AGGAAGTGATGGTGGCGCCCAAGATTGTTGCCTTAAATACAGCCAGCGGAAAATACCCGCGAA
AGTGGTCAGGAGTTATAGAAAACAGGAGCCTTCCCTGGGTTGTAGTATCCCCGCCATACTTTTC
CTCCCGAGAAAACGGAGCCAGGCCGAACTGTGCGCTGACCCTAAGGAACTTTGGGTGCAACAA
CTTATGCAACACCTGGATAAGACACCTTCTCCTCAAAAGCCAGCTCAGGGCtaG

Tail-less CCL21 (Mouse) (SEQ ID NO: 82)

ATGGCGCAAATGATGACCCTTTCCCTGCTGAGTCTTGTCCTCGCGCTCTGCATCCCGTGGACGCA
GGGGTCTGATGGGGGGGGCCAAGACTGTTGCCTGAAGTATTCACAAAAAAAGATACCGTACTCT
ATTGTCAGAGGGTACAGGAAGCAAGAACCCTCCTTGGGTTGCCCTATACCAGCAATTCTTTTCTC
CCCACGCAAGCATTCCAAACCAGAACTGTGTGCGAACCCCGAGGAGGGTTGGGTACAGAACTT
GATGCGAAGGCTTGACCAGCCCCCAGCCCCTGGCAAGCAGTCACCTGGGtaG

CCL19 (Mouse) (SEQ ID NO: 83)

ATGGCACCCCGCGTCACACCCTTGCTTGCTTTTTCTCTGCTTGTCCTCTGGACCTTCCCCGCTCCT
ACCCTTGGAGGAGCCAATGATGCCGAGGATTGCTGCCTGAGTGTTACACAAAGGCCAATACCAG
GGAATATAGTGAAGGCATTCCGGTATCTGCTCAATGAAGATGGGTGCAGAGTCCCCGCAGTTGT
CTTTACAACATTGCGAGGTTACCAGCTTTGTGCTCCCCAGACCAGCCTTGGGTAGATCGCATTA
TTCGCCGGTTGAAGAAGAGCTCAGCAAAGAATAAGGGCAATTCCACACGGAGAAGCCCCGTCT
CCtaG

CCL19 (Mouse) (SEQ ID NO: 84)

ATGAAATCAGCAGTCCTTTTCTTGCTCGGGATTATTTTTCTGGAACAATGTGGAGTGAGGGGAA
CACTCGTAATAAGAAACGCTCGGTGCTCATGCATATCAACATCACGGGGCACTATCCACTACAA
ATCCCTGAAGGATCTGAAGCAGTTCGCCCCAAGCCCTAACTGTAACAAGACCGAAATTATCGCA
ACTCTCAAAAATGGAGATCAGACTTGTCTTGACCCAGATTCAGCAAATGTCAAGAAGCTGATGA
AAGAGTGGGAAAAGAAGATTTCACAAAAAAAAAAGCAAAAACGCGGCAAGAAACATCAAAAG
AACATGAAAAACAGGAAACCTAAGACTCCCCAGTCAAGGAGAAGATCCCGCAAGCACCtaG

CXCL11 (Mouse) (SEQ ID NO: 85)

ATGAACAGAAAAGTTACCGCTATAGCACTTGCTGCCATAATATGGGCCACCGCAGCTCAAGGGT
TCCTGATGTTCAAGCAGGGCCGATGCCTCTGCATTGGCCCTGGAATGAAGGCCGTGAAAATGGC
CGAAATAGAAAAAGCTAGTGTCATATACCCCTCTAACGGTTGCGATAAAGTCGAGGTTATAGTC
ACAATGAAAGCTCATAAACGCCAACGCTGCCTCGACCCCCGGTCTAAGCAGGCTAGGCTCATAA
TGCAAGCAATCGAGAAGAAAAACiTTCTTAGACGGCAAAACATGtaG

CXCL10 (Mouse) (SEQ ID NO: 86)

ATGAACCCATCTGCCGCCGTTATTTTCTGTCTGATACTCCTTGGGCTGAGTGGCACACAAGGCAT
ACCCCTCGCCCGCACAGTCCGGTGTAATTGTATACATATTGACGACGGCCCTGTTAGAATGCGG
GCCATCGGTAAGCTGGAGATTATACCAGCAAGCCTTAGTTGTCCCAGGGTTGAAATCATAGCAA
CTATGAAAAAAAACGACGAACAAAGATGTTTGAATCCCGAGAGCAAGACAATCAAAAACCTTA
TGAAAGCATTTAGTCAAAAACGCTCTAAACGCGCTCCAtaG

CXCL10 (Human) (SEQ ID NO: 87)

ATGAATCAGACGGCAATCCTTATATGCTGCCTTATATTCCTTACTCTCTCAGGGATACAAGGGGT
ACCACTTTCTCGGACTGTTCGCTGCACTTGCATTTCAATATCTAACCAACCTGTAAATCCGCGGA
GCCTGGAAAAATTGGAGATTATACCTGCTTCTCAATTCTGCCCTCGGGTGGAAATCATCGCCACT
ATGAAGAAGAAGGGCGAGAAAAGGTGTCTGAATCCAGAGTCAAAGGCAATCAAAAACCTGCTG
AAAGCGGTGTCAAAGGAACGGTCCAAGAGATCACCCtaG

CXCL11-CXCL10 (Mouse) (SEQ ID NO: 88)

ATGAACAGGAAAGTAACAGCCATTGCATTGGCTGCCATCATCTGGGCCACCGCAGCACAGGGTT
TTCTGATGTTTAAGCAAGGGCGCTGTCTCTGTATAGGCCCAGGCATGAAGGCCGTGAAGATGGC
AGAGATTGAGAAGGCATCTGTGATTTATCCTTCTAACGGGTGCGATAAAGTCGAAGTTATTGTG
ACAATGAAGGCACACAAACGCCAACGGTGTTTGGACCCACGATCTAAACAGGCAAGATTGATT
ATGCAAGCCATCGAGAAAAAGAACTTTCTCCGAAGGCAAAATATGATCCCTTTGGCTCGGACAG
TGCGGTGTAACTGTATTCACATCGACGATGGGCCAGTACGGATGAGAGCAATAGGAAAGCTCG
AAATCATACCCGCCTCATTGTCTTGTCCCAGGGTGGAAATAATCGCCACTATGAAAAAGAACGA
TGAACAGAGGTGTCTCAACCCAGAGAGTAAGACTATCAAGAACCTTATGAAGGCATTCAGTCA
GAAGAGGTCAAAGCGAGCACCAtaG

XCL1 (Human) (SEQ ID NO: 89)

ATGAGACTTCTCATATTGGCGCTTCTCGGGATATGTTCTCTTACGGCATACATAGTTGAGGGGGT
GGGATCTGAGGTTAGCGATAAACGAACTTGTGTTAGTCTTACAACACAGAGGCTTCCAGTCTCC
AGGATAAAAACATATCGATAACTGAGGGATCTCTCAGAGCGGTCATCTTCATAACGAAGAGG
GGCCTGAAGGTCTGTGCTGACCCACAAGCGACTTGGGTAAGGACGTTGTGCGGAGCATGGAC
AGGAAGAGCAATACTCGCAACAACATGATCCAAACCAAACCTACGGGCACCCAACAGTCAACC
AATACTGCGGTAACATTGACGGGGtaG

TABLE 6-continued

Sequences encoding exemplary effector molecules

XCL1 (Mouse) (SEQ ID NO: 90)

ATGCGCCTCCTTCTGCTGACTTTTCTGGGTGTATGTTGCCTGACACCCTGGGTCGTAGAAGGAGT
AGGAACCGAGGTTCTGGAAGAGTCCTCATGTGTAAACTTGCAGACACAACGACTCCCCGTCCAA
AAAATCAAGACCTATATAATCTGGGAGGGGGCAATGCGGGCCGTCATTTTCGTGACTAAACGAG
GTCTCAAAATCTGCGCCGACCCCGAGGCTAAGTGGGTGAAGGCAGCCATTAAGACCGTGGATG
GGAGAGCCAGCACCAGAAAGAACATGGCCGAAACAGTACCTACTGGCGCACAGCGGTCAACCT
CAACTGCTATAACCTTGACAGGAtaG m sCD40L #1 (SEQ ID NO: 91)

ATGGAGACTGACACTCTGCTTCTGTGGGTGTTGCTGCTGTGGGTGCCTGGCAGTACAGGCGATA
TGCAACGAGGTGACGAGGACCCTCAAATCGCCGCCCATGTAGTCTCTGAAGCTAATAGCAACGC
TGCATCCGTCTTGCAGTGGGCAAAGAAAGGCTACTATACTATGAAGTCCAACTTGGTAATGCTT
GAAAACGGCAAGCAGTTGACTGTCAAGAGAGAGGGACTTTATTACGTCTATACCCAAGTCACAT
TCTGTAGCAATCGAGAACCCTCCTCACAGAGGCCTTTTATAGTGGGACTCTGGCTTAAACCAAG
TAGCGGCTCTGAGCGCATACTGTTGAAAGCCGCAAACACACACAGCTCTTCCCAACTCTGCGAG
CAGCAATCCGTGCATCTCGGTGGAGTATTTGAGCTTCAAGCCGGTGCCTCAGTGTTTGTGAACGT
CACTGAGGCCTCCCAGGTCATACATCGAGTTGGGTTCAGCTCCTTCGGCTTGCTCAAGCTCtaG m sCD40L #2 (SEQ ID NO: 92)

ATGGAAACTGATACATTGCTGCTCTGGGTTTTGCTGCTCTGGGTGCCTGGGAGTACAGGCGACA
TGAGGAGGCAGTTCGAGGATCTCGTTAAGGATATTACCCTTAATAAGGAGGAGAAGAAAGAAA
ACTCTTTTGAGATGCAACGAGGGGACGAAGATCCTCAGATCGCTGCTCACGTGGTCTCTGAAGC
TAACAGCAACGCCGCTTCTGTCCTCCAGTGGGCCAAGAAAGGTTATTACACCATGAAATCAAAC
CTTGTAATGCTTGAAAACGGGAAACAGCTTACAGTGAAGAGGGAAGGTCTTTACTACGTCTATA
CCCAGGTAACCTTCTGCTCAAACAGAGAACCATCAAGCCAGAGGCCATTCATAGTGGGGCTCTG
GCTCAAACCTTCCAGTGGCAGCGAGAGAATCTTGTTGAAAGCTGCTAATACACATAGTAGTAGC
CAGCTTTGCGAGCAACAGTCAGTCCACCTCGGGGGGGTGTTTGAGTTGCAAGCAGGGGCCTCAG
TATTCGTGAATGTCACTGAGGCTTCCCAGGTAATTCACAGGGTAGGCTTTAGTTCATTCGGTTTG
CTGAAGCTTtaG m sCD40L #3 (SEQ ID NO: 93)

ATGCGAAGAATGCAGCTTCTGCTCCTTATTGCTCTGAGTCTCGCCCTTGTCACCAACTCCGGGGA
CAGAATGAAACAAATCGAGGACAAAATTGAAGAAATACTGAGTAAAATATATCACATCGAAAA
CGAAATTGCACGCATTAAGAAATTGATTGGCGAACGCACCAGTGGCGGCTCTGGTGGCACCGG
AGGTTCAGGCGGGACCGGGGGCTCTGACAAAGTCGAAGAGGAGGTTAACCTTCATGAGGACTT
TGTGTTCATCAAGAAGCTGAAACGGTGCAATAAAGGAGAAGGTCTTTGAGCCTCCTTAATTGC
GAAGAGATGCGACGACAGTTCGAGGATCTGGTTAAGGACATTACACTTAATAAGGAAGAGAAA
AAGGAGAACTCTTTCGAAATGCAGCGCGGCGATGAAGATCCCCAGATAGCCGCCCATGTCGTCT
CTGAGGCCAACTCTAACGCAGCATCCGTCCTCCAGTGGGCTAAGAAAGGATATTATACTATGAA
AAGCAATTTGGTCATGCTCGAAAACGGTAAACAGCTCACTGTTAAGAGAGAAGGCCTCTATTAC
GTATATACTCAAGTAACTTTCTGTTCTAATAGGGAACCCTCCTCTCAAAGACCTTTTATCGTAGG
ACTCTGGTTGAAACCAAGTAGCGGTAGTGAAAGGATTCTGCTCAAAGCAGCTAATACTCACTCC
AGCAGTCAACTGTGCGAACAACAAAGCGTTCACCTCGGGGGCGTCTTTGAACTTCAGGCAGGTG
CCAGTGTTTTCGTCAACGTAACAGAAGCATCCCAGGTAATTCATCGAGTAGGGTTTTCTAGCTTT
GGTTTGCTGAAGCTGtaG anti-CD40 FGK4.5 (SEQ ID NO: 94)

ATGGAAACTGATCGCCTGTTGCTCTGGGTACTTCTTCTGTGGGTGCCTGGGTCCACTGGTGACAC
TGTACTTACACAATCACCCGCTTTGGCCGTTTCTCCTGGTGAACGGGTCACAATTAGTTGCCGAG
CTTCCGATTCTGTATCTACTCTTATGCATTGGTATCAACAAAAACCTGGTCAGCAGCCAAAATTG
CTCATTTATCTTGCTAGTCACTTGGAGTCCGGCGTACCTGCTGATTCAGCGGTAGTGGGTCTGG
CACAGATTTCACTTTGACCATAGATCCCGTGGAGGCCGATGACACTGCAACCTACTATTGCCAG
CAATCCTGGAACGACCCTTGGACTTTCGGCGGCGGCACCAAGCTGGAACTCAAGCGAGCAGAT
GCTGCCCCAACCGTTAGTATATTCCCACCCTCAACCGAACAACTCGCCACAGGAGGCGCTAGTG
TCGTGTGTCTTATGAACAATTTCTATCCACGAGACATTAGCGTCAAGTGGAAAATTGATGGGAC
AGAAAGGCGAGATGGAGTTTTGGATTCAGTAACAGACCAGGATTCAAAGGATTCTACCTATAGC
ATGAGCTCCACCTTGAGCCTGACCAAAGCTGATTATGAATCTCATAACCTGTATACTTGTGAAGT
GGTGCATAAGCTTCTAGCTCACCAGTGGTTAAATCTTTTAACCGCAACGAATGTCGGCGCAAG
AGGGGTTCCGGAGAGGGAAGGGGTAGTCTGCTCACCTGCGGCGATGTTGAAGAAAATCCTGGT
CCCATGGACATTCGGCTCTCTTTGGTATTCCTGGTACTTTTTATAAAGGGGGTGCAATGTGAAGT
CCAGCTCGTGGAAAGCGGTGGGGGCCTGGTTCAGCCCGGTCGCAGCCTTAAACTTAGTTGCGCA
GCATCCGGATTTACATTTTCTGACTATAACATGGCCTGGGTTCGACAGGCACCCAAAAAGGGC
TGGAGTGGGTCGCAACTATCATATACGATGGTTCCCGGACATACTATAGAGATTCAGTGAAGGG
GCGCTTTACAATAAGCAGGGACAATGCTAAGTCTACCTTGTATCTTCAGATGGACTCCCTGAGG
AGCGAAGATACAGCAACATATTATTGTGCTACAAACCGCTGGTTGCTGCTTCATTATTCGACTA
CTGGGGTCAGGGCGTCATGGTAACTGTATCAAGCGCCGAGACCACAGCCCCTTCTGTATATCCA
TTGGCACCAGGTACTGCTCTGAAATCCAACTCAATGGTAACCCTTGGATGTCTGGTTAAGGGTT
ATTTTCCCGAGCCCGTCACAGTTACTTGGAACTCTGGGGCCCTTTCTGCGGAGTCCATACCTTT
CCCGCCGTTTTGCAGAGTGGTCTGTACACCCTTACCTCAAGCGTCACAGTTCCATCTAGCACATG
GAGCTCCCAGGCAGTAACTTGTAATGTGGCCCATCCAGCCTCCTCAACTAAGGTAGATAAAAAG
ATCGTTCCCAGAGAATGCAATCCATGTGGATGCACCGGGTCTGAGGTCAGCAGTGTGTTCATTT
TCCCACCCAAGACTAAAGATGTATTGACTATTACTCTTACACCCAAAGTAACCTGCGTGGTGGTT
GATATTAGTCAAAATGATCCCGAGGTACGGTTCTCTTGGTTTATCGACGACGTCGAAGTACATA

TABLE 6-continued

Sequences encoding exemplary effector molecules

CAGCTCAGACACACGCTCCCGAGAAACAAAGCAATTCCACTCTTAGGAGCGTGTCCGAGTTGCC
AATCGTACATAGGGATTGGCTTAATGGCAAGACCTTTAAGTGTAAGGTCAATTCAGGGGCATTC
CCCGCACCAATAGAGAAGAGTATAAGCAAACCCGAGGGGACACCCAGAGGTCCACAGGTCTAT
ACAATGGCTCCCCCCAAGGAAGAGATGACCCAAAGTCAAGTCTCAATTACATGTATGGTGAAG
GGCTTTTATCCACCCGACATATACACTGAGTGGAAGATGAATGGACAGCCCCAAGAGAATTATA
AAAACACTCCCCCTACCATGGACACCGACGGGTCCTATTTTCTTTATAGTAAATTGAACGTGAA
AAAGGAGACCTGGCAACAAGGCAACACTTTCACCTGCTCCGTTCTTCACGAGGGCCTGCATAAT
CATCATACCGAAAAGTCTCTCAGTCATTCTCCAGGTAAGtaG

CD40L 2 (Human) (SEQ ID NO: 95)

ATGGAAACAGATACGTTGCTGTTGTGGGTACTTCTCCTTTGGGTCCCTGGCAGCACAGGGGACG
AGAATAGTTTCGAAATGCAGAAGGGCGACCAGAACCCACAGATCGCGGCTCACGTTATATCAG
AAGCAAGTAGTAAGACCACTTCCGTACTTCAGTGGGCTGAAAAAGGATATTACACCATGTCCAA
CAATCTCGTGACACTGGAGAACGGTAAACAACTTACGGTGAAACGACAGGGCCTCTATTACATC
TACGCTCAGGTGACATTCTGCTCAAATAGGGAGGCTTCTAGTCAAGCGCCCTTCATCGCCAGCC
TGTGCCTCAAATCTCCCGGCCGGTTCGAACGAATCCTGTTGCGAGCGGCCAATACCCATAGCTC
AGCTAAACCTTGCGGCCAGCAGAGTATTCATCTTGGTGGTGTGTTTGAACTTCAGCCGGGAGCA
TCTGTGTTCGTCAACGTAACGGACCCTAGCCAAGTGTCTCATGGGACAGGTTTTACATCCTTCGG
ACTCCTCAAGTTGtaG

Flt3L (Human) (SEQ ID NO: 96)

ATGACAGTTCTCGCGCCAGCTTGGAGTCCCACCACATACTTGCTTTTGCTTCTGCTTCTGTCCTCT
GGCCTGAGTGGGACCCAAGATTGTTCCTTTCAACATTCCCCAATTAGTTCTGATTTTGCAGTGAA
GATTAGAGAGCTCTCAGACTATCTGCTGCAAGATTATCCTGTCACAGTCGCTTCAAACCTGCAA
GACGAAGAGCTCTGCGGTGCCTTGTGGCGGTTGGTCTTGGCTCAAAGATGGATGGAGAGACTGA
AAACCGTAGCAGGCAGCAAGATGCAGGGTCTCCTGGAAAGGGTGAACACGGAAATCCATTTTG
TGACCAAGTGCGCGTTCCAGCCCCCACCGAGTTGTCTCCGGTTTGTTCAAACGAATATATCCCGG
TTGCTCCAGGAAACCTCAGAACAACTGGTGGCTTTGAAACCCTGGATCACAAGACAAAACTTTA
GTCGGTGCCTCGAACTCCAGTGCCAACCAGATTCTTCTACACTTCCCCCCCCGTGGTCCCCGCGC
CCGTTGGAAGCAACGGCCCCAtaG

TGFb TRAP (Human) (SEQ ID NO: 97)

ATGGCCTGGAGTCCTCTGTTTCTGACTCTTATAACTCACTGTGCCGGCAGTTGGGCTATACCCCC
TCATGTACAGAAGTCTGTAAACAACGACATGATTGTAACCGACAATAATGGCGCAGTGAAATTC
CCACAACTGTGTAAGTTCTGTGATGTACGGTTTAGTACATGCGACAATCAAAAAAGCTATATGT
CTAACTGCTCTATTACATCCATATGTGAAAAACCTCAGGAGGTGTGTGTTGCCGTTTGGCGAAA
AATGATGAGAATATCACACTGGAGACAGTATGTCATGACCCTAAACTGCCATACCATGATTTC
ATACTGGAGGACGCCGCCAGTCCTAAGTGCATTATGAAAGAGAAAAAGAAACCCGGTGAAACA
TTCTTTATGTGCTCTTGTAGCTCTGACGAGTGTAACGACAACATTATATTCAGCGAGGAGTACAA
TACAAGCAACCCCGATATACCACCTCACGTACAAAAAAGTGTCAACAACGATATGATTGTTACC
GACAATAACGGAGCTGTTAAGTTTCCTCAGTTGTGCAAGTTCTGCGATGTACGATTCTCTACCTG
CGACAACCAAAAGTCATGTATGTCTAACTGTTCCATAACCTCCATCTGCGAGAAGCCCCAGGAA
GTCTGCGTCGCCGTGTGGCGGAAAAACGACGAGAATATCACTCTTGAAACCGTTTGTCATGATC
CTAAACTGCCCTATCACGACTTTATTCTGGAAGATGCTGCTTCCCCTAAGTGTATCATGAAAGAA
AAGAAGAAACCTGGGGAGACATTCTTTATGTGTTCATGCTCCTCCGATGAGTGTAACGACAATA
TCATCTTCTCTGAGGAATACAACACTTCTAACCCTGATtaG

Fresolimumab (Human) (SEQ ID NO: 98)

ATGGCCTGGTCCCCTCTTTTTCTGACCCTCATCACACACTGTGCAGGCTCATGGGCTGAGACCGT
CTTGACCCAGTCCCCAGGAACTTTGTCTCTGTCTCCTGGTGAAAGAGCTACCCTTAGTTGTCGAG
CCTCTCAGTCCCTTGGTTCTAGCTATCTCGCTTGGTACCAGCAAAAGCCAGGCCAGGCCCCACG
ACTGCTGATCTACGAGCATCTTCACGGGCTCCCGGCATTCCCGATCGATTTTCCGGATCTGGTA
GTGGTACAGATTTCACACTGACCATATCTCGCCTGGAGCCCGAGGACTTTGCTGTTTATTATTGT
CAGCAGTACGCCGATTCTCCTATCACTTTTGGACAGGGAACCCGCCTGGAGATTAAGCGCACAG
TAGCAGCTCCATCCGTCTTTATCTTTCCACCATCAGATGAACAGCTCAAGAGTGGGACCGCAAG
TGTAGTATGCCTGCTGAACAATTTTTACCCTAGAGAGGCCAAAGTGCAGTGGAAGGTGGATAAC
GCCCTCCAGAGTGGCAATAGTCAAGAAAGTGTTACTGAGCAAGATAGTAAGGACTCTACATACT
CTTTGAGTTCTACTTTGACCCTGTCAAAAGCAGATTATGAAAAACATAAGGTGTATGCATGTGA
AGTTACACACCAAGGGTTGTCCTCTCCAGTTACAAAATCTTTTAATAGAGGAGAGTGCCGCCGC
AAACGCGGTAGTGGAGAAGGTCGAGGCTCACTCTTGACCTGTGGCGACGTGGAAGAAAATCCC
GGTCCTATGGATTGGACTTGGAGGGTATTTTGTCTTTTGGCAGTAACACCTGGAGCTCACCCCCA
AGTACAGCTCGTCCAATCTGGTGCCGAGGTTAAAAAGCCTGGAAGTTCAGTGAAGGTCTCTTGC
AAGGCATCTGGATACACCTTTTCATCAACGTCATATCCTGGGTACGGCAAGCCCCAGGACAGG
GACTTGAGTGGATGGGAGGGGTCATCCCCATCGTGGACATTGCTAATTACGCTCAGCGATTCAA
AGGGCGGGTTACTATAACTGCCGACGAGTCTACCTCAACTACCTACATGGAGTTGTCCTCTCTCC
GCTCCGAGGACACTGCTGTATATTACTGTGCCAGCACTCTCGGGTTGGTGTTGGATGCCATGGA
CTATTGGGGACAAGGAACCCTGGTGACAGTTAGCTCCGCAAGCACTAAAGGCCCTTCTGTTTTT
CCCTTGGCACCTTGTAGTAGGTCTACCTCTGAGTCTACAGCAGCACTTGGATGCTTGGTTAAGGA
CTATTTTCCCGAGCCAGTTACAGTCTCTTGGAACAGTGGTGCCCTCACAAGTGGGGTTCATACCT
TCCCCGCAGTCCTCCAGAGTAGTGGCCTTTACAGCCTCTCATCAGTTGTGACTGTTCCTAGTTCA
TCACTCGGTACTAAGACATATACATGTAACGTAGACCACAAGCCAAGCAACACAAAAGTAGAC
AAACGAGTCGAATCTAAGTATGGACCCCCTTGTCCCTCCTGTCCTGCTCCCGAGTTCCTTGGGGG
CCCTTCCGTGTTCTTGTTTCCTCCCAAGCCCAAGGATACCCTCATGATCTCACGAACCCCAGAGG
TAACATGTGTGGTTGTTGACGTAAGTCAGGAAGATCCCGAAGTGCAATTTAATTGGTACGTGGA

TABLE 6-continued

Sequences encoding exemplary effector molecules

TGGCGTCGAAGTCCATAACGCTAAAACAAAACCCCGAGAGGAACAATTCAATTCCACATATCG
GGTGGTGAGTGTATTGACCGTTCTTCACCAAGATTGGCTGAACGGCAAGGAGTATAAGTGTAAA
GTAAGCAACAAAGGTCTGCCAAGTAGCATAGAAAAAACAATATCTAAAGCTAAGGGCCAACCA
AGGGAACCACAAGTATATACATTGCCCCCCTCTCAGGAAGAGATGACAAAGAATCAAGTTAGC
CTGACCTGTTTGGTAAAGGGGTTCTATCCCTCAGATATAGCAGTCGAGTGGGAATCTAACGGCC
AGCCCGAGAATAATTATAAAACAACCCCCCCTGTGTTGGACTCAGACGGCAGCTTCTTTCTCTAT
TCACGGCTCACTGTTGATAAGTCCCGATGGCAGGAGGGGAATGTTTTCAGCTGTAGCGTGATGC
ACGAAGCTCTCCACAACCACTATACACAGAAAAGTTTGTCTTTGTCCCTTGGAAAAtaG

TGFb neutralizing peptide (Human) (SEQ ID NO: 99)

ATGAGTACATCCTTTCCAGAGCTGGATCTGGAGAATTTTGAGTATGACGACAGTGCCGAAGCCT
GCTACCTCGGGGACATAGTCGCATTCGGGACAATCTTTTTGTCTGTATTTTACGCCCTGGTGTTT
ACATTTGGCCTGGTTGGAAATCTGTTGGTCGTACTCGCTCTCACCAATTCCCGAAAACCCAAA
GTATAACAGACATATACCTGTTGAATCTGGCACTGAGTGACCTTTTGTTCGTCGCCACCCTTCCT
TTTTGGACACACTACCTTATCAGTCACGAGGGGCTTCATAATGCTATGTGCAAGCTCACTACTGC
CTTCTTCTTTATCGGATTCTTCGGGGGTATCTTTTTTATCACAGTTATTAGCATTGACCGATACCT
TGCCATAGTGCTCGCAGCCAACTCAATGAACAACCGCACCGTGCAGCATGGAGTGACTATTTCC
TTGGGTGTGTGGGCCGCTGCTATACTTGTCGCCAGCCCTCAATTCATGTTTACCAAAAGGAAAG
ACAATGAGTGCCTCGGAGATTACCCTGAGGTGTTGCAAGAAATGTGGCCTGTACTTCGAAATAG
CGAAGTGAATATACTCGGCTTTGCTCTTCCTCTGCTCATCATGTCATTCGTTATTTTCGAATAAT
CCAAACATTGTTCAGCTGTAAGAACCGAAAGAAAGCCCGCGCCGTACGCCTGATTCTGCTCGTT
GTGTTCGCCTTTTTTCTGTTTTGGACTCCTTACAACATAATGATATTCCTGGAGACTCTCAAATTC
TATAACTTTTTTTCCCTCCTGTGATATGAAAAGGGACCTTAGATTGGCTCTCAGTGTCACTGAAAC
AGTAGCCTTTAGCCATTGTTGTCTCAACCCTTTCATATATGCATTTGCAGGGGAAAAGTTCCGGC
GGTATCTCGGACATTTGTATCGGAAGTGCTTGGCCGTGTTGTGTGGTCATCCTGTCCATACCGGA
TTCTCTCCTGAGAGTCAACGGAGCCGCCAAGATTCAATCCTGTCCAGTTTCACTCACTATACTTC
AGAGGGGGATGGCAGCCTTCTGCTC

Kynureinase #1 (SEQ ID NO: 100)

ATGGAGACCGACACTTTGTTGCTGTGGGTACTTTTGTTGTGGGTCCCAGGATCTACCGGGGATAT
GGAACCCTCTCCTCTTGAACTGCCAGTAGACGCCGTGCGCCGCATTGCAGCCGAGTTGAATTGC
GATCCAACAGATGAACGCGTTGCCCTGAGGCTCGACGAAGAGGATAAATTGTCACATTTCAGGA
ACTGCTTTTACATTCCAAAGATGAGGGATCTTCCATCCATAGATCTTAGCCTCGTGTCCGAGGAT
GACGATGCCATATATTTCTTGGGAACAGTCTTGGGTTGCAGCCAAAAATGGTACGGACATATC
TCGAAGAGGAGCTGGACAAATGGGCTAAAATGGGTGCTTACGGCCACGACGTGGGAAAACGCC
CCTGGATAGTTGCGACGAATCTATCGTGAGTCTTATGAAAGATATAGTTGGAGCACATGAGAA
AGAAATTGCACTGATGAATGCCCTTACTATCAATCTGCATCTCCTCTTGCTTTCATTCTTTAAGCC
CACTCCTAAACGCCACAAAATACTTTTGGAAGCAAAAGCCTTTCCAAGCGACCACTACGTATT
GAGTCACAAATACAACTCCATGGACTTGATGTGGAAAAGTCTATGCGGATGGTAAAACCACGC
GAAGGCGAGGAGACCCTTCGAATGGAGGACATACTTGAGGTCATCGAAGAAGAAGGAGATAGT
ATAGCAGTTATCCTTTTCAGCGGGCTGCACTTCTACACAGGTCAACTCTTTAACATTCCAGCTAT
TACTAAGGCAGGCCACGCTAAAGGATGCTTCGTGGGCTTTGACCTTGCACACGCAGTAGGAAAC
GTAGAGCTCCGCTTGCACGATTGGGGCGTTGATTTCGCCTGCTGGTGTTCATATAAGTATCTTAA
CTCAGGAGCTGGTGGGTTGCAGGCGCATTCGTACACGAGAAACACGCTCATACCGTAAAGCCT
GCACTGGTAGGGTGGTTCGGACACGATCTCTCTACCCGCTTCAATATGGATAATAAACTCCAGC
TTATACCTGGCGCCAATGGATTCAGGATCTCAAATCCTCCTATTTTGCTCGTTTGCAGTTTGCAC
GCATCTCTTGAGGTGTTCCAGCAGGCTACCATGACTGCACTCCGCCGGAAGTCAATCCTTTTGAC
CGGATACTTGGAGTATATGCTGAAACATTATCACTCAAAAGATAACACTGAGAATAAGGGCCCC
ATAGTAAACATTATCACTCCATCTCGGGCTGAAGAGCGCGGCTGCCAACTCACATTGACTTTTTC
CATTCCCAAGAAGTCAGTGTTCAAAGAGTTGGAGAAACGGGGGGTTGTATGTGATAAGCGGGA
GCCAGATGGAATCCGCGTTGCCCCAGTCCCCCTCTATAATTCTTTTCACGATGTATACAAGTTTA
TTAGACTGCTGACAAGTATCTTGGACTCATCTGAGCGATCTtaG

Kynureinase #2 (SEQ ID NO: 101)

ATGGAACCCTCTCCTCTTGAACTGCCAGTAGACGCCGTGCGCCGCATTGCAGCCGAGTTGAATT
GCGATCCAACAGATGAACGCGTTGCCCTGAGGCTCGACGAAGAGGATAAATTGTCACATTTCAG
GAACTGCTTTTACATTCCAAAGATGAGGGATCTTCCATCCATAGATCTTAGCCTCGTGTCCGAGG
ATGACGATGCCATATATTTCTTGGGAACAGTCTTGGGTTGCAGCCAAAAATGGTACGGACATA
TCTCGAAGAGGAGCTGGACAAATGGGCTAAAATGGGTGCTTACGGCCACGACGTGGGAAAACG
CCCCTGGATAGTTGCGACGAATCTATCGTGAGTCTTATGAAAGATATAGTTGGAGCACATGAG
AAAGAAATTGCACTGATGAATGCCCTTACTATCAATCTGCATCTCCTCTTGCTTTCATTCTTTAA
GCCCACTCCTAAACGCCACAAAATACTTTTGGAAGCAAAAGCCTTTCCAAGCGACCACTACGCT
ATTGAGTCACAAATACAACTCCATGGACTTGATGTGGAAAAGTCTATGCGGATGGTAAAACCAC
GCGAAGGCGAGGAGACCCTTCGAATGGAGGACATACTTGAGGTCATCGAAGAAGAAGGAGATA
GTATAGCAGTTATCCTTTTCAGCGGGCTGCACTTCTACACAGGTCAACTCTTTAACATTCCAGCT
ATTACTAAGGCAGGCCACGCTAAAGGATGCTTCGTGGGCTTTGACCTTGCACACGCAGTAGGAA
ACGTAGAGCTCCGCTTGCACGATTGGGGCGTTGATTTCGCCTGCTGGTGTTCATATAAGTATCTT
AACTCAGGAGCTGGTGGGTTGCAGGCGCATTCGTACACGAGAAACACGCTCATACCGTAAAG
CCTGCACTGGTAGGGTGGTTCGGACACGATCTCTCTACCCGCTTCAATATGGATAATAAACTCC
AGCTTATACCTGGCGCCAATGGATTCAGGATCTCAAATCCTCCTATTTTGCTCGTTTGCAGTTTG
CACGCATCTCTTGAGGTGTTCCAGCAGGCTACCATGACTGCACTCCGCCGGAAGTCAATCCTTTT
GACCGGATACTTGGAGTATATGCTGAAACATTATCACTCAAAAGATAACACTGAGAATAAGGG
CCCCATAGTAAACATTATCACTCCATCTCGGGCTGAAGAGCGCGGCTGCCAACTCACATTGACT
TTTTCCATTCCCAAGAAGTCAGTGTTCAAAGAGTTGGAGAAACGGGGGGTTGTATGTGATAAGC

TABLE 6-continued

Sequences encoding exemplary effector molecules

GGGAGCCAGATGGAATCCGCGTTGCCCCAGTCCCCCTCTATAATTCTTTTCACGATGTATACAAG
TTTATTAGACTGCTGACAAGTATCTTGGACTCATCTGAGCGATCTtaG

Vegf (SEQ ID NO: 102)

ATGAATTTCTTGCTGAGCTGGGTGCATTGGACACTCGCATTGTTGCTGTACTTGCACCATGCCAA
GTGGTCCCAGGCTGCACCCACTACTGAGGGCGAGCAAAAGTCTCATGAGGTGATTAAATTTATG
GACGTTTACCAACGATCATACTGTCGGCCAATCGAAACCCTCGTAGATATATTCCAGGAGTACC
CAGACGAGATCGAATACATTTTCAAGCCCTCATGTGTCCCATTGATGCGATGTGCTGGGTGCTGT
AACGACGAAGCACTTGAATGTGTCCCCACCTCCGAGAGTAACATCACAATGCAAATAATGAGA
ATCAAGCCCCACCAATCCCAACATATCGGTGAAATGTCATTCCTTCAGCATTCCCGCTGCGAGT
GCCGGCCTAAGAAGGACCGCACCAAACCAGAGAACCATTGTGAACCCTGTTCTGAGAGACGGA
AGCACTTGTTCGTACAGGACCCTCAAACATGCAAGTGCAGCTGTAAGAATACCGACTCACGGTG
TAAAGCTAGGCAACTGGAGCTTAATGAAAGGACCTGCCGATGCGATAAACCCAGGAGGtaa

GM-CSF (SEQ ID NO: 103)

ATGTGGTTGCAGAATTTGCTCTTCCTGGGGATTGTGGTCTACAGCCTCTCCGCACCTACCCGCTC
TCCTATCACAGTTACAAGACCCTGGAAACATGTGGAGGCCATTAAAGAAGCATTGAATTTGTTG
GACGATATGCCCGTCACCCTGAATGAAGAAGTAGAAGTTGTTTCTAATGAGTTCAGCTTTAAAA
AATTGACCTGTGTGCAGACACGGCTTAAAATTTTTGAACAGGGACTTAGAGGGAAACTTTACTAA
GCTGAAGGGGGCACTTAACATGACAGCTTCTTATTATCAGACCTATTGTCCTCCAACACCTGAA
ACCGACTGTGAAACACAGGTAACCACTTACGCCGATTTTATTGATTCTTTGAAAACATTCCTCAC
CGATATACCATTTGAGTGTAAGAAGCCAGGCCAAAAGtaG

Anti-PD1 (SEQ ID NO: 104)

ATGGAAACTGACACACTTCTTCTGTGGGTCTTGCTCCTGTGGGTCCCAGGCTCTACTGGTGACAG
TCCTGATAGGCCATGGAACCCACCTACCTTTAGTCCAGCCTTGCTCGTCGTAACCGAAGGGGAC
AACGCTACATTCACCTGCTCTTTTAGCAATACTTCTGAGAGTTTTCATGTAGTCTGGCATCGGGA
GAGTCCATCCGGACAAACAGATACTTTGGCCGCTTTTCCAGAGGATAGGTCTCAACCTGGGCA
GACGCAAGGTTTCGAGTCACACAGCTTCCTAACGGGAGAGATTTTCACATGTCTGTAGTTCGGG
CACGCCGAAATGATTCTGGCACATATGTTTGCGGTGTGATCTCACTTGCTCCAAAGATTCAAATA
AAGGAGAGCCTTCGCGCCGAGTTGCGGGTGACTGAGCGGGAGCCCAAGTCCTGCGACAAACC
CATACTTGTCCACCCTGTGGCGGCGGGTCATCCGGTGGCGGGTCTGGGGGGCAACCAAGAGAG
CACAGGTATATACTCTTCCCCCCAGCAGAGAAGAAATGACAAAAAACCAAGTGTCCCTGACATG
TCTGGTTAAAGGATTTTATCCCAGTGACATTGCTGTAGAATGGGAATCCAATGGTCAACCCGAG
AATAACTACAAAACCACTCCTCCAGTATTGGACAGTGACGGTTCCTTCTTCCTCTATTCCAAACT
TACAGTGGATAAATCCCGCTGGCAGCAAGGGAATGTATTCAGCTGTAGTGTCATGCACGAAGCT
CTTCATAACCATTATACACAGAAATCTCTTTCCCTGAGCCCAGGTAAAtaG

Adenosine Deaminase (ADA) #1 (Mouse) (SEQ ID NO: 105)

ATGGAGACTGATACACTTTTGCTCTGGGTTTTGCTCTTGTGGGTACCAGGGTCTACTGGAGATGC
ACAAACTCCTGCATTCAACAAGCCTAAGGTAGAGCTTCATGTCCATTTGGACGGAGCCATAAAA
CCTGAAACCATACTCTATTTCGGCAAGAAACGGGGTATAGCACTTCCCGCTGATACCGTGGAAG
AGTTGAGAAATATCATTGGCATGGACAAACCTCTTAGCCTGCCTGGCTTTCTTGCAAAGTTCGAC
TACTATATGCCAGTTATAGCAGGGTGTAGAGAAGCAATAAAGCGAATCGCCTATGAGTTCGTTG
AGATGAAGGCTAAAGAAGGAGTTGTTTACGTGGAAGTCCGGTACTCACCTCATCTGCTTGCTAA
TAGCAAGGTGGACCCAATGCCATGGAATCAAACTGAAGGTGATGTAACCCCTGACGATGTGGTC
GATTTGGTCAATCAAGGTCTCCAAGAAGGCGAGCAGGCTTTCGGCATTAAGGTAAGAAGTATAT
TGTGCTGTATGCGACATCAACCTTCATGGTCCCTGGAGGTCCTCGAATTGTGCAAAAAGTACAA
TCAAAAAACAGTGGTCGCAATGGATCTCGCTGGAGATGAGACCATAGAAGGTTCCTCTCTTTTC
CCCGGTCATGTCGAAGCATATGAAGGGGCTGTCAAAAATGGTATCCACCGCACCGTCCACGCAG
GGGAAGTAGGGTCCCCAGAAGTAGTCAGGGAAGCCGTTGACATTTTGAAAACAGAAAGAGTCG
GGCATGGCTACCATACAATAGAGGACGAAGCCTTGTACAATCGACTTTTGAAAGAAAATATGCA
CTTCGAGGTCTGTCCCTGGAGTTCATATCTCACCGGAGCATGGGACCCCAAAACAACCCACGCC
GTCGTACGCTTCAAGAATGATAAGCAAACTACAGTTTGAATACAGATGATCCACTGATATTCA
AGTCAACACTTGACACTGACTACCAGATGACAAAAAAAGATATGGGTTTCACCGAAGAAGAGT
TCAAGAGATTGAACATTAACGCAGCAAAAAGCTCCTTCCTGCCAGAGGAAGAGAAAAAAGAAT
TGCTTGAAAGGTTGTATCGAGAATACCAA

Adenosine Deaminase (ADA) #2 (Mouse) (SEQ ID NO: 106)

ATGGCACAAACTCCAGCTTTTAATAAGCCCAAAGTGGAACTTCATGTTCATCTGGATGGGGCAA
TTAAGCCCGAAACTATATTGTACTTTGGCAAAAAGAGGGGTATTGCCCTGCCAGCAGATACCGT
TGAGGAGCTTCGCAACATCATTGGGATGGACAAGCCCCTCTCTCTGCCAGGTTTTCTCGCTAAAT
TCGATTATTATATGCCTGTTATTGCTGGTTGCCGGGAGGCCATCAAGAGGATAGCCTACGAGTTT
GTTGAGATGAAGGCCAAAGAGGGCGTGGTGTACGTAGAGGTCAGATACAGCCCTCACCTGCTT
GCCAACAGCAAGGTGGACCCAATGCCCTGGAACCAAACCGAGGGGGATGTCACTCCCGACGAC
GTTGTAGACCTCGTAAATCAGGGCCTTCAAGAGGGCGAGCAGGCATTTGGCATAAAAGTCCGGT
CTATACTCTGCTGTATGAGGCACCAACCCTCCTGGTCTTTGGAGGTACTTGAGTTGTGTAAGAAA
TACAATCAAAAGACTGTAGTCGCCATGGATCTTGCAGGCGATGAAACCATCGAGGGTAGCTCCT
TGTTCCCTGGACATGTTGAAGCCTACGAGGGGGCCGTAAAAATGGGATACACAGGACTGTCCA
CGCTGGTGAAGTCGGAAGCCCAGAGGTGGTAAGGGAGGCAGTTGACATACTCAAGACAGAGCG
GGTTGGACACGGATACCACACAATTGAGGACGAGGCCCTGTATAACCGCCTCCTCAAAGAGAA
CATGCATTTTGAGGTGTGTCCTTGGTCCAGCTACCTGACTGGTGCTTGGGACCCTAAAACAACTC
ACGCCGTGGTCCGGTTCAAGAACGATAAAGCCAATTACTCTTTGAATACCGACGACCCCCTCAT

TABLE 6-continued

Sequences encoding exemplary effector molecules

ATTCAAATCAACATTGGATACCGACTACCAAATGACCAAAAAGGATATGGGGTTTACTGAAGA
GGAGTTCAAGAGGCTCAACATAAATGCCGCTAAATCCTCCTTTCTCCCCGAGGAAGAAAAAAA
GAACTCCTTGAGCGGCTGTATAGGGAGTATCAA 4-1BBL #1 (Mouse) (SEQ ID NO: 107)

ATGGAAACAGATACACTCTTGCTCTGGGTACTGCTTCTGTGGGTCCCCGGCTCTACTGGGGATG
AAGATGATGTAACTACTACAGAAGAACTCGCTCCCGCTCTTGTCCCCCCACCCAAGGGTACCTG
CGCCGGTTGGATGGCTGGCATCCCAGGACATCCAGGTCACAACGGTACCCCCGGAAGAGATGG
TCGGGATGGAACTCCCGGCGAGAAGGGCGAAAAAGGGGATGCAGGGCTTCTGGGACCTAAAGG
TGAAACAGGGGACGTTGGAATGACTGGTGCAGAAGGGCCTCGCGGCTTTCCTGGCACCCCTGGG
AGGAAAGGAGAGCCCGGAGAGCTCCAGAGAACTGAACCTCGGCCTGCACTCACTATAACTACT
TCCCCTAATCTTGGGACCCGCGAGAACAACGCCGATCAGGTTACACCTGTAAGCCATATCGGGT
GCCCCAATACTACCCAGCAAGGGAGTCCCGTGTTCGCAAAGCTTTTGGCTAAAAACCAAGCATC
CCTGTGTAACACTACTCTTAATTGGCATTCACAAGACGGTGCTGGTAGCTCTTATCTTTCTCAGG
GGCTGCGGTACGAAGAAGATAAGAAGGAATTGGTTGTGGATTCTCCAGGACTCTATTATGTCTT
TCTCGAATTGAAGCTCAGTCCCACCTTCACAAACACTGGACACAAAGTCCAGGGCTGGGTAAGT
CTGGTACTCCAAGCAAAGCCCCAGGTTGACGATTTCGACAATTTGGCACTCACCGTAGAGCTTT
TCCCATGCTCCATGGAAAATAAACTTGTTGATCGGTCATGGTCACAGCTCTTGCTGCTTAAGGCA
GGGCATCGCCTCTCAGTGGGTCTGAGAGCTTATTTGCATGGTGCACAAGATGCTTACAGGGATT
GGGAATTGTCCTACCCAAACACTACAAGTTTCGGGTTGTTCCTTGTCAAACCTGATAACCCATGG
GAGtaG 4-1BBL #2 (Mouse) (SEQ ID NO: 108)

ATGGAAACTGATACACTCCTCCTGTGGGTCCTTCTTTTGTGGGTGCCCGGATCAACCGGCGATGG
CTGGATGGCAGGCATCCCAGGACACCCAGGACACAACGGTACTCCAGGTCGAGACGGTCGGGA
TGGGACTCCTGGGGAGAAAGGCGAGAAAGGGGACGCTGGTTTGCTCGGTCCTAAGGGGGAAAC
CGGGGATGTAGGAATGACAGGGGCTGAAGGGCCTCGGGGATTTCCTGGGACACCAGGCAGGAA
GGGTGAACCAGGGGAGGCCCTCCAGCGCACCGAGCCACGGCCAGCTCTGACCATAACAACAAG
TCCAAACCTGGGCACACGCGAAAACAATGCTGACCAGGTGACTCCTGTAAGTCACATCGGATGC
CCTAACACTACACAACAGGGCTCTCCTGTATTTGCAAAGCTTCTCGCAAAAAATCAAGCATCAC
TTTGTAATACAACCCTGAACTGGCATTCTCAGGACGGAGCAGGGTCCTCTTATTTGTCTCAAGGG
CTCCGCTACGAAGAAGATAAAAAGGAATTGGTTGTTGACAGTCCAGGTTTGTATTATGTGTTTTT
GGAACTTAAGCTGTCACCAACCTTCACTAACACCGGCCACAAGGTCCAAGGCTGGGTTAGTCTT
GTTTTGCAAGCCAAACCTCAAGTGGATGATTTTGACAATCTGGCTTTGACTGTTGAGCTTTTTCC
ATGCAGTATGGAGAATAAACTGGTTGATCGGTCATGGTCACAGCTCCTTCTGCTCAAGGCCGGA
CATAGGCTGAGTGTGGGACTTCGGGCCTACTTGCACGGCGCCCAGGACGCATACCGAGACTGGG
AACTCAGCTACCCTAACACAACTTCTTTTGGGTTGTTCCTTGTCAAACCCGATAATCCTTGGGAAt
aG

HPGE2 #1 (Mouse) (SEQ ID NO: 109)

ATGGAGACTGATACTTTGCTCCTGTGGGTTCTTCTCCTGTGGGTTCCTGGTTCCACAGGGGATAT
GCATGTCAATGGCAAGGTAGCACTCGTGACTGGGGCTGCACAGGGTATCGGGAAAGCTTTTGCC
GAGGCCCTGTTGCTGCATGGCGCCAAGGTCGCTTTGGTAGATTGGAACTTGGAGGCTGGAGTTA
AATGCAAAGCTGCACTCGACGAACAATTTGAGCCTCAAAAAACCCTCTTTGTGCAGTGTGACGT
TGCTGACCAAAAGCAACTCAGGGACACATTCAGGAAGGTCGTAGACCATTTCGGACGCCTCGAT
ATACTCGTTAATAATGCCGGGGTAAACAACGAAAAGAACTGGGAACAAACATTGCAAATCAAC
CTGGTAAGTGTCATTAGCGGAACTTATCTGGGTCTTGATTATATGAGCAAGCAGAACGGGGCG
AGGGCGGGATCATTATCAACATGTCAAGTCTTGCCGGATTGATGCCAGTTGCTCAGCAGCCTGT
TTACTGTGCCAGCAAGCACGGTATTATTGGGTTTACCCGGAGTGCCGCCATGGCCGCAAATCTT
ATGAAGAGTGGGGTAAGACTGAATGTTATCTGCCCAGGTTTCGTAGATACCCCAATCCTGGAGA
GCATCGAGAAGGAGGAAAATATGGGACAATACATTGAATATAAAGATCAAATCAAGGCTATGA
TGAAGTTCTACGGGGTTCTGCATCCATCCACAATTGCCAACGGGCTCATTAATCTGATTGAGGA
CGACGCCTTGAACGGAGCTATAATGAAAATCACAGCTTCCAAAGGCATTCACTTCCAAGATTAT
GATATATCACCCTTGCTTGTCAAGGCTCCTCTGACAAGT

HPGE2 #2 (Mouse) (SEQ ID NO: 110)

ATGCATGTCAATGGCAAGGTAGCACTCGTGACTGGGGCTGCACAGGGTATCGGGAAAGCTTTTG
CCGAGGCCCTGTTGCTGCATGGCGCCAAGGTCGCTTTGGTAGATTGGAACTTGGAGGCTGGAGT
TAAATGCAAAGCTGCACTCGACGAACAATTTGAGCCTCAAAAAACCCTCTTTGTGCAGTGTGAC
GTTGCTGACCAAAAGCAACTCAGGGACACATTCAGGAAGGTCGTAGACCATTTCGGACGCCTCG
ATATACTCGTTAATAATGCCGGGGTAAACAACGAAAAGAACTGGGAACAAACATTGCAAATCA
ACCTGGTAAGTGTCATTAGCGGAACTTATCTGGGTCTTGATTATATGAGCAAGCAGAACGGGGG
CGAGGGCGGGATCATTATCAACATGTCAAGTCTTGCCGGATTGATGCCAGTTGCTCAGCAGCCT
GTTTACTGTGCCAGCAAGCACGGTATTATTGGGTTTACCCGGAGTGCCGCCATGGCCGCAAATC
TTATGAAGAGTGGGGTAAGACTGAATGTTATCTGCCCAGGTTTCGTAGATACCCCAATCCTGGA
GAGCATCGAGAAGGAGGAAAATATGGGACAATACATTGAATATAAAGATCAAATCAAGGCTAT
GATGAAGTTCTACGGGGTTCTGCATCCATCCACAATTGCCAACGGGCTCATTAATCTGATTGAG
GACGACGCCTTGAACGGAGCTATAATGAAAATCACAGCTTCCAAAGGCATTCACTTCCAAGATT
ATGATATATCACCCTTGCTTGTCAAGGCTCCTCTGACAAGT

Additional Embodiments

Provided below are enumerated paragraphs describing specific embodiments:
1. An engineered cell comprising:
   a) a promoter; and
   b) an exogenous polynucleotide sequence comprising an expression cassette described in a formula, oriented from 5' to 3', comprising

S1-E1-L-S2-E2 wherein
   S1 comprises a polynucleotide sequence encoding a first signal peptide,
   E1 comprises a polynucleotide sequence encoding a first effector molecule,
   L comprises a linker polynucleotide sequence,
   S2 comprises a polynucleotide sequence encoding a second signal peptide,
   E2 comprises a polynucleotide sequence encoding a second effector molecule, and
   wherein the promoter is operably linked to the expression cassette, the first signal peptide is operably linked to the first effector molecule, and the second signal peptide is operably linked to the second effector molecule, and
   wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.
2. The engineered cell of paragraph 1, wherein the promoter comprises an exogenous promoter polynucleotide sequence.
3. The engineered cell of paragraph 1, wherein the promoter comprises an endogenous promoter.
4. The engineered cell of any one of paragraphs 1-3, wherein the promoter is operably linked to the expression cassette such that the polynucleotides are capable of being transcribed as a single polynucleotide comprising the formula S1-E1-L-S2-E2.
5. The engineered cell of paragraph 4, wherein the linker polynucleotide sequence is operably associated with the translation of the first effector molecule and the second effector molecule as separate polypeptides.
6. The engineered cell of paragraph 5, wherein the linker polynucleotide sequence encodes a 2A ribosome skipping tag.
7. The engineered cell of paragraph 6, wherein the 2A ribosome skipping tag is selected from the group consisting of: P2A, T2A, E2A, and F2A.
8. The engineered cell of paragraph 5, wherein the linker polynucleotide sequence encodes a T2A ribosome skipping tag.
9. The engineered cell of paragraph 5, the linker polynucleotide sequence encodes an Internal Ribosome Entry Site (IRES).
10. The engineered cell of any one of paragraphs 5-9, wherein the linker polynucleotide sequence encodes a cleavable polypeptide.
11. The engineered cell of paragraph 10, wherein the cleavable polypeptide comprises a Furin recognition polypeptide sequence.
12. The engineered cell of any one of paragraphs 5-9, wherein the linker polynucleotide sequence further encodes a Gly-Ser-Gly polypeptide sequence.
13. The engineered cell of any one of paragraphs 1-5, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus.
14. The engineered cell of any one of paragraphs 1-3, wherein the linker polynucleotide sequence encodes a second promoter,
   wherein the promoter is operably linked to the expression cassette such that a first polynucleotide comprising the formula S1-E1 is capable of being transcribed,
   wherein the second promoter is operably linked to the expression cassette such that a second polynucleotide comprising the formula S2-E2 is capable of being transcribed, and wherein the first and the second polynucleotide are separate polynucleotides.
15. The engineered cell of paragraph 14, wherein the promoter and the second promoter are identical.
16. The engineered cell of paragraph 14, wherein the promoter and the second promoter are different.
17. The engineered cell of any one of paragraphs 1-16, wherein the engineered cell is HLA-typed with reference to a subject in need of therapeutic treatment.
18. The engineered cell of any one of paragraphs 1-17, wherein the engineered cell is a human cell.
19. The engineered cell of paragraph 18, wherein the human cell is an isolated cell from a subject.
20. The engineered cell of paragraph 19, wherein the isolated cell is isolated from a tissue consisting of the group of: bone marrow, adipose tissue, the umbilical cord, fetal liver, muscle, and lung tissue.
21. The engineered cell of any one of paragraphs 1-20, wherein the engineered cell is a cultured cell.
22. The engineered cell of any one of paragraphs 1-21, wherein the engineered MSC comprises a cellular marker phenotype comprising the cellular markers CD105+, CD73+, and CD90+.
23. The engineered cell of paragraph 22, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof
24. The engineered cell of any one of paragraphs 1-21, wherein the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−.
25. The engineered cell of any one of paragraphs 22-24, wherein the cellular marker phenotype is determined or has been determined by flow-cytometry.
26. The engineered cell of any one of paragraphs 1-21, wherein the engineered cell comprises a T cell.
27. The engineered cell of any one of paragraphs 1-21, wherein the engineered cell comprises a NK cell.
28. The engineered cell of any one of paragraphs 1-21, wherein the engineered cell comprises a NKT cell.

29. The engineered cell of any of paragraphs 22-28, wherein the cellular marker phenotype further comprises a cellular marker comprising a cognate receptor or a cognate receptor ligand for the first effector molecule, the second effector molecule, or the first and second effector molecules expressed in the engineered cells.
30. The engineered cell of paragraph 29, wherein the receptor is selected from the group consisting of: IL12RB1, IL12RB2, CCL7, and combinations thereof
31. The engineered cell of any one of paragraphs 1-30, wherein the promoter and/or the second promoter comprises a constitutive promoter.
32. The engineered cell of paragraph 31, wherein the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb.
33. The engineered cell of any one of paragraphs 1-30, wherein the promoter comprises an SFFV promoter.
34. The engineered cell of any one of paragraphs 1-30, wherein the promoter and/or the second promoter comprises an inducible promoter.
35. The engineered cell of paragraph 34, wherein the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof
36. The engineered cell of any one of paragraphs 1-35, wherein the first signal peptide or the second signal peptide comprises a native signal peptide native to the first effector molecule or the second effector molecule, respectively.
37. The engineered cell of any one of paragraphs 1-36, wherein the first signal peptide or the second signal peptide comprises a non-native signal peptide non-native to the first effector molecule or the second effector molecule, respectively.
38. The engineered cell of paragraph 37, wherein the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21.
39. The engineered cell of any one of paragraphs 1-38, wherein the first signal peptide and the second signal peptide are identical.
40. The engineered cell of any one of paragraphs 1-39, wherein the polynucleotide sequence encoding the first signal peptide comprises a codon optimized polynucleotide sequence.
41. The engineered cell of any one of paragraphs 1-40, wherein the first secretion polypeptide is a human IL12 signal peptide.
42. The engineered cell of any one of paragraphs 1-40, wherein the polynucleotide sequence encoding the second signal peptide comprises a codon optimized polynucleotide sequence.
43. The engineered cell of any one of paragraphs 1-42, wherein the second secretion polypeptide is a human IL21 signal peptide.
44. The engineered cell of any one of paragraphs 1-42, wherein the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme.
45. The engineered cell of any one of paragraphs 1-44, wherein the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme.
46. The engineered cell of paragraph 45, wherein the therapeutic class of the first effector molecule and the second effector molecule are different.
47. The engineered cell of any one of paragraphs 1-46, wherein the first effector molecule and/or the second effector molecule is a modified effector molecule.
48. The engineered cell of paragraph 47, wherein the first effector molecule and/or the second effector molecule is modified to comprises a cell membrane tethering domain.
49. The engineered cell of paragraph 48, wherein the cell membrane tethering domain comprises a transmembrane-intracellular domain or a transmembrane domain.
50. The engineered cell of paragraph 48, wherein the cell membrane tethering domain comprises a cell surface receptor, or a cell membrane-bound portion thereof
51. The engineered cell of paragraph 50, wherein the modified effector molecule is a fusion protein that comprises the cell surface receptor, or a cell membrane-bound portion thereof
52. The engineered cell of any one of paragraphs 48-51, wherein the modified effector molecule further comprises a linker between the effector molecule and the cell membrane tethering domain.
53. The engineered cell of any one of paragraphs 47-52, wherein when expressed the modified effector molecule is tethered to a cell membrane of the engineered cell.
54. The engineered cell of any one of paragraphs 44-53, wherein the cytokine is selected from the group consisting of: IL12, IL7, IL21, IL18, IL15, Type I interferons, and Interferon-gamma.
55. The engineered cell of paragraph 54, wherein the IL12 cytokine is an IL12p70 fusion protein.
56. The engineered cell of any one of paragraphs 44-55, wherein the chemokine is selected from the group consisting of: CCL21a, CXCL10, CXCL11, CXCL13, CXCL10-11 fusion, CCL19, CXCL9, and XCL1.
57. The engineered cell of any one of paragraphs 44-56, wherein the growth factor is selected from the group consisting of: Flt3L and GM-CSF.
58. The engineered cell of any one of paragraphs 44-57, wherein the co-activation molecule is selected from the group consisting of: 4-1BBL and CD40L.
59. The engineered cell of any one of paragraphs 34-41, wherein the tumor microenvironment modifier is selected from the group consisting of: adenosine deaminase, TGF-beta inhibitors, immune checkpoint inhibitors, VEGF inhibitors, and HPGE2.
60. The engineered cell of paragraph 59, wherein the TGF-beta inhibitors are selected from the group consisting of: an anti-TGFbeta peptide, an anti-TGFbeta antibody, a TGFb-TRAP, and combinations thereof 61. The engineered cell of paragraph 59, wherein the immune checkpoint inhibitors comprise anti-PD-1 antibodies.

62. The engineered cell of paragraph 59, wherein the VEGF inhibitors comprise anti-VEGF antibodies, anti-VEGF peptides, or combinations thereof 63. The engineered cell of any one of paragraphs 1-59, wherein the first effector molecule and the second effector molecule are human-derived effector molecules.

64. The engineered cell of any one of paragraphs 1-63, wherein the first effector molecule comprises IL12.

65. The engineered cell of any one of paragraphs 1-63, wherein the first effector molecule comprises an IL12p70 fusion protein.

66. The engineered cell of paragraph 65, wherein the IL12p70 fusion protein is a human IL12p70 fusion protein.

67. The engineered cell of any one of paragraphs 64-66, wherein the second effector molecule comprises CCL21a.

68. The engineered cell of paragraph 67, wherein the CCL21a is a human CCL21a.

69. The engineered cell of any one of paragraphs 64-66, wherein the second effector molecule comprises IL7.

70. The engineered cell of paragraph 69, wherein the IL7 is a human IL7.

71. The engineered cell of any one of paragraphs 64-66, wherein the second effector molecule comprises IL21.

72. The engineered cell of paragraph 71, wherein the IL21 is a human IL21.

73. The engineered cell of any one of paragraphs 1-72, wherein the expression cassette further comprises an E3 comprising a polynucleotide sequence encoding a third effector molecule.

74. The engineered cell of paragraph 73, wherein the third effector molecule comprises Flt3L.

75. The engineered cell of paragraph 73, wherein the third effector molecule comprises anti-PD1.

76. The engineered cell of paragraph 75, wherein the expression cassette further comprises an E4 comprising a polynucleotide sequence encoding a fourth effector molecule.

77. The engineered cell of paragraph 76, wherein the fourth effector molecule comprises adenosine deaminase.

78. The engineered cell of paragraph 73, wherein the third effector molecule comprises adenosine deaminase.

79. The engineered cell of paragraph 73, wherein the third effector molecule comprises CD40L.

80. The engineered cell of paragraph 73, wherein the third effector molecule comprises a CXCL10-CXCL11 fusion protein.

81. The engineered cell of paragraph 73, wherein the third effector molecule comprises XCL1.

82. The engineered cell of paragraph 64, wherein the second effector molecule comprises Flt3L.

83. The engineered cell of paragraph 64, wherein the second effector molecule comprises a CXCL10-CXCL11 fusion protein.

84. The engineered cell of paragraph 64, wherein the second effector molecule comprises anti-PD1.

85. The engineered cell of paragraph 64, wherein the second effector molecule comprises CD40L.

86. The engineered cell of any one of paragraphs 1-63, wherein the first effector molecule comprises interferon-beta and the second effector molecule comprises Flt3L.

87. The engineered cell of any one of paragraphs 1-86, wherein the polynucleotide sequence encoding the first effector molecule comprises a codon optimized polynucleotide sequence.

88. The engineered cell of any one of paragraphs 1-87, wherein the polynucleotide sequence encoding the second effector molecule comprises a codon optimized polynucleotide sequence.

89. The engineered cell of any one of paragraphs 1-88, wherein the engineered cell comprises a polynucleotide sequence encoding the promoter and the expression cassette.

90. The engineered cell of paragraph 89, wherein the exogenous polynucleotide sequence comprises the sequence shown in SEQ ID NO: 144.

91. The engineered cell of any one of paragraphs 1-90, wherein the exogenous polynucleotide sequence is integrated into the genome of the engineered cell.

92. The engineered cell of any one of paragraphs 1-91, wherein the exogenous polynucleotide sequence comprises one or more viral vector polynucleotide sequences.

93. The engineered cell of paragraph 92, wherein the one or more viral vector polynucleotide sequences comprise lentiviral, retroviral, retrotransposon, or adenoviral polynucleotide sequences.

94. The engineered cell of any one of paragraphs 1-93, wherein the expression cassette further comprises following E2, an additional exogenous polynucleotide sequence comprising a formula, oriented from 5' to 3', comprising:

$(L-S-E)_X$ wherein
S comprises a polynucleotide sequence encoding a signal peptide,
E comprises a polynucleotide sequence encoding an effector molecule,
L comprises a linker polynucleotide sequence,
X=1 to 20
wherein the promoter is operably linked to the expression cassette, and wherein for each X the corresponding signal peptide is operably associated with the effector molecule.

95. An engineered cell comprising a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

96. The engineered cell of paragraph 95, wherein the construct comprises the polynucleotide sequence shown in SEQ ID NO: 144.

97. The engineered cell of paragraph 95 or paragraph 96, wherein the engineered cell is HLA-typed with reference to a subject in need of therapeutic treatment.

98. The engineered cell of any one of paragraphs 95-97, wherein the engineered cell is a human cell.

99. The engineered cell of paragraph 98, wherein the human cell is an isolated cell from a subject.

100. The engineered cell of paragraph 99, wherein the isolated cell is isolated from a tissue consisting of the group of: bone marrow, adipose tissue, the umbilical cord, fetal liver, muscle, and lung tissue.

101. The engineered cell of any one of paragraphs 95-100, wherein the engineered cell is a cultured cell.

102. The engineered cell of any one of paragraphs 95-101, wherein the engineered MSC comprises a cellular marker phenotype comprising the cellular markers CD105+, CD73+, and CD90+.

103. The engineered cell of paragraph 102, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof 104. The engineered cell of any one of paragraphs 95-101, wherein the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−.

105. The engineered cell of any one of paragraphs 95-101, wherein the engineered cell comprises a T cell.

106. The engineered cell of paragraph 105, wherein the T cell is a CD8+ T cell, a CD4+ T cell, a cytotoxic T lymphocyte (CTL), a viral-specific T cell, a gamma-delta T cell, or a T regulatory cell.

107. The engineered cell of any one of paragraphs 95-101, wherein the engineered cell comprises a NK cell.

108. The engineered cell of any one of paragraphs 95-101, wherein the engineered cell comprises a NKT cell.

109. The engineered cell of any one of paragraphs 95-101, wherein the engineered cell comprises a monocyte cell.

110. The engineered cell of any one of paragraphs 95-101, wherein the engineered cell comprises a macrophage.

111. The engineered cell of any one of paragraphs 95-101, wherein the engineered cell comprises a TIL.

112. The engineered cell of any one of paragraphs 95-111, wherein the exogenous polynucleotide sequence is integrated into the genome of the engineered cell.

113. The engineered cell of any one of paragraphs 95-112, wherein the exogenous polynucleotide sequence comprises one or more viral vector polynucleotide sequences.

114. The engineered cell of paragraph 113, wherein the one or more viral vector polynucleotide sequences comprise lentiviral, retroviral, retrotransposon, or adenoviral polynucleotide sequences.

115. The engineered cell of paragraph 113, wherein the one or more viral vector polynucleotide sequences comprise lentiviral polynucleotide sequences.

116. The engineered cell of any one of paragraphs 1-115, wherein the cell secretes each effector molecule.

117. The engineered cell of paragraph 116, wherein the first effector molecule is secreted at a ratio that is 10 fold higher relative to secretion of the second effector molecule.

118. The engineered cell of any one of paragraphs 1-117, wherein the cell further comprises an antigen recognizing receptor.

119. The engineered cell of paragraph 118, wherein the antigen recognizing receptor recognizes an antigen selected from the group consisting of: 5T4, ADAM9, ADGRE2, AFP, AXL, B7-H3, B7-H4, B7-H6, C4.4, CA6, Cadherin 3, Cadherin 6, CCR1, CCR4, CD117, CD123, CD131, CD133, CD138, CD142, CD166, CD25, CD244, CD30, CD300LF, CD33, CD352, CD37, CD38, CD44, CD56, CD66e, CD70, CD71, CD74, CD79b, CD80, CD93, CEA, CEACAM5, Claudin18.2, CLEC12A, cMet, CSPG4, CTLA, DLK1, DLL3, DR5, EGFR, EMB, ENPP3, EpCAM, EphA2, Ephrin A4, ETBR, FGFR2, FGFR3, FRalpha, FRb, FLT3, GAPT, GCC, GD2, GFRa4, gpA33, GPC3, gpNBM, GPRC5, HER2, IL-1RAP, IL-13R, IL-13Ra, IL-13Ra2, IL-8, IL-15, IL1RAP, Integrin aV, KIT, L1CAM, LAMP1, LAT2, Lewis Y, LeY, LILRA2, LILRB2, LIV-1, LRRC, LY6E, MCSP, Mesothelin, MLC1, MS4A3, MUC1, MUC16, MUC1C, MYADM, NaPi2B, Nectin 4, NKG2D, NOTCH3, NY ESO 1, Ovarin, P-cadherin, pan-Erb2, PIEZO1, PRAM1, PSCA, PSMA, PTK7, ROR1, S Aures, SCT, SLAMF7, SLC22A16, SLC17A9, SLITRK6, SPNS3, SSTR2, STEAP1, Survivin, TDGF1, TIM1, TROP2, VSTM1, and WT1

120. The engineered cell of paragraph 118 or paragraph 119, wherein the antigen recognizing receptor comprises an antigen-binding domain.

121. The engineered cell of paragraph 120, wherein the antigen-binding domain comprises an antibody, an antigen-binding fragment of an antibody, a F(ab) fragment, a F(ab') fragment, a single chain variable fragment (scFv), or a single-domain antibody (sdAb).

122. The engineered cell of paragraph 120, wherein the antigen-binding domain comprises a single chain variable fragment (scFv).

123. The engineered cell of paragraph 122, wherein the scFv comprises a heavy chain variable domain (VH) and a light chain variable domain (VL).

124. The engineered cell of paragraph 123, wherein the VH and VL are separated by a peptide linker.

125. The engineered cell of paragraph 124, wherein the scFv comprises the structure VH-L-VL or VL-L-VH, wherein VH is the heavy chain variable domain, L is the peptide linker, and VL is the light chain variable domain.

126. The engineered cell of any one of paragraphs 118-125, the antigen recognizing receptor is a chimeric antigen receptor (CAR) or T cell receptor (TCR).

127. The engineered cell of any one of paragraphs 118-125, the antigen recognizing receptor is a chimeric antigen receptor (CAR).
128. The engineered cell of paragraph 127, wherein the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.
129. The engineered cell of paragraph 127 or paragraph 128, wherein the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.
130. The engineered cell of any one of paragraphs 127-129, wherein the CAR comprises a spacer region between the antigen-binding domain and the transmembrane domain.
131. A population of cells, the population of cells comprising any of the engineered cells of any one of paragraphs 1-130.
132. The population of cells of paragraph 131, wherein the population of cells is enriched for the engineered cells.
133. The population of cells of paragraph 131 or paragraph 132, wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules.
134. The population of cells of paragraph 133, wherein the first effector molecule is IL12 or an IL12p70 fusion protein.
135. The population of cells of paragraph 134, wherein the population of cells enriched for the engineered cells express IL12 receptor β1 or increased levels thereof, IL12 receptor β2 or increased levels thereof, or IL12 receptor β1 and IL12 receptor β2 or increased levels thereof
136. The population of cells of any of paragraphs 133-135, wherein the second effector molecule is IL21.
137. The population of cells of any of paragraphs 133-135, wherein the second effector molecule is CCL21.
138. The population of cells of paragraph 137, wherein the population of cells enriched for the engineered cells express a CCL21 receptor or increased levels thereof
139. The population of cells of paragraph 138, wherein the CCL21 receptor is CCR7.
140. A method of stimulating a cell-mediated immune response to a tumor cell in a subject, the method comprising administering to a subject having a tumor a therapeutically effective dose of any of the engineered cells of any one of paragraphs 1-114 or the population of cells of any of paragraphs 131-139.
141. A method of providing an anti-tumor immunity in a subject, the method comprising administering to a subject in need thereof a therapeutically effective dose of any of the engineered cells of any one of paragraphs 1-114 or the population of cells of any of paragraphs 131-139.
142. A method of treating a subject having cancer, the method comprising administering to a subject having a tumor a therapeutically effective dose of any of the engineered cell of any one of paragraphs 1-114 or the population of cells of any of paragraphs 131-139.
143. A method of reducing tumor volume in a subject, the method comprising administering to a subject having a tumor a therapeutically effective dose of any of the engineered cells of any one of paragraphs 1-114 or the population of cells of any of paragraphs 131-139.
144. The method of any one of paragraphs 140-143, wherein the engineered cell is derived from the subject.
145. The method of any one of paragraphs 140-143, wherein the engineered cell is allogeneic with reference to the subject.
146. The method of any one of paragraphs 140-145, wherein the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.
147. The method of any one of paragraphs 140-145, wherein the tumor is an ovarian tumor.
148. The method of any one of paragraphs 140-147, wherein the tumor is a tumor located in a peritoneal space.
149. An engineered cell comprising:
  a) a promoter; and
  b) an exogenous polynucleotide sequence comprising an expression cassette described in a formula, oriented from 5' to 3', comprising:

$(L-S-E)_X$ wherein
  S comprises a polynucleotide sequence encoding a signal peptide,
  E comprises a polynucleotide sequence encoding an effector molecule,
  L comprises a linker polynucleotide sequence,
  X=2 to 20,
  wherein the promoter is operably linked to the expression cassette, wherein for the first iteration of the (L-S-E) unit L is absent, and wherein for each X the corresponding signal peptide is operably associated with the effector molecule, and
  wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

150. A population of cells comprising one or more engineered cells, wherein the one or more engineered cells comprise:
   a) a promoter; and
   b) an exogenous polynucleotide sequence comprising an expression cassette described in a formula, oriented from 5' to 3', comprising

S1-E1-L-S2-E2 wherein
   S1 comprises a polynucleotide sequence encoding a first signal peptide,
   E1 comprises a polynucleotide sequence encoding a first effector molecule,
   L comprises a linker polynucleotide sequence,
   S2 comprises a polynucleotide sequence encoding a second signal peptide,
   E2 comprises a polynucleotide sequence encoding a second effector molecule, and
   wherein the promoter is operably linked to the expression cassette, the first signal peptide is operably linked to the first effector molecule, and the second signal peptide is operably linked to the second effector molecule, and
   wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

151. A population of cells comprising one or more engineered cells, wherein the one or more engineered cells comprise:
   a) a promoter; and
   b) an exogenous polynucleotide sequence comprising an expression cassette described in a formula, oriented from 5' to 3', comprising

S1-E1-L-S2-E2 wherein
   S1 comprises a polynucleotide sequence encoding a first signal peptide,
   E1 comprises a polynucleotide sequence encoding a first effector molecule,
   L comprises a linker polynucleotide sequence,
   S2 comprises a polynucleotide sequence encoding a second signal peptide,
   E2 comprises a polynucleotide sequence encoding a second effector molecule, and
   wherein the promoter is operably linked to the expression cassette, the first signal peptide is operably linked to the first effector molecule, and the second signal peptide is operably linked to the second effector molecule, and
   wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and
   wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

152. The population of cells of paragraph 151, wherein the one or more engineered cells express a cognate receptor or cognate receptor ligand for the first effector molecule, the second effector molecule, or the first and second effector molecules expressed in the engineered cells.

153. The population of cells of paragraph 151 or paragraph 152, wherein the first effector molecule is IL12 or an IL12p70 fusion protein.

154. The population of cells of any of paragraphs 151-153, wherein the second effector molecule is IL21.

155. The population of cells of any of paragraphs 151-153, wherein the second effector molecule is CCL21.

156. A population of cells comprising one or more engineered cells, wherein the one or more engineered cells comprise a construct, wherein the construct comprises:
   a) an SFFV promoter; and
   b) an exogenous polynucleotide sequence comprising an expression cassette described in a formula, oriented from 5' to 3', comprising

S1-E1-L-S2-E2 wherein
   S1 comprises a polynucleotide sequence encoding a first signal peptide, wherein the first signal peptide is a human IL12 signal peptide;
   E1 comprises a polynucleotide sequence encoding a first effector molecule, wherein the first effector molecule is a human IL12p70 fusion protein;
   L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
   S2 comprises a polynucleotide sequence encoding a second signal peptide, wherein the second signal peptide is a human IL21 signal peptide;
   E2 comprises a polynucleotide sequence encoding a second effector molecule, wherein the second effector molecule is human IL21; and
   wherein the SFFV promoter is operably linked to the expression cassette, the first signal peptide is operably linked to the first effector molecule, and the second signal peptide is operably linked to the second effector molecule, and
   wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

157. A population of cells comprising one or more engineered cells, wherein the one or more engineered cells comprise a construct, wherein the construct comprises:

a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

158. The population of cells of paragraph 156 or paragraph 157, wherein the construct comprises the polynucleotide sequence shown in SEQ ID NO: 144.

159. A method of producing a population of cells enriched for one or more receptors or receptor ligands, comprising culturing one or more cells under conditions where the one or more cells are contacted with a first effector molecule, a second effector molecule, or a first and a second effector molecule, wherein the contacted cells express one or more cognate receptors or cognate receptor ligands for the first effector molecule, the second effector molecule, or the first and second effector molecules, and wherein the first effector molecule, the second effector molecule, or the first and the second effector molecules increase growth, viability, or growth and viability of the contacted cells relative to cells cultured in the absence of the first effector molecule, the second effector molecule, or the first and second effector molecules.

160. The method of paragraph 159, wherein the first effector molecule, the second effector molecule, or the first and second effector molecules are heterologously expressed in one or more cells, and the one or more cells are contacted with the first effector molecule, the second effector molecule, or the first and second effector molecules in an autocrine manner.

161. The method of paragraph 159, wherein the first effector molecule, the second effector molecule, or the first and second effector molecules are expressed in one or more additional cells, and the one or more cells are contacted with the first effector molecule, the second effector molecule, or the first and second effector molecules in an paracrine manner.

162. The method of paragraph 161, wherein the one or more additional cells are a feeder cells.

163. The method of paragraph 159, wherein the one or more cells are cultured in media.

164. The method of paragraph 163, wherein the one or more cells are contacted with the first effector molecule, the second effector molecule, or the first and second effector molecules by addition of a soluble first effector molecule, a soluble second effector molecule, or a soluble first and second effector molecules to the media.

165. The method of paragraph 163 or paragraph 164, wherein the soluble first effector molecule and/or soluble second effector molecule is a recombinant effector molecule.

166. The method of paragraph 159, wherein the one or more cells are cultured under adherent conditions.

167. The method of paragraph 166, wherein the one or more cells are adhered onto a surface.

168. The method of paragraph 167, wherein the adhered cells are contacted with the first effector molecule, the second effector molecule, or the first and second effector molecules by exposing the one or more cells to first effector molecule, the second effector molecule, or the first and second effector molecules is immobilized on the surface.

169. The method of any one of paragraphs 159-168, wherein the first effector molecule is IL12 or an IL12p70 fusion protein.

170. The method of paragraph 169, wherein the population of cells is enriched for IL12 receptor β1 (IL12Rβ1), enriched for IL12 receptor β2 (IL12Rβ2), or enriched for IL12Rβ1 and IL12Rβ2.

171. The method of paragraph 170, wherein the population of MSCs comprises a cellular marker phenotype comprising the cellular markers CD105+, CD73+, CD90+, IL12Rβ1+, and IL12Rβ2+.

172. The method of paragraph 171, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof 173. The method of paragraph 159, wherein the population of cells comprises a cell selected from the group consisting of: natural killer (NK) cells, NKT cells, innate lymphoid cells, mast cells, eosinophils, basophils, monocytes, macrophages, neutrophils, and dendritic cells, T cells, CD8+ T cells, CD4+ T cells, gamma-delta T cells, and T regulatory cells, and B cells.

174. The method of paragraph 173, wherein the population of cells comprises a T cell, a NK cell, a NKT cell, a monocyte, a macrophage, or a myeloid derived cell.

175. The method of any one of paragraphs 159-174, wherein the second effector molecule is IL21.

176. The method of any one of paragraphs 159-174, wherein the second effector molecule is CCL21.

177. The method of paragraph 176, wherein the population of cells is enriched for CCR7.
178. The method of paragraph 177, wherein the population of MSCs comprises a cellular marker phenotype comprising the cellular markers CD105+, CD73+, CD90+, IL12Rβ1+, IL12Rβ2+, and CCR7+.
179. The method of paragraph 178, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof
180. A population of cells enriched for one or more receptors or receptor ligands produced by the method of any one of paragraphs 159-179.
181. An exogenous polynucleotide sequence comprising a promoter and an expression cassette described in a formula, oriented from 5' to 3', comprising

E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule.
182. The exogenous polynucleotide sequence of paragraph 181, wherein the promoter comprises an exogenous promoter polynucleotide sequence.
183. The exogenous polynucleotide sequence of paragraph 181, wherein the promoter comprises an endogenous promoter.
184. The exogenous polynucleotide sequence of any one of paragraphs 181-183, wherein the promoter is operably linked to the expression cassette such that the polynucleotides are capable of being transcribed as a single polynucleotide comprising the formula S1-E1-L-S2-E2.
185. The exogenous polynucleotide sequence of paragraph 184, wherein the linker polynucleotide sequence is operably associated with the translation of the first effector molecule and the second effector molecule as separate polypeptides.
186. The exogenous polynucleotide sequence of paragraph 185, wherein the linker polynucleotide sequence encodes a 2A ribosome skipping tag.
187. The exogenous polynucleotide sequence of paragraph 186, wherein the 2A ribosome skipping tag is selected from the group consisting of: P2A, T2A, E2A, and F2A.
188. The exogenous polynucleotide sequence of paragraph 185, wherein the linker polynucleotide sequence encodes a T2A ribosome skipping tag.
189. The exogenous polynucleotide sequence of paragraph 185, the linker polynucleotide sequence encodes an Internal Ribosome Entry Site (IRES).
190. The exogenous polynucleotide sequence of any one of paragraphs 185-189, wherein the linker polynucleotide sequence encodes a cleavable polypeptide.
191. The exogenous polynucleotide sequence of paragraph 190, wherein the cleavable polypeptide comprises a Furin recognition polypeptide sequence.
192. The exogenous polynucleotide sequence of any one of paragraphs 185-191, wherein the linker polynucleotide sequence further encodes a Gly-Ser-Gly polypeptide sequence.
193. The exogenous polynucleotide sequence of any one of paragraphs 181-185, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus.
194. The exogenous polynucleotide sequence of any one of paragraphs 181-183, wherein the linker polynucleotide sequence encodes a second promoter,
wherein the promoter is operably linked to the expression cassette such that a first polynucleotide comprising the formula S1-E1 is capable of being transcribed,
wherein the second promoter is operably linked to the expression cassette such that a second polynucleotide comprising the formula S2-E2 is capable of being transcribed, and wherein the first and the second polynucleotide are separate polynucleotides.
195. The exogenous polynucleotide sequence of paragraph 194, wherein the promoter and the second promoter are identical.
196. The exogenous polynucleotide sequence of paragraph 194, wherein the promoter and the second promoter are different.
197. The exogenous polynucleotide sequence of any one of paragraphs 181-196, wherein the promoter and/or the second promoter comprises a constitutive promoter.
198. The exogenous polynucleotide sequence of paragraph 197, wherein the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb.
199. The exogenous polynucleotide sequence of any one of paragraphs 181-196, wherein the promoter comprises an SFFV promoter.
200. The exogenous polynucleotide sequence of any one of paragraphs 181-196, wherein the promoter and/or the second promoter comprises an inducible promoter.
201. The exogenous polynucleotide sequence of paragraph 200, wherein the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof
202. The exogenous polynucleotide sequence of any one of paragraphs 181-201, wherein the first signal peptide or the second signal peptide comprises a native signal peptide native to the first effector molecule or the second effector molecule, respectively.
203. The exogenous polynucleotide sequence of any one of paragraphs 181-202, wherein the first signal peptide or the second signal peptide comprises a non-native signal peptide non-native to the first effector molecule or the second effector molecule, respectively.
204. The exogenous polynucleotide sequence of paragraph 203, wherein the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21.

205. The exogenous polynucleotide sequence of any one of paragraphs 181-204, wherein the first signal peptide and the second signal peptide are identical.

206. The exogenous polynucleotide sequence of any one of paragraphs 181-205, wherein the polynucleotide sequence encoding the first signal peptide comprises a codon optimized polynucleotide sequence.

207. The exogenous polynucleotide sequence of any one of paragraphs 181-206, wherein the first secretion polypeptide is a human IL12 signal peptide.

208. The exogenous polynucleotide sequence of any one of paragraphs 181-206, wherein the polynucleotide sequence encoding the second signal peptide comprises a codon optimized polynucleotide sequence.

209. The exogenous polynucleotide sequence of any one of paragraphs 181-208, wherein the second secretion polypeptide is a human IL21 signal peptide.

210. The exogenous polynucleotide sequence of any one of paragraphs 181-208, wherein the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme.

211. The exogenous polynucleotide sequence of any one of paragraphs 181-210, wherein the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme.

212. The exogenous polynucleotide sequence of paragraph 211, wherein the therapeutic class of the first effector molecule and the second effector molecule are different.

213. The exogenous polynucleotide sequence of any one of paragraphs 181-212, wherein the first effector molecule and/or the second effector molecule is a modified effector molecule.

214. The exogenous polynucleotide sequence of paragraph 213, wherein the first effector molecule and/or the second effector molecule is modified to comprises a cell membrane tethering domain.

215. The exogenous polynucleotide sequence of paragraph 214, wherein the cell membrane tethering domain comprises a transmembrane-intracellular domain or a transmembrane domain.

216. The exogenous polynucleotide sequence of paragraph 214, wherein the cell membrane tethering domain comprises a cell surface receptor, or a cell membrane-bound portion thereof 217. The exogenous polynucleotide sequence of paragraph 216, wherein the modified effector molecule is a fusion protein that comprises the cell surface receptor, or a cell membrane-bound portion thereof 218. The exogenous polynucleotide sequence of any one of paragraphs 214-217, wherein the modified effector molecule further comprises a linker between the effector molecule and the cell membrane tethering domain.

219. The exogenous polynucleotide sequence of any one of paragraphs 213-218, wherein when expressed in a cell, the modified effector molecule is tethered to a cell membrane of the cell.

220. The exogenous polynucleotide sequence of any one of paragraphs 210-219 wherein the cytokine is selected from the group consisting of: IL12, IL7, IL21, IL18, IL15, Type I interferons, and Interferon-gamma.

221. The exogenous polynucleotide sequence of paragraph 220, wherein the IL12 cytokine is an IL12p70 fusion protein.

222. The exogenous polynucleotide sequence of any one of paragraphs 210-221, wherein the chemokine is selected from the group consisting of: CCL21a, CXCL10, CXCL11, CXCL13, CXCL10-11 fusion, CCL19, CXCL9, and XCL1.

223. The exogenous polynucleotide sequence of any one of paragraphs 210-222, wherein the growth factor is selected from the group consisting of: Flt3L and GM-CSF.

224. The exogenous polynucleotide sequence of any one of paragraphs 210-223, wherein the co-activation molecule is selected from the group consisting of: 4-1BBL and CD40L.

225. The exogenous polynucleotide sequence of any one of paragraphs 210-224, wherein the tumor microenvironment modifier is selected from the group consisting of: adenosine deaminase, TGFbeta inhibitors, immune checkpoint inhibitors, VEGF inhibitors, and HPGE2.

226. The exogenous polynucleotide sequence of paragraph 225, wherein the TGFbeta inhibitors are selected from the group consisting of: an anti-TGFbeta peptide, an anti-TGFbeta antibody, a TGFb-TRAP, and combinations thereof 227. The exogenous polynucleotide sequence of paragraph 225, wherein the immune checkpoint inhibitors comprise anti-PD-1 antibodies.

228. The exogenous polynucleotide sequence of paragraph 225, wherein the VEGF inhibitors comprise anti-VEGF antibodies, anti-VEGF peptides, or combinations thereof 229. The exogenous polynucleotide sequence of any one of paragraphs 181-225, wherein the first effector molecule and the second effector molecule are human-derived effector molecules.

230. The exogenous polynucleotide sequence of any one of paragraphs 181-229, wherein the first effector molecule comprises IL12.

231. The exogenous polynucleotide sequence of any one of paragraphs 181-229, wherein the first effector molecule comprises an IL12p70 fusion protein.

232. The exogenous polynucleotide sequence of paragraph 231, wherein the IL12p70 fusion protein is a human IL12p70 fusion protein.

233. The exogenous polynucleotide sequence of any one of paragraphs 230-232, wherein the second effector molecule comprises CCL21a.

234. The exogenous polynucleotide sequence of paragraph 233, wherein the CCL21a is a human CCL21a.

235. The exogenous polynucleotide sequence of any one of paragraphs 230-232, wherein the second effector molecule comprises IL7.

236. The exogenous polynucleotide sequence of paragraph 235, wherein the IL7 is a human IL7.

237. The exogenous polynucleotide sequence of any one of paragraphs 230-232, wherein the second effector molecule comprises IL21.

238. The exogenous polynucleotide sequence of paragraph 237, wherein the IL21 is a human IL21.

239. The exogenous polynucleotide sequence of any one of paragraphs 181-238, wherein the expression cassette further comprises an E3 comprising a polynucleotide sequence encoding a third effector molecule.

240. The exogenous polynucleotide sequence of paragraph 239, wherein the third effector molecule comprises Flt3L.

241. The exogenous polynucleotide sequence of paragraph 239, wherein the third effector molecule comprises anti-PD1.

242. The exogenous polynucleotide sequence of paragraph 241, wherein the expression cassette further comprises an E4 comprising a polynucleotide sequence encoding a fourth effector molecule.

243. The exogenous polynucleotide sequence of paragraph 242, wherein the fourth effector molecule comprises adenosine deaminase.

244. The exogenous polynucleotide sequence of paragraph 239, wherein the third effector molecule comprises adenosine deaminase.

245. The exogenous polynucleotide sequence of paragraph 239, wherein the third effector molecule comprises CD40L.

246. The exogenous polynucleotide sequence of paragraph 239, wherein the third effector molecule comprises a CXCL10-CXCL11 fusion protein.

247. The exogenous polynucleotide sequence of paragraph 239, wherein the third effector molecule comprises XCL1.

248. The exogenous polynucleotide sequence of paragraph 230, wherein the second effector molecule comprises Flt3L.

249. The exogenous polynucleotide sequence of paragraph 230, wherein the second effector molecule comprises a CXCL10-CXCL11 fusion protein.

250. The exogenous polynucleotide sequence of paragraph 230, wherein the second effector molecule comprises anti-PD1.

251. The exogenous polynucleotide sequence of paragraph 230, wherein the second effector molecule comprises CD40L.

252. The exogenous polynucleotide sequence of any one of paragraphs 181-229, wherein the first effector molecule comprises interferon-beta and the second effector molecule comprises Flt3L.

253. The exogenous polynucleotide sequence of any one of paragraphs 181-252, wherein the polynucleotide sequence encoding the first effector molecule comprises a codon optimized polynucleotide sequence.

254. The exogenous polynucleotide sequence of any one of paragraphs 181-253, wherein the polynucleotide sequence encoding the second effector molecule comprises a codon optimized polynucleotide sequence.

255. The exogenous polynucleotide sequence of any one of paragraphs 181-254, wherein the exogenous polynucleotide sequence comprises the polynucleotide sequence shown in SEQ ID NO: 144.

256. An exogenous polynucleotide sequence comprising an SFFV promoter and an expression cassette described in a formula, oriented from 5' to 3', comprising

S1-E1-L-S2-E2 wherein

S1 comprises a polynucleotide sequence encoding a first signal peptide, wherein the first signal peptide is a human IL12 signal peptide;

E1 comprises a polynucleotide sequence encoding a first effector molecule, wherein the first effector molecule is a human IL12p70 fusion protein;

L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;

S2 comprises a polynucleotide sequence encoding a second signal peptide, wherein the second signal peptide is a human IL21 signal peptide;

E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule.

257. The exogenous polynucleotide sequence of paragraph 256, wherein the polynucleotide sequence comprises the polynucleotide sequence shown in SEQ ID NO: 144.

258. An exogenous polynucleotide sequence comprising an SFFV promoter and an expression cassette described in a formula, oriented from 5' to 3', comprising

E1-L-S2-E2 wherein

S1 comprises a polynucleotide sequence encoding a first signal peptide, wherein the first signal peptide is a human IL12 signal peptide;

E1 comprises a polynucleotide sequence encoding a first effector molecule, wherein the first effector molecule is a human IL12p70 fusion protein;

L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;

S2 comprises a polynucleotide sequence encoding a second signal peptide, wherein the second signal peptide is a human IL21 signal peptide;

E2 comprises a polynucleotide sequence encoding a second effector molecule, wherein the second effector molecule is human IL21;

wherein the SFFV promoter is operably linked to the expression cassette, the first signal peptide is operably linked to the first effector molecule, and the second signal peptide is operably linked to the second effector molecule;

wherein the promoter is operably linked to the expression cassette such that the polynucleotides are capable of being transcribed as a single polynucleotide comprising the formula S1-E1-L-S2-E2; and wherein the polynucleotide sequence comprises the polynucleotide sequence shown in SEQ ID NO: 144.

259. The exogenous polynucleotide sequence of any one of paragraphs 181-258, wherein the exogenous polynucleotide sequence is encoded by a nucleic acid selected from the group consisting of: a DNA, a cDNA, an RNA, an mRNA, and a naked plasmid.

260. An expression vector comprising the exogenous polynucleotide sequence of any one of paragraphs 181-259.

261. The expression vector of paragraph 260, wherein the expression vector is a viral vector.

262. The expression vector of paragraph 261, wherein the viral vector is a lentiviral vector.

263. A composition comprising the exogenous polynucleotide sequence of any one of paragraphs 181-259, and a pharmaceutically acceptable carrier.

264. An isolated cell comprising the exogenous polynucleotide sequence of any one of paragraphs 181-259, the expression vector of any one of paragraphs 260-262, or the composition of paragraph 263.

265. The isolated cell of paragraph 264, wherein the isolated cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, an MSC, an induced pluripotent stem cell (iPSC), and an iPSC-derived cell.

266. The isolated cell of paragraph 264, wherein the isolated cell is an MSC.

267. The isolated cell of any one of paragraphs 264-266, wherein the exogenous polynucleotide sequence is integrated into the genome of the cell.

268. The isolated cell of any one of paragraphs 264-267, wherein the exogenous polynucleotide sequence comprises one or more viral vector polynucleotide sequences.

269. The isolated cell of paragraph 268, wherein the one or more viral vector polynucleotide sequences comprise lentiviral, retroviral, retrotransposon, or adenoviral polynucleotide sequences.

270. The isolated cell of paragraph 268, wherein the one or more viral vector polynucleotide sequences comprise lentiviral polynucleotide sequences.

271. The isolated cell of any one of paragraphs 264-270, wherein the engineered cell is HLA-typed with reference to a subject in need of therapeutic treatment.

272. The isolated cell of any one of paragraphs 264-271, wherein the engineered cell is a human cell.

273. The isolated cell of paragraph 272, wherein the human cell is an isolated cell from a subject.

274. The isolated cell of paragraph 273, wherein the isolated cell is isolated from a tissue consisting of the group of: bone marrow, adipose tissue, the umbilical cord, fetal liver, muscle, and lung tissue.

275. The isolated cell of any one of paragraphs 264-272, wherein the cell is a cultured cell.

276. The isolated cell of any one of paragraphs 264-275, wherein the cell comprises a cellular marker phenotype comprising the cellular markers CD105+, CD73+, and CD90+.

277. The isolated cell of paragraph 276, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof 278. The isolated cell of any one of paragraphs 264-275, wherein the cell comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−.

279. The isolated cell of any one of paragraphs 264-278, wherein the cellular marker phenotype further comprises a cellular marker comprising a cognate receptor or a cognate receptor ligand for the first effector molecule, the second effector molecule, or the first and second effector molecules expressed in the cell.

280. The isolated cell of paragraph 279, wherein the receptor is selected from the group consisting of: IL12RB1, IL12RB2, CCL7, and combinations thereof 281. The isolated cell of any one of paragraphs 264-280, wherein the cell secretes each effector molecule.

282. The isolated cell of paragraph 281, wherein the first effector molecule is secreted at a ratio that is 10 fold higher relative to secretion of the second effector molecule.

283. The isolated cell of any one of paragraphs 264-282, wherein the cell further comprises an antigen recognizing receptor.

284. The isolated cell of paragraph 283, wherein the antigen recognizing receptor comprises an antigen-binding domain.

285. The isolated cell of paragraph 284, wherein the antigen-binding domain comprises an antibody, an antigen-binding fragment of an antibody, a F(ab) fragment, a F(ab') fragment, a single chain variable fragment (scFv), or a single-domain antibody (sdAb).

286. The isolated cell of paragraph 284, wherein the antigen-binding domain comprises a single chain variable fragment (scFv).

287. The isolated cell of paragraph 286, wherein the scFv comprises a heavy chain variable domain (VH) and a light chain variable domain (VL).

288. The isolated cell of paragraph 287, wherein the VH and VL are separated by a peptide linker.

289. The isolated cell of paragraph 288, wherein the scFv comprises the structure VH-L-VL or VL-L-VH, wherein VH is the heavy chain variable domain, L is the peptide linker, and VL is the light chain variable domain.

290. The isolated cell of any one of paragraphs 283-289, the antigen recognizing receptor is a chimeric antigen receptor (CAR) or T cell receptor (TCR).

291. The isolated cell of any one of paragraphs 283-289, the antigen recognizing receptor is a chimeric antigen receptor (CAR).

292. The isolated cell of paragraph 291, wherein the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

293. The isolated cell of paragraph 291 or paragraph 292, wherein the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

294. The isolated cell of any one of paragraphs 291-293, wherein the CAR comprises a spacer region between the antigen-binding domain and the transmembrane domain.

295. A virus comprising the exogenous polynucleotide sequence of any one of paragraphs 181-259 or the expression vector of any one of paragraphs 260-262.

296. The virus of paragraph 295, wherein the virus is selected from the group consisting of: a lentivirus, a retrovirus, a retrotransposon, and an adenovirus.

297. The virus of paragraph 295, wherein the virus is a lentivirus.

298. A method of reducing tumor volume in a subject, the method comprising delivering to a subject having a tumor a composition comprising cells engineered to produce multiple effector molecules that modulate tumor-mediated immunosuppressive mechanisms, in an effective amount to reduce the volume of the tumor, wherein the engineered cells comprise:
a) a promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

299. A method of reducing tumor volume in a subject, the method comprising delivering to a subject having a tumor a composition comprising cells engineered to produce IL12 and IL21, in an effective amount to reduce the volume of the tumor, wherein the engineered cells comprise a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

300. The method of paragraph 299, wherein the construct comprises the polynucleotide sequence shown in SEQ ID NO: 144.

301. The method of any one of paragraphs 298-300, wherein the method further comprises administering a checkpoint inhibitor.

302. The method of paragraph 301, wherein the checkpoint inhibitor is an anti-PD-1 antibody, anti-PD-1L antibody or an anti-CTLA-4 antibody.

303. The method of any one of paragraphs 298-302, wherein the method further comprises administering an anti-CD40 antibody.

304. The method of any one of paragraphs 298-303, wherein the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.

305. The method of any one of paragraphs 298-303, wherein the tumor is an ovarian tumor.

306. The method of any one of paragraphs 298-303, wherein the tumor is a tumor located in a peritoneal space.

307. The method of any one of paragraphs 298-306, wherein the administering comprises systemic administration, intraperitoneal administration, or intratumoral administration 308. The method of any one of paragraphs 298-307, wherein the volume of the tumor is reduced by at least 25% relative to a control, optionally wherein the control is an unmodified cell.

309. The method of paragraph 307, wherein the volume of the tumor is reduced by at least 50% relative to a control, optionally wherein the control is an unmodified cell.

310. The method of paragraph 309, wherein the volume of the tumor is reduced by at least 75% relative to a control, optionally wherein the control is an unmodified cell.

311. A method of reducing tumor volume in a subject, the method comprising delivering to a subject having a tumor a composition capable of engineering an cell to produce multiple effector molecules that modulate tumor-mediated immunosuppressive mechanisms, in an effective amount to reduce the volume of the tumor, wherein each engineered cell comprises:
a) a promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

312. A method of reducing tumor volume in a subject, the method comprising delivering to a subject having a tumor a composition capable of engineering a cell to produce IL12 and IL21, in an effective amount to reduce the volume of the tumor, wherein the engineered cell comprises a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

313. The method of paragraph 312, wherein the construct comprises the polynucleotide sequence shown in SEQ ID NO: 144.

314. The method of any one of paragraphs 311-313, wherein the composition comprises a delivery system selected from the group consisting of: a viral system, a transposon system, and a nuclease genomic editing system.

315. The method of paragraph 314, wherein the viral system is selected from the group consisting of: a lentivirus, a retrovirus, a retrotransposon, and an adenovirus.

316. The method of paragraph 314, wherein the nuclease genomic editing system is selected from the group consisting of: a zinc-finger system, a TALEN system, and a CRISPR system.

317. The method of any one of paragraphs 311-316, wherein the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.

318. The method of any one of paragraphs 311-317, wherein the administering comprises systemic administration, intraperitoneal administration, or intratumoral administration.

EXAMPLES

Example 1

This Example describes the in vitro characterization of MSCs with individual and combination immunotherapy payloads. Direct anti-cancer effects of immunotherapy-expressing MSCs on cancer cells are first measured. Next, the effects of immunotherapy-expressing MSCs on co-cultures with primary immune cells (focusing on T cells) and cancer cells are measured. The immuno-stimulatory properties of immunotherapy-expressing MSCs are rank-ordered based on inflammatory biomarker panels in both mouse and human cell systems. Immunotherapy-expressing MSCs that significantly enhance cancer cell killing either on their own or together with T cells are identified, and the top candidates to advance to in vivo testing are selected.

Methods:

Immunotherapy-expressing MSCs are engineered to express the effector molecules listed in Table 1 are evaluated for their functional effects using in vitro models relevant to cancer therapy. Human ovarian cancer cells (e.g., OVCAR8 and SKOV3) and human immune cells isolated from circulating PBMCs are used to test the hMSCs expressing hITs. Mouse ovarian cancer cells (e.g., ID8) and mouse immune cells are used to test the mMSCs expressing mITs.

Checkpoint Inhibitors.

Cell-binding assays are used to verify the activity of the expressed antibodies. The targets of the antibodies, CTLA4 and PD1, both negatively regulate T cells, but they are upregulated at different stages of T-cell activation (Boutros C, et al. (2016) Nat Rev Clin Oncol 13(8):473-486; Valsecchi M E (2015) New Engl J Med 373(13):1270-1270). CTLA4 is briefly upregulated in the priming phase, whereas PD1 is consistently expressed in the effector phase of T cell activation (Pardoll D M (2012) Nat Rev Cancer 12(4):252-264; Legat A, et al. (2013) Front Immunol 4:455). Anti-CTLA4 antibody binds to CTLA4 on the T-cell surface, blocking CTLA4 from shutting down T-cell activation in the early stage, and the human anti-PD1 antibody binds to PD1, preventing tumor cells from inhibiting T-cell activity.

T cells are isolated from PBMC by negative selection using EASYSEP™ magnetic bead (STEMCELL Technologies). The isolated T cells are activated by Human T-Activator CD3/28 Dynabeads (Thermo Fisher) and expression of CTLA-4 and PD-1 is monitored over 5 days to select for optimal timing of expression for each surface marker. On the appropriate days, conditioned media from the MSCs expressing antibodies for CTLA-4 or PD-1, or control conditioned media from non-expressing MSCs, are applied to the activated T cells to validate direct cell-surface-receptor binding of these antibodies. Fluorochrome-labeled secondary detection antibodies together with flow cytometry should confirm binding.

Chemokines.

CCL21 chemokine functionality is confirmed using cell migration assays and isolated naive T cells, which express chemokine receptor CCR7 that is responsive to CCL21 chemotaxis. Specifically, CCL21-expressing or control MSCs are added to one compartment of a trans-well and then cell migration is assessed by isolated naive T cells from the other compartment, followed by enumeration of numbers of migrated T cells (Justus C R, et al. (2014) J Vis Exp (88)).

Cytokines.

The activity of IL2, IL12, and IL15 is measured. ELISA assays specific to IL2, IL12, and IL15 are used to detect levels of these cytokines in MSC supernatants. Functional bioactivity assays employ the CTLL-2 cell line to assess of IL2 or IL15-mediated proliferation, or the NKG cell line to assess IL12-mediated IFN-gamma production by MSC supernatants. Multiplexed cytokine profiling assays using LUMINEX® technology may also be used to assess cytokine expression and effects on immune cells.

STING Pathway.

STING pathway activation is measured with the constitutive STING mutant payload. Using LUMINEX® beads, the secretion of Type I interferons (e.g. IFN-alpha2 and IFN-beta) with expression of the STING mutant are profiled in MSCs.

Direct Effects of Immunotherapy-Expressing MSCs on Ovarian Cancer Cells.

Any direct effects of MSCs on ovarian cancer cell growth and viability are tested in vitro. For example, mMSC or hMSC candidates are co-cultured with the mouse ovarian cancer cell line (ID8) or human ovarian cancer cell lines (OVCAR8 and SKOV3) and cancer cell cytotoxicity is measured by the well-characterized lactate dehydrogenase (LDH) assay. After 24 hours of co-culture, the supernatants are collected and measured for LDH levels correlated to cellular death via an enzymatic reaction that is subsequently quantified by specific absorbance on a plate reader. Additionally, cancer cell numbers are assessed by counting live versus dead cells by Trypan Blue exclusion and live versus apoptotic/dead cells by flow cytometric measurement using Annexin-V and propidium iodide staining.

Effects of Immunotherapy-Expressing MSCs on T Cell and Ovarian Cancer Cell Co-Culture Systems.

Tests determine whether immunotherapy-expressing MSCs can stimulate immune cells, such as T cells, to have improved anti-cancer activity against ovarian cancer cells in vitro. Specifically, mMSC-mIT candidates are co-cultured with mouse splenocytes and the ID8 cancer cell line, or hMSC-hIT candidates are co-cultured with human PBMCs and the OVCAR8 or SKOV3 cell lines. The co-culture assays entail using PBMCs/splenocytes with the ovarian cancer cells, with or without the MSCs, and stimulation with anti-CD3/28 beads. To assess cancer cell death, 16 hour killing assays are performed using techniques such as LDH cytotoxicity measurements, combining dye-labeled ovarian cancer cells with non-labeled effector PBMCs/splenocytes at fixed ratios and assaying killing by flow cytometry (Jedema I, et al. (2004) Blood 103(7):2677-2682), and apoptosis readouts by flow cytometry using Annexin-V with propidium iodide. T cell activation/proliferation is specifically assay by CFSE cell division at 3-5 days and cytokine production of IFN-gamma at 1-3 days.

An alternative strategy to generate T cells expressing CTLA-4 and PD1 is to activate with phytohaemagglutinin (PHA) to express the cell surface receptors PD1 and CTLA4. On Day 3, ~99% of the activated T cells should express PD1 while ~15% of them should express CTLA4 (Pardoll D M (2012) Nat Rev Cancer 12(4):252-264; Legat A, et al. (2013) Front Immunol 4:455). On Day 10, the activated T cells should be in the effector phase, when CTLA4 expression is downregulated but PD1 expression is maintained. Direct cell-surface-receptor binding of these antibodies is evaluated. On Day 3 and Day 10 post-induction, MSCs with the respective checkpoint inhibitor antibody expression constructs are applied to the T cell cultures. Labeled detection antibodies are used together with flow cytometry to confirm binding. Commercial antibodies are used as controls.

Example 2

This Example describes the in vivo characterization of MSCs expressing immunotherapy payloads in a syngeneic ovarian cancer model. The anti-tumor efficacy of immunotherapy-expressing MSCs is characterized using syngeneic mouse models of ovarian cancer (mMSC-mIT with mouse immune system). Tumor homing of engineered MSCs and expression of individual and combinatorial immunotherapies in a syngeneic ovarian mouse model are measured. Ovarian tumor burden and mouse survival with engineered MSC treatments are also measured. This Example should demonstrate selective homing of engineered MSCs to the TME and localized production of immunotherapy factors in ovarian tumors versus other body sites. This Example should also demonstrate significant reductions in tumor burden and extension of mouse survival with immunotherapy-expressing engineered MSCs.

Methods:

The mouse ID8 cell line originated from spontaneous transformation of mouse ovarian epithelial surface cells (MOSE), is used to create a syngeneic ovarian tumor model (Roby K F, et al. (2000) Carcinogenesis 21(4):585-591). Derivatives of the ID8 cell line are also used (e.g., ID8-VEGF (ID8-Defb29/Vegf-a), ID8-P53DN, ID8-P53KO-PTEN KO, ID8-P53KO-BRCA2 KO, ID8-P53KO-BRCA1 KO, ID8-PD53KO-Nf1KO). The ID8 cell line is infected with a lentivirus expressing Renilla luciferase (rLuc) to allow for in vivo bioluminescence imaging that is orthogonal to MSCs expressing Firefly luciferase (ffLuc). Successful rLuc expression is confirmed in ID8 in vitro prior to establishing the syngeneic ovarian cancer model in mice. For the syngeneic model, $5 \times 10^5$ ID8 cells are injected into the peritoneal cavity of C57BL/6 mice between 6 to 8 weeks old (36, 54). MSCs are engineered as in Example 1, along with an ffLuc-expressing plasmid.

mMSC-mIT candidates are introduced into the syngeneic mouse model starting on day 25 (after tumor cell injection) at a dose of $10^6$ MSC per animal once per week for 5 weeks (Dembinski J L, et al. (2013) Cytotherapy 15(1):20-32). The ovarian tumor load and mMSC-mIT candidates are visualized over time through rLuc and ffLuc bioluminescence imaging, respectively, as well as histological analyses following terminal time points. Mice are euthanized when they develop signs of distress, such as body-weight loss, ruffled fur, poor body posture, distended abdomen, and jaundice. Survival curves for the mice are measured. Distal metastasis of tumor cells is quantified by bioluminescence imaging (BLI) and by necropsy at time of euthanasia. Immune system profiling and activity is measured at different time points as biomarkers of response to the therapy.

To assess for variability in the expected anti-tumor effects of the MSCs, the dose of ID8 cells used to establish the model is varied (e.g., increase the number of cells to $5 \times 10^6$), the dose of MSCs used is changed, and the time when MSCs are delivered after tumor establishment is modulated.

Even though mMSCs have been shown to home to ovarian tumors in mouse models, it is possible that some payloads disrupt this homing activity. In these instances, expression of these payloads may be engineered to be inducible. This can be achieved, for example, with a phlo-retin-inducible system (Gitzinger M, et al. (2009) Proc Natl Acad Sci USA 106(26):10638-10643). Alternatively, the Dimerizer system may be used to link a synthetic zinc-finger DNA-binding domain with a transactivator domain using a small molecule (Clackson T, et al. (1998) Proc Natl Acad Sci USA 95(18):10437-10442). Alternatively or additionally, inducible payload expression constructs that are triggered in the tumor microenvironment based on signals such as low $O_2$ may be constructed.

Lentiviral ffLuc constructs may also be used to infect MSCs.

Example 3

This Example describes the in vivo characterization of the efficacy of MSCs expressing immunotherapy payloads in xenograft models of human ovarian cancer in mice with human immune cells. The activity of engineered MSCs in human ovarian cancer models in immunodeficient mice that are engrafted with human immune cells via CD34+ cell transplants (hMSC-hIT with humanized immune system) is tested. Homing of engineered MSCs and expression of individual and combinatorial immunotherapies in human xenograft ovarian tumors in mice with human immune cells are measured. Ovarian tumor burden and mouse survival with engineered MSC treatments are also tested. This Example should demonstrate elevated homing of engineered MSCs and localized production of immunotherapy factors into human xenograft ovarian tumors versus other body sites in mice. This Example should also demonstrate significant reductions in tumor burden and extension of mouse survival with immunotherapy-expressing engineered MSCs correlating with changes in the immune system composition.

Methods.

To enable translation of engineered MSCs into human clinical trials, hMSC-hIT constructs are tested in humanized mouse models of human cancers. The effects of the immunotherapy-expressing hMSCs in mice are modeled by using xenografts of human ovarian cancer cell lines in immunodeficient mice (NSG) engrafted with CD34+ hematopoietic stem cells (HSCs).

For human ovarian cancer cells, OVCAR8 and SKOV3 cell lines are used. Similar assays as described in Example 3 are used to investigate tumor load and mouse survival over time.

Two alternative approaches may also be used. (1) Human T cells can be infused into the mice. (2) Human PBMCs can be infused into the mice.

```
Expression Vector: pL + MCS
                                                    (SEQ ID NO: 111)
ACGCGTGTAGTCTTATGCAATACTCTTGTAGTCTTGCAACATGGTAACGATGAGTTAGCAACATGC

CTTACAAGGAGAGAAAAAGCACCGTGCATGCCGATTGGTGGAAGTAAGGTGGTACGATCGTGCCT

TATTAGGAAGGCAACAGACGGGTCTGACATGGATTGGACGAACCACTGAATTGCCGCATTGCAGA

GATATTGTATTTAAGTGCCTAGCTCGATACAATAAACGGGTCTCTCTGGTTAGACCAGATCTGAGC

CTGGGAGCTCTCTGGCTAACTAGGGAACCCACTGCTTAAGCCTCAATAAAGCTTGCCTTGAGTGCT

TCAAGTAGTGTGTGCCCGTCTGTTGTGTGACTCTGGTAACTAGAGATCCCTCAGACCCTTTTAGTCA

GTGTGGAAAATCTCTAGCAGTGGCGCCCGAACAGGGACCTGAAAGCGAAAGGGAAACCAGAGCT

CTCTCGACGCAGGACTCGGCTTGCTGAAGCGCGCACGGCAAGAGGCGAGGGCGGCGACTGGTGA

GTACGCCAAAAATTTTGACTAGCGGAGGCTAGAAGGAGAGAGATGGGTGCGAGAGCGTCAGTATT
```

-continued

```
AAGCGGGGAGAATTAGATCGCGATGGGAAAAAATTCGGTTAAGGCCAGGGGGAAAGAAAAAAT
ATAAATTAAAACATATAGTATGGGCAAGCAGGGAGCTAGAACGATTCGCAGTTAATCCTGGCCTG
TTAGAAACATCAGAAGGCTGTAGACAAATACTGGGACAGCTACAACCATCCCTTCAGACAGGATC
AGAAGAACTTAGATCATTATATAATACAGTAGCAACCCTCTATTGTGTGCATCAAAGGATAGAGAT
AAAAGACACCAAGGAAGCTTTAGACAAGATAGAGGAAGAGCAAACAAAAGTAAGACCACCGCA
CAGCAAGCGGCCACTGATCTTCAGACCTGGAGGAGGAGATATGAGGGACAATTGGAGAAGTGAAT
TATATAAATATAAAGTAGTAAAAATTGAACCATTAGGAGTAGCACCCACCAAGGCAAAGAGAAGA
GTGGTGCAGAGAGAAAAAAGAGCAGTGGGAATAGGAGCTTTGTTCCTTGGGTTCTTGGGAGCAGC
AGGAAGCACTATGGGCGCAGCCTCAATGACGCTGACGGTACAGGCCAGACAATTATTGTCTGGTA
TAGTGCAGCAGCAGAACAATTTGCTGAGGGCTATTGAGGCGCAACAGCATCTGTTGCAACTCACA
GTCTGGGGCATCAAGCAGCTCCAGGCAAGAATCCTGGCTGTGGAAAGATACCTAAAGGATCAACA
GCTCCTGGGGATTTGGGGTTGCTCTGGAAAACTCATTTGCACCACTGCTGTGCCTTGGAATGCTAG
TTGGAGTAATAAATCTCTGGAACAGATTGGAATCACACGACCTGGATGGAGTGGGACAGAGAAAT
TAACAATTACACAAGCTTAATACACTCCTTAATTGAAGAATCGCAAAACCAGCAAGAAAAGAATG
AACAAGAATTATTGGAATTAGATAAATGGGCAAGTTTGTGGAATTGGTTTAACATAACAAATTGG
CTGTGGTATATAAAATTATTCATAATGATAGTAGGAGGCTTGGTAGGTTTAAGAATAGTTTTTGCT
GTACTTTCTATAGTGAATAGAGTTAGGCAGGGATATTCACCATTATCGTTTCAGACCCACCTCCCA
ACCCCGAGGGGACCCGACAGGCCCGAAGGAATAGAAGAAGAAGGTGGAGAGAGAGACAGAGAC
AGATCCATTCGATTAGTGAACGGATCTCGACGGTATCGGTTAACTTTTAAAAGAAAAGGGGGAT
TGGGGGGTACAGTGCAGGGGAAAGAATAGTAGACATAATAGCAACAGACATACAAACTAAAGAA
TTACAAAAACAAATTACAAAAATCAAAATTTTATCTCGACATGGTGGCGACCGGTAGCGCTAGCG
GATCGATAAGCTTGATATCGCCTGCAGCCGAATTCCTTGACTTGGGATCCGCGTCAAGTGGAGCAA
GGCAGGTGGACAGTCCTGCAGGCATGCGTGACTGACTGAGGCCGCGACTCTAGTTTAAACTGCGT
GACTGACTCTAGAAGATCCGGCAGTGCGGCCGCGTCGACAATCAACCTCTGGATTACAAAATTTGT
GAAAGATTGACTGGTATTCTTAACTATGTTGCTCCTTTTACGCTATGTGGATACGCTGCTTTAATGC
CTTTGTATCATGCTATTGCTTCCCGTATGGCTTTCATTTTCTCCTCCTTGTATAAATCCTGGTTGCTG
TCTCTTTATGAGGAGTTGTGGCCCGTTGTCAGGCAACGTGGCGTGGTGTGCACTGTGTTTGCTGAC
GCAACCCCCACTGGTTGGGGCATTGCCACCACCTGTCAGCTCCTTTCCGGGACTTTCGCTTTCCCCC
TCCCTATTGCCACGGCGGAACTCATCGCCGCCTGCCTTGCCCGCTGCTGGACAGGGGCTCGGCTGT
TGGGCACTGACAATTCCGTGGTGTTGTCGGGGAAATCATCGTCCTTTCCTTGGCTGCTCGCCTGTGT
TGCCACCTGGATTCTGCGCGGGACGTCCTTCTGCTACGTCCCTTCGGCCCTCAATCCAGCGGACCTT
CCTTCCCGCGGCCTGCTGCCGGCTCTGCGGCCTCTTCCGCGTCTTCGCCTTCGCCCTCAGACGAGTC
GGATCTCCCTTTGGGCCGCCTCCCCGCCTGGTACCTTTAAGACCAATGACTTACAAGGCAGCTGTA
GATCTTAGCCACTTTTTAAAAGAAAAGGGGGGACTGGAAGGGCTAATTCACTCCCAACGAAAATA
AGATCTGCTTTTTGCTTGTACTGGGTCTCTCTGGTTAGACCAGATCTGAGCCTGGGAGCTCTCTGGC
TAACTAGGGAACCCACTGCTTAAGCCTCAATAAAGCTTGCCTTGAGTGCTTCAAGTAGTGTGTGCC
CGTCTGTTGTGTGACTCTGGTAACTAGAGATCCCTCAGACCCTTTTAGTCAGTGTGGAAAATCTCTA
GCAGTAGTAGTTCATGTCATCTTATTATTCAGTATTTATAACTTGCAAAGAAATGAATATCAGAGA
GTGAGAGGAACTTGTTTATTGCAGCTTATAATGGTTACAAATAAAGCAATAGCATCACAAATTTCA
CAAATAAAGCATTTTTTTCACTGCATTCTAGTTGTGGTTTGTCCAAACTCATCAATGTATCTTATCA
TGTCTGGCTCTAGCTATCCCGCCCCTAACTCCGCCCAGTTCCGCCCATTCTCCGCCCCATGGCTGAC
```

-continued
```
TAATTTTTTTTATTTATGCAGAGGCCGAGGCCGCCTCGGCCTCTGAGCTATTCCAGAAGTAGTGAG
GAGGCTTTTTTGGAGGCCTAGACTTTTGCAGAGACGGCCCAAATTCGTAATCATGGTCATAGCTGT
TTCCTGTGTGAAATTGTTATCCGCTCACAATTCCACACAACATACGAGCCGGAAGCATAAAGTGTA
AAGCCTGGGGTGCCTAATGAGTGAGCTAACTCACATTAATTGCGTTGCGCTCACTGCCCGCTTTCC
AGTCGGGAAACCTGTCGTGCCAGCTGCATTAATGAATCGGCCAACGCGCGGGGAGAGGCGGTTTG
CGTATTGGGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGATAACTACGATACGG
GAGGGCTTACCATCTGGCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGC
TCCGGTTCCCAACGATCAAGGCGAGTTACATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGCAGCA
CTGCATAATTCTCTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAATACGGGATAATA
CCGCGCCACATAGCAGAACTTTAAAAGTGCTCATCATTGGAAAACGTTCTTCGGGGCGAAAACTCT
CAAGGATCTTACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAAACAAATAGGG
GTTCCGCGCACATTTCCCCGAAAAGTGCCACCTGACGTCTAAGAAACCATTATTATCATGACATTA
ACCTATAAAAATAGGCGTATCACGAGGCCCTTTCGTCTCGCGCGTTTCGGTGATGACGGTGAAAAC
CTCTGACACATGCAGCTCCCGGAGACGGTCACAGCTTGTCTGTAAGCGGATGCCGGGAGCAGACA
AGCCCGTCAGGGCGCGTCAGCGGGTGTTGGCGGGTGTCGGGGCTGGCTTAACTATGCGGCATCAG
AGCAGATTGTACTGAGAGTGCACCATATGCGGTGTGAAATACCGCACAGATGCGTAAGGAGAAAA
TACCGCATCAGGCGCCATTCGCCATTCAGGCTGCGCAACTGTTGGGAAGGGCGATCGGTGCGGGC
```

```
                                          -continued
CTCTTCGCTATTACGCCAGCTGGCGAAAGGGGGATGTGCTGCAAGGCGATTAAGTTGGGTAACGC

CAGGGTTTTCCCAGTCACGACGTTGTAAAACGACGGCCAGTGCCAAGCTG
```

Example 4. 4T1 Triple Negative Breast Carcinoma

In the following experiments, MSCs were engineered to express one of the following effector molecules, then administered, alone or in combinations, to an orthotopic breast cancer mouse model: IFNβ, IFNγ, IL12, IL15, IL36γ, IL7, TRAIL, cGAS, CCL21a, OX40L, CD40L, or HACv-PD1. In some examples, a checkpoint inhibitor (anti-CD40, anti-PD1, or anti-CTLA-4 antibody) was injected in combination with administration with the engineered MSCs.

MSC Homing

Figure 3:
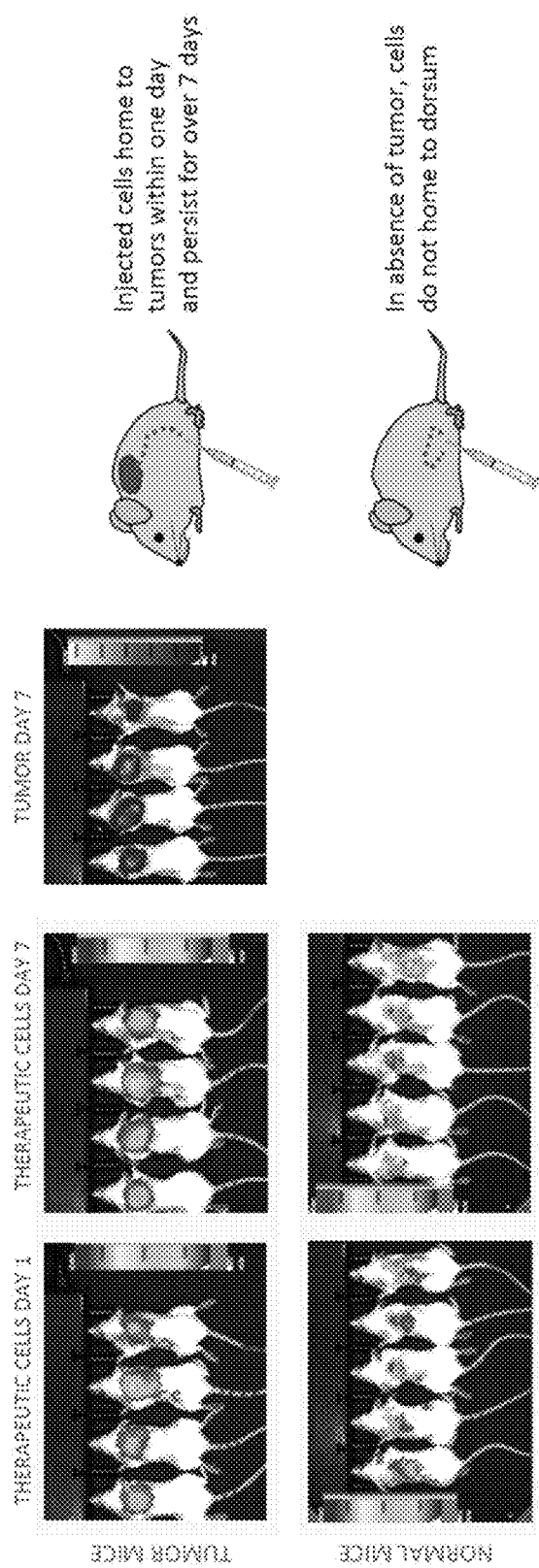
FIG. 3 shows data indicating that intraperitoneally injected murine BM-derived MSCs (BM-MSCs) home to the tumor site of 4T1 breast cancer cells in vivo. Fluorescently labeled BM-MSCs (therapeutic cells) were injected into mice bearing 4T1 breast tumor cells. The breast tumor cells express a luciferase reporter. The first top two panels on the left show imaging of therapeutic cells (BM-MSCs) in mice bearing tumors on day 1 and on day 7 after injection as indicated. The third top panel on the left shows imaging of tumor cells in mice bearing tumors on day 7 after injection. The bottom two panels on the left show imaging of therapeutic cells in normal mice not bearing tumors on day 1 and on day 7 after injection as indicated. A schematic showing the effect of tumors on homing of therapeutic cells is provided on the far right.

The following experiments demonstrate that murine MSCs home to tumors in an orthotopic mouse model of breast cancer. Luciferase-expressing 4T1 breast tumor cells ($5\times10^5$) were orthotopically implanted into the dorsal fat pad of female BALB/cJ mice. After 5 days, mice were intraperitoneally injected with 1 million fluorescently-labeled (with XenoLight DiR (Caliper Life Sciences)) murine BM-derived MSCs (BM-MSCs, therapeutic cells). At days 1 and 7 after MSC injection, fluorescence analysis was used to determine MSC localization using the Ami HT live animal imager (Spectral Instruments). On day 7, tumor localization and size was determined through the 4T1 cell's luciferase bioluminescence reporter using the Ami HT imager. As shown in FIG. 3, the injected MSCs co-localized to the site of the tumor, indicating that these cells do in fact specifically home in vivo to sites of 4T1 breast tumors. The injected MSCs home to tumors within one day and persist for over 7 days. In contrast, injected MSCs do not home to the dorsum in the absence of tumor in normal mice. These results suggest that MSCs can be used as a delivery vehicle for anti-cancer molecules, proteins or compounds.

Figure 11A:
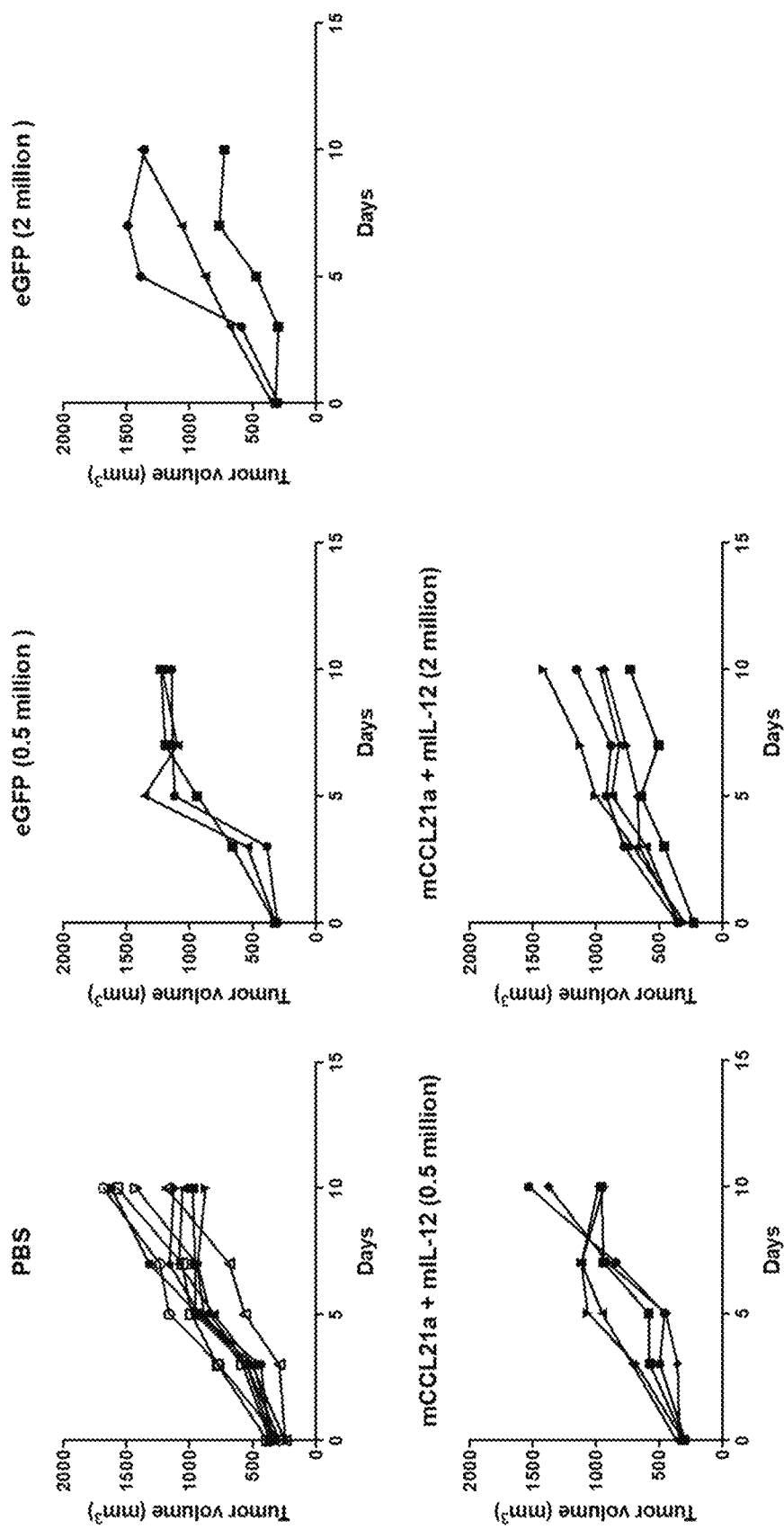
FIG. 11A shows that engineered human MSCs do not home to mouse 4T1 tumors. Each line of FIG. 11A represents an individual mouse.
Figure 11B:
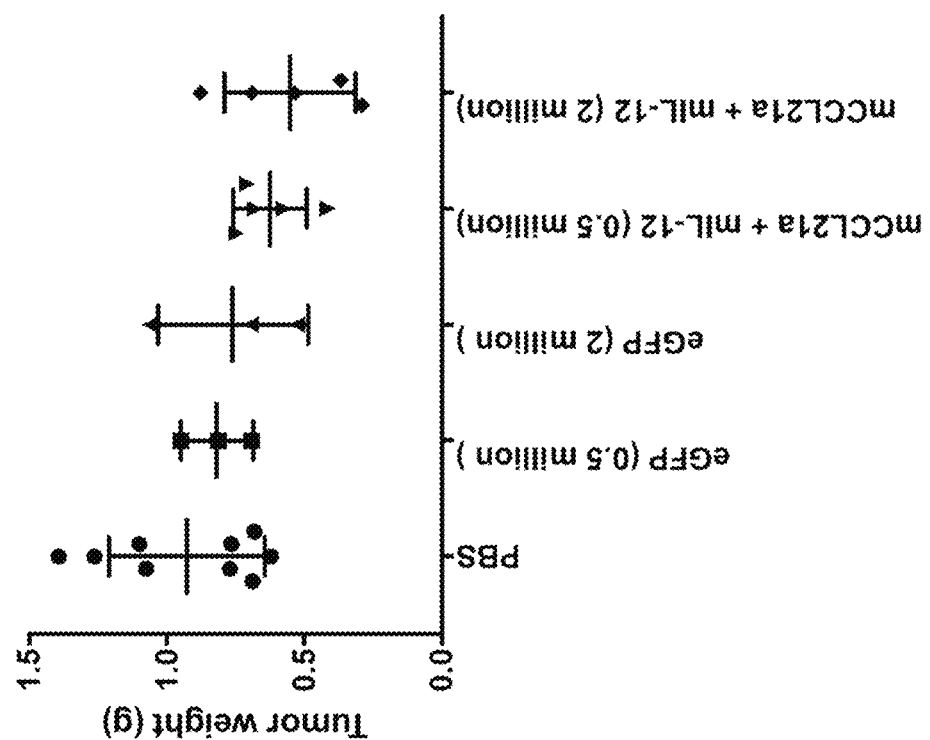
FIG. 11B shows that engineered human MSCs do not home to mouse 4T1 tumors.

To determine whether engineered human MSCs can home toward mouse tumors, different lines of engineered human MSC expressing either GFP, IL2 or CCL21a were injected into BALB/c mice with 4T1 tumors. Efficacy was determined by tumor volume from caliper measurement every other day. FIGS. 11A-11B show that human MSCs do not home to mouse 4T1 tumors.

In Vivo Efficacy

The following experiments demonstrate the in vivo efficacy of MSCs expressing immunotherapy effectors (payloads) in the orthotopic model of breast cancer. 4T1-Neo-Fluc mouse breast tumor cells (Imanis Life Sciences, $5\times10^5$ cells) were implanted orthotopically into the dorsal fat pad of female BALB/cJ mice (The Jackson Laboratory). Mice were then randomized into the treatment groups 5 days after tumor implantation. Mice received intraperitoneal injection of either control MSC growth media or engineered MSCs ($2\times10^6$ cells) expressing different immunotherapy effectors (payloads) once a week for two weeks. Each immunotherapy was expressed by a different MSC, and MSCs were combined (1:1 ratio) for combinatorial treatment. Tumor growth was monitored by caliper measurements every other day, and mouse weights were recorded twice weekly. Mice were euthanized 14 days after first MSC treatment and tissues were collected for further analysis.

Figure 4:
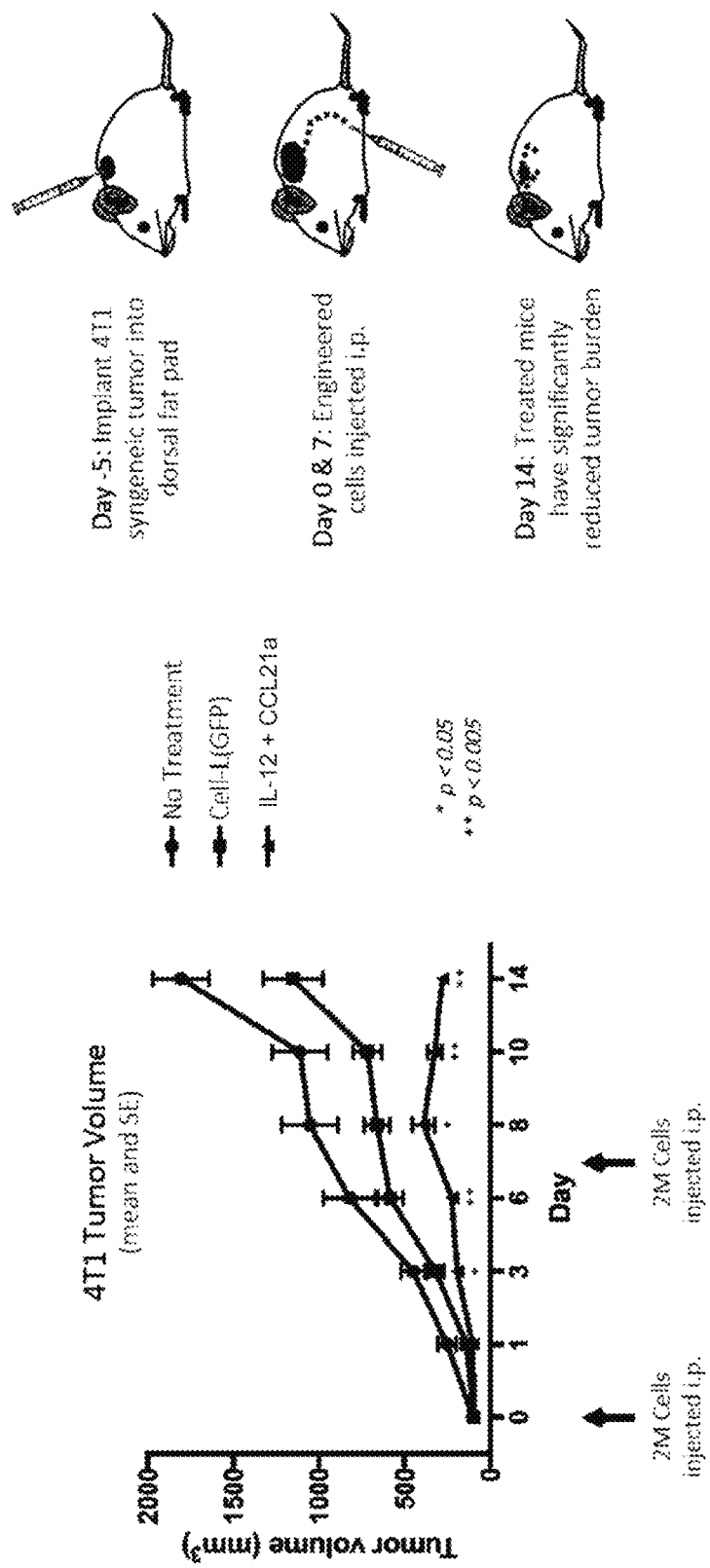
FIG. 4 shows data indicating that engineered MSCs expressing IL-12 and CCL21a induced significant tumor growth delay in an orthotopic mouse model of breast cancer. The chart on the left shows the effects of engineered MSCs on 4T1 breast tumor growth in mice (n=8). Each line in the chart represents tumor volume in mice receiving intraperitoneal injection of either control MSC growth media or engineered MSCs on day 0 and day 7. Mice received intraperitoneal injection of engineered MSCs expressing IL-12 and engineered MSCs expressing CCL21a. Tumor volume was determined by caliper measurements every other day. Data represent mean±SEM. *p<0.05, **p<0.005 as compared to control media group. The schematic on the right shows a timeline of treatment and the effect of engineered MSCs expressed combinatorial genes IL-12 and CCL21a on tumor burden in treated mice.

FIG. 4 shows that tumor growth was delayed in mice treated with engineered MSCs expressed combinatorial genes IL-12 and CCL21a compared to controls treated with media.

Figure 5A:
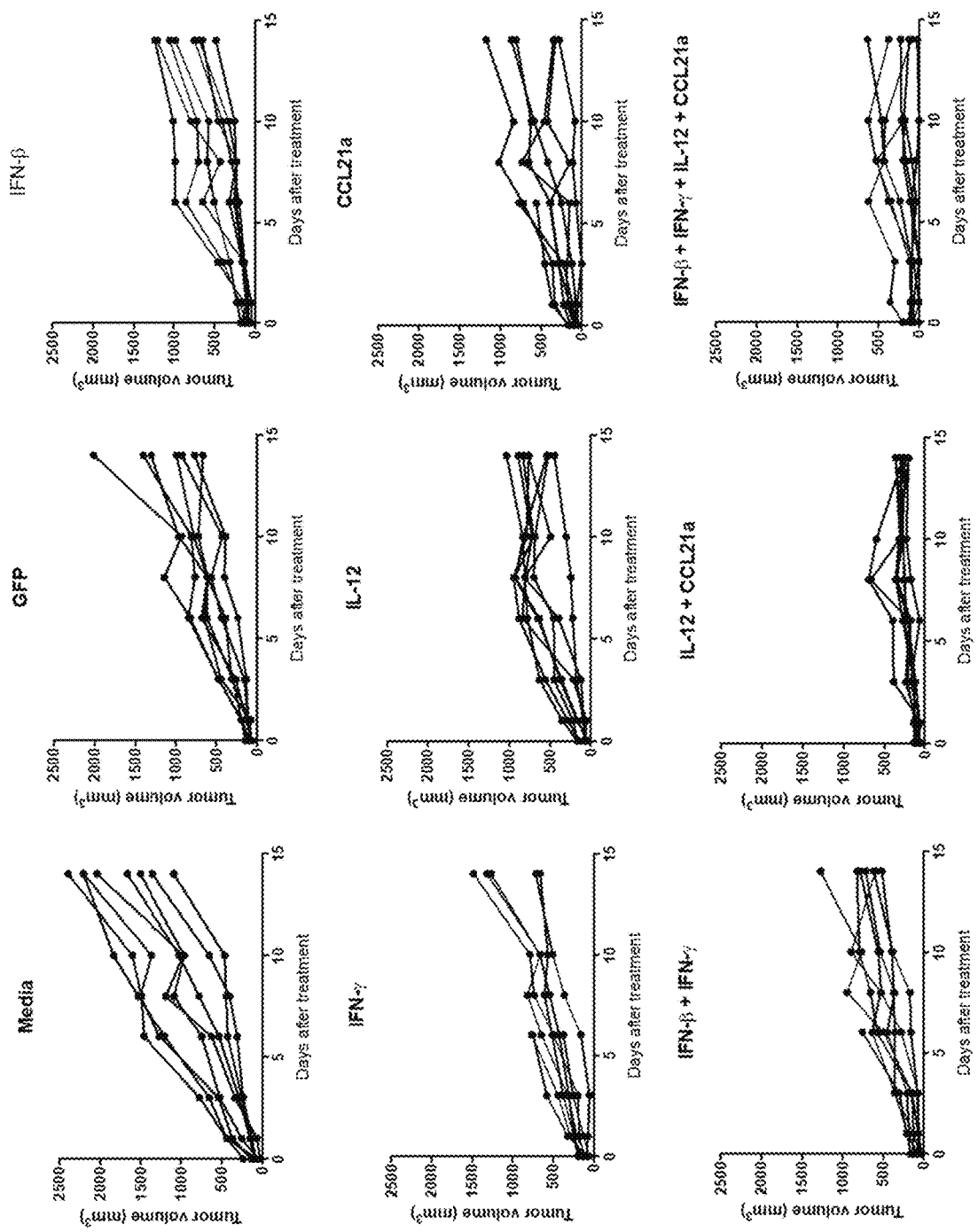
FIG. 5A includes data indicating that engineered MSCs expressing IFN-β, IFN-γ, IL-12, CCL21a, or combinations thereof inhibit tumor growth in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 5A represents an individual mouse.
Figure 5B:
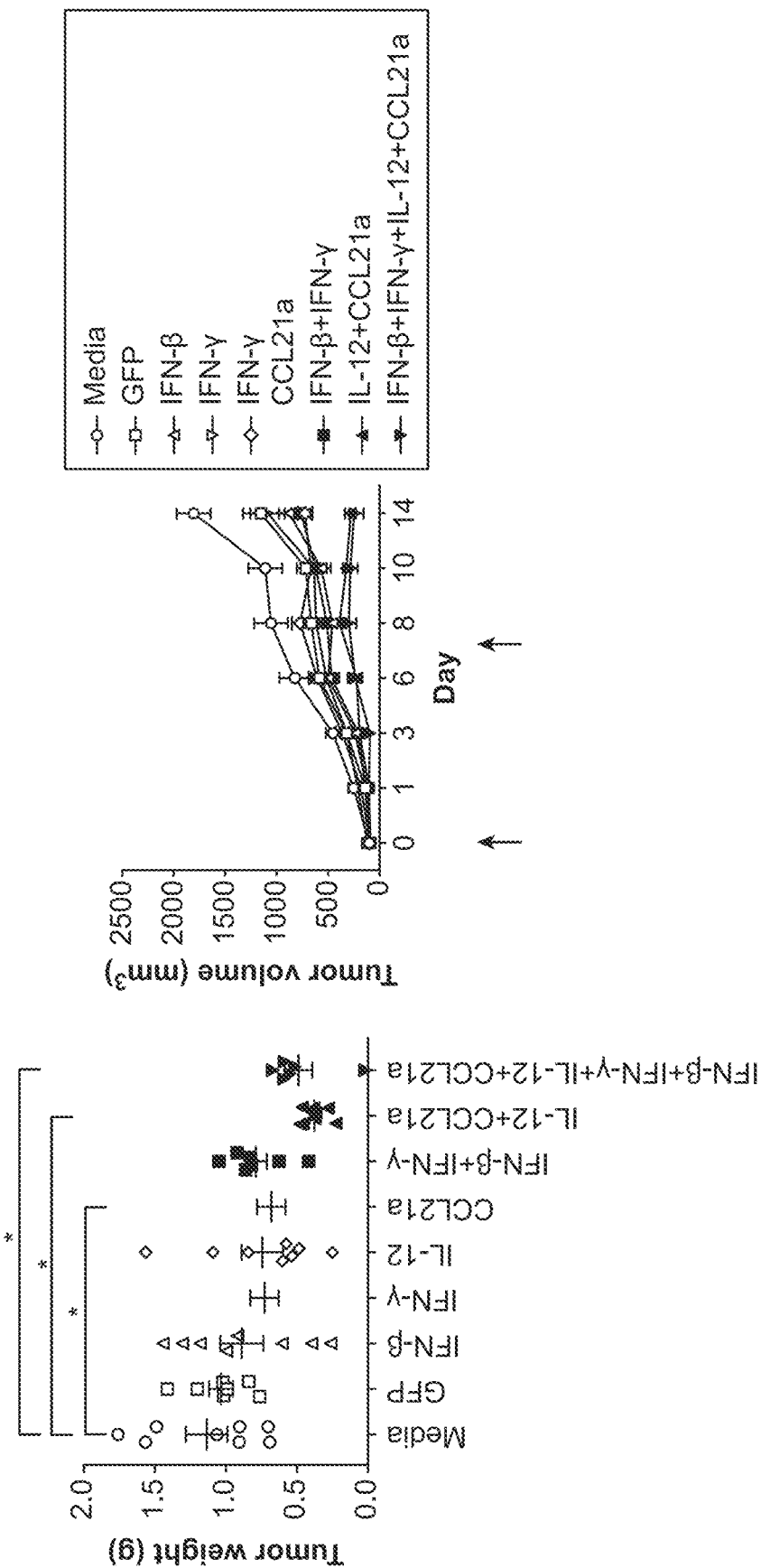
FIG. 5B includes data indicating that engineered MSCs expressing IFN-β, IFN-γ, IL-12, CCL21a, or combinations thereof inhibit tumor growth in an orthotopic mouse model of breast cancer (4T1 triple negative breast carcinoma). Each effector was expressed by a different MSC, and the MSCs were combined (at a 1:1 ratio) for combinatorial treatment. The left graph of FIG. 5B shows the tumor weight for individual mice in each treatment on day 14, and the mean±SEM for each treatment group. The right graph of FIG. 5B shows the tumor volume represented as mean±SEM for mice receiving each treatment over time.

FIGS. 5A-5C show that engineered MSCs that express single immunotherapy effectors (e.g., IFN-β, IFN-γ, IL-12 or CCL21a) inhibited growth of syngeneic 4T1 mouse tumors compared to media-treated mice. Surprisingly, a synergistic effect on tumor growth was observed when the immunotherapy effectors were combined, particularly the combination of IL-12 and CCL21a, and the combination of IFN-β, IFN-γ, IL-12 and CCL21a (FIGS. 5A-5C).

Figure 6A:
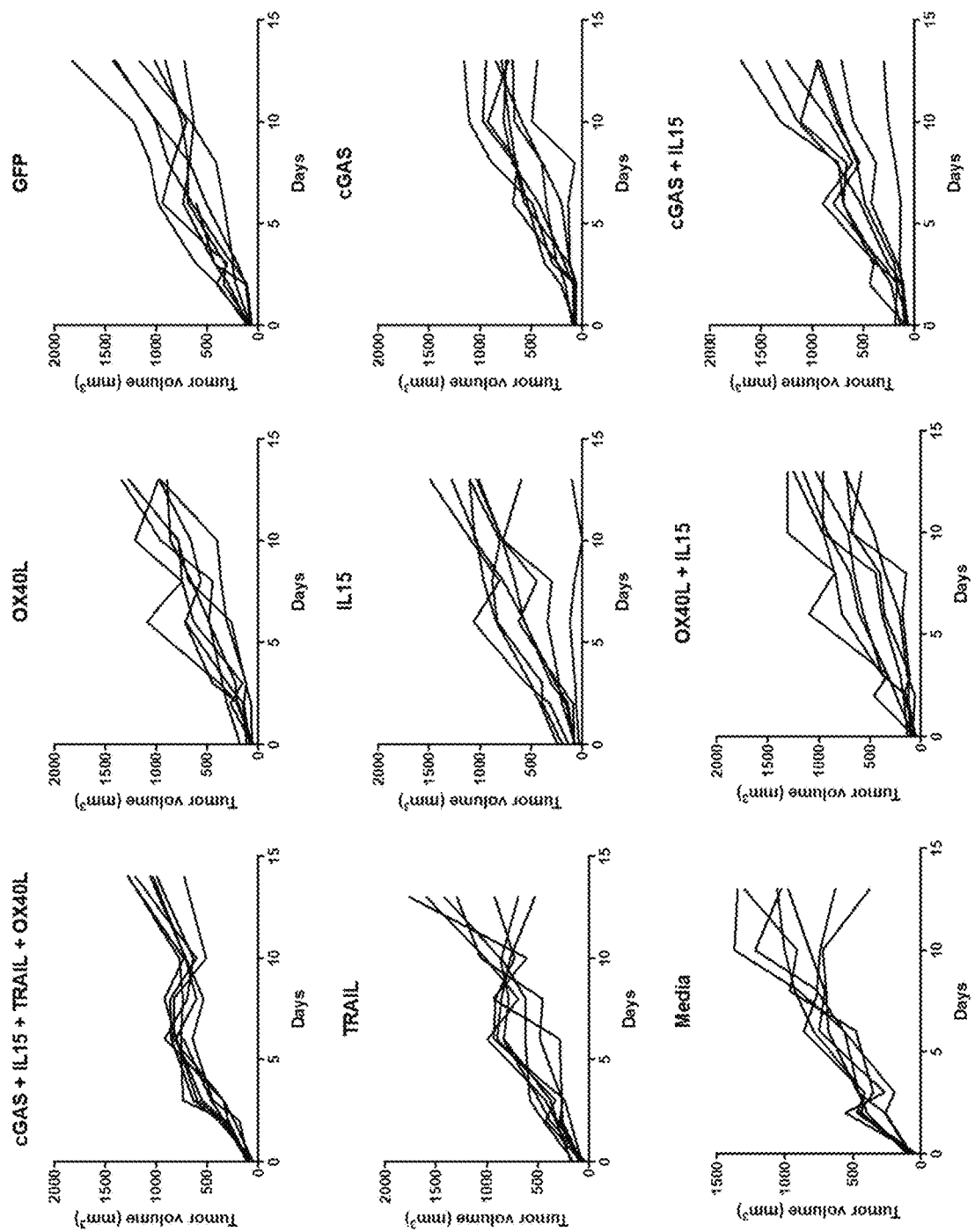
FIG. 6A includes data indicating that engineered MSCs expressing OX40L, TRAIL, IL15, cGAS, or combinations thereof do not inhibit tumor growth significantly in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 6A represents an individual mouse.
Figure 6B:
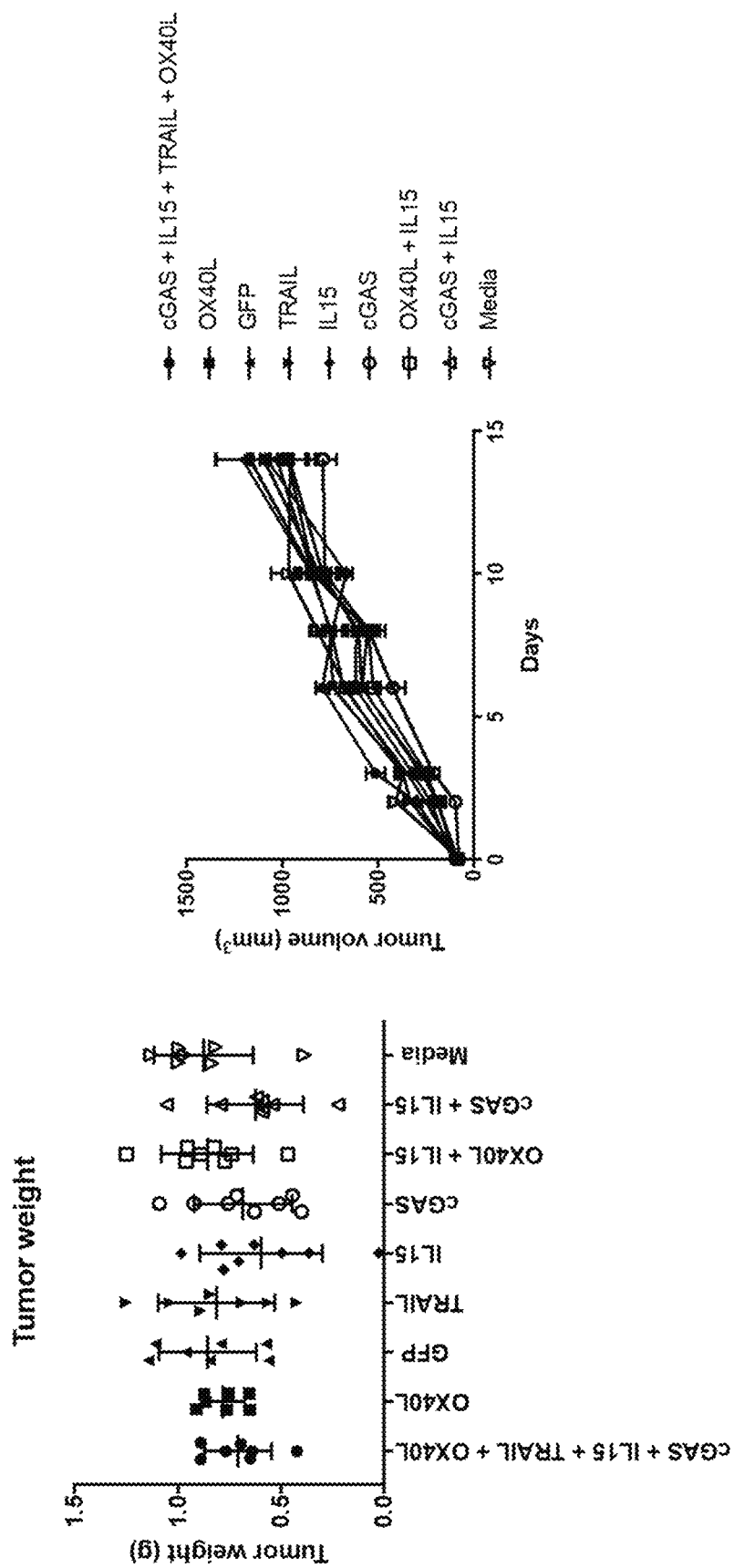
FIG. 6B includes data indicating that engineered MSCs expressing OX40L, TRAIL, IL15, cGAS, or combinations thereof do not inhibit tumor growth significantly in an orthotopic mouse model of breast cancer (4T1 triple negative breast carcinoma). Each effector was expressed by a different MSC, and the MSCs were combined (at a 1:1 ratio) for combinatorial treatment. The left graph of FIG. 6B shows the tumor weight for individual mice in each treatment, and the mean±SEM for each treatment group. The right graph of FIG. 6B shows tumor volume represented as mean±SEM for mice receiving each treatment over time.

FIGS. 6A-6B show that engineered MSCs expressing OX40L, TRAIL, IL15, cGAS, or combinations thereof do not inhibit tumor growth.

Figure 7A:
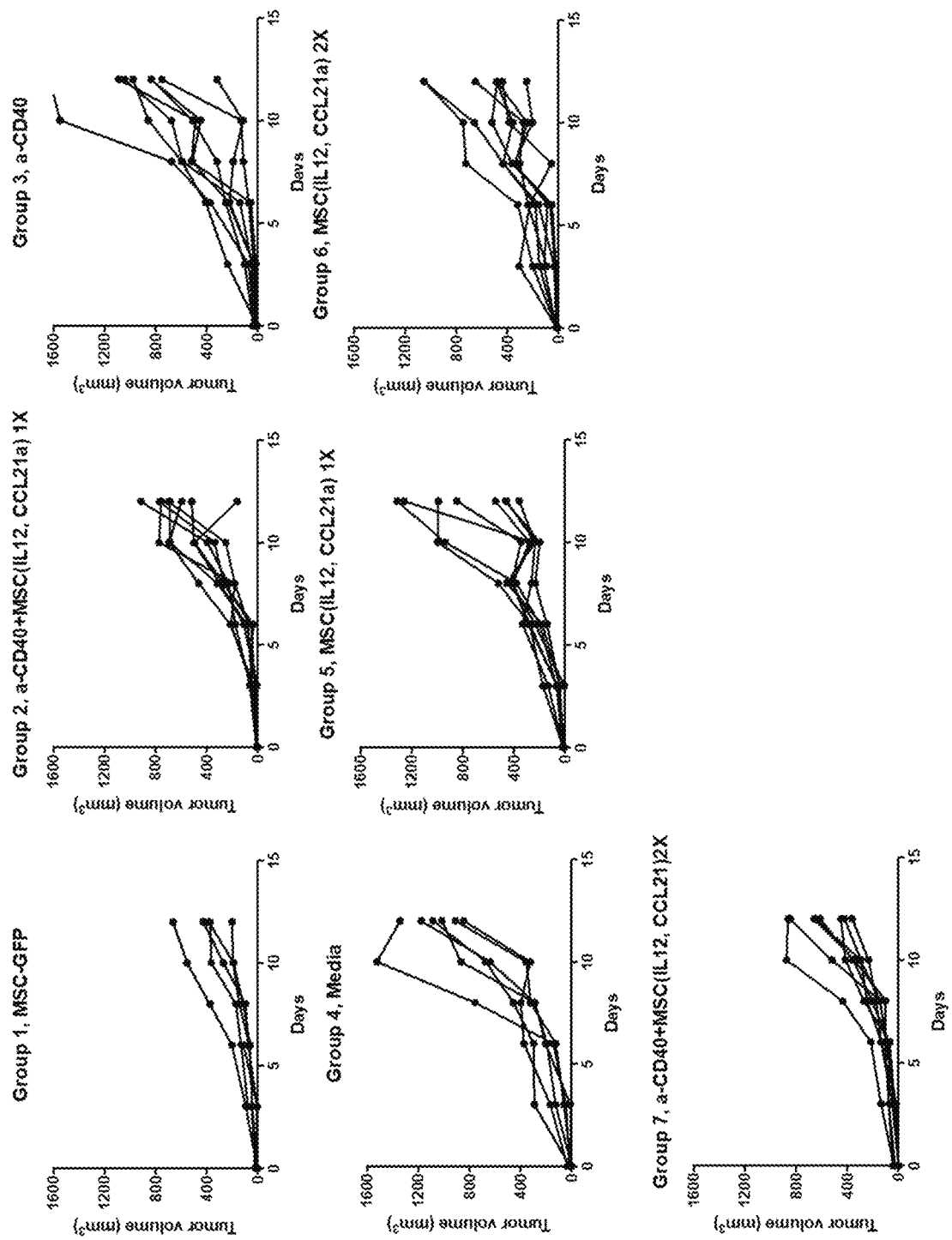
FIG. 7A includes data indicating that engineered MSCs expressing IL-12 and CCL21a inhibit tumor growth in an orthotopic mouse model of breast cancer (4T1 triple negative breast carcinoma); however the addition of anti-CD40 antibody does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 7A represents an individual mouse.
Figure 7B:
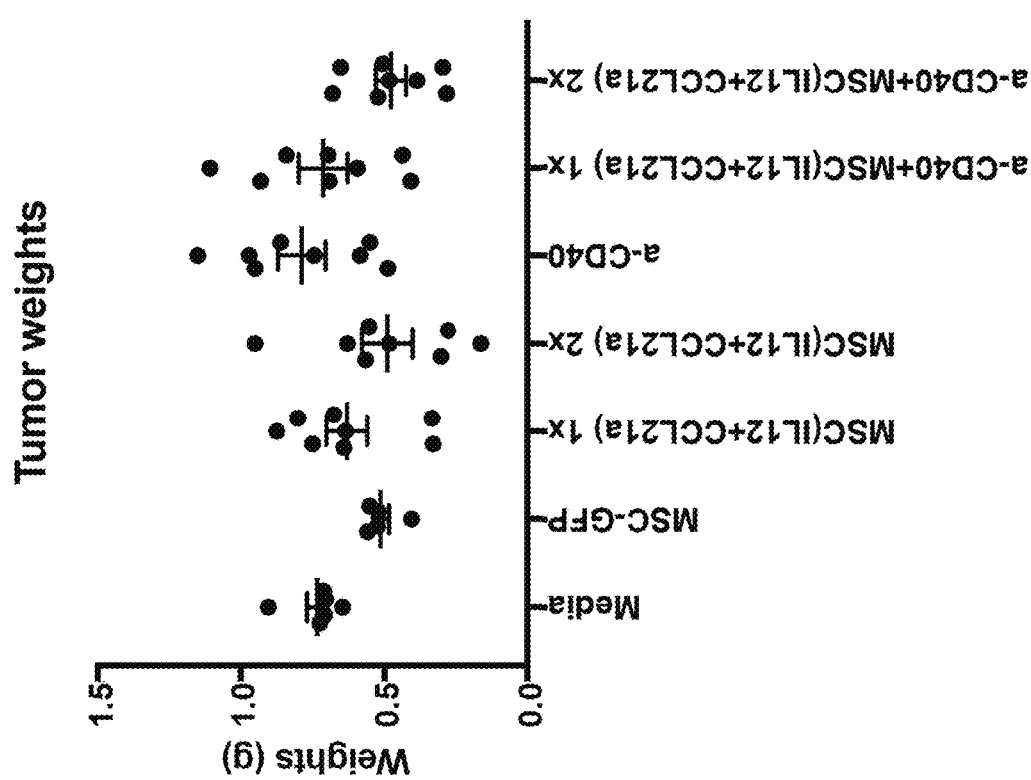
FIG. 7B includes data indicating that engineered MSCs expressing IL-12 and CCL21a inhibit tumor growth in an orthotopic mouse model of breast cancer (4T1 triple negative breast carcinoma); however the addition of anti-CD40 antibody does not reduce tumor growth. Each effector was expressed by a different MSC, and the MSCs were combined (at a 1:1 ratio) for combinatorial treatment.

FIGS. 7A-7B show that engineered MSCs expressing IL-12 and CCL21a inhibit tumor growth; however the addition of anti-CD40 antibody does not reduce tumor growth.

Figure 8A:
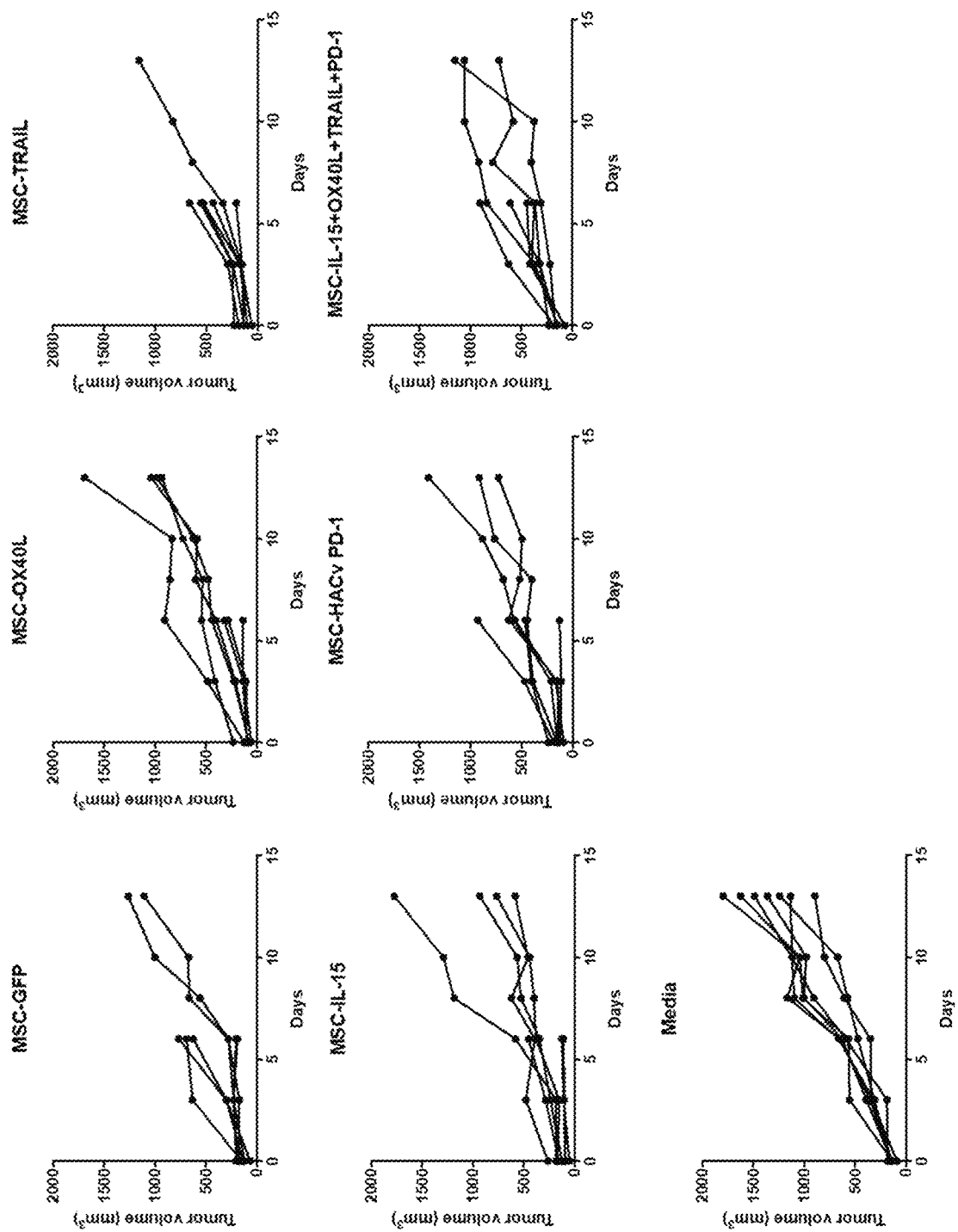
FIG. 8A includes data indicating that engineered MSCs expressing OX40L, TRAIL, IL15, HACvPD-1, or combinations thereof do not inhibit tumor growth significantly in an subcutaneous mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 8A represents an individual mouse.
Figure 8B:
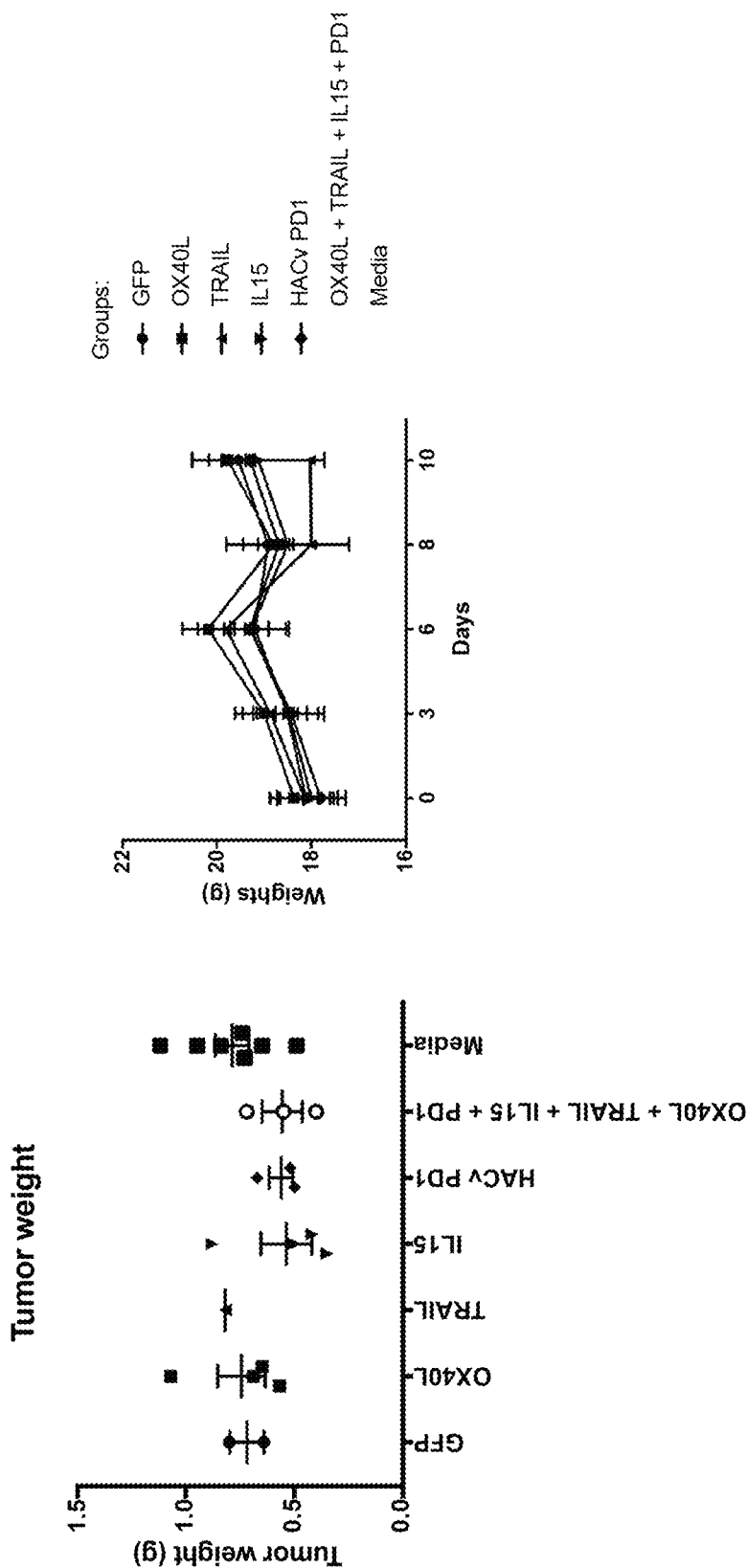
FIG. 8B includes data indicating that engineered MSCs expressing OX40L, TRAIL, IL15, HACvPD-1, or combinations thereof do not inhibit tumor growth significantly in an subcutaneous mouse model of breast cancer (4T1 triple negative breast carcinoma). Each effector was expressed by a different MSC, and the MSCs were combined (at a 1:1 ratio) for combinatorial treatment. The left graph of FIG. 8B shows the tumor weight for individual mice in each treatment, and the mean±SEM for each treatment group. The right graph of FIG. 8B shows body weight represented as mean±SEM for mice receiving each treatment over time.

FIGS. 8A-8B show that engineered MSCs expressing OX40L, TRAIL, IL15, HACvPD-1, or combinations thereof do not inhibit tumor growth significantly in a subcutaneous breast cancer model.

Figure 9A:
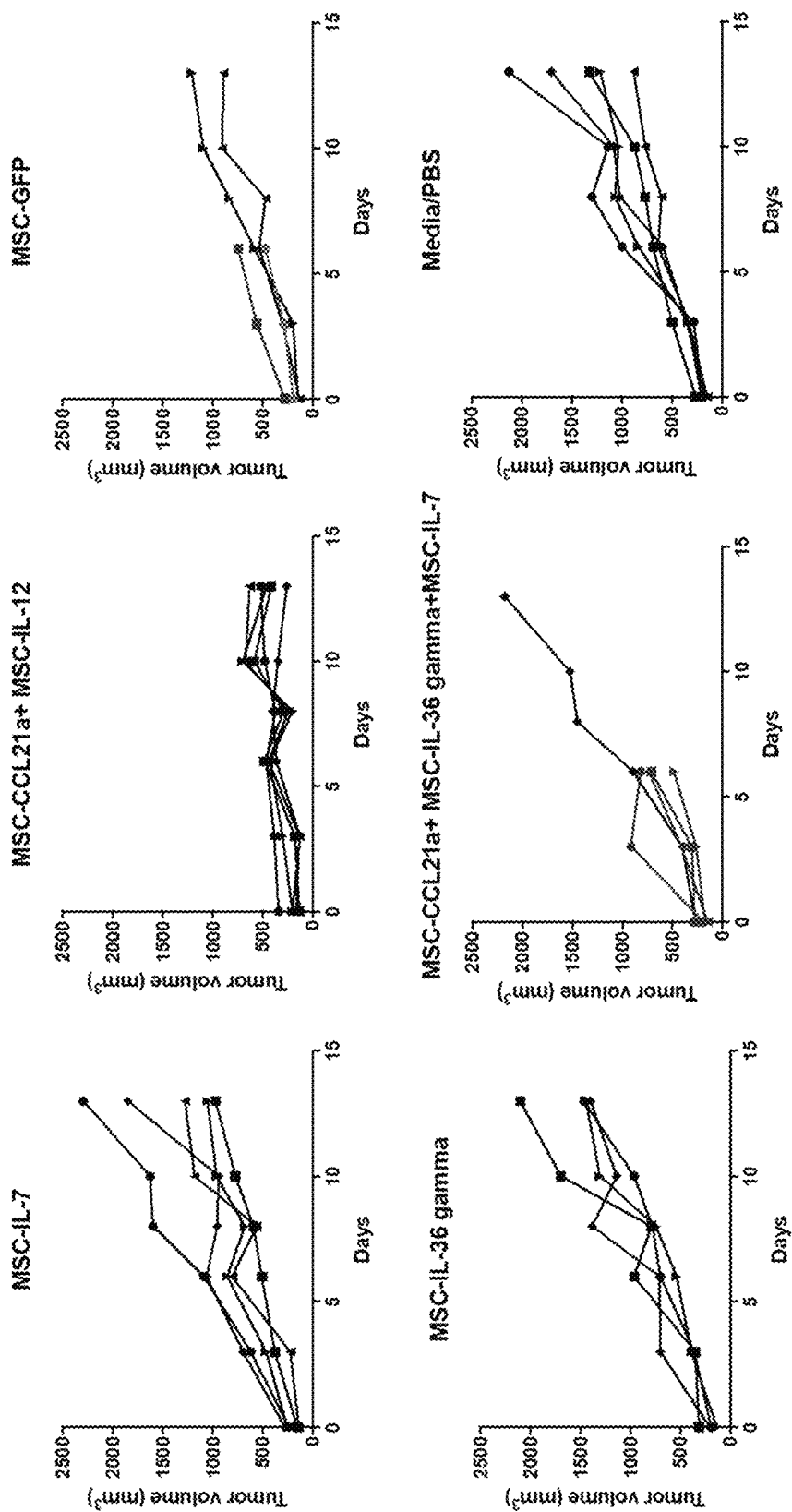
FIG. 9A includes data indicating that engineered MSCs expressing IL-12 and CCL21a inhibit tumor growth in an orthotopic mouse model of breast cancer (4T1 triple negative breast carcinoma); however the combination of MSCs expressing CCL21a, IL-36 gamma and IL-7 does not reduce tumor growth. Some of the effector combinations tested, however, may cause toxicity. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 9A represents an individual mouse.
Figure 9B:
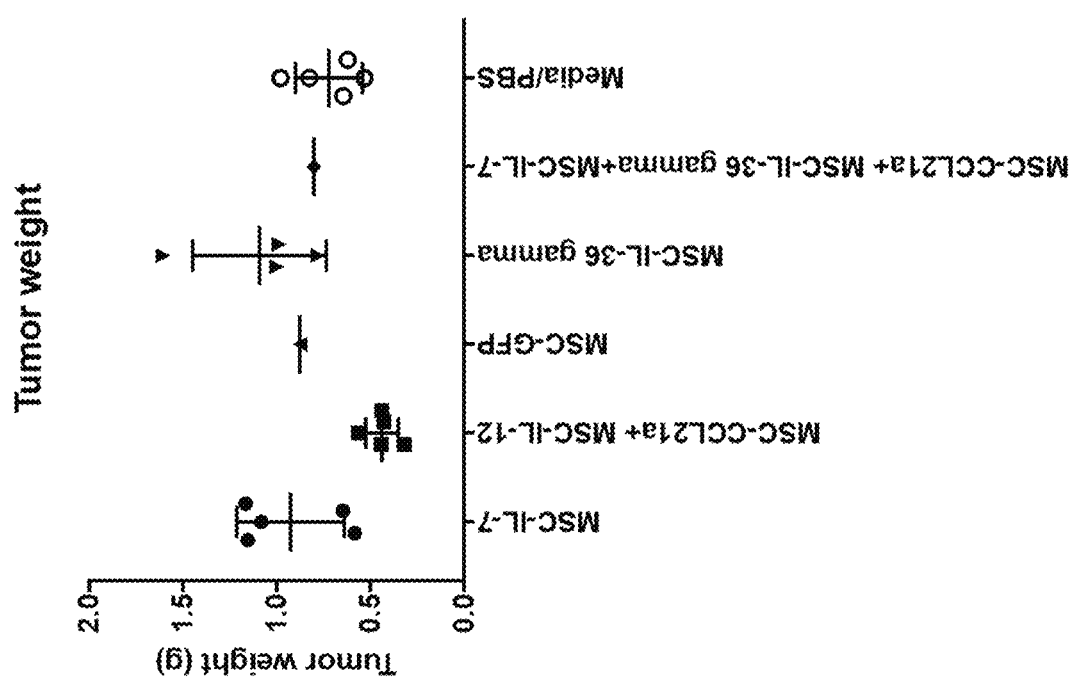
FIG. 9B includes data indicating that engineered MSCs expressing IL-12 and CCL21a inhibit tumor growth in an orthotopic mouse model of breast cancer (4T1 triple negative breast carcinoma); however the combination of MSCs expressing CCL21a, IL-36 gamma and IL-7 does not reduce tumor growth. Some of the effector combinations tested, however, may cause toxicity. Each effector was expressed by a different MSC, and the MSCs were combined (at a 1:1 ratio) for combinatorial treatment.

FIGS. 9A-9B show that engineered MSCs expressing IL-12 and CCL21a inhibit tumor growth; however the combination of MSCs expressing CCL21a, IL-36 gamma and IL-7 does not reduce tumor growth. Some of the effector combinations tested, however, may cause toxicity.

Dose Escalation

Figure 10A:
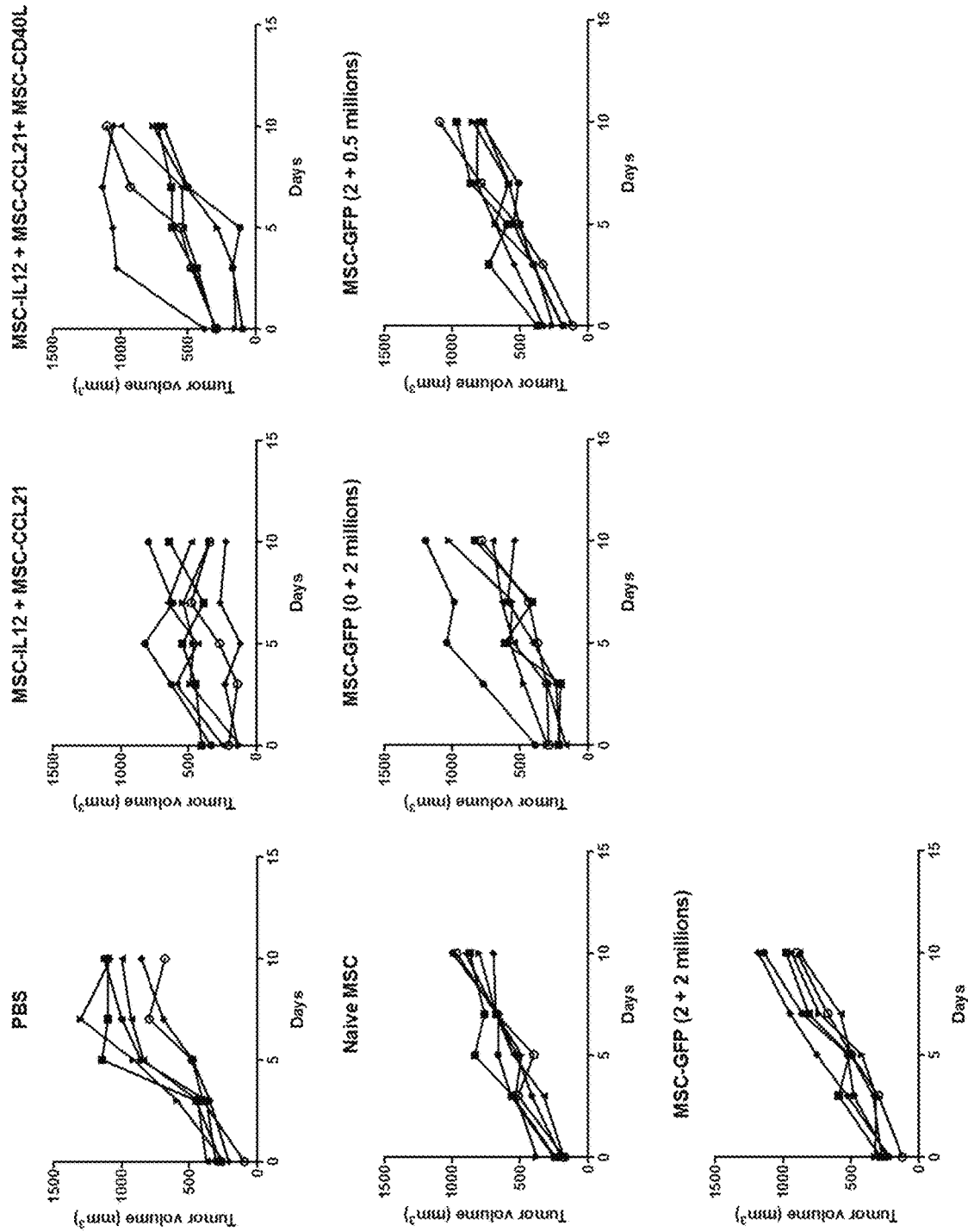
FIG. 10A includes data from a GFP dose escalation study for toxicity and screening.
Figure 10B:
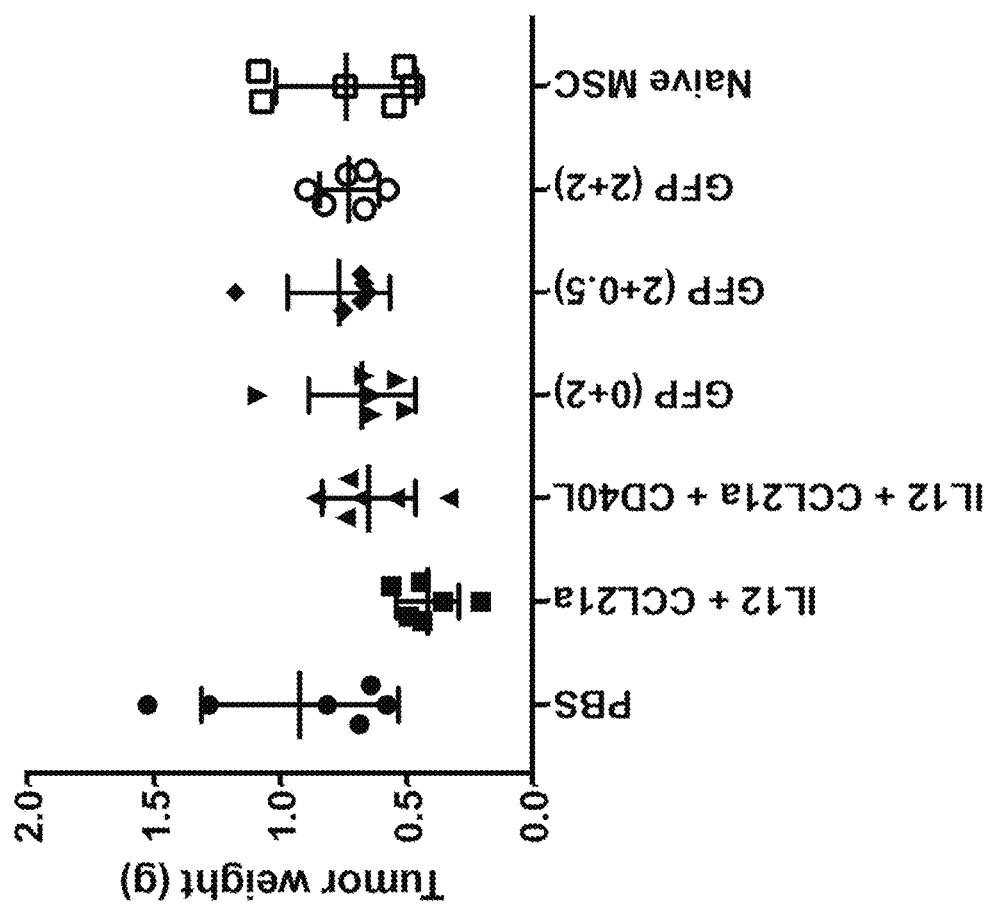
FIG. 10B includes data from a GFP dose escalation study for toxicity and screening. Each effector was expressed by a different MSC, and the MSCs were combined (at a 1:1 ratio) for combinatorial treatment.

A dose escalation study was performed. This experiment determined that engineered MSC cell expression GFP does not elicit toxicity (FIGS. 10A-10B).

Effect on Large Tumors

Figure 12:
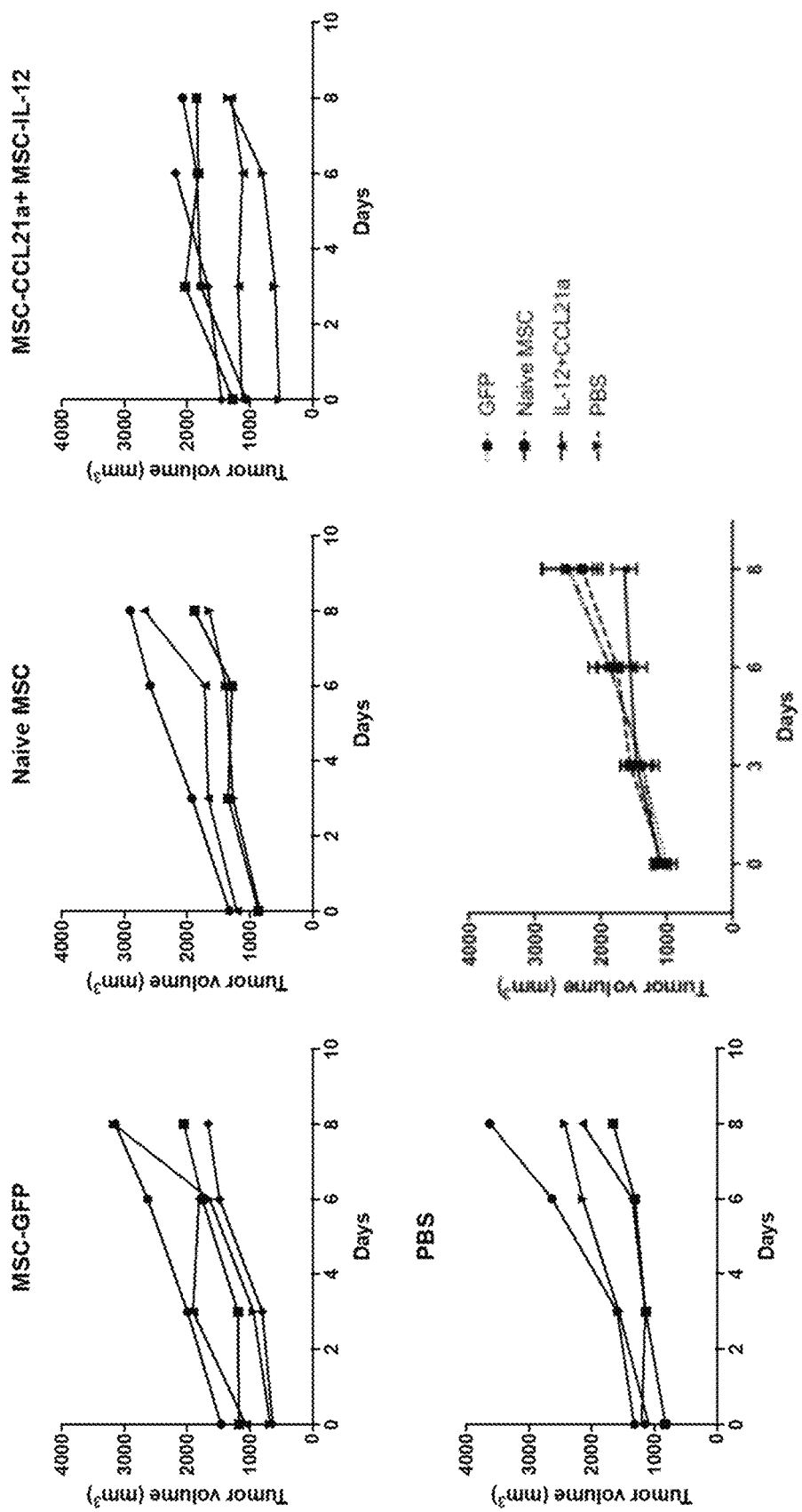
FIG. 12 includes data showing that IL-12 and CCL21a can reduce tumor expansion. Each line of FIG. 12 represents an individual mouse.

This experiment tested whether engineered mouse MSCs expressing IL12 and CCL21a can reduce tumor burden from larger tumor (>800 mm$^3$). Larger tumor are more difficult to treat than small tumor, and this experiment demonstrates this effector combination can reduce tumor expansion (FIGS. 12A-12B).

Checkpoint Inhibitors

Figure 13A:
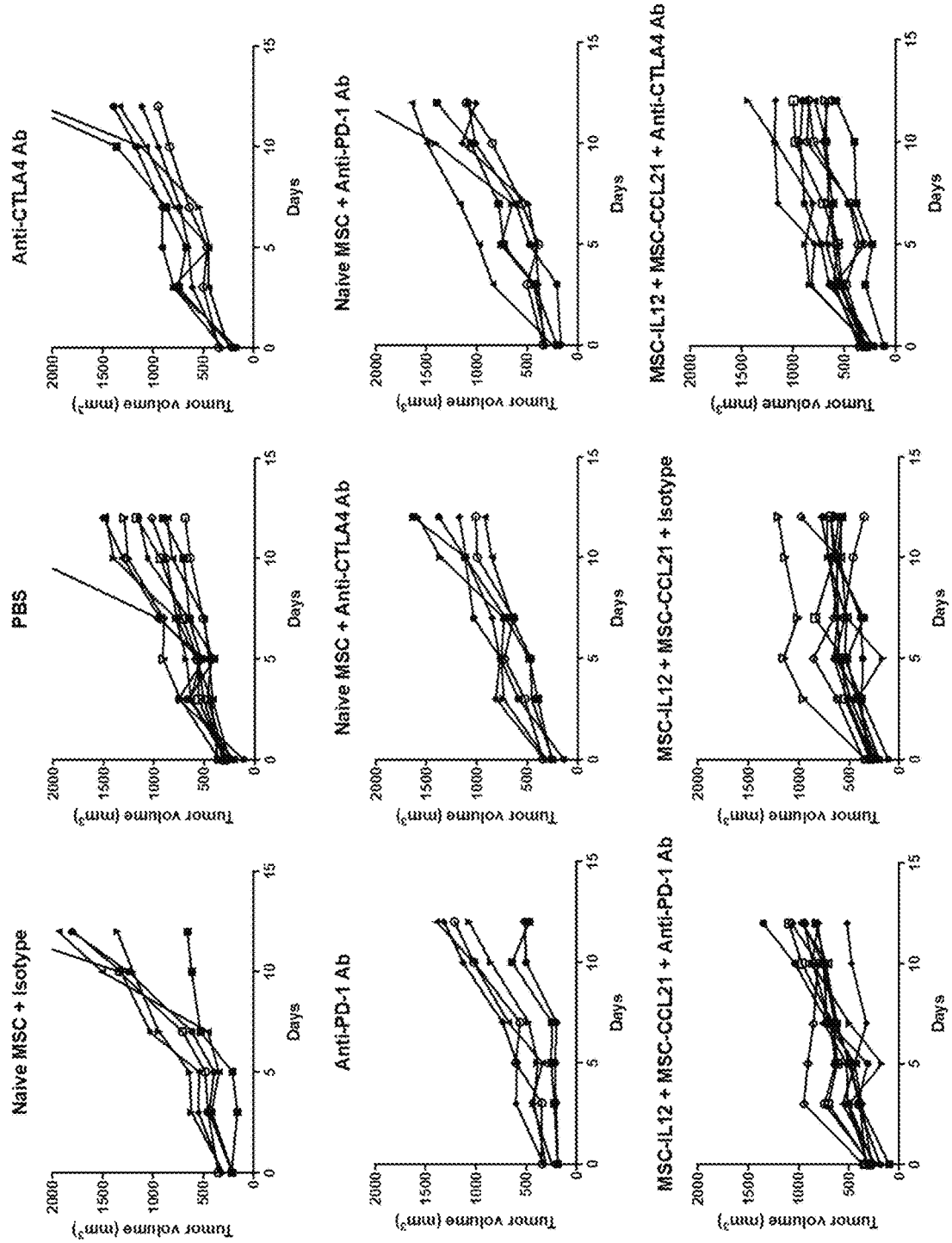
FIG. 13A includes data indicating that engineered MSCs expressing IL-12 and CCL21 are sufficient to inhibit tumor growth in an orthotopic mouse model of breast cancer (4T1 triple negative breast carcinoma), and the addition of a checkpoint inhibitor (anti-PD-1 antibody or anti-CTLA-4 antibody) did not increase efficacy. Each effector was expressed by a different MSC, and the MSCs were combined (at a 1:1 ratio) for combinatorial treatment, and the checkpoint inhibitor was injected separately. Each chart shows the effect of engineered MSCs expressing the indicated immunotherapies alone or in combination on the growth of 4T1 breast tumors in mice (n=6-8). Each line of FIG. 13A represents an individual mouse.
Figure 13B:
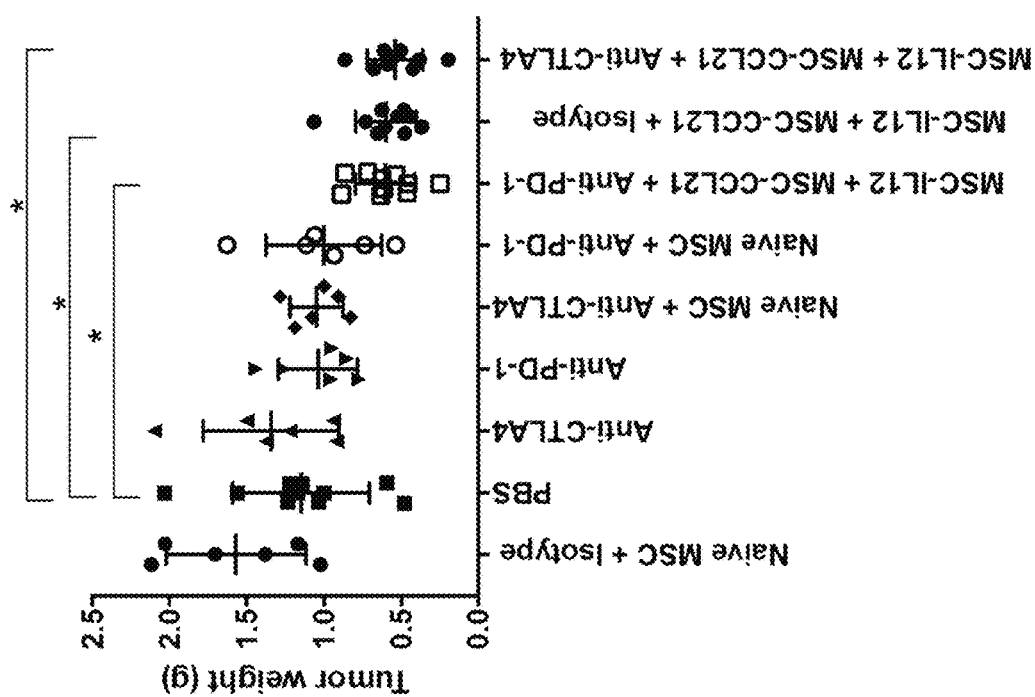
FIG. 13B includes data indicating that engineered MSCs expressing IL-12 and CCL21 are sufficient to inhibit tumor growth in an orthotopic mouse model of breast cancer (4T1 triple negative breast carcinoma), and the addition of a checkpoint inhibitor (anti-PD-1 antibody or anti-CTLA-4 antibody) did not increase efficacy. Each effector was expressed by a different MSC, and the MSCs were combined (at a 1:1 ratio) for combinatorial treatment, and the checkpoint inhibitor was injected separately.

FIG. 13A shows that engineered MSCs expressing IL-12 and CCL21 are sufficient to inhibit tumor growth, although the addition of a checkpoint inhibitor (anti-PD-1 antibody or anti-CTLA-4 antibody) by injection did not increase efficacy in a subcutaneous tumor model.

Example 5. CT26 Colorectal Carcinoma

In the following experiments, MSCs were engineered to express one of the following effector molecules, then administered, alone or in combinations, to a colorectal carcinoma mouse model: IFNβ, IL12, IL15, IL36γ, IL7, CCL21a, HACv-PD1, or 41BB. In some examples, a checkpoint inhibitor (anti-CD40 or anti-CTLA-4 antibody) was injected in combination with administration with the engineered MSCs.

Figure 14:
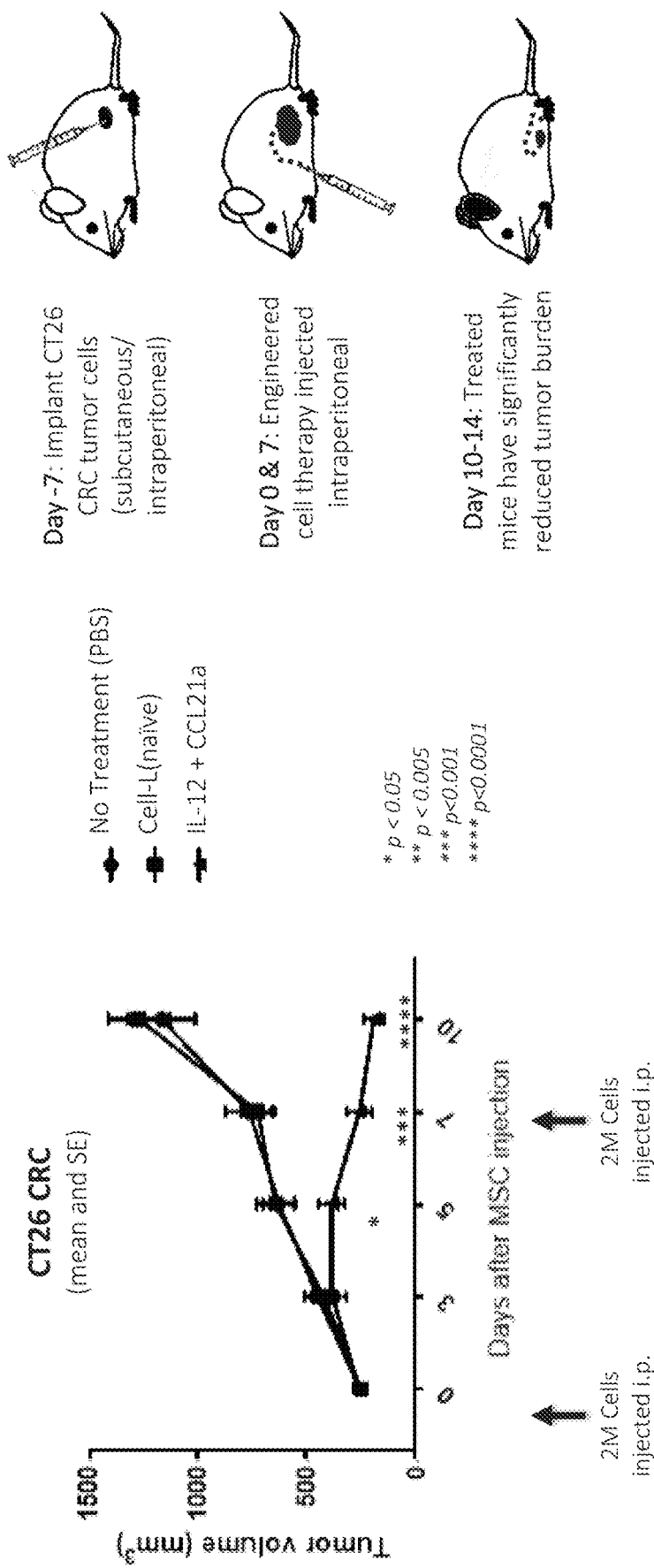
FIG. 14 shows data indicating that engineered MSCs expressing IL-12 and CCL21a induced significant tumor growth delay in a mouse model of colorectal cancer. The graph on the left shows the effects of engineered MSCs on CT26 colorectal tumor growth in mice (n=8). Each line in the chart represents tumor volume in mice receiving intraperitoneal injection of either control MSC growth media or engineered MSCs on day 0 and day 7. Mice received intraperitoneal injection of engineered MSCs expressing IL-12 and engineered MSCs expressing CCL21a. Tumor volume was determined by caliper measurements every other day. Data represent mean±SEM. *$p<0.05$, **$p<0.005$ as compared to control media group. The schematic on the right shows a timeline of treatment and the effect of engineered MSCs expressed combinatorial genes IL-12 and CCL21a on tumor burden in treated mice.

FIG. 14 shows that engineered MSCs expressing IL-12 and CCL21a induced significant tumor growth delay.

Figure 15:
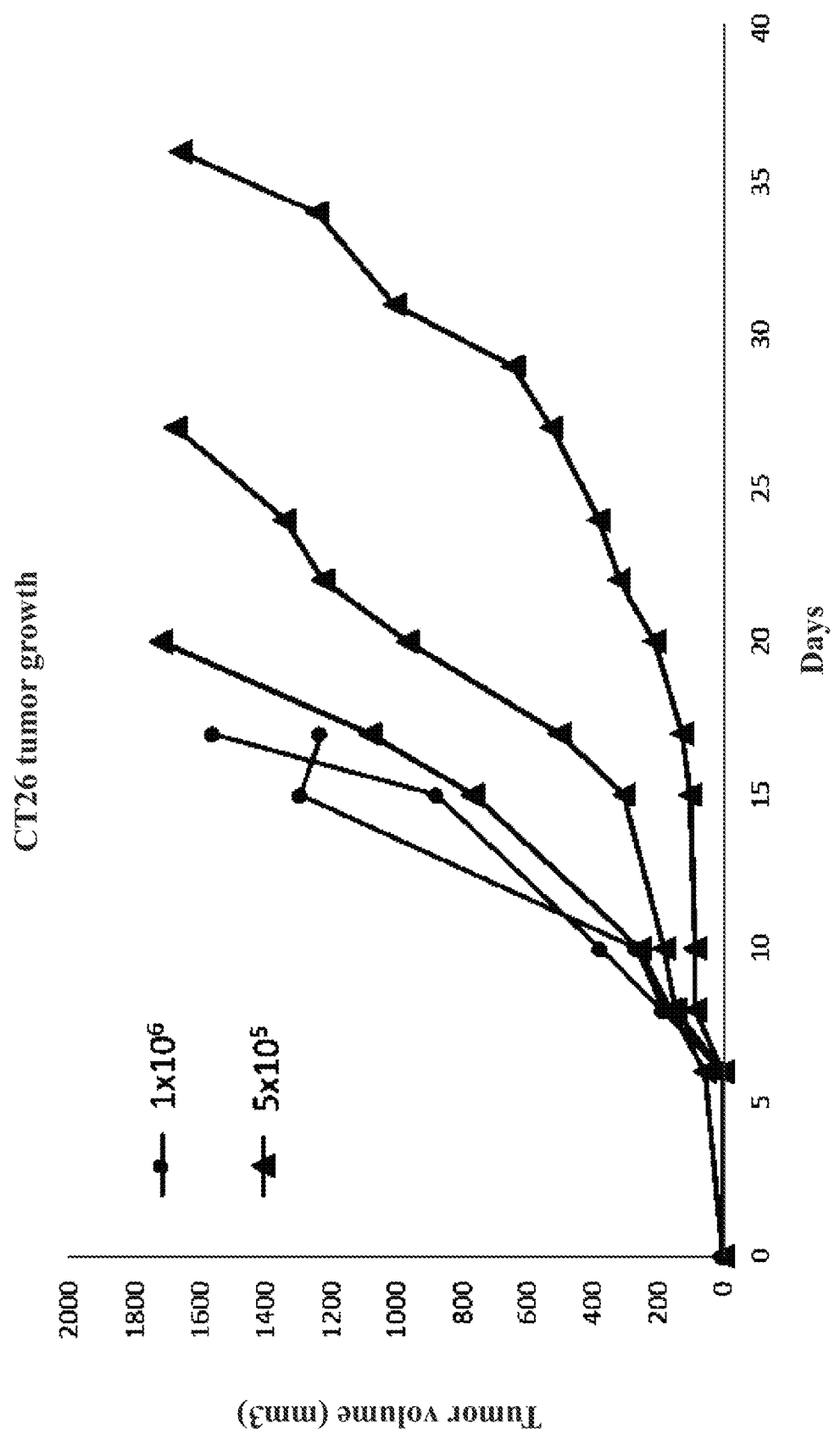
FIG. 15 is a graph showing tumor growth kinetics in the CT26 mouse model to determine optimal time for dosing the engineered MSC cells.

FIG. 15 shows tumor growth kinetics in the CT26 mouse model to determine optimal time for dosing the engineered MSC cells.

In Vivo Efficacy

Figure 16A:
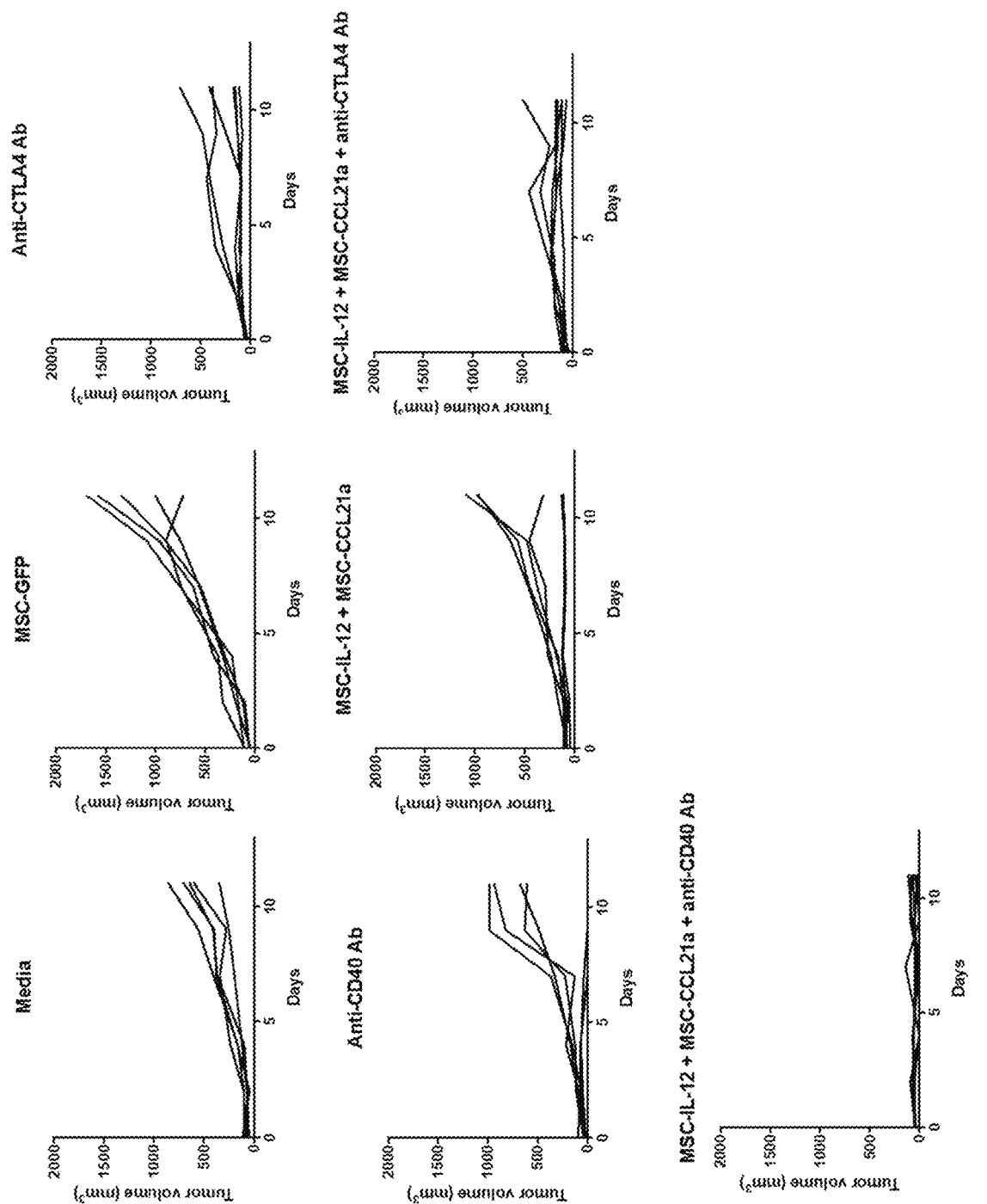
FIG. 16A includes data indicating the effects of engineered MSCs expressing IL-12 and CCL21a combined with anti-CD40 or anti-CTLA4 antibodies on average tumor growth in a syngeneic mouse model of colon cancer. Mice bearing CT26 colon tumors were treated with one of seven treatments (n=5-6 per treatment group). MSC-IL-12+MSC-CCL21a indicates treatment with engineered cells expressing IL-12 and with engineered cells expressing CCL21a (at a 1:1 ratio) for combinatorial treatment. Each line of FIG. 16A represents an individual mouse.
Figure 16B:
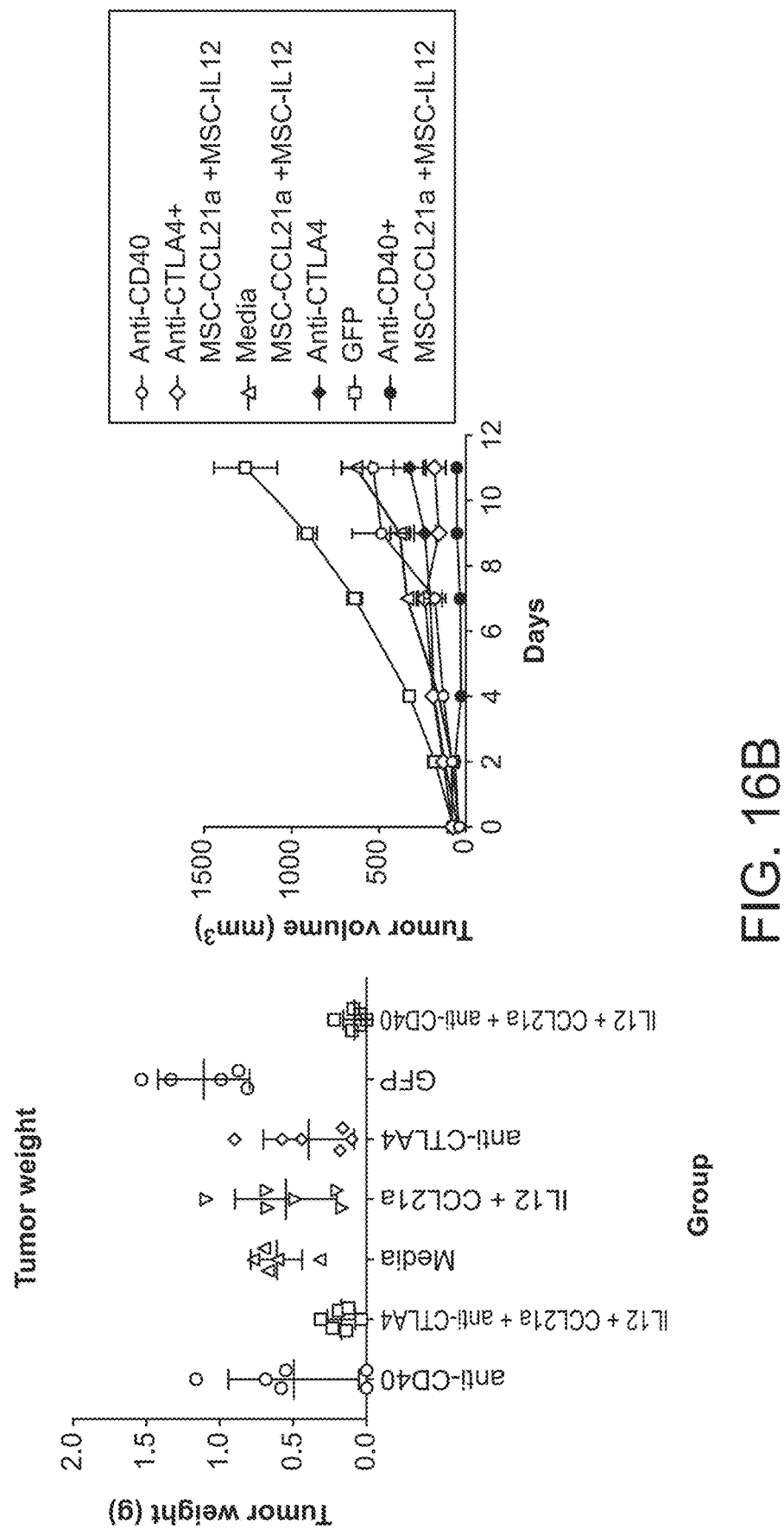
FIG. 16B includes data indicating the effects of engineered MSCs expressing IL-12 and CCL21a combined with anti-CD40 or anti-CTLA4 antibodies on average tumor growth in a syngeneic mouse model of colon cancer. Mice bearing CT26 colon tumors were treated with one of seven treatments (n=5-6 per treatment group). MSC-IL-12+MSC-CCL21a indicates treatment with engineered cells expressing IL-12 and with engineered cells expressing CCL21a (at a 1:1 ratio) for combinatorial treatment. The left graph of FIG. 16B shows the tumor weight for individual mice in each treatment, and the mean±SEM for each treatment group. The right graph of FIG. 16B shows the tumor volume represented as mean±SEM for mice receiving each treatment over time.

The following experiments demonstrate the in vivo efficacy of MSCs expressing immunotherapy effectors (payloads) in the subcutaneous mouse model of colon (colorectal) cancer. CT26-Neo-Fluc mouse colon cancer cells (Imanis Life Sciences, 5×10$^5$) were injected subcutaneously into the flanks of female BALB/cJ mice (The Jackson Laboratory). Seven days after tumor implantation, mice were then randomized into the following treatment groups: control MSC growth media, engineered MSCs (MSC-12+CCL21a), anti-CD40 antibody, anti-CTLA4 antibody (Bio X cell), MSC-12+CCL21a in combination with anti-CD40 antibody or MSC-12+CCL21a in combination with anti-CTLA4 antibody. Engineered MSCs (2×10$^6$ cells) were injected intraperitoneally (ip) once a week for two weeks (Day 0 and 7). Anti-CD40 antibodies were injected ip (100 μg) on Days 0 and 3. Anti-CTLA4 antibodies were injected ip (100 μg) on Days 0, 3 and 7. Tumor growth was monitored by caliper measurements every other day, and mouse weights were recorded twice weekly. Mice were euthanized 11 days after first MSC treatment and tumors were collected and weighed. The tumor weight of individual mice in each treatment group was measured and the results are shown in the bottom left of FIG. 16B (left graph). The average tumor volume of each treatment group was monitored over time (FIG. 16B, right graph). Treatment Groups 2 (IL-12+CCL21a+anti-CTLA4 antibody), 4 (IL-12+CCL21a) and 7 (IL-12+CCL21a+anti-CD40 antibody) inhibited the average growth of CT26 colon tumors compared to GFP-treated mice (FIG. 16B, right graph). Similar results were observed when the tumor volume of individual mice in each treatment group was measured over time (FIG. 16A). Therefore, combinatorial treatment with MSCs expressing immunotherapies inhibited the growth of colon cancer cells in vivo.

Figure 18A:
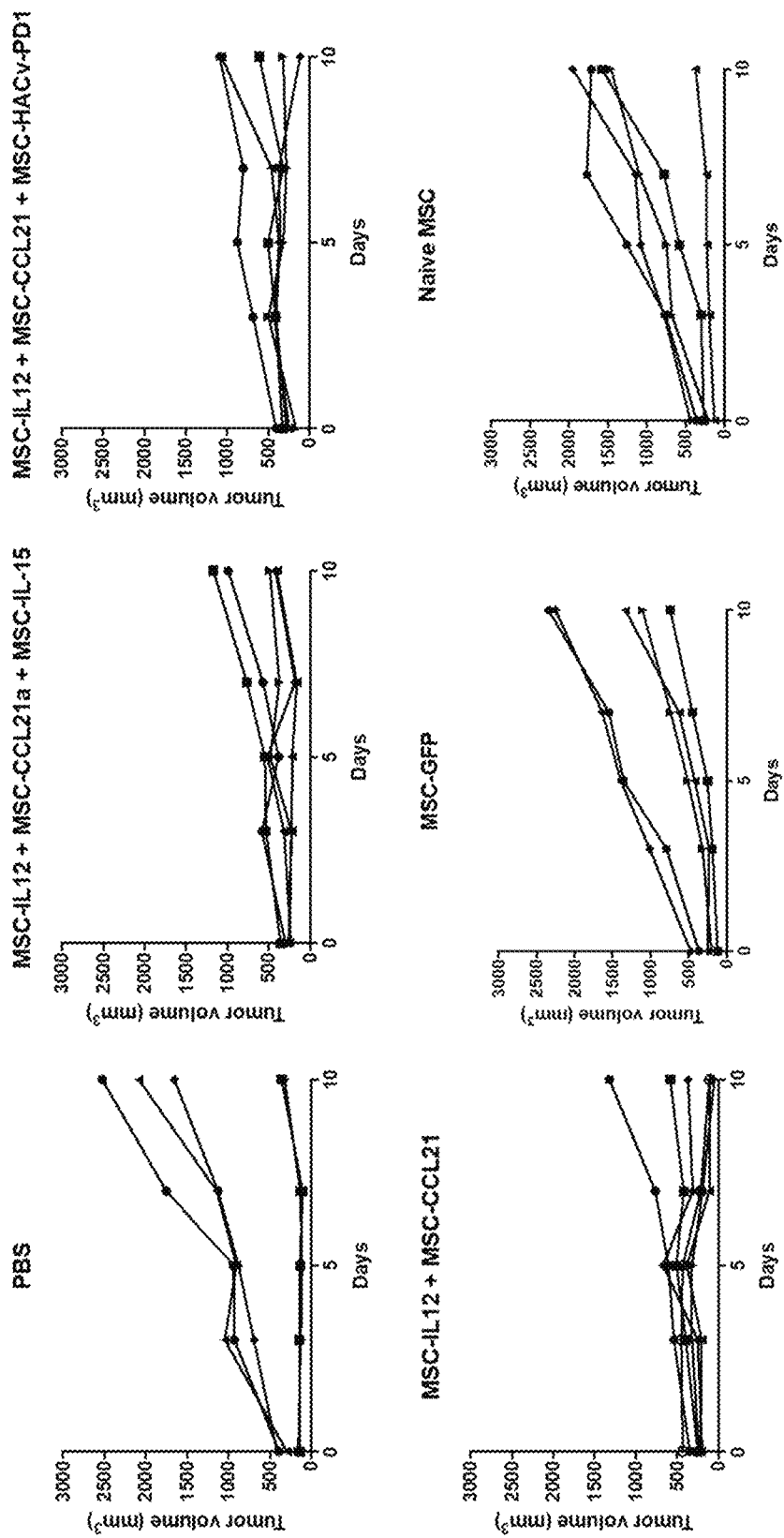
FIG. 18A includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 colorectal tumors in mice (n=6-8). Each line of FIG. 18A represents an individual mouse.
Figure 18B:
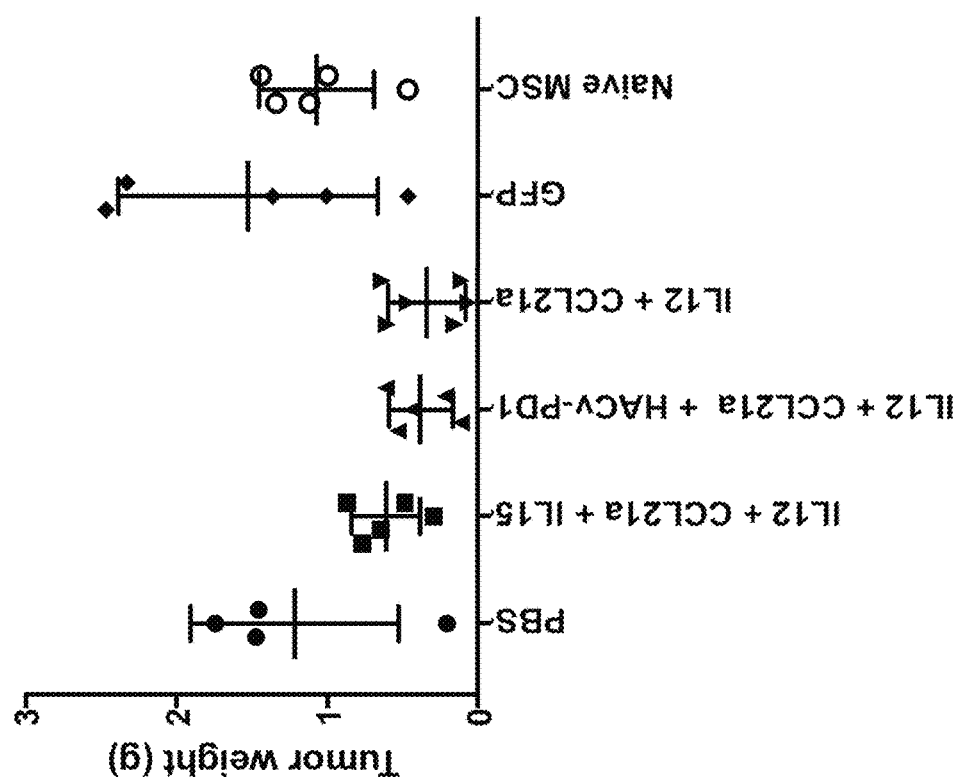
FIG. 18B includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 18C:
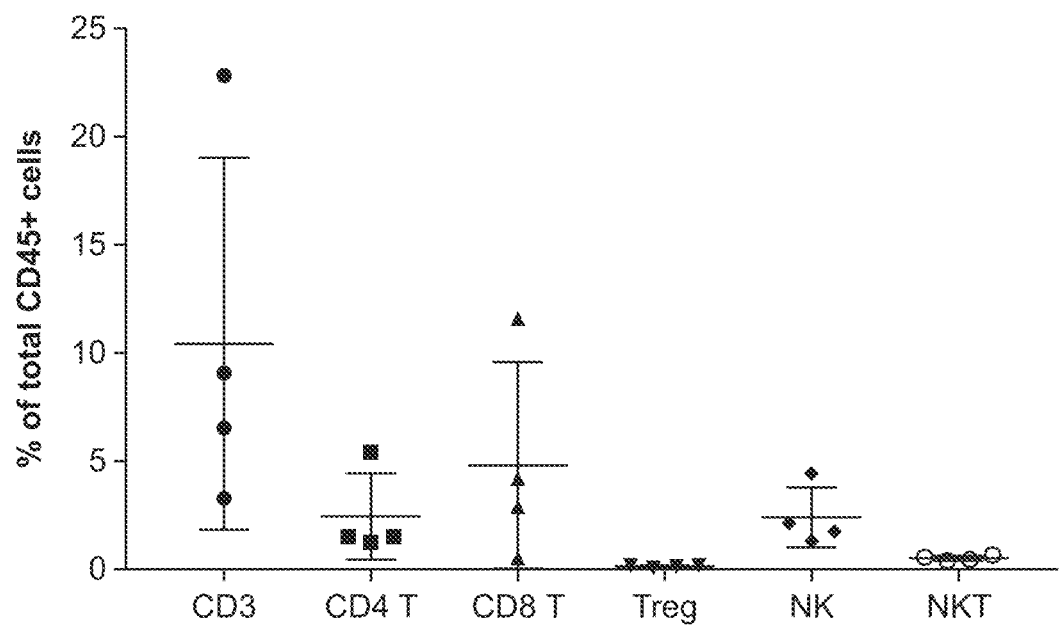
FIG. 18C includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 18C:
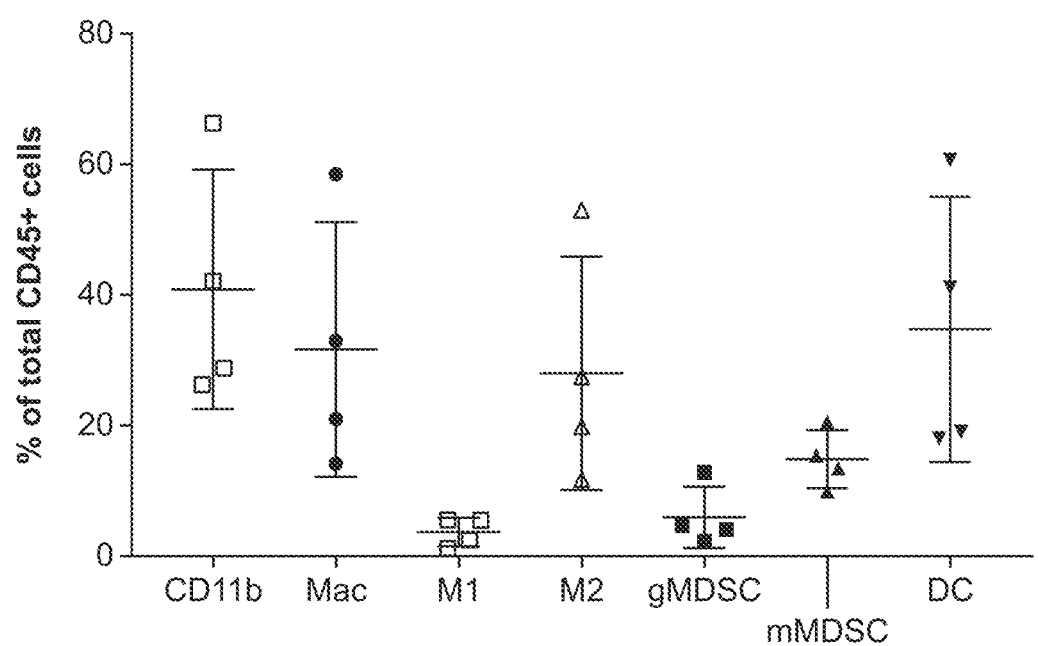
Figure 18D:
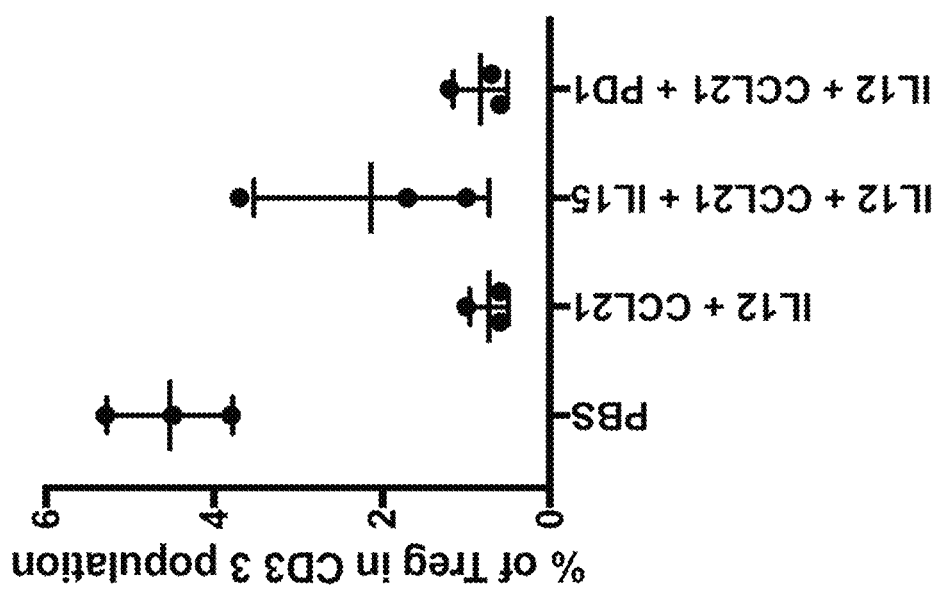
FIG. 18D includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 18E:
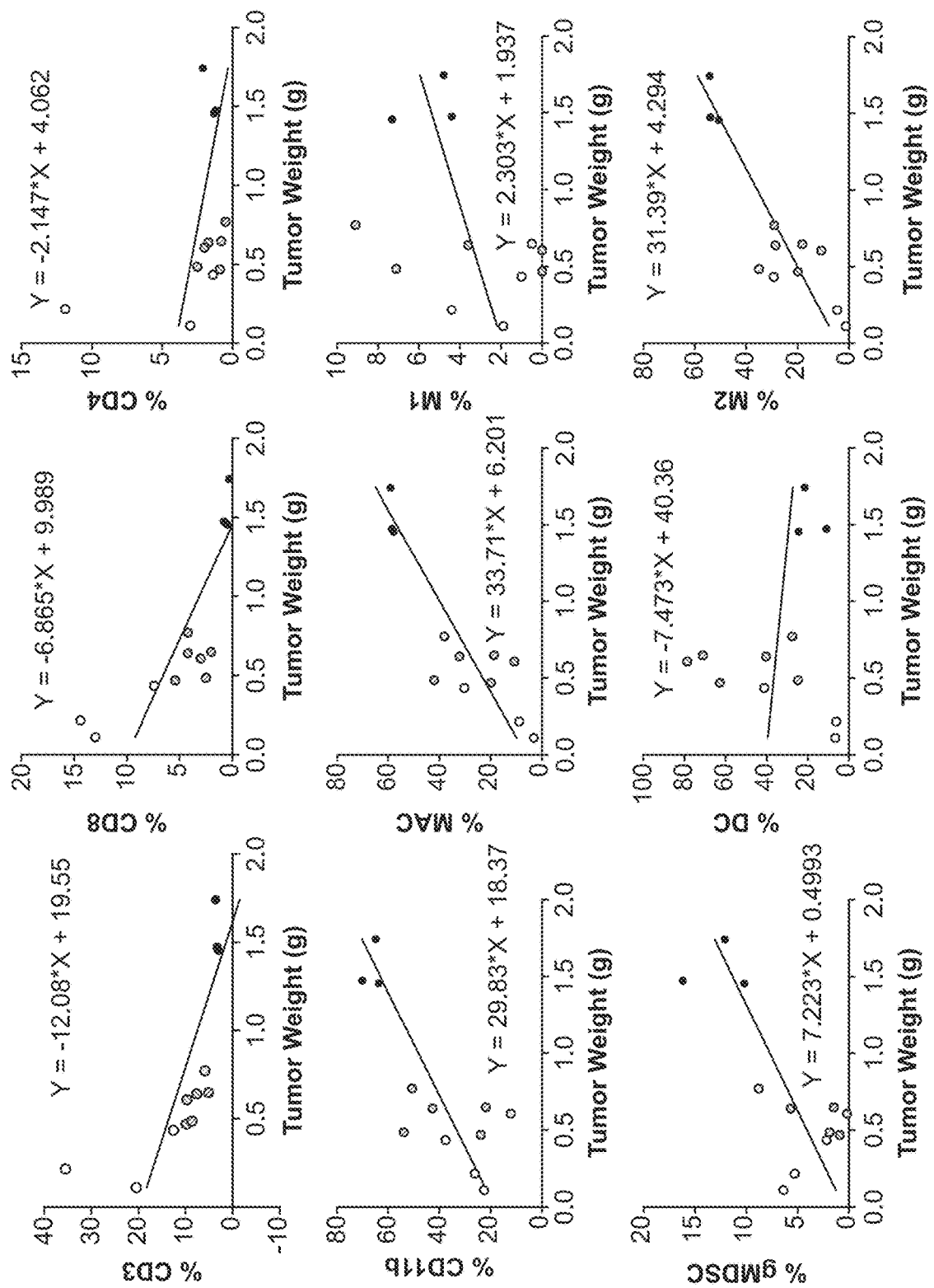
FIG. 18E includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 19:
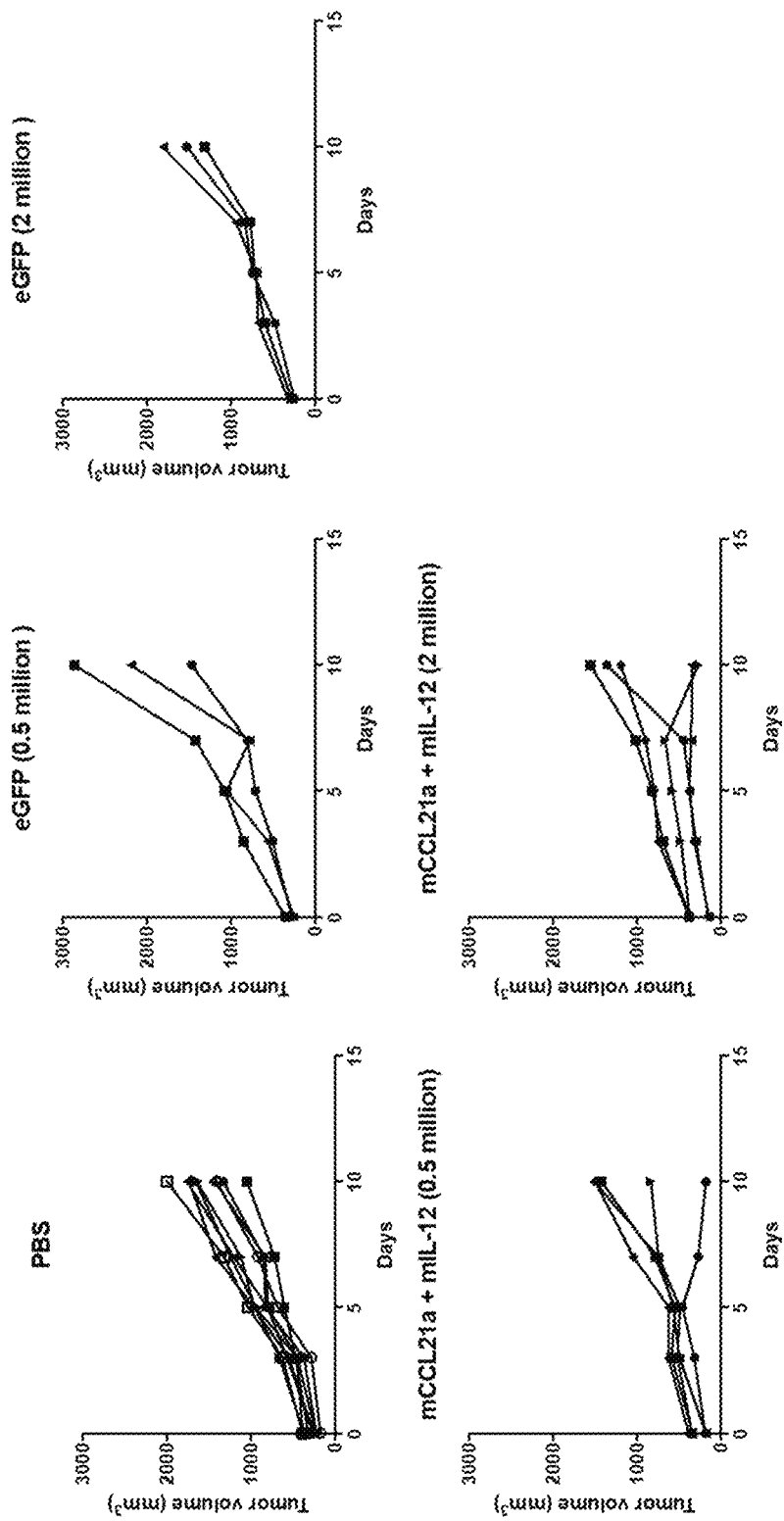
FIG. 19 shows the tumor volume for individual mice in each treatment. Efficacy was determined by tumor volume from caliper measurement every other day.

FIG. 18A shows that engineered MSCs expressing IL-12, CCL21a, and either IL15 or HACvPD-1 inhibit tumor growth significantly in a mouse model of colorectal cancer. FIG. 18B shows the tumor weight for individual mice in each treatment. FIG. 18C is a representative graph of the infiltrating immune population within the tumor microenvironment. FIG. 18D shows the percentage of regulatory T cells (Treg) in the total CD3 population. There was a significant decrease in the numbers of Tregs in the tumor microenvironment treated with engineered MSC-IL2 and CCL21a. FIG. 18E correlates the percentage of immune infiltration with tumor weight. Samples with increase in lymphocytes (CD3+) were found to correlate with low tumor weight, while samples with high myeloid (CD11b+) infiltration were correlated with higher tumor burden.

Long-Term Survival

Figure 17A:
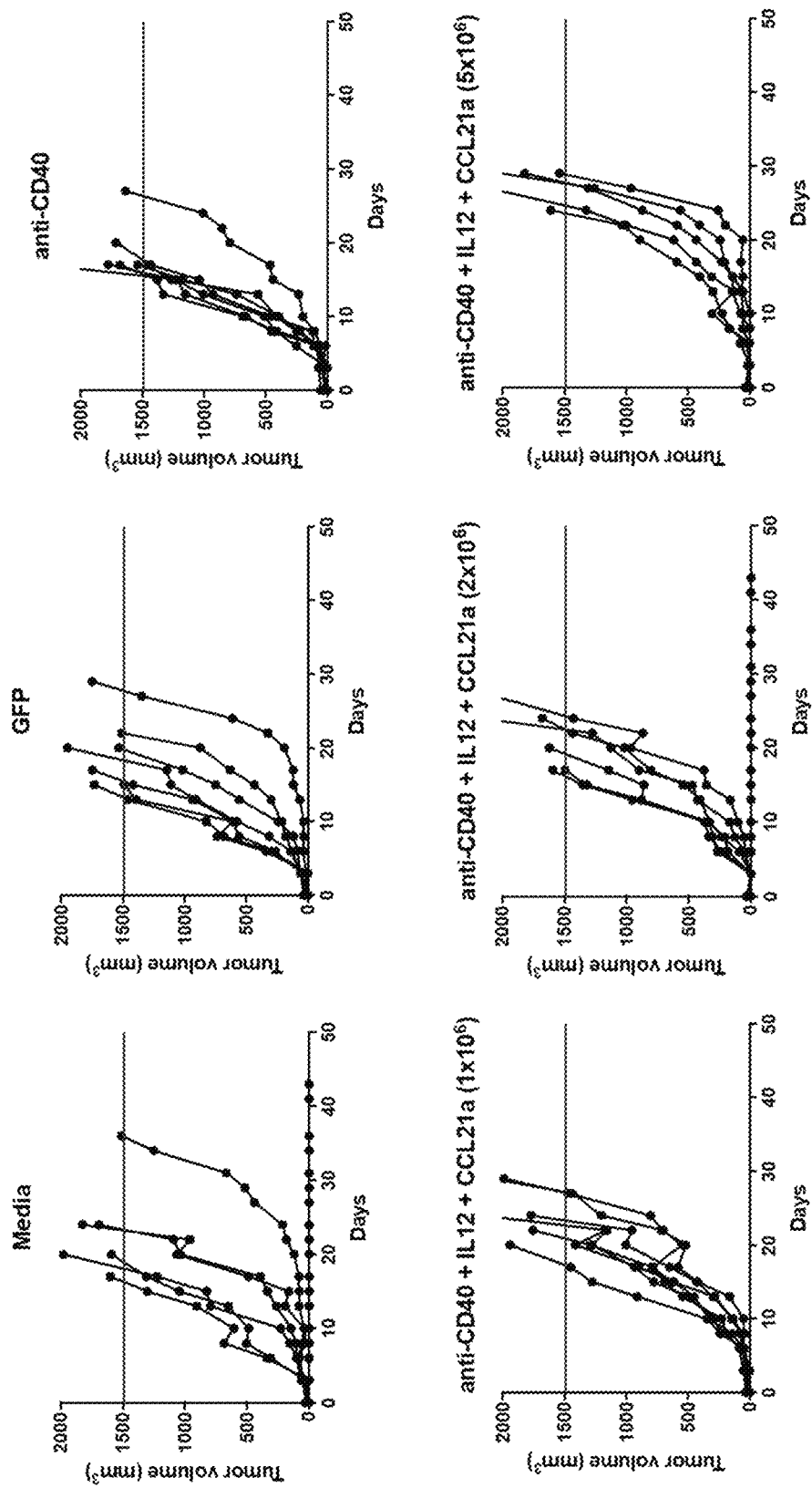
FIG. 17A includes data from a dose-dependent long-term survival study.
Figure 17B:
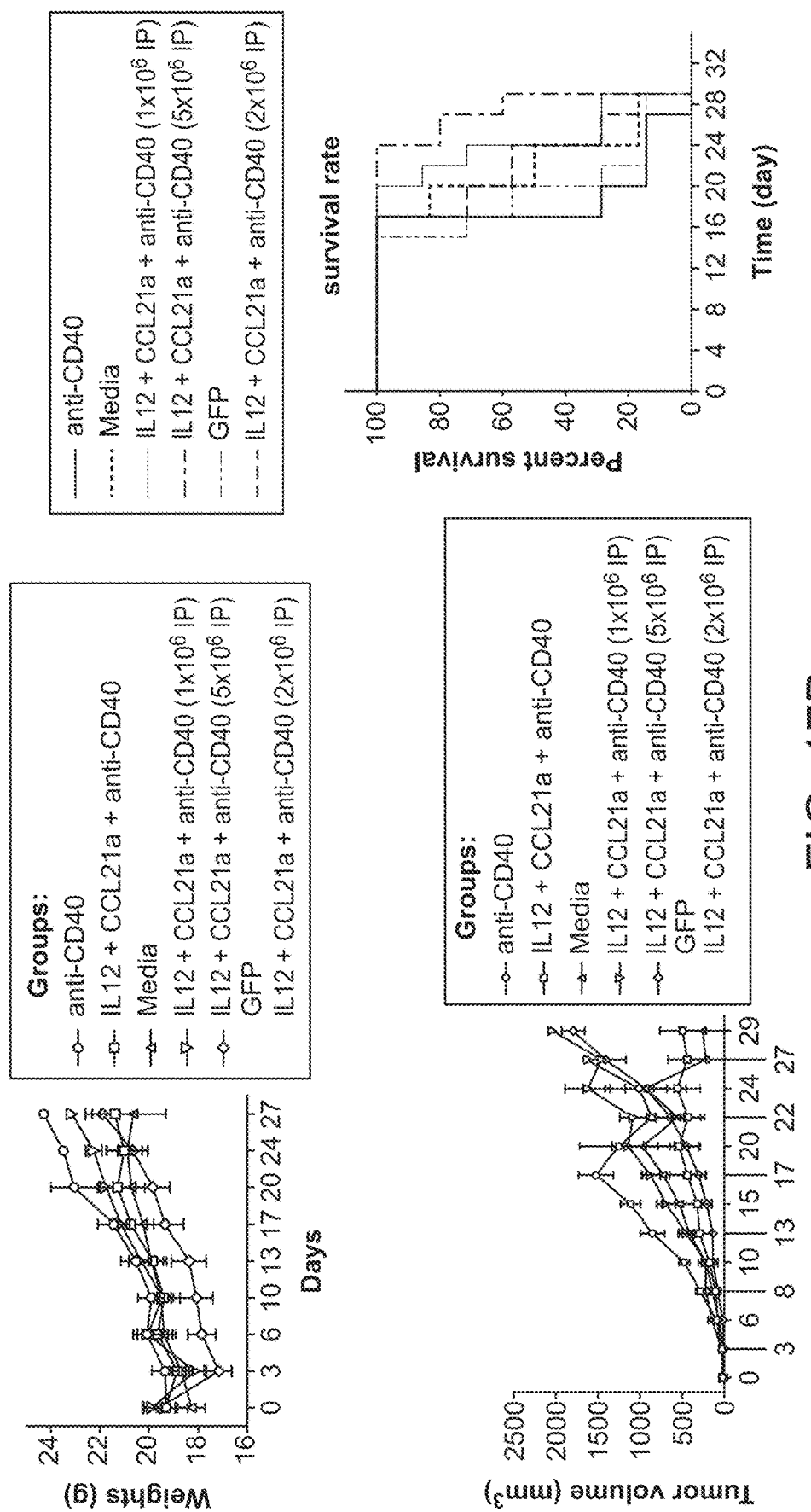
FIG. 17B includes data from a dose-dependent long-term survival study.

Mice were dosed twice with different concentration of engineered MSC-IL12 and CCL21a therapy in combination with injected anti-CD40 antibody. After the second dose, tumor volume was monitored twice a week until tumor burden is greater than 1500 mm$^3$ and the mice were sacrificed. FIG. 17A shows the tumor volume of the individual group. FIG. 17B, left graph, tracks the mice weight and tumor volume from individual group over time. FIG. 17B, right graph, shows the survival plot of the different groups.

MSC Efficacy

Figure 20:
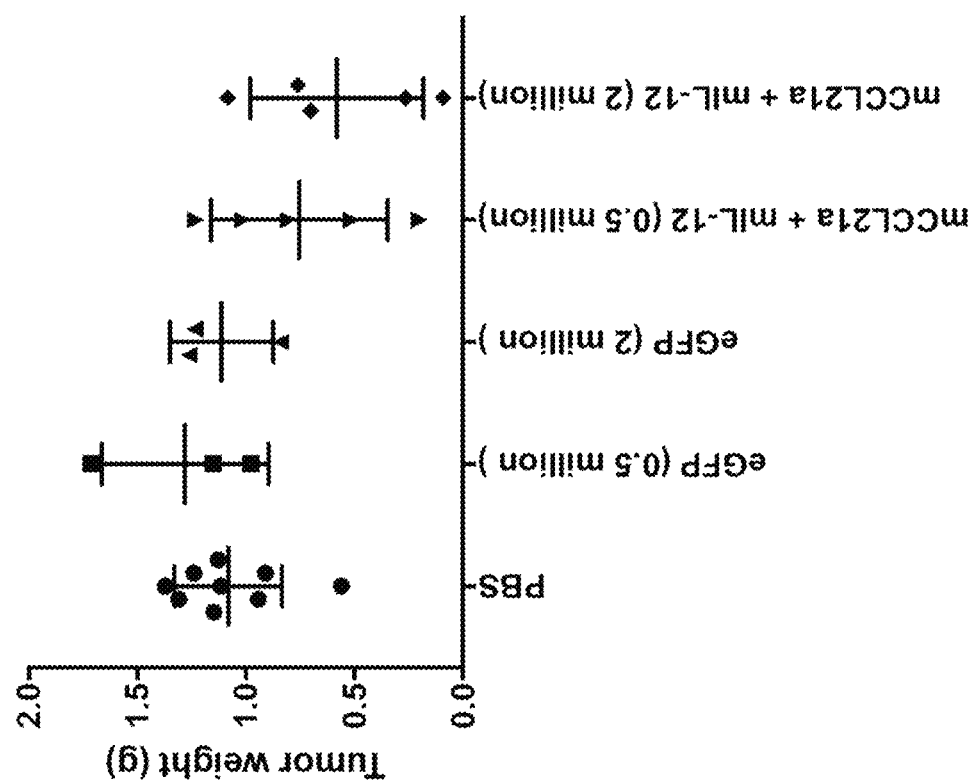
FIG. 20 shows the tumor weight for individual mice in each treatment, and the mean±SEM for each treatment group. Efficacy was determined by tumor weight.

FIG. 20A shows the tumor volume for individual mice in each treatment. FIG. 20B shows the tumor weight for individual mice in each treatment. Efficacy was determined by tumor volume from caliper measurement every other day.

Tumor Growth Kinetics

Figure 21A:
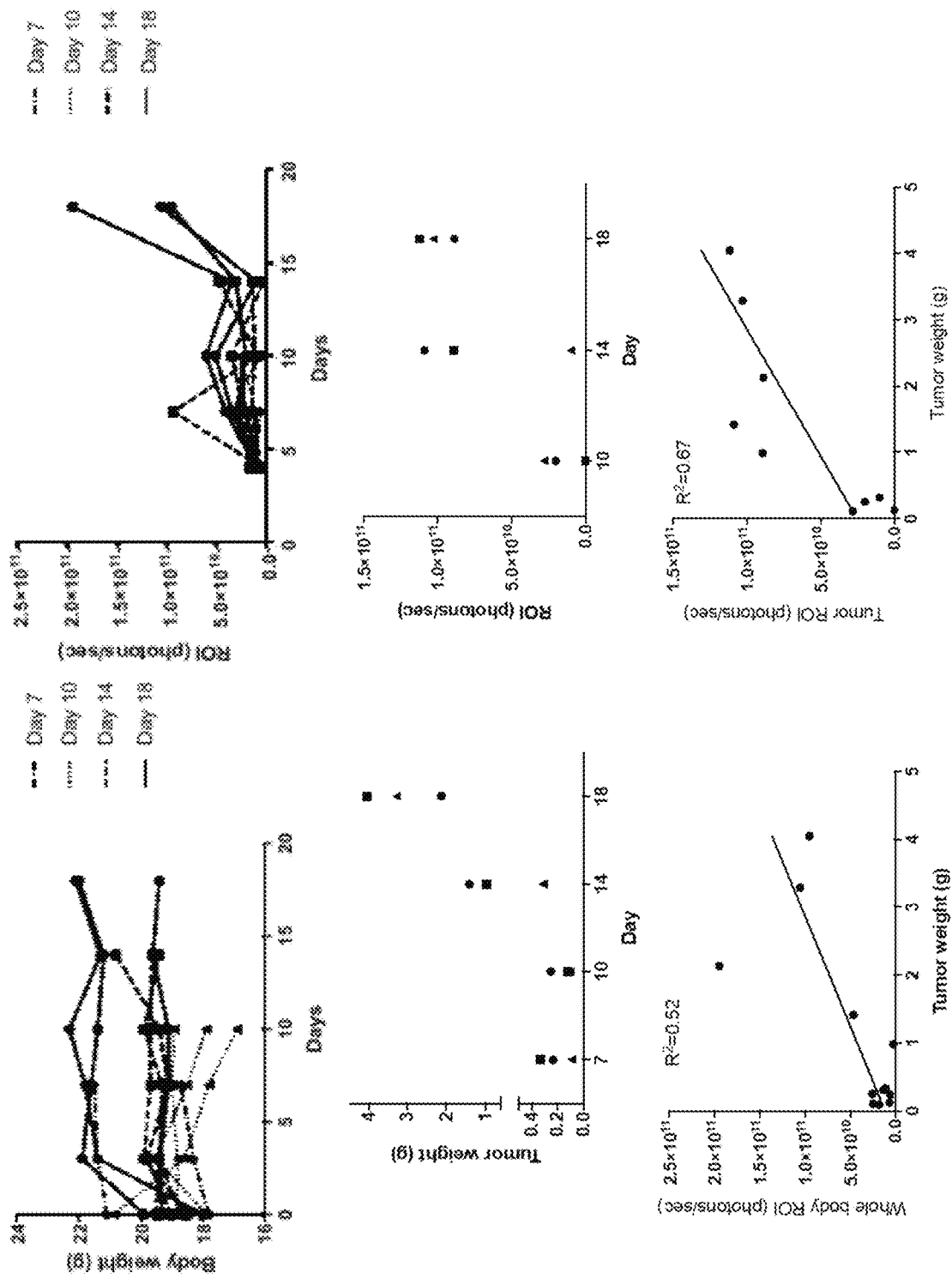
FIG. 21A shows the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth. The first row of FIG. 21A measures the mice body weight (left panel) and ROI (right panel) with an IVIS imager to monitor tumor burden. The second row monitors the tumor weight (left panel) and the ROI (right panel) of the tumor of individual mice in each group. The third row correlates the tumor weight with either whole body ROI (left panel) or tumor ROI (right panel).
Figure 21B:
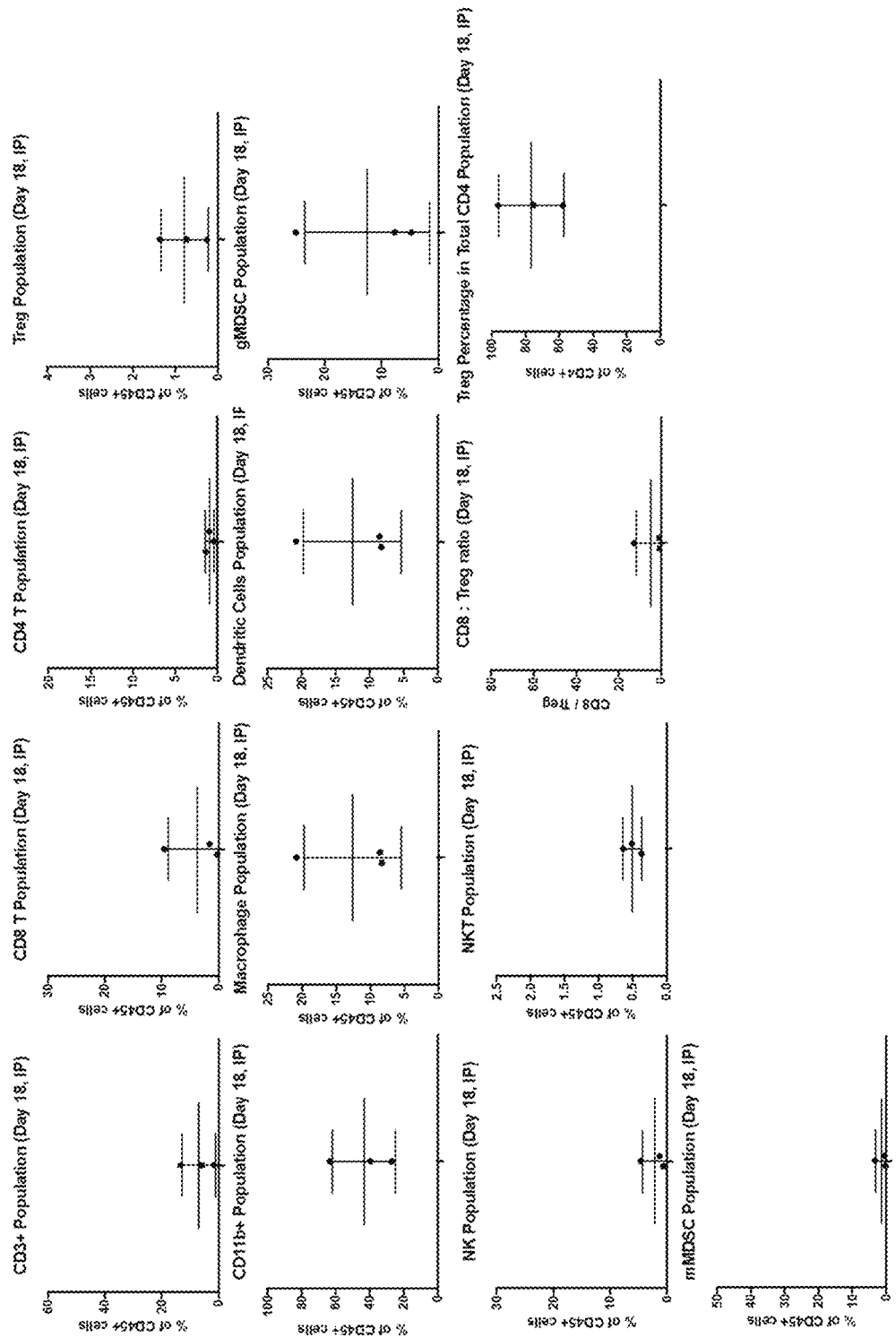
FIG. 21B shows the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth.

FIGS. 21A-21B show the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth. The first row of FIG. 21A measures the mice body weight and ROI with an IVIS imager to monitor tumor burden. The second row monitors the tumor weight and the ROI of the tumor of individual mice in each group. The third row correlates the tumor weight with either whole body ROI or tumor ROI. FIG. 21B shows the immune profile of three (3) mice in the day 18 group to better understand the tumor microenvironment.

Tumor Infiltrate Statistics/Immune Percentage/Tumor Weight

Subcutaneous Mouse Model

Figure 22A:
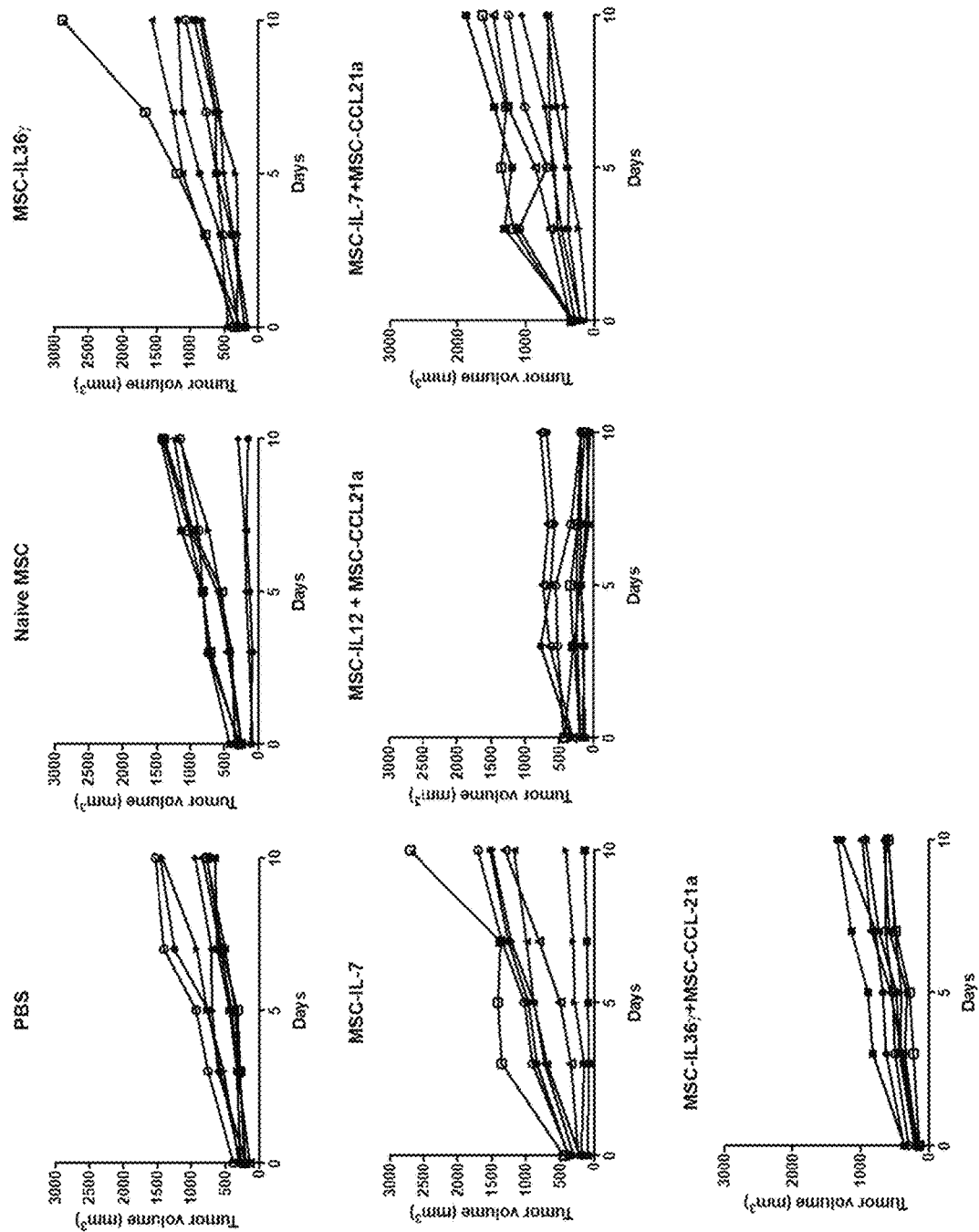
FIG. 22A includes data indicating that engineered MSCs expressing IL-12 and CCL21a inhibit tumor growth in a subcutaneous mouse model of colorectal cancer; however the combination of MSCs expressing CCL21a and IL-36 gamma or IL-7 does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 colon tumors in mice (n=6-8). Each line of FIG. 22A represents an individual mouse.
Figure 22B:
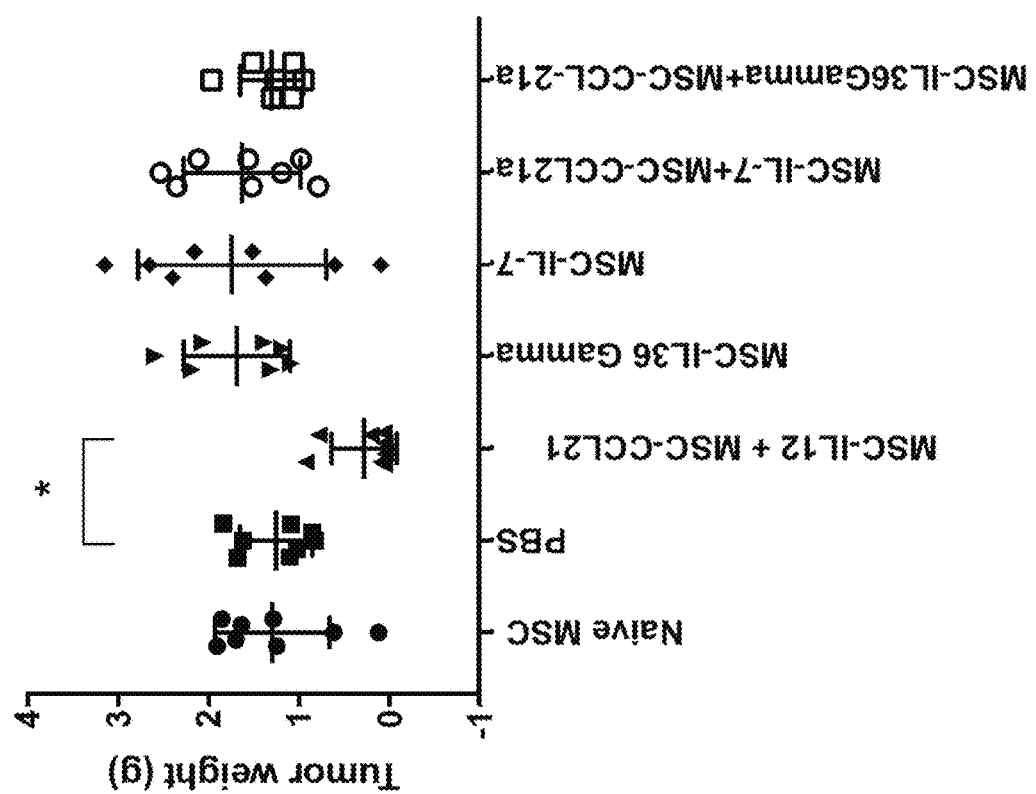
FIG. 22B includes data indicating that engineered MSCs expressing IL-12 and CCL21a inhibit tumor growth in a subcutaneous mouse model of colorectal cancer; however the combination of MSCs expressing CCL21a and IL-36 gamma or IL-7 does not reduce tumor growth. Each effector was expressed by a different MSC, and the MSCs were combined (at a 1:1 ratio) for combinatorial treatment.
Figure 23A:
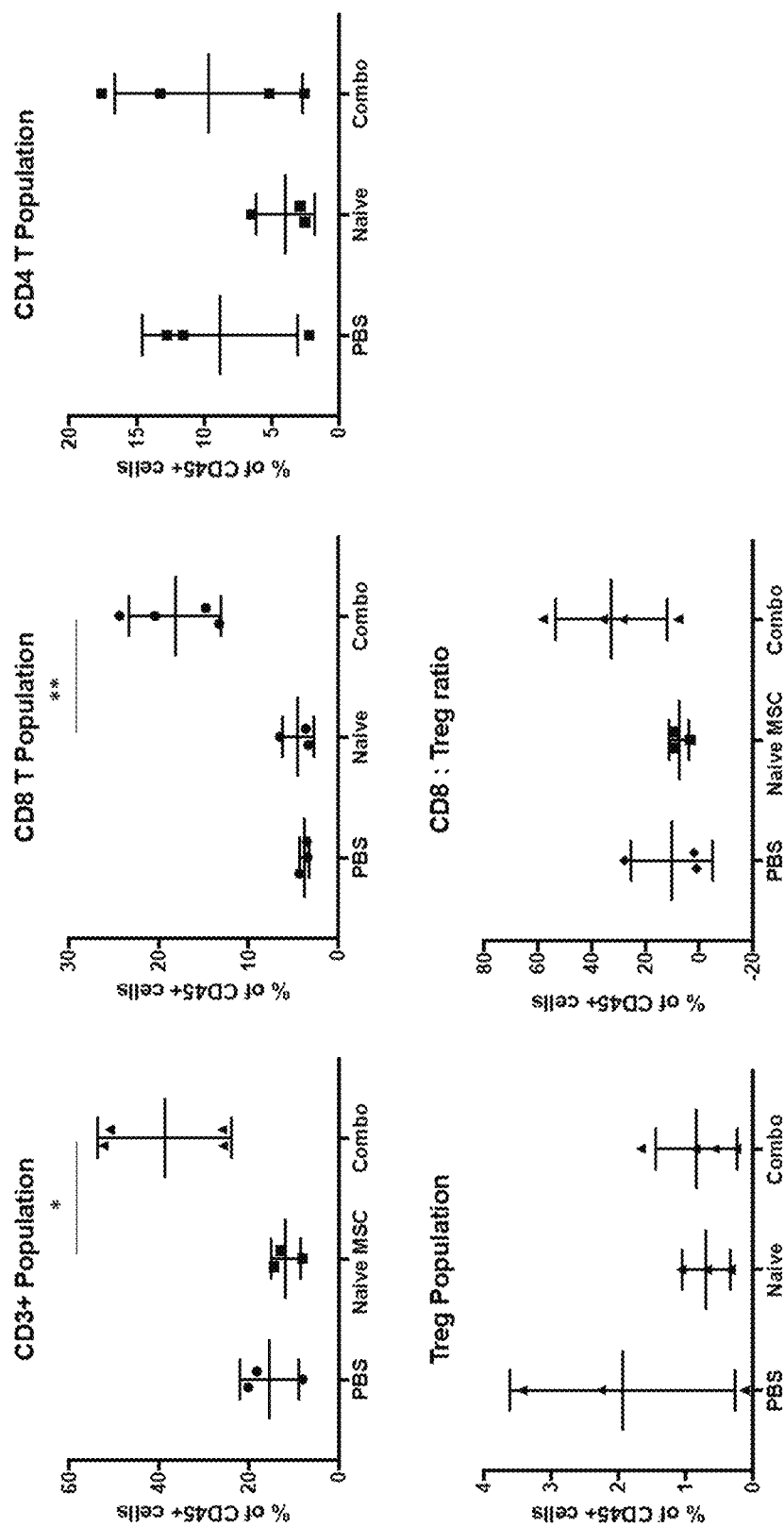
FIG. 23A includes tumor immune infiltrate statistics from the experiment represented by FIGS. 22A-22B. Three mice were selected from PBS, Naïve MSC, and MSC-IL12+ MSC-CCL21a (combo) group to run flow cytometry to immune profile tumor microenvironment.
Figure 23B:
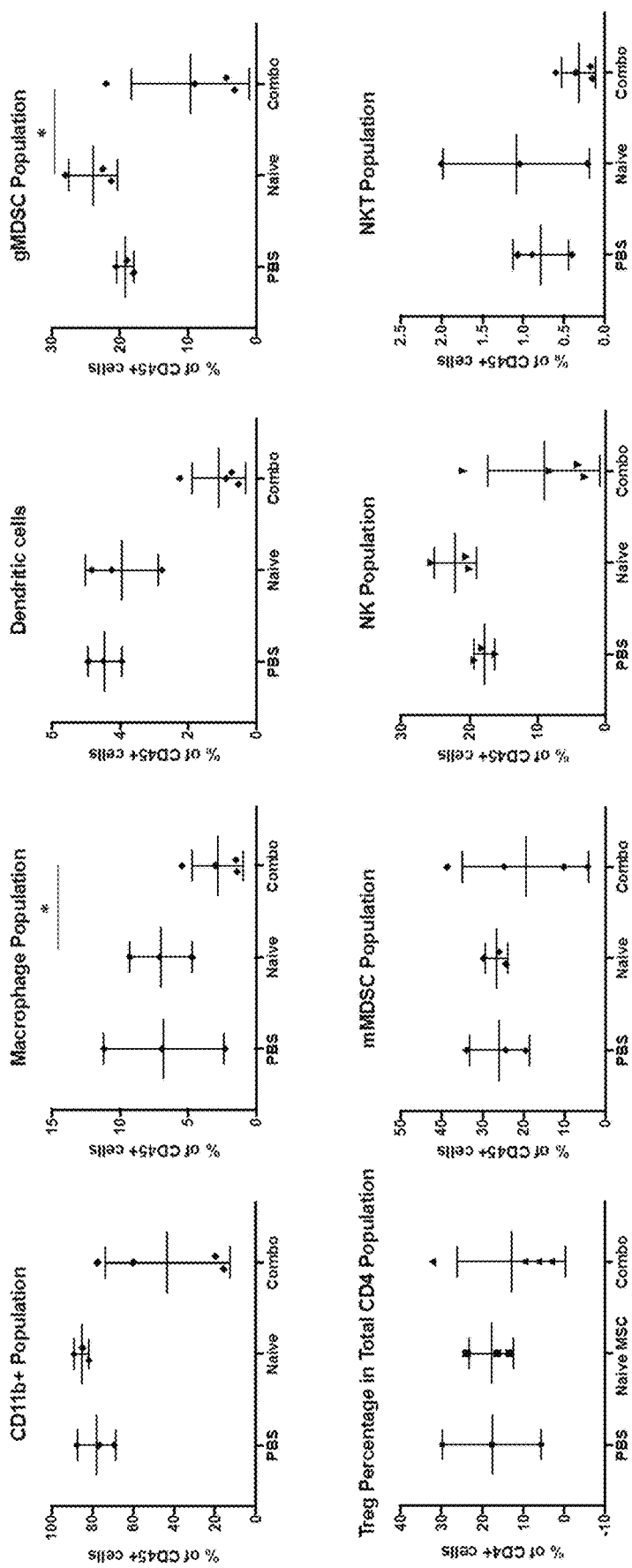
FIG. 23B includes tumor immune infiltrate statistics from the experiment represented by FIGS. 22A-22B. Three mice were selected from PBS, Naïve MSC, and MSC-IL12+ MSC-CCL21a (combo) group to run flow cytometry to immune profile tumor microenvironment.

FIG. 22A includes data indicating that engineered MSCs expressing IL-12 and CCL21a inhibit tumor growth in an subcutaneous mouse model of colorectal cancer; however the combination of MSCs expressing CCL21a and IL-36 gamma or IL-7 does not reduce tumor growth. FIGS. 23A-23B include the tumor immune infiltrate statistics. Three mice were selected from PBS, Naïve MSC, and MSC-IL12+MSC-CCL21a (combo) group to run flow cytometry to immune profile tumor microenvironment. FIG. 23A shows a significant increase in infiltrating CD3 and CD8 cytotoxic T population in the combo group compared to the group dosed with naïve MSC. FIG. 23B shows a significant reduction in granulocytic myeloid-derived suppressor cells (gMDSCs) and macrophage population in the combo group compared to group treated with Naïve MSC.

Figure 24A:
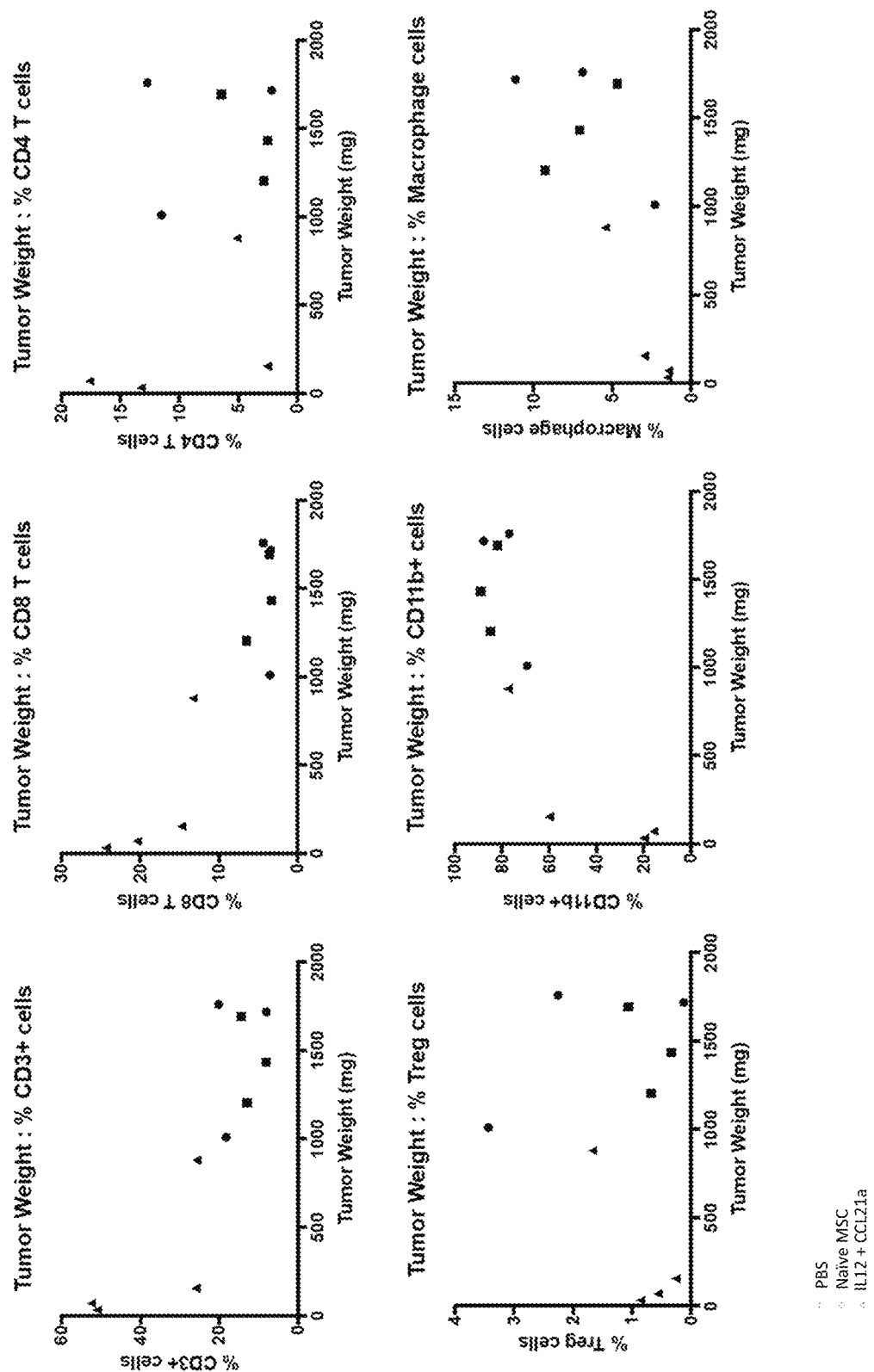
FIG. 24A includes data relating to immune percentage and tumor weight, relating to the experiments represented by FIGS. 22A-22B.
Figure 24B:
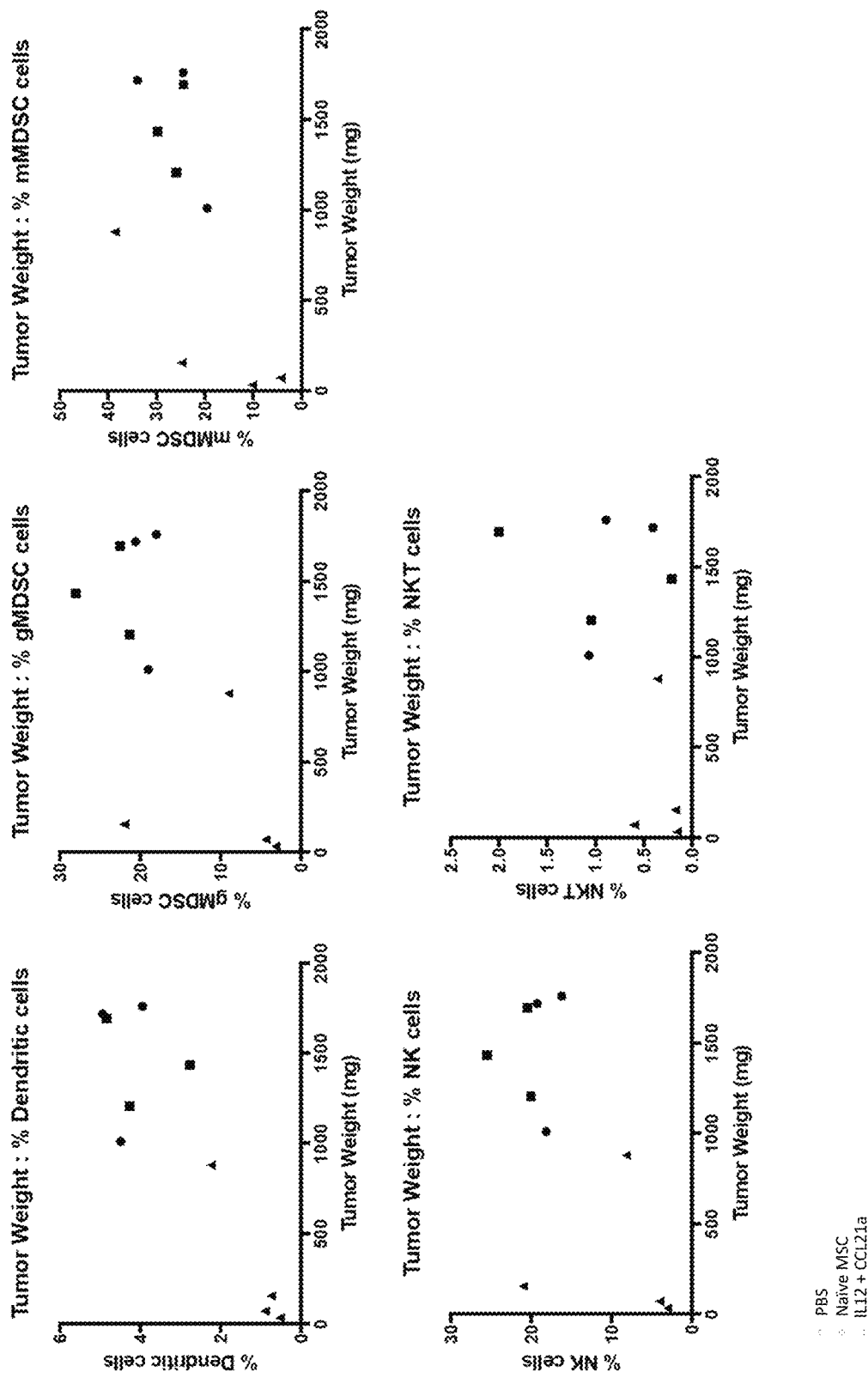
FIG. 24B includes data relating to immune percentage and tumor weight, relating to the experiments represented by FIGS. 22A-22B.

FIGS. 24A-24B include data relating to immune percentage and tumor weight, showing that samples with more CD3+ and CD8+ T cells (top left and center graph) correlate strongly with a decrease in tumor weight. These figures also show that samples with fewer CD11b myeloid cells, including macrophage, dendritic cells, and MDSC, display lower tumor burden (lower center and right graph of FIG. 24A and upper row of FIG. 24B).

Orthotopic Mouse Model

Figure 26A:
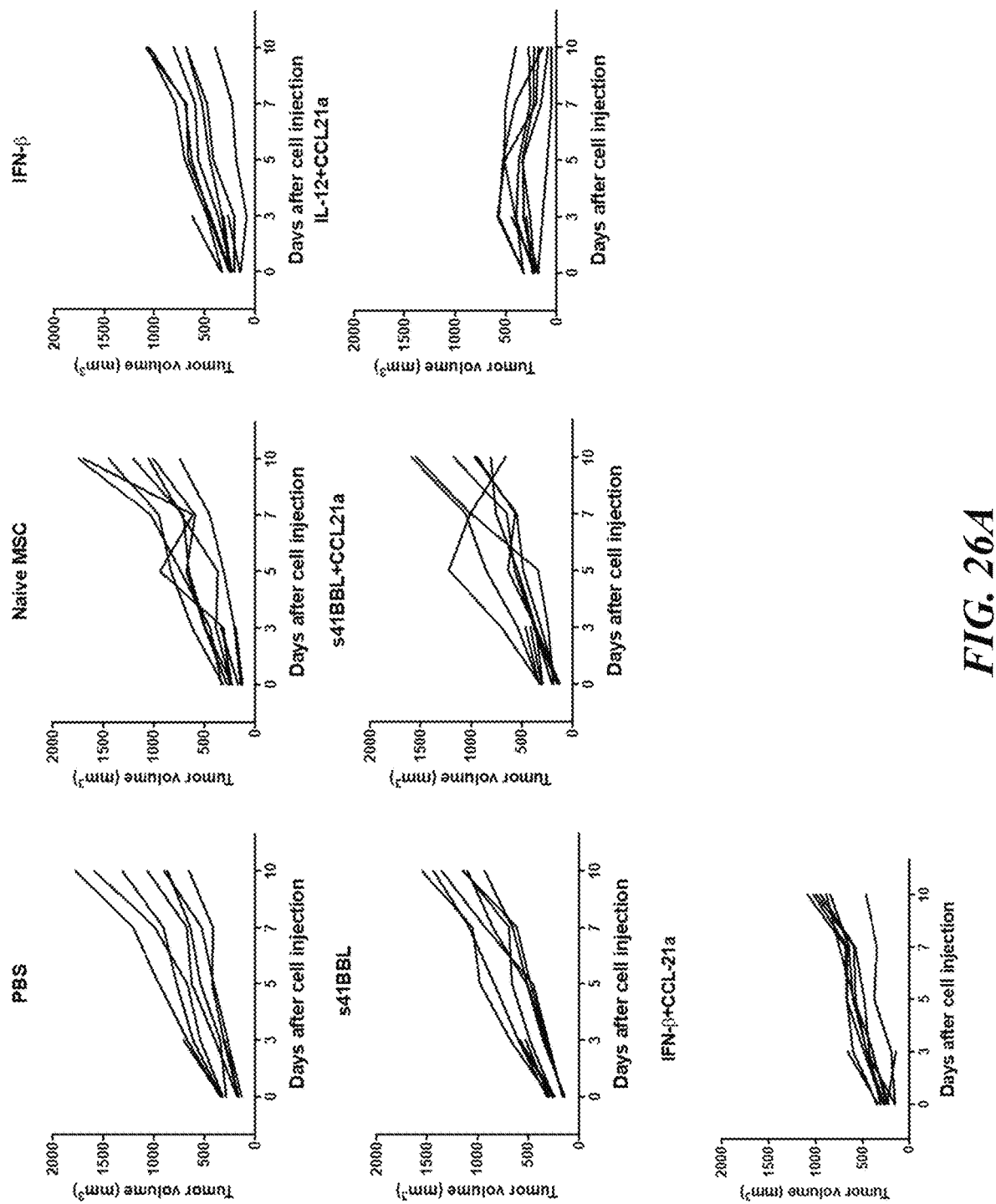
FIG. 26A includes data indicating that engineered combination treatment MSC-IL-12+MSC-CCL21a, or MSC-CCL21a+MSC-IFN-β, inhibit tumor growth in a subcutaneous mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 tumors in mice (n=6-8). Each line of FIG. 26A represents an individual mouse.
Figure 26B:
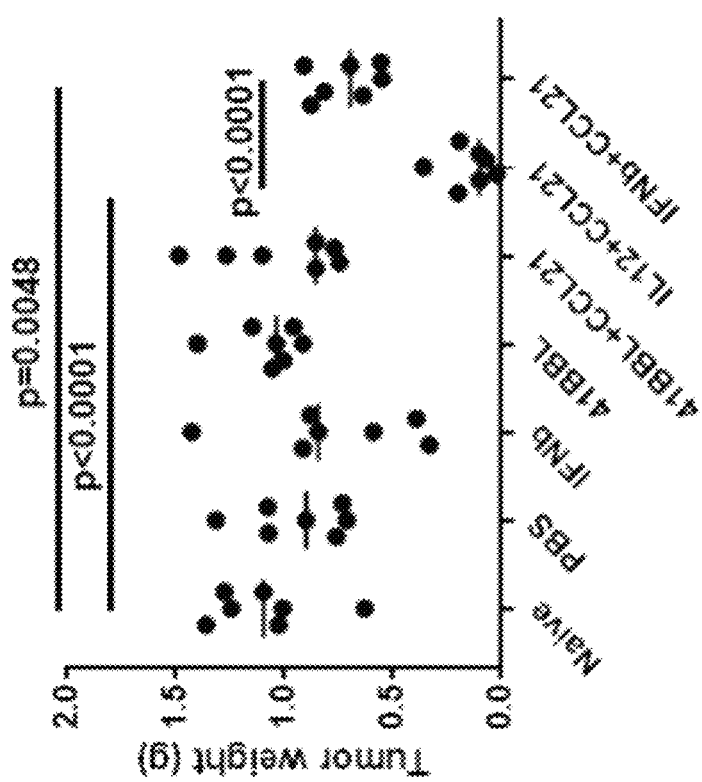
FIG. 26B includes data indicating that engineered combination treatment MSC-IL-12+MSC-CCL21a, or MSC-CCL21a+MSC-IFN-β, inhibit tumor growth in a subcutaneous mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment.

FIG. 26A shows that engineered MSCs expressing IL-12 and CCL21a, or CCL21a and IFN-β, inhibit tumor growth in an orthotopic mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 26A represents an individual mouse. FIG. 26B shows the tumor weight for individual mice in each treatment. MSC-IL12+MSC-CCL21a shows best efficacy compared to mice injected with naïve MSC. Treatment efficacy was also observed in the group treated with MSC-IFNb+MSC-CCL21a.

Figure 27A:
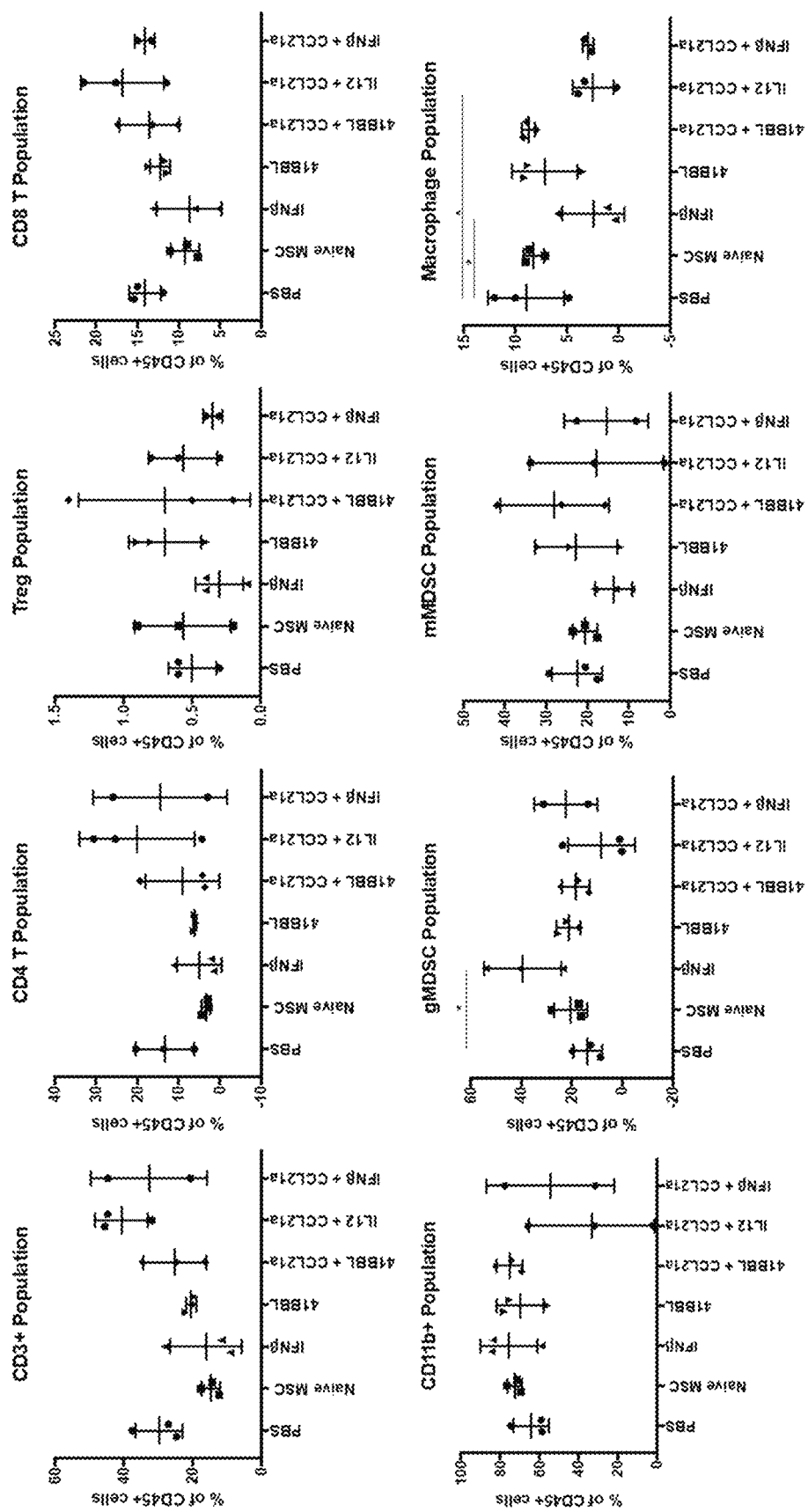
FIG. 27A provides additional data from the experiment represented by FIGS. 26A-26B.
Figure 27B:
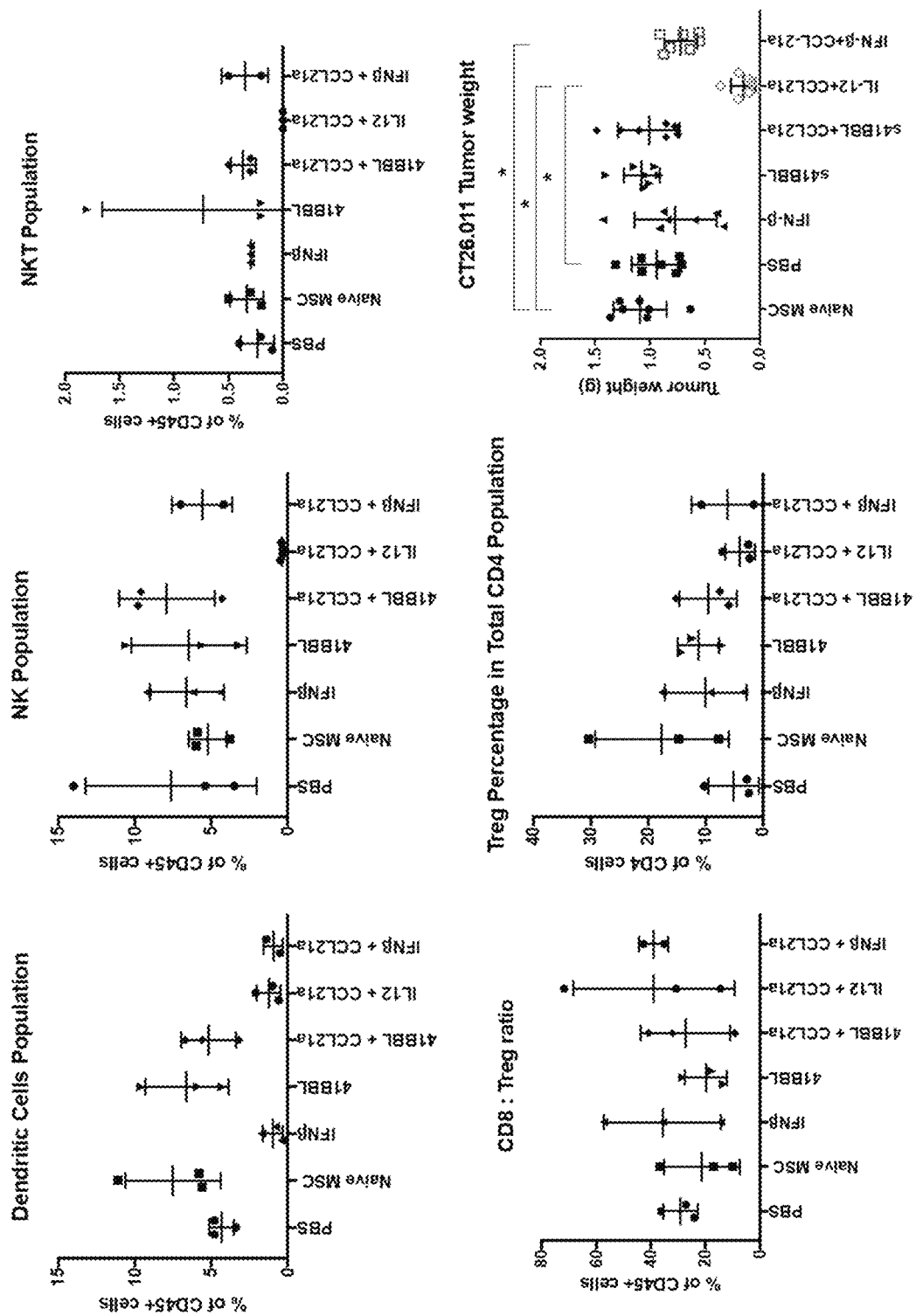
FIG. 27B provides additional data from the experiment represented by FIGS. 26A-26B.

FIGS. 27A-27B are graphs that show immune profiles of each group treated with indicated engineered MSC. A consistent decrease in macrophage population was observed after treating with MSC-IL12+MSC-CCL21a (FIG. 27A). A general trend of increased infiltration in CD3+ population and decreased infiltration in CD11b+ population was also observed when compared to group treated with MSC-IL12+MSC-CCL21a against naïve MSC (FIG. 27A and FIG. 27B).

Figure 28A:
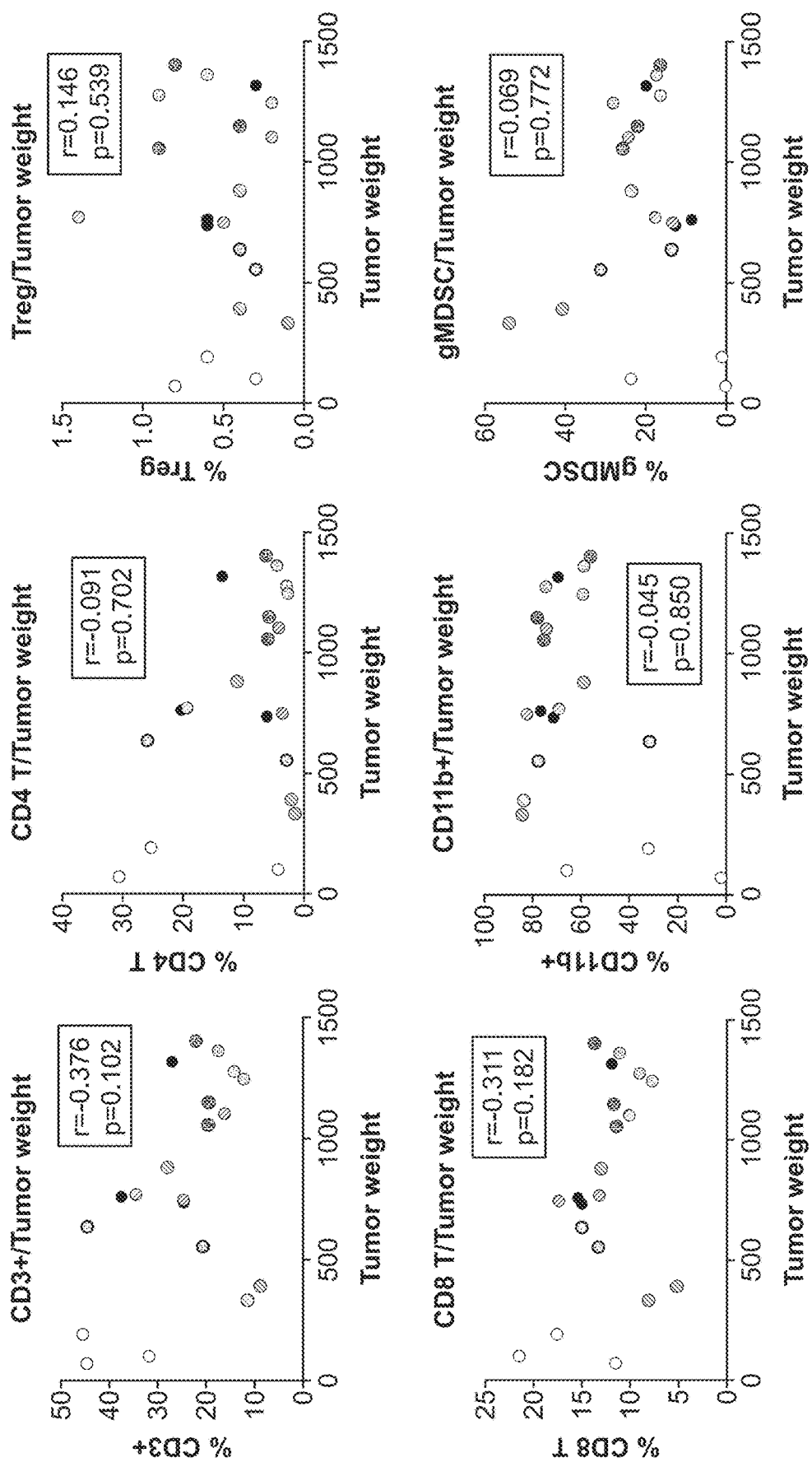
FIG. 28A also provides additional data from the experiment represented by FIGS. 26A-26B.
Figure 28B:
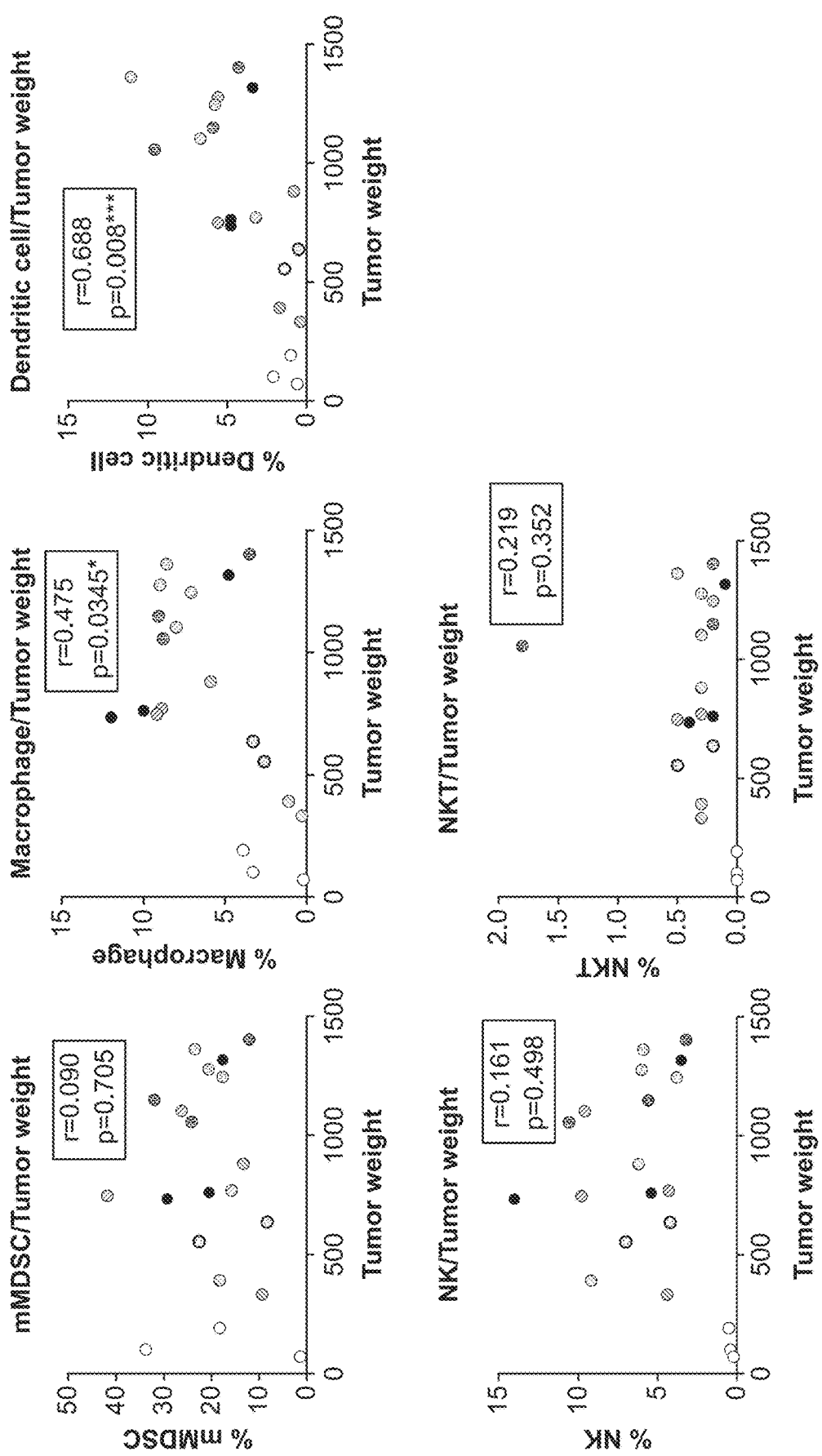
FIG. 28B also provides additional data from the experiment represented by FIGS. 26A-26B.

FIG. 28A-28B show the correlation of immune infiltration with tumor weight. Samples with low macrophage and dendritic cells have lower tumor burden (FIG. 28B, top center and top right). FIG. 28C shows the average tumor weight from each group. Statistical significance was observed with both MSC-IL12+MSC-CCL21a, or MSC-IFNb+MSC-CCL21a compared with naïve MSC.

Figure 29:
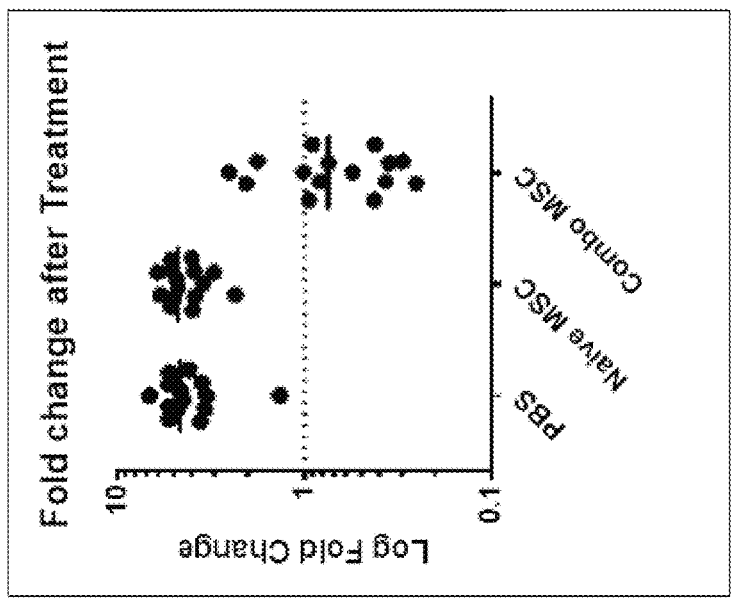
Figure 29:
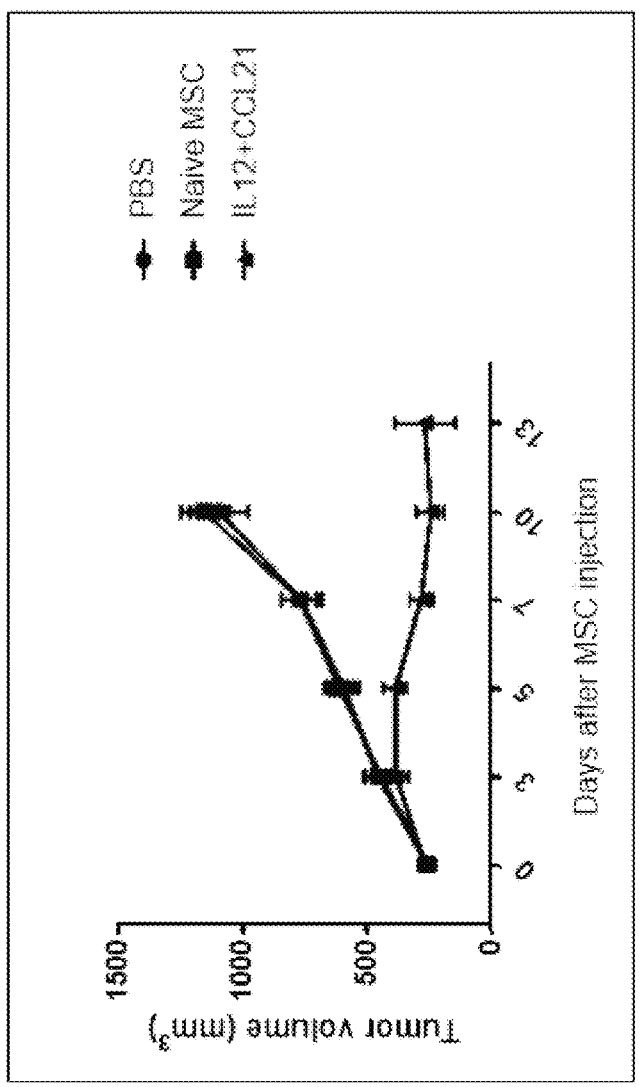

FIG. 29 shows graphs combining the in vivo data from the colorectal cancer models above (FIG. 22A and FIG. 26A). The combined CT26 data from FIG. 22A and FIG. 26A capture three groups: tumor only (PBS), treated with naïve MSC, and treated with MSC-IL12+MSC-CCL21a.

Figure 30A:
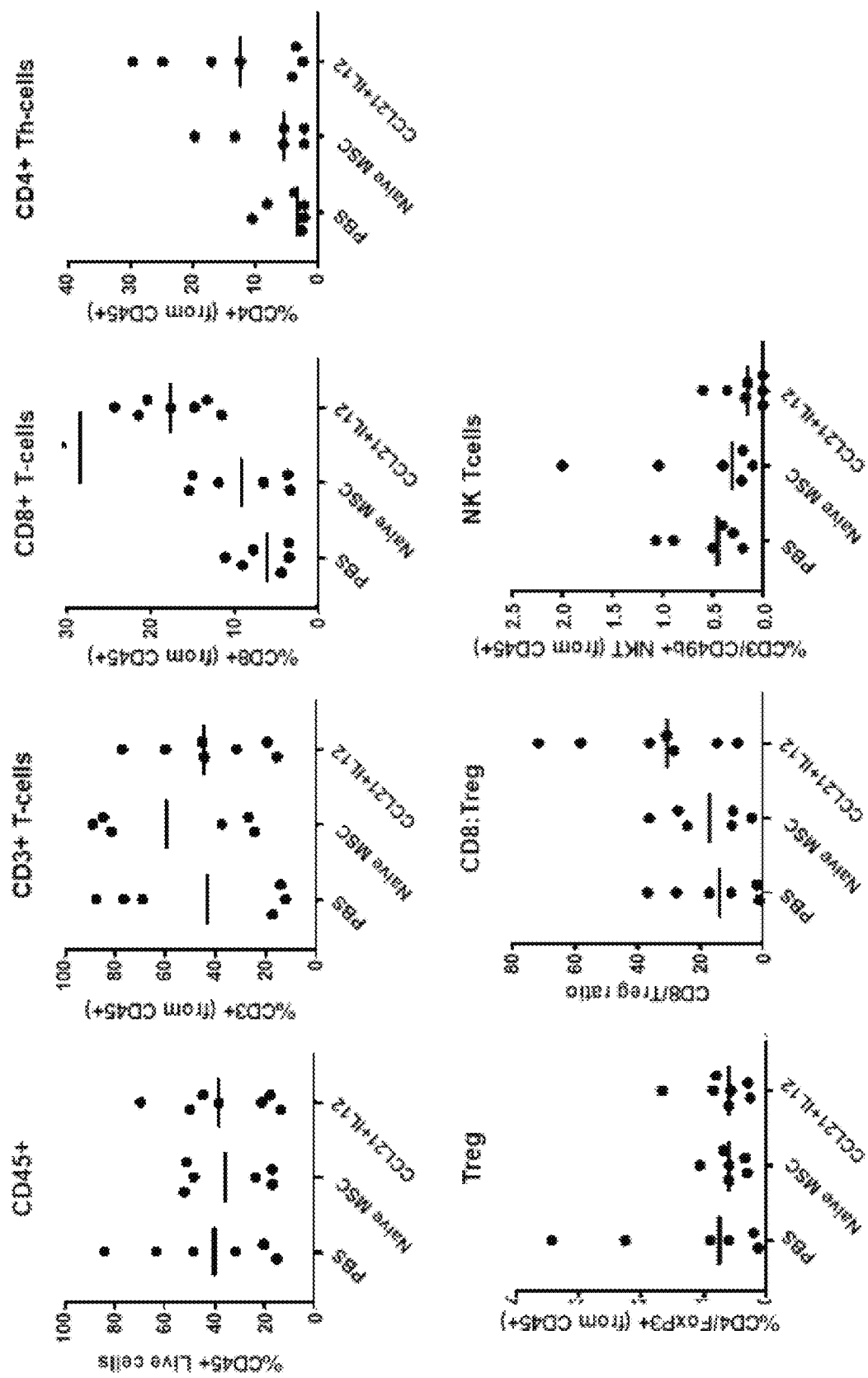
FIG. 30A also shows combined data from FIG. 22A and FIG. 26A. The graphs show the average number of immune infiltration from the flow cytometry experiment data. Statistical significance was observed in CD8+ T, demonstrating the ability of MSC-IL12+MSC-CCL21a to repolarize tumor microenvironment and allow more cytotoxic T cell infiltration.
Figure 30B:
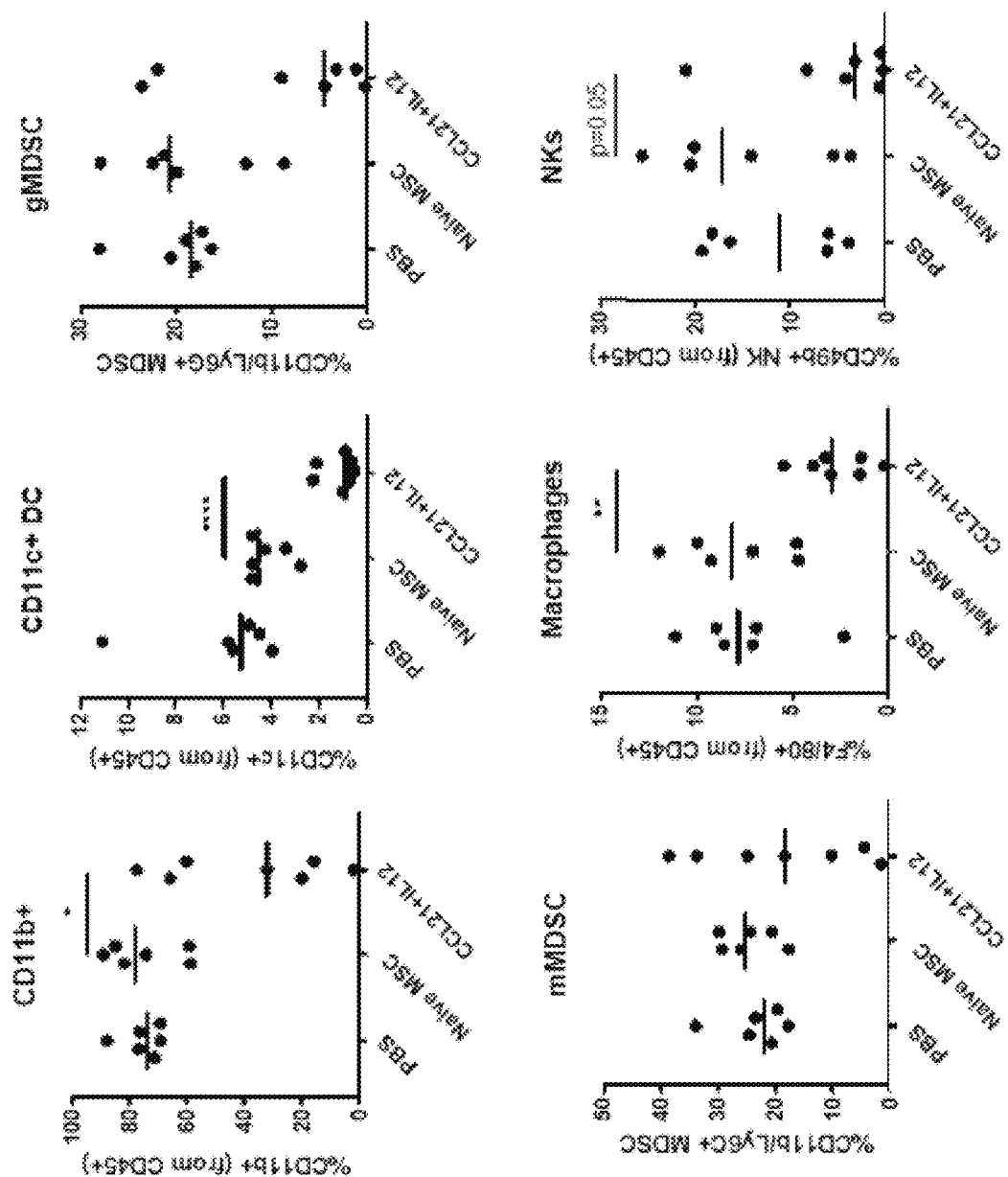
FIG. 30B also shows combined data from FIG. 22A and FIG. 26A. The graphs show the average number of immune infiltration from the flow cytometry experiment data. There was a reduction in CD11b+ myeloid population infiltration in the groups that were treated by MSC-IL12+MSC-CCL21a. The data collected show that the dendritic cells and the macrophage population was statistical significance.

FIGS. 30A-30C also show combined data from FIG. 22A and FIG. 26A. The graphs show the average number of immune infiltration from the flow cytometry experiment data. Statistical significance was observed in CD8+ T from FIG. 30A, demonstrating the ability of MSC-IL12+MSC-CCL21a to repolarize tumor microenvironment and allow more cytotoxic T cell infiltration. Furthermore, there was a reduction in CD11b+ myeloid population infiltration in the groups that were treated by MSC-IL12+MSC-CCL21a (FIG. 30B). The data collected using dendritic cells and the macrophage population was statistical significance.

Figure 25A:
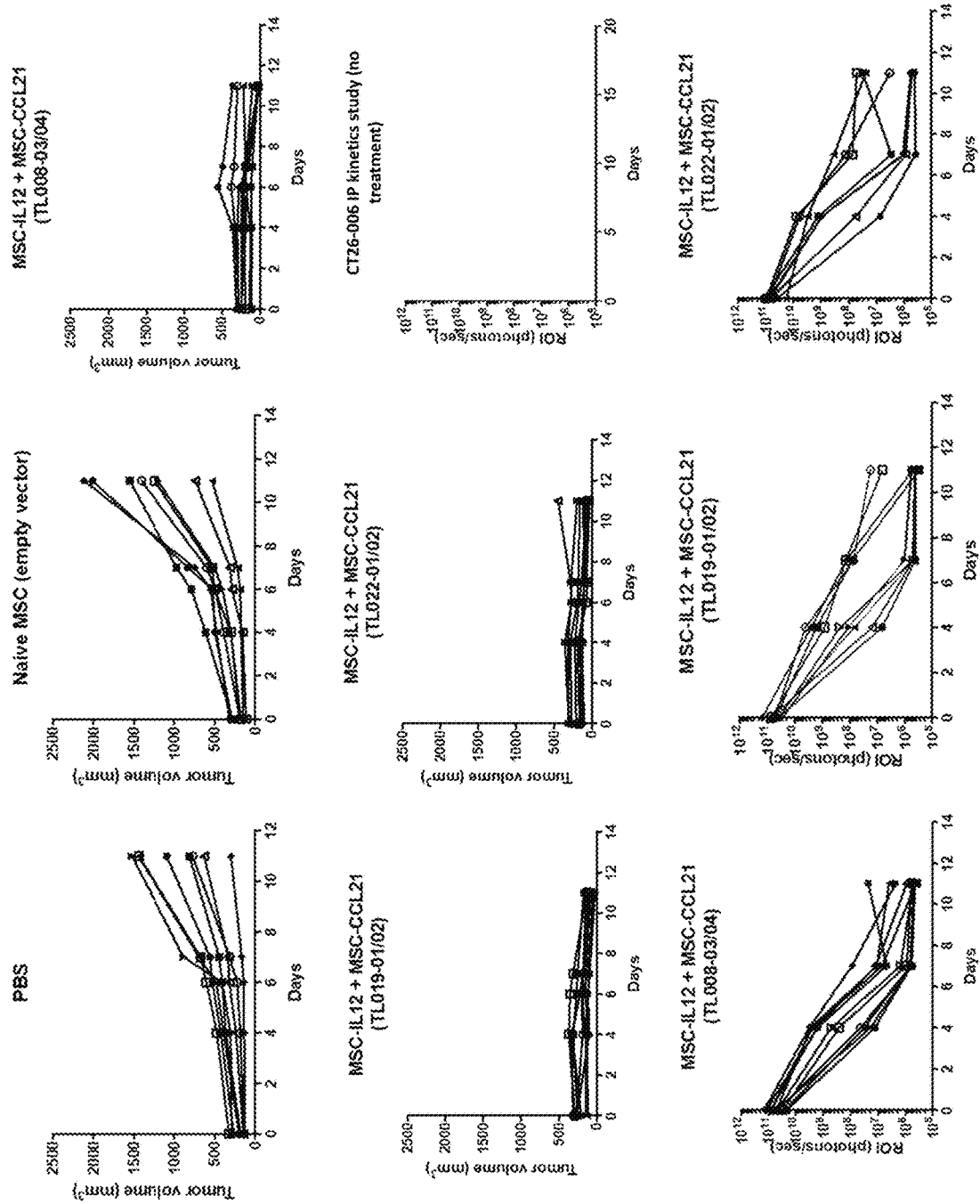
FIG. 25A includes data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot).
Figure 25B:
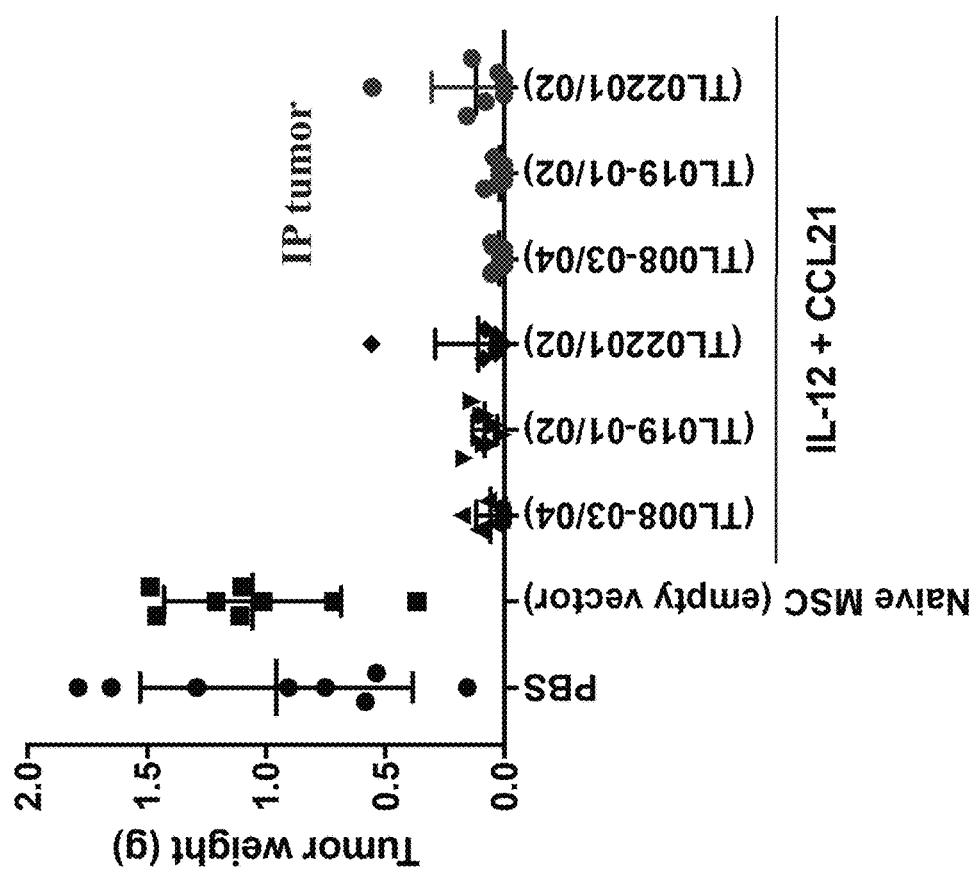
FIG. 25B includes data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02.

IL12 and CCL21a Therapy in Intraperitoneal and Subcutaneous Mouse Models of Colorectal Cancer FIGS. 25A-25B include data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot). FIG. 25A shows that all three lots of MSC-IL12+MSC-CCL21a can reduce tumor burden in both subcutaneous and intraperitoneal model (first 5 graphs are from the SC model and last 3 are from the IP model). Tumors from all mice were collected on day 11. FIG. 25B shows the average tumor weight from each group.

Example 6. MSC Combination Cytokine Therapy Methods

The following methods were used in experiments, as indicated.
Methods:
MSC Culturing
Bone-marrow derived C57BL/6 and Balb/C murine MSCs (mMSCs) were purchased from Cyagen (Cat. No. MUBMX-01001 and MUCMX-01001, respectively). mMSC culturing media was composed of: MEM Corning Cat #10-022-CV (500 ml)+MSC FBS Gibco Cat #12662-029 (final conc 10%)+L-Glut (200 mM) Stem cell 07100 (Final conc 2 mM)+PenStrep 100×VWR Cat #97063-708 (Final conc 1×)+murine FGF Peprotech Cat #450-33-100uG (Final conc-1:10,000 dilution). TrypLE Express was purchased (ThermoFisher—#12604021). PBS did not contain magnesium, calcium, or phenol red.
mMSCs were passaged according to the protocol below:
1. mMSCs should be passaged at 70-90% confluency.
2. Aspirate media from dish/flask.
3. Rinse plate with PBS (e.g. 2 mL for 10 cm dish, 3 ml for 15 cm dish).
4. Add TrypLE Express (e.g. 2 mL for 10 cm dish, 3 ml for 15 cm dish)
5. Incubate for 3-4 minutes at 37 degrees.
6. Knock plate on side to dislodge cells. Confirm by microscopy that most cells have been dislodged.
7. Wash cells off plate using media (e.g. 8 mL for 10 cm dish).
8. Place cells in 15 conical and centrifuge 400×g for 5 min.
9. Aspirate media.
10. Resuspend cells in appropriate media and plate cells into fresh plates/flasks.
Note: 70% confluent cells can be
split 1:3. 90% confluent cells can be split 1:4. Alternatively, cells can be plated at 3000-5000 cells/cm2.
Bone-marrow derived human MSCs were purchased (RoosterBank-hBM-1M-XF, RoosterBio). Various hMSC culturing media were purchased: Xeno-free hMSC media—(RoosterBio—#KT-016); +FBS (serum-containing) hMSC media (Lonza—MSCGM media—#PT-3001). TrypLE Express was purchased (ThermoFisher—#12604021). PBS did not contain magnesium, calcium, or phenol red.
hMSCs were passaged according to the exemplary protocol below:
1. hMSCs should be passaged at 70-90% confluency.
2. Aspirate media from dish/flask.
3. Rinse plate with PBS (e.g. 2 mL for 10 cm dish).
4. Add TrypLE Express (e.g. 2 mL for 10 cm dish)
5. Incubate for 3-4 minutes at 37 degrees or 5 minutes RT.
6. Knock plate on side to dislodge cells. Confirm by microscopy that most cells have been dislodged.
7. Wash cells off plate using Lonza MSCGM media (e.g. 8 mL for 10 cm dish).
8. Place cells in 15 conical and centrifuge 400×g for 5 min.
9. Aspirate media.
10. Resuspend cells in Rooster xeno-free media and plate cells into fresh plates/flasks. Note: 70% confluent cells can be split 1:3. 90% confluent cells can be split 1:4. Alternatively, cells can be plated at 3000-5000 cells/cm2.
hMSCs were thawed according to the exemplary protocol below:
1. Pre-warm hMSC media to 37°.
2. Remove hMSC aliquot from liquid nitrogen.
3. Thaw by holding the tube 1/2 submerged in 37° bath for 60-90 seconds, until 2/3 of the frozen sample has thawed.
4. Wipe the tube with 70% ethanol to sterilize tube.
5. Add 0.5 mL media to the cryotube, gently pipette 2-3 times, and then transfer cells into 9 mL media (10 mL total) in 15 mL conical tube.
6. Centrifuge 400×g for 5 min.
7. Aspirate media, and then gently resuspend pellet in appropriate volume of Rooster xeno-free media. Plate cells at a concentration of 3000-5000 cells/cm2.

Lentiviral Production

Lentivirus was produced using: Lenti-X 293T packaging cell line (Clontech, Cat #632180); LX293T Complete growth medium, without antibiotics; DMEM, hi-glucose; 1 mM Sodium Pyruvate; 10% FBS, heat-inactivated; Opti-Mem I Reduced Serum Media (Gibco/Thermo Fisher; Cat #31985); FuGene HD (Promega, Cat #E2311); Envelope, Packaging, and Transfer Vector plasmids; VSV-G-pseudotyped envelope vector (pMD2.G); Packaging vector that contains Gag, Pol, Rev, and Tat that can be used with 2nd and 3rd generation transfer vectors (psMAX2). 293T(FT) cells from 90% confluent 10 cm dishes were lifted and dispensed at 1:3 dilution late in the afternoon the day before transfection and incubated cells as normal overnight at 37° C., 5% CO2 (cells should be 60-85% confluent the next day at time of transfection).

A transfection reaction was prepped for each 10 cm dish according to the protocol below:
1. Prep transfection reaction for each 10 cm dish in a separate 1.7 mL tube.
2. Add 900 uL Opti-Mem I at RT.
3. Add 9 ug vector backbone (containing gene of interest) per reaction.
4. Add Bug packaging vector per reaction.
5. Add 1 ug envelope vector per reaction (pMD2.G).
6. Mix thoroughly by quickly vortexing for 3 seconds.
7. Add 55 uL Fugene HD per reaction.
8. Mix by quickly pipetting up and down 20-30 times.

9. Let sit at RT for 10 min (allowing DNA complexes to form).
10. Slowly add mixture in dropwise manner around the dish, then mix by gently rocking back-forth and up-down for 5-10 seconds (do not swirl).
11. Place dish into virus incubator.

Viral supernatants were harvested on days 2 and 3 using a serological pipette. Cellular debris was removed using a Millipore steriflip 0.45 um filters. A Lenti-X Concentrator (Cat. Nos. 631231 & 631232) was used according to the protocol: 1) Combine 1 volume of Lenti-X Concentrator with 3 volumes of clarified supernatant. Mix by gentle inversion; 2) Incubate mixture on ice or at 4° C. for 30 minutes to overnight; (3) Centrifuge sample at 1,500×g for 45 minutes at 4° C.; (4) Carefully remove and discard supernatant, taking care not to disturb the pellet; (5) Gently resuspend the pellet in 1/10 to 1/100th of the original volume using sterile PBS+0.1% BSA.

Vectors

Figure 31:
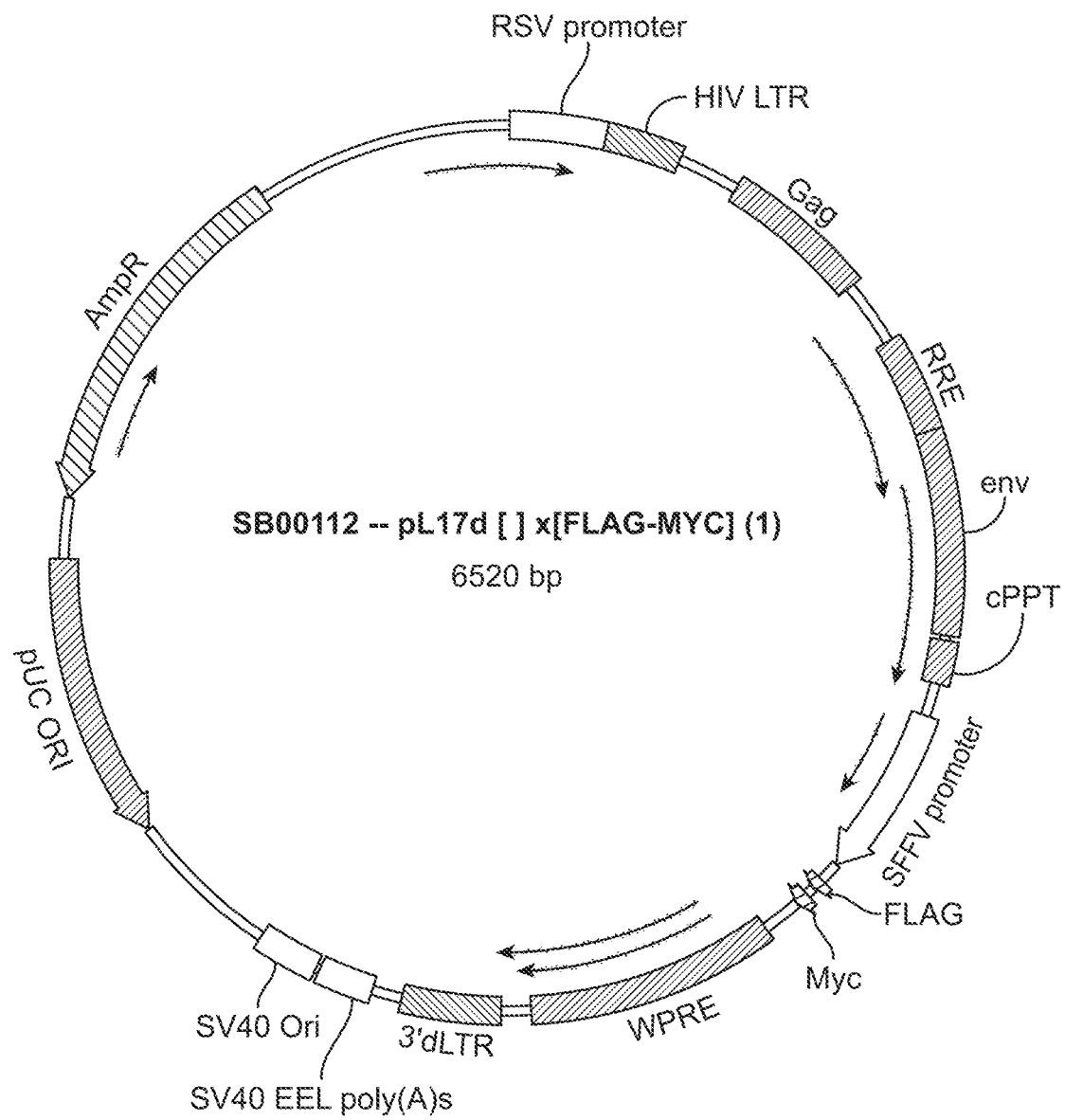
FIG. 31 shows the vector map of pL17D.

Cytokine expression cassettes were cloned into a pL17D, the vector map of which is shown in FIG. 31 with salient features annotated; e.g., a SFFV promoter; a FLAG and MYC epitope tag; LTRs, etc.

Lentiviral Transduction

Murine MSCs were seeded in 6-well plates and infected when cells were 50% confluent. Virus was added at the appropriate MOI and incubated for 3 hours to transduce cells. Following infection, fresh media was added to the cells.

Human MSCs were transduced following the exemplary protocol below:
1. 200,000 human MSCs were plated in each well of 6-well plate, in 2 mL xeno-free human MSC media.
2. After 2 hours, the media was removed and replaced with 1 mL of PBS.
3. Appropriate amount of virus was added to each well, as indicate by MOI below, and cells were incubated with virus for 3 hours with occasional rocking, at 37 degrees and 5% CO2.
4. Virus was removed after 3 hours, plates were washed with media, and then the MSCs were cultured normally (as noted above) until cells reached senescence. Cells were counted at each passage, so that total cell numbers could be determined.

Example 7: MSC Combination Cytokine Therapy (CT26)

In the following example, balb/c mMSCs were engineered to express various cytokines using the lentiviral transduction method described in Example 6.

Figure 32:
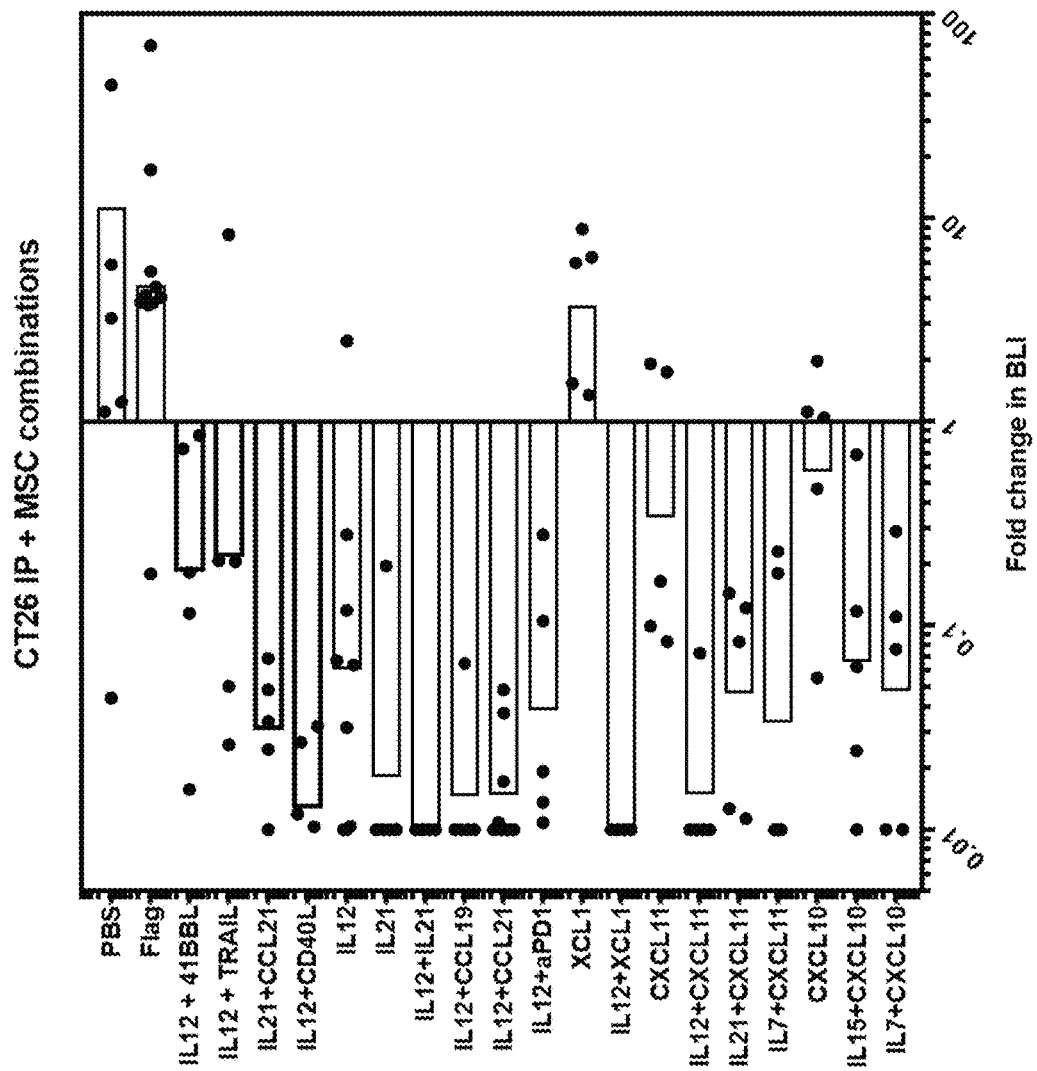
FIG. 32 shows MSCs engineered to express different effector molecules either alone or in combination and their efficacy in reducing CT26 tumor burden in an IP tumor model as assessed by BLI levels.

CT26 tumor cells ($5×10^4$ cells in 100 µl) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. Mice were randomized into treatment groups and treated with intraperitoneally delivered mMSCs ($1×10^6$) expressing effector molecules as single agent or as a combination of mMSCs to deliver a combination of agents. MSC-Flag-Myc and PBS were used as a negative control. Tumor burden was assessed at day 12 and 17. Bioluminescent signal (photons/second) was normalized for each individual mouse relative to the initial signal (pre-treatment). Reduction of BLI signal by more than 100 fold (0.01) was equivalent to a complete cure (no tumor was evident at the time of necropsy). As shown in FIG. 32, MSCs engineered to express different effector molecules either alone or in combination demonstrated efficacy in reducing CT26 tumor burden in an IP tumor model as assessed by BLI levels.

Example 8: MSC Combination Cytokine Therapy (B16F10)

In the following example, C57BL/6 mMSCs were engineered to express various cytokines using the lentiviral transduction method described in Example 6.

Figure 33:
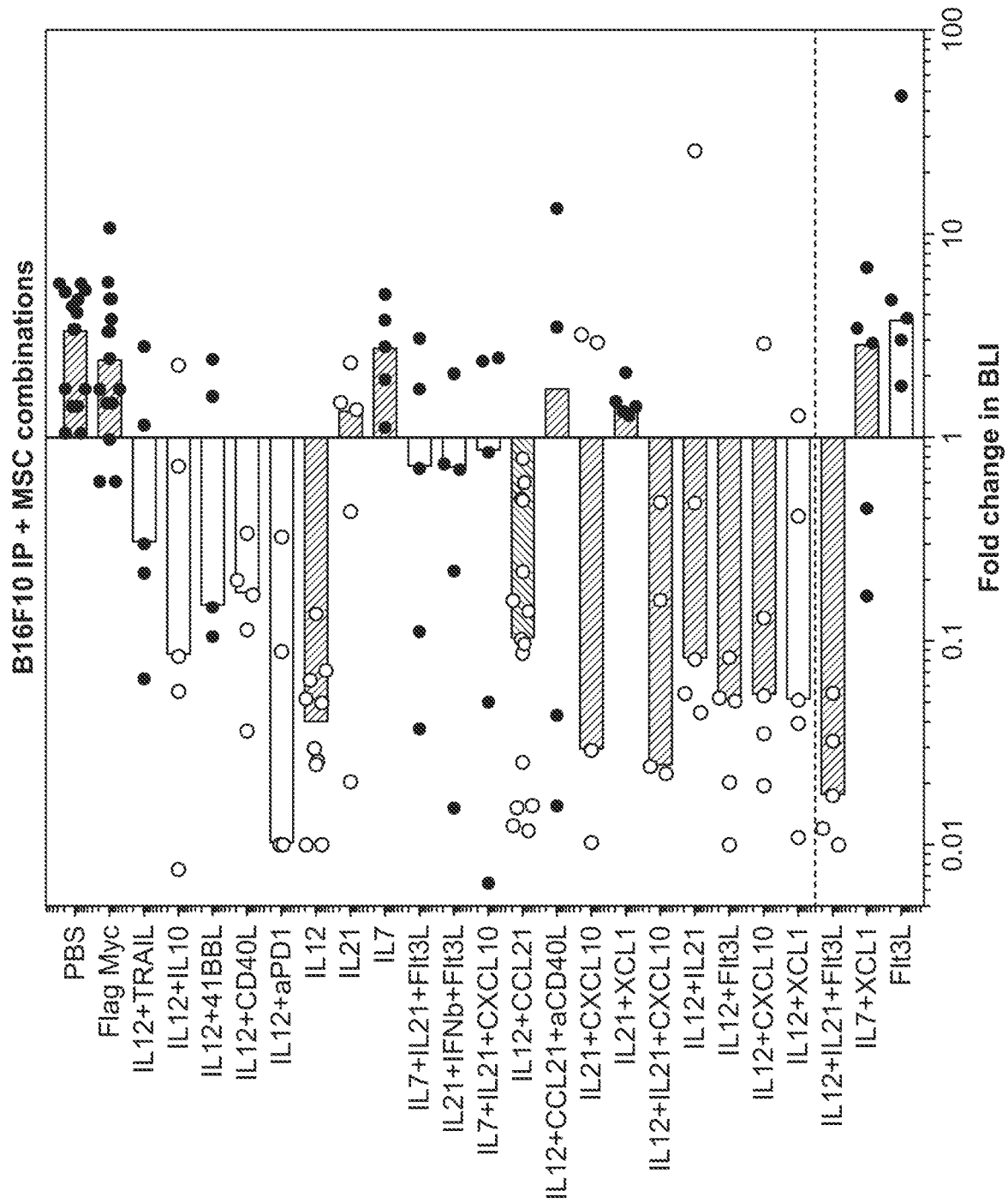
FIG. 33 shows MSCs engineered to express different effector molecules either alone or in combination and their efficacy in reducing B16F10 tumor burden in an IP tumor model as assessed by BLI levels.

B16F10 tumor cells ($5×10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with intraperitoneally delivered mMSCs ($1×10^6$) expressing effector molecules as single agent or as a combination of mMSCs to deliver a combination of agents. MSC-Flag-Myc and PBS were used as a negative control. Tumor burden was assessed at day 12 and 17. Bioluminescent signal (photons/second) was normalized for each individual mouse relative to the initial signal (pre-treatment). Reduction of BLI signal by more than 100 fold (0.01) was equivalent to a complete cure (no tumor was evident at the time of necropsy). As shown in FIG. 33, MSCs engineered to express different effector molecules either alone or in combination demonstrated efficacy in reducing B16F10 tumor burden in an IP tumor model as assessed by BLI levels.

Example 9: Engineered Human MSC Cytokine Production

Figure 34:
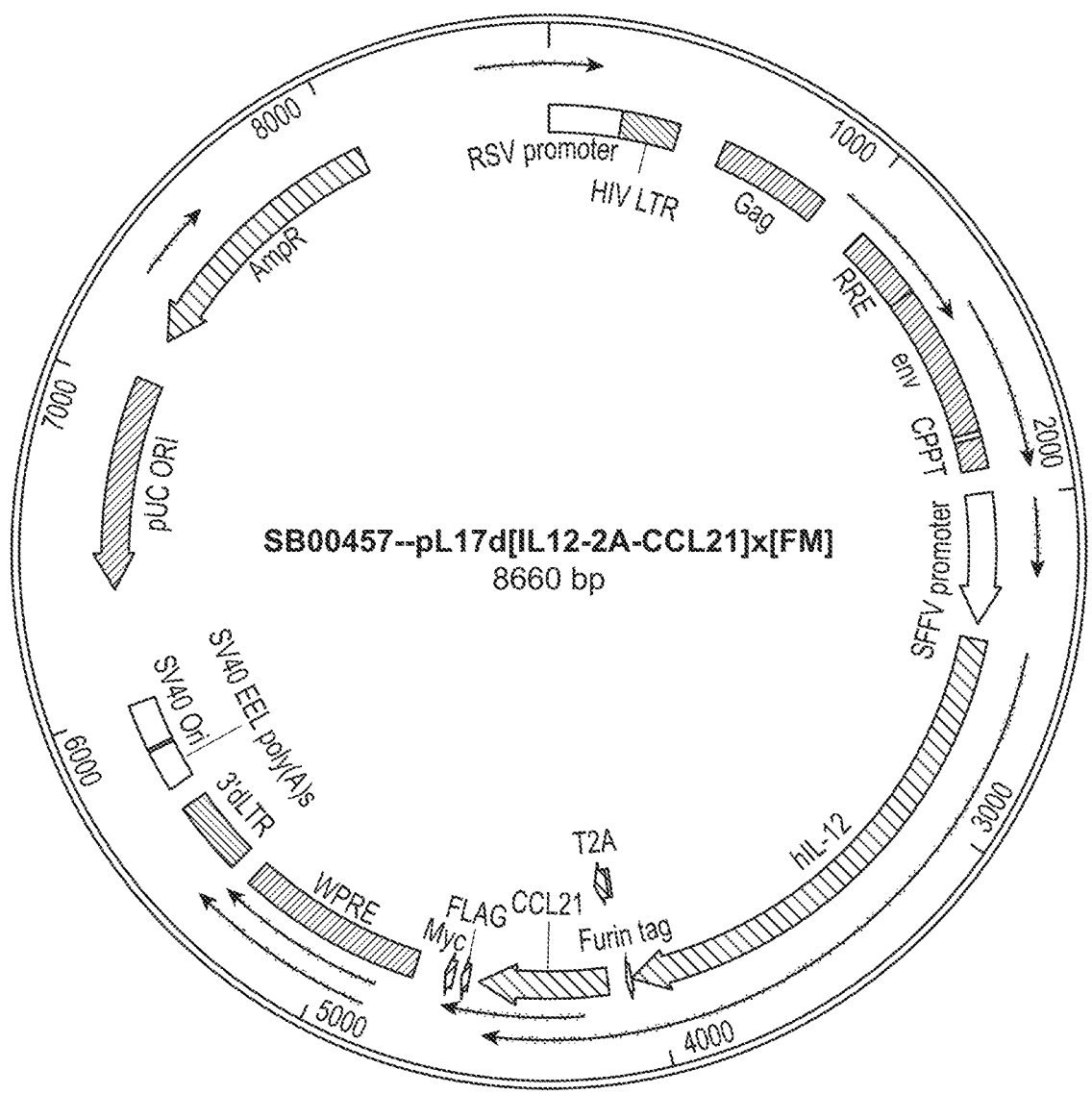
FIG. 34 shows the lentiviral expression vector map for expression of human IL12 (p70) and human CCL21a from a single lentiviral expression vector.

In the following example, bone-marrow derived hMSCs (derived from 3 human volunteer healthy donors) were engineered to express human IL12 (p70) and human CCL21a from a single lentiviral expression vector using the lentiviral transduction method described in Example 6. The lentiviral expression vector (schematic vector map of which is shown in FIG. 34) used a 2A ribosome skipping elements to express both cytokines from a single transcript.

Figure 35A:
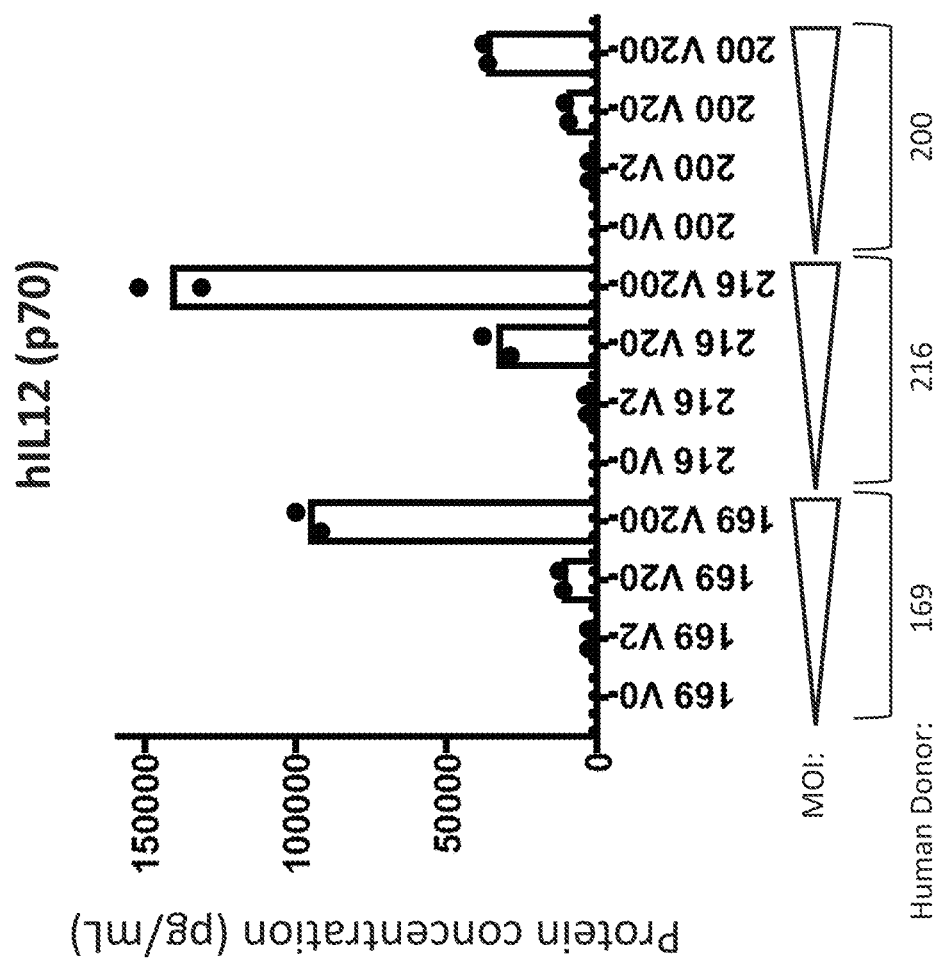
FIG. 35A shows production by engineered hMSCs of hIL12, as assessed by cytokine ELISA.
Figure 35B:
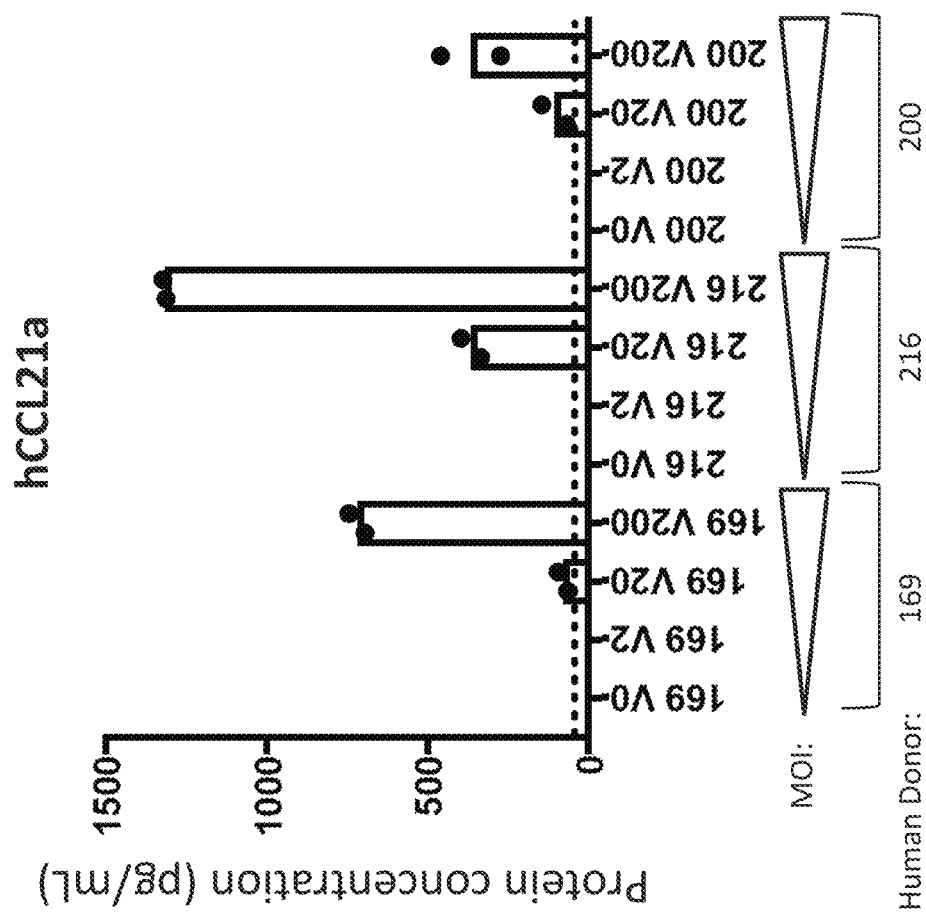
FIG. 35B shows production by engineered hMSCs of hCCL21a, as assessed by cytokine ELISA.

As shown in FIG. 35, engineered hMSCs were able to produce both hIL12 (FIG. 35A) and hCCL21a (FIG. 35B), as assessed by cytokine ELISA. Notably, protein secretion was correlated with the amount of viral particles (MOI) used during the transduction of MSCs.

Example 10: Engineered Human MSC Functional Assessment

Figure 36A:
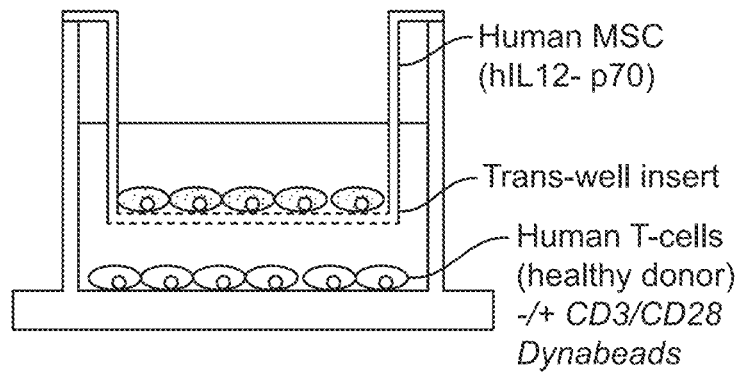
FIG. 36A shows a schematic of a transwell assay for assessing functional T cell modulation by hIL12 produced from MSCs.
Figure 36B:
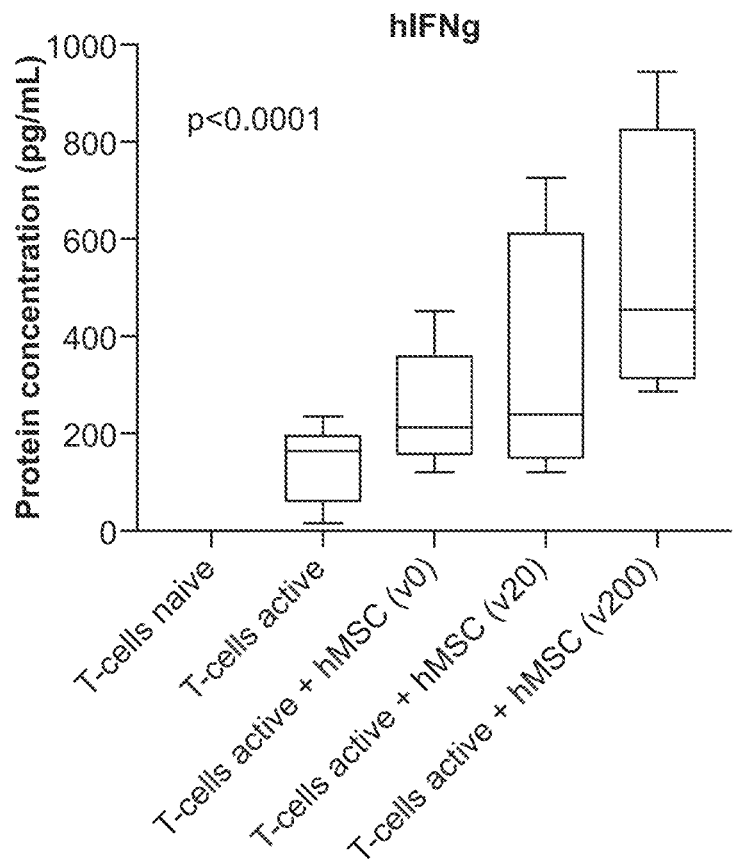
FIG. 36B shows a transwell assay demonstrating functional T cell modulation by hIL12 produced from MSCs as assessed by IFNγ production.

In the following example, bone-marrow derived hMSCs were engineered to express human IL12 (p70) using the lentiviral transduction method described in Example 6. Engineered hMSCs were co-cultured into 0.4 µm transwell inserts with human T-cells isolated from healthy blood donors (a schematic representation of the transwell assay is shown in FIG. 36A). To assess IL12 induced Th1 polarization on activated naïve T-cells, IFNγ production by T-cells was measured by ELISA on the supernatant collected from the lower compartment (T-cells). As shown in FIG. 36B, IFNγ production was increased in a MOI dose-dependent manner by co-culturing CD3 T-cells with hMSCs expressing IL12p70.

Example 11: MSCs Home to Tumors in an IP Model

Figure 37A:
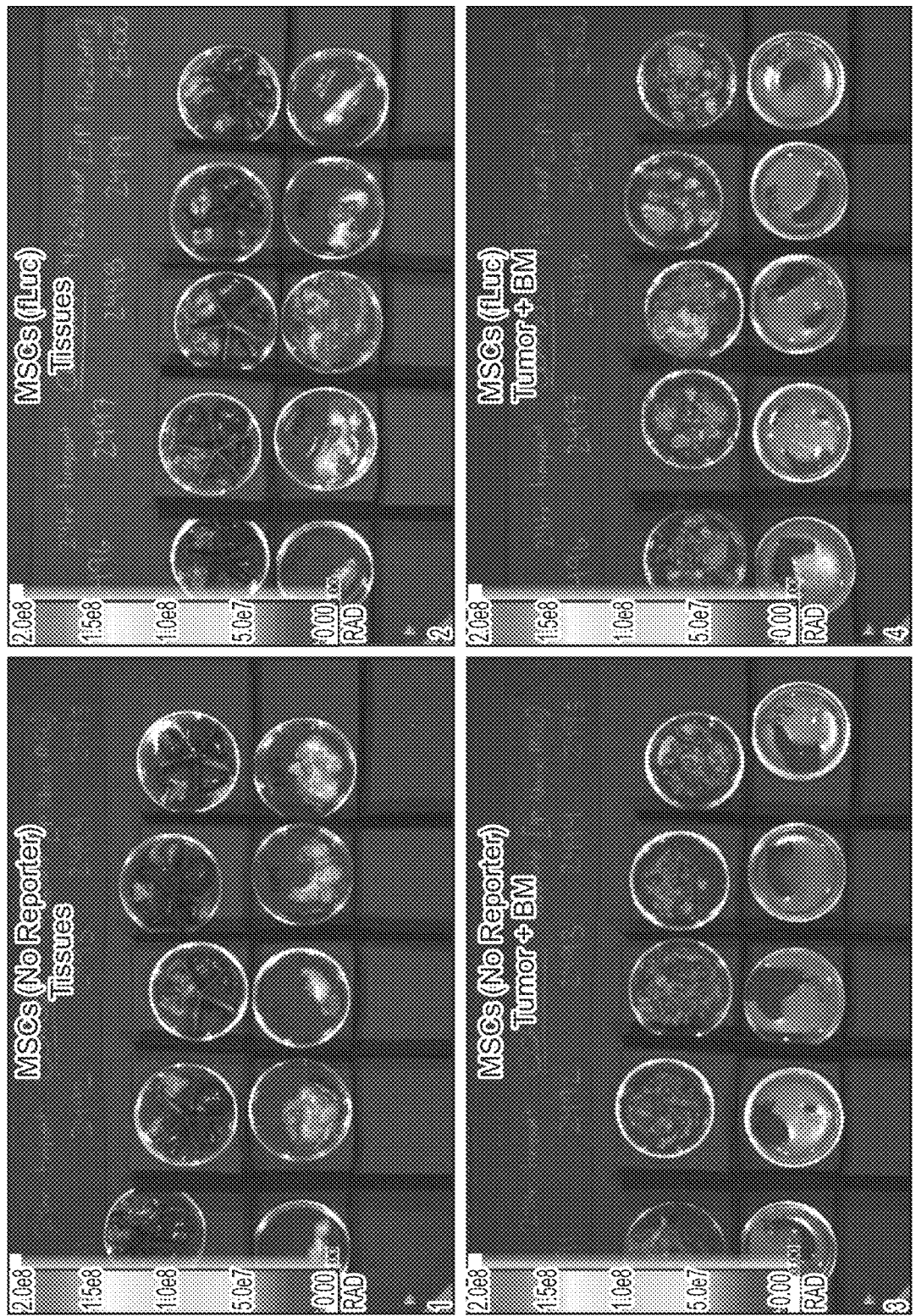
FIG. 37A shows homing to tumors by MSCs in IP tumor-bearing mice tumors as assessed by bioluminescence imaging.
Figure 37B:
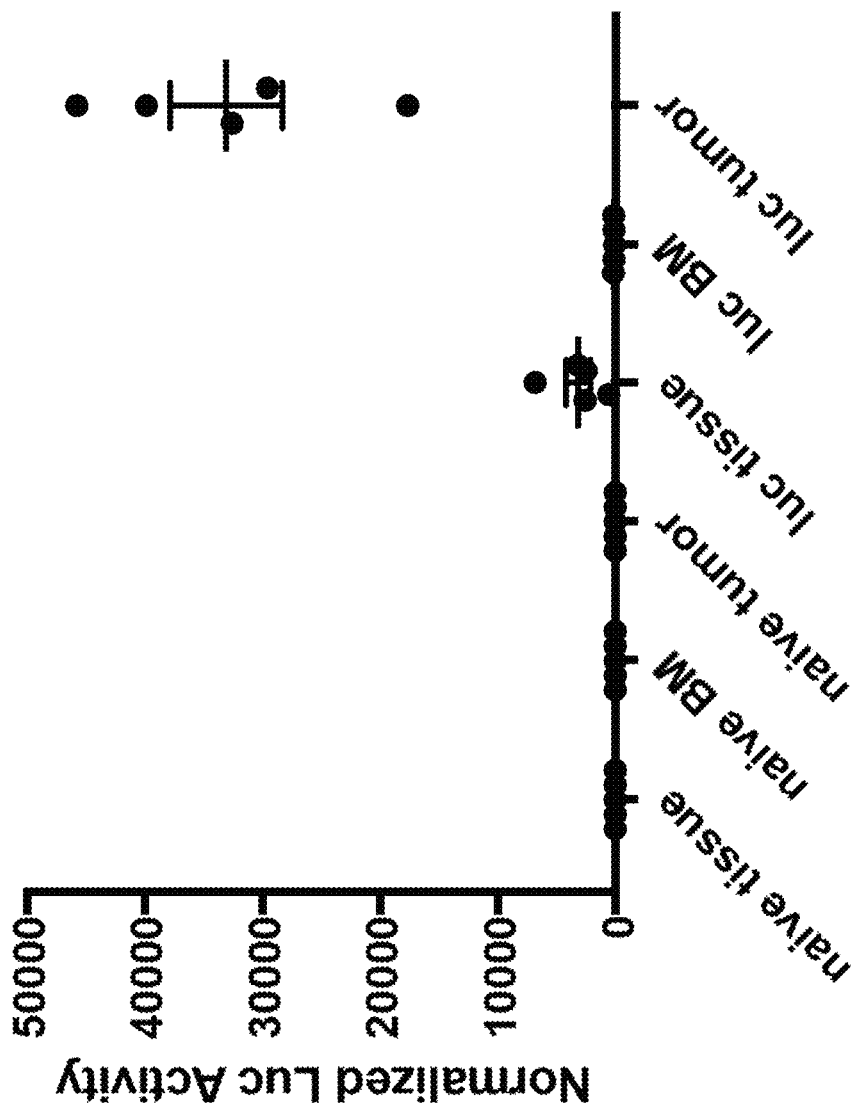
FIG. 37B shows homing to tumors by MSCs in IP tumor-bearing mice tumors as assessed by bioluminescence imaging.
Figure 37C:
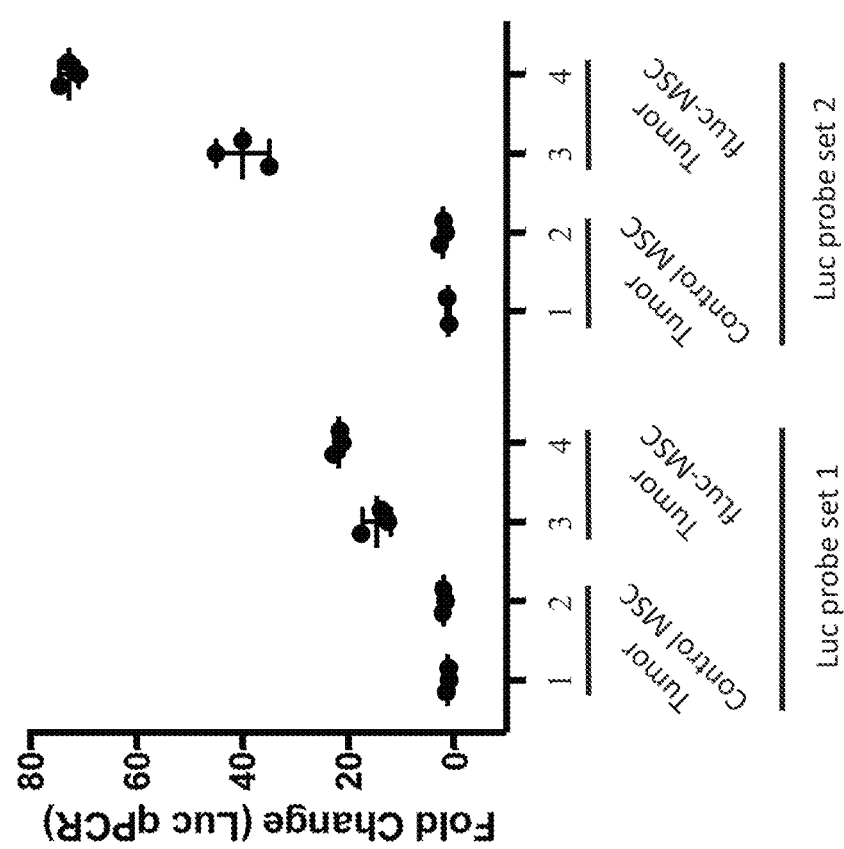
FIG. 37C shows homing to tumors by MSCs in IP tumor-bearing mice tumors as assessed by bioluminescence imaging.
Figure 37D:
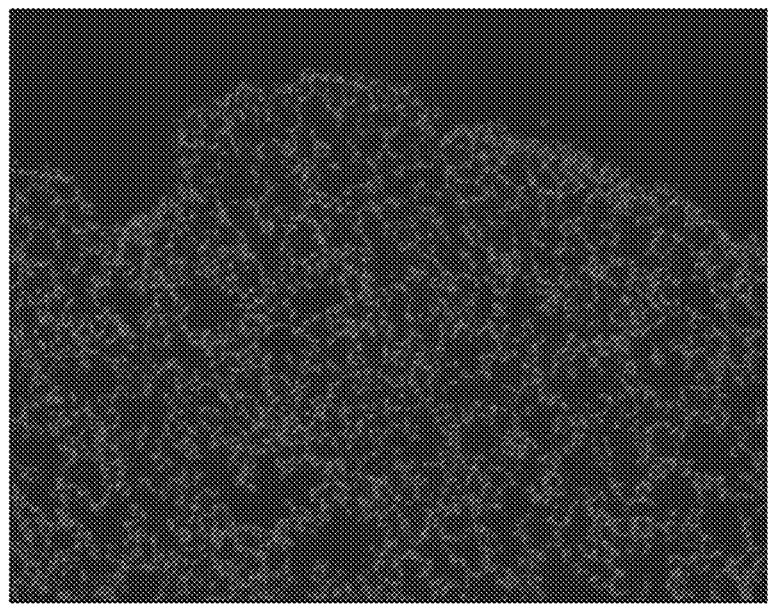
FIG. 37D shows homing to tumors by MSCs in IP tumor-bearing mice tumors as assessed by bioluminescence imaging.
Figure 37D:
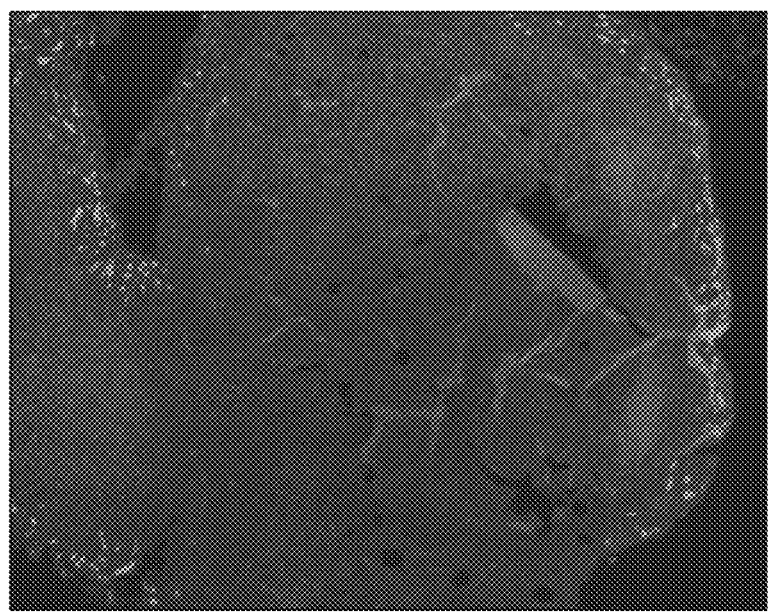

In the following example, balb/c MSCs ($2\times10^6$ cells) expressing fLUC were injected IP into CT-26 IP tumor-bearing mice. Mice were euthanized and tissues were collected 24 hours after injection. As shown in FIG. 37, fLUC-MSCs were significantly enriched in the tumors as detected by bioluminescence imaging (images shown in FIG. 37A, quantification of images in FIG. 37B), quantitative real time PCR (FIG. 37C), and fluorescence microscopy against firefly luciferase (FIG. 37D).

Figure 37E:
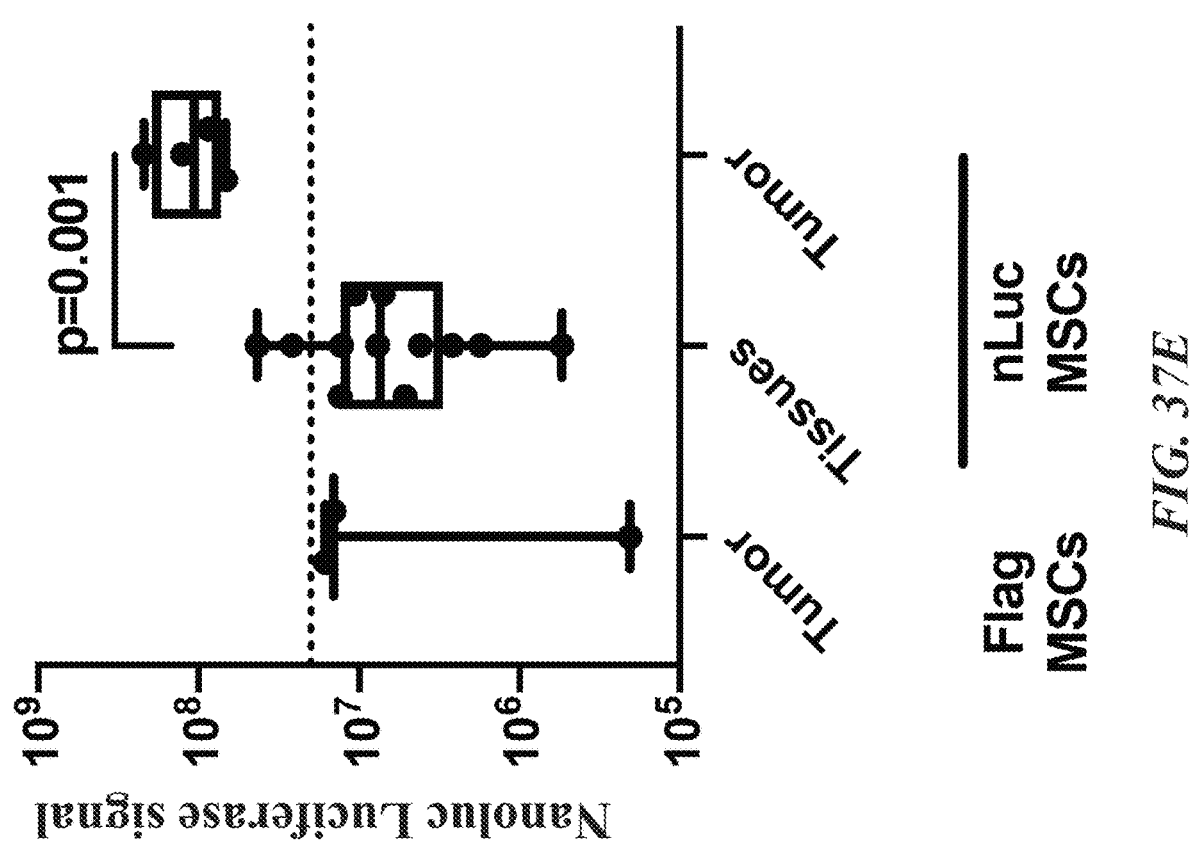
FIG. 37E shows homing to tumors by MSCs in IP tumor-bearing mice tumors as assessed by bioluminescence imaging.

Additionally, C57Bl/6 mice were implanted with $5\times10^4$ B16F10-fLUC cells IP. 7 days after tumor implantation, $1\times10^6$ C57Bl/6 murine BM-MSCs engineered to express Nanoluc-EGFP were injected IP. Mice were euthanized at 24 hours post injection of MSCs and peritoneal organs (stomach, kidney, liver, colon, spleen, pancreas, omentum/tumor, ovaries and Fallopian tubes) were imaged ex-vivo for nanoluc signaling (NanoGlo Substrate Kit, Vendor: Promega, Catalog No.: N1110). As shown in FIG. 37E, murine MSC nanoluc signal was preferentially enriched in the tumor compared to the other organs in the peritoneal cavity in a B16F10 tumor model.

Example 12: IL12 Producing MSCs Reduce CT26 Tumor Burden in an IP Model

In the following example, balb/c mMSCs were engineered to express murine IL12p70 using the lentiviral transduction method described in Example 6.

Figure 38:
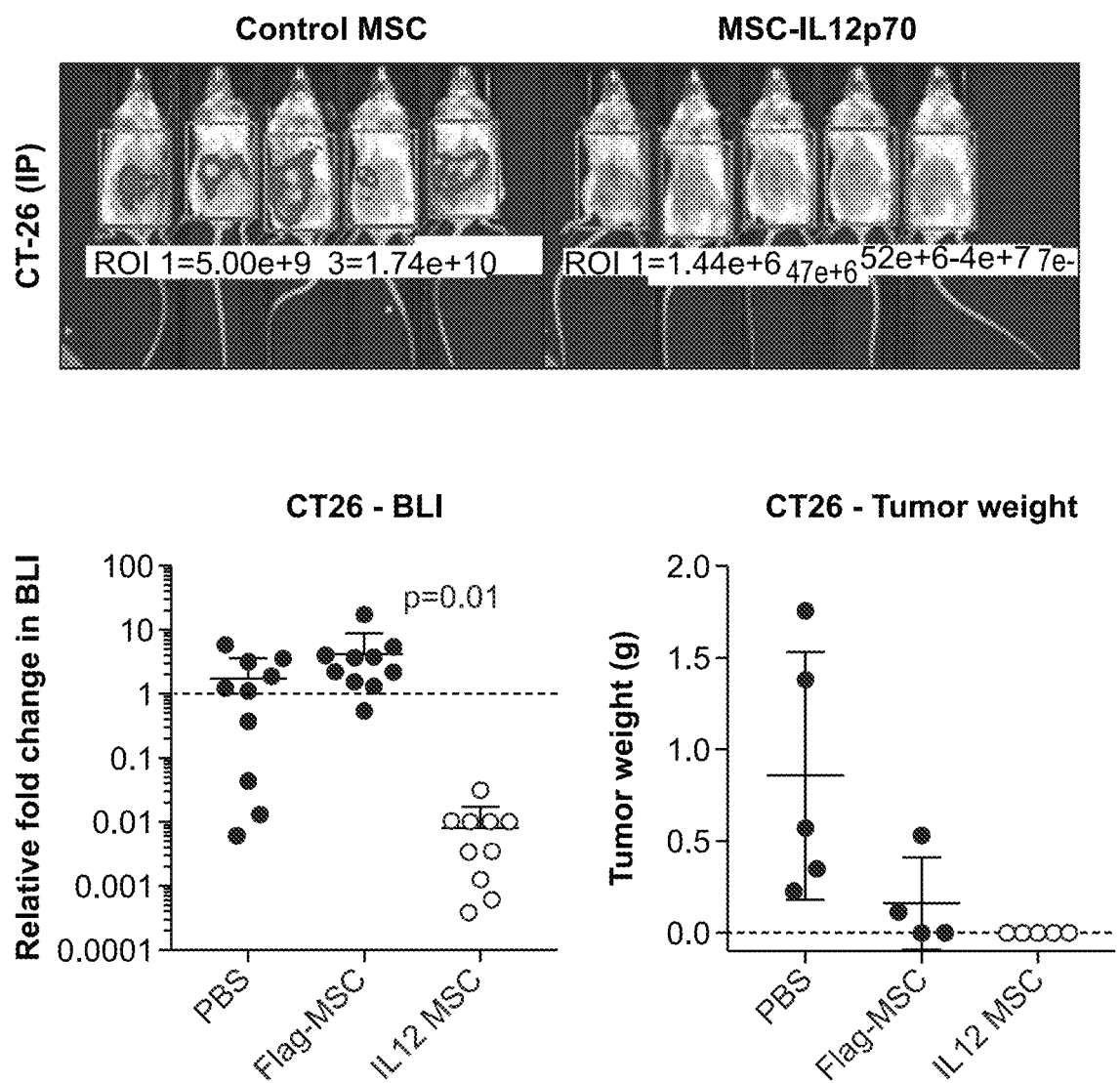
FIG. 38 shows IL12p70 expressing MSCs leading to reduction in tumor burden as assessed by BLI (top panels—images; and bottom left panel—individual mice in each treatment and the mean±SEM for each treatment group) and a complete elimination of detectable intraperitoneal tumors by tumor weight for individual mice in each treatment, and the mean±SEM for each treatment group (bottom right panel) in a CT26 IP model.

CT26 tumor cells ($5\times10^4$ cells in 100 µl) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. Mice were randomized into treatment groups and treated with intraperitoneally delivered mMSCs ($1\times10^6$ cells) expressing IL12p70. MSC-Flag-Myc and PBS were used as a negative control. As shown in FIG. 38, IL12p70 expressing MSCs led to reduction in tumor burden as assessed by BLI (top panels and bottom left panel) and a complete elimination of detectable intraperitoneal tumors by tumor weight (bottom right panel) in a CT26 model.

Example 13: IL12 Producing MSCs Reduce B16F10 Tumor Burden in an IP Model

Figure 39:
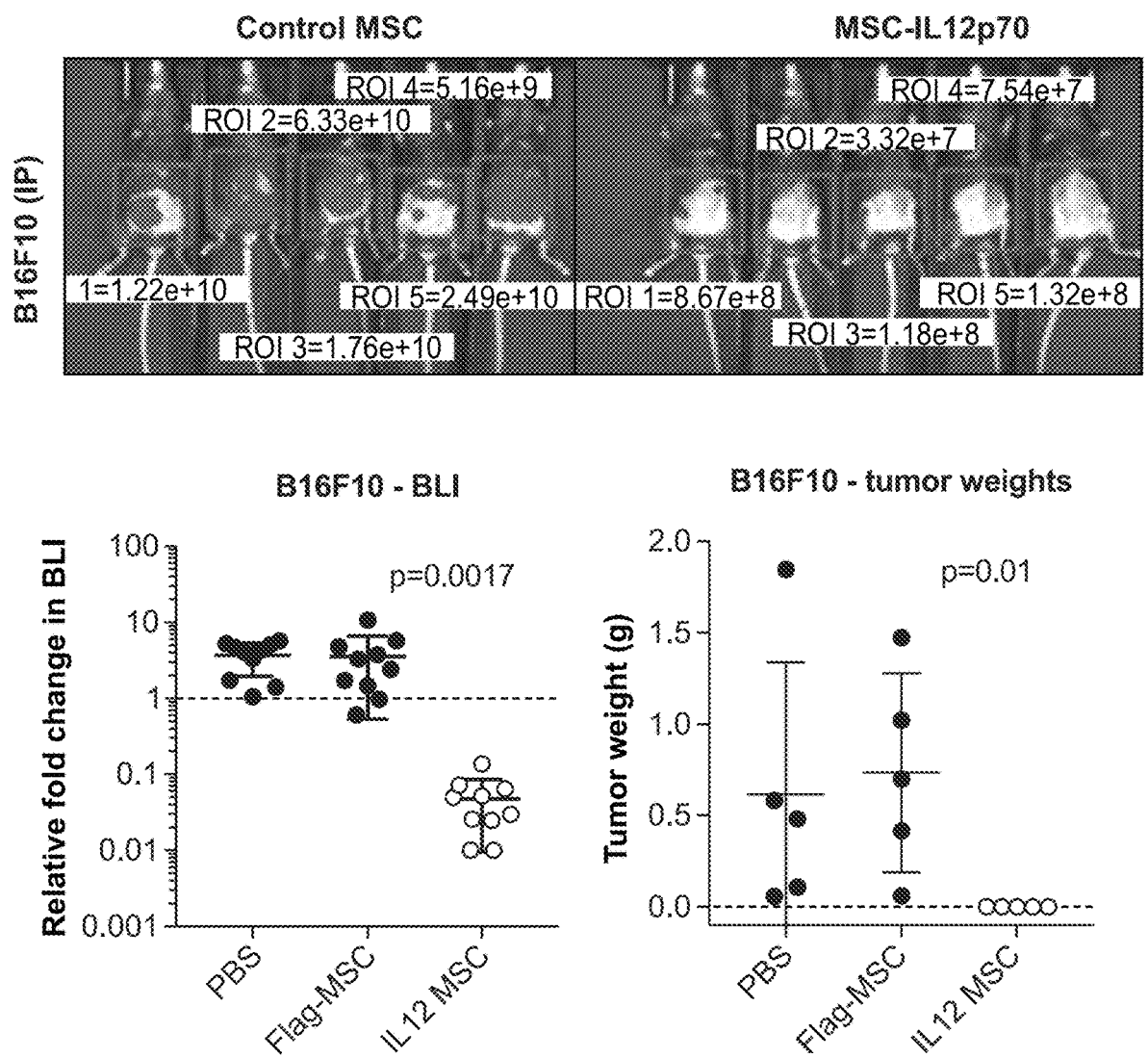
FIG. 39 shows IL12p70 expressing MSCs leading to reduction in tumor burden as assessed by BLI (top panels—images; and bottom left panel—individual mice in each treatment and the mean±SEM for each treatment group) and a complete elimination of detectable intraperitoneal tumors by tumor weight for individual mice in each treatment, and the mean±SEM for each treatment group (bottom right panel) in a B16F10 IP model.

In the following example, C57BL/6 mMSCs were engineered to express murine IL12p70 using the lentiviral transduction method described in Example 6. B16F10 tumor cells ($5\times10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with intraperitoneally delivered mMSCs $1\times10^6$ expressing IL12p70. MSC-Flag-Myc and PBS were used as a negative control. As shown in FIG. 39, IL12p70 expressing MSCs led to reduction in tumor burden as assessed by BLI (top panels and bottom left panel) and a complete elimination of detectable intraperitoneal tumors by tumor weight (bottom right panel) in a B16F10 model.

Example 14: MSCs Producing IL12 and CCL21a Reduce Tumor Burden and Prolong Survival in a CT26 IP Tumor Model In the following example, balb/c mMSCs were engineered to express murine IL12 (p70) and murine CCL21a from a single lentiviral expression vector. The lentiviral expression vector used a 2A ribosome skipping elements to express both cytokines from a single transcript using the lentiviral transduction method described in Example 6.

Figure 40A:
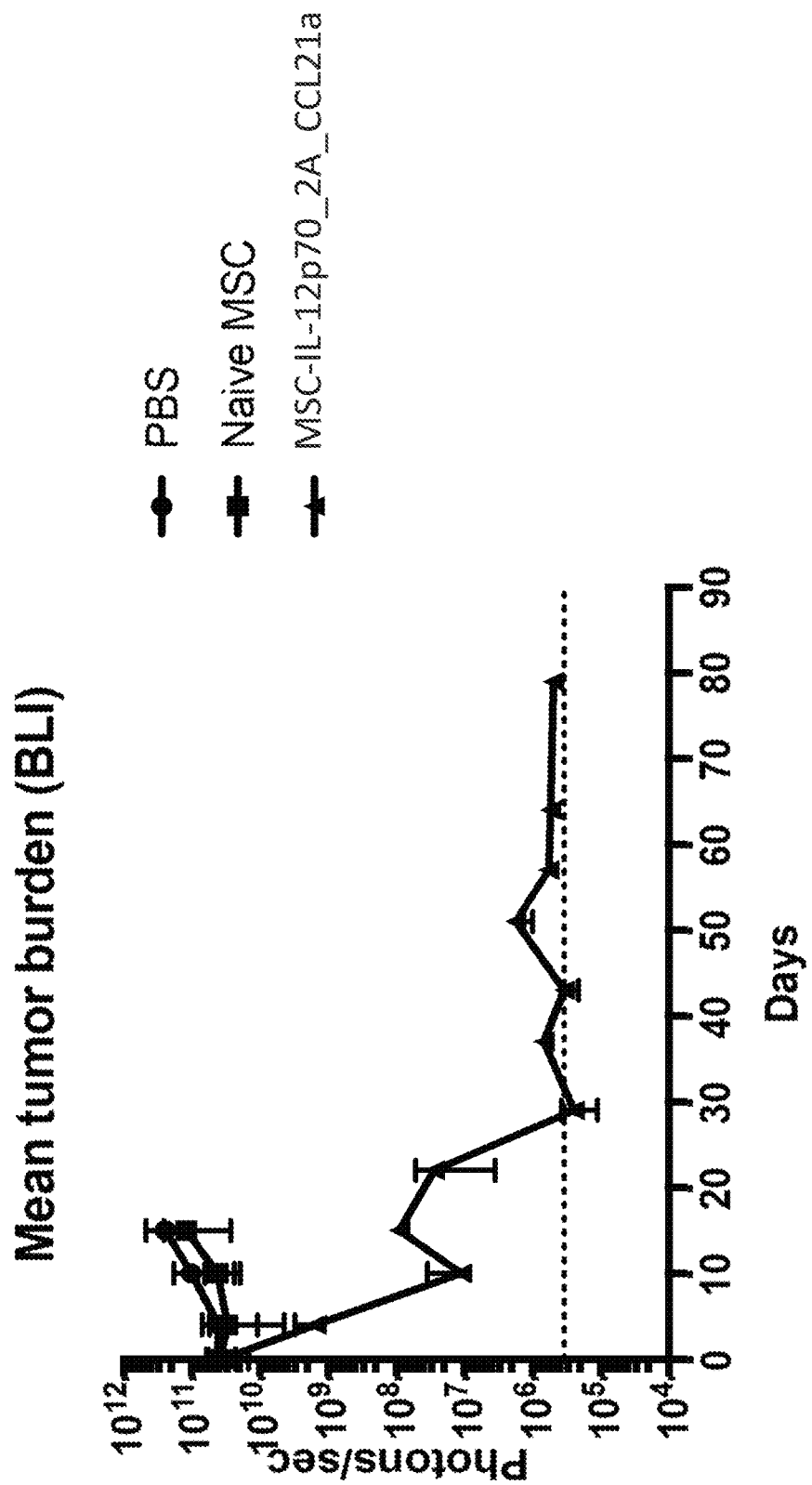
FIG. 40A shows IL12p70/CCL21a expressing MSCs leading to reduction in tumor burden as assessed by BLI in a CT26 IP model.
Figure 40B:
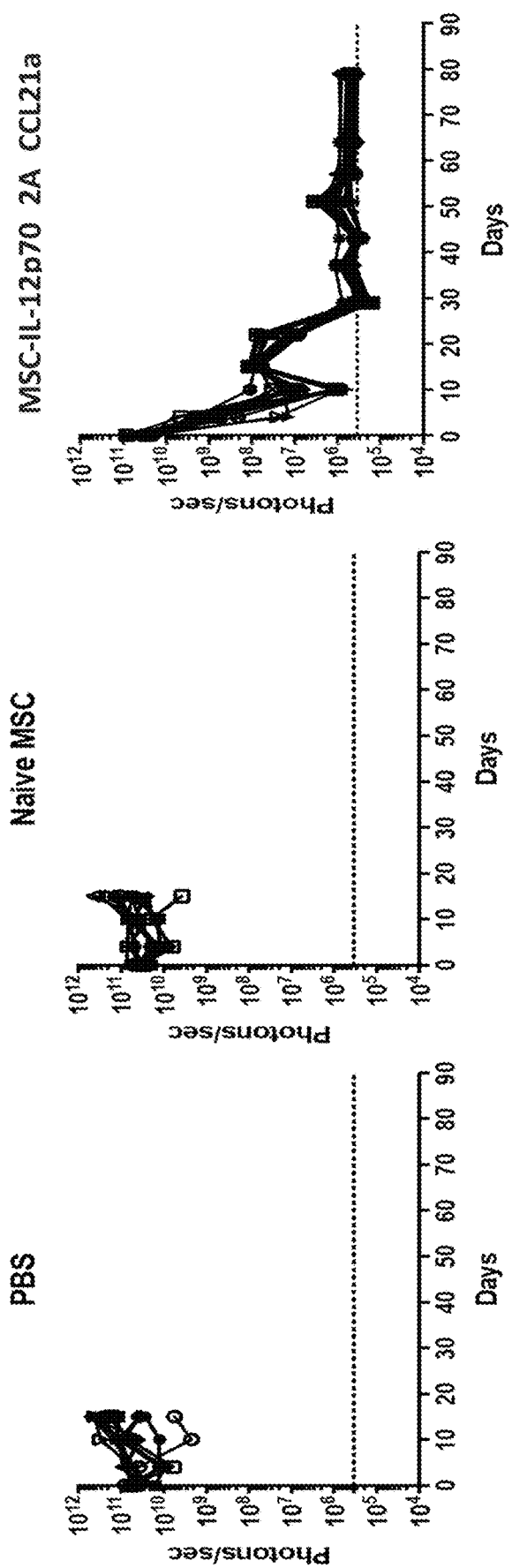
FIG. 40B shows IL12p70/CCL21a expressing MSCs leading to reduction in tumor burden as assessed by BLI in a CT26 IP model.
Figure 40C:
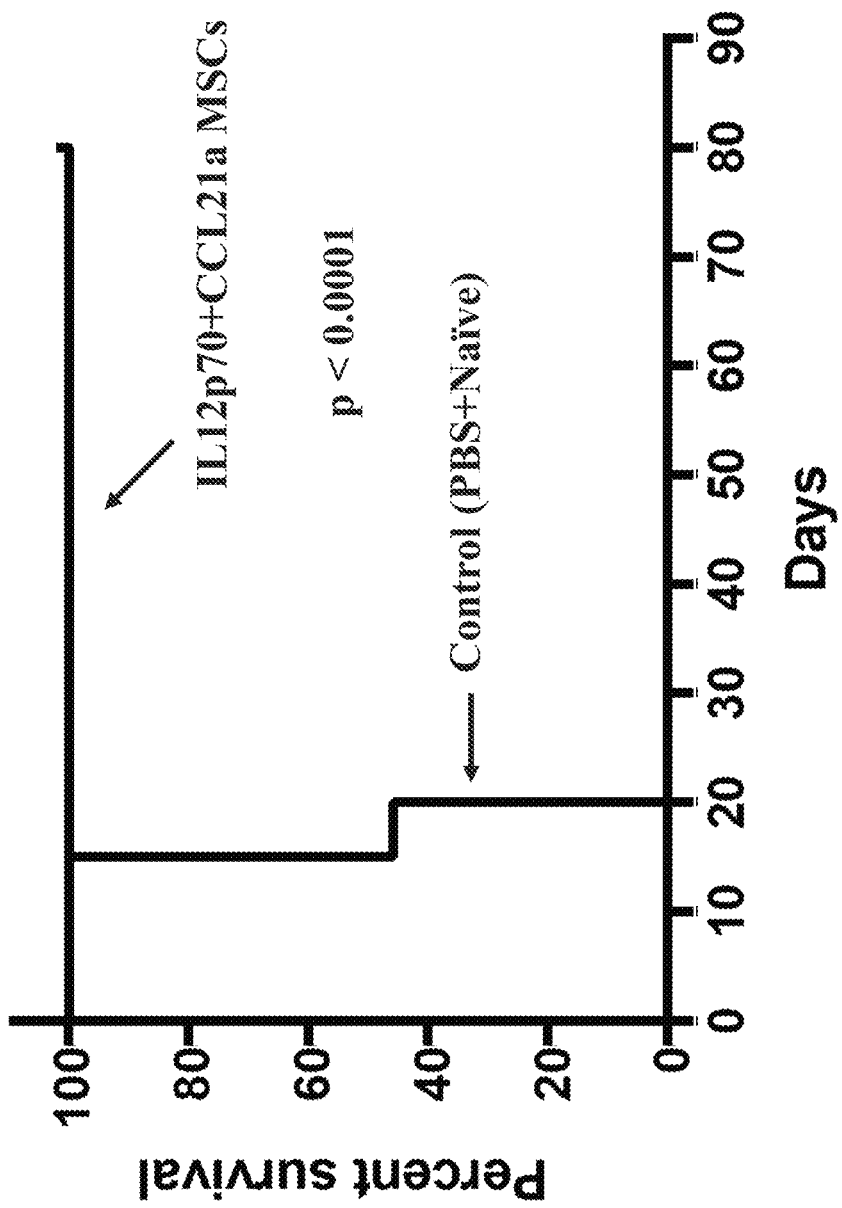
FIG. 40C shows treatment with IL12p70/CCL21a expressing MSCs led to prolonged survival (100% survival greater than 90 days), while control treated mice all died or were euthanized by Day 20.

CT26 tumor cells ($1\times10^6$ cells) modified to constitutively express luciferase enzyme (Cat no: CL043, Lot no: CL-IM147 Imanis Life Sciences) were injected into the peritoneal space of immunocompetent balb/c mice (age 6-8 weeks). One week after tumor implantation, tumor burden was measured by luciferase imaging (BLI) using an AMI imager. Mice were randomized into treatment groups and treated with intraperitoneally delivered mMSCs $1\times10^6$ expressing IL12p70 and CCL21a by the same MSC ("MSC-IL-12p70_2A_CCL21a"). MSC-Flag-Myc and PBS were used as a negative control. As shown in FIG. 40, IL12p70/CCL21a expressing MSCs led to reduction in tumor burden as assessed by BLI (top panels and bottom left panel) and a complete elimination of detectable intraperitoneal tumors by tumor weight (bottom right panel) in a CT26 model. FIG. 40A demonstrates the mean tumor burden as assessed by BLI for PBS treated (circle), MSC-Flag-Myc ("Naïve MSC" square), and IL12p70/CCL21a expressing MSCs (triangle). FIG. 40B demonstrates the tumor burden in individual mice as assessed by BLI for PBS treated, MSC-Flag-Myc ("Naïve MSC"), and IL12p70/CCL21a expressing MSCs (left, middle, and right panels, respectively). Notably, as shown in FIG. 40C, treatment with IL12p70/CCL21a expressing MSCs led to prolonged survival (100% survival greater than 90 days), while control treated mice all died or were euthanized by Day 20.

Example 15: MSCs Producing IL12 and IL21 Reduce Tumor Burden and Prolong Survival in a B16F10 IP Tumor Model In the following example, C57BL/6 mMSCs were engineered to express murine IL12 (p70) or murine IL21 (i.e., each MSC engineered to express only a single agent) using the lentiviral transduction method described in Example 6.

Figure 41:
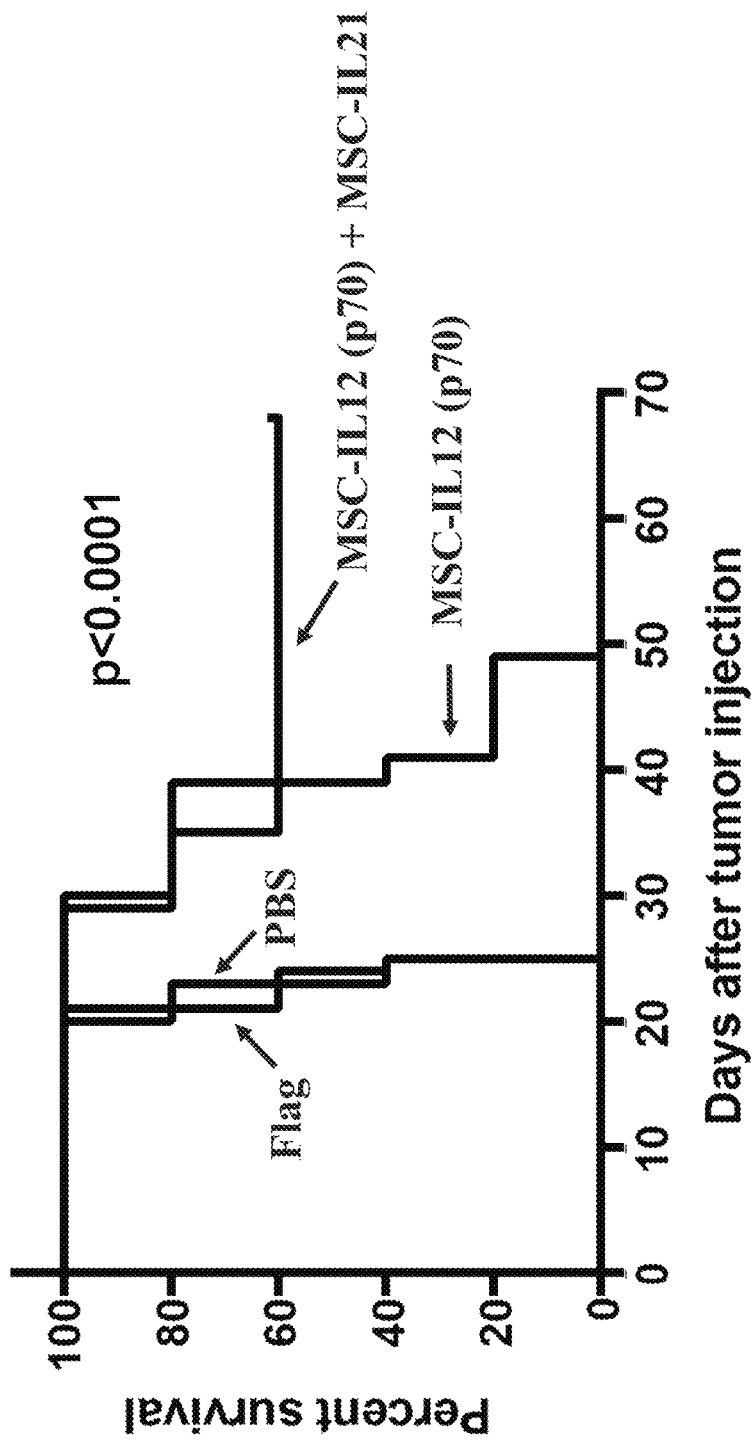
FIG. 41 shows treatment with IL12p70 expressing MSCs led to prolonged survival.

B16F10 tumor cells ($5\times10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with intraperitoneally delivered mMSCs ($1\times10^6$ cells) expressing IL12p70 in combination with mMSCs ($1\times10^6$ cells) expressing IL21, or mMSCs ($1\times10^6$ cells) expressing IL12p70 alone. MSC-Flag-Myc and PBS were used as a negative control. As shown in FIG. 41, treatment with IL12p70 expressing MSCs led to prolonged survival relative to control treated mice but all mice still all died or were euthanized by Day 50. In contrast, treatment with IL12p70 expressing MSCs in combination with IL21 expressing MSCs led to prolonged survival relative to treatment with IL12p70 expressing MSCs (60% survival past 60 days). Thus, IL21 expression by MSCs enhanced the efficacy of IL12p70 expressing MSCs.

Example 16: Allogeneic MSCs Producing IL12 and CCL21a Reduce Tumor Burden and Prolong Survival in a CT26 IP Tumor Model In the following example, balb/c mMSCs (syngeneic) and C57BL/6 mMSCs (allogeneic) were engineered to express murine IL12 (p70) and murine CCL21a from a single lentiviral expression vector. The lentiviral expression vector used a 2A ribosome skipping elements to express both cytokines from a single transcript using the lentiviral transduction method described in Example 6.

Figure 1:
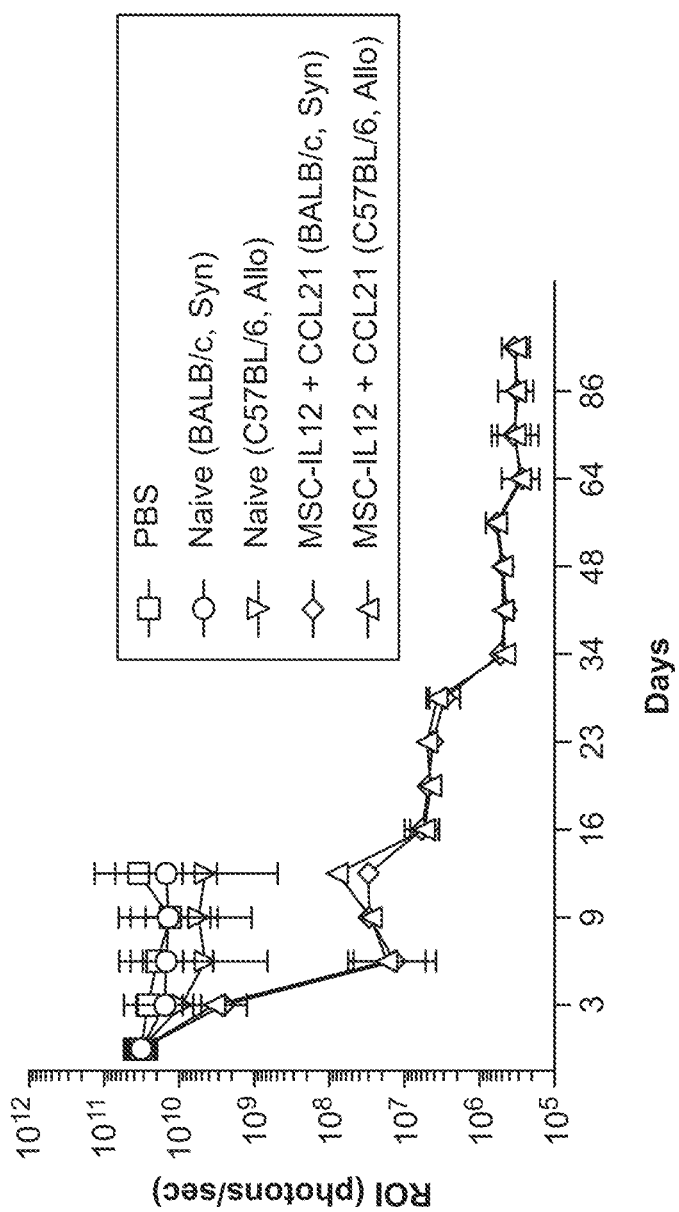
FIG. 1 shows treatment using syngeneic and allogeneic MSCs expressing IL12p70/CCL21a in a CT26 model.
Figure 2A:
FIG. 2A shows rechallenge of tumor free mice with CT26 tumors previously treated using syngeneic and allogeneic MSCs expressing IL12p70/CCL21a in a CT26 model.
Figure 2B:
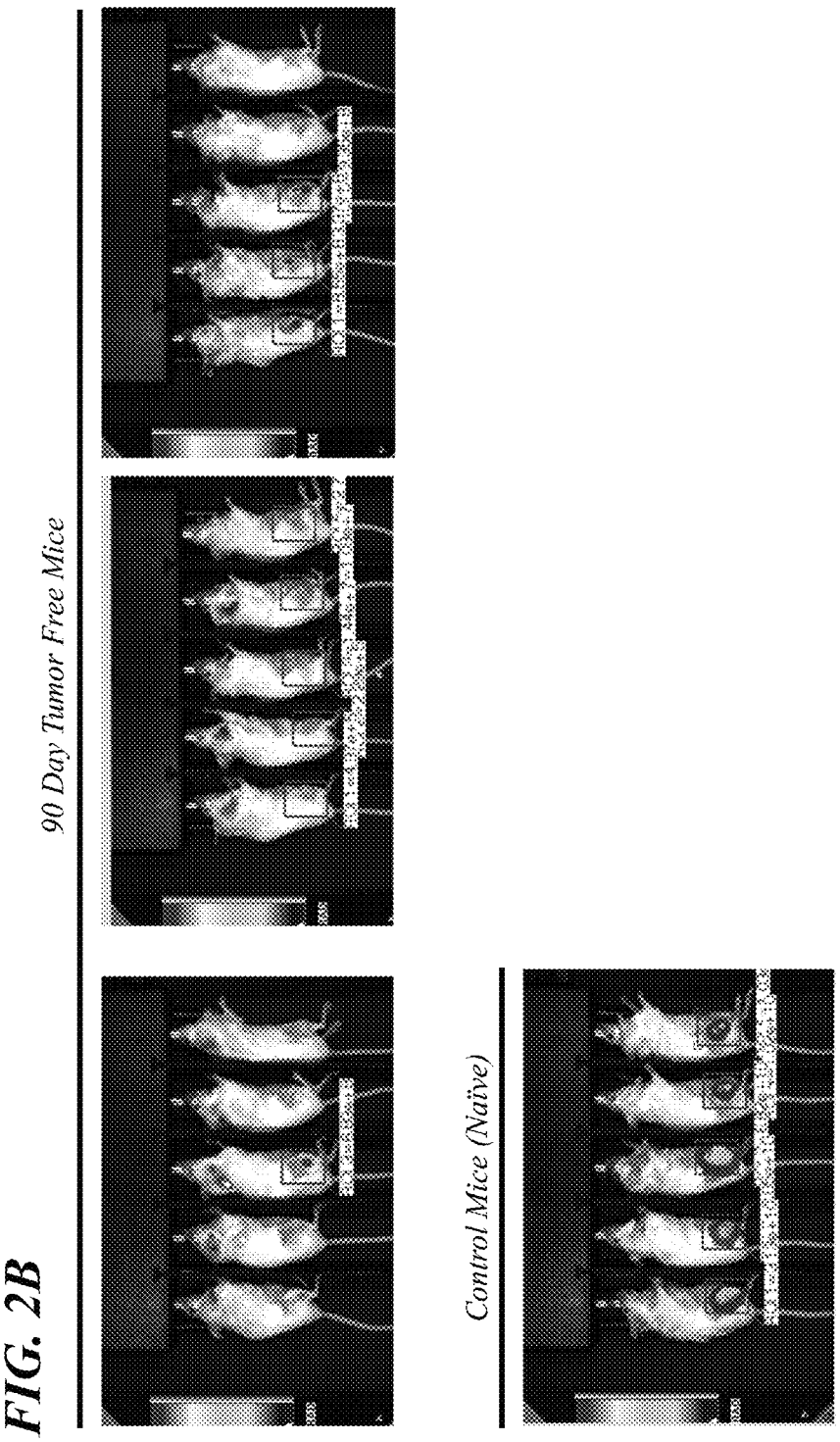
FIG. 2B shows rechallenge of tumor free mice with CT26 tumors previously treated using syngeneic and allogeneic MSCs expressing IL12p70/CCL21a in a CT26 model.

CT26 tumor cells ($1 \times 10^6$ cells) modified to constitutively express luciferase enzyme (Cat no: CL043, Lot no: CL-IM147 Imanis Life Sciences) were injected into the peritoneal space of immunocompetent balb/c mice (age 6-8 weeks). One week after tumor implantation, tumor burden was measured by luciferase imaging (BLI) using an AMI imager. Mice were randomized into treatment groups and treated with intraperitoneally delivered mMSCs ($1 \times 10^6$ cells) expressing IL12p70 and CCL21a by the same MSC ("MSC-IL12+CCL21"). Both balb/c control mMSCs (syngeneic) and C57BL/6 control mMSCs (allogeneic) were engineered to express MSC-Flag-Myc ("Naïve"). PBS was also used as a negative control. As shown in FIG. 1, both syngeneic and allogeneic MSCs expressing IL12p70/CCL21a led to reduction in tumor burden as assessed by BLI in a CT26 model, while control treatments did not. Additionally, mice that were previously treated with mMSCs expressing IL12p70 and CCL21a in both syngeneic and allogeneic models and were determined to be tumor free for 90 days were subsequently challenged with CT26 tumor cells ($0.5 \times 10^6$ cells in 100 µl PBS) implanted subcutaneously in the thigh, as schematized in FIG. 2A. As shown in FIG. 2B, tumor free mice rejected the tumor implant in contrast to naïve control mice where the tumor became established. Thus, treatment with MSCs expressing IL12p70/CCL21a led to prolonged tumor burden reduction as well as immunological memory.

Example 17: MSCs Producing IL12 and CCL21a Demonstrate Enhanced Growth Relative to Unmodified Cells In the following example, human MSCs from 3 different donors were engineered at different multiplicity of infections (MOIs) to express and secrete human IL-12 and human CCL21a from a single lentiviral expression vector. The lentiviral expression vector used a 2A ribosome skipping elements to express both cytokines from a single transcript using the lentiviral transduction method described in Example 6.

Figure 42A:
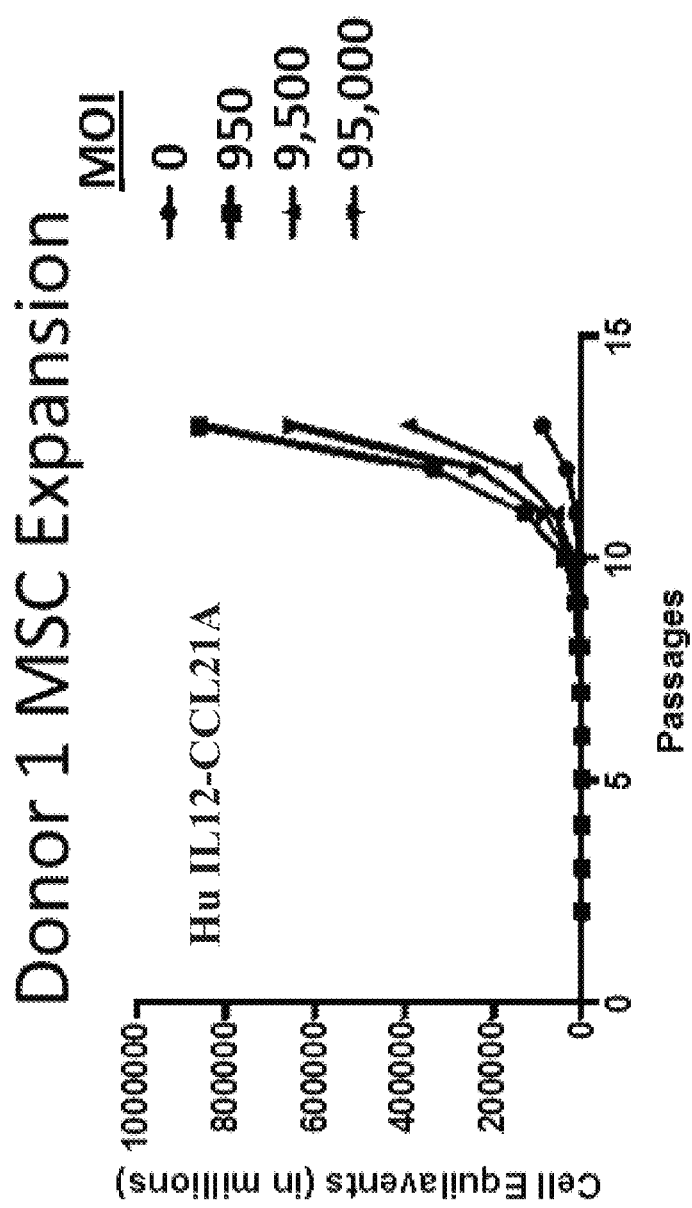
FIG. 42A shows relative growth of genetically engineered MSCs across different MOIs (95000, 9500, 950, or uninfected) in Donor 1.
Figure 42B:
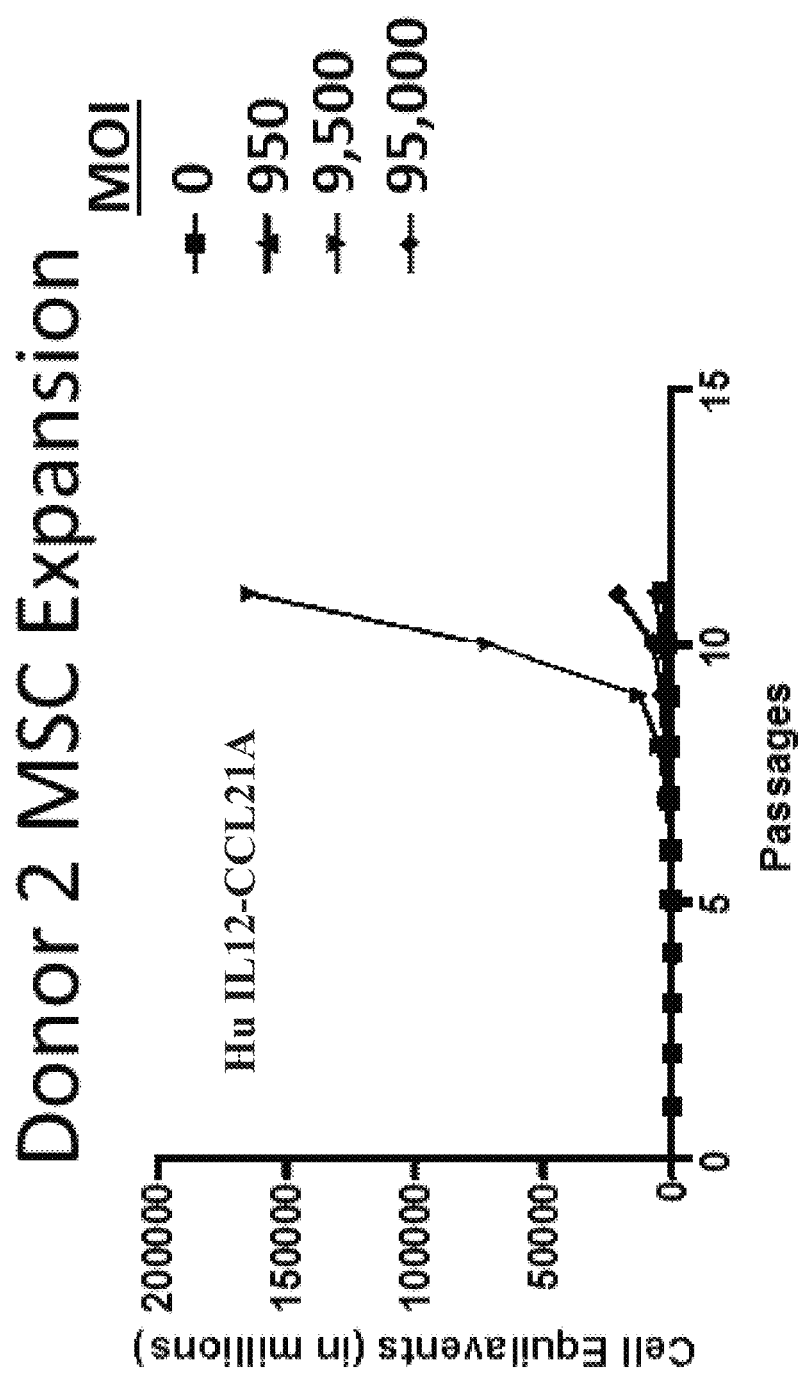
FIG. 42B shows relative growth of genetically engineered MSCs across different MOIs (95000, 9500, 950, or uninfected) in Donor 2.
Figure 42C:
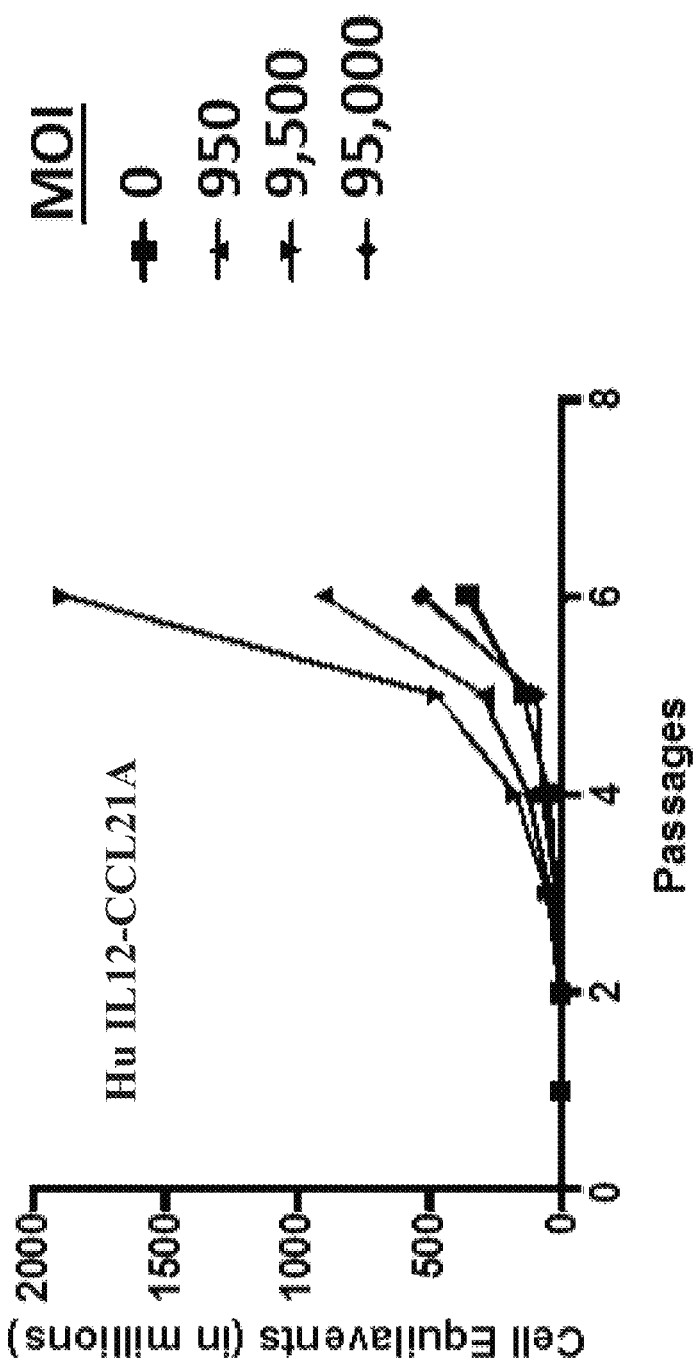
FIG. 42C shows relative growth of genetically engineered MSCs across different MOIs (95000, 9500, 950, or uninfected) in Donor 3.

As shown in FIG. 42, the genetically engineered MSCs (MOI=95000, 9500, or 950) exhibited enhanced cell expansion and growth compared to the non-genetically engineered human MSCs (MOI=0) in the three donors tested (FIG. 42A, Donor 1; FIG. 42B, Donor 2; FIG. 42C, Donor 3). Human MSCs genetically engineered with lentivirus to express GFP did not show a similar enhanced cell expansion or growth phenotype (data not shown).

Example 18: Selection of Promoter for Sustained Protein Expression in Human Bone-Marrow MSCs (BM-MSCs)

In the following example, various promoters were tested for driving expression of a reporter EGFP construct in human MSCs. Promoters tested were CMV, SFFV, EF1a, EF1a-LTR, EFS, MND, PGK, UbC (see Table 4). Cells were transduced using equivalent MOI (multiplicity of infection) using the lentiviral transduction method described in Example. EGFP percentage and Median Fluorescence Intensity (MFI) were quantified over serial passages using flow cytometry.

Figure 43:
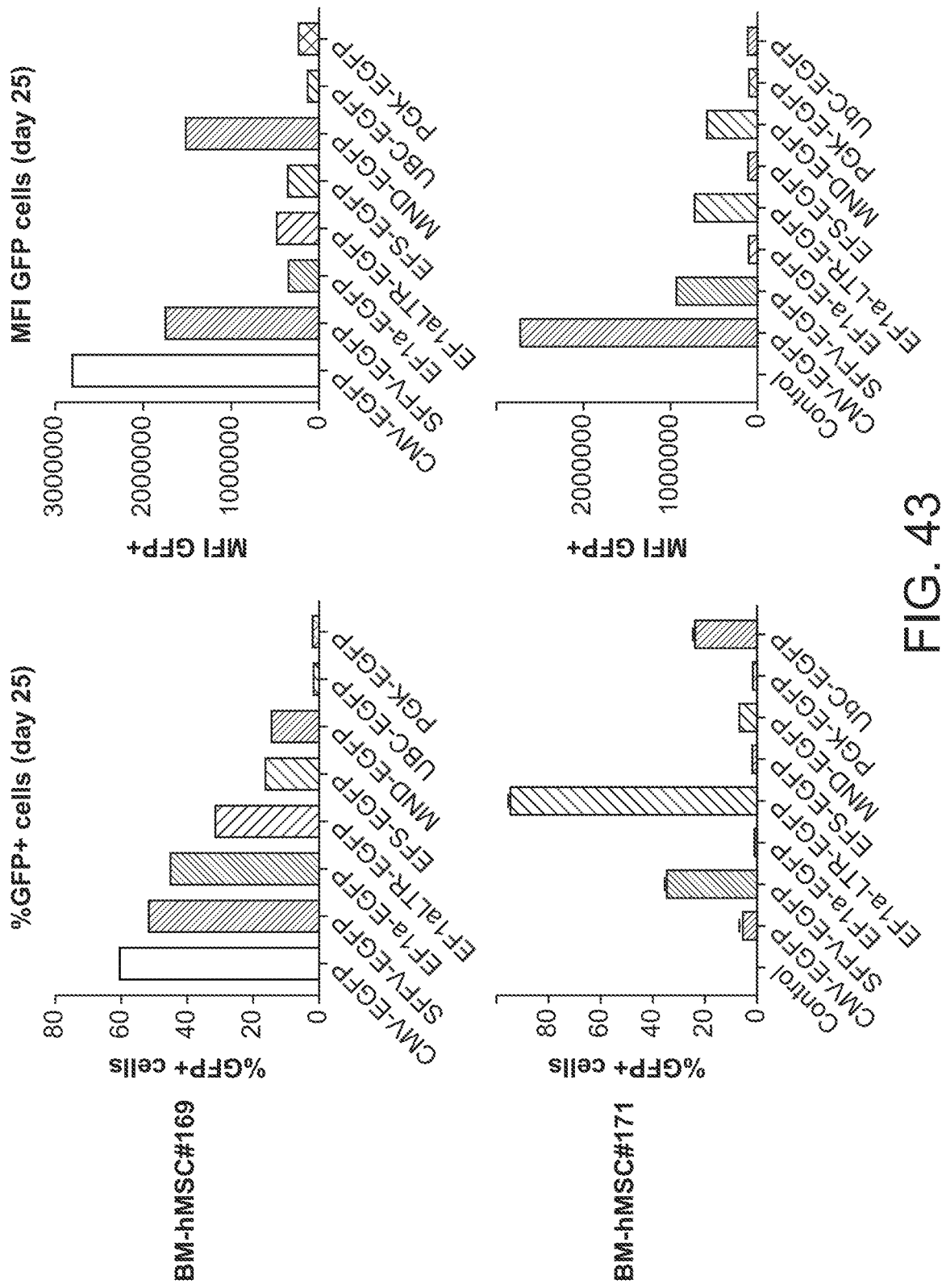
FIG. 43 shows two independent human BM-MSC cell lines from 2 different donors (top and bottom row, respectively) that were transduced with constructs containing various promoters driving EGFP expression. Percent GFP (left panels) and MFI (right panels) of engineered cells at day 25 post transduction is shown.

As shown in FIG. 43, two independent human BM-MSC cell lines from 2 different donors (top and bottom row, respectively were engineered and percent GFP (left panels) and MFI (right panels) of engineered cells was assessed at day 25 post transduction. The SFFV promoter demonstrated GFP expression in both cell lines by both GFP percentage and MFI.

Figure 44:
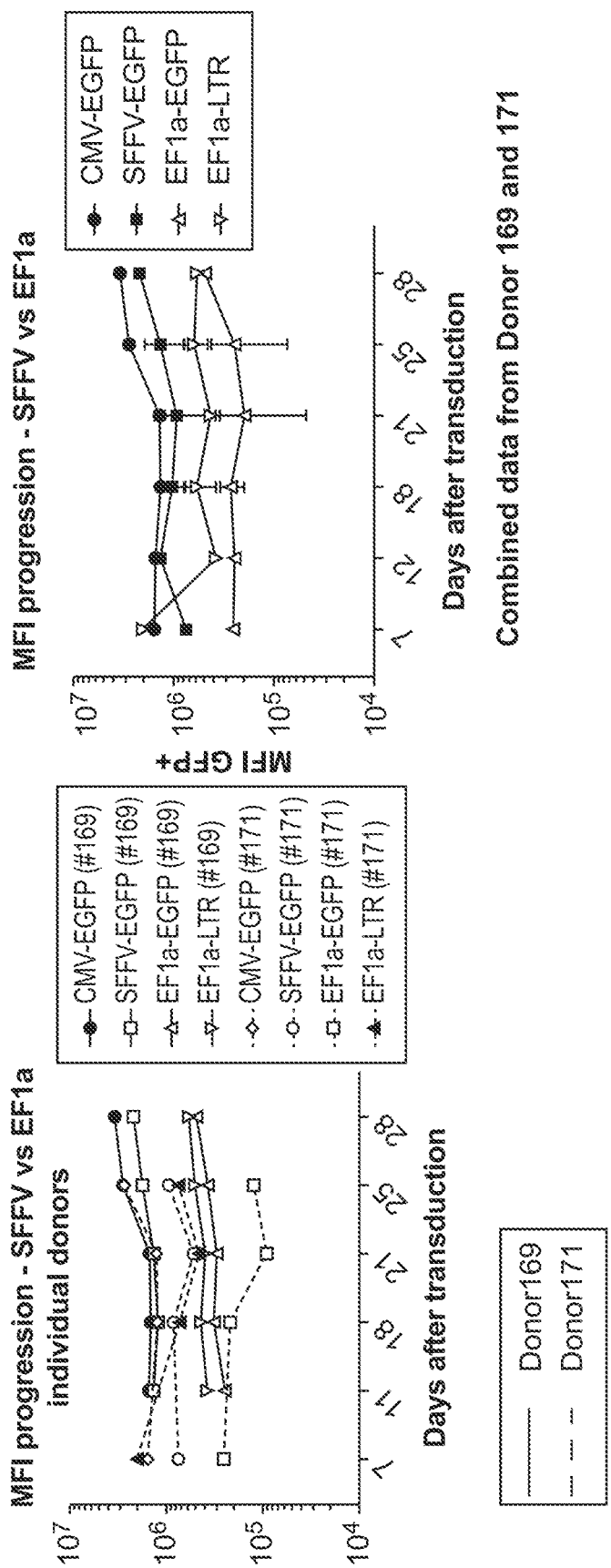
FIG. 44 shows two independent human BM-MSC cell lines from 2 different donors that were transduced with constructs containing various promoters driving EGFP expression. Shown is EGFP MFI tracked over time (day 7 to day 28 post-transduction) for either the two independent human BM-MSC cell lines individually (left panel) or with data from the two independent human BM-MSC cell lines combined (right panel).

As shown in FIG. 44, EGFP MFI was tracked over time (day 7 to day 28 post-transduction) for either the two independent human BM-MSC cell lines individually (left panel) or with data from the two independent human BM-MSC cell lines combined (right panel). Protein expression was stable over time during more than 28 days. Additionally, in comparison to EF1a promoters, SFFV promoter consistently drove almost ten-fold more protein expression as quantified by MFI.

Example 19: Engineering Human MSCs to Produce IL12 and IL21

In the following example, human bone-marrow MSCs were stably transduced to express IL12p70 and IL21 from various constructs using the lentiviral transduction method described in Example 6. Cells were expanded for 3 to 4 passages post-transduction and $0.2 \times 10^6$ cells were seeded in 6-well plates in 4 mL of media. Conditioned media was collected after 24 hours and ELISAs were performed to determine the IL-12 and IL-21 concentrations produced.

Various constructs were tested with different combinations and/or arrangements of promoter-signal sequence 1-cytokine 1-2A linker-signal sequence 2—cytokine 2. The combinations tested are described below in Table 7. Specific details of construct SB00880 are presented below in Table 8.

TABLE 7

| IL-12 and IL-21 Expression Constructs | | | | |
|---|---|---|---|---|
| Construct Name (SB#) | Promoter | Insert | Backbone | Codon Optimization |
| SB00743 | SFFV_1 | IL12ss-IL12 | pL23d | None |
| SB00763 | EFa1 (pEF6) | IL12ss-IL 12-fT2A*-IL21ss-IL21 | pL40g | None |
| SB00765 | EFa1 (pEF6) | IL12ss-IL 12-fT2A-IL12ss-IL21 | pL40g | None |
| SB00766 | EFa1 (pEF6) | IL12ss-IL 12-fT2A-IL8ss-IL21 | pL40g | None |
| SB00767 | EF1a (pEF6) | IL12ss-IL12-fT2A-IL21 | pL40g | None |
| SB00768 | EFa1 (pEF6) | IL21ss-IL21-fT2A-IL12ss-IL12 | pL40g | None |
| SB00769 | EFa1 (pEF6) | IL12ss-IL21-fT2A-IL12ss-IL12 | pL40g | None |

TABLE 7-continued

IL-12 and IL-21 Expression Constructs

| Construct Name (SB#) | Promoter | Insert | Backbone | Codon Optimization |
|---|---|---|---|---|
| SB00770 | EFa1 (pEF6) | IL6ss-IL21-fT2A-IL12ss-IL12 | pL40g | None |
| SB00771 | EF1a (pEF6) | IL8ss-IL21-fT2A-IL12ss-IL12 | pL40g | None |
| SB00772 | EF1a (pEF6) | IL21ss-IL21-fT2A-IL12 | pL40g | None |
| SB00773 | EF1a (pEF6) | IL12ss-IL21-fT2A-IL12 | pL40g | None |
| SB00774 | EF1a (pEF6) | IL6ss-IL21-fT2A-IL12 | pL40g | None |
| SB00775 | EF1a (pEF6) | IL8ss-IL21-fT2A-IL12 | pL40g | None |
| SB00772 | EF1a (pEF6) | IL21ss-IL21-fT2A-IL12 | pL40g | None |
| SB00620 | SFFV_1 | IL2ss-IL21 | pL17d | None |
| SB00838 | SFFV_1 | IL12ss-IL12-fT2A-IL21ss-IL21 | pL41g | None |
| SB00839 | SFFV_1 | IL12ss-IL12-fT2A-IL8ss-IL21 | pL41g | None |
| SB00840 | SFFV_1 | IL12ss-IL12-fT2A-IL21 | pL41g | None |
| SB00841 | SFFV_1 | IL21ss-IL21-fT2A-IL12ss-IL12 | pL41g | None |
| SB00843 | SFFV_1 | IL21ss-IL21-fT2A-IL12 | pL41g | None |
| SB00844 | SFFV_1 | IL8ss-IL21-fT2A-IL12 | pL41g | None |
| SB00868 | SFFV_1 | IL12ss-IL12 | pL41g | Yes |
| SB00870 | EF1a (pEF6) | IL12ss-IL12-fT2A-IL21ss-IL21 | pL40g | Yes |
| SB00872 | EF1a (pEF6) | IL12ss-IL12-fT2A-IL21 | pL40g | Yes |
| SB00869 | EF1a (pEF6) | IL21ss-IL21-fT2A-IL12ss-IL12 | pL40g | Yes |
| SB00871 | EF1a (pEF6) | IL21ss-IL21-fT2A-IL12 | pL40g | Yes |
| SB00879 | SFFV_1 | IL21ss-IL21-fT2A-IL12ss-IL12 | pL41g | Yes |
| SB00880 | SFFV_1 | IL12ss-IL12-fT2A-IL21ss-IL21 | pL41g | Yes |
| SB00881 | SFFV_1 | IL21ss-IL21-fT2A-IL12 | pL41g | Yes |
| SB00882 | SFFV_1 | IL12ss-IL12-fT2A-IL21 | pL41g | Yes |
| SB00862 | SFFV_1 | IL21ss-IL21 | pL23d | None |
| SB00863 | SFFV_1 | IL2ss-IL21 | pL41g | Yes |
| SB00968 | SFFV_1 | IL2ss-IL21-fT2A-IL12ss-IL12 | pL41g | Yes |
| SB00969 | SFFV_1 | IL8ss-IL21-fT2A-IL12ss-IL12 | pL41g | Yes |
| SB00970 | SFFV_1 | IL12ss-IL12-fT2A-IL2ss-IL21 | pL41g | Yes |
| SB00971 | SFFV_1 | IL12ss-IL12-fT2A-IL8ss-IL21 | pL41g | Yes |
| SB00862 + SB00743 | SFFV_1 | Co-transduction IL12 + IL21 | pL41g | None |
| SB00868 + 863 | SFFV_1 | Co-transduction IL12 + IL21 (IL2ssIL21) | pL41g | Yes |

*fT2A refers to Furin-T2A

TABLE 8

SB00880 Expression Construct Sequences

SFFV promoter (SEQ ID NO: 17)

```
GTAACGCCATTTTGCAAGGCATGGAAAAATACCAAACCAAGAATAGAGAAGTTCAGATCAAGG
GCGGGTACATGAAAATAGCTAACGTTGGGCCAAACAGGATATCTGCGGTGAGCAGTTTCGGCCC
CGGCCCGGGGCCAAGAACAGATGGTCACCGCAGTTTCGGCCCCGGCCCGAGGCCAAGAACAGA
TGGTCCCCAGATATGGCCCAACCCTCAGCAGTTTCTTAAGACCCATCAGATGTTTCCAGGCTCCC
CCAAGGACCTGAAATGACCCTGCGCCTTATTTGAATTAACCAATCAGCCTGCTTCTCGCTTCTGT
TCGCGCGCTTCTGCTTCCCGAGCTCTATAAAAGAGCTCACAACCCCTCACTCGGCGCGCCAGTCC
TCCGACAGACTGAGTCGCCCGGG
```

Human IL-12 signal sequence; codon optimized (nucleic acid) (SEQ ID NO: 32)

```
ATGTGCCATCAGCAACTCGTCATCTCCTGGTTCTCCCTTGTGTTCCTCGCTTCCCCTCTGGTCGCC
```

Human IL-12 signal sequence (amino acid) (SEQ ID NO: 112)

MCHQQLVISWFSLVFLASPLVA

Human IL-12 protein without signal sequence; codon optimized (nucleic acid) (SEQ ID NO: 136)

```
ATTTGGGAACTGAAGAAGGACGTCTACGTGGTCGAGCTGGATTGGTACCCGGACGCCCCTGGAG
AAATGGTCGTGCTGACTTGCGATACGCCAGAAGAGGACGGCATAACCTGGACCCTGGATCAGA
GCTCCGAGGTGCTCGGAAGCGGAAAGACCCTGACCATTCAAGTCAAGGAGTTCGGCGACGCGG
GCCAGTACACTTGCCACAAGGGTGGCGAAGTGCTGTCCCACTCCCTGCTGCTGCTGCACAAGAA
AGAGGATGGAATCTGGTCCACTGACATCCTCAAGGACCAAAAAGAACCGAAGAACAAGACCTT
CCTCCGCTGCGAAGCCAAGAACTACAGCGGTCGGTTCACCTGTTGGTGGCTGACGACAATCTCC
ACCGACCTGACTTTCTCCGTGAAGTCGTCACGGGGATCAAGCGATCCTCAGGGCGTGACCTGTG
GAGCCGCCACTCTGTCCGCCGAGAGAGTCAGGGGAGACAACAAGGAATATGAGTACTCCGTGG
AATGCCAGGAGGACAGCGCCTGCCCTGCCGCGGGAAGAGTCCCTGCCTATCGAGGTCATGGTCGA
TGCCGTGCATAAGCTGAAATACGAGAACTACACTTCCTCCTTCTTTATCCGCGACATCATCAAGC
CTGACCCCCCCAAGAACTTGCAGCTGAAGCCACTCAAGAACTCCCGCCAAGTGGAAGTGTCTTG
GGAATATCCAGACACTTGGAGCACCCCGCACTCATACTTCTCGCTCACTTTCTGTGTGCAAGTGC
```

TABLE 8-continued

SB00880 Expression Construct Sequences

AGGGAAAGTCCAAACGGGAGAAGAAAGACCGGGTGTTCACCGACAAAACCTCCGCCACTGTGA
TTTGTCGGAAGAACGCGTCAATCAGCGTCCGGGCGCAGGATAGATACTACTCGTCCTCCTGGAG
CGAATGGGCCAGCGTGCCTTGTTCCGGTGGCGGATCAGGCGGAGGTTCAGGAGGAGGCTCCGG
AGGAGGTTCCCGGAACCTCCCTGTGGCAACCCCCGACCCTGGAATGTTCCCGTGCCTACACCAC
TCCCAAAACCTCCTGAGGGCTGTGTCGAACATGTTGCAGAAGGCCCGCCAGACCCTTGAGTTCT
ACCCCTGCACCTCGGAAGAAATTGATCACGAGGACATCACCAAGGACAAGACCTCGACCGTGG
AAGCCTGCCTGCCGCTGGAACTGACCAAGAACGAATCGTGTCTGAACTCCCGCGAGACAAGCTT
TATCACTAACGGCAGCTGCCTGGCGTCGAGAAAGACCTCATTCATGATGGCGCTCTGTCTTTCCT
CGATCTACGAAGATCTGAAGATGTATCAGGTCGAGTTCAAGACCATGAACGCCAAGCTGCTCAT
GGACCCCAAGCGGCAGATCTTCCTGGACCAGAATATGCTCGCCGTGATTGATGAACTGATGCAG
GCCCTGAATTTCAACTCCGAGACTGTGCCTCAAAAGTCCAGCCTGGAAGAACCGGACTTCTACA
AGACCAAGATCAAGCTGTGCATCCTGTTGCACGCTTTCCGCATTCGAGCCGTGACCATTGACCG
CGTGATGTCCTACCTGAACGCCAGT

Human IL-12 protein without signal sequence (amino acid)
(SEQ ID NO: 137); p35 subunit in bold; p40 subunit in italics

*IWELKKDVYVVELDWYPDAPGEMVVLTCDTPEEDGITWTLDQSSEVLGSGKTLTIQVKEFGDAGQYTCHK*
*GGEVLSHSLLLLHKKEDGIWSTDILKDQKEPKNKTFLRCEAKNYSGRFTCWWLTTISTDLTFSVKSSRGSSD*
*PQGVTCGAATLSAERVRGDNKEYEYSVECQEDSACPAAEESLPIEVMVDAVHKLKYENYTSSFFIRDIIKPD*
*PPKNLQLKPLKNSRQVEVSWEYPDTWSTPHSYFSLTFCVQVQGKSKREKKDRVFTDKTSATVICRKNASISV*
*RAQDRYYSSSWSEWASVPCSGGGSGGGSGGGSGGGS*__RNLPVATPDPGMFPCLHHSQNLLRAVSNM__
__LQKARQTLEFYPCTSEEIDHEDITKDKTSTVEACLPLELTKNESCLNSRETSFITNGSCLASRKT__
__SFMMALCLSSIYEDLKMYQVEFKTMNAKLLMDPKRQIFLDQNMLAVIDELMQALNFNSETVP__
__QKSSLEEPDFYKTKIKLCILLHAFRIRAVTIDRVMSYLNAS__

Human IL-12 protein with signal sequence (amino acid)
(SEQ ID NO: 138); p35 subunit in bold; p40 subunit in italics MCHQQLVISWFSLVFLASPLVA*IWELKKDVYVVELDWYPDAPGEMVVLTCDTPEEDGITWTLDQSSEVL*
*GSGKTLTIQVKEFGDAGQYTCHKGGEVLSHSLLLLHKKEDGIWSTDILKDQKEPKNKTFLRCEAKNYSGR*
*FTCWWLTTISTDLTFSVKSSRGSSDPQGVTCGAATLSAERVRGDNKEYEYSVECQEDSACPAAEESLPIEVM*
*VDAVHKLKYENYTSSFFIRDIIKPDPPKNLQLKPLKNSRQVEVSWEYPDTWSTPHSYFSLTFCVQVQGKSKR*
*EKKDRVFTDKTSATVICRKNASISVRAQDRYYSSSWSEWASVPCSGGGSGGGSGGGSGGGS*__RNLPVATPD__
__PGMFPCLHHSQNLLRAVSNMLQKARQTLEFYPCTSEEIDHEDITKDKTSTVEACLPLELTKNES__
__CLNSRETSFITNGSCLASRKTSFMMALCLSSIYEDLKMYQVEFKTMNAKLLMDPKRQIFLDQN__
__MLAVIDELMQALNFNSETVPQKSSLEEPDFYKTKIKLCILLHAFRIRAVTIDRVMSYLNAS__

Furin-T2A Linker (nucleic acid) (SEQ ID NO: 139)

AGACGGAAACGCGGAAGCGGAGAGGGCAGAGGCTCGCTGCTTACATGCGGGGACGTGGAAGA
GAACCCCGGTCCG

Furin-T2A Linker (amino acid) (SEQ ID NO: 140)

RRKRGSGEGRGSLLTCGDVEENPGP

Human IL-21 signal sequence; codon optimized (nucleic acid)
(SEQ ID NO: 55)

ATGGAACGCATTGTGATCTGCCTGATGGTCATCTTCCTGGGCACCTTAGTGCACAAGTCGAGCA
GC

Human IL-21 signal sequence (amino acid) (SEQ ID NO: 135)

MERIVICLMVIFLGTLVHKSSS

Human IL-21 protein without signal sequence; codon optimized
(nucleic acid) (SEQ ID NO: 141)

CAGGGACAGGACAGGCACATGATTAGAATGCGCCAGCTCATCGATATCGTGGACCAGTTGAAG
AACTACGTGAACGACCTGGTGCCCGAGTTCCTGCCGGCCCCCGAAGATGTGGAAACCAATTGCG
AATGGTCGGCATTTTCCTGCTTTCAAAAGGCACAGCTCAAGTCCGCTAACACCGGGAACAACGA
ACGGATCATCAACGTGTCCATCAAAAAGCTGAAGCGGAAGCCTCCCTCCACCAACGCCGGACG
GAGGCAGAAGCATAGGCTGACTTGCCCGTCATGCGACTCCTACGAGAAGAAGCCGCCGAAGGA
GTTCCTGGAGCGGTTCAAGTCGCTCCTGCAAAAGATGATTCATCAGCACCTGTCCTCCCGGACTC
ATGGGTCTGAGGATTCA

Human IL-21 protein without signal sequence (amino acid)
(SEQ ID NO: 142)

QGQDRHMIRMRQLIDIVDQLKNYVNDLVPEFLPAPEDVETNCEWSAFSCFQKAQLKSANTGNNERII
NVSIKKLKRKPPSTNAGRRQKHRLTCPSCDSYEKKPPKEFLERFKSLLQKMIHQHLSSRTHGSEDS

TABLE 8-continued

SB00880 Expression Construct Sequences

Human IL-21 protein with signal sequence (amino acid)
(SEQ ID NO: 143)

MERIVICLMVIFLGTLVHKSSSQGQDRHMIRMRQLIDIVDQLKNYVNDLVPEFLPAPEDVETNCEWS
AFSCFQKAQLKSANTGNNERIINVSIKKLKRKPPSTNAGRRQKHRLTCPSCDSYEKKPPKEFLERFKS
LLQKMIHQLSSRTHGSEDS

SB00880 Cassette (SFFV-IL12ss-IL12-fT2A-IL21ss-IL21)
(SEQ ID NO: 144)

```
GTAACGCCATTTTGCAAGGCATGGAAAAATACCAAACCAAGAATAGAGAAGTTCAGATCAAGG
GCGGGTACATGAAAATAGCTAACGTTGGGCCAAACAGGATATCTGCGGTGAGCAGTTTCGGCCC
CGGCCCGGGGCCAAGAACAGATGGTCACCGCAGTTTCGGCCCCGGCCCGAGGCCAAGAACAGA
TGGTCCCCAGATATGGCCCAACCCTCAGCAGTTTCTTAAGACCCATCAGATGTTTCCAGGCTCCC
CCAAGGACCTGAAATGACCCTGCGCCTTATTTGAATTAACCAATCAGCCTGCTTCTCGCTTCTGT
TCGCGCGCTTCTGCTTCCCGAGCTCTATAAAAGAGCTCACAACCCCTCACTCGGCGCGCCAGTCC
TCCGACAGACTGAGTCGCCCGGGGGATCCGCGGAATTCGCCGCCACCATGTGCCATCAGCAACT
CGTCATCTCCTGGTTCTCCCTTGTGTTCCTCGCTTCCCCTCTGGTCGCCATTTGGGAACTGAAGAA
GGACGTCTACGTGGTCGAGCTGGATTGGTACCCGGACGCCCCTGGAGAAATGGTCGTGCTGACT
TGCGATACGCCAGAAGAGGACGGCATAACCTGGACCCTGGATCAGAGATCCGAGGTGCTCGGA
AGCGGAAAGACCCTGACCATTCAAGTCAAGGAGTTCGGCGACGCGGGCCAGTACACTTGCCAC
AAGGGTGGCGAAGTGCTGTCCCACTCCCTGCTGCTGCTGCACAAGAAAGAGGATGGAATCTGGT
CCACTGACATCCTCAAGGACCAAAAGAACCGAAGAACAAGACCTTCCTCCGCTGCGAAGCCA
AGAACTACAGCGGTCGGTTCACCTGTTGGTGGCTGACGACAATCTCCACCGACCTGACTTTCTCC
GTGAAGTCGTCACGGGGATCAAGCGATCCTCAGGGCGTGACCTGTGGAGCCGCCACTCTGTCCG
CCGAGAGAGTCAGGGGAGACAACAAGGAATATGAGTACTCCGTGGAATGCCAGGAGGACAGC
GCCTGCCCTGCCGCGGAAGAGTCCCTGCCTATCGAGGTCATGGTCGATGCCGTGCATAAGCTGA
AATACGAGAACTACACTTCCTCCTTCTTTATCCGCGACATCATCAAGCCTGACCCCCCCAAGAAC
TTGCAGCTGAAGCCACTCAAGAACTCCCGCCAAGTGGAAGTGTCTTGGGAATATCCAGACACTT
GGAGCACCCCGCACTCATACTTCTCGCTCACTTTCTGTGTGCAAGTGCAGGGAAAGTCCAAACG
GGAGAAGAAAGACCGGGTGTTCACCGACAAAACCTCCGCCACTGTGATTTGTCGGAAGAACGC
GTCAATCAGCGTCCGGGCGCAGGATAGATACTACTCGTCCTCCTGGAGCGAATGGGCCAGCGTG
CCTTGTTCCGGTGGCGGATCAGGCGGAGGTTCAGGAGGAGGCTCCGGAGGAGGTTCCCGGAAC
CTCCCTGTGGCAACCCCCGACCCTGGAATGTTCCCGTGCCTACACCACTCCCAAACCTCCTGAG
GGCTGTGTCGAACATGTTGCAGAAGGCCCGCCAGACCCTTGAGTTCTACCCCTGCACCTCGGAA
GAAATTGATCACGAGGACATCACCAAGGACAAGACCTCGACCGTGGAAGCCTGCCTGCCGCTG
GAACTGACCAAGAACGAATCGTGTCTGAACTCCCGCGAGACAAGCTTTATCACTAACGGCAGCT
GCCTGGCGTCGAGAAAGACCTCATTCATGATGGCGCTCTGTCTTTCCTGATCTACGAAGATCTG
AAGATGTATCAGGTCGAGTTCAAGACCATGAACGCCAAGCTGCTCATGGACCCGAAGCGGCAG
ATCTTCCTGGACCAGAATATGCTCGCCGTGATTGATGAACTGATGCAGGCCCTGAATTTCAACTC
CGAGACTGTGCCTCAAAAGTCCAGCCTGGAAGAACCGGACTTCTACAAGACCAAGATCAAGCT
GTGCATCCTGTTGCACGCTTTCCGCATTCGAGCCGTGACCATTGACCGCGTGATGTCCTACCTGA
ACGCCAGTAGACGGAAACGCGGAAGCGGAGAGGGCAGAGGCTCGCTGCTTACATGCGGGGACG
TGGAAGAGAACCCCGGTCCGATGGAACGCATTGTGATCTGCCTGATGGTCATCTTCCTGGGCAC
CTTAGTGCACAAGTCGAGCAGCCAGGGACAGGACAGGCACATGATTAGAATGCGCCAGCTCAT
CGATATCGTGGACCAGTTGAAGAACTACGTGAACGACCTGGTGCCCGAGTTCCTGCCGGCCCCC
GAAGATGTGGAAACCAATTGCGAATGGTCGGCATTTTCCTGCTTTCAAAAGGCACAGCTCAAGT
CCGCTAACACCGGGAACAACGAACGGATCATCAACGTGTCCATCAAAAAGCTGAAGCGGAAGC
CTCCCTCCACCAACGCCGGACGGAGGCAGAAGCATAGGCTGACTTGCCCGTCATGCGACTCCTA
CGAGAAGAAGCCGCCGAAGGAGTTCCTGGAGCGGTTCAAGTCGCTCCTGCAAAAGATGATTCA
TCAGCACCTGTCCTCCCGGACTCATGGGTCTGAGGATTCATGA
```

SB00880 Full Vector (PL41g + SB00880 Cassette)
(SEQ ID NO: 145)

```
TGACTCCTGCGCAGTCCAAAAAAAAAGGCTCCAAAAGGAGCCTTTAATTGTATCGGTGGGCCCT
TAGAAAACTCATCGAGCATCAAATGAAACTGCAATTTATTCATATCAGGATTATCAATACCAT
ATTTTTGAAAAAGCCGTTTCTGTAATGAAGGAGAAAACTCACCGAGGCAGTTCCATAGGATGGC
AAGATCCTGGTATCGGTCTGCGATTCCGACTCGTCCAACATCAATACAACCTATTAATTTCCCCT
CGTCAAAAATAAGGTTATCAAGTGAGAAATCACCATGAGTGACGACTGAATCCGGTGAGAATG
GCAAAAGCTTATGCATTTCTTTCCAGACTTGTTCAACAGGCCAGCCATTACGCTCGTCATCAAAA
TCACTCGCATCAACCAAACCGTTATTCATTCGTGATTGCGCCTGAGCGAGACGAAATACGCGAT
CGCTGTTAAAGGACAATTACAAACAGGAATCGAATGCAACCGGCGCAGGAACACTGCCAGCG
CATCAACAATATTTTCACCTGAATCAGGATATTCTTCTAATACCTGGAATGCTGTTTTCCCGGGG
ATCGCAGTGGTGAGTAACCATGCATCATCAGGAGTACGGATAAAATGCTTGATGGTCGGAAGA
GGCATAAATTCCGTCAGCCAGTTTAGTCTGACCATCTCATCTGTAACATCATTGGCAACGCTACC
TTTGCCATGTTTCAGAAACAACTCTGGCGCATCGGGCTTCCCATACAATCGATAGATTGTCGCAC
CTGATTGCCCGACATTATCGCGAGCCCATTTATACCCATATAAATCAGCATCCATGTTGGAATTT
AATCGCGGCCTCGAGCAAGACGTTTCCCGTTGAATATGGCTCATAACACCCCTTGTATTACTGTT
TATGTAAGCAGACAGTTTTATTGTTCATGATGATATATTTTTATCTTGTGCAATGTAACATCAGA
GATTTTGAGACACAACGTGGTTTAAACAAATAGTCAAAGCCTCCGGCGACTAGTCGGGGTCAT
TAGTTCATAGCCCATATATGGAGTTCCGCGTTACATAACTTACGGTAAATGGCCCGCCTGGCTGA
CCGCCCAACGACCCCCGCCCATTGACGTCAATAATGACGTATGTTCCCATAGTAACGCCAATA
GGACTTTCCATTGACGTCAATGGGTGGAGTATTTACGGTAAACTGCCCACTTGGCAGTACATCA
AGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGG
```

TABLE 8-continued

SB00880 Expression Construct Sequences

```
ACTTTCCAAAATGTCGTAACAACTCCGCCCCATTGACGCAAATGGGCGGTAGGCGTGTACGGTG
GGAGGTCTATATAAGCAGAGCTGGTTTAGTGAACCGGGTCTCTCTGGTTAGACCAGATTTGAGC
CTGGGAGCTCTCTGGCTAACTAGGGAACCCACTGCTTAAGCCTCAATAAAGCTTGCCTTGAGTG
CTTCAAGTAGTGTGTGCCCGTCTGTTGTGTGACTCTGGTAACTAGAGATCCCTCAGACCCTTTTA
GTCAGTGTGGAAAATCTCTAGCAGTGGCGCCCGAACAGGGACCTGAAAGCGAAAGGGAAACCA
GAGGAGCTCTCTCGACGCAGGACTCGGCTTGCTGAAGCGCGCACGGCAAGAGGCGAGGGGCGG
CGACTGCAGAGTACGCCAAAATTTTGACTAGCGGAGGCTAGAAGGACGAGAGATGGGTGCGAGA
GCGTCAGTATTAAGCGGGGGAAAATAGCGGCCGCCACAATTTTAAAAGAAAAGGGGGGATTGG
GGGGTACAGTGCAGGGGAAGAATAGTAGACATAATAGCAACAGACATACAAACTAAAGAATT
ACAAAAACAAATTACAAAAATTCAAATTTTCGGGGGATCCGTAACGCCATTTTGCAAGGCATGG
AAAAATACCAAACCAAGAATAGAGAAGTTCAGATCAAGGGCGGGTACATGAAAATAGCTAACG
TTGGGCCAAACAGGATATCTGCGGTGAGCAGTTTCGGCCCCGGCCCGGGGCCAAGAACAGATG
GTCACCGCAGTTTCGGCCCCGGCCCGAGGCCAAGAACAGATGGTCCCCAGATATGGCCCAACCC
TCAGCAGTTTCTTAAGACCCATCAGATGTTTCCAGGCTCCCCCAAGGACCTGAAATGACCCTGC
GCCTTATTTGAATTAACCAATCAGCCTGCTTCTCGCTTCTGTTCGCGCTTCTGCTTCCCGAGCT
CTATAAAAGAGCTCACAACCCCTCACTCGGCGCGCCAGTCCTCCGACAGACTGAGTCGCCCGGG
GGATCCGCGGAATTCGCCGCCACCATGTGCCATCAGCAACTCGTCATCTCCTGGTTCTCCCTTGT
GTTCCTCGCTTCCCCTCTGGTCGCCATTTGGGAACTGAAGAAGGACGTCTACGTGGTCGAGCTG
GATTGGTACCCGGACGCCCTGGAGAAATGGTCGTGCTGACTTGCGATACGCCAGAAGAGGAC
GGCATAACCTGGACCCTGGATCAGAGCTCCGAGGTGCTCGGAAGCGGAAAGACCCTGACCATT
CAAGTCAAGGAGTTCGGCGACGCGGGCCAGTACACTTGCCACAAGGGTGGCGAAGTGCTGTCC
CACTCCCTGCTGCTGCTGCACAAGAAAGAGGATGGAATCTGGTCCACTGACATCCTCAAGGACC
AAAAAGAACCGAAGAACAAGACCTTCCTCCGCTGCGAAGCCAAGAACTACAGCGGTCGGTTCA
CCTGTTGGTGGCTGACGACAATCTCCACCGACCTGACTTTCTCCGTGAAGTCGTCACGGGGATC
AAGCGATCCTCAGGGCGTGACCTGTGGAGCCGCCACTCTGTCCGCCGAGAGAGTCAGGGGAGA
CAACAAGGAATATGAGTACTCCGTGGAATGCCAGGAGGACAGCGCCTGCCCTGCCGCGGAAGA
GTCCCTGCCTATCGAGGTCATGGTCGATGCCGTGCATAAGCTGAAATACGAGAACTACACTTCC
TCCTTCTTTATCCGCGACATCATCAAGCCTGACCCCCCCAAGAACTTGCAGCTGAAGCCACTCAA
GAACTCCCGCCAAGTGGAAGTGTCTTGGGAATATCCAGACACTTGGAGCACCCCGCACTCATAC
TTCTCGCTCACTTTCTGTGTGCAAGTGCAGGGAAAGTCCAAACGGGAGAAGAAAGACCGGGTGT
TCACCGACAAAACCTCCGCCACTGTGATTTGTCGGAAGAACGCGTCAATCAGCGTCCGGGCGCA
GGATAGATACTACTCGTCCTCCTGGAGCGAATGGGCCAGCGTGCCTTGTTCCGGTGGCGGATCA
GGCGGAGGTTCAGGAGGAGGCTCCGGAGGAGGTTCCCGGAACCTCCCTGTGGCAACCCCCGAC
CCTGGAATGTTCCCGTGCCTACACCACTCCCAAAACCTCCTGAGGGCTGTGTCGAACATGTTGC
AGAAGGCCCGCCAGACCCTTGAGTTCTACCCCTGCACCTCGGAAGAAATTGATCACGAGGACAT
CACCAAGGACAAGACCTCGACCGTGGAAGCCTGCCTGCCGCTGGAACTGACCAAGAACGAATC
GTGTCTGAACTCCCGCGAGACAAGCTTTATCACTAACGGCAGCTGCCTGGCGTCGAGAAAGACC
TCATTCATGATGGCGCTCTGTCTTTCCTCGATCTACGAAGATCTGAAGATGTATCAGGTCGAGTT
CAAGACCATGAACGCCAAGCTGCTCATGGACCCGAAGCGGCAGATCTTCCTGGACCAGAATAT
GCTCGCCGTGATTGATGAACTGATGCAGGCCCTGAATTTCAACTCCGAGACTGTGCCTCAAAAG
TCCAGCCTGGAAGAACCGGACTTCTACAAGACCAAGATCAAGCTGTGCATCCTGTTGCACGCTT
TCCGCATTCGAGCCGTGACCATTGACCGCGTGATGTCCTACCTGAACGCCAGTAGACGGAAACG
CGGAAGCGGAGAGGGCAGAGGCTCGCTGCTTACATGCGGGGACGTGGAAGAGAACCCCGGTCC
GATGGAACGCATTGTGATCTGCCTGATGGTCATCTTCCTGGGCACCTTAGTGCACAAGTGCAGC
AGCCAGGGACAGGACAGGCACATGATTAGAATGCGCCAGCTCATCGATATCGTGGACCAGTTG
AAGAACTACGTGAACGACCTGGTGCCCGAGTTCCTGCCGGCCCCCGAAGATGTGGAAACCAATT
GCGAATGGTCGGCATTTTCCTGCTTTCAAAAGGCACAGCTCAAGTCCGCTAACACCGGGAACAA
CGAACGGATCATCAACGTGTCATCAAAAAGCTGAAGCGGAAGGCCTCCCTCCACCAACGCCGG
ACGGAGGCAGAAGCATAGGCTGACTTGCCCGTCATGCGACTCCTACGAGAAGAAGCCGCCGAA
GGAGTTCCTGGAGCGGTTCAAGTCGCTCCTGCAAAAGATGATTCATCAGCACCTGTCCTCCCGG
ACTCATGGGTCTGAGGATTCATGAGGTTAGTCGACAATCAACCTCTGGATTACAAAATTTGTGA
AAGATTGACTGGTATTCTTAACTATGTTGCTCCTTTTACGCTATGTGGATACGCTGCTTTAATGCC
TTTGTATCATGCTATTGCTTCCCGTATGGCTTTCATTTTCTCCTCCTTGTATAAATCCTGGTTGCTG
TCTCTTTATGAGGAGTTGTGGCCCGTTGTCAGGCAACGTGGCGTGGTGTGCACTGTGTTTGCTGA
CGCAACCCCCACTGGTTGGGGCATTGCCACCACCTGTCAGCTCCTTTCCGGGACTTTCGCTTTCC
CCCTCCCTATTGCCACGGCGGAACTCATCGCCGCCTGCCTTGCCCGCTGCTGGACAGGGGCTCG
GCTGTTGGGCACTGACAATTCCGTGGTGTTGTCGGGGAAATCATCGTCCTTTCCTTGGCTGCTCG
CCTGTGTTGCCACCTGGATTCTGCGCGGGACGTCCTTCTGCTACGTCCCTTCGGCCCTCAATCCA
GCGGACCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCTTAGTACTGGTACCTTTAAGACCAATG
ACTTACAAGGCAGCTGTAGATCTTAGCCACTTTTTAAAAGAAAAGGGGGGACTGGAAGGGCTA
ATTCACTCCCAACGAAGACAAGATTCCGGAATTTATTTGTGAAATTTGTGATGCTATTGCTTTAT
TTGTAAACCGGTGCAGCTGCTTTTTGCCTGTACTGGGTCTCTCTGGTTAGACCAGATCTGAGCCT
GGGAGCTCTCTGGCTAACTAGGGAACCCACTGCTTAAGCCTCAATAAAGCTTGCCTTGAGTGCT
TCAAGTAGTGTGTGCCCGTCTGTTGTGTGACTCTGGTAACTAGAGATCCCTCAGACCCTTTTAGT
CAGTGTGGAAAATCTCTAGCATCTAGAGTATGCAAAGCATGCATCTCAATTAGTCAGCAACCAG
GTGTGGAAAGTCCCAGGCTCCCCAGCAGGCAGAAGTATGCAAAGCATGCATCTCAATTAGTCA
GCAACCATAGTCCCGCCCCTAACTCCGCCCATCCCGCCCCTAACTCCGCCCAGTTCCGCCCATTC
TCCGCCCCATGGCTGACTAATTTTTTTTATTTATGCAGAGGCCGAGGCCGCCTCGGCCTCTGAGC
TATTCCAGAAGTAGTGAGGAGGCTTTTTTGGAGGCCTAGGCTAGGATCATAATCAGCCATACC
ACATTTGTAGAGGTTTTACTTGCTTTAAAAAACCTCCCACACCTCCCCCTGAACCTGAAACATAA
AATGAATGCAATTGTTGTTGTTAACTTGTTTATTGCAGCTTATAATGGTTACAAATAAAGCAATA
GCATCACAAATTTCACAAATAAAGCATTTTTTCACTGCATTCTAGTTGTGGTTTGTCCAAACTC
ATCAATGTATCTTATCATGTCTGCTAGCCGGGCTTTTTTTCTTAGGCCTTCTTCCGCTTCCTCGC
TCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATAC
```

TABLE 8-continued

SB00880 Expression Construct Sequences

```
CAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCG
CTGCCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGA
AGTGGTGGCCTAACTACGGCTACACTAGAAGAACAGTATTTGGTATCTGCGCTCTGCTGAAGCC
AGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGC
GATCTGTCTATTTCGTTCATCCATAGTTGCC
```

Figure 45:
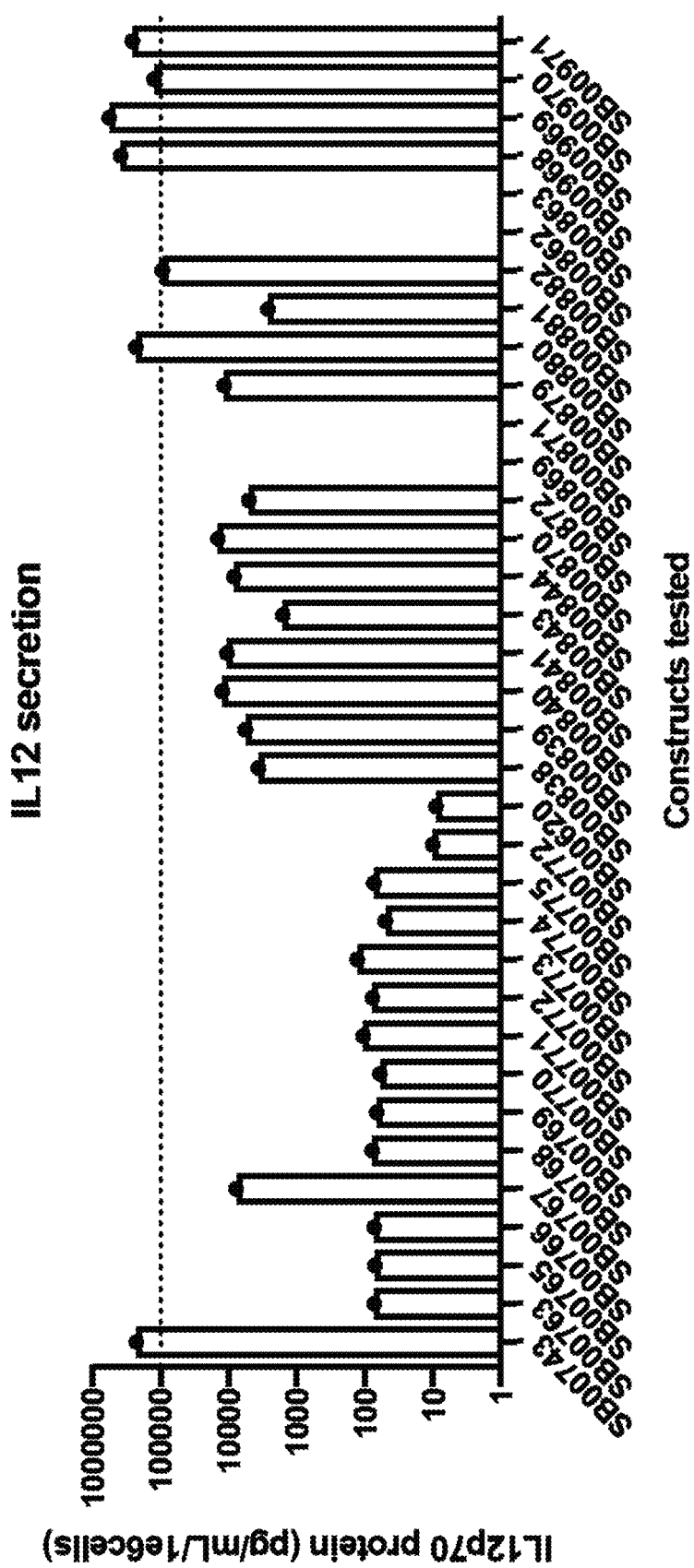
FIG. 45 shows secretion of IL-12p70 by engineered MSCs as assessed by ELISA.
Figure 46:
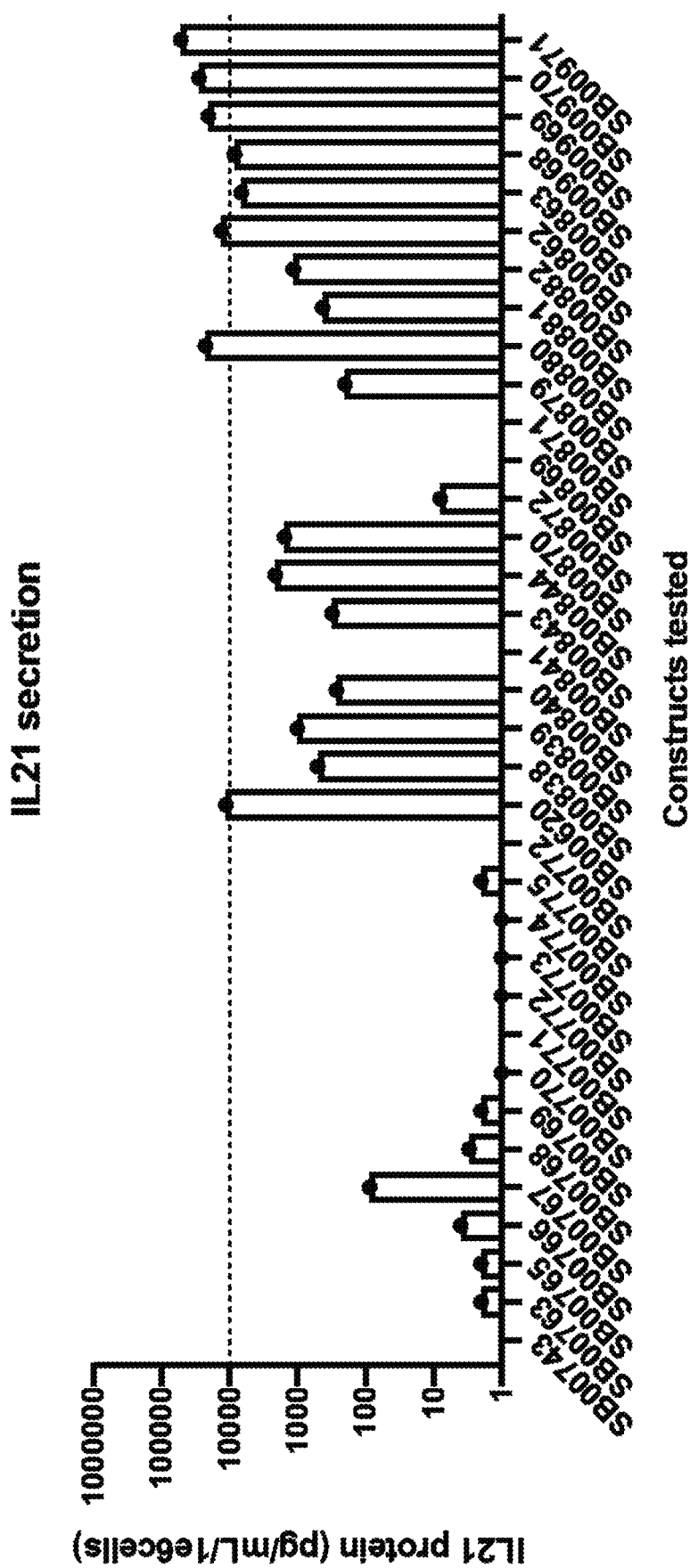
FIG. 46 shows secretion of IL-21 by engineered MSCs as assessed by ELISA.
Figure 47:
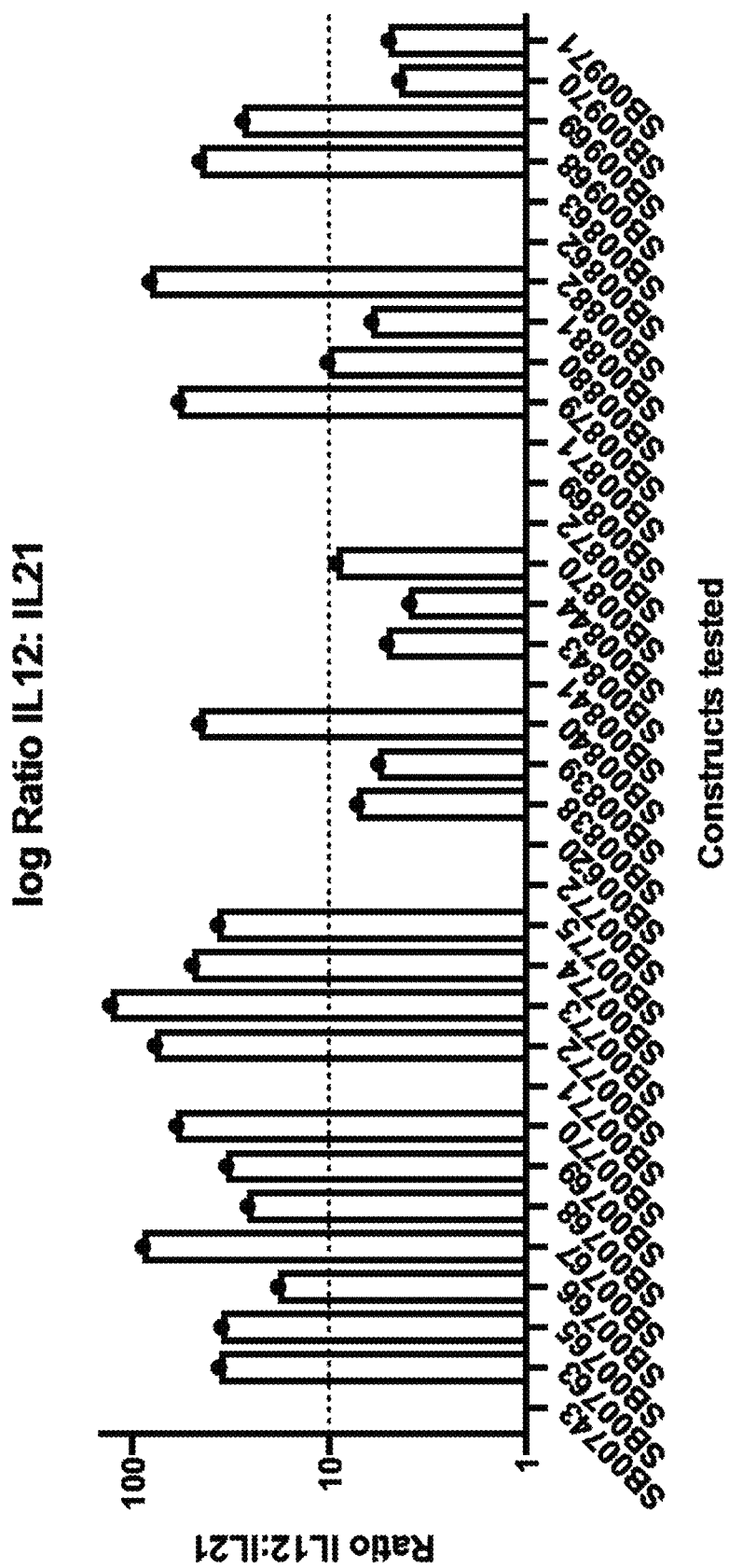
FIG. 47 shows the ratio of secreted IL-12p70 to IL-21 by engineered MSCs as assessed by ELISA.

Secretion of IL-12p70 and IL-21 by engineered MSCs are shown in FIG. 45 and FIG. 46, respectively, as assessed by ELISA. SB00880 demonstrated expression of both cytokines by engineered MSCs at higher levels than the majority of constructs tested. Additionally, the ratio of IL-12 to IL-21 was determined, as assessed by ELISA and shown in FIG. 47. MSCs engineered using SB00880 demonstrated a 10 fold higher ratio of IL-12p70 relative to IL-21. Notably, a ratio of 10:1 has demonstrated pre-clinical efficacy (data not shown).

Figure 48:
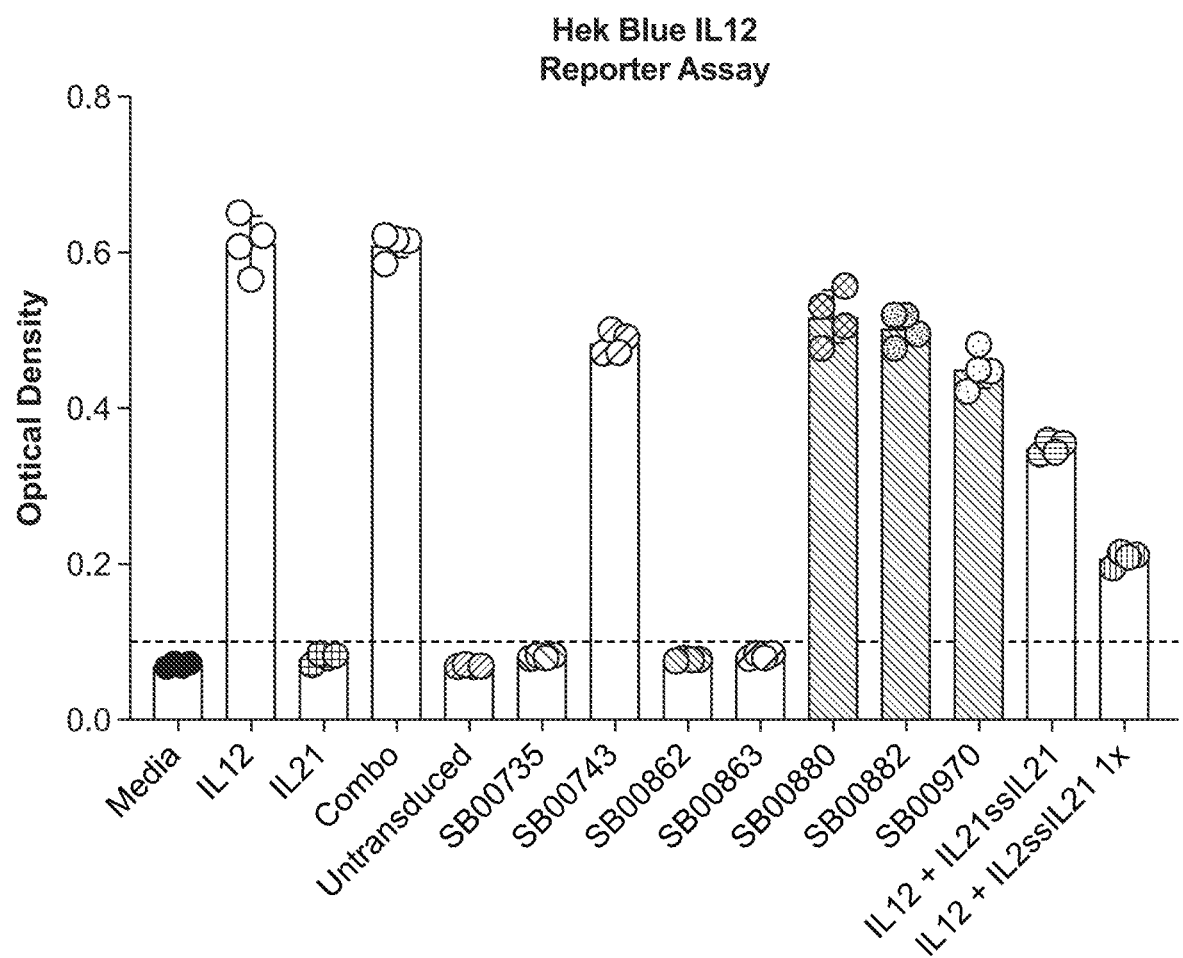
FIG. 48 shows results of a functional reporter assay for IL-12p70 using HEK-293T cells with a STAT4-SEAP reporter to assess cytokine production and secretion by engineered MSCs.

Functional assays demonstrating expression of IL-12p70 by engineered MSCs were performed. HEK-293T cells with a STAT4-SEAP reporter, which reports IL12p70 binding to its receptor and signaling through the JAK-STAT4 pathway, were used to determine potency and activity of IL12p70 produced by engineered hMSCs. Engineered MSCs were cultured for 24 hours and media was collected and incubated with HEK-293T STAT4-SEAP reporter cells. SEAP production was determined with spectrophotometer. As shown in FIG. 48, all constructs that encode IL-12 demonstrated reporter activity indicating functional IL12p70 signaling.

Figure 49:
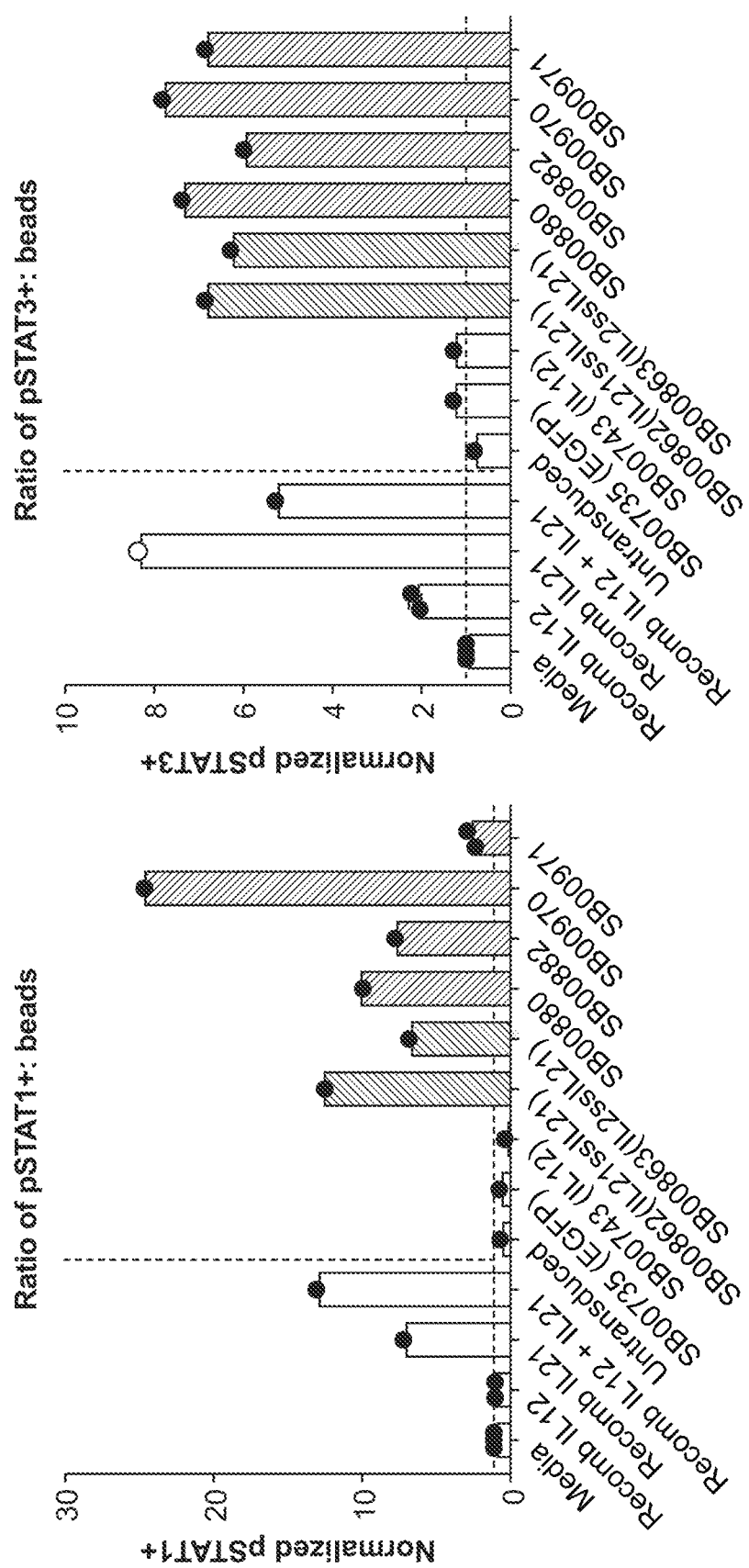
FIG. 49 shows a results of a functional reporter assay for IL-21 using intracellular phospho-flow to quantify phospho-STAT1 (left panel) and phospho-STAT3 (right panel) in NK-92 human natural killer cells to assess cytokine production and secretion by engineered MSCs.

Functional assays demonstrating expression of IL-21 by engineered MSCs were performed. NK-92 human natural killer cells were used to determine function of IL-21 produced by engineered hMSCs. Engineered hMSCs were cultured for 24 hours and conditioned media was collected and used to treat NK-92 cells that were deprived from IL-2. Intracellular phospho-flow was performed to quantify phospho-STAT1 and phospho-STAT3 activation as a readout for IL-21 activity. As shown in FIG. 49, all constructs that encode IL-21 demonstrated STAT1 (left panel) and STAT3 (right panel) phosphorylation indicating functional IL-21 signaling.

Figure 50:
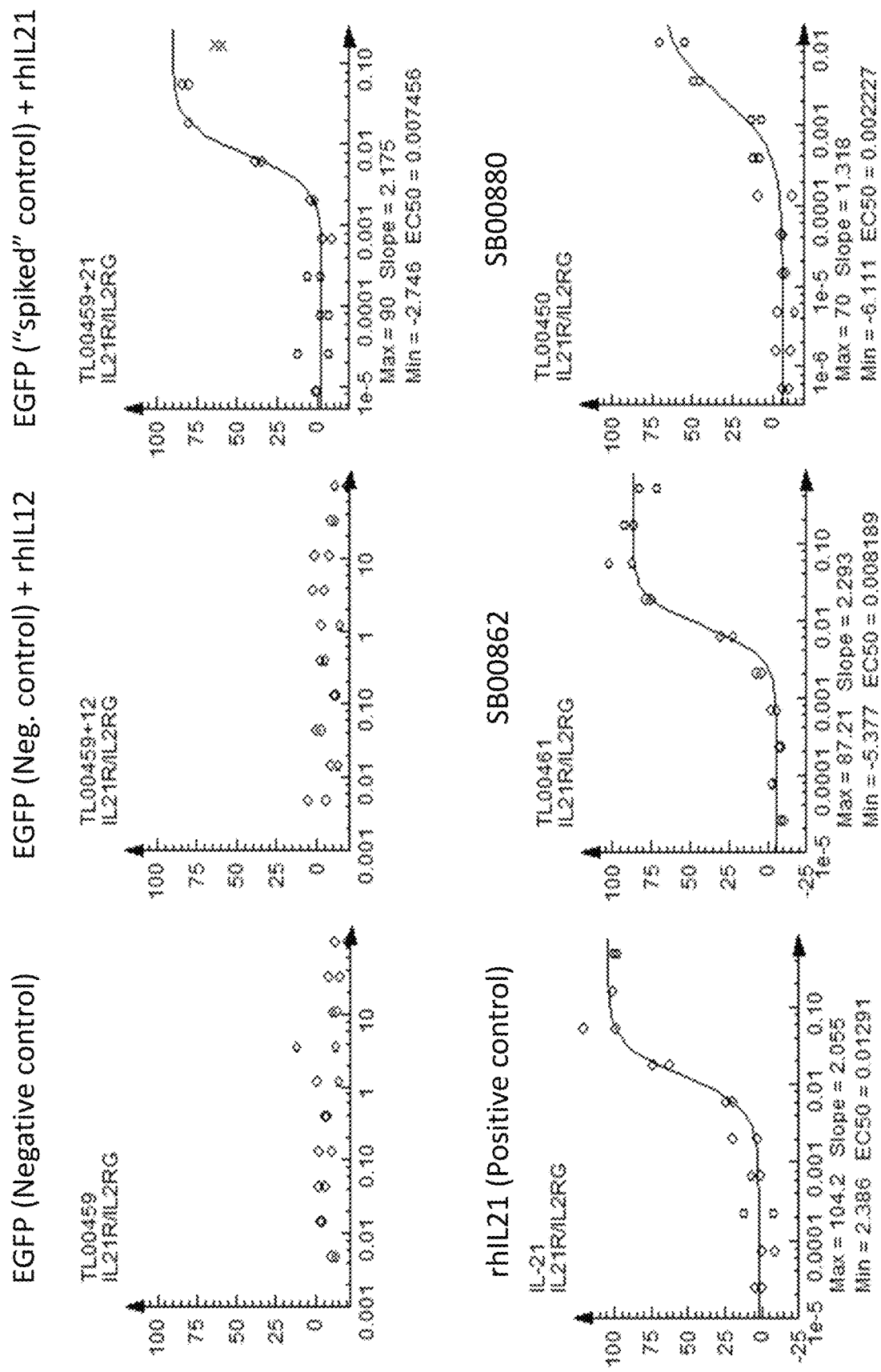
FIG. 50 shows results of a functional reporter assay for IL-12 using a IL21R-U2OS IL21R/IL2RG dimerization reporter to assess cytokine production and secretion by engineered MSCs.

Functional assays for IL-21 was also performed using a IL21R-U2OS IL21R/IL2RG dimerization reporter (PathHunter® U2OS IL21R/IL2RG Dimerization Cell Line, DiscoverX Cat. No: 93-1035C3). Reporter cells were incubated with conditioned media from engineered human MSCs or the appropriate positive (recombinant cytokine) or negative controls. As shown in FIG. 50, all constructs that encode IL-21 demonstrated dimerization.

Example 20: Engineered MSC Efficacy in CT26 Tumor Model

In the following example, balb/c mMSCs were engineered to express each of the various murine immune effectors shown in FIG. 51A using the lentiviral transduction method described in Example 6. Each MSC was engineered to express only a single agent. CT26 tumor cells ($5 \times 10^4$ cells in 100 µl) modified to constitutively express luciferase enzyme (Cat no: CL043, Lot no: CL-IM147 Imanis Life Sciences) were injected into the peritoneal space of immunocompetent balb/c female mice (age 6-8 weeks). One week after tumor implantation, tumor burden was measured by luciferase imaging (BLI) using an AMI imager. Mice were randomized into treatment groups and treated with intraperitoneally delivered engineered mMSCs ($1 \times 10^6$ cells). MSC-Flag-Myc and PBS were used as a negative control.

Figure 51A:
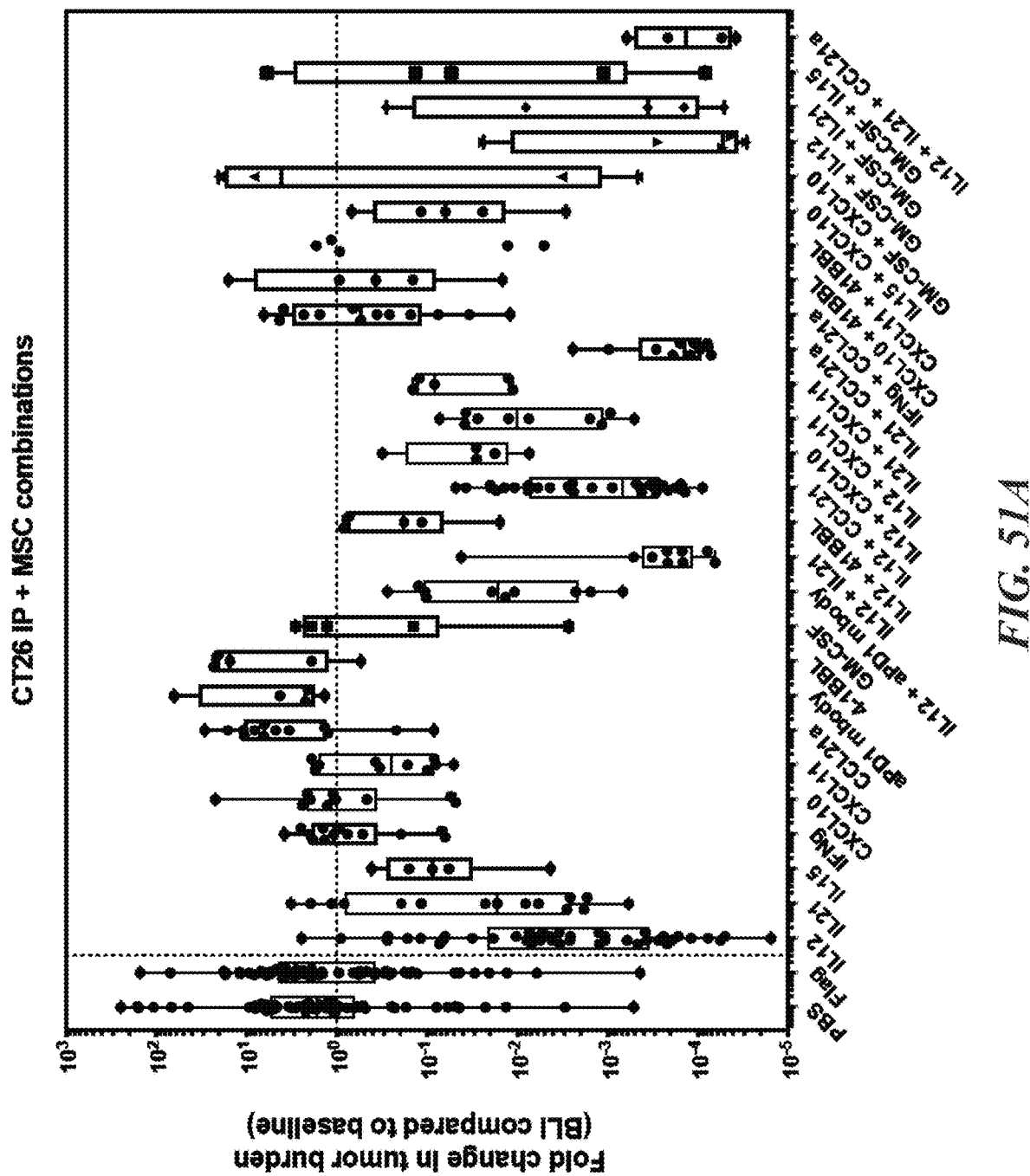
FIG. 51A shows MSCs engineered to express different effector molecules either alone or in combination and their efficacy in reducing CT26 tumor burden in an IP tumor model as assessed by BLI levels.

As shown in FIG. 51A, significant reductions in tumor burden were achieved with select effector-producing engineered-MSCs and select effector-producing engineered-MSCs in a CT26 syngeneic tumor model. Tumor burden fold change was calculated for each individual mouse by normalization of post-treatment BLI (day 10) vs pre-treatment BLI. All the cases where tumor burden fold change was lower than 1 (dotted line) represent tumor burden reduction. The top MSC-effectors that achieved significant reduction in tumor burden were: IL12, IL15, IL12+anti-PD1(microbody), IL12+IL21, IL12+CCL21a, IL12+CXCL10, IL12+CXCL11, IL21+CXCL11, IL21+CCL21a, IL15+CXCL10, GM-CSF+IL12, IL12+IL21+CCL21a.

Example 21: Engineered MSC Efficacy in B16F10 Tumor Model

In the following example, C57BL/6 mMSCs were engineered to express each of the various murine immune effectors shown in FIG. 51B using the lentiviral transduction method described in Example 6. Each MSC was engineered to express only a single agent. B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 female mice (age 6-8 weeks). One week after tumor implantation, tumor burden was measured by luciferase imaging (BLI) using an AMI imager. Mice were randomized into treatment groups and treated with intraperitoneally delivered mMSCs $1 \times 10^6$ expressing immune-modulatory cytokines or chemokines such as IL12p70. MSC-Flag-Myc and PBS were used as a negative control.

Figure 51B:
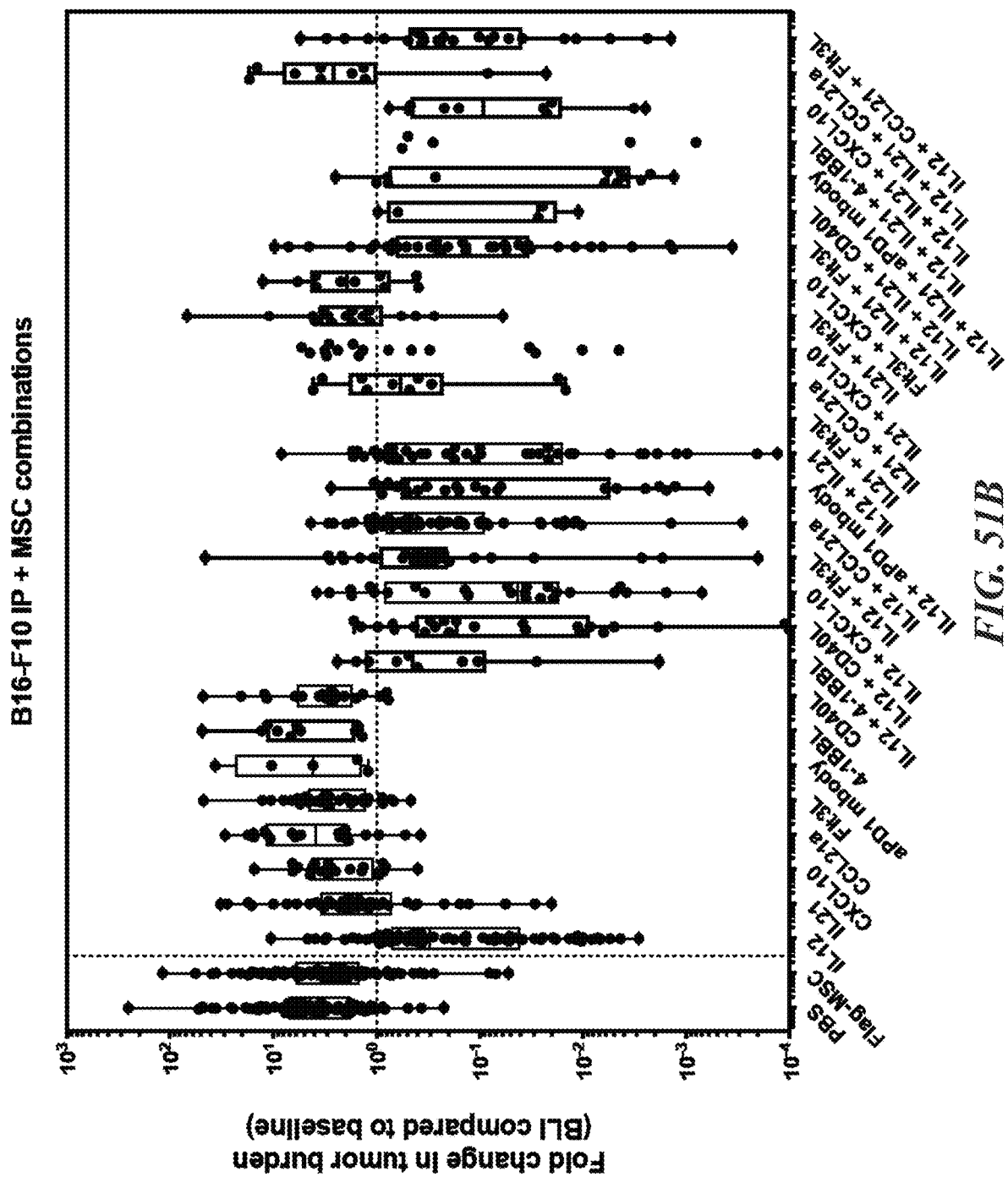
FIG. 51B shows MSCs engineered to express different effector molecules either alone or in combination and their efficacy in reducing B16F10 tumor burden in an IP tumor model as assessed by BLI levels.

As shown in FIG. 51B, significant reductions in tumor burden were achieved with select effector-producing engineered-MSCs and select effector-producing engineered-MSCs in a CT26 syngeneic tumor model. Selected effectors or combinations were achieving significant reduction in tumor burden: IL12, IL12+CD40L, IL12+CXCL10, IL12+IL21, IL12+IL21+Flt3L, IL12+IL21+CXCL10, IL12+CCL21a+Flt3L.

Example 22: IL12 Producing MSCs Reduce CT26 Tumor Burden in an IP Model

In the following example, balb/c mMSCs were engineered to express murine IL12p70 or murine IL21 (i.e., each MSC engineered to express only a single agent) using the lentiviral transduction method described in Example 6. CT26 tumor cells ($5 \times 10^4$ cells in 100 µl) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. In addition, tumor weights were determined at the time of termination (day 17 post tumor implant). Mice were randomized into treatment groups and treated with intraperitoneally delivered mMSCs ($1 \times 10^6$ cells). MSC-Flag-Myc and PBS were used as a negative control. Experimental cohorts included: murine IL12-expressing murine MSCs, murine IL21-expressing murine MSCs, and combination treatment of murine IL12-expressing murine MSCs and murine IL21-expressing murine MSCs ($1 \times 10^6$ cells delivered for each in the combination).

Figure 52A:
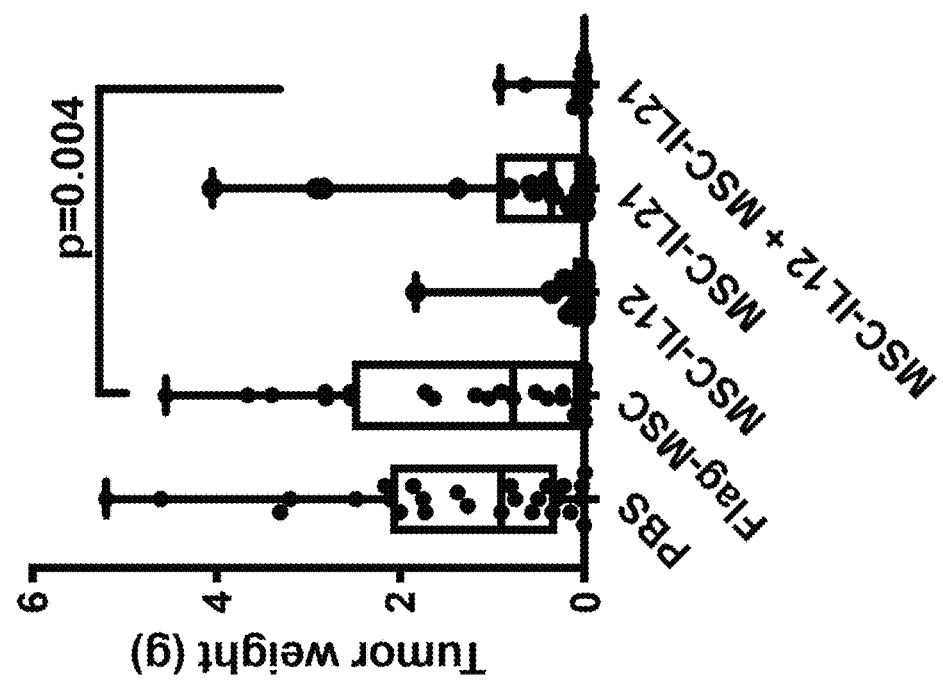
FIG. 52A shows efficacy of treatment using IL12p70-expressing MSCs, IL21-expressing MSCs, and the combination of IL12p70 and IL21-expressing MSCs as assessed by BLI for individual mice in each treatment, and the mean±SEM for each treatment group (left panel) and by tumor weight for individual mice in each treatment, and the mean±SEM for each treatment group (right panel) in a CT26 model.
Figure 52A:
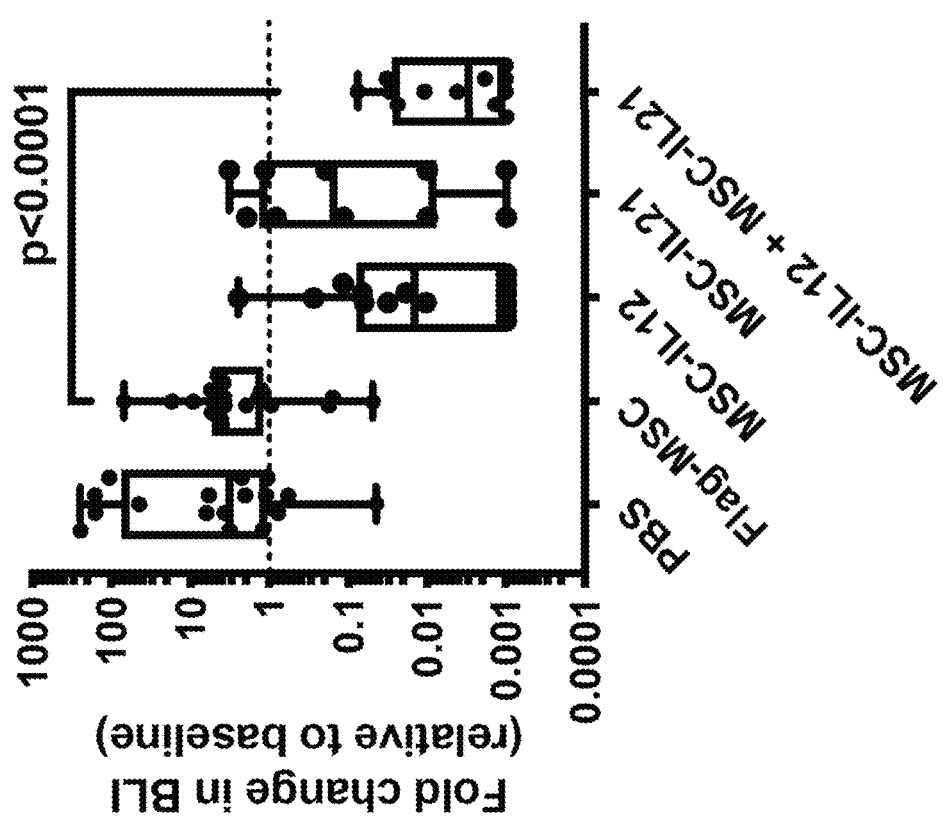
Figure 52B:
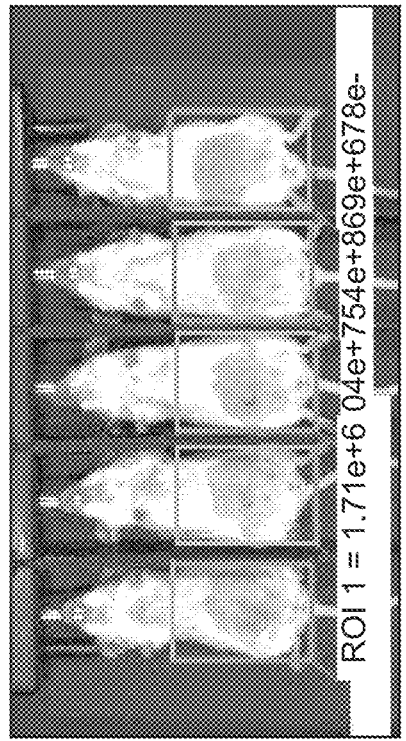
FIG. 52B shows efficacy of treatment using IL12p70-expressing MSCs, IL21-expressing MSCs, and the combination of IL12p70 and IL21-expressing MSCs in a CT26 model.
Figure 52B:
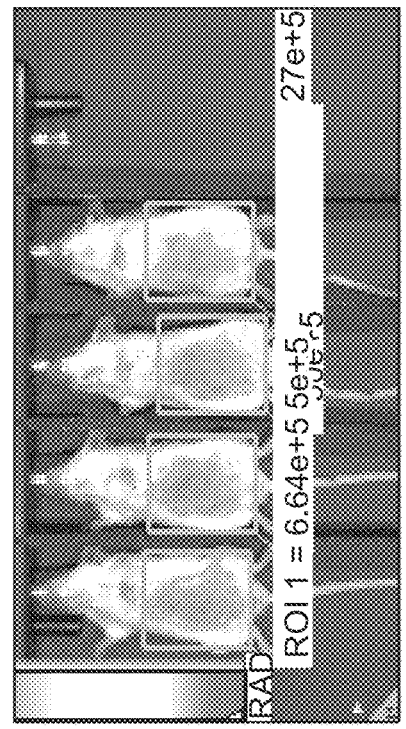
Figure 52B:
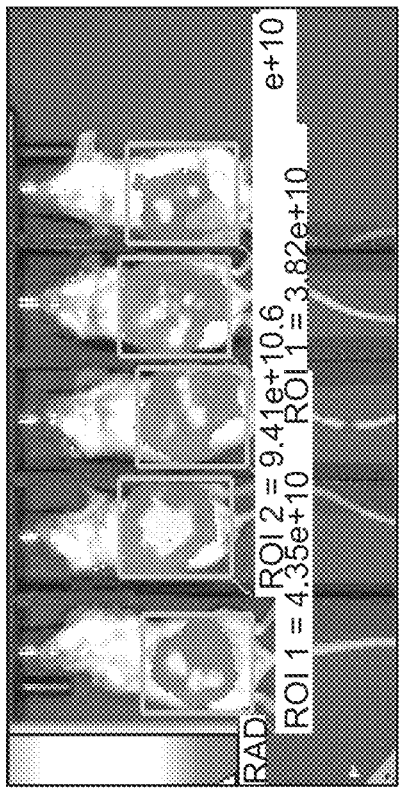
Figure 52B:
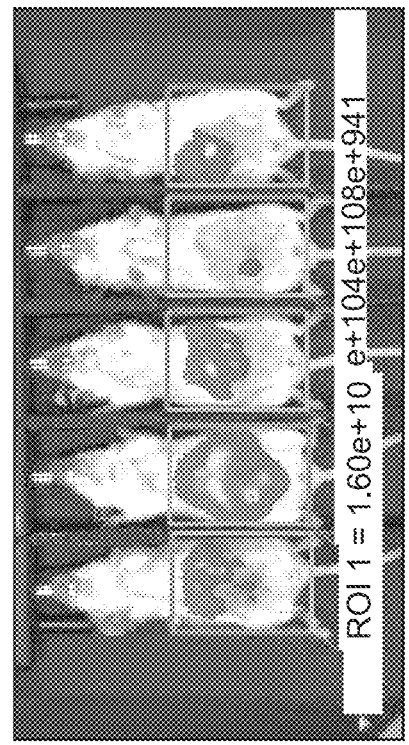

As shown in FIG. 52A and FIG. 52B, the groups receiving IL12p70-expressing MSCs, IL21-expressing MSCs, and the combination of IL12p70 and IL21-expressing MSCs led to reduction in tumor burdens as assessed by BLI (FIG. 52A left panel) and by tumor weight (FIG. 52A right panel) in a CT26 model, including a significant reduction in the combination treatment, relative to the controls. FIG. 52B demonstrates the BLI luciferase measurements of individual mice (results summarized in FIG. 52A left panel).

Figure 53A:
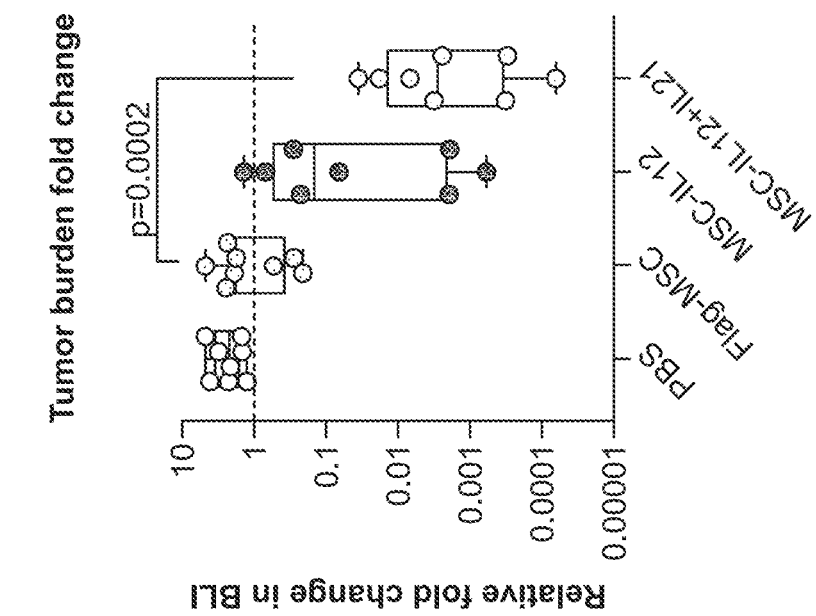
FIG. 53A shows efficacy of treatment using a lower dose of IL12p70-expressing MSCs, and the combination of IL12p70 and IL21-expressing MSCs as assessed by BLI; individual BLI measurements of mice—left panel; summary of BLI measurements for individual mice in each treatment, and the mean±SEM for each treatment group—right panel).
Figure 53A:
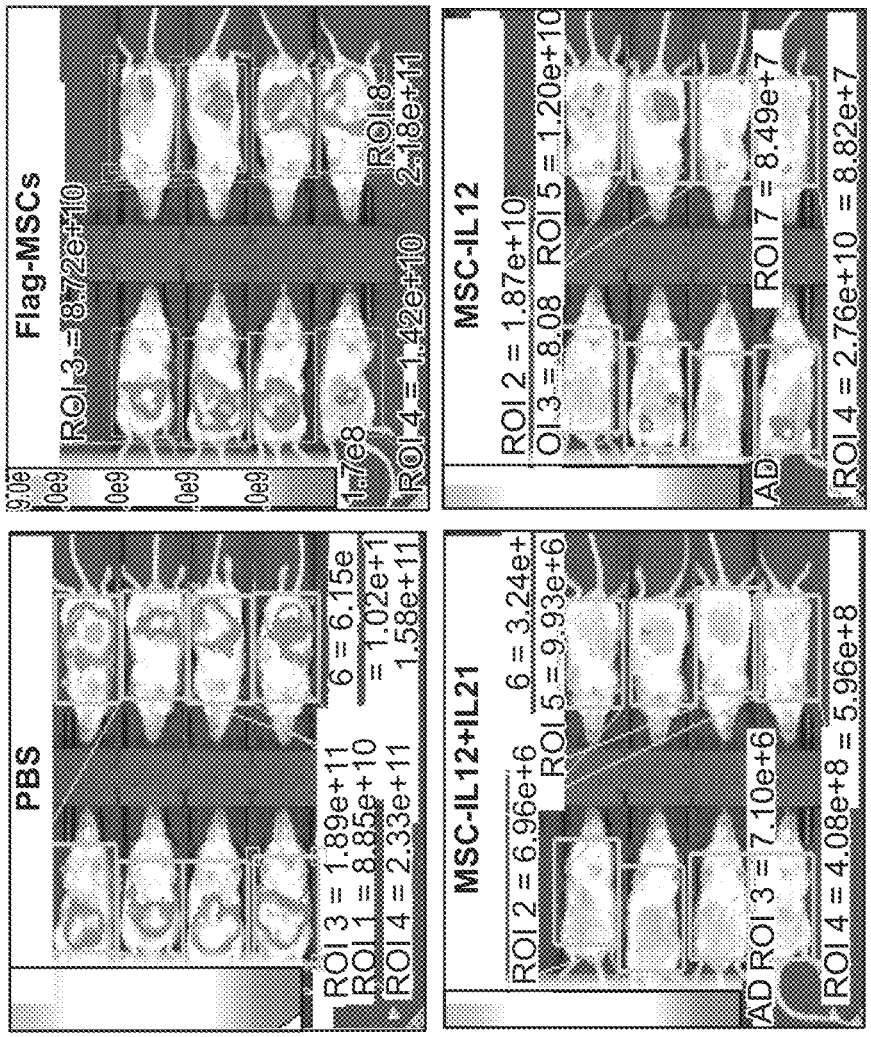
Figure 53B:
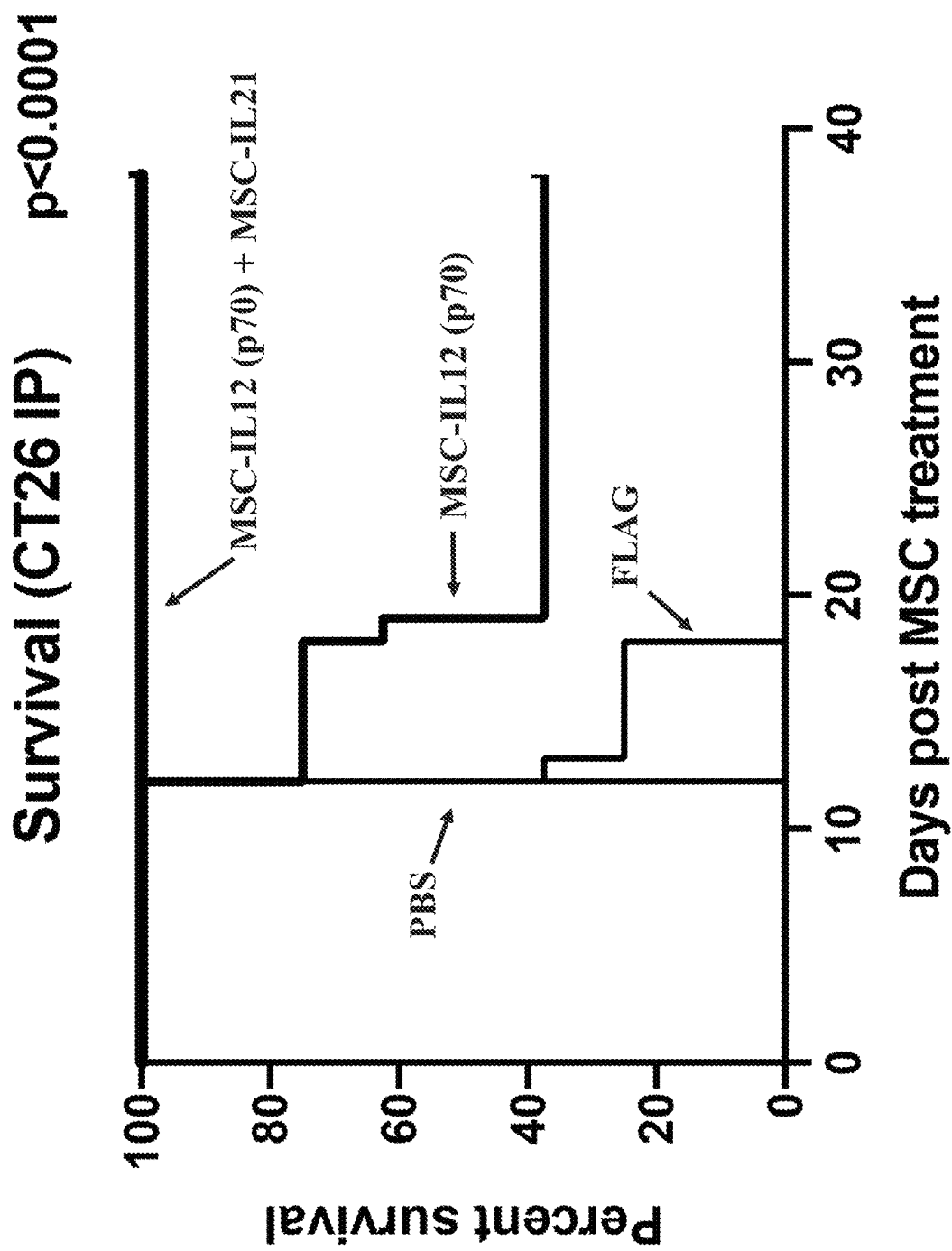
FIG. 53B shows efficacy of treatment using a lower dose of IL12p70-expressing MSCs, and the combination of IL12p70 and IL21-expressing MSCs.

The above experiment was repeated with the modification of delivering a lower dose of engineered mMSCs ($1 \times 10^5$ cells). As shown in FIG. 53A, the groups receiving IL12p70-expressing MSCs, and the combination of IL12p70 and IL21-expressing MSCs led to reduction in tumor burdens as assessed by BLI (FIG. 53A; individual BLI measurements of mice—left panel; summary of BLI measurements—right panel) in a CT26 model, including a significant reduction in the combination treatment, relative to the controls. Additionally, the combination treatment demonstrated increased efficacy relative to groups receiving IL12p70-expressing MSCs alone. As shown in FIG. 53B, treatment with $1 \times 10^5$ IL12p70 expressing MSCs in combination with $1 \times 10^5$ IL21 expressing MSCs led to tumor-free survival up to 40 days in all mice treated (n=8; median survival not reached). In contrast, treatment with $1 \times 10^5$ IL12p70 expressing MSCs alone only resulted in a 25% survival rate by day 40 (n=8; median survival 19 days). Control groups treated with PBS for FLAG-MSCs resulted in a 0% survival rate by day 40 (n=8 each; median survival 12 days each). Thus, IL21 expression by MSCs enhanced the efficacy of IL12p70 expressing MSCs.

Example 23: IL12 Producing MSCs Reduce B16F10 Tumor Burden in an IP Model

In the following example, C57BL/6 mMSCs were engineered to express murine IL12p70 or murine IL21 (i.e., each MSC engineered to express only a single agent) using the lentiviral transduction method described in Example 6. B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. In addition, tumor weights were determined at the time of termination (day 17 post tumor implant). Mice were randomized into treatment groups and treated with intraperitoneally delivered mMSCs ($1 \times 10^6$ cells). MSC-Flag-Myc and PBS were used as a negative control. Experimental cohorts included: murine IL12-expressing murine MSCs, murine IL21-expressing murine MSCs, and combination treatment of murine IL12-expressing murine MSCs and murine IL21-expressing murine MSCs ($1 \times 10^6$ cells delivered for each in the combination).

Figure 54:
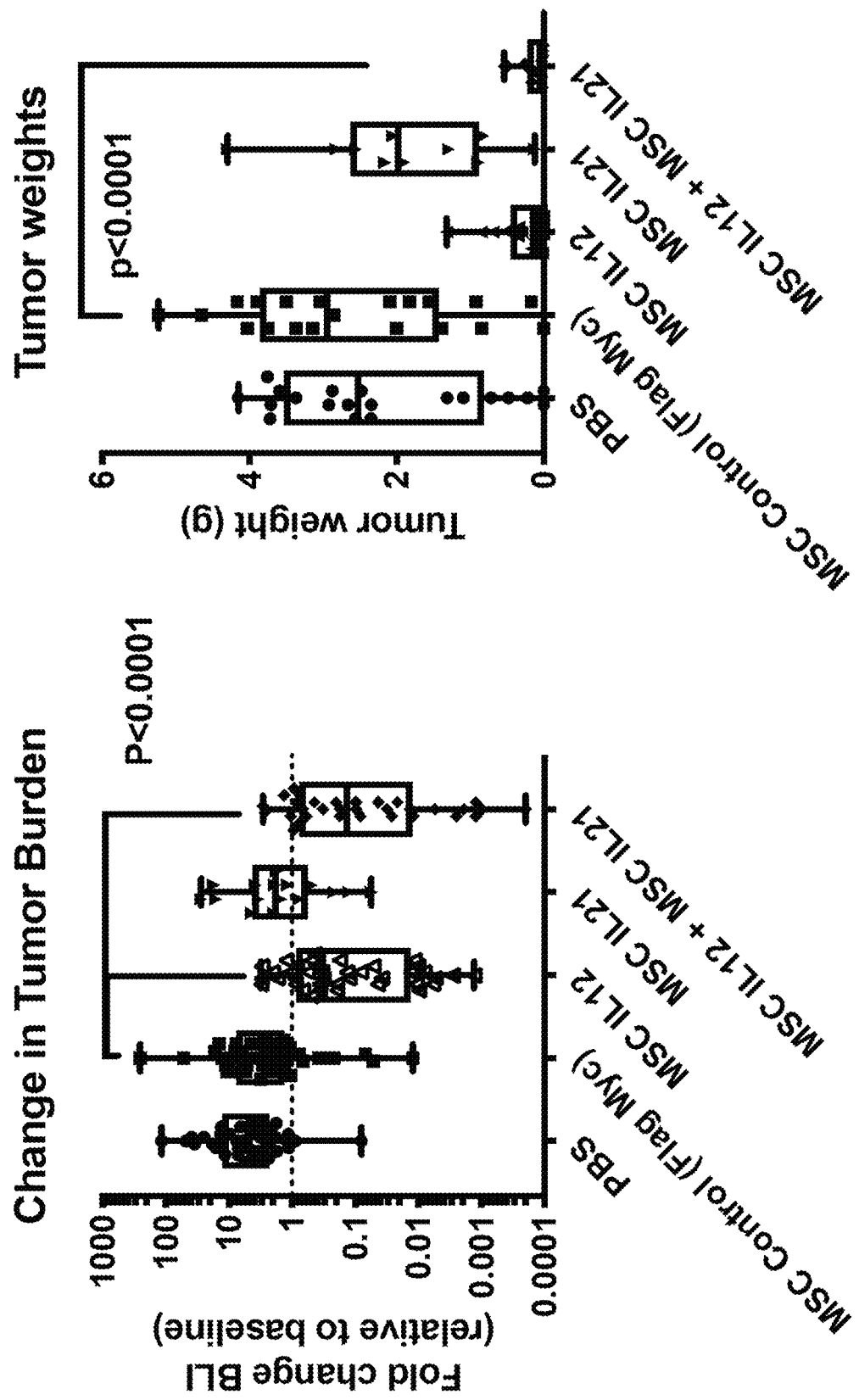
FIG. 54 shows efficacy of treatment using IL12p70-expressing MSCs, IL21-expressing MSCs, and the combination of IL12p70 and IL21-expressing MSCs as assessed by BLI for individual mice in each treatment, and the mean±SEM for each treatment group (left panel) and by tumor weight for individual mice in each treatment, and the mean±SEM for each treatment group (right panel) in a B16F10 model.
Figure 55:
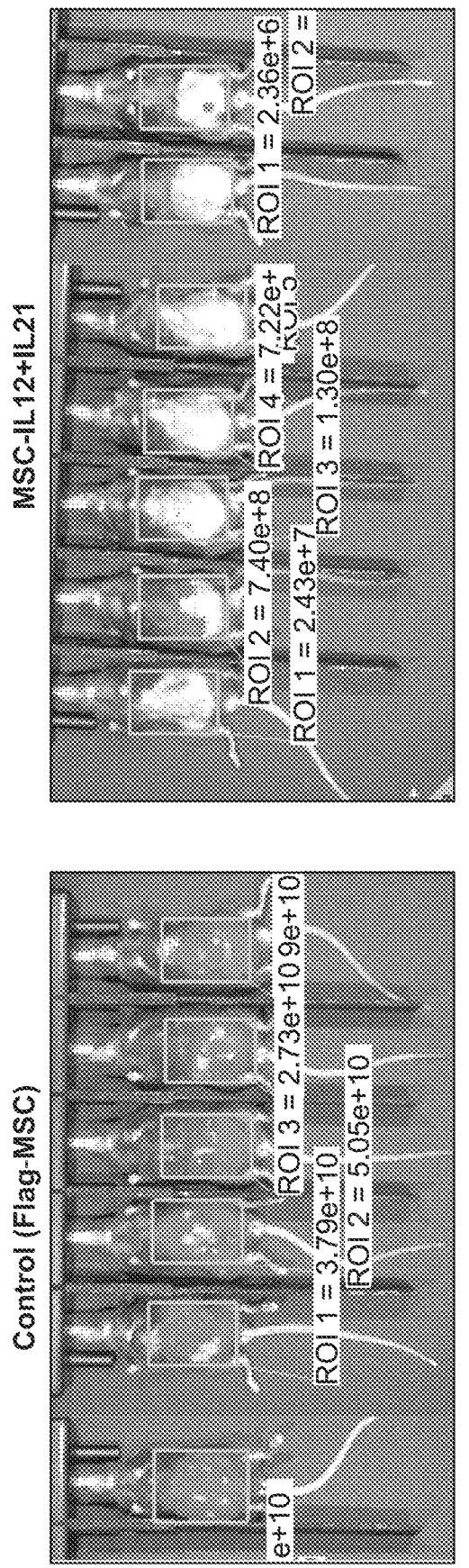
FIG. 55 demonstrates the BLI luciferase measurements of individual mice of following treatment using control FLAG-expressing MSCs (left panel) and the combination of IL12-expressing MSCs and IL21-expressing MSCs (right panel) in a B16F10 model.

As shown in FIG. 54 and FIG. 55, the groups receiving IL12p70-expressing MSCs, and the combination of IL12p70 and IL21-expressing MSCs led to reduction in tumor burdens as assessed by BLI (FIG. 54 left panel) and by tumor weight (FIG. 54 right panel) in a B16F10 model, including a significant reduction in the combination treatment, relative to the controls. Notably, IL21-expressing MSCs alone did not demonstrate a significant reduction in tumor burden or tumor weight. FIG. 55 demonstrates the BLI luciferase measurements of individual mice for the control FLAG-expressing MSCs and the combination of IL12-expressing MSCs and IL21-expressing MSCs (results summarized in FIG. 54 left panel).

Example 24: MSCs Producing IL12 and IL21 Prolong Tumor-Free Survival in a B16F10 IP Tumor Model and Survive Tumor Rechallenge In the following example, C57BL/6 mMSCs were engineered to express murine IL12 (p70) or murine IL21 (i.e., each MSC engineered to express only a single agent) using the lentiviral transduction method described in Example 6. B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). Mice were randomized into treatment groups and treated with intraperitoneally delivered mMSCs ($1 \times 10^6$ cells). MSC-Flag-Myc and PBS were used as a negative control. Experimental cohorts included: murine IL12-expressing murine MSCs, murine IL21-expressing murine MSCs, and combination treatment of murine IL12-expressing murine MSCs and murine IL21-expressing murine MSCs ($1 \times 10^6$ cells delivered for each in the combination).

Figure 56:
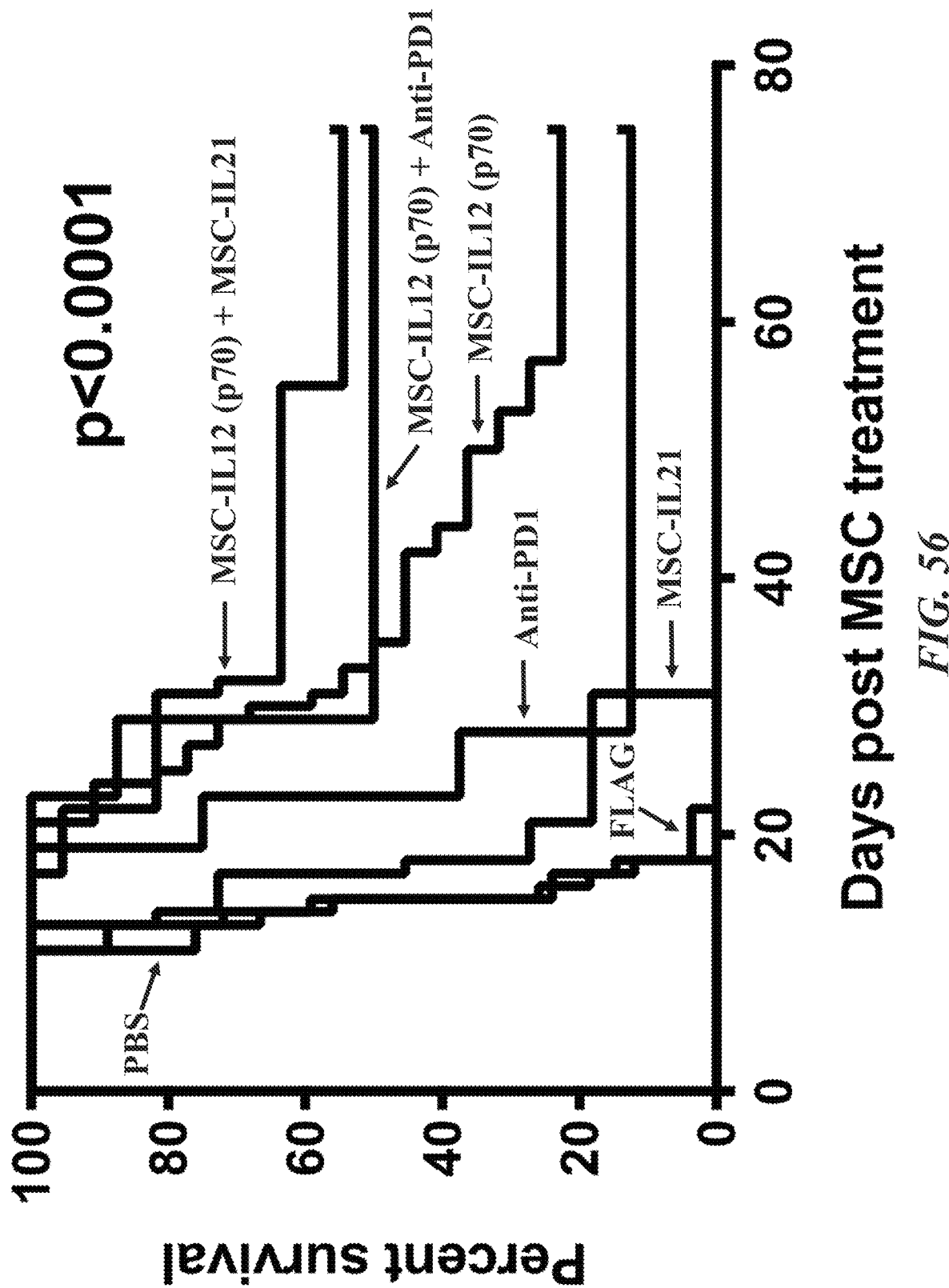
FIG. 56 shows survival curves of the treatment groups receiving IL12p70-expressing MSCs, IL21-expressing MSCs, the combination of IL12p70 and IL21-expressing MSCs, anti-PD1, or the combination of IL12p70 and anti-PD1.

As shown in FIG. 56, treatment with IL12p70 expressing MSCs led to prolonged survival (median survival 27 days post-treatment) relative to control treated mice (median survival of 8 days post-treatment for both PBS treated and FLAG-expressing MSCs). Treatment with IL12p70 expressing MSCs in combination with IL21 expressing MSCs led to prolonged survival (54.5% survival; median survival not reached) relative to treatment with IL12p70 expressing MSCs alone. Thus, IL21 expression by MSCs enhanced the efficacy of IL12p70 expressing MSCs.

Figure 57A:
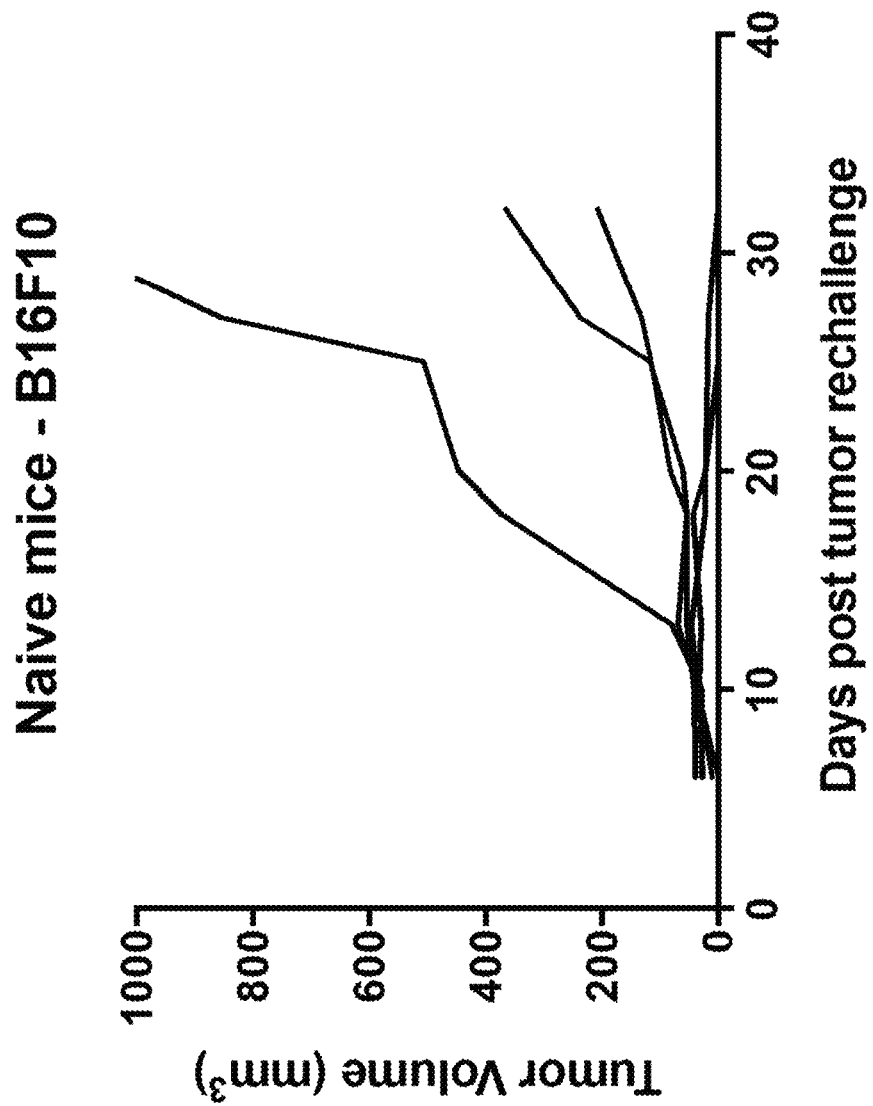
FIG. 57A shows survival curves of mice following tumor rechallenge.
Figure 57B:
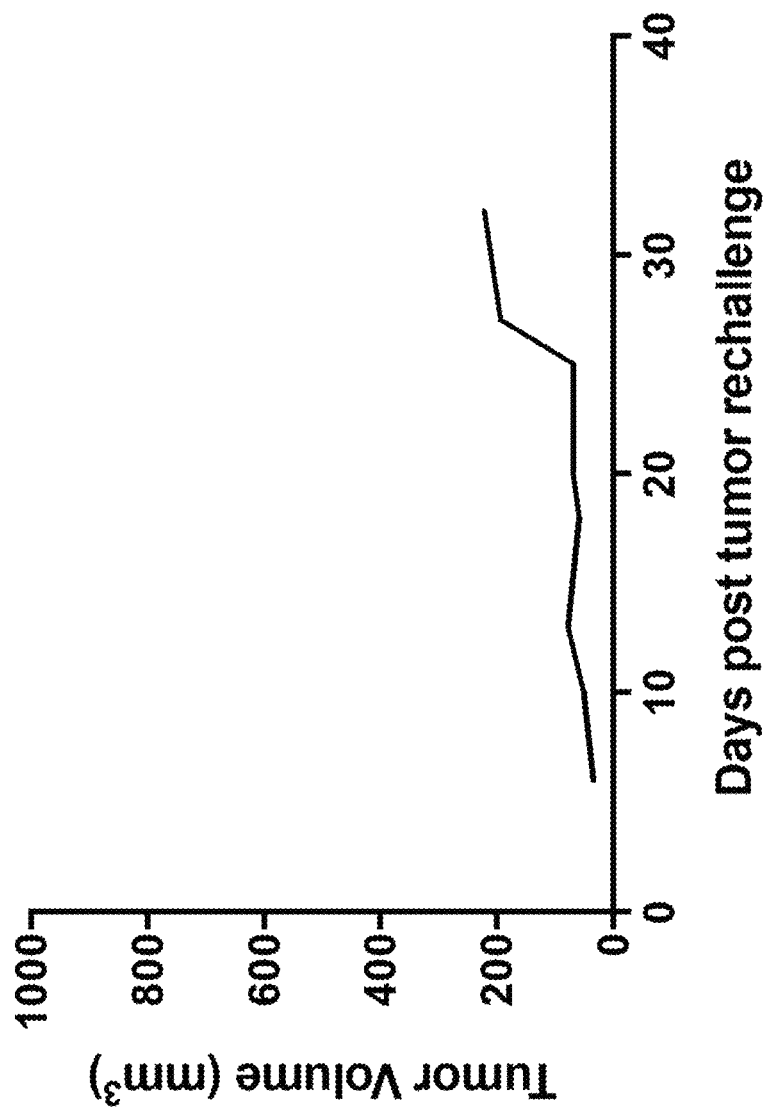
FIG. 57B shows survival curves of mice following tumor rechallenge.
Figure 57C:
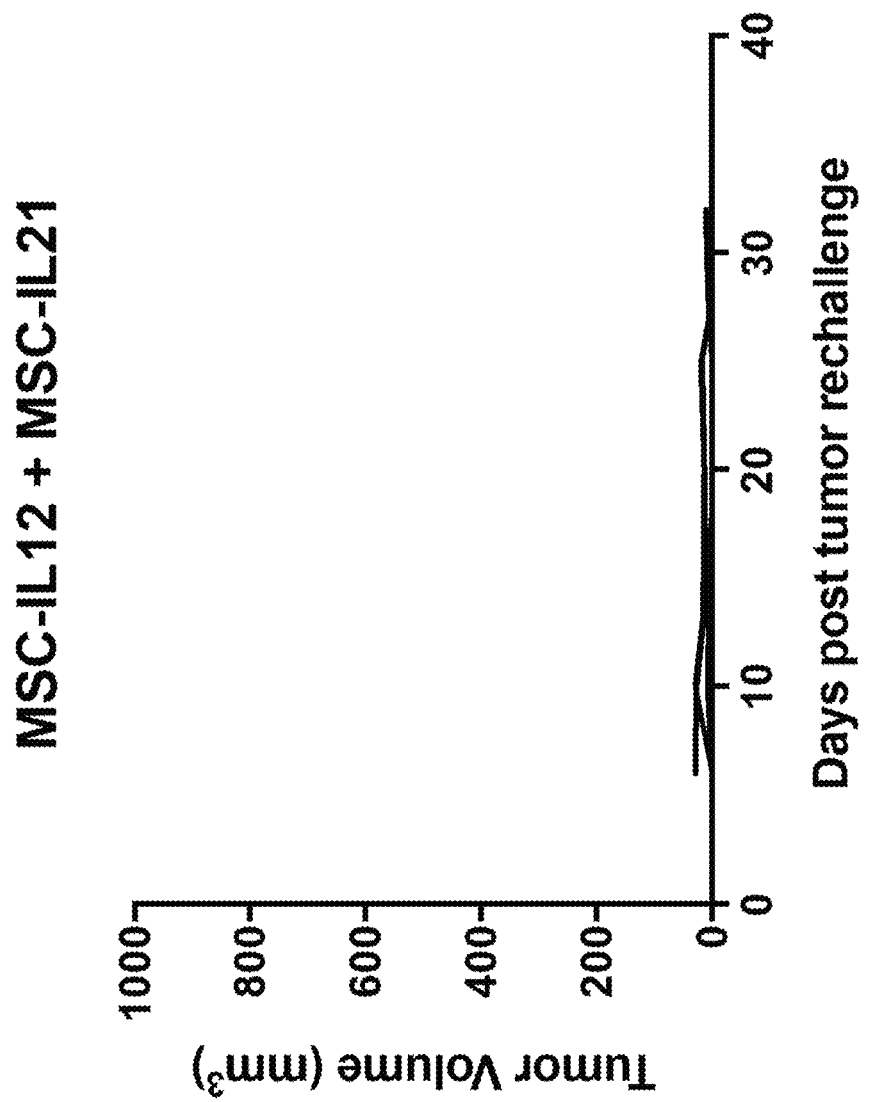
FIG. 57C shows survival curves of mice following tumor rechallenge.

Additionally, mice that were tumor-free for more than 90 days were subsequently re-challenged with B16-F10 tumor cells implanted in the flank ($1 \times 10^6$ cells). Naïve un-treated mice were implanted at the same time as controls. Subcutaneous tumor burden was measured by caliper. As shown in FIG. 57C, all mice (n=4) that previously received the combination treatment of IL12-expressing MSCs and IL21-expressing MSCs survived rejected the newly implanted tumor, indicating that the treatment resulted in achievement of anti-tumor immune memory. Mice that previously received the treatment of IL12-expressing MSCs alone had a 50% tumor-rejection rate (2 out of 4 mice; FIG. 57B). In contrast, tumor were established in 60% of naïve mice (3 out of 5 mice; FIG. 57A).

Example 25: MSCs Producing IL12 in Combination with Immune Checkpoint Therapy Prolong Survival in a B16F10 IP Tumor Model In the following example, C57BL/6 mMSCs were engineered to express murine IL12 (p70) using the lentiviral transduction method described in Example 6. B16F10 tumor cells ($5\times10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). Mice were randomized into treatment groups and treated with IP administration of anti-PD1 antibody (clone RMP1-14) at a dose of 200 mg/kg alone or in combination with low dose (1e5) of IL12-expressing murine MSCs.

As shown in FIG. 56, treatment with anti-PD1 alone resulted in a 12.5% survival rate and median survival of 23 days (FIG. 56 "Anti-PD1"; 1 out of 8 mice had long term tumor-free survival). In contrast, the combined treatment of anti-PD1 with IL12p70 expressing MSCs resulted in a 50% survival rate (FIG. 56 "MSC-IL12 (p70)+Anti-PD1"; 4 out of 8 mice had long term tumor-free survival; median survival not yet established). Thus, IL12 expression by MSCs enhanced the efficacy of anti-PD1 immune checkpoint therapy and convert a checkpoint refractory or resistant model (B16F10) into responsive.

Example 26: MSCs Producing Both IL12 and IL21 Reduce Tumor Burden in a CT26 IP Tumor Model In the following example, balb/c mMSCs were engineered to express murine IL12 (p70) and murine IL21 from a single lentiviral expression vector. The lentiviral expression vector used a 2A ribosome skipping elements to express both cytokines from a single transcript using the lentiviral transduction method described in Example 6. CT26 tumor cells ($1\times10^5$ cells in 100 µl) modified to constitutively express luciferase enzyme (Cat no: CL043, Lot no: CL-IM147 Imanis Life Sciences) were injected into the peritoneal space of immunocompetent female balb/c mice (age 6-8 weeks). One week after tumor implantation, tumor burden was measured by luciferase imaging (BLI) using an AMI imager. Mice were randomized into treatment groups and treated IP with different amounts of mMSCs ranging from $1\times10^4$ to $1\times10^6$ cells. MSC-Flag-Myc ($1\times10^6$ cells) and PBS were used as a negative control.

Figure 58A:
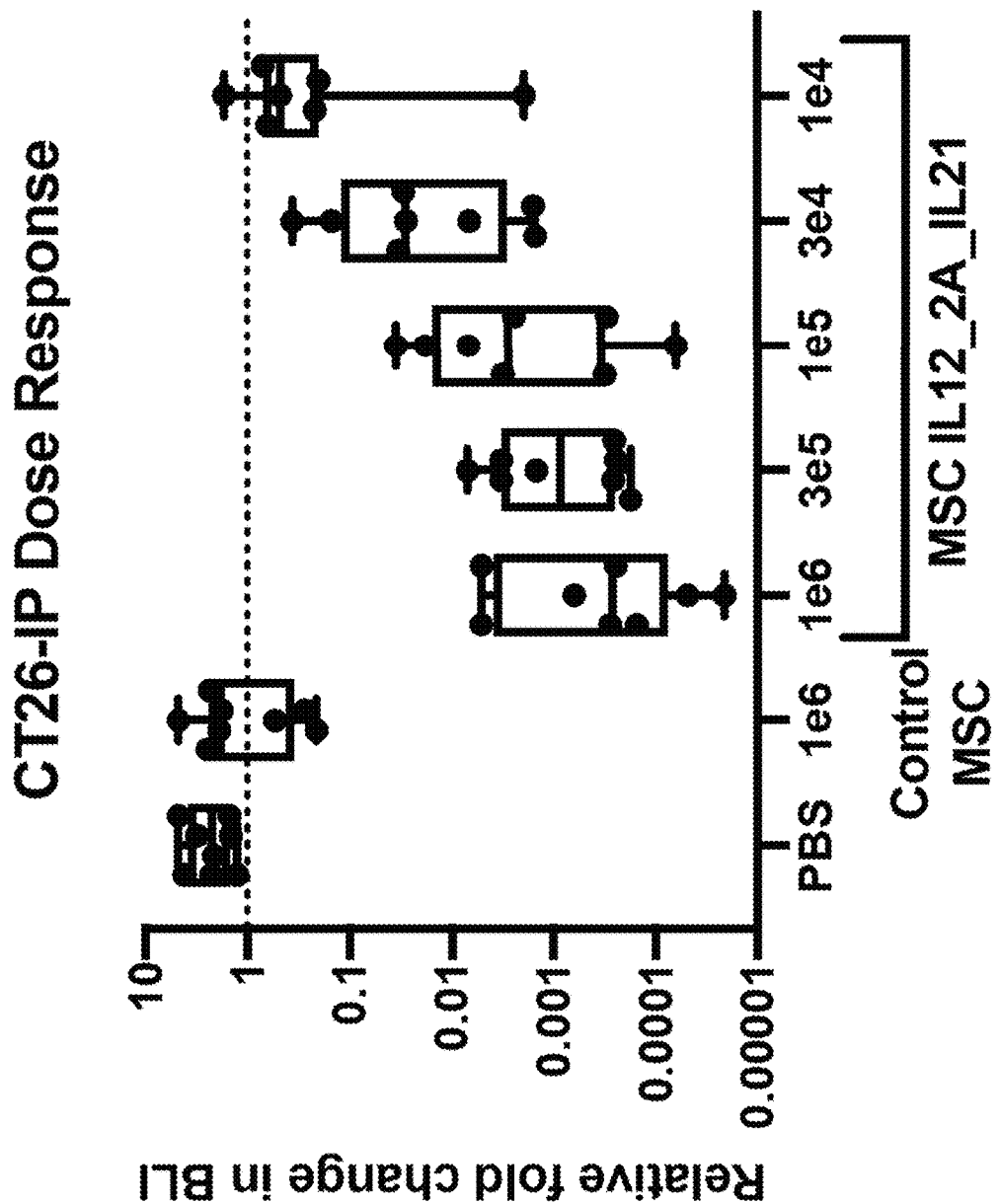
FIG. 58A shows dose-dependent efficacy of treatment using mMSCs engineered to express murine IL12 (p70) and murine IL21 from a single lentiviral expression vector in a CT26 tumor model.
Figure 58B:
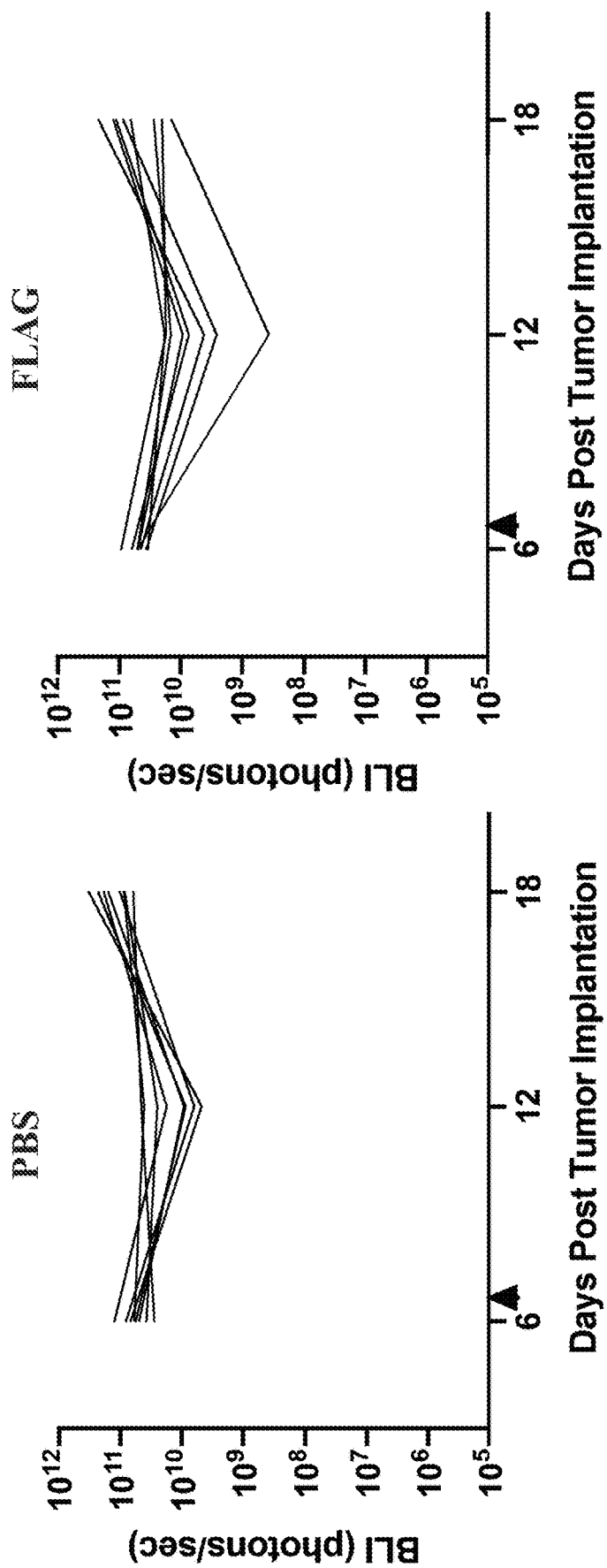
FIG. 58B shows dose-dependent efficacy of treatment using mMSCs engineered to express murine IL12 (p70) and murine IL21 from a single lentiviral expression vector in a CT26 tumor model.
Figure 58C:
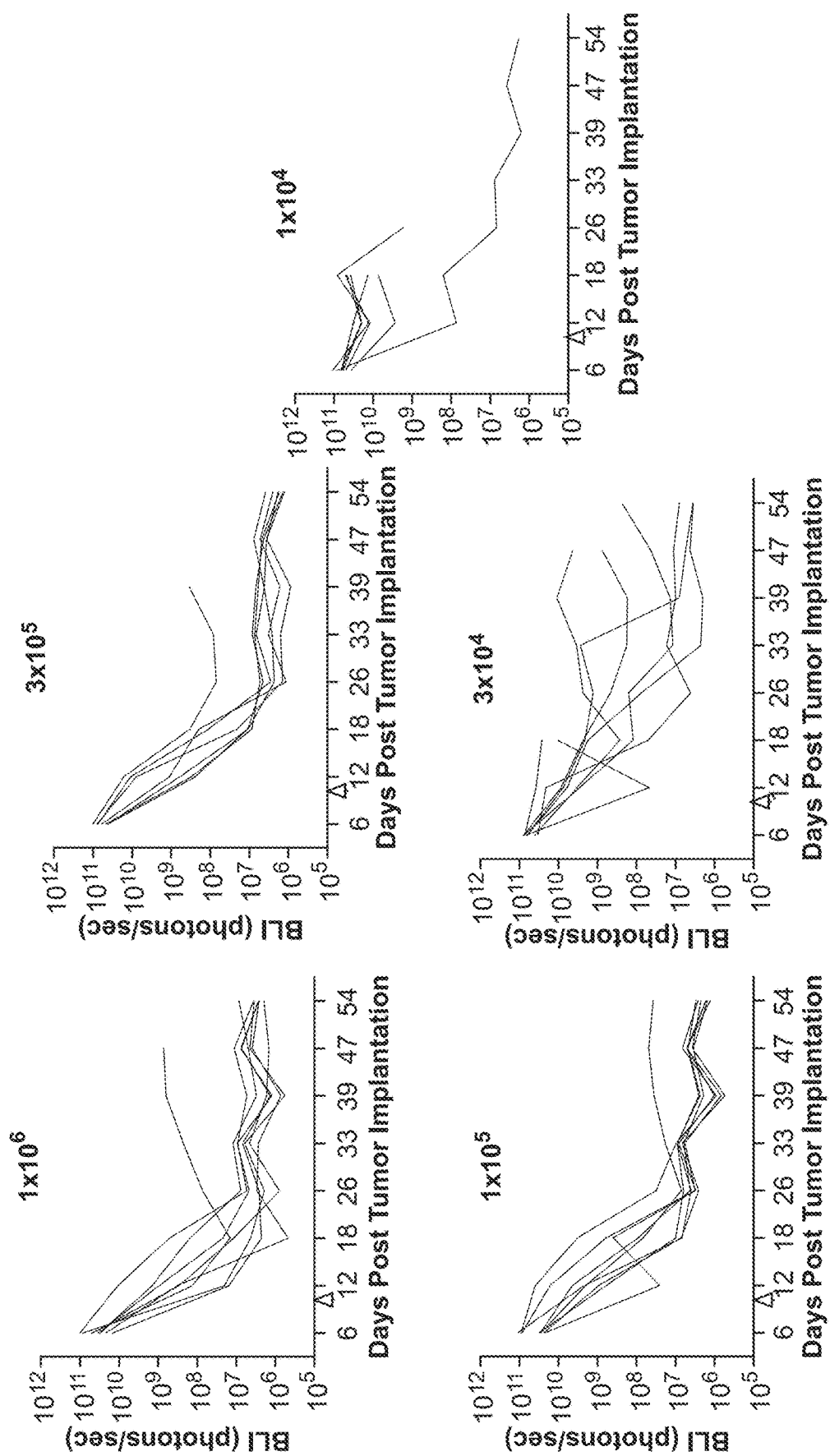
FIG. 58C shows dose-dependent efficacy of treatment using mMSCs engineered to express murine IL12 (p70) and murine IL21 from a single lentiviral expression vector in a CT26 tumor model.
Figure 58D:
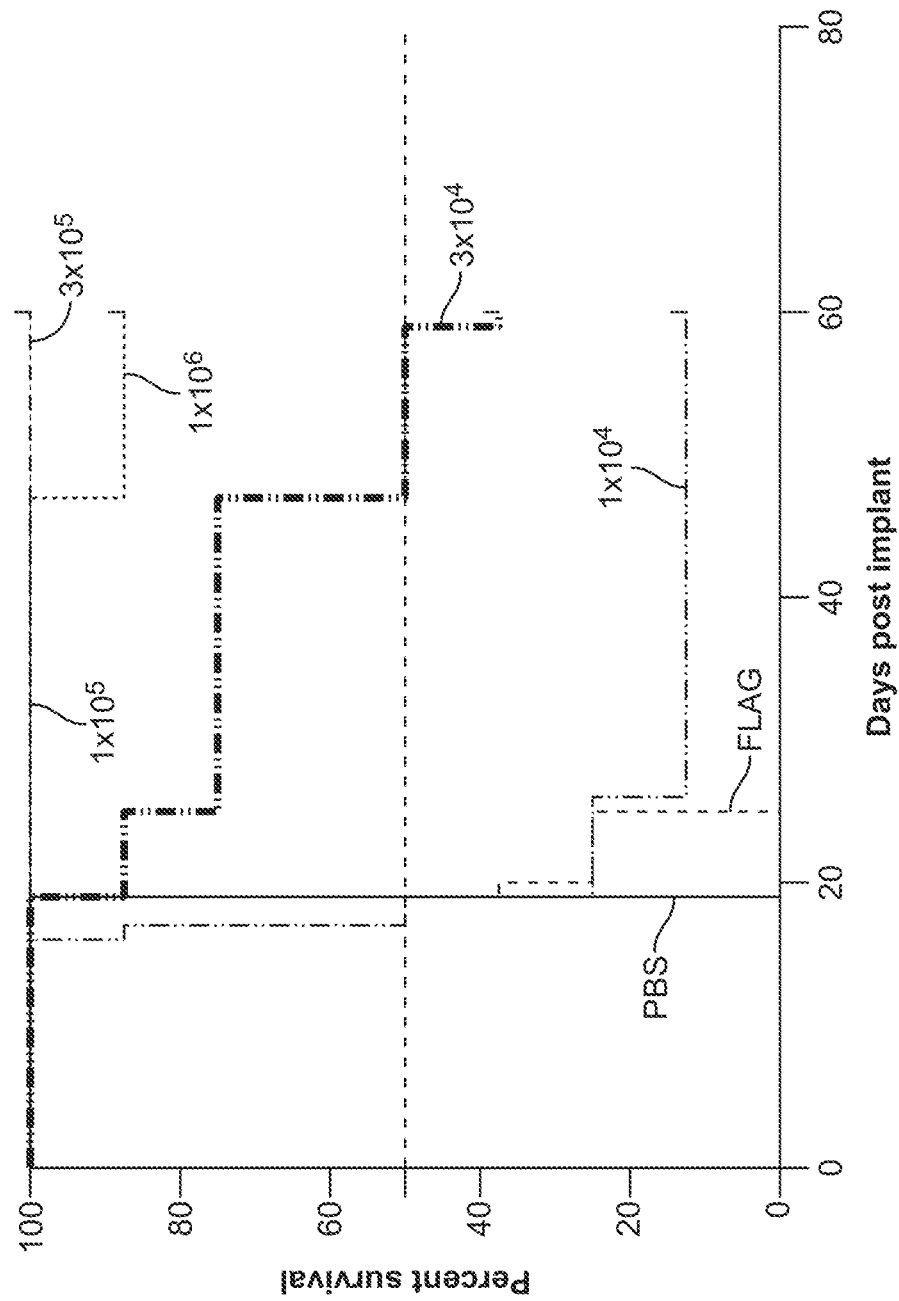
FIG. 58D shows dose-dependent efficacy of treatment using mMSCs engineered to express murine IL12 (p70) and murine IL21 from a single lentiviral expression vector in a CT26 tumor model.

As shown in FIG. 58A-C, anti-tumor activity was observed in a dose-dependent manner of MSCs expressing both IL12 and IL21, as assessed by BLI (FIG. 58A normalized day 17 vs day 7; FIG. 58B and FIG. 58C BLI over time for individual mice). No efficacy was observed in control FLAG or PBS mice (FIG. 58A and FIG. 58B). In contrast, minimal efficacy was observed at a dose of $1\times10^4$, with efficacy increasing at each increased dose (FIG. 58A and FIG. 58C). As shown in FIG. 58D, long term tumor-free survival up to 60 days post tumor implant was observed in a dose-dependent manner, with mice treated with $1\times10^6$ to $1\times10^5$ having significantly extended tumor-free survival (Median survival post-implant: PBS/FLAG—19 days; $1\times10^6$ to $1\times10^5$—not reached; $3\times10^4$—53 days; $1\times10^4$—18-19 days).

Example 27: MSCs Producing Both IL12 and IL21 Reduce Tumor Burden in a B16F10 IP Tumor Model In the following example, C57BL/6 mMSCs were engineered to express murine IL12 (p70) and murine IL21 from a single lentiviral expression vector. The lentiviral expression vector used a 2A ribosome skipping elements to express both cytokines from a single transcript using the lentiviral transduction method described in Example 6. B16F10 tumor cells ($5\times10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with different amounts of mMSCs ranging from $1\times10^5$ to $1\times10^7$ cells). MSC-Flag-Myc ($3\times10^6$ cells) and PBS were used as a negative control. Some groups were treated with multiple doses separated by 5 days (treatment on day 7, 12 and 17 post tumor-implant).

Figure 59A:
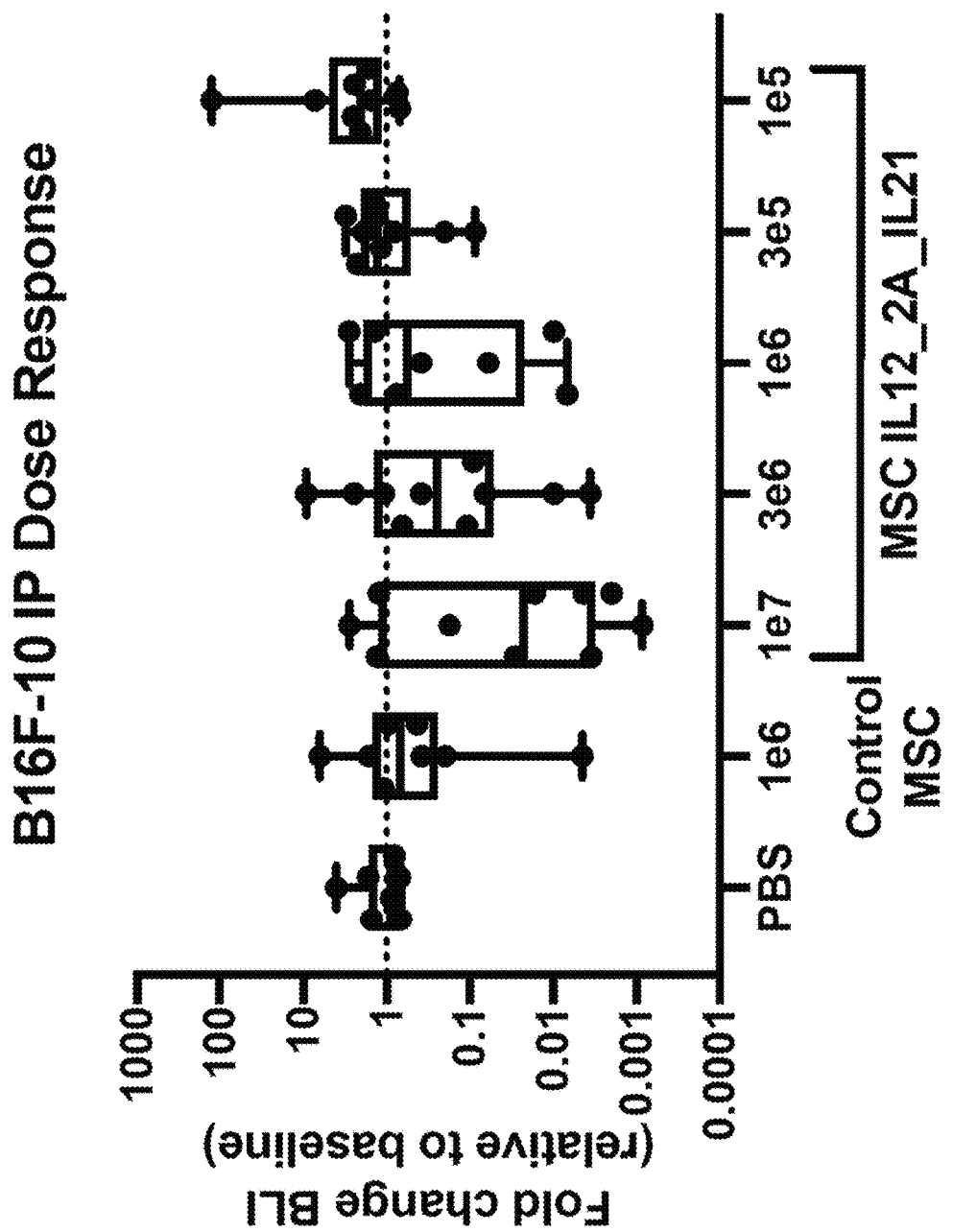
FIG. 59A shows dose-dependent efficacy of treatment using mMSCs engineered to express murine IL12 (p70) and murine IL21 from a single lentiviral expression vector in a B16F10 tumor model.
Figure 59B:
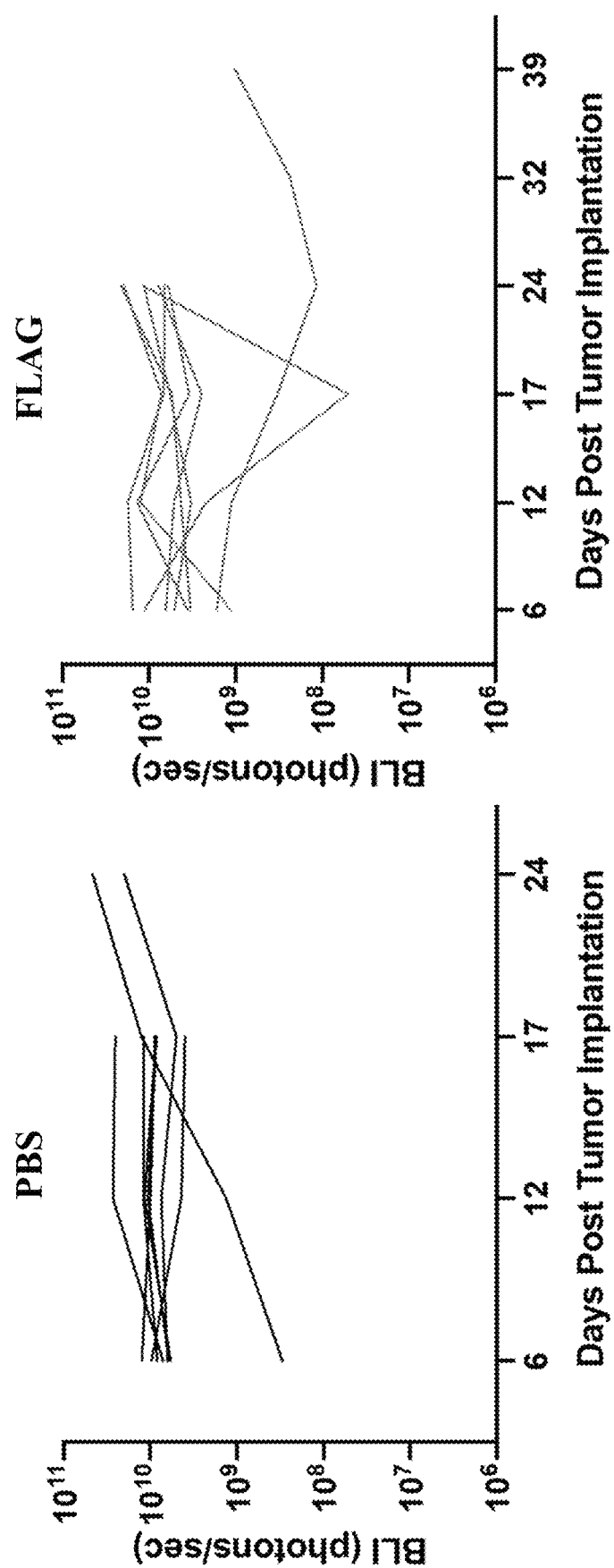
FIG. 59B shows efficacy of treatment using control FLAG mMSCs (right) or PBS (left) in a B16F10 tumor model.
Figure 59C:
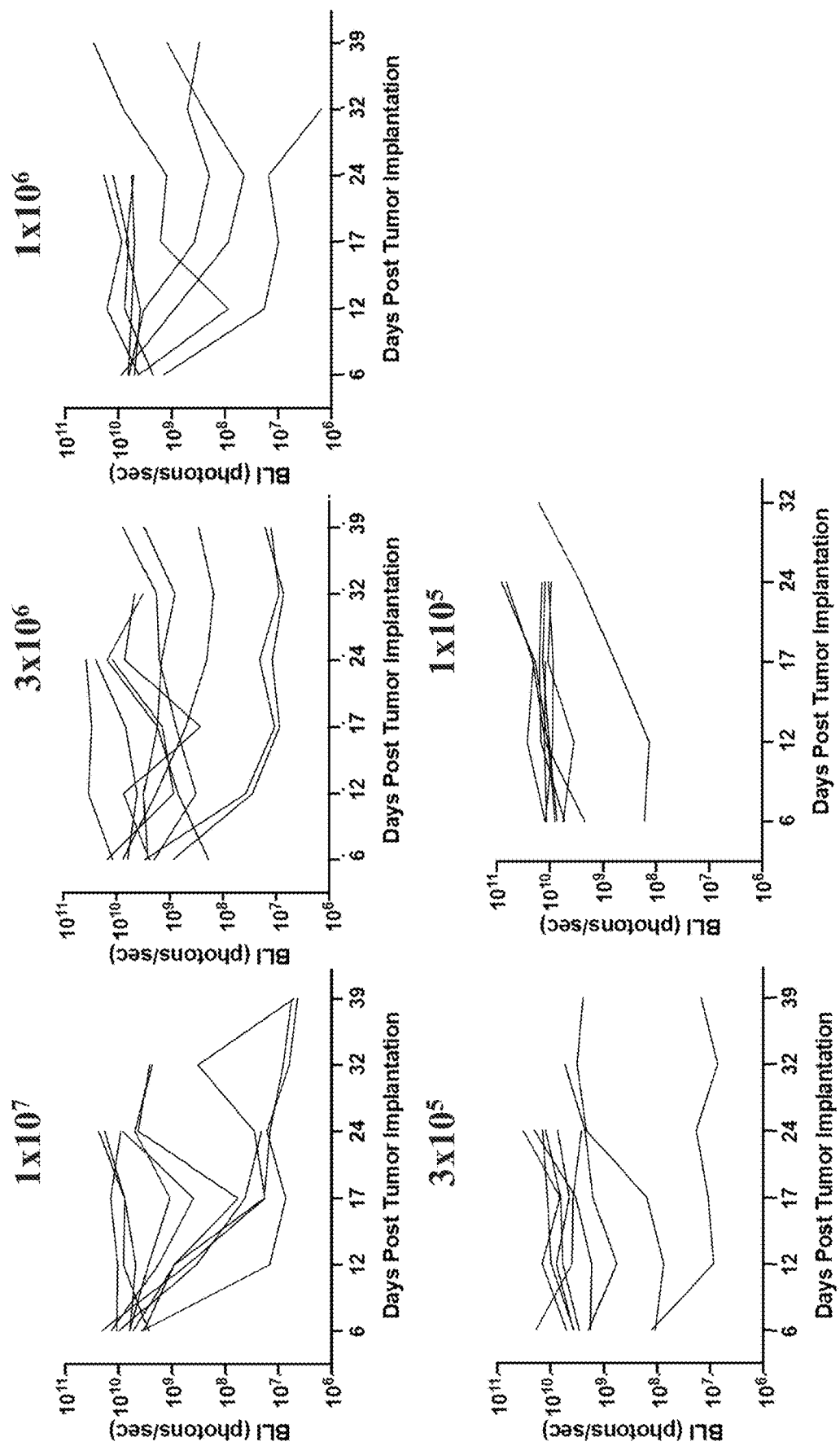
FIG. 59C shows dose-dependent efficacy of treatment using mMSCs engineered to express murine IL12 (p70) and murine IL21 from a single lentiviral expression vector in a B16F10 tumor model.
Figure 59D:
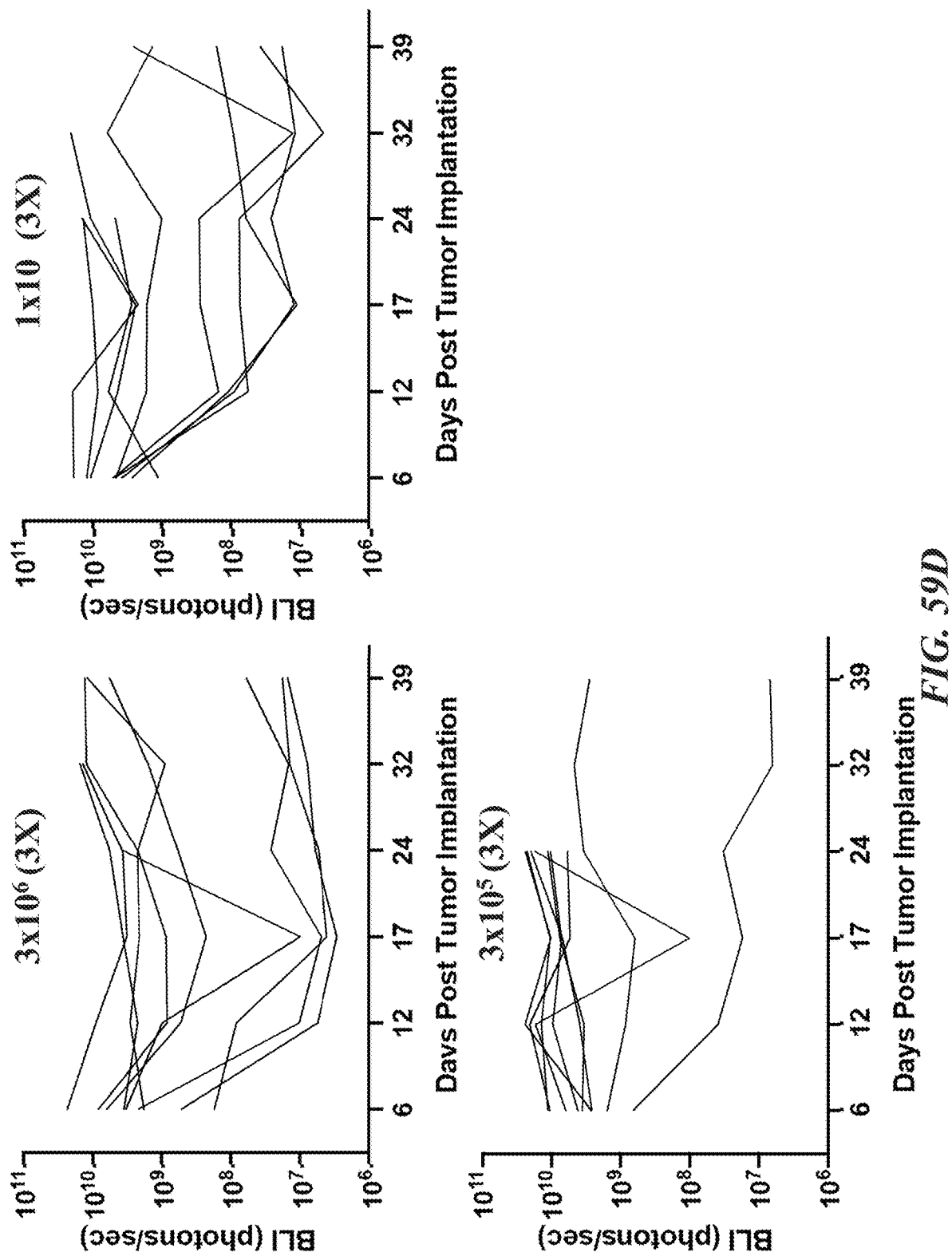
FIG. 59D shows dose-dependent efficacy of treatment using mMSCs engineered to express murine IL12 (p70) and murine IL21 from a single lentiviral expression vector in a B16F10 tumor model.
Figure 59E:
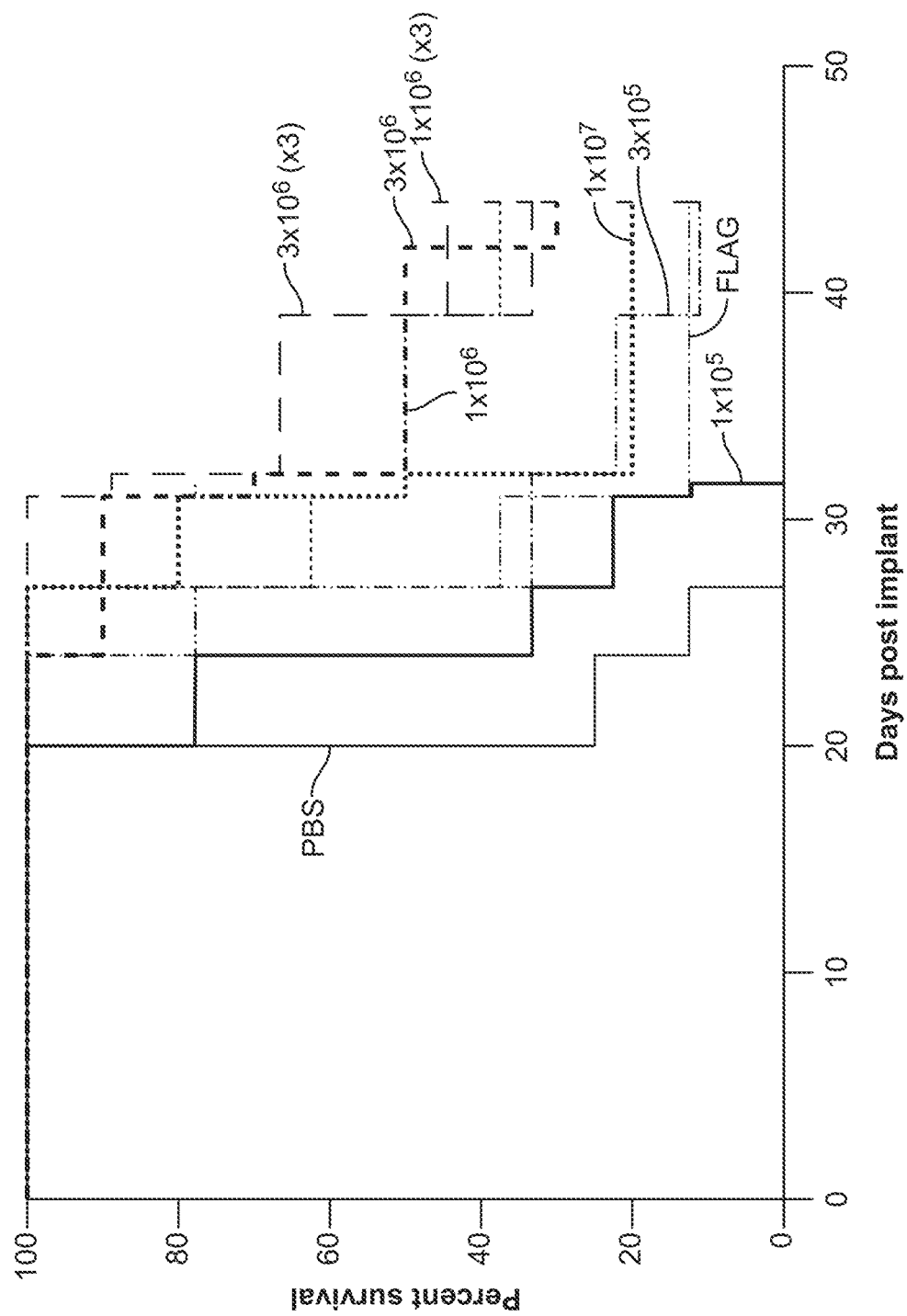
FIG. 59E shows dose-dependent efficacy of treatment using mMSCs engineered to express murine IL12 (p70) and murine IL21 from a single lentiviral expression vector in a B16F10 tumor model.

As shown in FIG. 59A-D, anti-tumor activity was observed in a dose-dependent manner of MSCs expressing both IL12 and IL21, as assessed by BLI (FIG. 59A normalized day 17 vs day 7; FIG. 59B-D BLI over time for individual mice). No efficacy was observed in control FLAG or PBS mice (FIG. 59A and FIG. 59B). No efficacy was also observed at doses of $1\times10^5$ or $3\times10^5$ cells (FIG. 59A and FIG. 59C). In contrast, minimal efficacy was observed at a dose of $1\times10^6$, with efficacy increasing at each increased dose (FIG. 59A and FIG. 59C). Efficacy was also observed following multiple administrations of higher doses (FIG. 59D). As shown in FIG. 59E, long term tumor-free survival was observed in a dose-dependent manner, and also observed following multiple administrations of higher doses (Median survival post-implant: PBS—20 days; FLAG ($\times3$)—27 days; $1\times10^7$—31.5 days; $3\times10^6$—36 days; $3\times10^6$ ($\times3$)—39 days; $1\times10^6$—33 days; $1\times10^6$ ($\times3$)—39 days; $3\times10^5$—27 days; $3\times10^5$ ($\times3$)—27 days [curve overlaps with $3\times10^5$ treatment]; $1\times10^5$—24 days).

Example 28: MSCs Producing Both IL12 and IL21 Reduce Tumor Burden in a MC-38 IP Tumor Model In the following example, C57BL/6 mMSCs were engineered to express murine IL12 (p70) and murine IL21 from a single lentiviral expression vector. The lentiviral expression vector used a 2A ribosome skipping elements to express both cytokines from a single transcript using the lentiviral transduction method described in Example 6. MC-38 tumor cells were transduced with fLUC-EGFP construct and sorted based on EGFP fluorescence, then $5\times10^5$ cells were injected into the peritoneal space of immunocompetent C57BL/6 (age 6-8 weeks). Nine days after tumor implantation, tumor burden was measured by luciferase imaging (BLI) using an AMI imager. Mice were randomized into treatment groups and treated with different amounts of mMSCs ranging from $3\times10^4$ to $1\times10^6$ cells. MSC-Flag-Myc and PBS were used as a negative control.

Figure 60A:
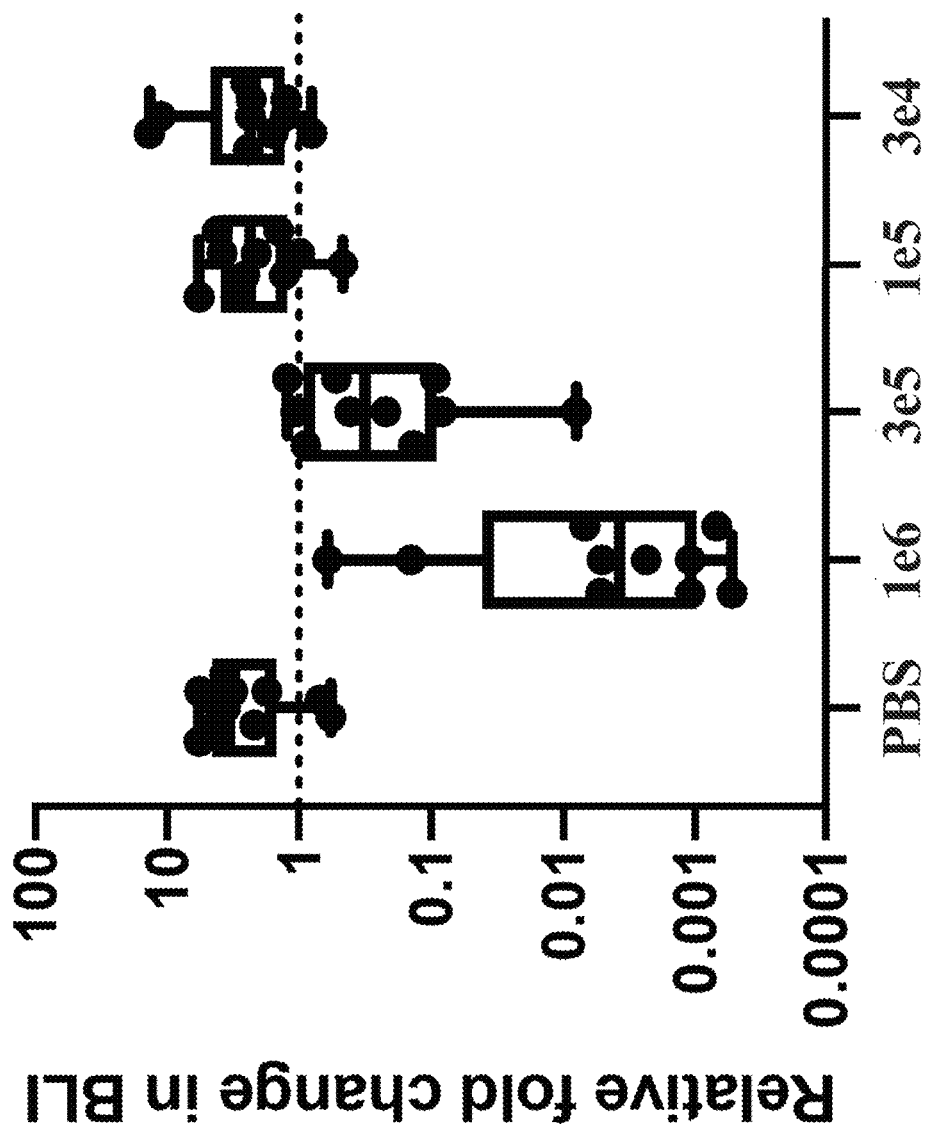
FIG. 60A shows dose-dependent efficacy of treatment using mMSCs engineered to express murine IL12 (p70) and murine IL21 from a single lentiviral expression vector in a MC-38 tumor model.
Figure 60B:
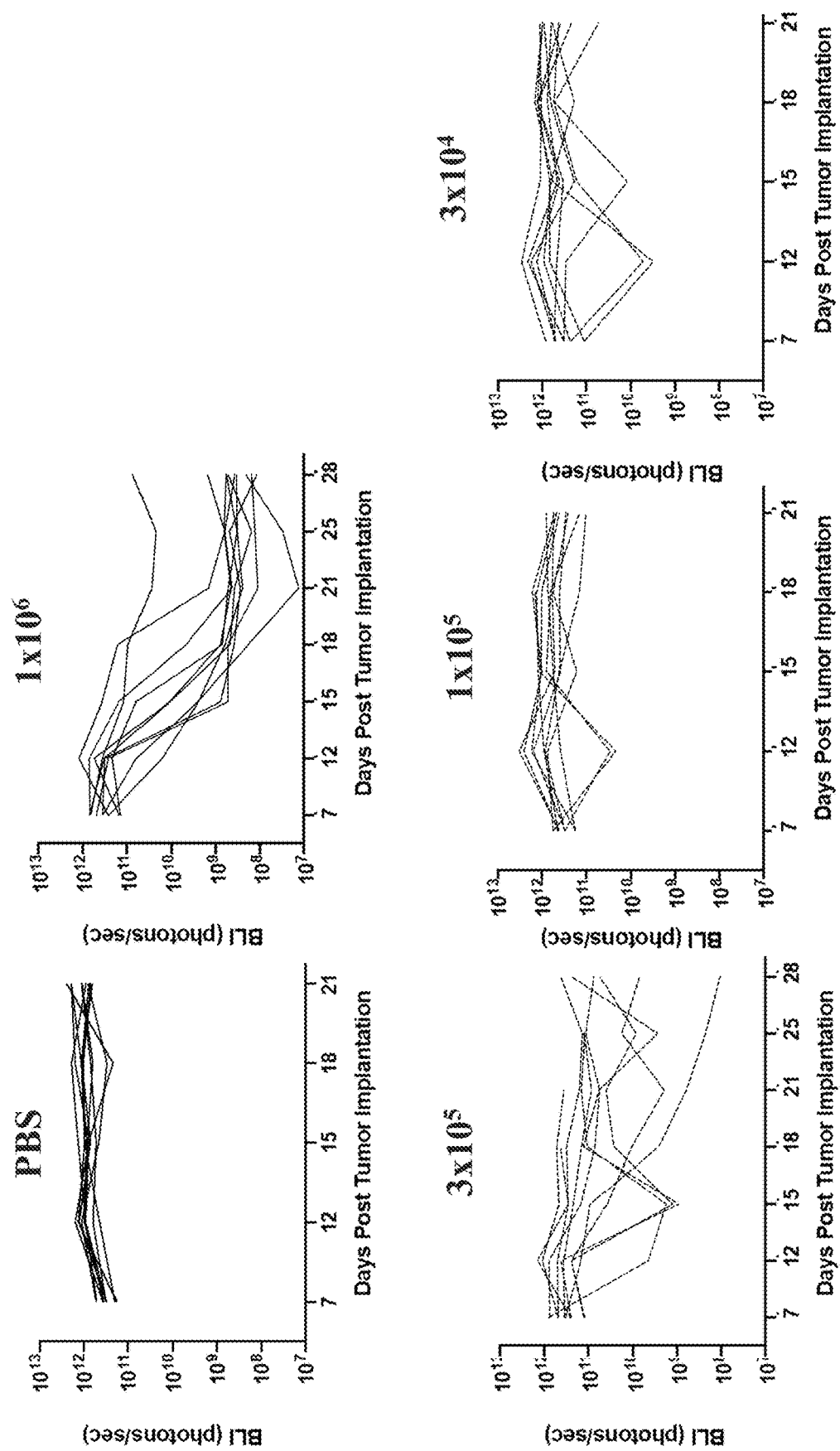
FIG. 60B shows dose-dependent efficacy of treatment using mMSCs engineered to express murine IL12 (p70) and murine IL21 from a single lentiviral expression vector in a MC-38 tumor model.
Figure 60C:
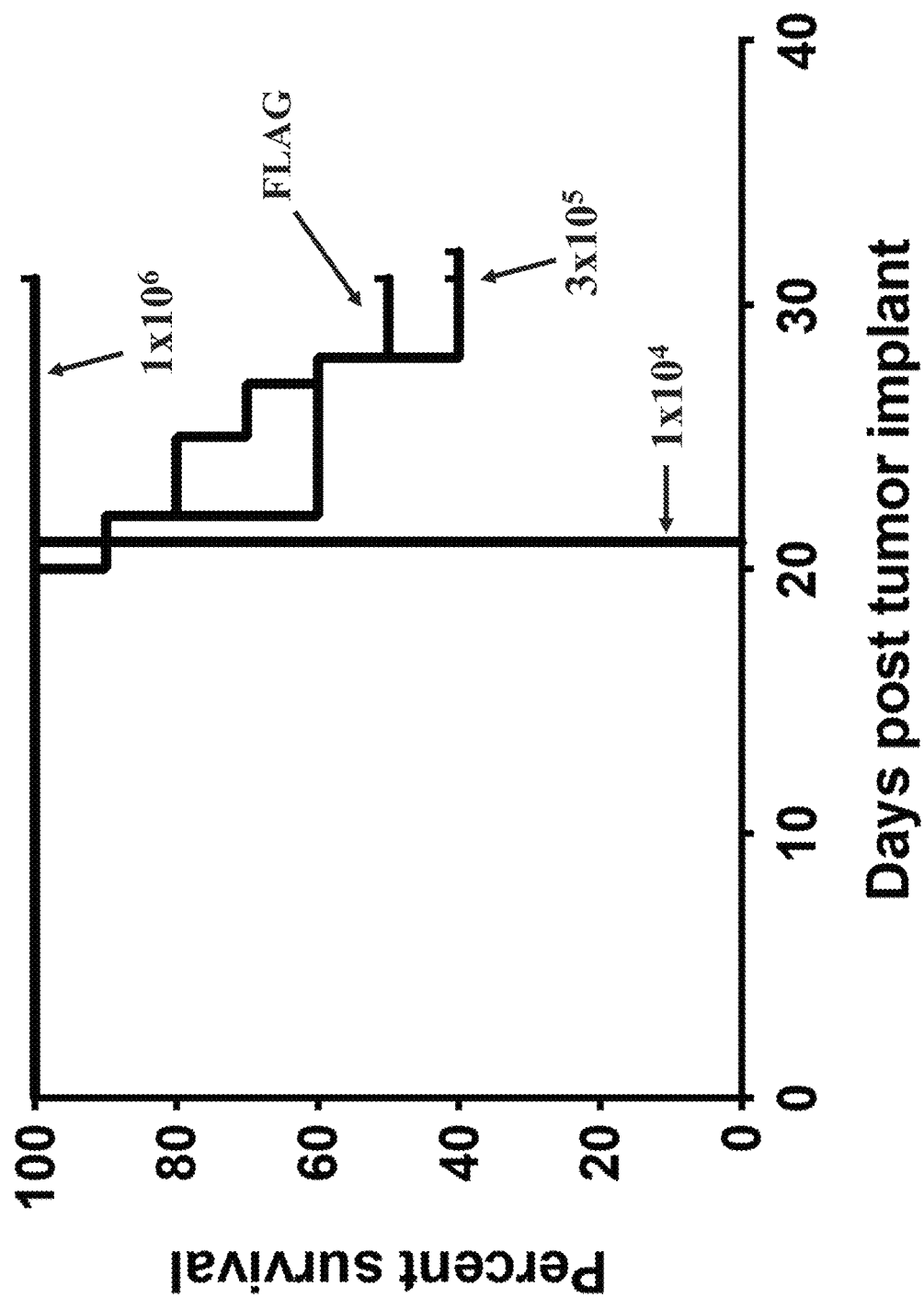
FIG. 60C shows dose-dependent efficacy of treatment using mMSCs engineered to express murine IL12 (p70) and murine IL21 from a single lentiviral expression vector in a MC-38 tumor model.

As shown in FIG. 60A and FIG. 60B, anti-tumor activity was observed in a dose-dependent manner of MSCs expressing both IL12 and IL21, as assessed by BLI (FIG. 60A normalized day 18 vs day 9; FIG. 60B BLI over time for individual mice). No efficacy was observed in control FLAG or PBS mice (FIG. 60A and FIG. 60B). No efficacy was also observed at doses of $1\times10^5$ or $3\times10^4$ cells (FIG. 60A and FIG. 60B). In contrast, minimal efficacy was observed at a dose of $3\times10^5$, with efficacy increasing at an increased dose of $1\times10^6$ cells (FIG. 60A and FIG. 60B). As shown in FIG. 60C, long term tumor-free survival was observed in a dose-dependent manner, with all mice treated with $1\times10^6$ cells surviving past at least day 30 (Median survival post-implant: PBS—21 days; FLAG—29 days; 1×10$^6$—not reached; 3×10$^5$—28 days; 1×10$^5$—21 days; 3×10$^4$—21 days [PBS, 1×10$^5$, and 3×10$^4$ overlap). Accordingly, mMSCs engineered to express murine IL12 (p70) and murine IL21 demonstrated efficacy in a MC-38 tumor model.

Example 29: Human MSCs Home to Tumors in an IP Model

In the following example, NSG mice were implanted with OVCAR8-fLUC cells IP. 14-21 days after tumor implantation, 1×10$^6$ human BM-MSCs engineered to express Nanoluc-EGFP were delivered IP. Mice were euthanized at 24 hours post injection of MSCs and peritoneal organs (stomach, kidney, liver, colon, spleen, pancreas, omentum/tumor, ovaries and Fallopian tubes) were imaged ex-vivo for Nano-Luc signaling (NanoGlo Substrate Kit, Vendor: Promega, Catalog No.: N1110). Human MSCs were imaged by EGFP fluorescence in tumor sections collected at 24 hours as well as 22 days post injection.

Figure 61A:
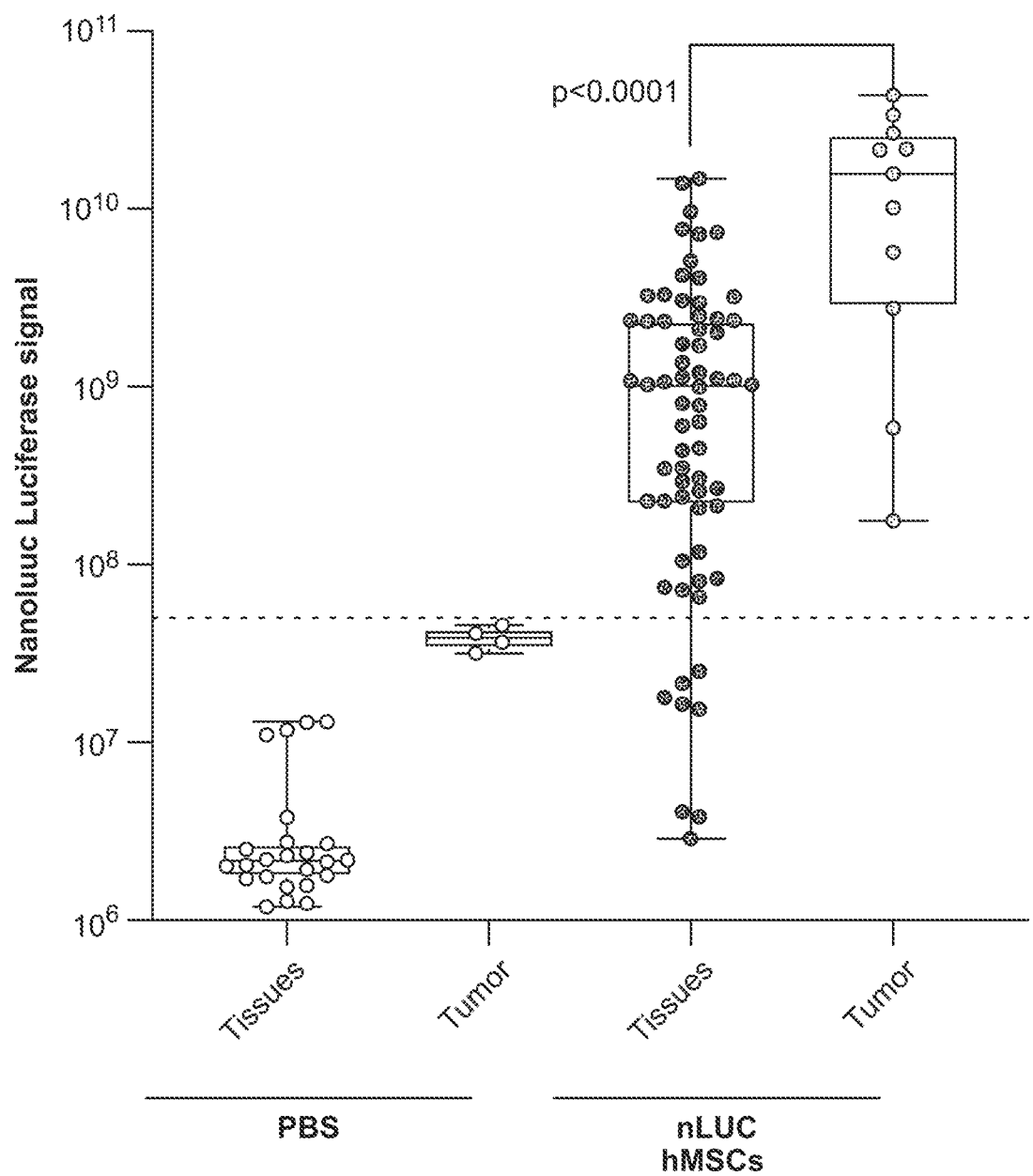
FIG. 61A shows preferential homing of human MSCs.
Figure 61B:
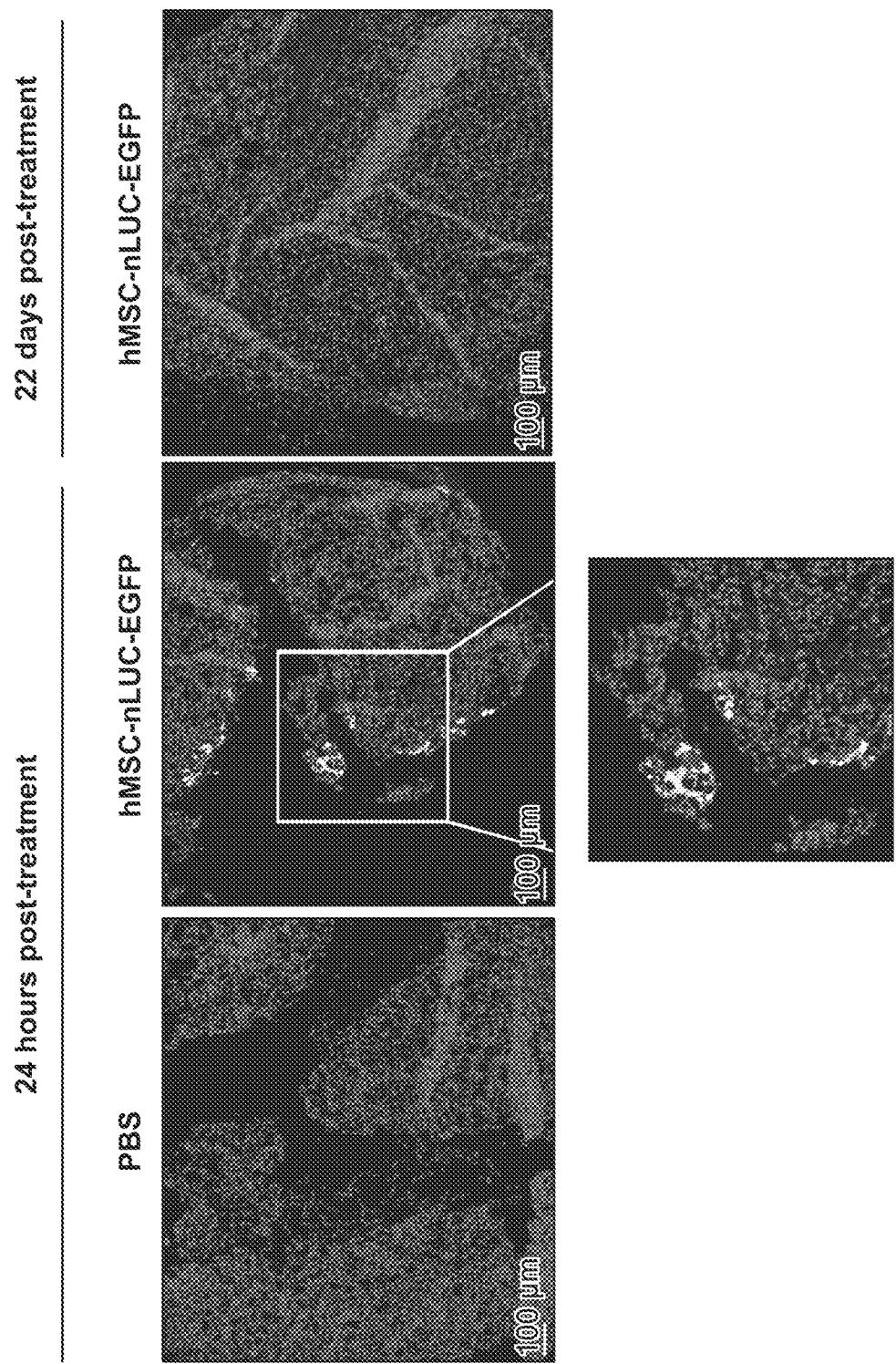
FIG. 61B shows preferential homing of human MSCs.

As shown in FIG. 61A and FIG. 61B, human MSC NanoLuc signal was preferentially enriched in the tumor compared to the other organs in the peritoneal cavity (FIG. 61A summarized luciferase quantification; FIG. 61B representative images of luciferase signal). Additionally, persistence of MSCs was lower than 22 days, with no cells being detected at the latest time point (FIG. 61B right most panel).

Example 30: Biodistribution and PK of Effector Cytokines

In the following example, biodistribution and PK of effector cytokines produced by engineered MSCs was assessed.

In a first experiment, NSG mice were implanted with 5×10$^6$ OVCAR8-fLUC tumor cells IP. 21-27 days after tumor implantation, mice were randomized based on tumor burden measured by BLI and treated with 1×10$^6$ hMSCs engineered to express human IL12 (p70) and human IL21 from a single lentiviral expression vector. The lentiviral expression vector used a 2A ribosome skipping elements to express both cytokines from a single transcript using the lentiviral transduction method described in Example 6. Mice were euthanized at 16-24 hours or 3, 4 and 7 days post MSC treatment and peritoneal fluid was collected via IP lavage by injecting 1 mL of PBS into the peritoneal space and collecting it. Serum was separated from whole blood after intracardiac puncture. ELISA (R&D systems) was used to determine the protein amount in each compartment (peritoneal fluid vs serum) for each time point and treatment type.

Figure 62A:
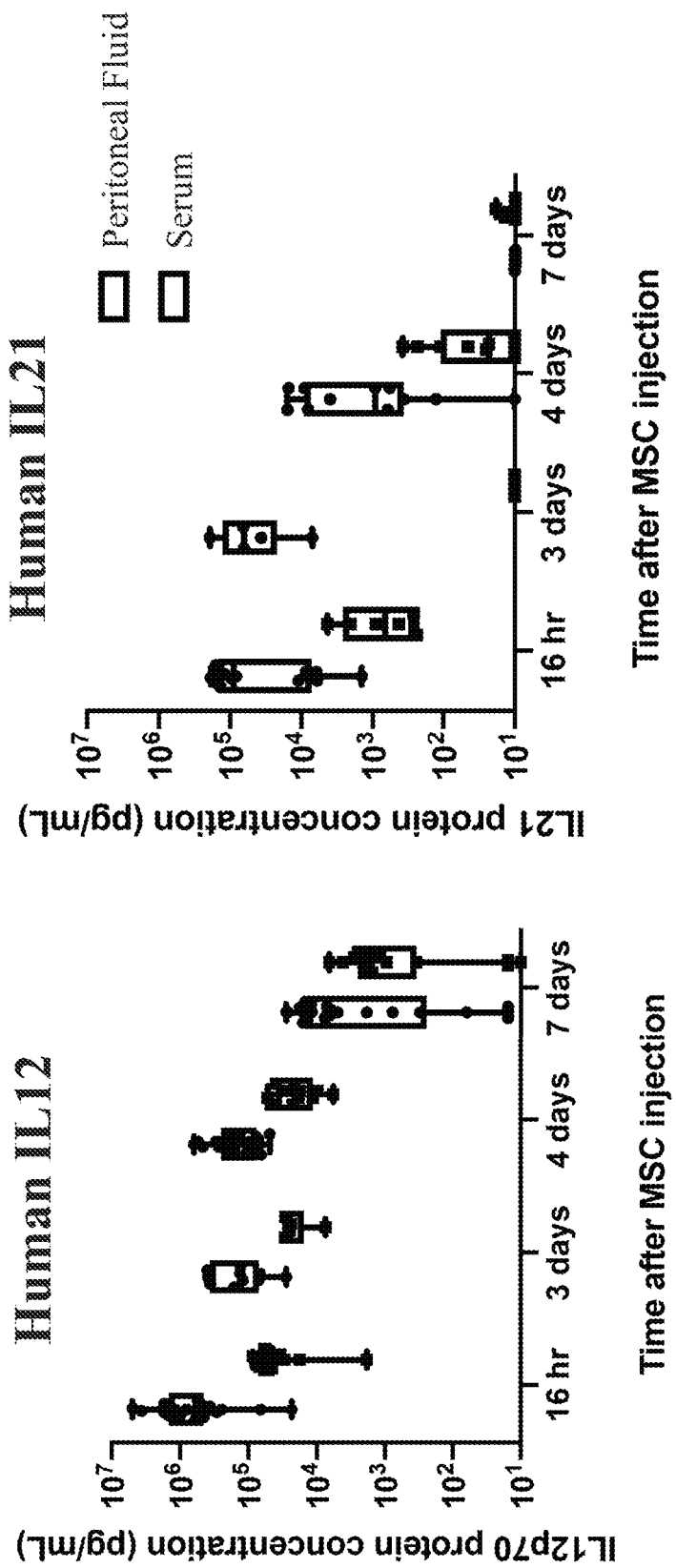
FIG. 62A shows production of human IL12 (left panel) and human IL21 (right panel) in the peritoneal fluid (left column for each respective time point) and serum (right column for each respective time point) in a OVCAR8 model for individual mice in each treatment, and the mean±SEM for each treatment group.

As shown in FIG. 62A, transient production of both human IL12 (left panel) and human IL21 (right panel) was observed in both the peritoneal fluid (left column for each respective time point) and serum (right column for each respective time point). At least a 10 fold increased protein abundance was observed in the peritoneal space (local) compared to systemic (serum), demonstrating localized delivery of cytokines by engineered MSCs.

In another experiment, balb/c mMSCs were engineered to express murine IL12p70 or murine IL21 (i.e., each MSC engineered to express only a single agent) using the lentiviral transduction method described in Example 6. CT26-fLUC tumor cells (1×10$^5$ cells in 100 μl) were injected into the peritoneal space of immunocompetent balb/c (age 6-8 weeks). Murine IL12-expressing murine MSCs and murine IL21-expressing murine MSCs (1×10$^6$ cells delivered for each in the combination) were delivered IP. Mice were euthanized at 24 or 72 hours post MSC treatment and peritoneal fluid was collected via IP lavage by injecting 1 mL of PBS into the peritoneal space and collecting it. Serum was separated from whole blood after intracardiac puncture. Luminex (Millipore) was used to determine the protein amount in each compartment (peritoneal fluid vs serum) for each time point and treatment type.

Figure 62B:
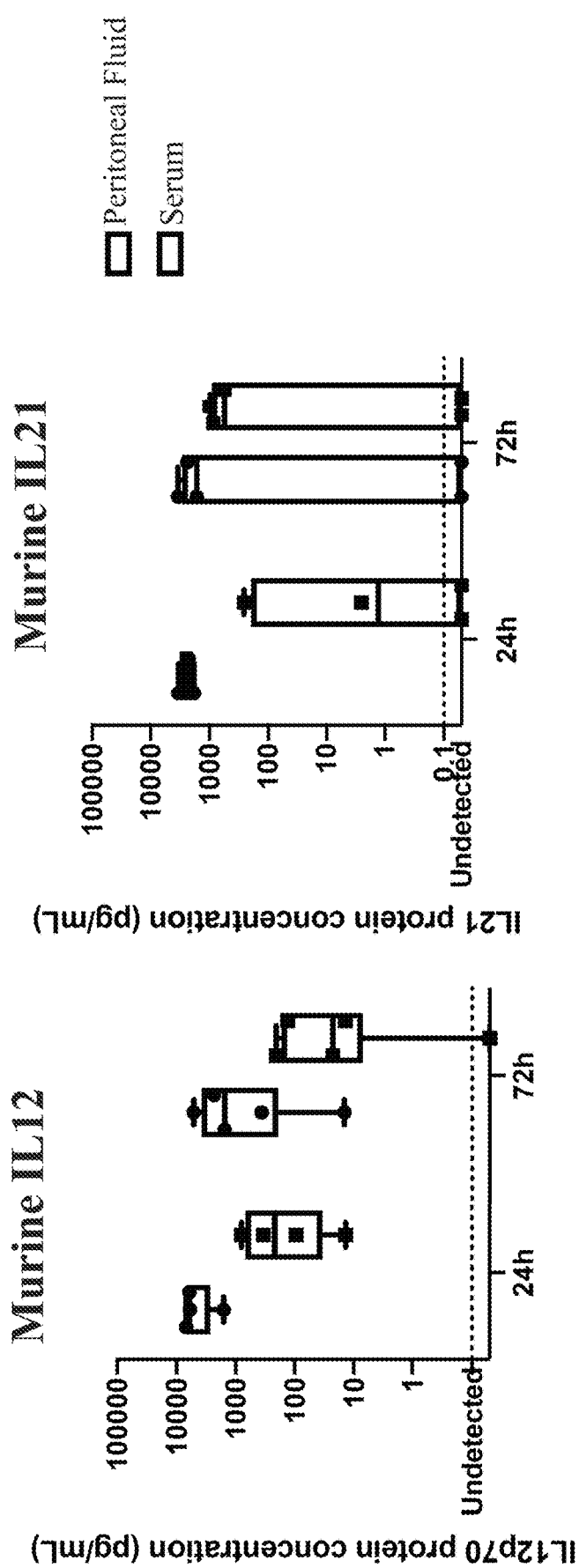
FIG. 62B shows transient production of murine IL12 (left panel) and murine IL21 (right panel) in the peritoneal fluid (left column for each respective time point) and serum (right column for each respective time point) in a CT26 model for individual mice in each treatment, and the mean±SEM for each treatment group.

As shown in FIG. 62B, transient production of both murine IL12 (left panel) and murine IL21 (right panel) was observed in both the peritoneal fluid (left column for each respective time point) and serum (right column for each respective time point). At least a 10 fold increased protein abundance was observed in the peritoneal space (local) compared to systemic (serum), demonstrating localized delivery of cytokines by engineered MSCs.

Example 31: Comparison of MSC Treatment and Recombinant Cytokine Treatment in a CT26 IP Tumor Model In the following example, balb/c mMSCs were engineered to express murine IL12 (p70) and murine IL21 from a single lentiviral expression vector. Balb/c mMSCs were also engineered to express either murine IL12 (p70) or murine IL21. The lentiviral expression vector used a 2A ribosome skipping elements to express both cytokines from a single transcript using the lentiviral transduction method described in Example 6. CT26 tumor cells (1×10$^5$ cells in 100 μl) modified to constitutively express luciferase enzyme (Cat no: CL043, Lot no: CL-IM147 Imanis Life Sciences) were injected into the peritoneal space of immunocompetent female balb/c mice (age 6-8 weeks). One week after tumor implantation, tumor burden was measured by luciferase imaging (BLI) using an AMI imager. For MSC treated mice, mice were randomized into treatment groups and treated with intraperitoneally delivered mMSCs (1×10$^6$ cells), receiving murine IL12-expressing murine MSCs, murine IL21-expressing murine MSCs, or murine IL12 and IL21-expressing murine MSCs, with MSC-Flag-Myc and PBS were used as a negative control. Additionally, treatment groups also included mice receiving a bolus dose of the respective recombinant cytokines at a dose of 4-times the amount produced by MSCs in vitro (measured by ELISA—recombinant IL12: 5 ug/mouse; Recombinant IL21: 0.4 ug/mouse). Tumor burden was measured by fLUC BLI across time points and mice were euthanized when reaching endpoint criteria due to tumor burden. Kaplan Meier survival curves were determined to calculate tumor-free survival.

Figure 63A:
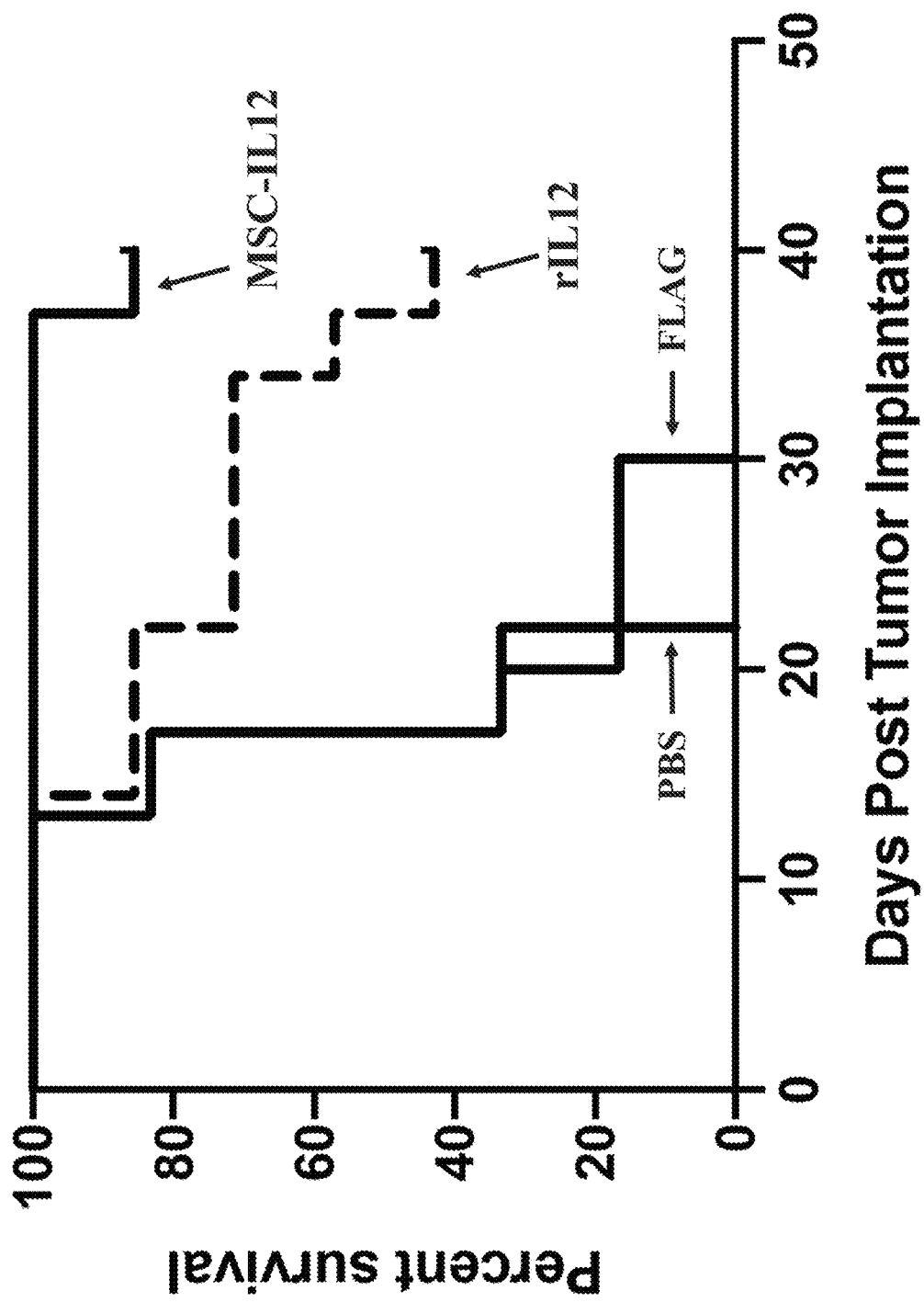
FIG. 63A shows efficacy of mice either treated with MSCs engineered to produce cytokines or treated with recombinant cytokine therapy in a CT26 model.
Figure 63B:
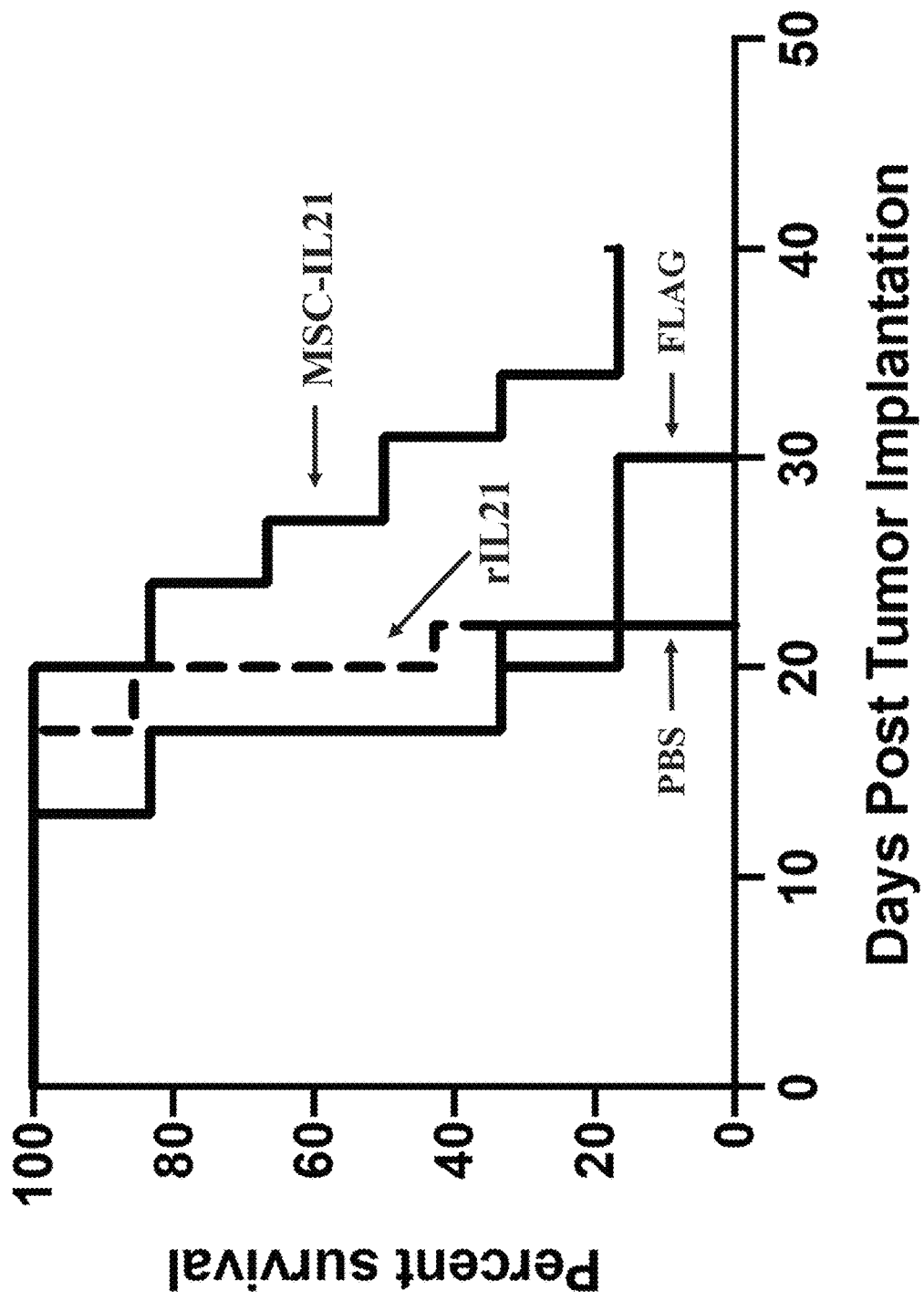
FIG. 63B shows efficacy of mice either treated with MSCs engineered to produce cytokines or treated with recombinant cytokine therapy in a CT26 model.
Figure 63D:
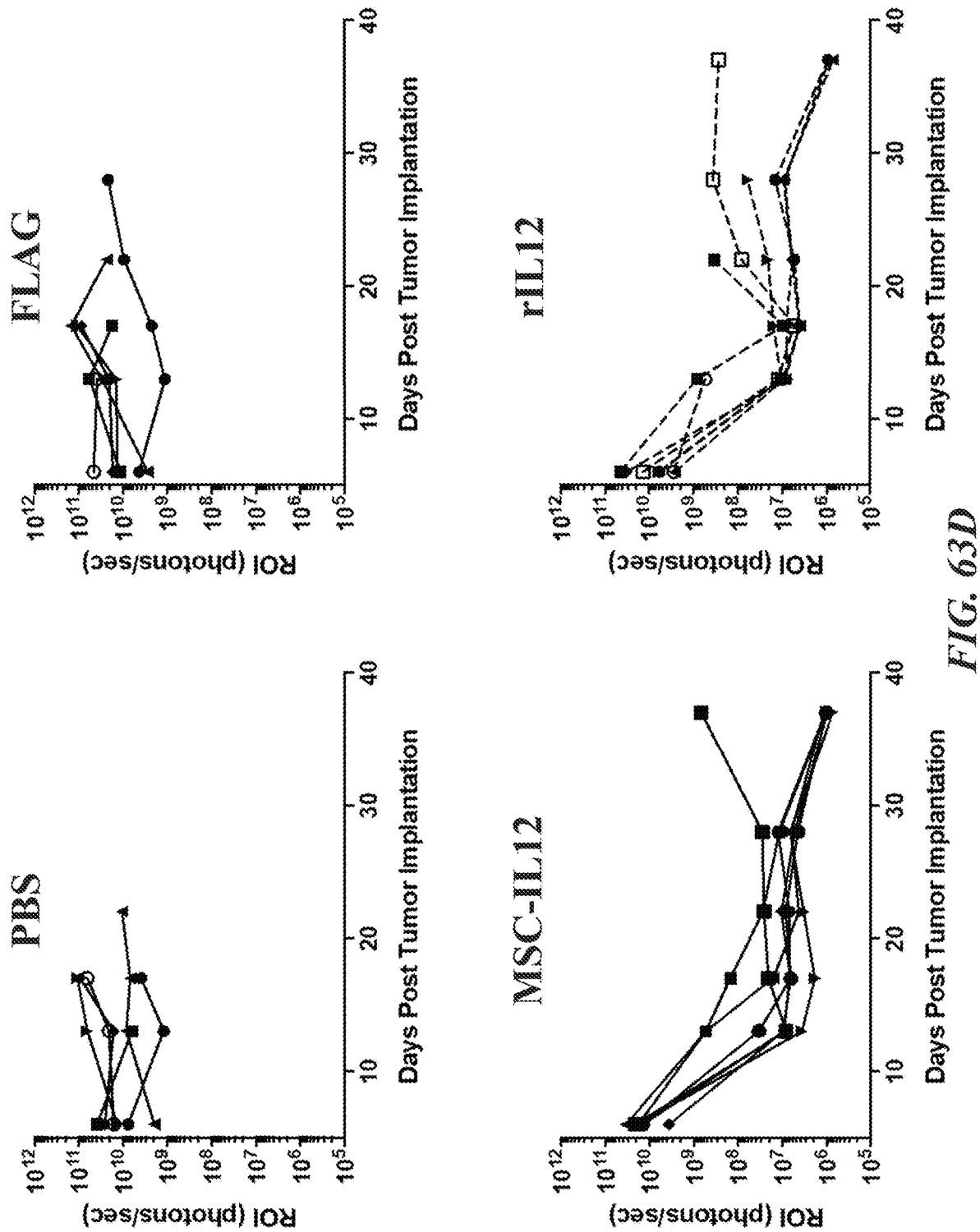
FIG. 63D shows efficacy of mice either treated with MSCs engineered to produce cytokines or treated with recombinant cytokine therapy in a CT26 model.
Figure 63E:
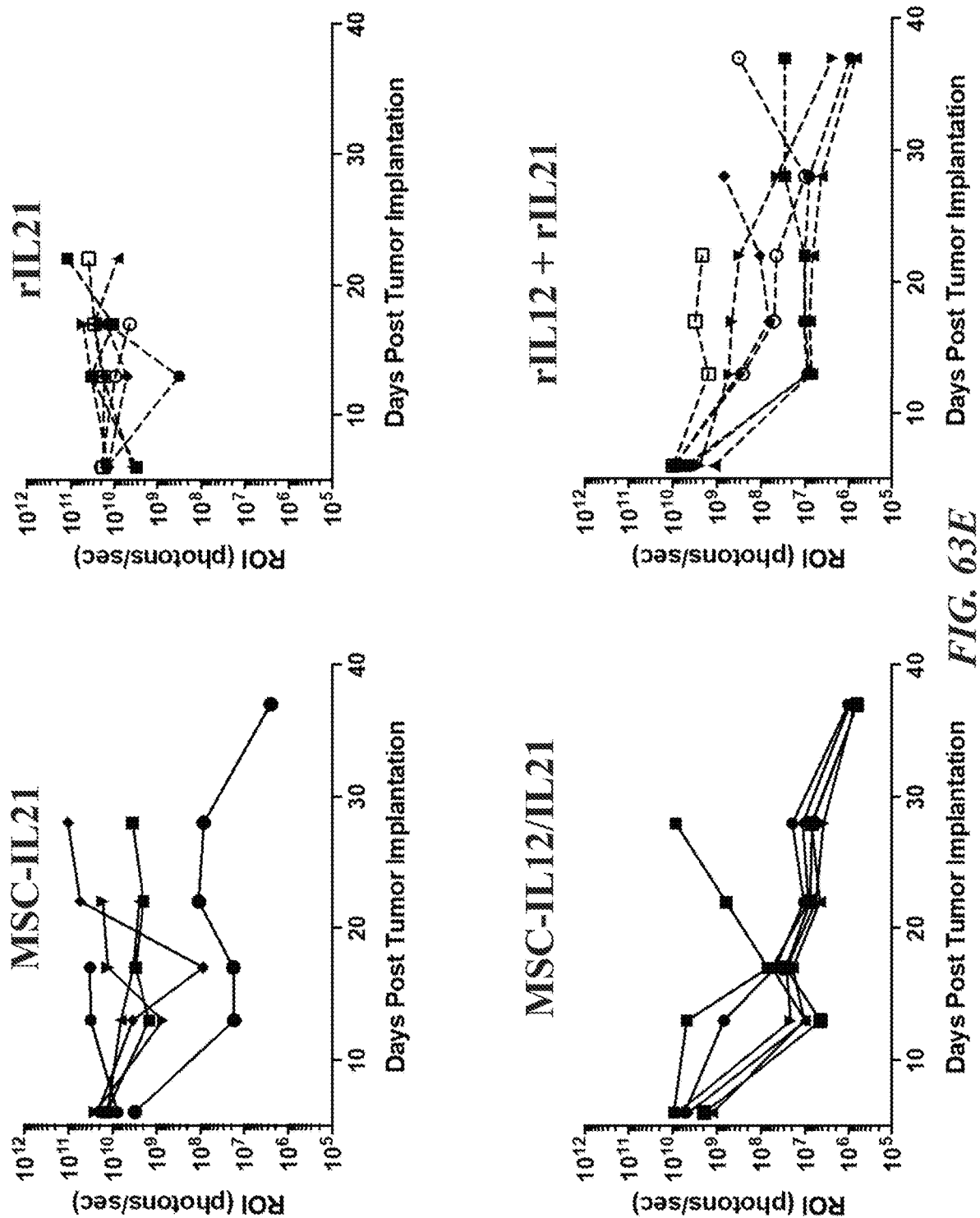
FIG. 63E shows efficacy of mice either treated with MSCs engineered to produce cytokines or treated with recombinant cytokine therapy in a CT26 model.

As shown in FIG. 63A-C, mice treated with MSCs engineered to produce cytokines outperformed recombinant cytokine therapy in terms of prolonged tumor-free survival, in all cases (FIG. 63A—MSC-IL12 vs rIL12; FIG. 63B—MSC-IL21 vs rIL21; FIG. 63C—MSC-IL12/IL21 vs rIL12+rIL21). Additionally, as shown in FIG. 63D-E, mice treated with MSCs engineered to produce cytokines outperformed recombinant cytokine therapy as assessed by tumor burden BLI), in all cases (FIG. 63D bottom row—MSC-IL12 vs rIL12; FIG. 63E top row—MSC-IL21 vs rIL21; FIG. 63E bottom row—MSC-IL12/IL21 vs rIL12+rIL21).

Example 32: Comparison of MSC Treatment and Recombinant Cytokine Treatment in a B16F10 IP Tumor Model In the following example, C57BL/6 mMSCs were engineered to express murine IL12 (p70) and murine IL21 from a single lentiviral expression vector. C57BL/6 mMSCs were also engineered to express either murine IL12 (p70) or murine IL21. The lentiviral expression vector used a 2A ribosome skipping elements to express both cytokines from a single transcript using the lentiviral transduction method described in Example 6. B16F10 tumor cells ($1\times10^5$ cells in 100 µl) modified to constitutively express luciferase enzyme (Cat no: CL043, Lot no: CL-IM147 Imanis Life Sciences) were injected into the peritoneal space of immunocompetent female balb/c mice (age 6-8 weeks). One week after tumor implantation, tumor burden was measured by luciferase imaging (BLI) using an AMI imager. For MSC treated mice, mice were randomized into treatment groups and treated with intraperitoneally delivered mMSCs ($3\times10^6$ cells) engineered to express both IL12 and IL21-expressing murine MSCs, with MSC-Flag-Myc and PBS were used as a negative control. Additionally, treatment groups also included mice receiving a bolus dose of the respective recombinant cytokines at a dose of 4-times the amount produced by MSCs in vitro (measured by ELISA—recombinant IL12: 3 ug/mouse; Recombinant IL21: 0.03 ug/mouse). Tumor burden was measured by tumor weight at day 7 post treatment and mice were euthanized when reaching endpoint criteria due to tumor burden. Kaplan Meier survival curves were determined to calculate tumor-free survival.

Figure 64A:
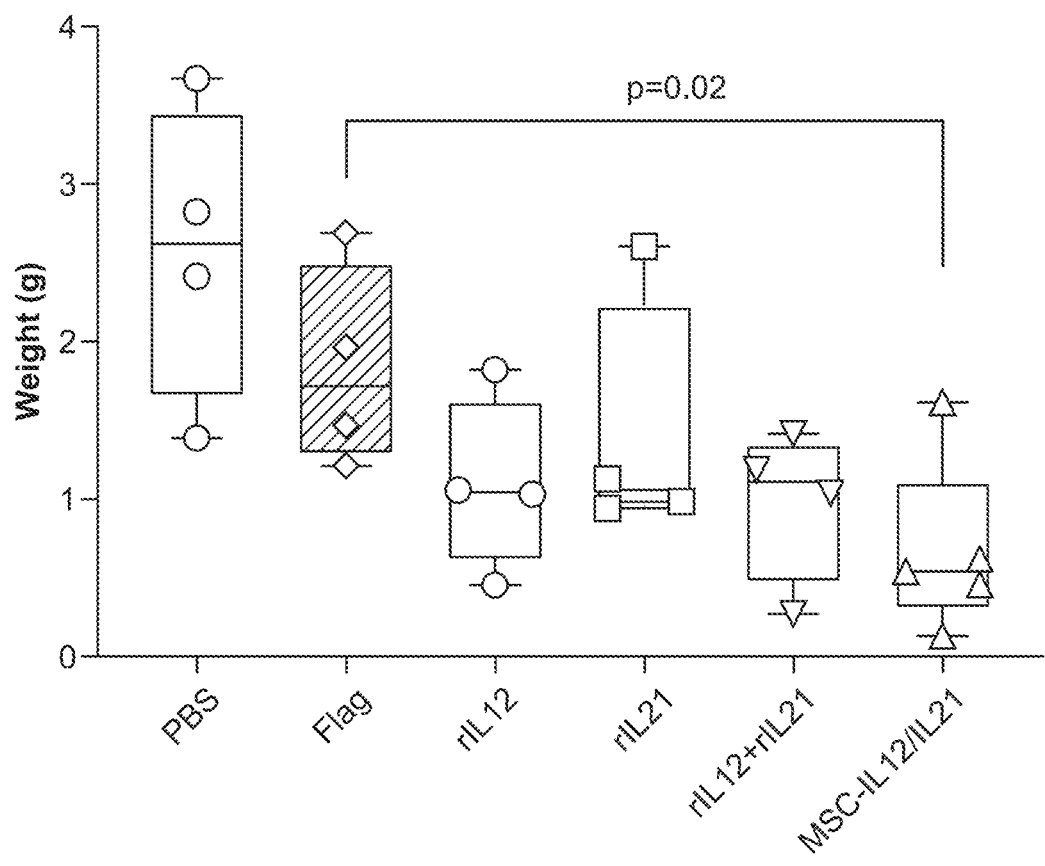
FIG. 64A shows efficacy of mice either treated with MSCs engineered to produce cytokines or treated with recombinant cytokine therapy in a B16F10 model.

As shown in FIG. 64A, mice treated with MSCs engineered to produce both IL12 and IL21 outperformed recombinant cytokine therapy as assessed by tumor weight. Additionally, as shown in FIG. 64B, mice treated with MSCs engineered to produce both IL12 and IL21 outperformed recombinant cytokine therapy as assessed by tumor-free prolonged survival.

Example 33: Immune Profile Following Treatment with MSCs Producing Both IL12 and IL21 in a CT26 IP Tumor Model In the following example, balb/c mMSCs were engineered to express murine IL12p70 or murine IL21 (i.e., each MSC engineered to express only a single agent) using the lentiviral transduction method described in Example 6. CT26 tumor cells ($1\times10^5$ cells) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. Mice were randomized into treatment groups and treated with a intraperitoneally delivered combination treatment of murine IL12-expressing murine MSCs and murine IL21-expressing murine MSCs ($1\times10^6$ cells delivered for each in the combination), or MSC-Flag-Myc and PBS as a negative controls. Mice were euthanized and organs collected at 72 hours after treatment. Multicolor flow cytometry was used to characterize immune infiltrates in response to treatment.

As shown in FIG. 65A and FIG. 65B, T-cell subsets and activation markers (CD3, CD4, CD8, CD8/CD38+, CD8/IFNg+, CD8/Gzmb+, NK/Gzmb+ and ratio CD8:Tregs-FoxP3) were significantly increased in the peritoneal fluid after treatment with MSCs-IL12+MSCs IL21. Additionally, as shown in FIG. 65C, antigen-presenting cells such as dendritic cells (CD11c/MHC-II hi, CD86+, CD103+, CD11b+) were also significantly increased in peritoneal tumor-draining lymph nodes after treatment with MSC-IL12+MSC-IL21. Accordingly, combination treatment of murine IL12-expressing murine MSCs and murine IL21-expressing murine MSCs demonstrated an activated immune profile.

Example 34: Optimization of Signal Peptide Sequences

In the following example, effector molecules are modified to replace their native signal peptide sequence with an exogenous signal peptide sequence (see Table 5 for exemplary signal peptide sequences that are tested). Modified effector molecules are tested for functional improvements such as improved expression and maintained secretion, such as in particular environments (e.g., tumor microenvironments). Functional performance for the modified effector molecules is also tested in tumor models (e.g., improved ability to clear tumors, improved ability to clear tumors in different environments, or improved ability to clear different types of tumors).

Example 35: Enrichment of Engineered MSCs

In the following example, MSCs are engineered to express effector molecules within a population of cells that include unmodified cells, such as unmodified MSCs. The engineered MSCs are enriched within the population by contacting the engineered MSCs with a growth factor (such as the effector molecules described in Table 1) such that those engineered MSCs that are enriched are a sub-population of engineered MSCs that express a receptor or receptor ligand for the growth factor. The sub-population of engineered MSCs of interest are contacted with the growth factor in various manners:
1. In an autocrine manner by genetically engineering the MSCs themselves to express the factors.
2. In a paracrine manner by genetically engineering feeder or support cells to express the factors and supply those factors to the MSCs, or by using conditioned media containing the factors from the feeder or support cells (such as 293 Ts) engineered to express these factors.
3. In an endocrine manner, by injecting recombinant protein or nucleic acid versions of these factors into patients following MSC transplantation.
4. Via addition of soluble recombinant protein versions of these factors to the MSC culture conditions.
5. Via coating of the tissue culture plate/flask surfaces used for MSC propagation with recombinant versions of these factors.

REFERENCES

1. Kidd S, et al. (2009) Stem Cells 27(10):2614-2623.
2. Dembinski J L, et al. (2013) Cytotherapy 15(1):20-32.
3. Siegel R L, et al. (2016) CA Cancer J Clin 66(1):7-30.
4. Dizon D M J (2010) Gynecol Oncol 116(3).
5. Woo S R, et al. (2015) Trends Immunol 36(4):250-256.
6. Hamanishi J, et al. (2016) Int Immunol 28(7):339-348.
7. Li S, et al. (2012) Oncolytic Virother 1:1-21.
8. Koneru M, et al. (2015) J Transl Med 13:102.
9. Cruz C R, et al. (2010) Cytotherapy 12(6):743-749.
10. Li Y Q, et al. (2013) PLoS One 8(10):e76379.
11. Wiedemann G M, et al. (2016) Oncoimmunology 5(9): e1175794.
12. Squillaro T, et al. (2016) Cell Transplant 25(5):829-848.
13. Studeny M, et al. (2004) J Natl Cancer Inst 96(21):1593-1603.
14. Ling X, et al. (2010) Cancer Microenviron 3(1):83-95.

15. Schukur L, et al. (2015) Sci Transl Med 7(318): 318ra201.
16. Howlader N N A, Krapcho M, Garshell J, Miller D, Altekruse S F, Kosary C L, Yu M, Ruhl J, Tatalovich Z, Mariotto A, Lewis D R, Chen H S, Feuer E J and Cronin K A. (2015).
17. Lengyel E (2010) Am J Pathol 177(3):1053-1064.
18. McGuire W P, et al. (1996) The New England journal of medicine 334(1):1-6.
19. McGuire W P, et al. (1989) Annals of internal medicine 111(4):273-279.
20. Adams S F & Benencia F (2015) Future Oncology 11(9):1293-1296.
21. Maude S L, et al. (2014) N Engl J Med 371(16):1507-1517.
22. Bargou R, et al. (2008) Science 321(5891):974-977.
23. Kershaw M H, et al. (2014) Clin Trans Immunol 3:e16.
24. Gilham D E, et al. (2012) Trends Mol Med 18(7):377-384.
25. Klinger M, et al. (2012) Blood 119(26):6226-6233.
26. Fu J, et al. (2015) Sci Transl Med 7(283):283ra252.
27. Moynihan K D, et al. (2016) Nat Med 22(12):1402-1410.
28. Mohammadi M, et al. (2016) Cancer Gene Ther 23(9): 285-286.
29. Wang D, et al. (2013) Cell Transplant 22(12):2267-2277.
30. Nowakowski A, et al. (2016) Stem Cells Int 2016: 4956063.
31. Sun Z, et al. (2014) J Hematol Oncol 7:14.
32. Ando M, et al. (2015) Stem Cell Reports 5(4):597-608.
33. Zhao Q, et al. (2015) Proc Natl Acad Sci USA 112(2): 530-535.
34. Xie C, et al. (2013) Br J Cancer 109(5):1198-1205.
35. Parker B S, et al. (2016) Nat Rev Cancer 16(3):131-144.
36. Roby K F, et al. (2000) Carcinogenesis 21(4):585-591.
37. Sharma A D, et al. (2015) J Vis Exp (95):e52242.
38. Waterman R S, et al. (2012) PLoS One 7(9):e45590.
39. Dubinett S M, et al. (2010) Cancer J 16(4):325-335.
40. Tang E D & Wang C Y (2015) PLoS One 10(3): e0120090.
41. Cieri N, et al. (2013) Blood 121(4):573-584.
42. Fitzgerald K A, et al. (2003) Nat Immunol 4(5):491-496.
43. Wong A S, et al. (2016) Proc Natl Acad Sci USA 113(9):2544-2549.
44. Wong A S, et al. (2015) Nat Biotechnol 33(9):952-961.
45. Nissim L, et al. (2014) Mol Cell 54(4):698-710.
46. Deng P, et al. (2016) Neural Regen Res 11(5):702-705.
47. Beegle J R, et al. (2016) Mol Ther Methods Clin Dev 3:16053.
48. Boutros C, et al. (2016) Nat Rev Clin Oncol 13(8):473-486.
49. Valsecchi M E (2015) New Engl J Med 373(13):1270-1270.
50. Pardoll D M (2012) Nat Rev Cancer 12(4):252-264.
51. Legat A, et al. (2013) Front Immunol 4:455.
52. Justus C R, et al. (2014) J Vis Exp (88).
53. Jedema I, et al. (2004) Blood 103(7):2677-2682.
54. Peng D, et al. (2015) Nature 527(7577):249-253.
55. Gitzinger M, et al. (2009) Proc Natl Acad Sci USA 106(26):10638-10643.
56. Clackson T, et al. (1998) Proc Natl Acad Sci USA 95(18):10437-10442.
57. Siuti P, et al. (2013) Nature Biotechnology 31(5):448-452.
58. Farzadfard F & Lu T K (2014) Science 346(6211): 1256272.
59. Perli S D, et al. (2016) Science 353(6304).
60. Roquet N, et al. (2016) Science 353(6297):aad8559.
61. Wong A S L, et al. (2016) Proceedings of the National Academy of Sciences.
62. Gardner T S, et al. (2000) Nature 403(6767):339-342.
63. Deans T L, et al. (2007) Cell 130(2):363-372.
64. Warren L, et al. (2010) Cell Stem Cell 7(5):618-630.
65. Yang B X, et al. (2015) Cell 163(1):230-245.
66. Kumar R M, et al. (2014) Nature 516(7529):56-61.
67. Zhang J, et al. (2016) Cell Stem Cell 19(1):66-80.
68. Cahan P, et al. (2014) Cell 158(4):903-915.
69. Doulatov S, et al. (2013) Cell Stem Cell 13(4):459-470.
70. Kim K, et al. (2011) Nat Biotechnol 29(12):1117-1119.
71. Chavez A, et al. (2016) Nat Methods 13(7):563-567.
72. Slomovic S & Collins J J (2015) Nat Methods 12(11): 1085-1090.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An engineered mesenchymal stem cell (MSC) comprising:
   a) a promoter; and
   b) an exogenous polynucleotide sequence comprising an expression cassette described in a formula, oriented from 5' to 3', comprising

S1-E1-L-S2-E2 wherein
   S1 comprises a polynucleotide sequence encoding a first signal peptide,
   E1 comprises a polynucleotide sequence encoding a first effector molecule,
   L comprises a linker polynucleotide sequence,
   S2 comprises a polynucleotide sequence encoding a second signal peptide,
   E2 comprises a polynucleotide sequence encoding a second effector molecule,
   wherein the promoter is operably linked to the expression cassette, the first signal peptide is operably linked to the first effector molecule, and the second signal peptide is operably linked to the second effector molecule, and
   wherein the first effector molecule comprises an IL12P70 fusion protein and the second effector molecule comprises CCL21a, IL7, IL11S, IL21, Flt3L, an anti-PD1 antibody, CD40L, or a CXCL10-CXCL11 fusion protein.

2. The engineered MSC claim 1, wherein the promoter is operably linked to the expression cassette such that the polynucleotides are capable of being transcribed as a single polynucleotide comprising the formula S1–E1–L–S2–E2.

3. The engineered MSC of claim 2, wherein the linker polynucleotide sequence is operably associated with the translation of the first effector molecule and the second effector molecule as separate polypeptides.

4. The engineered MSC of claim 1, wherein the linker polynucleotide sequence encodes a 2A ribosome skipping tag.

5. The engineered MSC of claim 1, wherein the engineered MSC is a human cell, wherein the human cell comprises a cellular marker phenotype comprising CD105+, CD73+, CD90+, CD45-, CD34-, CD14-; a cellular marker phenotype comprising CD105+, CD73+, CD90+, CD11b-, CD79α-; a cellular marker phenotype comprising CD105+, CD73+, CD90+, CD19-, HLA class II-; or a cellular marker phenotype comprising CD73+, CD90+, CD105+, and CD166+, CD11b-, CD14-, CD19-, CD34-, CD45-, and HLA-DR-.

6. The engineered MSC of claim 1, wherein the promoter comprises a constitutive promoter or an inducible promoter.

7. The engineered MSC of claim 1, wherein:
   the first signal peptide comprises a native signal peptide native to the first effector molecule; or
   the second signal peptide comprises a native signal peptide native to the second effector molecule; or
   the first signal peptide comprises a non-native signal peptide non-native to the first effector molecule; or
   the second signal peptide comprises a non-native signal peptide non-native to the second effector molecule, respectively; or any combination thereof.

8. The engineered MSC of claim 1, wherein the exogenous polynucleotide sequence comprises one or more viral vector polynucleotide sequences.

9. A population of cells, wherein the population of cells comprises one or more engineered MSCs of claim 1.

10. A pharmaceutical composition comprising a pharmaceutically acceptable carrier and one or more engineered MSCs of claim 1.

11. An engineered mesenchymal stem cell (MSC) comprising:
    a) an SFFV promoter; and
    b) an exogenous polynucleotide sequence comprising an expression cassette described in a formula, oriented from 5' to 3', comprising

S1-E1-L-S2-E2 wherein
    S1 comprises a polynucleotide sequence encoding a first signal peptide, wherein the first signal peptide is a human IL12 signal peptide;
    E1 comprises a polynucleotide sequence encoding a first effector molecule, wherein the first effector molecule is a human IL12p70 fusion protein;
    L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
    S2 comprises a polynucleotide sequence encoding a second signal peptide, wherein the second signal peptide is a human IL21 signal peptide;
    E2 comprises a polynucleotide sequence encoding a second effector molecule, wherein the second effector molecule is human IL21; and
    wherein the SFFV promoter is operably linked to the expression cassette, the first signal peptide is operably linked to the first effector molecule, and the second signal peptide is operably linked to the second effector molecule.

12. The engineered MSC of claim 11, wherein the engineered MSC is a human cell, wherein the human cell comprises a cellular marker phenotype comprising CD105+, CD73+, CD90+, CD45-, CD34-, CD14-; a cellular marker phenotype comprising CD105+, CD73+, CD90+, CD11b-, CD79α-; a cellular marker phenotype comprising CD105+, CD73+, CD90+, CD19-, HLA class II-; or a cellular marker phenotype comprising CD73+, CD90+, CD105+, and CD166+, CD11b-, CD14-, CD19-, CD34-, CD45-, and HLA-DR-.

13. The engineered MSC of claim 11, wherein the exogenous polynucleotide sequence comprises one or more viral vector polynucleotide sequences.

14. A population of cells, wherein the population of cells comprises one or more engineered MSCs of claim 11.

15. A pharmaceutical composition comprising a pharmaceutically acceptable carrier and one or more engineered MSCs of claim 11.

16. An engineered mesenchymal stem cell (MSC) comprising an exogenous polynucleotide sequence comprising the polynucleotide sequence shown in SEQ ID NO: 144.

17. The engineered MSC of claim 16, wherein the engineered MSC is a human bone-marrow derived MSC.

18. The engineered MSC of claim 16, wherein the engineered MSC is a human cell, wherein the human cell comprises a cellular marker phenotype comprising CD105+, CD73+, CD90+, CD45-, CD34-, CD14-; a cellular marker phenotype comprising CD105+, CD73+, CD90+, CD11b-, CD79α-; a cellular marker phenotype comprising CD105+, CD73+, CD90+, CD19-, HLA class II-; or a cellular marker phenotype comprising CD73+, CD90+, CD105+, and CD166+, CD11b-, CD14-, CD19-, CD34-, CD45-, and HLA-DR-.

19. The engineered MSC of claim 16, wherein the exogenous polynucleotide sequence comprises one or more viral vector polynucleotide sequences.

20. The engineered MSC of claim 19, wherein the one or more viral vector polynucleotide sequences comprises lentiviral vector polynucleotide sequences.

21. The engineered MSC of claim 20, wherein the exogenous polynucleotide sequence comprises SEQ ID NO: 145.

22. The engineered MSC of claim 16, wherein the exogenous polynucleotide sequence comprises is capable of expressing a higher ratio of secreted IL-12p70 relative to secreted IL-21.

23. A population of cells, wherein the population of cells comprises one or more engineered MSCs of claim 16.

24. A pharmaceutical composition comprising a pharmaceutically acceptable carrier and one or more engineered MSCs of claim 16.

25. A pharmaceutical composition comprising the population of cells of claim 23 and a pharmaceutically acceptable carrier.

26. A pharmaceutical composition comprising a pharmaceutically acceptable carrier and one or more engineered MSCs of claim 17.

27. A pharmaceutical composition comprising a pharmaceutically acceptable carrier and one or more engineered MSCs of claim 18.

28. A pharmaceutical composition comprising a pharmaceutically acceptable carrier and one or more engineered MSCs of claim 19.

29. A pharmaceutical composition comprising a pharmaceutically acceptable carrier and one or more engineered MSCs of claim 20.

30. A pharmaceutical composition comprising a pharmaceutically acceptable carrier and one or more engineered MSCs of claim 21.

31. A pharmaceutical composition comprising a pharmaceutically acceptable carrier and one or more engineered MSCs of claim 22.

* * * * *

SEQUENCE LISTING

<160> NUMBER OF SEQ ID NOS: 145

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 1
agagggtata taatggaagc tcgacttcca g                                31

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaatttcc ggggactttc cgggaatttc cggggacttt ccgggaattt cc         52

<210> SEQ ID NO 3
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caccagacag tgacgtcagc tgccagatcc catggccgtc atactgtgac gtctttcaga   60
caccccattg acgtcaatgg gagaa                                        85

<210> SEQ ID NO 4
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggaggaaaaa ctgtttcata cagaaggcgt ggaggaaaaa ctgtttcata cagaaggcgt   60
ggaggaaaaa ctgtttcata cagaaggcgt                                   90

<210> SEQ ID NO 5
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggatgtcca tattaggaca tctaggatgt ccatattagg acatctagga tgtccatatt   60
aggacatcta ggatgtccat attaggacat ctaggatgtc catattagga catct       115

<210> SEQ ID NO 6
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
agtatgtcca tattaggaca tctaccatgt ccatattagg acatctacta tgtccatatt   60
aggacatctt gtatgtccat attaggacat ctaaaatgtc catattagga catct       115
```

```
<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgagtcagtg actcagtgag tcagtgactc agtgagtcag tgactcag                    48

<210> SEQ ID NO 8
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
agatcaaagg gtttaagatc aaagggctta agatcaaagg gtataagatc aaagggccta       60
agatcaaagg gactaagatc aaagggttta agatcaaagg gcttaagatc aaagggccta      120

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtctagacgt ctagacgtct agacgtctag ac                                     32

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagacacaga cacagacaca gaca                                              24

<210> SEQ ID NO 11
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggatccggta ctcgagatct gcgatctaag taagcttggc attccggtac tgttggtaaa       60
gccac                                                                   65

<210> SEQ ID NO 12
<211> LENGTH: 588
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 12

```
gttgacattg attattgact agtattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccattgacgc   540
aaatgggcgg taggcgtgta cggtgggagg tctatataag cagagctc              588
```

<210> SEQ ID NO 13
<211> LENGTH: 1179
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
ggctccggtg cccgtcagtg ggcagagcgc acatcgccca cagtcccga gaagttgggg    60
ggaggggtcg gcaattgaac cggtgcctag agaaggtggc gcggggtaaa ctgggaaagt   120
gatgccgtgt actggctccg ccttttccc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acggggtatg gcccttgcgt gccttgaatt   300
acttccacct ggctgcagta cgtgattctt gatcccgagc ttcgggttgg aagtgggtgg   360
gagagttcga ggccttgcgc ttaaggagcc ccttcgcctc gtgcttgagt tgaggcctgg   420
cctgggcgct ggggccgccg cgtgcgaatc tggtggcacc ttcgcgcctg tctcgctgct   480
ttcgataagt ctctagccat ttaaaatttt tgatgacctg ctgcgacgct ttttttctgg   540
caagatagtc ttgtaaatgc gggccaagat ctgcacactg gtatttcggt ttttggggcc   600
gcgggcggcg acggggcccg tgcgtcccag cgcacatgtt cggcgaggcg gggcctgcga   660
gcgcgaccac cgagaatcgg acgggggtag tctcaagctg gccggcctgc tctggtgcct   720
gtcctcgcgc cgccgtgtat cgccccgccc cgggcggcaa ggctggcccg gtcggcacca   780
gttgcgtgag cggaaagatg gccgcttccc ggtcctgctg cagggagctc aaaatggagg   840
acgcggcgct cgggagagcg gcgggtgag tcacccacac aaaggaaaag ggcctttccg   900
tcctcagccg tcgcttcatg tgactccacg gagtaccggg cgccgtccag cacctcgat    960
tagttctcga gcttttggag tacgtcgtct ttaggttggg gggagggtt ttatgcgatg   1020
gagtttcccc acactgagtg ggtggagact gaagttaggc cagcttggca cttgatgtaa   1080
ttctccttgg aattgccct ttttgagttt ggatcttggt tcattctcaa gcctcagaca   1140
gtggttcaaa gtttttttct tccatttcag gtgtcgtga                         1179
```

<210> SEQ ID NO 14
<211> LENGTH: 544
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 14
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gccttttcc cgagggtggg ggagaaccgt      180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctac                                                                  544

<210> SEQ ID NO 15
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tttatttagt ctccagaaaa agggggaat gaaagacccc acctgtaggt ttggcaagct       60
aggatcaagg ttaggaacag agagacagca gaatatgggc caaacaggat atctgtggta     120
agcagttcct gccccggctc agggccaaga acagttggaa cagcagaata tgggccaaac     180
aggatatctg tggtaagcag ttcctgcccc ggctcagggc caagaacaga tggtccccag     240
atgcggtccc gcccctcagca gtttctagag aaccatcaga tgtttccagg gtgccccaag    300
gacctgaaat gaccctgtgc cttatttgaa ctaaccaatc agttcgcttc tcgcttctgt     360
tcgcgcgctt ctgctccccg agctcaataa aagagccca                            399

<210> SEQ ID NO 16
<211> LENGTH: 511
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ggggttgggg ttgcgccttt tccaaggcag ccctgggttt gcgcagggac gcggctgctc      60
tgggcgtggt tccgggaaac gcagcggcgc cgaccctggg tctcgcacat tcttcacgtc     120
cgttcgcagc gtcacccgga tcttcgccgc taccttgtg ggcccccggg cgacgcttcc      180
tgctccgccc ctaagtcggg aaggttcctt gcggttcgcg gcgtgccgga cgtgacaaac     240
ggaagccgca cgtctcacta gtaccctcgc agacggacag cgccagggag caatggcagc     300
gcgccgaccg cgatgggctg tggccaatag cggctgctca gcggggcgcg ccgagagcag     360
cggccgggaa ggggcggtgc gggaggcggg gtgtggggcg gtagtgtggg ccctgttcct     420 gcccgcgcg tgttccgcat tctgcaagcc tccgagcgc acgtcggcag tcggctccct      480
cgttgaccga atcaccgacc tctctccca g                                    511
```

<210> SEQ ID NO 17
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gtaacgccat tttgcaaggc atggaaaaat accaaaccaa gaatagagaa gttcagatca      60
agggcgggta catgaaaata gctaacgttg gccaaacag  gatatctgcg gtgagcagtt     120
tcggccccgg cccggggcca agaacagatg gtcaccgcag tttcggcccc ggcccgaggc     180
caagaacaga tggtccccag atatggccca accctcagca gtttcttaag acccatcaga    240
tgtttccagg ctcccccaag gacctgaaat gaccctgcgc cttatttgaa ttaaccaatc    300
agcctgcttc tcgcttctgt tcgcgcgctt ctgcttcccg agctctataa aagagctcac    360 aaccccctcac tcggcgcgcc agtcctccga cagactgagt cgcccggg                 408
```

<210> SEQ ID NO 18
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
ctgtggaatg tgtgtcagtt agggtgtgga aagtccccag gctccccagc aggcagaagt      60
atgcaaagca tgcatctcaa ttagtcagca accaggtgtg gaaagtcccc aggctcccca    120
gcaggcagaa gtatgcaaag catgcatctc aattagtcag caaccatagt cccgcccta    180 actccgccca tcccgcccct aactccgccc agttccgccc attctccgcc ccatggctga    240
ctaatttttt ttatttatgc agaggccgag gccgcctctg cctctgagct attccagaag    300
tagtgaggag gcttttttgg aggcctaggc ttttgcaaaa agct                       344
```

<210> SEQ ID NO 19
<211> LENGTH: 1229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gcgccgggtt ttggcgcctc ccgcgggcgc cccctcctc  acggcgagcg ctgccacgtc      60
agacgaaggg cgcaggagcg ttcctgatcc ttccgcccgg acgctcagga cagcggcccg    120
ctgctcataa gactcggcct tagaaccca  gtatcagcag aaggacattt taggacggga    180
cttgggtgac tctagggcac tggttttctt tccagagagc ggaacaggcg aggaaaagta    240
gtcccttctc ggcgattctg cggagggatc tccgtggggc ggtgaacgcc gatgattata    300
taaggacgcg ccgggtgtgg cacagctagt tccgtcgcag ccgggatttg ggtcgcggtt    360
cttgtttgtg gatcgctgtg atcgtcactt ggtgagttgc gggctgctgg gctgccgggg    420
gctttcgtgg ccgccgggcc gctcggtggg acggaagcgt gtggagagac cgccaagggc    480
tgtagtctgg gtccgcgagc aaggttgccc tgaactgggg gttgggggga gcgcacaaaa    540
tggcggctgt tcccgagtct tgaatggaag acgcttgtaa ggcgggctgt gaggtcgttg    600
aaacaaggtg gggggcatgg tgggcggcaa gaacccaagg tcttgaggcc ttcgctaatg    660
```

```
cgggaaagct cttattcggg tgagatgggc tggggcacca tctggggacc ctgacgtgaa    720
gtttgtcact gactggagaa ctcgggtttg tcgtctggtt gcgggggcgg cagttatgcg    780
gtgccgttgg gcagtgcacc cgtacctttg ggagcgcgcg cctcgtcgtg tcgtgacgtc    840
acccgttctg ttggcttata atgcaggggt gggccacctg ccggtaggtg tgcggtaggc    900
ttttctccgt cgcaggacgc agggttcggg cctagggtag gctctcctga atcgacaggc    960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcaccttt gaaatgtaa tcatttgggt caatatgtaa    1140
ttttcagtgt tagactagta aagcttctgc aggtcgactc tagaaaattg tccgctaaat   1200
tctggccgtt tttggctttt ttgttagac                                     1229
```

<210> SEQ ID NO 20
<211> LENGTH: 1179
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccacct ggctgcagta cgtgattctt gatcccgagc ttcgggttgg aagtgggtgg    360
gagagttcga ggccttgcgc ttaaggagcc ccttcgcctc gtgcttgagt tgaggcctgg    420
cctgggcgct ggggccgccg cgtgcgaatc tggtggcacc ttcgcgcctg tctcgctgct    480
ttcgataagt ctctagccat ttaaaatttt tgatgacctg ctgcgacgct ttttttctgg    540
caagatagtc ttgtaaatgc gggccaagat ctgcacactg gtatttcggt ttttggggcc    600
gcgggcggcg acggggcccg tgcgtcccag cgcacatgtt cggcgaggcg gggcctgcga    660
gcgcggccac cgagaatcgg acgggggtag tctcaagctg gccggcctgc tctggtgcct    720
ggtctcgcgc cgccgtgtat cgccccgccc tgggcggcaa ggctggcccg gtcggcacca    780
gttgcgtgag cggaaagatg gccgcttccc ggccctgctg cagggagctc aaaatggagg    840
acgcggcgct cgggagagcg ggcgggtgag tcacccacac aaaggaaaag ggcctttccg    900
tcctcagccg tcgcttcatg tgactccacg gagtaccggg cgccgtccag gcacctcgat    960
tagttctcga gcttttggag tacgtcgtct ttaggttggg gggagggggtt ttatgcgatg   1020 gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gttttttttct tccatttcag gtgtcgtga                          1179
```

<210> SEQ ID NO 21
<211> LENGTH: 1718
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
actagttatt aatagtaatc aattacgggg tcattagttc atagcccata tatggagttc    60
cgcgttacat aacttacggt aaatggcccg cctggctgac cgcccaacga cccccgccca   120
ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc ccctattga cgtcaatgac ggtaaatggc ccgcctggca ttatgcccag   300
tacatgacct tatgggactt tcctacttgg cagtacatct acgtattagt catcgctatt   360
accatggtcg aggtgagccc cacgttctgc ttcactctcc ccatctcccc ccctccccca   420
cccccaattt tgtatttatt tattttttaa ttattttgtg cagcgatggg ggcgggggg    480
ggggggggc gcgcgccagg cggggcgggg cggggcgagg ggcggggcgg ggcgaggcgg   540
agaggtgcgg cggcagccaa tcagagcggc gcgctccgaa agtttccttt tatggcgagg   600
cggcggcggc ggcggcccta taaaagcga agcgcgcggc gggcggggag tcgctgcgac   660
gctgccttcg cccgtgccc cgctccgccg ccgcctcgcg ccgcccgccc cggctctgac   720
tgaccgcgtt actcccacag gtgagcgggc gggacggccc ttctcctccg gctgtaatt   780
agcgcttggt ttaatgacgg cttgtttctt ttctgtggct gcgtgaaagc cttgaggggc   840
tccgggaggg ccctttgtgc gggggagcg gctcggggg tgcgtgcgtg tgtgtgtgcg   900
tggggagcgc cgcgtgcggc tccgcgctgc ccggcggctg tgagcgctgc gggcgcggcg   960
cggggctttg tgcgctccgc agtgtgcgcg aggggagcgc ggccggggc ggtgccccgc  1020
ggtgcggggg gggctgcgag gggaacaaag gctgcgtgcg gggtgtgtgc gtggggggt  1080
gagcagggg tgtgggcgcg tcggtcgggc tgcaaccccc cctgcacccc cctccccgag  1140
ttgctgagca cggcccggct tcgggtgcgg ggctccgtac ggggcgtggc gcggggctcg  1200
ccgtgccggg cgggggtgg cggcaggtgg gggtgccggg cggggcgggg ccgcctcggg  1260
ccggggaggg ctcgggggag gggcgcgcg gcccccggag cgccggcggc tgtcgaggcg  1320
cggcgagccg cagccattgc cttttatggt aatcgtgcga gagggcgcag ggacttcctt  1380
tgtcccaaat ctgtgcggag ccgaaatctg ggaggcgccg ccgcacccc tctagcgggc  1440
gcggggcgaa gcggtgcggc gccggcagga aggaaatggg cggggagggc cttcgtgcgt  1500
cgccgcgccg ccgtcccctt ctccctctcc agcctcgggg ctgtccgcgg gggacggct  1560
gccttcgggg gggacggggc agggcggggt tcggcttctg gcgtgtgacc ggcggctcta  1620
gagcctctgc taaccatgtt catgccttct tcttttttcct acagctcctg gcaacgtgc  1680
tggttattgt gctgtctcat cattttggca aagaattc                           1718
```

<210> SEQ ID NO 22
<211> LENGTH: 212
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22

```
gggcagagcg cacatcgccc acagtccccg agaagttggg gggagggtc ggcaattgaa    60
ccggtgccta gagaaggtgg cgcggggtaa actgggaaag tgatgtcgtg tactggctcc   120
gccttttcc cgagggtggg ggagaaccgt atataagtgc agtagtcgcc gtgaacgttc   180
tttttcgcaa cgggtttgcc gccagaacac ag                                  212
```

<210> SEQ ID NO 23
<211> LENGTH: 2379
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

| | | | | | |
|---|---|---|---|---|---|
| ccactagttc | catgtcctta | tatggactca | tctttgccta | ttgcgacaca | cactcaatga | 60 |
| acacctacta | cgcgctgcaa | agagcccgc | aggcctgagg | tgcccccacc | tcaccactct | 120 |
| tcctattttt | gtgtaaaaat | ccagcttctt | gtcaccacct | ccaaggaggg | ggaggaggag | 180 |
| gaaggcaggt | tcctctaggc | tgagccgaat | gccctctgt | ggtcccacgc | cactgatcgc | 240 |
| tgcatgccca | ccacctgggt | acacacagtc | tgtgattccc | ggagcagaac | ggaccctgcc | 300 |
| cacccggtct | tgtgtgctac | tcagtggaca | gacccaaggc | aagaaagggt | gacaaggaca | 360 |
| gggtcttccc | aggctggctt | tgagttccta | gcaccgcccc | gccccaatc | ctctgtggca | 420 |
| catggagtct | tggtccccag | agtcccccag | cggcctccag | atggtctggg | agggcagttc | 480 |
| agctgtggct | gcgcatagca | gacatacaac | ggacggtggg | cccagaccca | ggctgtgtag | 540 |
| acccagcccc | ccgccccgc | agtgcctagg | tcacccacta | cgccccagg | cctggtcttg | 600 |
| gctgggcgtg | actgttaccc | tcaaaagcag | gcagctccag | ggtaaaaggt | gccctgccct | 660 |
| gtagagccca | ccttccttcc | cagggctgcg | gctgggtagg | tttgtagcct | tcatcacggg | 720 |
| ccacctccag | ccactggacc | gctggcccct | gccctgtcct | ggggagtgtg | gtcctgcgac | 780 |
| ttctaagtgg | ccgcaagcca | cctgactccc | caacaccac | actctacctc | tcaagcccag | 840 |
| gtctctccct | agtgacccac | ccagcacatt | tagctagctg | agccccacag | ccagaggtcc | 900 |
| tcaggccctg | ctttcagggc | agttgctctg | aagtcggcaa | ggggggagtga | ctgcctggcc | 960 |
| actccatgcc | ctccaagagc | tccttctgca | ggagcgtaca | gaacccaggg | ccctggcacc | 1020 |
| cgtgcagacc | ctggcccacc | ccacctgggc | gctcagtgcc | caagagatgt | ccacacctag | 1080 |
| gatgtcccgc | ggtgggtggg | gggcccgaga | gacgggcagg | ccggggcag | gcctggccat | 1140 |
| gcggggccga | accgggcact | gcccagcgtg | gggcgcgggg | gccacggcgc | gcgccccag | 1200 |
| ccccgggcc | cagcacccca | aggcggccaa | cgccaaaact | ctccctcctc | ctcttcctca | 1260 |
| atctcgctct | cgctctttt | tttttcgca | aaaggagggg | agaggggta | aaaaaatgct | 1320 |
| gcactgtgcg | gcgaagccgg | tgagtgagcg | gcgcggggcc | aatcagcgtg | cgccgttccg | 1380 |
| aaagttgcct | tttatggctc | gagcggccgc | ggcggcgccc | tataaaaccc | agcggcgcga | 1440 |
| cgcgccacca | ccgccgagac | cgcgtccgcc | ccgcgagcac | agagcctcgc | ctttgccgat | 1500 |
| ccgccgcccg | tccacacccg | ccgccaggta | agcccggcca | gccgaccggg | gcaggcggct | 1560 |
| cacggcccgg | ccgcaggcgg | ccgcggcccc | ttcgcccgtg | cagagccgcc | gtctgggccg | 1620 |
| cagcgggggg | cgcatggggg | gggaaccgga | ccgccgtggg | gggcgcggga | gaagcccctg | 1680 |
| ggcctccgga | gatgggggac | accccacgcc | agttcggagg | cgcgaggccg | cgctcgggag | 1740 |
| gcgcgctccg | ggggtgccgc | tctcggggcg | ggggcaaccg | gcggggtctt | tgtctgagcc | 1800 |
| gggctcttgc | caatggggat | cgcagggtgg | gcgcggcgga | gccccgcca | ggcccggtgg | 1860 |
| gggctggggc | gccattgcgc | gtgcgcgctg | gtcctttggg | cgctaactgc | gtgcgcgctg | 1920 |
| ggaattggcg | ctaattgcgc | gtgcgcgctg | ggactcaagg | cgctaactgc | gcgtgcgttc | 1980 |
| tggggcccgg | ggtgccgcgg | cctggctgg | ggcgaaggcg | ggctcggccg | gaaggggtgg | 2040 |
| ggtcgccgcg | gctcccgggc | gcttgcgcgc | acttcctgcc | cgagccgctg | gccgcccgag | 2100 |

```
ggtgtggccg ctgcgtgcgc gcgcgccgac ccggcgctgt ttgaaccggg cggaggcggg    2160
gctggcgccc ggttgggagg gggttggggc ctggcttcct gccgcgcgcc gcggggacgc    2220
ctccgaccag tgtttgcctt ttatggtaat aacgcggccg gcccggcttc ctttgtcccc    2280
aatctgggcg cgcgccggcg cccctggcg gcctaaggac tcggcgcgcc ggaagtggcc    2340
agggcggggg cgacctcggc tcacagcgcg cccggctat                          2379
```

<210> SEQ ID NO 24
<211> LENGTH: 529
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gttgatttcc ttcatccctg gcacacgtcc aggcagtgtc gaatccatct ctgctacagg     60
ggaaaacaaa taacatttga gtccagtgga gaccgggagc agaagtaaag ggaagtgata    120 accccagag cccggaagcc tctggaggct gagacctcgc cccccttgcg tgatagggcc     180
tacggagcca catgaccaag gcactgtcgc ctccgcacgt gtgagagtgc agggccccaa    240
gatggctgcc aggcctcgag gcctgactct tctatgtcac ttccgtaccg gcgagaaagg    300
cgggccctcc agccaatgag gctgcggggc gggccttcac cttgataggc actcgagtta    360
tccaatggtg cctgcgggcc ggagcgacta ggaactaacg tcatgccgag ttgctgagcg    420
ccggcaggcg gggccggggc ggccaaacca atgcgatggc cggggcggag tcgggcgctc    480
tataagttgt cgataggcgg gcactccgcc ctagtttcta aggaccatg              529
```

<210> SEQ ID NO 25
<211> LENGTH: 794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
agttccccaa ctttcccgcc tctcagcctt tgaaagaaag aaaggggagg gggcaggccg     60
cgtgcagtcg cgagcggtgc tgggctccgg ctccaattcc ccatctcagt cgctcccaaa   120
gtccttctgt ttcatccaag cgtgtaaggg tccccgtcct tgactcccta gtgtcctgct   180
gcccacagtc cagtcctggg aaccagcacc gatcacctcc catcgggcca atctcagtcc    240
cttcccccct acgtcgggc ccacacgctc ggtgcgtgcc cagttgaacc aggcggctgc    300
ggaaaaaaaa agcggggag aaagtagggc ccggctacta gcggttttac gggcgcacgt    360
agctcaggcc tcaagacctt gggctgggac tggctgagcc tggcgggagg cggggtccga    420
gtcaccgcct gccgccgcgc ccccggtttc tataaattga gccgcagcc tcccgcttcg     480 ctctctgctc ctcctgttcg acagtcagcc gcatcttctt ttgcgtcgcc aggtgaagac    540
gggcggagag aaacccggga ggctaggac ggcctgaagg cggcagggggc gggcgcaggc     600 cggatgtgtt cgcgccgctg cggggtgggc ccggcggcc tccgcattgc aggggcgggc     660
ggaggacgtg atgcggcgcg ggctgggcat ggaggcctgg tgggggaggg gaggggaggc    720
gtgggtgtcg gccggggcca ctaggcgctc actgttctct ccctccgcgc agccgagcca    780
catcgctgag acac                                                      794
```

<210> SEQ ID NO 26
<211> LENGTH: 532
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
agtgcggtta ccagcggaaa tgcctcgggg tcagaagtcg caggagagat agacagctgc     60
tgaaccaatg ggaccagcgg atggggcgga tgttatctac cattggtgaa cgttagaaac    120
gaatagcagc caatgaatca gctgggggg cggagcagtg acgtttattg cggaggggc     180 cgcttcgaat cggcggcggc cagcttggtg gcctgggcca atgaacggcc tccaacgagc    240
agggccttca ccaatcggcg gcctccacga cggggctggg ggagggtata taagccgagt    300
aggcgacggt gaggtcgacg ccggccaaga cagcacagac agattgacct attgggtgt     360 ttcgcgagtg tgagggggaa gcgccgcggc ctgtatttct agacctgccc ttcgcctggt    420
tcgtggcgcc ttgtgacccc gggccccctgc cgcctgcaag tcggaaattg cgctgtgctc    480
ctgtgctacg gcctgtggct ggactgcctg ctgctgccca actggctggc ac            532
```

<210> SEQ ID NO 27
<211> LENGTH: 701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
tagtttcatc accaccgcca cccccccgcc ccccgccat ctgaaagggt tctaggggat      60
ttgcaacctc tctcgtgtgt ttcttctttc cgagaagcgc cgccacacga gaaagctggc    120
cgcgaaagtc gtgctggaat cacttccaac gaaaccccag gcatagatgg gaaagggtga    180
agaacacgtt gccatggcta ccgtttcccc ggtcacggaa taaacgctct ctaggatccg    240
gaagtagttc cgccgcgacc tctctaaaag gatggatgtg ttctctgctt acattcattg    300
gacgttttcc cttagaggcc aaggccgccc aggcaaaggg gcggtcccac gcgtgagggg    360
cccgcggagc catttgattg gagaaaagct gcaaaccctg accaatcgga aggagccacg    420
cttcgggcat cggtcaccgc acctggacag ctccgattgg tggacttccg cccccctca     480 cgaatcctca ttgggtgccg tgggtgcgtg gtgcggcgcg attggtgggt tcatgttcc    540 cgtccccgc ccgcgagaag tgggggtgaa aagcggcccg acctgcttgg ggtgtagtgg     600
gcggaccgcg cggctggagg tgtgaggatc cgaacccagg ggtgggggt ggaggcggct     660 cctgcgatcg aagggactt gagactcacc ggccgcacgt c                         701
```

<210> SEQ ID NO 28
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gggccgccca ctcccccttc ctctcagggt ccctgtcccc tccagtgaat cccagaagac     60
tctggagagt tctgagcagg gggcggcact ctggcctctg attggtccaa ggaaggctgg    120
ggggcaggac gggaggcgaa aaccctggaa tattcccgac ctggcagcct catcgagctc    180
```

```
ggtgattggc tcagaaggga aaaggcgggt ctccgtgacg acttataaaa gcccaggggc    240
aagcggtccg gataacggct agcctgagga gctgctgcga cagtccacta ccttttttcga   300 gagtgactcc cgttgtccca aggcttccca gagcgaacct gtgcggctgc aggcaccggc    360
gcgtcgagtt tccggcgtcc ggaaggaccg agctcttctc gcggatccag tgttccgttt    420 ccagcccca atctcagagc ggagccgaca gagagcaggg aaccc                     465
```

<210> SEQ ID NO 29
<211> LENGTH: 538
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gccccacccc cgtccgcgtt acaaccggga ggcccgctgg gtcctgcacc gtcaccctcc    60
tccctgtgac cgcccacctg atacccaaac aactttctcg cccctccagt ccccagctcg   120
ccgagcgctt gcggggagcc acccagcctc agtttcccca gccccgggcg gggcgagggg   180
cgatgacgtc atgccggcgc gcggcattgt ggggcgggggc gaggcgggggc gccgggggga   240 gcaacactga gacgccattt tcggcggcgg gagcggcgca ggcggccgag cgggactggc   300
tgggtcggct gggctgctgg tgcgaggagc cgcggggctg tgctcggcgg ccaaggggac   360
agcgcgtggg tggccgagga tgctgcgggg cggtagctcc ggcgcccctc gctggtgact   420
gctgcgccgt gcctcacaca gccgaggcgg gctcggcgca cagtcgctgc tccgcgctcg   480
cgcccggcgg cgctccaggt gctgacagcg cgagagagcg cggcctcagg agcaacac    538
```

<210> SEQ ID NO 30
<211> LENGTH: 1091
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ttccagagct ttcgaggaag gtttcttcaa ctcaaattca tccgcctgat aattttctta    60
tattttccta aagaaggaag agaagcgcat agaggagaag ggaaataatt ttttaggagc   120
ctttcttacg gctatgagga attttggggct cagttgaaaa gcctaaactg cctctcggga   180
ggttgggcgc ggcgaactac tttcagcggg gcacggagac ggcgtctacg tgaggggtga   240
taagtgacgc aacactcgtt gcataaattt gcgctccgcc agcccggagc atttaggggc   300 ggttggctttt gttgggtgag cttgtttgtg tccctgtggg tggacgtggt tggtgattgg   360
caggatcctg gtatccgcta acaggtactg gcccacagcc gtaaagacct gcggggcgt    420 gagagggggg aatgggtgag gtcaagctgg aggcttcttg ggttgggtg ggccgctgag   480 gggaggggag ggcgaggtga cgcgacaccc ggcctttctg ggagagtggg ccttgttgac   540 ctaaggggggg cgagggcagt tggcacgcgc acgcgccgac agaaactaac agacattaac   600
caacagcgat tccgtcgcgt ttacttggga ggaaggcgga aaagaggtag tttgtgtggc   660
ttctggaaac cctaaatttg gaatcccagt atgagaatgg tgtcccttct tgtgtttcaa   720
tgggattttt acttcgcgag tcttgtgggt ttggttttgt tttcagtttg cctaacaccg   780
tgcttaggtt tgaggcagat tggagttcgg tcgggggagt ttgaatatcc ggaacagtta   840
gtggggaaag ctgtggacgc ttggtaagag agcgctctgg attttccgct gttgacgttg   900
```

```
aaaccttgaa tgacgaattt cgtattaagt gacttagcct tgtaaaattg aggggaggct    960
tgcggaatat taacgtattt aaggcatttt gaaggaatag ttgctaattt tgaagaatat   1020
taggtgtaaa agcaagaaat acaatgatcc tgaggtgaca cgcttatgtt ttacttttaa   1080
actaggtcac c                                                        1091

<210> SEQ ID NO 31
<211> LENGTH: 66
<212> TYPE: DNA
<213> ORGANISM: Homo sapiens

<400> SEQUENCE: 31
atgtgtcacc agcagctcgt tatatcctgg tttagtttgg tgtttctcgc ttcacccctg     60
gtggca                                                                66

<210> SEQ ID NO 32
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atgtgccatc agcaactcgt catctcctgg ttctcccttg tgttcctcgc ttcccctctg     60
gtcgcc                                                                66

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgcaactgc tgtcatgtat cgcactcatc ctggcgctgg ta                        42

<210> SEQ ID NO 34
<211> LENGTH: 60
<212> TYPE: DNA
<213> ORGANISM: Homo sapiens

<400> SEQUENCE: 34
atgtatcgga tgcaactttt gagctgcatc gcattgtctc tggcgctggt gacaaattcc     60

<210> SEQ ID NO 35
<211> LENGTH: 45
<212> TYPE: DNA
<213> ORGANISM: Homo sapiens

<400> SEQUENCE: 35
atgaatctct tgctcatact tacgtttgtc gctgctgccg ttgcg                     45

<210> SEQ ID NO 36
<211> LENGTH: 51
<212> TYPE: DNA
<213> ORGANISM: Unknown
<220> FEATURE:
<223> OTHER INFORMATION: Description of Unknown:
      Gaussia Luciferase sequence
```

```
<400> SEQUENCE: 36
atgggcgtga aggtcttgtt tgcccttatc tgcatagctg ttgcggaggc g        51

<210> SEQ ID NO 37
<211> LENGTH: 72
<212> TYPE: DNA
<213> ORGANISM: Homo sapiens

<400> SEQUENCE: 37
atgccgatgg ggagccttca acctttggca acgctttatc ttctggggat gttggttgct    60
agttgccttg gg                                                        72

<210> SEQ ID NO 38
<211> LENGTH: 63
<212> TYPE: DNA
<213> ORGANISM: Mus sp.

<400> SEQUENCE: 38
atggaaactg acacgttgtt gctgtgggta ttgctcttgt gggtcccagg atctacgggc    60
gac                                                                  63

<210> SEQ ID NO 39
<211> LENGTH: 66
<212> TYPE: DNA
<213> ORGANISM: Homo sapiens

<400> SEQUENCE: 39
atggatatga gggttcccgc ccagcttttg gggctgcttt tgttgtggct tcgaggggct    60
cggtgt                                                               66

<210> SEQ ID NO 40
<211> LENGTH: 48
<212> TYPE: DNA
<213> ORGANISM: Unknown
<220> FEATURE:
<223> OTHER INFORMATION: Description of Unknown:
      VSV-G sequence

<400> SEQUENCE: 40
atgaagtgtc tgttgtacct ggcgtttctg ttcattggtg taaactgt              48

<210> SEQ ID NO 41
<211> LENGTH: 84
<212> TYPE: DNA
<213> ORGANISM: Homo sapiens

<400> SEQUENCE: 41
atgaatatca aggaagtcc gtggaagggt agtctcctgc tgctcctcgt atctaacctt    60
ctcctttgtc aatccgtggc accc                                           84

<210> SEQ ID NO 42
<211> LENGTH: 54
<212> TYPE: DNA
<213> ORGANISM: Homo sapiens

<400> SEQUENCE: 42
atgaaatggg taacattcat atcacttctc tttctgttca gctctgcgta ttct          54
```

```
<210> SEQ ID NO 43
<211> LENGTH: 57
<212> TYPE: DNA
<213> ORGANISM: Homo sapiens

<400> SEQUENCE: 43
atgacaaggc ttactgtttt ggctctcctc gctggactct tggcttcctc ccgagca      57

<210> SEQ ID NO 44
<211> LENGTH: 51
<212> TYPE: DNA
<213> ORGANISM: Homo sapiens

<400> SEQUENCE: 44
atgagggctt ggattttttt tctgctctgc cttgccggtc gagccctggc g            51

<210> SEQ ID NO 45
<211> LENGTH: 48
<212> TYPE: DNA
<213> ORGANISM: Homo sapiens

<400> SEQUENCE: 45
atgcctcttc tgcttttgct tcctcttttg tgggcaggtg ccctcgca                48

<210> SEQ ID NO 46
<211> LENGTH: 87
<212> TYPE: DNA
<213> ORGANISM: Homo sapiens

<400> SEQUENCE: 46
atgaactctt tctcaacctc tgcgtttggt ccggtcgctt tctcccttgg gctcctgctt   60
gtcttgccag cagcgtttcc tgcgcca                                       87

<210> SEQ ID NO 47
<211> LENGTH: 60
<212> TYPE: DNA
<213> ORGANISM: Homo sapiens

<400> SEQUENCE: 47
atgacaagta aactggcggt agccttgctc gcggcctttt tgatttccgc agcccttgt    60

<210> SEQ ID NO 48
<211> LENGTH: 69
<212> TYPE: DNA
<213> ORGANISM: Homo sapiens

<400> SEQUENCE: 48
atgaaggtaa gtgcagcgtt gctttgcctt ctcctcattg cagcgacctt tattcctcaa   60
gggctggcc                                                           69

<210> SEQ ID NO 49
<211> LENGTH: 78
<212> TYPE: DNA
<213> ORGANISM: Homo sapiens

<400> SEQUENCE: 49
atgggagcgg cagctagaac acttcgactt gcccttgggc tcttgctcct tgcaaccctc   60
cttagacctg ccgacgca                                                 78
```

```
<210> SEQ ID NO 50
<211> LENGTH: 63
<212> TYPE: DNA
<213> ORGANISM: Homo sapiens

<400> SEQUENCE: 50
atgtcaccgt tgttgcggag attgctgttg ccgcactttt tgcaactggc tcctgctcaa    60
gcc                                                                  63

<210> SEQ ID NO 51
<211> LENGTH: 63
<212> TYPE: DNA
<213> ORGANISM: Homo sapiens

<400> SEQUENCE: 51
atgaataacc tgctctgttg tgcgctcgtg ttcctggaca tttctataaa atggacaacg    60
caa                                                                  63

<210> SEQ ID NO 52
<211> LENGTH: 69
<212> TYPE: DNA
<213> ORGANISM: Homo sapiens

<400> SEQUENCE: 52
atgcaaatgt ctcctgccct tacctgtctc gtacttggtc ttgcgctcgt atttggagag    60
ggatcagcc                                                            69

<210> SEQ ID NO 53
<211> LENGTH: 102
<212> TYPE: DNA
<213> ORGANISM: Homo sapiens

<400> SEQUENCE: 53
atggcaaggg ctgcactcag tgctgccccg tctaatccca gattgcttcg agttgcattg    60
cttcttctgt tgctggttgc agctggtagg agagcagcgg gt                      102

<210> SEQ ID NO 54
<211> LENGTH: 63
<212> TYPE: DNA
<213> ORGANISM: Homo sapiens

<400> SEQUENCE: 54
atgaatgcaa aagtcgtggt cgtgctggtt ttggttctga cggcgttgtg tcttagtgat    60
ggg                                                                  63

<210> SEQ ID NO 55
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atggaacgca ttgtgatctg cctgatggtc atcttcctgg gcaccttagt gcacaagtcg    60
agcagc                                                               66

<210> SEQ ID NO 56
<211> LENGTH: 1626
<212> TYPE: DNA
<213> ORGANISM: Homo sapiens
```

<400> SEQUENCE: 56

```
atgtgccatc agcagcttgt catatcttgg ttttcacttg tattcctggc cagcccttttg      60
gttgcgatct gggagctcaa gaaggatgtg tacgttgtag agctggactg gtaccccgat     120
gctcccggtg agatggtcgt tttgacatgt gacactccag aagaggacgg tattacgtgg     180
actctggacc agtcctccga agttcttggt tctggtaaga ctctgactat ccaggtgaaa     240
gaatttgggg atgcgggaca atacacatgc cacaagggag cgaggtgtt gtctcatagt      300
ttgctgcttc tccacaagaa agaggatgga atctggagca ccgacatact caaggatcaa     360
aaggaaccca aaataagac atttctgcga tgtgaggcta agaactatag tggccgcttc      420
acttgttggt ggctgactac catcagcaca gatctcacgt tttcagtaaa aagtagtaga     480
ggttcaagtg atcctcaagg ggtaacgtgc ggtgctgcaa cactgtctgc tgaacgcgta     540
agaggagata ataaggagta cgagtattcc gtagaatgcc aagaggacag tgcttgtcct     600
gcggccgagg agtctctccc aatagaagtg atggtggacg cggtgcataa actgaaatat     660
gagaactaca caagcagttt ttttataaga gatatcatca agcccgatcc gccgaagaat     720
ttgcaactta aaccgcttaa aaactcacgc caggttgaag tatcctggga gtatccggat     780
acatggtcaa caccacacag ctattttttcc cttaccttct gtgtgcaggt ccaagggaag    840
agcaaaaggg agaagaagga cagggtattc actgataaaa cttccgcgac ggtcatctgc    900
cgaaaaaacg ctagtatatc tgtacgggcg caggataggg actatagttc ttcttggtct    960
gagtgggcct cagttccgtg ctctggggga ggaagtggag agggtccggc ggtggaagc     1020
gggggaggga gtcgcaactt gccagtggct acaccagatc caggcatgtt tccatgtctg    1080
catcattccc agaatctcct gagagcggtg tcaaatatgc tccaaaaagc gagacaaaca    1140
ctggaatttt acccgtgtac cagtgaggag attgatcacg aggacataac caaggacaag    1200
acctcaactg tagaagcgtg tttgccgctg gagttgacta agaatgagtc ctgcctcaat    1260
tccagagaaa cttcattcat tactaacggc agttgtcttg catcccggaa aacgtccttt    1320
atgatggccc tttgccttag ttcaatttac gaggatctta aaatgtatca agtggagttt    1380
aaaaccatga atgctaaact tcttatggac cccaaacgac aaattttttct ggatcagaat   1440
atgcttgccg tgatagacga actcatgcag gcgcttaatt ttaactccga aacagttcca    1500
caaaaatcta gccttgaaga acctgatttt tataaaacga agattaaact gtgtatcctg    1560
ctgcatgcct ttcgcatccg agctgtcaca atcgataggg ttatgtccta ccttaacgcg    1620
agctag                                                              1626
```

<210> SEQ ID NO 57
<211> LENGTH: 1623
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atgtgccatc agcaactcgt catctcctgg ttctcccttg tgttcctcgc ttccctctg       60
gtcgccattt gggaactgaa gaaggacgtc tacgtggtcg agctggattg gtaccggac     120
gccctggag aaatggtcgt gctgacttgc gatacgccag aagaggacgg cataacctgg      180
accctggatc agagctccga ggtgctcgga agcggaaaga ccctgaccat tcaagtcaag    240
gagttcggcg acgcgggcca gtacacttgc cacaagggtg gcgaagtgct gtcccactcc    300
```

```
ctgctgctgc tgcacaagaa agaggatgga atctggtcca ctgacatcct caaggaccaa      360
aaagaaccga agaacaagac cttcctccgc tgcgaagcca agaactacag cggtcggttc      420
acctgttggt ggctgacgac aatctccacc gacctgactt tctccgtgaa gtcgtcacgg      480
ggatcaagcg atcctcaggg cgtgacctgt ggagccgcca ctctgtccgc cgagagagtc      540
aggggagaca acaaggaata tgagtactcc gtggaatgcc aggaggacag cgcctgccct      600
gccgcggaag agtccctgcc tatcgaggtc atggtcgatg ccgtgcataa gctgaaatac      660
gagaactaca cttcctcctt ctttatccgc gacatcatca agcctgaccc ccccaagaac      720
ttgcagctga agccactcaa gaactcccgc caagtggaag tgtcttggga atatccagac      780
acttggagca ccccgcactc atacttctcg ctcactttct gtgtgcaagt gcagggaaag      840
tccaaacggg agaagaaaga ccgggtgttc accgacaaaa cctccgccac tgtgatttgt      900
cggaagaacg cgtcaatcag cgtccgggcg caggatagat actactcgtc ctcctggagc      960
gaatgggcca gcgtgccttg ttccggtggc ggatcaggcg gaggttcagg aggaggctcc     1020
ggaggaggtt cccggaacct ccctgtggca accccgacc ctggaatgtt cccgtgccta     1080
caccactccc aaaacctcct gagggctgtg tcgaacatgt gcagaaggc ccgccagacc     1140 cttgagttct accctgcac ctcggaagaa attgatcacg aggacatcac caaggacaag     1200
acctcgaccg tggaagcctg cctgccgctg gaactgacca gaacgaatc gtgtctgaac     1260 tcccgcgaga caagctttat cactaacggc agctgcctgg cgtcgagaaa gacctcattc     1320
atgatggcgc tctgtctttc ctcgatctac gaagatctga agatgtatca ggtcgagttc     1380
aagaccatga acgccaagct gctcatggac ccgaagcggc agatcttcct ggaccagaat     1440
atgctcgccg tgattgatga actgatgcag gccctgaatt caactccga gactgtgcct     1500 caaaagtcca gcctggaaga accggacttc tacaagacca agatcaagct gtgcatcctg     1560
ttgcacgctt tccgcattcg agccgtgacc attgaccgcg tgatgtccta cctgaacgcc     1620
agt                                                                    1623
```

<210> SEQ ID NO 58
<211> LENGTH: 1635
<212> TYPE: DNA
<213> ORGANISM: Mus sp.

<400> SEQUENCE: 58

```
atgtgtccac agaagctgac aataagttgg tttgccattg tcctcctggt gagcccactc       60
atggcaatgt gggaactcga aaaggatgtc tacgtggtag aagtagattg gactccagac      120
gcgccagggg agacagtgaa tttgacatgt gacacaccag aagaagatga cattacatgg      180
acatctgacc aacgccatgg cgtaataggg agtgggaaaa cactcacgat cacagttaaa      240
gagttcttgg atgctggtca atatacttgc cataaaggcg gcgagacact cagccactca      300
catttgcttt tgcataaaaa agagaatggc atttggagca ctgaaatact taagaacttt      360
aagaacaaga catttctcaa gtgtgaggcc cctaattaca gcggcaggtt cacgtgctca      420
tggctggtcc agcgcaacat ggacctcaag tttaacataa aatcttcttc ctcttcacct      480
gactccagag ctgttacttg cggcatggct ctctgagcg cagaaaaagt aacgttggat      540
caaagagact acgaaaagta ctctgtttct tgtcaagagg atgttacgtg cccgacggcc      600
gaagaaacgc ttccaattga actcgcgttg aagctcgcc aacaaacaa gtatgaaaac      660 tacagtacaa gcttctttat acgggatata attaaacccg atcccccaa gaacttgcaa      720 atgaaaccac ttaagaacag ccaggtggaa gtttcctggg agtatccaga ctcatggagt      780
```

```
actcctcaca gctattttc tctgaaattc tttgtaagga tacaacggaa gaaagagaag      840
atgaaagaga ccgaggaggg ttgtaatcag aagggagcgt ttctcgtgga gaaaacgtct      900
accgaagtcc aatgtaaagg tggcaatgtg tgcgtccaag ctcaggatag atactataat      960
tcaagttgct ccaagtgggc ctgtgttcca tgccgcgttc ggagcggggg aggtagcgga     1020
ggaggtagtg ggggtgggtc aggaggaggg agtcgagtta tcccggtgtc aggccccgca     1080
cgctgcttga gccagagtcg caacctcctt aagacaacag atgacatggt gaaaacagca     1140
cgcgaaaagc ttaaacacta ctcttgtacg gcggaggata ttgatcacga ggatattacc     1200
cgagaccaaa ctagcacttt gaaaacctgt ctgccccttg aacttcataa aaatgagagc     1260
tgtctggcta cacgagagac gtcaagtacg actaggggca gctgtctccc gccgcaaaag     1320
acaagcctca tgatgacgct ctgtttgggt tccatttacg aggacttgaa aatgtatcaa     1380
acggagttcc aggctataaa tgcggcgttg cagaaccata accatcaaca aattatactt     1440
gataaaggca tgttggtggc gattgatgaa ctcatgcaga gtctcaatca caacggggaa     1500
acgttgagac agaaaccccc agtcggtgaa gcggacccat atcgagtaaa aatgaagctc     1560
tgcattctgc ttcacgcatt cagcactaga gttgttacca tcaaccgggt aatgggatat     1620
ctctccagtg cgtag                                                      1635
```

<210> SEQ ID NO 59
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
atggaacgca ttgtgatctg cctgatggtc atcttcctgg gcaccttagt gcacaagtcg       60
agcagccagg gacaggacag gcacatgatt agaatgcgcc agctcatcga tatcgtggac      120
cagttgaaga actacgtgaa cgacctggtg cccgagttcc tgccggcccc cgaagatgtg      180
gaaaccaatt gcgaatggtc ggcatttttcc tgctttcaaa aggcacagct caagtccgct      240
aacaccggga acaacgaacg gatcatcaac gtgtccatca aaaagctgaa gcggaagcct      300
ccctccacca cgccggacg gaggcagaag cataggctga cttgcccgtc atgcgactcc      360
tacgagaaga agccgccgaa ggagttcctg gagcggttca gtcgctcct gcaaaagatg      420 attcatcagc acctgtcctc ccggactcat gggtctgagg attca                      465
```

<210> SEQ ID NO 60
<211> LENGTH: 2163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atgtgccatc agcaactcgt catctcctgg ttctcccttg tgttcctcgc ttcccctctg       60
gtcgccattt gggaactgaa gaaggacgtc tacgtggtcg agctggattg taccccggac      120
gcccctggag aaatggtcgt gctgacttgc gatacgccag aagaggacgg cataacctgg      180
accctggatc agagctccga ggtgctcgga agcggaaaga ccctgaccat tcaagtcaag      240
gagttcggcg acgcgggcca gtacacttgc cacaagggtg cgaagtgct gtcccactcc      300 ctgctgctgc tgcacaagaa agaggatgga atctggtcca ctgacatcct caaggaccaa      360
```

| | |
|---|---|
| aaagaaccga agaacaagac cttcctccgc tgcgaagcca agaactacag cggtcggttc | 420 |
| acctgttggt ggctgacgac aatctccacc gacctgactt tctccgtgaa gtcgtcacgg | 480 |
| ggatcaagcg atcctcaggg cgtgacctgt ggagccgcca ctctgtccgc cgagagagtc | 540 |
| aggggagaca caaggaata tgagtactcc gtggaatgcc aggaggacag cgcctgccct | 600 |
| gccgcggaag agtccctgcc tatcgaggtc atggtcgatg ccgtgcataa gctgaaatac | 660 |
| gagaactaca cttcctcctt ctttatccgc gacatcatca agcctgaccc cccaagaac | 720 |
| ttgcagctga agccactcaa gaactcccgc caagtggaag tgtcttggga atatccagac | 780 |
| acttggagca ccccgcactc atacttctcg ctcactttct gtgtgcaagt gcagggaaag | 840 |
| tccaaacggg agaagaaaga ccgggtgttc accgacaaaa cctccgccac tgtgatttgt | 900 |
| cggaagaacg cgtcaatcag cgtccgggcg caggatagat actactcgtc ctcctggagc | 960 |
| gaatgggcca gcgtgccttg ttccggtggc ggatcaggcg gaggttcagg aggaggctcc | 1020 |
| ggaggaggtt cccggaacct ccctgtggca accccgacc ctggaatgtt cccgtgccta | 1080 |
| caccactccc aaaacctcct gagggctgtg tcgaacatgt tgcagaaggc ccgccagacc | 1140 |
| cttgagttct accctgcac ctcggaagaa attgatcacg aggacatcac caaggacaag | 1200 |
| acctcgaccg tggaagcctg cctgccgctg aactgacca agaacgaatc gtgtctgaac | 1260 |
| tcccgcgaga caagctttat cactaacggc agctgcctgg cgtcgagaaa gacctcattc | 1320 |
| atgatggcgc tctgtctttc ctcgatctac gaagatctga agatgtatca ggtcgagttc | 1380 |
| aagaccatga acgccaagct gctcatggac ccgaagcggc agatcttcct ggaccagaat | 1440 |
| atgctcgccg tgattgatga actgatgcag gccctgaatt caactccga gactgtgcct | 1500 |
| caaaagtcca gcctggaaga accggacttc tacaagacca agatcaagct gtgcatcctg | 1560 |
| ttgcacgctt ccgcattccg agccgtgacc attgaccgcg tgatgtccta cctgaacgcc | 1620 |
| agtagacgga aacgcggaag cggagagggc agaggctcgc tgcttacatg cggggacgtg | 1680 |
| gaagagaacc ccggtccgat ggaacgcatt gtgatctgcc tgatggtcat cttcctgggc | 1740 |
| accttagtgc acaagtcgag cagccaggga caggacaggc acatgattag aatgcgccag | 1800 |
| ctcatcgata tcgtggacca gttgaagaac tacgtgaacg acctggtgcc cgagttcctg | 1860 |
| ccggcccccg aagatgtgga aaccaattgc gaatggtcgg catttttcctg ctttcaaaag | 1920 |
| gcacagctca gtccgctaa caccgggaac aacgaacgga tcatcaacgt gtccatcaaa | 1980 |
| aagctgaagc ggaagcctcc ctccaccaac gccggacgga ggcagaagca taggctgact | 2040 |
| tgcccgtcat gcgactccta cgagaagaag ccgccgaagg agttcctgga gcggttcaag | 2100 |
| tcgctcctgc aaaagatgat tcatcagcac ctgtcctccc ggactcatgg gtctgaggat | 2160 |
| tca | 2163 |

<210> SEQ ID NO 61
<211> LENGTH: 2103
<212> TYPE: DNA
<213> ORGANISM: Homo sapiens

<400> SEQUENCE: 61

| | |
|---|---|
| atgtgccatc agcagcttgt catatcttgg ttttcacttg tattcctggc cagcccttg | 60 |
| gttgcgatct gggagctcaa gaaggatgtg tacgttgtag agctggactg gtaccccgat | 120 |
| gctcccggtg agatggtcgt tttgacatgt gacactccag aagaggacgg tattacgtgg | 180 |
| actctggacc agtcctccga agttcttggt tctggtaaga ctctgactat ccaggtgaaa | 240 |
| gaatttgggg atgcgggaca atacacatgc cacaagggag gcgaggtgtt gtctcatagt | 300 |

```
ttgctgcttc tccacaagaa agaggatgga atctggagca ccgacatact caaggatcaa        360
aaggaaccca aaataagac atttctgcga tgtgaggcta agaactatag tggccgcttc         420
acttgttggt ggctgactac catcagcaca gatctcacgt tttcagtaaa aagtagtaga        480
ggttcaagtg atcctcaagg ggtaacgtgc ggtgctgcaa cactgtctgc tgaacgcgta        540
agaggagata ataaggagta cgagtattcc gtagaatgcc aagaggacag tgcttgtcct       600
gcggccgagg agtctctccc aatagaagtg atggtggacg cggtgcataa actgaaatat       660
gagaactaca caagcagttt ttttataaga gatatcatca agcccgatcc gccgaagaat       720
ttgcaactta aaccgcttaa aaactcacgc caggttgaag tatcctggga gtatccggat       780
acatggtcaa caccacacag ctatttttcc cttaccttct gtgtgcaggt ccaagggaag       840
agcaaaaggg agaagaagga cagggtattc actgataaaa cttccgcgac ggtcatctgc       900
cgaaaaaacg ctagtatatc tgtacgggcg caggataggt actatagttc ttcttggtct       960
gagtgggcct cagttccgtg ctctggggga ggaagtggag gagggtccgg cggtggaagc      1020
gggggaggga gtcgcaactt gccagtggct acaccagatc caggcatgtt tccatgtctg      1080
catcattccc agaatctcct gagagcggtg tcaaatatgc tccaaaaagc gagacaaaca      1140
ctggaatttt acccgtgtac cagtgaggag attgatcacg aggacataac caaggacaag      1200
acctcaactg tagaagcgtg tttgccgctg gagttgacta agaatgagtc ctgcctcaat      1260
tccagagaaa cttcattcat tactaacggc agttgtcttg catcccggaa aacgtccttt      1320
atgatggccc tttgccttag ttcaatttac gaggatctta aaatgtatca agtggagttt      1380
aaaaccatga atgctaaact tcttatggac cccaaacgac aaattttctt ggatcagaat      1440
atgcttgccg tgatagacga actcatgcag gcgcttaatt ttaactccga aacagttcca      1500
caaaaatcta gccttgaaga acctgatttt tataaaacga agattaaaact gtgtatcctg      1560 ctgcatgcct ttcgcatccg agctgtcaca atcgataggg ttatgtccta ccttaacgcg      1620
agccggcgca agaggggttc cggagaggga aggggtagtc tgctcacctg cggcgatgtt      1680
gaagaaaatc ctggtcccat ggcgcaaagt ctggctcttt cactcctgat cctggtcttg      1740
gccttcggga ttccgaggac ccaaggaagt gatggtggcg cccaagattg ttgccttaaa      1800
tacagccagc ggaaaatacc cgcgaaagtg gtcaggagtt atagaaaaca ggagccttcc      1860
ctgggttgta gtatccccgc catacttttc ctcccgagaa aacggagcca ggccgaactg      1920
tgcgctgacc ctaaggaact ttgggtgcaa caacttatgc aacacctgga taagacacct      1980
tctcctcaaa agccagctca gggctgccga aaagatagag gcgcctcaaa aaccggaaaa      2040
aagggcaaag gttctaaagg atgtaagcgg actgaacgct ctcaaacgcc taaagggccg      2100
tag                                                                     2103
```

<210> SEQ ID NO 62
<211> LENGTH: 2109
<212> TYPE: DNA
<213> ORGANISM: Mus sp.

<400> SEQUENCE: 62

```
atgtgtccac agaagctgac aataagttgg tttgccattg tcctcctggt gagcccactc         60
atggcaatgt gggaactcga aaaggatgtc tacgtggtag aagtagattg gactccagac       120
gcgccagggg agacagtgaa tttgacatgt gacacaccag aagaagatga cattacatgg       180
acatctgacc aacgccatgg cgtaataggg agtgggaaaa cactcacgat cacagttaaa       240
gagttcttgg atgctggtca atatacttgc cataaaggcg gcgagacact cagccactca       300
```

| | |
|---|---|
| catttgcttt tgcataaaaa agagaatggc atttggagca ctgaaatact taagaacttt | 360 |
| aagaacaaga catttctcaa gtgtgaggcc cctaattaca gcggcaggtt cacgtgctca | 420 |
| tggctggtcc agcgcaacat ggacctcaag tttaacataa aatcttcttc ctcttcacct | 480 |
| gactccagag ctgttacttg cggcatggct tctctgagcg cagaaaaagt aacgttggat | 540 |
| caaagagact acgaaaagta ctctgttcct tgtcaagagg atgttacgtg cccgacggcc | 600 |
| gaagaaacgc ttccaattga actcgcgttg gaagctcgcc aacaaaacaa gtatgaaaac | 660 |
| tacagtacaa gcttctttat acgggatata attaaacccg atcccccaa gaacttgcaa | 720 |
| atgaaaccac ttaagaacag ccaggtggaa gtttcctggg agtatccaga ctcatggagt | 780 |
| actcctcaca gctattttc tctgaaattc tttgtaagga tacaacggaa gaaagagaag | 840 |
| atgaaagaga ccgaggaggg ttgtaatcag aagggagcgt ttctcgtgga gaaaacgtct | 900 |
| accgaagtcc aatgtaaagg tggcaatgtg tgcgtccaag ctcaggatag atactataat | 960 |
| tcaagttgct ccaagtgggc ctgtgttcca tgccgcgttc ggagcggggg aggtagcgga | 1020 |
| ggaggtagtg ggggtgggtc aggaggaggg agtcgagtta tcccggtgtc aggccccgca | 1080 |
| cgctgcttga gccagagtcg caacctcctt aagacaacag atgacatggt gaaaacagca | 1140 |
| cgcgaaaagc ttaaacacta ctcttgtacg gcggaggata ttgatcacga ggatattacc | 1200 |
| cgagaccaaa ctagcacttt gaaaacctgt ctgccccttg aacttcataa aaatgagagc | 1260 |
| tgtctggcta cacgagagac gtcaagtacg actaggggca gctgtctccc gccgcaaaag | 1320 |
| acaagcctca tgatgacgct ctgtttgggt tccatttacg aggacttgaa aatgtatcaa | 1380 |
| acggagttcc aggctataaa tgcggcgttg cagaaccata accatcaaca aattatactt | 1440 |
| gataaaggca tgttggtggc gattgatgaa ctcatgcaga gtctcaatca caacggggaa | 1500 |
| acgttgagac agaaaccccc agtcggtgaa gcggacccat atcgagtaaa aatgaagctc | 1560 |
| tgcattctgc ttcacgcatt cagcactaga gttgttacca tcaaccgggt aatgggatat | 1620 |
| ctctccagtg cgcggcgcaa gaggggttcc ggagagggaa ggggtagtct gctcacctgc | 1680 |
| ggcgatgttg aagaaaatcc tggtcccatg gcgcaaatga tgacccttc cctgctgagt | 1740 |
| cttgtcctcg cgctctgcat cccgtggacg caggggtctg atgggggggg ccaagactgt | 1800 |
| tgcctgaagt attcacaaaa aaagatacccg tactctattg tcagagggta caggaagcaa | 1860 |
| gaaccctcct tgggttgccc tataccagca attcttttct ccccacgcaa gcattccaaa | 1920 |
| ccagaactgt gtgcgaaccc cgaggagggt tgggtacaga acttgatgcg aaggcttgac | 1980 |
| cagcccccag cccctggcaa gcagtcacct gggtgcagaa aaaacagagg tacttcaaag | 2040 |
| agcggcaaga aaggcaaagg gagtaaagga tgtaaaagaa cggagcagac ccagccttca | 2100 |
| cgaggctag | 2109 |

<210> SEQ ID NO 63
<211> LENGTH: 2109
<212> TYPE: DNA
<213> ORGANISM: Mus sp.

<400> SEQUENCE: 63

| | |
|---|---|
| atggcgcaaa tgatgaccct ttccctgctg agtcttgtcc tcgcgctctg catcccgtgg | 60 |
| acgcaggggt ctgatggggg gggccaagac tgttgcctga agtattcaca aaaaaagata | 120 |
| ccgtactcta ttgtcagagg gtacaggaag caagaaccct ccttgggttg ccctatacca | 180 |
| gcaattcttt tctccccacg caagcattcc aaaccagaac tgtgtgcgaa ccccgaggag | 240 |
| ggttgggtac agaacttgat gcgaaggctt gaccagcccc cagcccctgg caagcagtca | 300 |

```
cctgggtgca gaaaaaacag aggtacttca aagagcggca agaaaggcaa agggagtaaa        360
ggatgtaaaa gaacggagca gacccagcct tcacgaggcc ggcgcaagag gggttccgga        420
gagggaaggg gtagtctgct cacctgcggc gatgttgaag aaaatcctgg tcccatgtgt        480
ccacagaagc tgacaataag ttggtttgcc attgtcctcc tggtgagccc actcatggca        540
atgtgggaac tcgaaaagga tgtctacgtg gtagaagtag attggactcc agacgcgcca        600
ggggagacag tgaatttgac atgtgacaca ccagaagaag atgacattac atggacatct        660
gaccaacgcc atggcgtaat agggagtggg aaaacactca cgatcacagt taaagagttc        720
ttggatgctg gtcaatatac ttgccataaa ggcggcgaga cactcagcca ctcacatttg        780
ctttttgcata aaaagagaa tggcatttgg agcactgaaa tacttaagaa ctttaagaac        840
aagacatttc tcaagtgtga ggcccctaat tacagcggca ggttcacgtg ctcatggctg        900
gtccagcgca acatggacct caagtttaac ataaaatctt cttcctcttc acctgactcc        960
agagctgtta cttgcggcat ggcttctctg agcgcagaaa agtaacgtt ggatcaaaga       1020
gactacgaaa agtactctgt ttcttgtcaa gaggatgtta cgtgcccgac ggccgaagaa       1080
acgcttccaa ttgaactcgc gttggaagct cgccaacaaa acaagtatga aaactacagt       1140
acaagcttct ttatacggga tataattaaa cccgatcccc ccaagaactt gcaaatgaaa       1200
ccacttaaga acagccaggt ggaagttttcc tgggagtatc cagactcatg gagtactcct       1260
cacagctatt tttctctgaa attctttgta aggatacaac ggaagaaaga gaagatgaaa       1320
gagaccgagg agggttgtaa tcagaaggga gcgtttctcg tggagaaaac gtctaccgaa       1380
gtccaatgta aagtggcaa tgtgtgcgtc caagctcagg atagatacta taattcaagt       1440
tgctccaagt gggcctgtgt tccatgccgc gttcggagcg ggggaggtag cggaggaggt       1500
agtgggggtg ggtcaggagg agggagtcga gttatcccgg tgtcaggccc cgcacgctgc       1560
ttgagccaga gtcgcaacct ccttaagaca acagatgaca tggtgaaaac agcacgcgaa       1620
aagcttaaac actactcttg tacggcggag gatattgatc acgaggatat tacccgagac       1680
caaactagca ctttgaaaac ctgtctgccc cttgaacttc ataaaaatga gagctgtctg       1740
gctacacgag agacgtcaag tacgactagg ggcagctgtc tcccgccgca aaagacaagc       1800
ctcatgatga cgctctgttt gggttccatt tacgaggact tgaaaatgta tcaaacggag       1860
ttccaggcta taaatgcggc gttgcagaac cataaccatc aacaaattat acttgataaa       1920
ggcatgttgg tggcgattga tgaactcatg cagagtctca atcacaacgg ggaaacgttg       1980
agacagaaac ccccagtcgg tgaagcggac ccatatcgag taaaaatgaa gctctgcatt       2040
ctgcttcacg cattcagcac tagagttgtt accatcaacc gggtaatggg atatctctcc       2100
agtgcgtag                                                              2109
```

<210> SEQ ID NO 64
<211> LENGTH: 465
<212> TYPE: DNA
<213> ORGANISM: Mus sp.

<400> SEQUENCE: 64

```
atgtttcatg tgtccttcag gtacatattt ggtatcccac cacttatatt ggtgctcttg         60
cctgtaacca gctctgaatg tcatataaaa gacaaggagg gcaaagcata cgagtccgta        120
ttgatgatct caatcgatga acttgacaag atgacaggga ccgattctaa ttgtccaaat        180
aacgagccaa acttctttcg gaaacacgtg tgtgatgata caaagaagc tgcttttctt        240
aacagagctg ccagaaaact caagcagttc ctcaagatga atatatccga ggaatttaac        300
```

| | |
|---|---|
| gtgcatctcc tcacagtatc tcagggaact caaacccttg taaactgcac ttctaaggag | 360 |
| gagaagaatg tcaaagagca gaagaaaaat gatgcatgtt ttttgaaacg gctgttgagg | 420 |
| gagatcaaaa catgctggaa taaaatcctc aagggctcaa tttag | 465 |

<210> SEQ ID NO 65
<211> LENGTH: 1428
<212> TYPE: DNA
<213> ORGANISM: Homo sapiens

<400> SEQUENCE: 65

| | |
|---|---|
| atggaaacag acacattgct gctttgggta ttgttgctct gggtgcctgg atcaacagga | 60 |
| aactgggtaa acgtaatttc agatctgaag aagatcgagg accttattca atccatgcac | 120 |
| atcgatgcca ctctctacac cgaaagcgac gttcacccat cttgcaaggt gaccgctatg | 180 |
| aaatgtgaat tgttggaact tcaggtaatt tctctggaga gcggcgatgc ctcaatacat | 240 |
| gacaccgttg aaaatcttat catccttgct aatgattcac tctctagtaa tgggaacgta | 300 |
| acagagagcg ggtgtaagga gtgtgaagaa ctggaggaga aaacattaa ggaattttg | 360 |
| cagtcattcg tccatatagt gcaaatgttc ataaacactt ccagaagaaa gcgaggctct | 420 |
| ggggaggggc gaggctctct gctgacctgt ggggatgtag aagagaatcc aggtcccatg | 480 |
| gaccggctga ccagctcatt cctgcttctg attgtgccag cctacgtgct ctccatcaca | 540 |
| tgtcctcccc aatgagcgt cgagcatgct gacatctggg tgaagtcata ctccttgtac | 600 |
| agcagagaga gatacatttg taattccgga ttcaagcgca aggccggcac ctcctctctg | 660 |
| acagagtgcg tccttaacaa agcaaccaac gtagcacatt ggaccacacc atccttgaag | 720 |
| tgcatacgag aacctaaatc ttgcgataag actcatactt gtccaccttg tccagcccca | 780 |
| gaactgcttg gcggaccctc agtattttg ttcccaccaa agccaaaaga cacactcatg | 840 |
| atatccagaa ctcctgaggt gacctgtgtc gttgtagacg tttcccacga agatcctgaa | 900 |
| gtaaaattca actggtacgt ggatggggtc gaagtccata cgccaagac taaaccaagg | 960 |
| gaggaacagt ataactctac ttaccgagta gtttctgtgt tgaccgtgct gcaccaggac | 1020 |
| tggttgaacg gaaggagta caaatgcaag gtgagcaata agctctgcc cgcaccaatc | 1080 |
| gaaaagacaa tatctaaggc caaggggcag ccacgagagc cccaggtata cactgcca | 1140 |
| ccctcacgcg atgaattgac taagaaccag gtttccctga cctgtcttgt aaaaggtttc | 1200 |
| taccctccg acatagctgt tgagtgggaa agtaacgggc agccagagaa caattacaag | 1260 |
| acaactccac ccgttcttga tagcgatgga tcatttttc tgtattccaa actcactgtc | 1320 |
| gataaaagtc gctggcagca aggcaatgtt tttagctgct cagtcatgca cgaagcactg | 1380 |
| cataatcact acacacaaaa aagtttgtcc cttagccctg gtaagtag | 1428 |

<210> SEQ ID NO 66
<211> LENGTH: 1080
<212> TYPE: DNA
<213> ORGANISM: Homo sapiens

<400> SEQUENCE: 66

| | |
|---|---|
| atgtactcaa tgcagttggc ctcctgtgta acattgacct tggtcctctt ggtcaacagc | 60 |
| aattggatcg atgtacgcta cgacttggag aagattgagt cccttataca gagtatacac | 120 |
| atagatacaa ccttgtatac tgacagtgac ttccatccca gctgtaaagt gactgcaatg | 180 |
| aactgttttt tgttggagtt gcaagtaatt ctgcatgaat acagcaacat gaccctcaat | 240 |

```
gaaaccgtta ggaatgtcct ttatctcgca aattctactc tgagtagcaa taagaatgtt    300
gccgaaagcg gctgcaagga gtgcgaagaa ctggaggaaa aaactttcac cgagtttctc    360
cagagtttca tcagaattgt ccaaatgttc attaatacaa gtagtggtgg tgggagcggg    420
ggtggaggca gtgggggagg tgggagcgga ggtggagggt ccggagggg gagccttcaa    480 ggcactactt gtcctccacc cgtatccatc gagcacgccg atattcgagt taaaaattat    540
agtgttaata gcagagaacg atacgtctgc aactcagggt ttaagagaaa ggccggaact    600
tcaactctca tagaatgcgt gattaataag aatactaacg tcgcacattg gactactccc    660
agtctcaagt gcatacgcga tccatctctc gctcattact caccagtacc tacagtggtt    720
actcctaagg tgacctctca gcccgaatca ccatctccca gcgcaaaaga gcctgaggcc    780
tttctcccta aatcagacac tgctatgact acagaaacag ccataatgcc aggaagccgg    840
ctgacaccat ctcaaactac cagcgcaggc acaactggga ctggctccca caaaagctca    900
cgcgcaccaa gtctcgccgc aacaatgaca ttggagccta cagccagcac atctcttaga    960
atcacagaaa tttctcccca cagtagcaag atgaccaagg tggcaattag taccagcgtc   1020
cttcttgtag gagctggagt tgtgatggca ttttggcat ggtatatcaa aagcaggtag   1080

<210> SEQ ID NO 67
<211> LENGTH: 489
<212> TYPE: DNA
<213> ORGANISM: Mus sp.

<400> SEQUENCE: 67
atgaagatcc tcaagccata catgcgaaac actagtatta gctgttactt gtgttttctg     60
ctgaatagtc atttttttgac tgaagcagga atccatgtat ttatactcgg ttgtgtgtct    120
gtaggtctgc caaagactga ggctaattgg attgacgtgc gctatgatct tgaaaaaata    180
gagtccttga ttcaatcaat acacatcgat accactctct acaccgacag tgatttccat    240
ccttcctgca aggtaacagc tatgaattgc ttcctcctgg agctccaagt cattctccat    300
gagtactcca acatgacttt gaacgaaact gtaagaaacg tattgtatct ggctaatagc    360
accttgtcta gtaacaaaaa tgtggcagag agcggctgca aagaatgtga agaattggaa    420
gagaaaacat ttacagagtt cctgcaatcc tttattcgca tcgtccaaat gtttatcaat    480
acctcttag                                                            489

<210> SEQ ID NO 68
<211> LENGTH: 438
<212> TYPE: DNA
<213> ORGANISM: Mus sp.

<400> SEQUENCE: 68
atgtattcca tgcaacttgc cagttgtgta acccttactc tcgtcctgct cgttaattcc     60
gctggtgcta actggataga tgttcgatac gatctggaaa agattgagtc ccttatccaa    120
tccattcata tagataccac cctttatact gacagcgact ccatccttc ttgcaaggtg     180 accgctatga attgtttcct gctggaactc caagttattc tgcatgaata ctctaatatg    240
acacttaacg agaccgtaag aaatgttctc tatctcgcta atagtacttt gagctcaaat    300
aagaacgtgg ccgagtctgg gtgtaaggaa tgcgaagagc tggaagaaaa gacattcacc    360
gagtttctcc agtctttcat acggattgtg cagatgtttta tcaacacatc agattacaaa    420
gacgacgatg ataagtag                                                  438
```

```
<210> SEQ ID NO 69
<211> LENGTH: 579
<212> TYPE: DNA
<213> ORGANISM: Mus sp.

<400> SEQUENCE: 69
atggcagcca tgtctgagga ctcttgtgtg aactttaaag aaatgatgtt catagacaat      60
acactctact ttatacctga ggagaatgga gatttggaat ctgacaactt tggcaggctg     120
cattgcacta ccgcagttat ccgaaacatc aacgatcagg tactgtttgt tgataaaaga     180
caacctgtat tcgaggacat gaccgacata gatcagtctg cctcagagcc cagactagg     240 cttatcatct atatgtacaa ggacagcgaa gtacgaggcc tggctgttac actctcagtc     300
aaagactcta agatgagcac cctgtcatgc aagaacaaaa ttatcagttt tgaggagatg     360
gacccacctg aaaacataga tgacattcag tcagacctca tttttttttca aaagcgggta     420 ccaggacaca acaaaatgga atttgaatca tcactctacg aaggacattt ccttgcatgc     480
cagaaagagg atgacgcatt caaattgatc ctgaaaaaaa aggacgaaaa tggtgataaa     540
tcagtcatgt ttacattgac caatcttcac caaagttag                            579

<210> SEQ ID NO 70
<211> LENGTH: 579
<212> TYPE: DNA
<213> ORGANISM: Mus sp.

<400> SEQUENCE: 70
atggctgcaa tgtctgaaga tagctgtgtc aactttaagg agatgatgtt cattgataat      60
actttgtact ttatacctga agaaaatgga gaccttgagt cagacaactt cgggagactg     120
cactgcacaa ctgccgttat ccgaaacata aatgatcaag tattgttcgt ggacaaaaga     180
caaccagtct ttgaggatat gacagacatc gaccaatccg catctgaacc tcagactagg     240
ctgatcatct atatgtacgc cgactccgaa gtaagaggcc ttgctgtgac acttagtgtt     300
aaggatagta agatgagcac actgtcctgt aagaataaga ttatatcttt tgaagagatg     360
gaccctcccg agaacataga tgacatccag agcgacttga tcttctttca gaagcgagtg     420
ccaggccata caagatgga atttgaatca tctctttatg aaggccattt cctcgcatgt     480
caaaaggagg acgatgcctt caagctcatt ctgaaaaaaa aagacgagaa cggtgataag     540
agcgtgatgt tcactctgac aaatctgcac cagtcatag                            579

<210> SEQ ID NO 71
<211> LENGTH: 534
<212> TYPE: DNA
<213> ORGANISM: Homo sapiens

<400> SEQUENCE: 71
atgtatcgca tgcaactcct gtcctgcatt gctctgagct tggctttggt aaccaactca      60
tacttcggga aactggagag taaactctcc gtaatcagga atcttaatga ccaagtattg     120
tttattgacc agggcaaccg cccgttgttc gaggatatga ctgattctga ctgtcgggat     180
aacgctccga gaactatctt tatcatttca atgtacaagg acagccaacc gcggggtatg     240
gctgtgacaa tcagtgtcaa atgtgagaag atttccacgc tgtcctgcga aacaagata      300 atttcttcca agaaatgaa ccccctgac aatataaagg atacaaagag tgatatcatc     360 ttcttcaga ggtccgtgcc cggccacgat aataagatgc aatttgaaag ttcatcttat     420
```

```
gagggggtact ttttggcatg cgagaaagaa agggatctct tcaagttgat cctgaagaag    480
gaggacgaat tgggcgaccg ctccatcatg ttcacagtcc agaacgagga ctag           534
```

<210> SEQ ID NO 72
<211> LENGTH: 534
<212> TYPE: DNA
<213> ORGANISM: Homo sapiens

<400> SEQUENCE: 72

```
atgtaccgca tgcagctcct gagttgtatt gccctttccc tcgctctcgt taccaattct    60
tacttcggta agcttgcctc taaactctct gttattagga acttgaacga ccaagtcctt    120
ttcatagacc aagggaacag accactgttt gaagatatga cggatagcga ttgccgagat    180 aatgcccta ggacgatttt tatcattagt atgtatgcgg actctcaacc gaggggatg      240 gccgttacta taagtgtgaa atgcgagaaa atatcaacgc tcagttgtga aacaaaatc     300 ataagtttca aggagatgaa tccacctgat aacatcaaag acactaagtc tgatattata    360
tttttccaac gaagtgttcc gggacacgat aacaaaatgc aatttgagag ctcctcatac    420
gagggctact cctcgcgtg tgagaaagaa agggatttgt taagcttat cctcaagaaa      480 gaggacgagt tggggatcg gagcataatg tttaccgtac agaatgagga ctag            534
```

<210> SEQ ID NO 73
<211> LENGTH: 441
<212> TYPE: DNA
<213> ORGANISM: Mus sp.

<400> SEQUENCE: 73

```
atggagcgga cactcgtgtg tcttgtcgta atttttctcg ggacagtcgc acacaagtcc    60
tcaccccagg gtcctgatcg ccttctcata cgcctccgac atttgatcga cattgtagag    120
cagctcaaaa tttacgagaa tgacctcgat cccgagcttt tgagtgctcc ccaagacgtt    180
aagggtcatt gcgagcacgc agcttttgct tgcttccaga aggccaagtt gaaaccaagc    240
aaccctggta ataataagac tttcatcatc gacttggtcg cccaactccg aaggaggctg    300 cctgccggc gcggaggaaa aaaacaaaag catattgcaa agtgtccttc atgtgattca     360
tacgaaaagc ggactcccaa agagttcttg gaaaggttga atggcttct tcagaagatg     420 attcatcaac atttgtcata g                                              441
```

<210> SEQ ID NO 74
<211> LENGTH: 564
<212> TYPE: DNA
<213> ORGANISM: Homo sapiens

<400> SEQUENCE: 74

```
atgaccaaca atgccttttt gcaaattgcc ctgcttttgt gttttagcac taccgcattg    60
agcatgtcat ataacctcct cggcttcctt cagagatcat caaactttca gtgtcagaaa    120
ctgctttggc aacttaatgg caggctcgaa tattgtctga agatcggat gaatttcgac     180 attccagaag aaataaaaca gcttcaacaa ttccagaaag gacgccgc cctgactatt      240 tacgagatgc tccagaatat cttcgccatt tccggcagg acagctcatc cacggggtgg    300
aatgagacta ttgtagaaaa tcttctggct aatgtgtacc atcaaattaa tcacctcaaa    360
acggtgcttg aggaaaaact tgaaaaggaa gatttcacac ggggcaagtt gatgtcctcc    420
ctgcacctta acgatactca cggcaggatt cttcattact tgaaggctaa ggagtatagc    480
```

```
cattgcgcgt ggacaattgt acgggtagaa atactgcgaa acttttattt catcaaccgg    540
ctcactggat accttagaaa ttag                                            564

<210> SEQ ID NO 75
<211> LENGTH: 549
<212> TYPE: DNA
<213> ORGANISM: Mus sp.

<400> SEQUENCE: 75
atgaacaatc ggtggatact ccacgccgca tttctcctct gctttagcac gacggccctg     60
tccatcaact acaaacagct tcagttgcag gagcggacta cataaggaa gtgccaggaa    120 ctgctggaac agcttaatgg taaaattaat cttacatacc gagctgactt caaaattcct    180
atggaaatga ccgagaagat gcagaaatcc tacgcgcat cgccatcca ggaaatgctc     240 cagaacgtat ttctcgtgtt ccgcaataat ttctcttcta cgggttggaa cgaaaccatt    300
gttgttagac tgcttgacga actgcatcag caaaccgtgt tccttaaaac cgtgcttgag    360
gagaagcagg aggagcgcct gacttgggag atgtctagta ccgcacttca cttgaaatcc    420
tactactggc gcgttcagcg gtatctgaag ctgatgaagt ataactcata cgcctggatg    480
gtagtgcgcg cagagatctt cagaaacttt cttatcatcc ggcgactgac ccgaaacttt    540
cagaattag                                                             549

<210> SEQ ID NO 76
<211> LENGTH: 501
<212> TYPE: DNA
<213> ORGANISM: Homo sapiens

<400> SEQUENCE: 76
atgaagtaca ctagctatat attggccttc cagctttgca tcgtattggg tagcctcgga     60
tgctattgcc aagacccgta tgtcaaagaa gccgaaaatc tcaaaaagta tttcaatgcc    120
ggacactcag acgtcgcgga taacggtaca ctgtttcttg gcatcctgaa aaattggaag    180
gaagagagtg acagaaaaat aatgcagtca caaatagtgt cctttactt taagctgttc    240 aaaaatttca aggatgacca agtatccag aagagtgttg aaactatcaa agaggacatg    300
aatgtgaaat tctttaacag taataagaag aagcgcgatg acttcgagaa actcactaat    360
tacagcgtaa cggatcttaa cgtccaacgc aaggcaatcc acgagcttat acaggtaatg    420
gctgagctta gtcccgcagc caagacaggg aagagaaaaa ggtctcaaat gcttttccgg    480
ggccggcgag cttcacaata g                                               501

<210> SEQ ID NO 77
<211> LENGTH: 468
<212> TYPE: DNA
<213> ORGANISM: Mus sp.

<400> SEQUENCE: 77
atgaacgcta cgcattgcat cctcgcactc caattgttcc tcatggctgt gtcagggtgt     60
tactgtcacg gtactgtcat agaaagcctc gaatccctga taactatttt taacagtagc    120
ggtatagatg tagaagaaaa gtctctcttt cttgacatct ggaggaattg gcaaaaggat    180
ggagacatga agattctcca atctcagatt atatcatttt acttgaggct ttttgaggtt    240
ctgaaggata accaggcgat cagcaataat atcagcgtaa ttgaatctca ccttattaca    300
```

| | |
|---|---|
| acatttttct caaattccaa ggcaaagaaa gatgctttca tgtctatcgc gaaatttgag | 360 |
| gtgaacaatc ctcaggtaca aaggcaagcc tttaacgagc tgattagagt tgtacatcag | 420 |
| ttgttgcccg aaagtagtct tagaaaacgc aaacggagcc gatgctag | 468 |

<210> SEQ ID NO 78
<211> LENGTH: 570
<212> TYPE: DNA
<213> ORGANISM: Mus sp.

<400> SEQUENCE: 78

| | |
|---|---|
| atggcaaggt tgtgcgcttt tctcatggta ctggctgtgc tctcctattg gcctacttgt | 60 |
| tctctgggat gcgacttgcc acagacccac aatctgcgga ataagagggc tctgactctg | 120 |
| ctggtgcaaa tgagacggct ctctccactt agctgtttga agatagaaa ggatttcggg | 180 |
| ttcccccagg agaaggtgga tgcccagcag atcaagaagg cacaggctat ccccgtcctt | 240 |
| tccgagctga cccagcaaat tttgaacatc tttacaagta aggatagttc agctgcatgg | 300 |
| aataccacac ttttggattc tttttgtaac gatctgcatc agcagctgaa cgatctccag | 360 |
| ggatgcctga tgcagcaagt cggcgtgcaa gaatttccac tcacccagga ggacgctctg | 420 |
| ctcgcagtgc gaaagtattt tcaccgaatt accgtgtacc tccgggagaa aaagcattca | 480 |
| ccctgcgctt gggaagtagt cagggccgaa gtatggagag cccttagtag ctccgctaat | 540 |
| gtactgggcc ggttgcggga agagaaatag | 570 |

<210> SEQ ID NO 79
<211> LENGTH: 405
<212> TYPE: DNA
<213> ORGANISM: Homo sapiens

<400> SEQUENCE: 79

| | |
|---|---|
| atggcgcaaa gtctggctct ttcactcctg atcctggtct tggccttcgg gattccgagg | 60 |
| acccaaggaa gtgatggtgg cgcccaagat tgttgcctta atacagcca gcggaaaata | 120 |
| cccgcgaaag tggtcaggag ttatagaaaa caggagcctt ccctgggttg tagtatcccc | 180 |
| gccatacttt tcctcccgag aaaacggagc caggccgaac tgtgcgctga ccctaaggaa | 240 |
| ctttgggtgc aacaacttat gcaacacctg ataagacac cttctcctca aaagccagct | 300 |
| cagggctgcc gaaagatag aggcgcctca aaaaccggaa aaaagggcaa aggttctaaa | 360 |
| ggatgtaagc ggactgaacg ctctcaaacg cctaaagggc cgtag | 405 |

<210> SEQ ID NO 80
<211> LENGTH: 402
<212> TYPE: DNA
<213> ORGANISM: Mus sp.

<400> SEQUENCE: 80

| | |
|---|---|
| atggcgcaaa tgatgaccct ttccctgctg agtcttgtcc tcgcgctctg catcccgtgg | 60 |
| acgcaggggt ctgatggggg gggccaagac tgttgcctga agtattcaca aaaaaagata | 120 |
| ccgtactcta ttgtcagagg gtacaggaag caagaaccct ccttgggttg ccctatacca | 180 |
| gcaattcttt tctccccacg caagcattcc aaaccagaac tgtgtgcgaa ccccgaggag | 240 |
| ggttgggtac agaacttgat gcgaaggctt gaccagcccc cagcccctgg caagcagtca | 300 |
| cctgggtgca gaaaaacag aggtacttca aagagcggca gaaaggcaa agggagtaaa | 360 |
| ggatgtaaaa gaacggagca gacccagcct tcacgaggct ag | 402 |

```
<210> SEQ ID NO 81
<211> LENGTH: 309
<212> TYPE: DNA
<213> ORGANISM: Homo sapiens

<400> SEQUENCE: 81
atggcgcaaa gtctggctct ttcactcctg atcctggtct tggccttcgg gattccgagg      60
acccaaggaa gtgatggtgg cgcccaagat tgttgcctta aatacagcca gcggaaaata     120
cccgcgaaag tggtcaggag ttatagaaaa caggagcctt ccctgggttg tagtatcccc     180
gccatacttt tcctcccgag aaaacggagc caggccgaac tgtgcgctga ccctaaggaa     240
ctttgggtgc aacaacttat gcaacacctg gataagacac cttctcctca aaagccagct     300
cagggctag                                                              309

<210> SEQ ID NO 82
<211> LENGTH: 309
<212> TYPE: DNA
<213> ORGANISM: Mus sp.

<400> SEQUENCE: 82
atggcgcaaa tgatgaccct tccctgctg agtcttgtcc tcgcgctctg catcccgtgg       60
acgcaggggt ctgatggggg gggccaagac tgttgcctga agtattcaca aaaaaagata     120
ccgtactcta ttgtcagagg gtacaggaag caagaaccct ccttgggttg ccctatacca     180
gcaattcttt tctccccacg caagcattcc aaaccagaac tgtgtgcgaa ccccgaggag     240
ggttgggtac agaacttgat gcgaaggctt gaccagcccc cagcccctgg caagcagtca     300
cctgggtag                                                              309

<210> SEQ ID NO 83
<211> LENGTH: 327
<212> TYPE: DNA
<213> ORGANISM: Mus sp.

<400> SEQUENCE: 83
atggcacccc gcgtcacacc cttgcttgct ttttctctgc ttgtcctctg gaccttcccc      60
gctcctaccc ttggaggagc caatgatgcc gaggattgct gcctgagtgt tacacaaagg     120
ccaataccag ggaatatagt gaaggcattc cggtatctgc tcaatgaaga tgggtgcaga     180
gtccccgcag ttgtctttac aacattgcga ggttaccagc tttgtgctcc cccagaccag     240
ccttgggtag atcgcattat tcgccggttg aagaagagct cagcaaagaa taagggcaat     300
tccacacgga gaagccccgt ctcctag                                          327

<210> SEQ ID NO 84
<211> LENGTH: 381
<212> TYPE: DNA
<213> ORGANISM: Mus sp.

<400> SEQUENCE: 84
atgaaatcag cagtccttt cttgctcggg attattttc tggaacaatg tggagtgagg       60
ggaacactcg taataagaaa cgctcggtgc tcatgcatat caacatcacg gggcactatc     120
cactacaaat ccctgaagga tctgaagcag ttcgccccaa gcctaactg taacaagacc     180 gaaattatcg caactctcaa aaatggagat cagacttgtc ttgacccaga ttcagcaaat     240
gtcaagaagc tgatgaaaga gtgggaaaag aagatttcac aaaaaaaaaa gcaaaaacgc     300
```

```
ggcaagaaac atcaaaagaa catgaaaaac aggaaaccta agactcccca gtcaaggaga      360
agatcccgca agacaaccta g                                                381
```

<210> SEQ ID NO 85
<211> LENGTH: 303
<212> TYPE: DNA
<213> ORGANISM: Mus sp.

<400> SEQUENCE: 85

```
atgaacagaa aagttaccgc tatagcactt gctgccataa tatgggccac cgcagctcaa       60
gggttcctga tgttcaagca gggccgatgc ctctgcattg ccctggaat gaaggccgtg       120 aaaatggccg aaatagaaaa agctagtgtc atataccccct ctaacggttg cgataaagtc      180
gaggttatag tcacaatgaa agctcataaa cgccaacgct gcctcgaccc ccggtctaag      240
caggctaggc tcataatgca agcaatcgag aagaaaaact ttcttagacg gcaaaacatg      300
tag                                                                    303
```

<210> SEQ ID NO 86
<211> LENGTH: 297
<212> TYPE: DNA
<213> ORGANISM: Mus sp.

<400> SEQUENCE: 86

```
atgaacccat ctgccgccgt tatttctgt ctgatactcc ttgggctgag tggcacacaa       60 ggcataccccc tcgcccgcac agtccggtgt aattgtatac atattgacga cggccctgtt     120
agaatgcggg ccatcggtaa gctggagatt ataccagcaa gccttagttg tcccagggtt     180
gaaatcatag caactatgaa aaaaacgac gaacaaagat gtttgaatcc cgagagcaag     240
acaatcaaaa accttatgaa agcatttagt caaaaacgct ctaaacgcgc tccatag         297
```

<210> SEQ ID NO 87
<211> LENGTH: 297
<212> TYPE: DNA
<213> ORGANISM: Homo sapiens

<400> SEQUENCE: 87

```
atgaatcaga cggcaatcct tatatgctgc cttatattcc ttactctctc agggatacaa       60
ggggtaccac tttctcggac tgttcgctgc acttgcattt caatatctaa ccaacctgta     120
aatccgcgga gcctggaaaa attggagatt ataccctgctt ctcaattctg ccctcgggtg     180
gaaatcatcg ccactatgaa gaagaagggc gagaaaaggt gtctgaatcc agagtcaaag     240
gcaatcaaaa acctgctgaa agcggtgtca aggaacggt ccaagagatc accctag         297
```

<210> SEQ ID NO 88
<211> LENGTH: 534
<212> TYPE: DNA
<213> ORGANISM: Mus sp.

<400> SEQUENCE: 88

```
atgaacagga agtaacagc cattgcattg ctgccatca tctgggccac cgcagcacag        60
ggttttctga tgtttaagca agggcgctgt ctctgtatag gccaggcat gaaggccgtg      120 aagatggcag agattgagaa ggcatctgtg atttatcctt ctaacgggtg cgataaagtc     180
gaagttattg tgacaatgaa ggcacacaaa cgccaacggt gtttggaccc acgatctaaa     240
caggcaagat tgattatgca agccatcgag aaaaagaact ttctccgaag gcaaaatatg     300
atccctttgg ctcggacagt gcggtgtaac tgtattcaca tcgacgatgg gccagtacgg     360
```

```
atgagagcaa taggaaagct cgaaatcata cccgcctcat tgtcttgtcc cagggtggaa      420
ataatcgcca ctatgaaaaa gaacgatgaa cagaggtgtc tcaacccaga gagtaagact      480
atcaagaacc ttatgaaggc attcagtcag aagaggtcaa agcgagcacc atag            534
```

<210> SEQ ID NO 89
<211> LENGTH: 345
<212> TYPE: DNA
<213> ORGANISM: Homo sapiens

<400> SEQUENCE: 89

```
atgagacttc tcatattggc gcttctcggg atatgttctc ttacggcata catagttgag       60
ggggtgggat ctgaggttag cgataaacga acttgtgtta gtcttacaac acagaggctt      120
ccagtctcca ggataaaaac atatacgata actgagggat ctctcagagc ggtcatcttc      180
ataacgaaga ggggcctgaa ggtctgtgct gacccacaag cgacttgggt aagggacgtt      240
gtgcggagca tggacaggaa gagcaatact cgcaacaaca tgatccaaac caaacctacg      300
ggcacccaac agtcaaccaa tactgcggta acattgacgg ggtag                     345
```

<210> SEQ ID NO 90
<211> LENGTH: 345
<212> TYPE: DNA
<213> ORGANISM: Mus sp.

<400> SEQUENCE: 90

```
atgcgcctcc ttctgctgac ttttctgggt gtatgttgcc tgacaccctg ggtcgtagaa       60
ggagtaggaa ccgaggttct ggaagagtcc tcatgtgtaa acttgcagac acaacgactc      120
cccgtccaaa aaatcaagac ctatataatc tgggaggggg caatgcgggc cgtcattttc      180
gtgactaaac gaggtctcaa aatctgcgcc gaccccgagg ctaagtgggt gaaggcagcc      240
attaagaccg tggatgggag agccagcacc agaaagaaca tggccgaaac agtacctact      300
ggcgcacagc ggtcaacctc aactgctata accttgacag gatag                      345
```

<210> SEQ ID NO 91
<211> LENGTH: 513
<212> TYPE: DNA
<213> ORGANISM: Unknown
<220> FEATURE:
<223> OTHER INFORMATION: Description of Unknown:
      m_sCD40L #1 sequence

<400> SEQUENCE: 91

```
atggagactg acactctgct tctgtgggtg ttgctgctgt gggtgcctgg cagtacaggc       60
gatatgcaac gaggtgacga ggaccctcaa atcgccgccc atgtagtctc tgaagctaat      120
agcaacgctg catccgtctt gcagtgggca aagaaaggct actatactat gaagtccaac      180
ttggtaatgc ttgaaaacgg caagcagttg actgtcaaga gagggact ttattacgtc       240 tatacccaag tcacattctg tagcaatcga gaaccctcct cacagaggcc ttttatagtg      300
ggactctggc ttaaaccaag tagcggctct gagcgcatac tgttgaaagc cgcaaacaca      360
cacagctctt cccaactctg cgagcagcaa tccgtgcatc tcgtggagt atttgagctt      420 caagccggtg cctcagtgtt tgtgaacgtc actgaggcct cccaggtcat acatcgagtt      480
gggttcagct ccttcggctt gctcaagctc tag                                   513
```

<210> SEQ ID NO 92
<211> LENGTH: 588
<212> TYPE: DNA
<213> ORGANISM: Unknown
<220> FEATURE:
<223> OTHER INFORMATION: Description of Unknown:
      m_sCD40L #2 sequence

<400> SEQUENCE: 92

| | | | | | |
|---|---|---|---|---|---|
| atggaaactg | atacattgct | gctctgggtt | ttgctgctct | gggtgcctgg | gagtacaggc | 60 |
| gacatgagga | ggcagttcga | ggatctcgtt | aaggatatta | cccttaataa | ggaggagaag | 120 |
| aaagaaaact | cttttgagat | gcaacgaggg | gacgaagatc | ctcagatcgc | tgctcacgtg | 180 |
| gtctctgaag | ctaacagcaa | cgccgcttct | gtcctccagt | gggccaagaa | aggttattac | 240 |
| accatgaaat | caaaccttgt | aatgcttgaa | aacgggaaac | agcttacagt | gaagagggaa | 300 |
| ggtcttact | acgtctatac | ccaggtaacc | ttctgctcaa | acagagaacc | atcaagccag | 360 |
| aggccattca | tagtggggct | ctggctcaaa | ccttccagtg | gcagcgagag | aatcttgttg | 420 |
| aaagctgcta | atacacatag | tagtagccag | ctttgcgagc | aacagtcagt | ccacctcggg | 480 |
| ggggtgtttg | agttgcaagc | agggcctca | gtattcgtga | atgtcactga | ggcttcccag | 540 |
| gtaattcaca | gggtaggctt | tagttcattc | ggtttgctga | agcttag | | 588 |

<210> SEQ ID NO 93
<211> LENGTH: 849
<212> TYPE: DNA
<213> ORGANISM: Unknown
<220> FEATURE:
<223> OTHER INFORMATION: Description of Unknown:
      m_sCD40L #3 sequence

<400> SEQUENCE: 93

| | | | | | |
|---|---|---|---|---|---|
| atgcgaagaa | tgcagcttct | gctccttatt | gctctgagtc | tcgcccttgt | caccaactcc | 60 |
| ggggacagaa | tgaaacaaat | cgaggacaaa | attgaagaaa | tactgagtaa | aatatatcac | 120 |
| atcgaaaacg | aaattgcacg | cattaagaaa | ttgattggcg | aacgcaccag | tggcggctct | 180 |
| ggtggcaccg | gaggttcagg | cgggaccggg | ggctctgaca | agtcgaaga | ggaggttaac | 240 |
| cttcatgagg | actttgtgtt | catcaagaag | ctgaaacggt | gcaataaagg | agaaggttct | 300 |
| ttgagcctcc | ttaattgcga | agagatgcga | cgacagttcg | aggatctggt | taaggacatt | 360 |
| acacttaata | aggaagagaa | aaaggagaac | tctttcgaaa | tgcagcgcgg | cgatgaagat | 420 |
| ccccagatag | ccgcccatgt | cgtctctgag | gccaactcta | acgcagcatc | cgtcctccag | 480 |
| tgggctaaga | aaggatatta | tactatgaaa | agcaatttgg | tcatgctcga | aaacggtaaa | 540 |
| cagctcactg | ttaagagaga | aggcctctat | tacgtatata | ctcaagtaac | tttctgttct | 600 |
| aatagggaac | cctcctctca | aagacctttt | atcgtaggac | tctggttgaa | accaagtagc | 660 |
| ggtagtgaaa | ggattctgct | caaagcagct | aatactcact | ccagcagtca | actgtgcgaa | 720 |
| caacaaagcg | ttcacctcgg | gggcgtcttt | gaacttcagg | caggtgccag | tgttttcgtc | 780 |
| aacgtaacag | aagcatccca | ggtaattcat | cgagtagggt | tttctagctt | tggtttgctg | 840 |
| aagctgtag | | | | | | 849 |

<210> SEQ ID NO 94
<211> LENGTH: 2160
<212> TYPE: DNA
<213> ORGANISM: Unknown
<220> FEATURE:
<223> OTHER INFORMATION: Description of Unknown:
      anti-CD40_FGK4.5 sequence

<400> SEQUENCE: 94

```
atggaaactg atcgcctgtt gctctgggta cttcttctgt gggtgcctgg gtccactggt      60
gacactgtac ttacacaatc acccgctttg ccgtttctc ctggtgaacg ggtcacaatt      120
agttgccgag cttccgattc tgtatctact cttatgcatt ggtatcaaca aaaacctggt     180
cagcagccaa aattgctcat ttatcttgct agtcacttgg agtccggcgt acctgctcga     240
ttcagcggta gtgggtctgg cacagatttc actttgacca tagatcccgt ggaggccgat     300
gacactgcaa cctactattg ccagcaatcc tggaacgacc cttggacttt cggcggcggc     360
accaagctgg aactcaagcg agcagatgct gccccaaccg ttagtatatt cccaccctca     420
accgaacaac tcgccacagg aggcgctagt gtcgtgtgtc ttatgaacaa tttctatcca     480
cgagacatta gcgtcaagtg gaaaattgat gggacagaaa ggcgagatgg agttttggat     540
tcagtaacag accaggattc aaaggattct acctatagca tgagctccac cttgagcctg     600
accaaagctg attatgaatc tcataacctg tatacttgtg aagtggtgca taagacttct     660
agctcaccag tggttaaatc tttttaaccgc aacgaatgtc ggcgcaagag gggttccgga     720
gagggaaggg gtagtctgct cacctgcggc gatgttgaag aaaatcctgg tcccatggac     780
attcggctct ctttggtatt cctggtactt tttataaagg gggtgcaatg tgaagtccag     840
ctcgtggaaa gcggtggggg cctggttcag cccggtcgca gccttaaaact tagttgcgca     900
gcatccggat ttcatttttc tgactataac atggcctggg ttcgacaggc acccaaaaaa     960
gggctggagt gggtcgcaac tatcatatac gatggttccc ggacatacta tagagattca    1020
gtgaaggggc gctttacaat aagcaggac aatgctaagt ctaccttgta tcttcagatg     1080
gactccctga ggagcgaaga tacagcaaca tattattgtg ctacaaaccg ctggttgctg    1140
cttcattatt tcgactactg gggtcagggc gtcatggtaa ctgtatcaag cgccgagacc    1200
acagccctt ctgtatatcc attggcacca ggtactgctc tgaaatccaa ctcaatggta     1260
acccttggat gtctggttaa gggttatttt cccgagcccg tcacagttac ttggaactct    1320
ggggcccttt ctagcggagt ccataccttt cccgccgttt gcagagtgg tctgtacacc     1380
cttacctcaa gcgtcacagt tccatctagc acatggagct cccaggcagt aacttgtaat    1440
gtggcccatc cagcctcctc aactaaggta gataaaaaga tcgttcccag agaatgcaat    1500
ccatgtggat gcaccgggtc tgaggtcagc agtgtgttca ttttcccacc caagactaaa    1560
gatgtattga ctattactct tacacccaaa gtaacctgcg tggtggttga tattagtcaa    1620
aatgatcccg aggtacggtt ctcttggttt atcgacgacg tcgaagtaca tacagctcag    1680
acacacgctc ccgagaaaca aagcaattcc actcttagga gcgtgtccga gttgccaatc    1740
gtacataggg attggcttaa tggcaagacc tttaagtgta aggtcaattc agggcattc    1800
cccgcaccaa tagagaagag tataagcaaa cccgagggga cacccagagg tccacaggtc    1860
tatacaatgg ctccccccaa ggaagagatg acccaaagtc aagtctcaat tacatgtatg    1920
gtgaagggct tttatccacc cgacatatac actgagtgga agatgaatgg acagcccaa     1980
gagaattata aaacactcc ccctaccatg acaccgacg ggtcctattt tctttatagt     2040
aaattgaacg tgaaaaagga gacctggcaa caaggcaaca cttttcacctg ctccgttctt    2100
cacgagggcc tgcataatca tcataccgaa aagtctctca gtcattctcc aggtaagtag    2160
```

<210> SEQ ID NO 95
<211> LENGTH: 528
<212> TYPE: DNA
<213> ORGANISM: Homo sapiens

<400> SEQUENCE: 95

```
atggaaacag atacgttgct gttgtgggta cttctccttt gggtccctgg cagcacaggg      60
gacgagaata gtttcgaaat gcagaagggc gaccagaacc cacagatcgc ggctcacgtt     120
atatcagaag caagtagtaa gaccacttcc gtacttcagt gggctgaaaa aggatattac     180
accatgtcca acaatctcgt gacactggag aacggtaaac aacttacggt gaaacgacag     240
ggcctctatt acatctacgc tcaggtgaca ttctgctcaa ataggaggc ttctagtcaa      300
gcgcccttca tcgccagcct gtgcctcaaa tctcccggcc ggttcgaacg aatcctgttg     360
cgagcggcca atacccatag ctcagctaaa ccttgcggcc agcagagtat tcatcttggt     420
ggtgtgtttg aacttcagcc gggagcatct gtgttcgtca acgtaacgga ccctagccaa     480
gtgtctcatg ggacaggttt tacatccttc ggactcctca agttgtag                  528
```

<210> SEQ ID NO 96
<211> LENGTH: 540
<212> TYPE: DNA
<213> ORGANISM: Homo sapiens

<400> SEQUENCE: 96

```
atgacagttc tcgcgccagc ttggagtccc accacatact tgcttttgct tctgcttctg      60
tcctctggcc tgagtgggac ccaagattgt tcctttcaac attccccaat tagttctgat     120
tttgcagtga agattagaga gctctcagac tatctgctgc aagattatcc tgtcacagtc     180
gcttcaaacc tgcaagacga agagctctgc ggtgccttgt ggcggttggt cttggctcaa     240
agatggatgg agagactgaa accgtagca ggcagcaaga tgcagggtct cctggaaagg      300
gtgaacacgg aaatccattt tgtgaccaag tgcgcgttcc agccccccacc gagttgtctc    360
cggtttgttc aaacgaatat atcccggttg ctccaggaaa cctcagaaca actggtggct     420
ttgaaacccct ggatcacaag acaaaacttt agtcggtgcc tcgaactcca gtgccaacca    480
gattcttcta cacttccccc cccgtggtcc ccgcgcccgt ggaagcaac ggccccatag      540
```

<210> SEQ ID NO 97
<211> LENGTH: 876
<212> TYPE: DNA
<213> ORGANISM: Homo sapiens

<400> SEQUENCE: 97

```
atggcctgga gtcctctgtt tctgactctt ataactcact gtgccggcag ttgggctata      60
cccctcatg tacagaagtc tgtaaacaac gacatgattg taaccgacaa taatggcgca     120
gtgaaattcc cacaactgtg taagttctgt gatgtacggt ttagtacatg cgacaatcaa     180
aaaagctgta tgtctaactg ctctattaca tccatatgtg aaaaacctca ggaggtgtgt     240
gttgccgttt ggcgaaaaaa tgatgagaat atcacactgg agacagtatg tcatgaccct     300
aaactgccat accatgattt catactggag gacgccgcca gtcctaagtg cattatgaaa     360
gagaaaaaga aacccggtga acattctttt atgtgctctt gtagctctga cgagtgtaac     420
gacaacatta tattcagcga ggagtacaat acaagcaacc ccgatatacc acctcacgta     480
caaaaaagtg tcaacaacga tatgattgtt accgacaata acggagctgt taagtttcct     540
cagttgtgca agttctgcga tgtacgattc tctacctgcg acaaccaaaa gtcatgtatg     600
tctaactgtt ccataaccctc catctgcgag aagcccagg aagtctgcgt cgccgtgtgg      660
cggaaaaacg acgagaatat cactcttgaa accgtttgtc atgatcctaa actgccctat     720
cacgacttta ttctggaaga tgctgcttcc cctaagtgta tcatgaaaga aaagaagaaa     780
```

```
cctggggaga cattctttat gtgttcatgc tcctccgatg agtgtaacga caatatcatc    840
ttctctgagg aatacaacac ttctaaccct gattag                              876

<210> SEQ ID NO 98
<211> LENGTH: 2178
<212> TYPE: DNA
<213> ORGANISM: Homo sapiens

<400> SEQUENCE: 98
atggcctggt cccctctttt tctgaccctc atcacacact gtgcaggctc atgggctgag     60
accgtcttga cccagtcccc aggaactttg tctctgtctc tggtgaaag agctacccctt    120 agttgtcgag cctctcagtc ccttggttct agctatctcg cttggtacca gcaaaagcca    180
ggccaggccc cacgactgct gatctacgga gcatcttcac gggctcccgg cattcccgat    240
cgattttccg gatctggtag tggtacagat ttcacactga ccatatctcg cctggagccc    300
gaggactttg ctgtttatta ttgtcagcag tacgccgatt ctcctatcac ttttggacag    360
ggaacccgcc tggagattaa gcacacagta gcagctccat ccgtctttat ctttccacca    420
tcagatgaac agctcaagag tgggaccgca agtgtagtat gcctgctgaa caattttac    480 cctagagagg ccaaagtgca gtggaaggtg ataacgcccc tccagagtgg caatagtcaa    540
gaaagtgtta ctgagcaaga tagtaaggac tctacatact ctttgagttc tacttttgacc    600 ctgtcaaaag cagattatga aaacataag gtgtatgcat gtgaagttac acaccaaggg    660
ttgtcctctc cagttacaaa atctttaat agaggagagt gccgccgcaa acgcggtagt    720
ggagaaggtc gaggctcact cttgacctgt ggcgacgtgg aagaaaatcc cggtcctatg    780
gattggactt ggagggtatt ttgtcttttg gcagtaacac ctggagctca cccccaagta    840
cagctcgtcc aatctggtgc cgaggttaaa aagcctggaa gttcagtgaa ggtctcttgc    900
aaggcatctg gatacaccct ttcatctaac gtcatatcct gggtacggca gcccccagga    960
cagggacttg agtggatggg aggggtcatc cccatcgtgg acattgctaa ttacgctcag   1020
cgattcaaag gcgggttac tataactgcc gacgagtcta cctcaactac ctacatggag   1080
ttgtcctctc tccgctccga ggacactgct gtatattact gtgccagcac tctcgggttg   1140
gtgttggatg ccatggacta ttggggacaa ggaaccctgg tgacagttag ctccgcaagc   1200
actaaaggcc cttctgtttt tcccttggca ccttgtagta ggtctacctc tgagtctaca   1260
gcagcacttg gatgcttggt taaggactat tttcccgagc cagttacagt ctcttggaac   1320
agtggtgccc tcacaagtgg ggttcatacc ttccccgcag tcctccagag tagtggcctt   1380
tacagcctct catcagttgt gactgttcct agttcatcac tcggtactaa gacatataca   1440
tgtaacgtag accacaagcc aagcaacaca aaagtagaca aacgagtcga atctaagtat   1500
ggaccccctt gtccctcctg tcctgctccc gagttccttg ggggcccttc cgtgttcttg   1560
tttcctccca gcccaaggga taccctcatg atctcacgaa ccccagaggt aacatgtgtg   1620
gttgttgacg taagtcagga agatcccgaa gtgcaattta attggtacgt ggatggcgtc   1680
gaagtccata cgctaaaac aaaacccgga gaggaacaat tcaattccac atatcgggtg   1740
gtgagtgtat tgaccgttct tcaccaagat tggctgaacg gcaaggagta taagtgtaaa   1800
gtaagcaaca aggtctgcc aagtagcata gaaaaaacaa tatctaaagc taagggccaa   1860
ccaagggaac cacaagtata tacattgccc ccctctcagg aagagatgac aaagaatcaa   1920
gttagcctga cctgtttggt aaaggggttc tatccctcag atatagcagt cgagtgggaa   1980
tctaacggcc agcccgagaa taattataaa acaaccccc ctgtgttgga ctcagacggc   2040
```

| | |
|---|---|
| agcttctttc tctattcacg gctcactgtt gataagtccc gatggcagga ggggaatgtt | 2100 |
| ttcagctgta gcgtgatgca cgaagctctc cacaaccact atacacagaa aagtttgtct | 2160 |
| ttgtcccttg gaaaatag | 2178 |

<210> SEQ ID NO 99
<211> LENGTH: 1062
<212> TYPE: DNA
<213> ORGANISM: Homo sapiens

<400> SEQUENCE: 99

| | |
|---|---|
| atgagtacat cctttccaga gctggatctg gagaattttg agtatgacga cagtgccgaa | 60 |
| gcctgctacc tcggggacat agtcgcattc gggacaatct ttttgtctgt attttacgcc | 120 |
| ctggtgttta catttggcct ggttggaaat ctgttggtcg tactcgctct caccaattcc | 180 |
| cgaaaaccca aaagtataac agacatatac ctgttgaatc tggcactgag tgaccttttg | 240 |
| ttcgtcgcca cccttccttt ttggacacac taccttatca gtcacgaggg gcttcataat | 300 |
| gctatgtgca agctcactac tgccttcttc tttatcggat tcttcggggg tatctttttt | 360 |
| atcacagtta ttagcattga ccgatacctt gccatagtgc tcgcagccaa ctcaatgaac | 420 |
| aaccgcaccg tgcagcatgg agtgactatt tccttgggtg tgtgggccgc tgctatactt | 480 |
| gtcgccagcc ctcaattcat gtttaccaaa aggaaagaca atgagtgcct cggagattac | 540 |
| cctgaggtgt tgcaagaaat gtggcctgta cttcgaaata cgaagtgaa tatactcggc | 600 |
| tttgctcttc ctctgctcat catgtcattc tgttattttc gaataatcca acattgttc | 660 |
| agctgtaaga accgaaagaa agcccgcgcc gtacgcctga ttctgctcgt tgtgttcgcc | 720 |
| ttttttctgt tttggactcc ttacaacata atgatattcc tggagactct caaattctat | 780 |
| aacttttttc cctcctgtga tatgaaaagg gaccttagat tggctctcag tgtcactgaa | 840 |
| acagtagcct ttagccattg ttgtctcaac ccttcatat atgcatttgc aggggaaaag | 900 |
| ttccggcggt atctcggaca tttgtatcgg aagtgcttgg ccgtgttgtg tggtcatcct | 960 |
| gtccataccg gattctctcc tgagagtcaa cggagccgcc aagattcaat cctgtccagt | 1020 |
| ttcactcact atacttcaga gggggatggc agccttctgc tc | 1062 |

<210> SEQ ID NO 100
<211> LENGTH: 1458
<212> TYPE: DNA
<213> ORGANISM: Unknown
<220> FEATURE:
<223> OTHER INFORMATION: Description of Unknown:
      Kynureinase #1 sequence

<400> SEQUENCE: 100

| | |
|---|---|
| atggagaccg acactttgtt gctgtgggta cttttgttgt gggtcccagg atctaccggg | 60 |
| gatatggaac cctctcctct tgaactgcca gtagacgccg tgcgccgcat tgcagccgag | 120 |
| ttgaattgcg atccaacaga tgaacgcgtt gccctgaggc tcgacgaaga ggataaaattg | 180 |
| tcacatttca ggaactgctt ttacattcca aagatgaggg atcttccatc catagatctt | 240 |
| agcctcgtgt ccgaggatga cgatgccata tattttcttg gaacagtct tgggttgcag | 300 |
| ccaaaaatgg tacggacata tctcgaagag gagctggaca aatgggctaa atgggtgct | 360 |
| tacggccacg acgtgggaaa acgcccctgg atagttggcg acgaatctat cgtgagtctt | 420 |
| atgaaagata tagttggagc acatgagaaa gaaattgcac tgatgaatgc ccttactatc | 480 |
| aatctgcatc tcctcttgct ttcattcttt aagcccactc ctaaacgcca caaaatactt | 540 |

```
ttggaagcaa aagcctttcc aagcgaccac tacgctattg agtcacaaat acaactccat    600
ggacttgatg tggaaaagtc tatgcggatg gtaaaaccac gcgaaggcga ggagacccct    660
cgaatggagg acatacttga ggtcatcgaa gaagaaggag atagtatagc agttatcctt    720
ttcagcgggc tgcacttcta cacaggtcaa ctctttaaca ttccagctat tactaaggca    780
ggccacgcta aggatgcttc gtgggctttt gaccttgcac acgcagtagg aaacgtagag    840
ctccgcttgc acgattgggg cgttgatttc gcctgctggt gttcatataa gtatcttaac    900
tcaggagctg gtgggttggc aggcgcattc gtacacgaga acacgctca taccgtaaag    960 cctgcactgg tagggtggtt cggacacgat ctctctaccc gcttcaatat ggataataaa   1020
ctccagctta tacctggcgc caatggattc aggatctcaa atcctcctat tttgctcgtt   1080
tgcagtttgc acgcatctct tgaggtgttc cagcaggcta ccatgactgc actccgccgg   1140
aagtcaatcc ttttgaccgg atacttggag tatatgctga acattatca ctcaaaagat   1200 aacactgaga ataagggccc catagtaaac attatcactc catctcgggc tgaagagcgc   1260
ggctgccaac tcacattgac tttttccatt cccaagaagt cagtgttcaa agagttggag   1320
aaacgggggg ttgtatgtga taagcgggag ccagatggaa tccgcgttgc cccagtcccc   1380
ctctataatt cttttcacga tgtatacaag tttattagac tgctgacaag tatcttggac   1440
tcatctgagc gatcttag                                                 1458

<210> SEQ ID NO 101
<211> LENGTH: 1395
<212> TYPE: DNA
<213> ORGANISM: Unknown
<220> FEATURE:
<223> OTHER INFORMATION: Description of Unknown:
      Kynureinase #2 sequence

<400> SEQUENCE: 101
atggaaccct ctcctcttga actgccagta gacgccgtgc gccgcattgc agccgagttg     60
aattgcgatc aacagatga acgcgttgcc ctgaggctcg acgaagagga taaattgtca    120
catttcagga actgctttta cattccaaag atgagggatc ttccatccat agatcttagc    180
ctcgtgtccg aggatgacga tgccatatat tttcttggga cagtcttgg gttgcagcca    240 aaaatggtac ggacatatct cgaagaggag ctggacaaat gggctaaaat gggtgcttac    300
ggccacgacg tggaaaaacg cccctggata gttggcgacg aatctatcgt gagtcttatg    360
aaagatatag ttggagcaca tgagaaagaa attgcactga tgaatgccct tactatcaat    420
ctgcatctcc tcttgctttc attctttaag cccactccta acgccacaa aatacttttg    480 gaagcaaaag cctttccaag cgaccactac gctattgagt cacaaataca actccatgga    540
cttgatgtgg aaaagtctat gcggatggta aaaccacgcg aaggcgagga ccccttcga    600 atggaggaca tacttgaggt catcgaagaa gaaggagata gtagcagt tatccttttc    660 agcgggctgc acttctacac aggtcaactc tttaacattc agctattac taaggcaggc    720 cacgctaaag gatgcttcgt gggctttgac cttgcacacg cagtaggaaa cgtagagctc    780
cgcttgcacg attgggggcgt tgatttcgcc tgctggtgtt catataagta tcttaactca    840
ggagctggtg ggttggcagg cgcattcgta cacgagaaac acgctcatac cgtaaagcct    900
gcactggtag ggtggttcgg acacgatctc tctacccgct tcaatatgga taataaactc    960
cagcttatac ctggcgccaa tggattcagg atctcaaatc ctcctatttt gctcgtttgc   1020
agtttgcacg catctcttga ggtgttccag caggctacca tgactgcact ccgccggaag   1080
```

-continued

| | |
|---|---|
| tcaatcctttt tgaccggata cttggagtat atgctgaaac attatcactc aaaagataac | 1140 |
| actgagaata agggcccat agtaaacatt atcactccat ctcgggctga agagcgcggc | 1200 |
| tgccaactca cattgactttt ttccattccc aagaagtcag tgttcaaaga gttggagaaa | 1260 |
| cgggggggttg tatgtgataa gcgggagcca gatggaatcc gcgttgcccc agtcccccctc | 1320 |
| tataattctt ttcacgatgt atacaagttt attagactgc tgacaagtat cttggactca | 1380 |
| tctgagcgat cttag | 1395 |

<210> SEQ ID NO 102
<211> LENGTH: 573
<212> TYPE: DNA
<213> ORGANISM: Unknown
<220> FEATURE:
<223> OTHER INFORMATION: Description of Unknown:
    VEGF sequence

<400> SEQUENCE: 102

| | |
|---|---|
| atgaatttct tgctgagctg ggtgcattgg acactcgcat tgttgctgta cttgcaccat | 60 |
| gccaagtggt cccaggctgc acccactact gagggcgagc aaaagtctca tgaggtgatt | 120 |
| aaatttatgg acgtttacca acgatcatac tgtcggccaa tcgaaaccct cgtagatata | 180 |
| ttccaggagt acccagacga gatcgaatac atttttcaagc cctcatgtgt cccattgatg | 240 |
| cgatgtgctg ggtgctgtaa cgacgaagca cttgaatgtg tccccacctc cgagagtaac | 300 |
| atcacaatgc aaataatgag aatcaagccc caccaatccc aacatatcgg tgaaatgtca | 360 |
| ttccttcagc attcccgctg cgagtgccgg cctaagaagg accgcaccaa accagagaac | 420 |
| cattgtgaac cctgttctga gagacggaag cacttgttcg tacaggaccc tcaaacatgc | 480 |
| aagtgcagct gtaagaatac cgactcacgg tgtaaagcta ggcaactgga gcttaatgaa | 540 |
| aggacctgcc gatgcgataa acccaggagg taa | 573 |

<210> SEQ ID NO 103
<211> LENGTH: 426
<212> TYPE: DNA
<213> ORGANISM: Unknown
<220> FEATURE:
<223> OTHER INFORMATION: Description of Unknown:
    GM-CSF sequence

<400> SEQUENCE: 103

| | |
|---|---|
| atgtggttgc agaatttgct cttcctgggg attgtggtct acagcctctc cgcacctacc | 60 |
| cgctctccta tcacagttac aagaccctgg aaacatgtgg aggccattaa agaagcattg | 120 |
| aatttgttgg acgatatgcc cgtcacccctg aatgaagaag tagaagttgt ttctaatgag | 180 |
| ttcagcttta aaaattgac ctgtgtgcag acacggctta aaatttttga acagggactt | 240 |
| agaggaaact ttactaagct gaaggggggca cttaacatga cagcttctta ttatcagacc | 300 |
| tattgtcctc caacacctga aaccgactgt gaaacacagg taaccactta cgccgattt | 360 |
| attgattctt tgaaaacatt cctcaccgat ataccatttg agtgtaagaa gccaggccaa | 420 |
| aagtag | 426 |

<210> SEQ ID NO 104
<211> LENGTH: 822
<212> TYPE: DNA
<213> ORGANISM: Unknown
<220> FEATURE:
<223> OTHER INFORMATION: Description of Unknown:
    Anti-PD1 sequence

<400> SEQUENCE: 104

```
atggaaactg acacacttct tctgtgggtc ttgctcctgt gggtcccagg ctctactggt      60
gacagtcctg ataggccatg aacccacct acctttagtc cagccttgct cgtcgtaacc     120
gaagggaca acgctacatt cacctgctct tttagcaata cttctgagag ttttcatgta     180
gtctggcatc gggagagtcc atccggacaa acagatactt tggccgcttt tccagaggat    240
aggtctcaac ctgggcaaga cgcaaggttt cgagtcacac agcttcctaa cgggagagat    300
tttcacatgt ctgtagttcg ggcacgccga aatgattctg cacatatgt ttgcggtgtg     360
atctcacttg ctccaaagat tcaaataaag gagagcctc gcgccgagtt gcgggtgact     420
gagcgggagc ccaagtcctg cgacaaaacc catacttgtc caccctgtgg cggcgggtca    480
tccggtggcg ggtctggggg gcaaccaaga gagccacagg tatatactct tccccccagc    540
agagaagaaa tgacaaaaaa ccaagtgtcc ctgacatgtc tggttaaagg atttatccc     600
agtgacattg ctgtagaatg ggaatccaat ggtcaacccg agaataacta caaaaccact    660
cctccagtat tggacagtga cggttccttc ttcctctatt ccaaacttac agtggataaa    720
tcccgctggc agcaagggaa tgtattcagc tgtagtgtca tgcacgaagc tcttcataac    780
cattatacac agaaatctct ttccctgagc ccaggtaaat ag                       822
```

<210> SEQ ID NO 105
<211> LENGTH: 1116
<212> TYPE: DNA
<213> ORGANISM: Mus sp.

<400> SEQUENCE: 105

```
atggagactg atacactttt gctctgggtt ttgctcttgt gggtaccagg gtctactgga      60
gatgcacaaa ctcctgcatt caacaagcct aaggtagagc ttcatgtcca tttggacgga    120
gccataaaac ctgaaaccat actctatttc ggcaagaaac ggggtatagc acttcccgct    180
gataccgtgg aagagttgag aaatatcatt ggcatggaca aacctcttag cctgcctggc    240
tttcttgcaa agttcgacta ctatatgcca gttatagcag ggtgtagaga agcaataaag    300
cgaatcgcct atgagttcgt tgagatgaag gctaagaag gagttgttta cgtggaagtc     360
cggtactcac ctcatctgct tgctaatagc aaggtggacc caatgccatg gaatcaaact    420
gaaggtgatg taaccctga cgatgtggtc gatttggtca atcaaggtct ccaagaaggc    480
gagcaggctt tcggcattaa ggtaagaagt atattgtgct gtatgcgaca tcaaccttca    540
tggtccctgg aggtcctcga attgtgcaaa aagtacaatc aaaaaacagt ggtcgcaatg    600
gatctcgctg gagatgagac catagaaggt tcctctcttt tccccggtca tgtcgaagca    660
tatgaagggg ctgtcaaaaa tggtatccac cgcaccgtcc acgcagggga agtagggtcc    720
ccagaagtag tcagggaagc cgttgacatt tgaaaacag aaagagtcgg gcatggctac     780
catacaatag aggacgaagc cttgtacaat cgacttttga agaaaatat gcacttcgag     840
gtctgtccct ggagttcata tctcaccgga gcatgggacc ccaaaacaac ccacgccgtc    900
gtacgcttca agaatgataa ggcaaactac agtttgaata cagatgatcc actgatattc    960
aagtcaacac ttgacactga ctaccagatg acaaaaaaag atatgggttt caccgaagaa   1020
gagttcaaga gattgaacat taacgcagca aaaagctcct tcctgccaga ggaagagaaa   1080
aaagaattgc ttgaaaggtt gtatcgagaa taccaa                             1116
```

```
<210> SEQ ID NO 106
<211> LENGTH: 1056
<212> TYPE: DNA
<213> ORGANISM: Mus sp.

<400> SEQUENCE: 106
atggcacaaa ctccagcttt aataagccc  aaagtggaac ttcatgttca tctggatggg    60
gcaattaagc ccgaaactat attgtacttt ggcaaaaaga ggggtattgc cctgccagca   120
gataccgttg aggagcttcg caacatcatt gggatggaca agcccctctc tctgccaggt   180
tttctcgcta aattcgatta ttatatgcct gttattgctg gttgccggga ggccatcaag   240
aggatagcct acgagtttgt tgagatgaag gccaaagagg gcgtggtgta cgtagaggtc   300
agatacagcc ctcacctgct tgccaacagc aaggtggacc caatgccctg aaccaaacc   360 gaggggatg tcactcccga cgacgttgta gacctcgtaa atcagggcct tcaagagggc    420
gagcaggcat ttggcataaa agtccggtct atactctgct gtatgaggca ccaaccctcc   480
tggtctttgg aggtacttga gttgtgtaag aaatacaatc aaaagactgt agtcgccatg   540
gatcttgcag gcgatgaaac catcgagggt agctccttgt tccctggaca tgttgaagcc   600 tacgagggg ccgtaaaaaa tgggatacac aggactgtcc acgctggtga agtcggaagc    660
ccagaggtgg taaggggaggc agttgacata ctcaagacag agcgggttgg acacggatac   720
cacacaattg aggacgaggc cctgtataac cgcctcctca agagaacat gcattttgag    780 gtgtgtcctt ggtccagcta cctgactggt gcttgggacc ctaaaacaac tcacgccgtg   840
gtccggttca agaacgataa agccaattac tctttgaata ccgacgaccc cctcatattc   900
aaatcaacat tggataccga ctaccaaatg accaaaaagg atatgggggtt tactgaagag   960 gagttcaaga ggctcaacat aaatgccgct aaatcctcct ttctccccga ggaagaaaaa  1020
aaagaactcc ttgagcggct gtataggagg tatcaa                            1056

<210> SEQ ID NO 107
<211> LENGTH: 966
<212> TYPE: DNA
<213> ORGANISM: Mus sp.

<400> SEQUENCE: 107
atggaaacag atacactctt gctctgggta ctgcttctgt gggtccccgg ctctactggg    60
gatgaagatg atgtaactac tacagaagaa ctcgctcccg ctcttgtccc cccacccaag   120
ggtacctgcg ccggttggat ggctggcatc ccaggacatc caggtcacaa cggtacccc    180 ggaagagatg gtcgggatgg aactcccggc gagaagggcg aaaaagggga tgcagggctt   240
ctgggaccta aggtgaaac aggggacgtt ggaatgactg gtgcagaagg gcctcgcggc    300
tttcctggca cccctgggag gaaggagag cccggagagc tccagagaac tgaacctcgg   360
cctgcactca ctataactac ttccccctaat cttgggaccc gcgagaacaa cgccgatcag   420
gttacacctg taagccatat cgggtgcccc aatactaccc agcaagggag tcccgtgttc   480
gcaaagcttt tggctaaaaa ccaagcatcc ctgtgtaaca ctactcttaa ttggcattca   540
caagacggtg ctggtagctc ttatctttct caggggctgc ggtacgaaga agataagaag   600
gaattggttg tggattctcc aggactctat tatgtctttc tcgaattgaa gctcagtccc   660 acccttcacaa acactggaca caaagtccag ggctgggtaa gtctggtact ccaagcaaag   720
ccccaggttt acgatttcga caatttggca ctcaccgtag agcttttccc atgctccatg   780
gaaaataaac ttgttgatcg gtcatggtca cagctcttgc tgcttaaggc agggcatcgc   840
```

```
ctctcagtgg gtctgagagc ttatttgcat ggtgcacaag atgcttacag ggattgggaa      900
ttgtcctacc caaacactac aagtttcggg ttgttccttg tcaaacctga taacccatgg      960
gagtag                                                                 966
```

<210> SEQ ID NO 108
<211> LENGTH: 900
<212> TYPE: DNA
<213> ORGANISM: Mus sp.

<400> SEQUENCE: 108

```
atggaaactg atacactcct cctgtgggtc cttcttttgt gggtgcccgg atcaaccggc       60
gatggctgga tggcaggcat cccaggacac ccaggacaca acggtactcc aggtcgagac      120
ggtcgggatg ggactcctgg ggagaaaggc gagaagggg acgctggttt gctcggtcct      180
aaggggaaaa ccggggatgt aggaatgaca ggggctgaag ggcctcgggg atttcctggg      240
acaccaggca ggaagggtga accagggag ccctccagc gcaccgagcc acggccagct      300
ctgaccataa caacaagtcc aaacctgggc acacgcgaaa acaatgctga ccaggtgact      360
cctgtaagtc acatcggatg ccctaacact acacaacagg gctctcctgt atttgcaaag      420
cttctcgcaa aaaatcaagc atcactttgt aatacaaccc tgaactggca ttctcaggac      480
ggagcagggt cctcttattt gtctcaaggg ctccgctacg aagaagataa aaaggaattg      540
gttgttgaca gtccaggttt gtattatgtg tttttggaac ttaagctgtc accaaccttc      600
actaacaccg ccacaaggt ccaaggctgg gttagtcttg ttttgcaagc caaacctcaa      660
gtggatgatt ttgacaatct ggcttttgact gttgagcttt ttccatgcag tatggagaat      720
aaactggttg atcggtcatg gtcacagctc cttctgctca aggccggaca taggctgagt      780
gtgggacttc gggcctactt gcacggcgcc caggacgcat accgagactg ggaactcagc      840
taccctaaca caacttcttt tgggttgttc cttgtcaaac ccgataatcc ttgggaatag      900
```

<210> SEQ ID NO 109
<211> LENGTH: 870
<212> TYPE: DNA
<213> ORGANISM: Mus sp.

<400> SEQUENCE: 109

```
atggagactg atactttgct cctgtgggtt cttctcctgt gggttcctgg ttccacaggg       60
gatatgcatg tcaatggcaa ggtagcactc gtgactgggg ctgcacaggg tatcgggaaa      120
gcttttgccg aggccctgtt gctgcatggc gccaaggtcg ctttggtaga ttggaacttg      180
gaggctggag ttaaatgcaa agctgcactc gacgaacaat ttgagcctca aaaaaccctc      240
tttgtgcagt gtgacgttgc tgaccaaaag caactcaggg acacattcag gaaggtcgta      300
gaccatttcg gacgcctcga tatactcgtt aataatgccg gggtaaacaa cgaaaagaac      360
tgggaacaaa cattgcaaat caacctggta agtgtcatta gcggaactta tctgggtctt      420
gattatatga gcaagcagaa cggggcgag ggcgggatca ttatcaacat gtcaagtctt      480
gccggattga tgccagttgc tcagcagcct gtttactgtg ccagcaagca cggtattatt      540
gggtttaccc ggagtgccgc catggccgca atcttatga agagtggggt aagactgaat      600
gttatctgcc caggttttcgt agatacccca atcctggaga gcatcgagaa ggaggaaaat      660
atgggacaat acattgaata taaagatcaa atcaaggcta tgatgaagtt ctacggggtt      720
ctgcatccat ccacaattgc caacgggctc attaatctga ttgaggacga cgccttgaac      780
```

```
ggagctataa tgaaaatcac agcttccaaa ggcattcact tccaagatta tgatatatca    840
cccttgcttg tcaaggctcc tctgacaagt                                     870

<210> SEQ ID NO 110
<211> LENGTH: 807
<212> TYPE: DNA
<213> ORGANISM: Mus sp.

<400> SEQUENCE: 110
atgcatgtca atggcaaggt agcactcgtg actggggctg cacagggtat cgggaaagct     60
tttgccgagg ccctgttgct gcatggcgcc aaggtcgctt tggtagattg aacttggag    120 gctggagtta aatgcaaagc tgcactcgac gaacaatttg agcctcaaaa acccctcttt   180
gtgcagtgtg acgttgctga ccaaaagcaa ctcaggaca cattcaggaa ggtcgtagac    240
catttcggac gcctcgatat actcgttaat aatgccgggg taaacaacga aaagaactgg   300
gaacaaacat tgcaaatcaa cctggtaagt gtcattagcg aacttatct gggtcttgat    360 tatatgagca agcagaacgg gggcgagggc gggatcatta tcaacatgtc aagtcttgcc   420
ggattgatgc cagttgctca gcagcctgtt tactgtgcca gcaagcacgg tattattggg   480
tttacccgga gtgccgccat ggccgcaaat cttatgaaga gtggggtaag actgaatgtt   540
atctgcccag gtttcgtaga tacccccaatc ctggagagca tcgagaagga ggaaaatatg   600
ggacaataca ttgaatataa agatcaaatc aaggctatga tgaagttcta cggggttctg   660
catccatcca caattgccaa cgggctcatt aatctgattg aggacgacgc cttgaacgga   720
gctataatga aaatcacagc ttccaaaggc attcacttcc aagattatga tatatcaccc   780
ttgcttgtca aggctcctct gacaagt                                        807

<210> SEQ ID NO 111
<211> LENGTH: 6029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga   180
attgccgcat tgcagagata ttgtatttaa gtgcctagct cgatacaata acgggtctc    240 tctggttaga ccagatctga gcctgggagc tctctggcta actagggaac ccactgctta   300
agcctcaata aagcttgcct tgagtgcttc aagtagtgtg tgcccgtctg ttgtgtgact   360
ctggtaacta gagatccctc agacccttt agtcagtgtg aaaatctct agcagtggcg    420 cccgaacagg gacctgaaag cgaaagggaa accagagctc tctcgacgca ggactcggct   480
tgctgaagcg cgcacggcaa gaggcgaggg gcggcgactg gtgagtacgc caaaaatttt   540
gactagcgga ggctagaagg agagagatgg gtgcgagagc gtcagtatta agcggggag    600 aattagatcg cgatgggaaa aaattcggtt aaggccaggg ggaaagaaaa aatataaatt   660
aaaacatata gtatgggcaa gcagggagct agaacgattc gcagttaatc ctggcctgtt   720
agaaacatca gaaggctgta gacaaatact gggacagcta caaccatccc ttcagacagg   780
atcagaagaa cttagatcat tatataatac agtagcaacc ctctattgtg tgcatcaaag   840
```

```
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
cttttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg ggatttgggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca gggggaaagaa tagtagacat   1860
aatagcaaca gacatacaaa ctaaagaatt acaaaaacaa attacaaaaa tcaaaatttt   1920
atctcgacat ggtggcgacc ggtagcgcta gcggatcgat aagcttgata tcgcctgcag   1980
ccgaattcct tgacttggga tccgcgtcaa gtggagcaag gcaggtggac agtcctgcag   2040
gcatgcgtga ctgactgagg ccgcgactct agtttaaact gcgtgactga ctctagaaga   2100
tccggcagtg cggccgcgtc gacaatcaac ctctggatta caaaatttgt gaaagattga   2160
ctggtattct taactatgtt gctcctttta cgctatgtgg atacgctgct ttaatgcctt   2220
tgtatcatgc tattgcttcc cgtatggctt tcattttctc ctccttgtat aaatcctggt   2280
tgctgtctct ttatgaggag ttgtggcccg ttgtcaggca acgtggcgtg gtgtgcactg   2340
tgtttgctga cgcaaccccc actggttggg gcattgccac cacctgtcag ctcctttccg   2400
ggactttcgc tttccccctc cctattgcca cggcggaact catcgccgcc tgccttgccc   2460
gctgctggac aggggctcgg ctgttgggca ctgacaattc cgtggtgttg tcggggaaat   2520
catcgtcctt tccttggctg ctcgcctgtg ttgccacctg gattctgcgc gggacgtcct   2580
tctgctacgt cccttcggcc ctcaatccag cggaccttcc ttcccgcggc ctgctgccgg   2640
ctctgcggcc tcttccgcgt cttcgccttc gccctcagac gagtcggatc tccctttggg   2700
ccgcctcccc gcctggtacc tttaagacca atgacttaca aggcagctgt agatcttagc   2760
cactttttaa aagaaaaggg gggactggaa gggctaattc actcccaacg aaaataagat   2820
ctgcttttg cttgtactgg gtctctctgg ttagaccaga tctgagcctg ggagctctct   2880
ggctaactag ggaacccact gcttaagcct caataaagct tgccttgagt gcttcaagta   2940
gtgtgtgccc gtctgttgtg tgactctggt aactagagat ccctcagacc cttttagtca   3000
gtgtggaaaa tctctagcag tagtagttca tgtcatctta ttattcagta tttataactt   3060
gcaaagaaat gaatatcaga gagtgagagg aacttgttta ttgcagctta taatggttac   3120
aaataaagca atagcatcac aaatttcaca aataaagcat ttttttcact gcattctagt   3180
tgtggtttgt ccaaactcat caatgtatct tatcatgtct ggctctagct atcccgcccc   3240
```

```
taactccgcc cagttccgcc cattctccgc cccatggctg actaattttt tttatttatg    3300
cagaggccga ggccgcctcg gcctctgagc tattccagaa gtagtgagga ggcttttttg    3360
gaggcctaga cttttgcaga gacggcccaa attcgtaatc atggtcatag ctgtttcctg    3420
tgtgaaattg ttatccgctc acaattccac acaacatacg agccggaagc ataaagtgta    3480
aagcctgggg tgcctaatga gtgagctaac tcacattaat tgcgttgcgc tcactgcccg    3540
ctttccagtc gggaaacctg tcgtgccagc tgcattaatg aatcggccaa cgcgcgggga    3600
gaggcggttt gcgtattggg cgctcttccg cttcctcgct cactgactcg ctgcgctcgg    3660
tcgttcggct gcggcgagcg gtatcagctc actcaaaggc ggtaatacgg ttatccacag    3720
aatcagggga taacgcagga aagaacatgt gagcaaaagg ccagcaaaag gccaggaacc    3780
gtaaaaaggc cgcgttgctg gcgtttttcc ataggctccg ccccctgac gagcatcaca    3840 aaaatcgacg ctcaagtcag aggtggcgaa acccgacagg actataaaga taccaggcgt    3900
ttccccctgg aagctccctc gtgcgctctc ctgttccgac cctgccgctt accggatacc    3960
tgtccgcctt tctcccttcg ggaagcgtgg cgctttctca tagctcacgc tgtaggtatc    4020
tcagttcggt gtaggtcgtt cgctccaagc tgggctgtgt gcacgaaccc cccgttcagc    4080
ccgaccgctg cgccttatcc ggtaactatc gtcttgagtc aacccggta agacacgact    4140 tatcgccact ggcagcagcc actggtaaca ggattagcag agcgaggtat gtaggcggtg    4200
ctacagagtt cttgaagtgg tggcctaact acggctacac tagaaggaca gtatttggta    4260
tctgcgctct gctgaagcca gttaccttcg aaaaagagt tggtagctct tgatccggca    4320
aacaaaccac cgctggtagc ggtggttttt tgtttgcaa gcagcagatt acgcgcagaa    4380
aaaaaggatc tcaagaagat cctttgatct tttctacggg gtctgacgct cagtggaacg    4440
aaaactcacg ttaagggatt ttggtcatga gattatcaaa aaggatcttc acctagatcc    4500
ttttaaatta aaaatgaagt tttaaatcaa tctaaagtat atatgagtaa acttggtctg    4560
acagttacca atgcttaatc agtgaggcac ctatctcagc gatctgtcta tttcgttcat    4620
ccatagttgc ctgactcccc gtcgtgtaga taactacgat acgggagggc ttaccatctg    4680
gccccagtgc tgcaatgata ccgcgagacc cacgctcacc ggctccagat ttatcagcaa    4740
taaaccagcc agccggaagg gccgagcgca gaagtggtcc tgcaacttta tccgcctcca    4800
tccagtctat taattgttgc cgggaagcta gagtaagtag ttcgccagtt aatagtttgc    4860
gcaacgttgt tgccattgct acaggcatcg tggtgtcacg ctcgtcgttt ggtatggctt    4920
cattcagctc cggttcccaa cgatcaaggc gagttacatg atccccatg ttgtgcaaaa    4980 aagcggttag ctccttcggt cctccgatcg ttgtcagaag taagttggcc gcagtgttat    5040
cactcatggt tatggcagca ctgcataatt ctcttactgt catgccatcc gtaagatgct    5100
tttctgtgac tggtgagtac tcaaccaagt cattctgaga atagtgtatg cggcgaccga    5160
gttgctcttg cccggcgtca atacgggata ataccgcgcc acatagcaga actttaaaag    5220
tgctcatcat tggaaaacgt tcttcggggc gaaaactctc aaggatctta ccgctgttga    5280
gatccagttc gatgtaaccc actcgtgcac ccaactgatc ttcagcatct tttactttca    5340
ccagcgtttc tgggtgagca aaaacaggaa ggcaaaatgc cgcaaaaaag ggaataaggg    5400
cgacacggaa atgttgaata ctcatactct tcctttttca atattattga agcatttatc    5460
agggttattg tctcatgagc ggatacatat ttgaatgtat ttagaaaaat aaacaaatag    5520
gggttccgcg cacatttccc cgaaaagtgc cacctgacgt ctaagaaacc attattatca    5580
tgacattaac ctataaaaat aggcgtatca cgaggccctt tcgtctcgcg cgtttcggtg    5640
```

```
atgacggtga aaacctctga cacatgcagc tcccggagac ggtcacagct tgtctgtaag   5700
cggatgccgg gagcagacaa gcccgtcagg gcgcgtcagc gggtgttggc gggtgtcggg   5760
gctggcttaa ctatgcggca tcagagcaga ttgtactgag agtgcaccat atgcggtgtg   5820
aaataccgca cagatgcgta aggagaaaat accgcatcag gcgccattcg ccattcaggc   5880
tgcgcaactg ttgggaaggg cgatcggtgc gggcctcttc gctattacgc cagctggcga   5940
aagggggatg tgctgcaagg cgattaagtt gggtaacgcc agggttttcc cagtcacgac   6000
gttgtaaaac gacggccagt gccaagctg                                    6029
```

<210> SEQ ID NO 112
<211> LENGTH: 22
<212> TYPE: PRT
<213> ORGANISM: Homo sapiens

<400> SEQUENCE: 112

Met Cys His Gln Gln Leu Val Ile Ser Trp Phe Ser Leu Val Phe Leu
1               5                   10                  15

Ala Ser Pro Leu Val Ala
            20

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Met Gln Leu Leu Ser Cys Ile Ala Leu Ile Leu Ala Leu Val
1               5                   10

<210> SEQ ID NO 114
<211> LENGTH: 20
<212> TYPE: PRT
<213> ORGANISM: Homo sapiens

<400> SEQUENCE: 114

Met Tyr Arg Met Gln Leu Leu Ser Cys Ile Ala Leu Ser Leu Ala Leu
1               5                   10                  15

Val Thr Asn Ser
            20

<210> SEQ ID NO 115
<211> LENGTH: 15
<212> TYPE: PRT
<213> ORGANISM: Homo sapiens

<400> SEQUENCE: 115

Met Asn Leu Leu Leu Ile Leu Thr Phe Val Ala Ala Ala Val Ala
1               5                   10                  15

<210> SEQ ID NO 116
<211> LENGTH: 17
<212> TYPE: PRT
<213> ORGANISM: Unknown
<220> FEATURE:
<223> OTHER INFORMATION: Description of Unknown:
      Gaussia Luciferase sequence

```
<400> SEQUENCE: 116

Met Gly Val Lys Val Leu Phe Ala Leu Ile Cys Ile Ala Val Ala Glu
1               5                   10                  15
Ala

<210> SEQ ID NO 117
<211> LENGTH: 24
<212> TYPE: PRT
<213> ORGANISM: Homo sapiens

<400> SEQUENCE: 117

Met Pro Met Gly Ser Leu Gln Pro Leu Ala Thr Leu Tyr Leu Leu Gly
1               5                   10                  15

Met Leu Val Ala Ser Cys Leu Gly
            20

<210> SEQ ID NO 118
<211> LENGTH: 21
<212> TYPE: PRT
<213> ORGANISM: Mus sp.

<400> SEQUENCE: 118

Met Glu Thr Asp Thr Leu Leu Leu Trp Val Leu Leu Leu Trp Val Pro
1               5                   10                  15

Gly Ser Thr Gly Asp
            20

<210> SEQ ID NO 119
<211> LENGTH: 22
<212> TYPE: PRT
<213> ORGANISM: Homo sapiens

<400> SEQUENCE: 119

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 120
<211> LENGTH: 16
<212> TYPE: PRT
<213> ORGANISM: Unknown
<220> FEATURE:
<223> OTHER INFORMATION: Description of Unknown:
      VSV-G sequence

<400> SEQUENCE: 120

Met Lys Cys Leu Leu Tyr Leu Ala Phe Leu Phe Ile Gly Val Asn Cys
1               5                   10                  15

<210> SEQ ID NO 121
<211> LENGTH: 28
<212> TYPE: PRT
<213> ORGANISM: Homo sapiens

<400> SEQUENCE: 121

Met Asn Ile Lys Gly Ser Pro Trp Lys Gly Ser Leu Leu Leu Leu Leu
1               5                   10                  15

Val Ser Asn Leu Leu Leu Cys Gln Ser Val Ala Pro
            20                  25
```

<210> SEQ ID NO 122
<211> LENGTH: 18
<212> TYPE: PRT
<213> ORGANISM: Homo sapiens

<400> SEQUENCE: 122

Met Lys Trp Val Thr Phe Ile Ser Leu Leu Phe Leu Phe Ser Ser Ala
1               5                   10                  15

Tyr Ser

<210> SEQ ID NO 123
<211> LENGTH: 19
<212> TYPE: PRT
<213> ORGANISM: Homo sapiens

<400> SEQUENCE: 123

Met Thr Arg Leu Thr Val Leu Ala Leu Leu Ala Gly Leu Leu Ala Ser
1               5                   10                  15

Ser Arg Ala

<210> SEQ ID NO 124
<211> LENGTH: 17
<212> TYPE: PRT
<213> ORGANISM: Homo sapiens

<400> SEQUENCE: 124

Met Arg Ala Trp Ile Phe Phe Leu Leu Cys Leu Ala Gly Arg Ala Leu
1               5                   10                  15

Ala

<210> SEQ ID NO 125
<211> LENGTH: 16
<212> TYPE: PRT
<213> ORGANISM: Homo sapiens

<400> SEQUENCE: 125

Met Pro Leu Leu Leu Leu Leu Pro Leu Leu Trp Ala Gly Ala Leu Ala
1               5                   10                  15

<210> SEQ ID NO 126
<211> LENGTH: 29
<212> TYPE: PRT
<213> ORGANISM: Homo sapiens

<400> SEQUENCE: 126

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro
            20                  25

<210> SEQ ID NO 127
<211> LENGTH: 20
<212> TYPE: PRT
<213> ORGANISM: Homo sapiens

<400> SEQUENCE: 127

Met Thr Ser Lys Leu Ala Val Ala Leu Leu Ala Ala Phe Leu Ile Ser
1               5                   10                  15

Ala Ala Leu Cys
            20

<210> SEQ ID NO 128
<211> LENGTH: 23
<212> TYPE: PRT
<213> ORGANISM: Homo sapiens

<400> SEQUENCE: 128

Met Lys Val Ser Ala Ala Leu Leu Cys Leu Leu Leu Ile Ala Ala Thr
1               5                   10                  15

Phe Ile Pro Gln Gly Leu Ala
            20

<210> SEQ ID NO 129
<211> LENGTH: 26
<212> TYPE: PRT
<213> ORGANISM: Homo sapiens

<400> SEQUENCE: 129

Met Gly Ala Ala Ala Arg Thr Leu Arg Leu Ala Leu Gly Leu Leu Leu
1               5                   10                  15

Leu Ala Thr Leu Leu Arg Pro Ala Asp Ala
            20                  25

<210> SEQ ID NO 130
<211> LENGTH: 21
<212> TYPE: PRT
<213> ORGANISM: Homo sapiens

<400> SEQUENCE: 130

Met Ser Pro Leu Leu Arg Arg Leu Leu Leu Ala Ala Leu Leu Gln Leu
1               5                   10                  15

Ala Pro Ala Gln Ala
            20

<210> SEQ ID NO 131
<211> LENGTH: 21
<212> TYPE: PRT
<213> ORGANISM: Homo sapiens

<400> SEQUENCE: 131

Met Asn Asn Leu Leu Cys Cys Ala Leu Val Phe Leu Asp Ile Ser Ile
1               5                   10                  15

Lys Trp Thr Thr Gln
            20

<210> SEQ ID NO 132
<211> LENGTH: 23
<212> TYPE: PRT
<213> ORGANISM: Homo sapiens

<400> SEQUENCE: 132

Met Gln Met Ser Pro Ala Leu Thr Cys Leu Val Leu Gly Leu Ala Leu
1               5                   10                  15

Val Phe Gly Glu Gly Ser Ala
            20

<210> SEQ ID NO 133
<211> LENGTH: 34
<212> TYPE: PRT
<213> ORGANISM: Homo sapiens -continued

<400> SEQUENCE: 133

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly

<210> SEQ ID NO 134
<211> LENGTH: 21
<212> TYPE: PRT
<213> ORGANISM: Homo sapiens

<400> SEQUENCE: 134

Met Asn Ala Lys Val Val Val Val Leu Val Leu Val Leu Thr Ala Leu
1               5                   10                  15

Cys Leu Ser Asp Gly
            20

<210> SEQ ID NO 135
<211> LENGTH: 22
<212> TYPE: PRT
<213> ORGANISM: Homo sapiens

<400> SEQUENCE: 135

Met Glu Arg Ile Val Ile Cys Leu Met Val Ile Phe Leu Gly Thr Leu
1               5                   10                  15

Val His Lys Ser Ser Ser
            20

<210> SEQ ID NO 136
<211> LENGTH: 1557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

| | |
|---|---|
| atttgggaac tgaagaagga cgtctacgtg gtcgagctgg attggtaccc ggacgcccct | 60 |
| ggagaaatgg tcgtgctgac ttgcgatacg ccagaagagg acggcataac ctggaccctg | 120 |
| gatcagagct ccgaggtgct cggaagcgga aagaccctga ccattcaagt caaggagttc | 180 |
| ggcgacgcgg gccagtacac ttgccacaag ggtggcgaag tgctgtccca ctccctgctg | 240 |
| ctgctgcaca gaaagagga tggaatctgg tccactgaca tcctcaagga ccaaaaagaa | 300 |
| ccgaagaaca agaccttcct ccgctgcgaa gccaagaact acagcggtcg gttcacctgt | 360 |
| tggtggctga cgacaatctc caccgacctg actttctccg tgaagtcgtc acggggatca | 420 |
| agcgatcctc agggcgtgac ctgtggagcc gccactctgt ccgccgagag agtcagggga | 480 |
| gacaacaagg aatatgagta ctccgtggaa tgccaggagg acagcgcctg ccctgccgcg | 540 |
| gaagagtccc tgcctatcga ggtcatggtc gatgccgtgc ataagctgaa atacgagaac | 600 |
| tacacttcct ccttctttat ccgcgacatc atcaagcctg accccccaa gaacttgcag | 660 |
| ctgaagccac tcaagaactc ccgccaagtg gaagtgtctt gggaatatcc agacacttgg | 720 |
| agcacccgc actcatactt ctcgctcact ttctgtgtgc aagtgcaggg aaagtccaaa | 780 |
| cgggagaaga aagaccgggt gttcaccgac aaaacctccg ccactgtgat ttgtcggaag | 840 |
| aacgcgtcaa tcagcgtccg ggcgcaggat agatactact cgtcctcctg gagcgaatgg | 900 |

```
gccagcgtgc cttgttccgg tggcggatca ggcggaggtt caggaggagg ctccggagga    960
ggttcccgga acctcctgt ggcaacccc gaccctggaa tgttcccgtg cctacaccac     1020
tcccaaaacc tcctgagggc tgtgtcgaac atgttgcaga aggcccgcca gacccttgag   1080
ttctacccct gcacctcgga agaaattgat cacgaggaca tcaccaagga caagacctcg   1140
accgtggaag cctgcctgcc gctggaactg accaagaacg aatcgtgtct gaactcccgc   1200
gagacaagct ttatcactaa cggcagctgc ctggcgtcga aaagacctc attcatgatg    1260
gcgctctgtc tttcctcgat ctacgaagat ctgaagatgt atcaggtcga gttcaagacc   1320
atgaacgcca agctgctcat ggacccgaag cggcagatct tcctggacca gaatatgctc   1380
gccgtgattg atgaactgat gcaggccctg aatttcaact ccgagactgt gcctcaaaag   1440
tccagcctgg aagaaccgga cttctacaag accaagatca agctgtgcat cctgttgcac   1500
gctttccgca ttcgagccgt gaccattgac cgcgtgatgt cctacctgaa cgccagt      1557
```

<210> SEQ ID NO 137
<211> LENGTH: 519
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 137

```
Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240
```

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
        260                 265                 270

Ser Ala Thr Val Ile Cys Arg Lys Asn Ala Ser Ile Ser Val Arg Ala
        275                 280                 285

Gln Asp Arg Tyr Tyr Ser Ser Trp Ser Glu Trp Ala Ser Val Pro
        290                 295                 300

Cys Ser Gly Gly Gly Ser Gly Gly Ser Gly Gly Ser Gly Gly
305                 310                 315                 320

Gly Ser Arg Asn Leu Pro Val Ala Thr Pro Asp Pro Gly Met Phe Pro
                325                 330                 335

Cys Leu His His Ser Gln Asn Leu Leu Arg Ala Val Ser Asn Met Leu
            340                 345                 350

Gln Lys Ala Arg Gln Thr Leu Glu Phe Tyr Pro Cys Thr Ser Glu Glu
        355                 360                 365

Ile Asp His Glu Asp Ile Thr Lys Asp Lys Thr Ser Thr Val Glu Ala
        370                 375                 380

Cys Leu Pro Leu Glu Leu Thr Lys Asn Glu Ser Cys Leu Asn Ser Arg
385                 390                 395                 400

Glu Thr Ser Phe Ile Thr Asn Gly Ser Cys Leu Ala Ser Arg Lys Thr
                405                 410                 415

Ser Phe Met Met Ala Leu Cys Leu Ser Ser Ile Tyr Glu Asp Leu Lys
            420                 425                 430

Met Tyr Gln Val Glu Phe Lys Thr Met Asn Ala Lys Leu Leu Met Asp
        435                 440                 445

Pro Lys Arg Gln Ile Phe Leu Asp Gln Asn Met Leu Ala Val Ile Asp
450                 455                 460

Glu Leu Met Gln Ala Leu Asn Phe Asn Ser Glu Thr Val Pro Gln Lys
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asp Arg Val
            500                 505                 510

Met Ser Tyr Leu Asn Ala Ser
            515

<210> SEQ ID NO 138
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

```
Glu Phe Gly Asp Ala Gly Gln Tyr Thr Cys His Lys Gly Gly Val
                85                  90                  95
Leu Ser His Ser Leu Leu Leu His Lys Lys Glu Asp Gly Ile Trp
            100                 105                 110
Ser Thr Asp Ile Leu Lys Asp Gln Lys Glu Pro Lys Asn Lys Thr Phe
            115                 120                 125
Leu Arg Cys Glu Ala Lys Asn Tyr Ser Gly Arg Phe Thr Cys Trp Trp
130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
            180                 185                 190
Cys Gln Glu Asp Ser Ala Cys Pro Ala Ala Glu Glu Ser Leu Pro Ile
        195                 200                 205
Glu Val Met Val Asp Ala Val His Lys Leu Lys Tyr Glu Asn Tyr Thr
    210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
            260                 265                 270
Phe Cys Val Gln Val Gln Gly Lys Ser Lys Arg Glu Lys Lys Asp Arg
        275                 280                 285
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Gly Ser Gly Gly Gly Ser
                325                 330                 335
Gly Gly Gly Ser Gly Gly Gly Ser Arg Asn Leu Pro Val Ala Thr Pro
            340                 345                 350
Asp Pro Gly Met Phe Pro Cys Leu His His Ser Gln Asn Leu Leu Arg
        355                 360                 365
Ala Val Ser Asn Met Leu Gln Lys Ala Arg Gln Thr Leu Glu Phe Tyr
    370                 375                 380
Pro Cys Thr Ser Glu Glu Ile Asp His Glu Asp Ile Thr Lys Asp Lys
385                 390                 395                 400
Thr Ser Thr Val Glu Ala Cys Leu Pro Leu Glu Leu Thr Lys Asn Glu
                405                 410                 415
Ser Cys Leu Asn Ser Arg Glu Thr Ser Phe Ile Thr Asn Gly Ser Cys
            420                 425                 430
Leu Ala Ser Arg Lys Thr Ser Phe Met Met Ala Leu Cys Leu Ser Ser
        435                 440                 445
Ile Tyr Glu Asp Leu Lys Met Tyr Gln Val Glu Phe Lys Thr Met Asn
    450                 455                 460
Ala Lys Leu Leu Met Asp Pro Lys Arg Gln Ile Phe Leu Asp Gln Asn
465                 470                 475                 480
Met Leu Ala Val Ile Asp Glu Leu Met Gln Ala Leu Asn Phe Asn Ser
                485                 490                 495
```

```
Glu Thr Val Pro Gln Lys Ser Ser Leu Glu Pro Asp Phe Tyr Lys
            500                 505                 510
Thr Lys Ile Lys Leu Cys Ile Leu Leu His Ala Phe Arg Ile Arg Ala
        515                 520                 525
Val Thr Ile Asp Arg Val Met Ser Tyr Leu Asn Ala Ser
    530                 535                 540
```

<210> SEQ ID NO 139
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139

```
agacggaaac gcggaagcgg agagggcaga ggctcgctgc ttacatgcgg ggacgtggaa      60
gagaaccccg gtccg                                                      75
```

<210> SEQ ID NO 140
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

```
Arg Arg Lys Arg Gly Ser Gly Glu Gly Arg Gly Ser Leu Leu Thr Cys
1               5                   10                  15
Gly Asp Val Glu Glu Asn Pro Gly Pro
            20                  25
```

<210> SEQ ID NO 141
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

```
cagggacagg acaggcacat gattagaatg cgccagctca tcgatatcgt ggaccagttg      60
aagaactacg tgaacgacct ggtgcccgag ttcctgccgg cccccgaaga tgtggaaacc     120
aattgcgaat ggtcggcatt ttcctgcttt caaaaggcac agctcaagtc cgctaacacc     180
gggaacaacg aacggatcat caacgtgtcc atcaaaaagc tgaagcggaa gcctccctcc     240
accaacgccg gacggaggca gaagcatagg ctgacttgcc cgtcatgcga ctcctacgag     300
aagaagccgc cgaaggagtt cctggagcgg ttcaagtcgc tcctgcaaaa gatgattcat     360
cagcacctgt cctcccggac tcatgggtct gaggattca                            399
```

<210> SEQ ID NO 142
<211> LENGTH: 133
<212> TYPE: PRT
<213> ORGANISM: Homo sapiens

<400> SEQUENCE: 142

```
Gln Gly Gln Asp Arg His Met Ile Arg Met Arg Gln Leu Ile Asp Ile
1               5                   10                  15
Val Asp Gln Leu Lys Asn Tyr Val Asn Asp Leu Val Pro Glu Phe Leu
            20                  25                  30
```

```
Pro Ala Pro Glu Asp Val Glu Thr Asn Cys Glu Trp Ser Ala Phe Ser
         35                  40                  45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
             85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
        130

<210> SEQ ID NO 143
<211> LENGTH: 155
<212> TYPE: PRT
<213> ORGANISM: Homo sapiens

<400> SEQUENCE: 143

Met Glu Arg Ile Val Ile Cys Leu Met Val Ile Phe Leu Gly Thr Leu
 1               5                  10                  15

Val His Lys Ser Ser Ser Gln Gly Gln Asp Arg His Met Ile Arg Met
             20                  25                  30

Arg Gln Leu Ile Asp Ile Val Asp Gln Leu Lys Asn Tyr Val Asn Asp
         35                  40                  45

Leu Val Pro Glu Phe Leu Pro Ala Pro Glu Asp Val Glu Thr Asn Cys
 50                  55                  60

Glu Trp Ser Ala Phe Ser Cys Phe Gln Lys Ala Gln Leu Lys Ser Ala
 65                  70                  75                  80

Asn Thr Gly Asn Asn Glu Arg Ile Ile Asn Val Ser Ile Lys Lys Leu
             85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
        115                 120                 125

Phe Leu Glu Arg Phe Lys Ser Leu Leu Gln Lys Met Ile His Gln His
        130                 135                 140

Leu Ser Ser Arg Thr His Gly Ser Glu Asp Ser
145                 150                 155

<210> SEQ ID NO 144
<211> LENGTH: 2598
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
gtaacgccat tttgcaaggc atggaaaaat accaaaccaa gaatagagaa gttcagatca      60
agggcgggta catgaaaata gctaacgttg gccaaacag atatctgcg gtgagcagtt      120 tcggccccgg cccgggggcca agaacagatg gtcaccgcag tttcggcccc ggcccgaggc      180
caagaacaga tggtccccag atatggccca accctcagca gtttcttaag acccatcaga      240
tgtttccagg ctcccccaag gacctgaaat gaccctgcgc cttatttgaa ttaaccaatc      300
```

| | |
|---|---|
| agcctgcttc tcgcttctgt tcgcgcgctt ctgcttcccg agctctataa aagagctcac | 360 |
| aaccgctcac tcggcgcgcc agtcctccga cagactgagt cgcccggggg atccgcggaa | 420 |
| ttcgccgcca ccatgtgcca tcagcaactc gtcatctcct ggttctccct tgtgttcctc | 480 |
| gcttcccctc tggtcgccat ttgggaactg aagaaggacg tctacgtggt cgagctggat | 540 |
| tggtacccgg acgcccctgg agaaatggtc gtgctgactt gcgatacgcc agaagaggac | 600 |
| ggcataacct ggaccctgga tcagagctcc gaggtgctcg gaagcggaaa gaccctgacc | 660 |
| attcaagtca aggagttcgg cgacgcgggc cagtacactt gccacaaggg tggcgaagtg | 720 |
| ctgtccccact ccctgctgct gctgcacaag aaagaggatg gaatctggtc cactgacatc | 780 |
| ctcaaggacc aaaaagaacc gaagaacaag accttcctcc gctgcgaagc caagaactac | 840 |
| agcggtcggt tcacctgttg gtggctgacg acaatctcca ccgacctgac tttctccgtg | 900 |
| aagtcgtcac ggggatcaag cgatcctcag ggcgtgacct gtggagccgc cactctgtcc | 960 |
| gccgagagag tcaggggaga caacaaggaa tatgagtact ccgtggaatg ccaggaggac | 1020 |
| agcgcctgcc ctgccgcgga agagtccctg cctatcgagg tcatggtcga tgccgtgcat | 1080 |
| aagctgaaat acgagaacta cacttcctcc ttctttatcc gcgacatcat caagcctgac | 1140 |
| ccccccaaga acttgcagct gaagccactc aagaactccc gccaagtgga agtgtcttgg | 1200 |
| gaatatccag acacttggag caccccgcac tcatacttct cgctcacttt ctgtgtgcaa | 1260 |
| gtgcagggaa agtccaaacg ggagaagaaa gaccgggtgt tcaccgacaa acctccgcc | 1320 |
| actgtgattt gtcggaagaa cgcgtcaatc agcgtccggg cgcaggatag atactactcg | 1380 |
| tcctcctgga gcgaatgggc cagcgtgcct tgttccggtg gcggatcagg cggaggttca | 1440 |
| ggaggaggct ccggaggagg ttcccggaac ctccctgtgg caaccccga ccctggaatg | 1500 |
| ttcccgtgcc tacaccactc ccaaaacctc ctgagggctg tgtcgaacat gttgcagaag | 1560 |
| gcccgccaga cccttgagtt ctaccctgc acctcggaag aaattgatca cgaggacatc | 1620 |
| accaaggaca agacctcgac cgtggaagcc tgcctgccgc tggaactgac caagaacgaa | 1680 |
| tcgtgtctga actcccgcga gacaagcttt atcactaacg gcagctgcct ggcgtcgaga | 1740 |
| aagacctcat tcatgatggc gctctgtctt tcctcgatct acgaagatct gaagatgtat | 1800 |
| caggtcgagt tcaagaccat gaacgccaag ctgctcatgg acccgaagcg gcagatcttc | 1860 |
| ctggaccaga atatgctcgc cgtgattgat gaactgatgc aggccctgaa tttcaactcc | 1920 |
| gagactgtgc ctcaaaagtc cagcctggaa gaaccggact tctacaagac caagatcaag | 1980 |
| ctgtgcatcc tgttgcacgc tttccgcatt cgagccgtga ccattgaccg cgtgatgtcc | 2040 |
| tacctgaacg ccagtagacg gaaacgcgga agcggagagg gcagaggctc gctgcttaca | 2100 |
| tgcgggggacg tggaagagaa ccccggtccg atggaacgca ttgtgatctg cctgatggtc | 2160 |
| atcttcctgg gcaccttagt gcacaagtcg agcagccagg gacaggacag gcacatgatt | 2220 |
| agaatgcgcc agctcatcga tatcgtggac cagttgaaga actacgtgaa cgacctggtg | 2280 |
| cccgagttcc tgccggcccc cgaagatgtg gaaaccaatt gcgaatggtc ggcattttcc | 2340 |
| tgctttcaaa aggcacagct caagtccgct aacaccggga acaacgaacg gatcatcaac | 2400 |
| gtgtccatca aaaagctgaa gcggaagcct ccctccacca acgccggacg gaggcagaag | 2460 |
| cataggctga cttgcccgtc atgcgactcc tacgagaaga agccgccgaa ggagttcctg | 2520 |
| gagcggttca agtcgctcct gcaaaagatg attcatcagc acctgtcctc ccggactcat | 2580 |
| gggtctgagg attcatga | 2598 |

<210> SEQ ID NO 145
<211> LENGTH: 7213
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

| | | | | | |
|---|---|---|---|---|---|
| tgactcctgc | gcagtccaaa | aaaaaaggct | ccaaaaggag | cctttaattg | tatcggtggg | 60 |
| cccttagaaa | aactcatcga | gcatcaaatg | aaactgcaat | ttattcatat | caggattatc | 120 |
| aataccatat | ttttgaaaaa | gccgtttctg | taatgaagga | gaaaactcac | cgaggcagtt | 180 |
| ccataggatg | gcaagatcct | ggtatcggtc | tgcgattccg | actcgtccaa | catcaataca | 240 |
| acctattaat | ttcccctcgt | caaaaataag | gttatcaagt | gagaaatcac | catgagtgac | 300 |
| gactgaatcc | ggtgagaatg | gcaaaagctt | atgcatttct | ttccagactt | gttcaacagg | 360 |
| ccagccatta | cgctcgtcat | caaaatcact | cgcatcaacc | aaaccgttat | tcattcgtga | 420 |
| ttgcgcctga | gcgagacgaa | atacgcgatc | gctgttaaaa | ggacaattac | aaacaggaat | 480 |
| cgaatgcaac | cggcgcagga | acactgccag | cgcatcaaca | atattttcac | ctgaatcagg | 540 |
| atattcttct | aatacctgga | atgctgtttt | cccggggatc | gcagtggtga | gtaaccatgc | 600 |
| atcatcagga | gtacggataa | aatgcttgat | ggtcggaaga | ggcataaatt | ccgtcagcca | 660 |
| gtttagtctg | accatctcat | ctgtaacatc | attggcaacg | ctacctttgc | catgtttcag | 720 |
| aaacaactct | ggcgcatcgg | gcttcccata | caatcgatag | attgtcgcac | ctgattgccc | 780 |
| gacattatcg | cgagcccatt | tatacccata | taaatcagca | tccatgttgg | aatttaatcg | 840 |
| cggcctcgag | caagacgttt | cccgttgaat | atggctcata | acaccccttg | tattactgtt | 900 |
| tatgtaagca | gacagtttta | ttgttcatga | tgatatattt | ttatcttgtg | caatgtaaca | 960 |
| tcagagattt | tgagacacaa | cgtggtttaa | acaaatagtc | aaaagcctcc | ggcgactagt | 1020 |
| cggggtcatt | agttcatagc | ccatatatgg | agttccgcgt | tacataactt | acggtaaatg | 1080 |
| gcccgcctgg | ctgaccgccc | aacgaccccc | gcccattgac | gtcaataatg | acgtatgttc | 1140 |
| ccatagtaac | gccaataggg | actttccatt | gacgtcaatg | ggtggagtat | ttacggtaaa | 1200 |
| ctgcccactt | ggcagtacat | caagtgtatc | atatgccaag | tacgccccct | attgacgtca | 1260 |
| atgacggtaa | atggcccgcc | tggcattatg | cccagtacat | gaccttatgg | gactttccta | 1320 |
| cttggcagta | catctacgta | ttagtcatcg | ctattaccat | ggtgatgcgg | ttttggcagt | 1380 |
| acatcaatgg | gcgtggatag | cggtttgact | cacggggatt | tccaagtctc | caccccattg | 1440 |
| acgtcaatgg | gagtttgttt | tggcaccaaa | atcaacggga | ctttccaaaa | tgtcgtaaca | 1500 |
| actccgcccc | attgacgcaa | atgggcggta | ggcgtgtacg | gtgggaggtc | tatataagca | 1560 |
| gagctggttt | agtgaaccgg | gtctctctgg | ttagaccaga | tttgagcctg | ggagctctct | 1620 |
| ggctaactag | gaacccact | gcttaagcct | caataaagct | tgccttgagt | gcttcaagta | 1680 |
| gtgtgtgccc | gtctgttgtg | tgactctggt | aactagagat | ccctcagacc | cttttagtca | 1740 |
| gtgtggaaaa | tctctagcag | tggcgcccga | acagggacct | gaaagcgaaa | gggaaaccag | 1800 |
| aggagctctc | tcgacgcagg | actcggcttg | ctgaagcgcg | cacggcaaga | ggcgaggggc | 1860 |
| ggcgactgca | gagtacgcca | aaattttgac | tagcggaggc | tagaaggaga | gagatgggtg | 1920 |
| cgagagcgtc | agtattaagc | gggggaaaat | agcggccgcc | acaattttaa | aagaaagggg | 1980 |
| gggattgggg | ggtacagtgc | aggggaaaga | atagtagaca | taatagcaac | agacatacaa | 2040 |
| actaaagaat | tacaaaaaca | aattacaaaa | attcaaattt | tcggggggatc | cgtaacgcca | 2100 |

```
ttttgcaagg catggaaaaa taccaaacca agaatagaga agttcagatc aagggcgggt    2160
acatgaaaat agctaacgtt gggccaaaca ggatatctgc ggtgagcagt ttcggccccg    2220
gcccggggcc aagaacagat ggtcaccgca gtttcggccc cggcccgagg ccaagaacag    2280
atggtcccca gatatggccc aaccctcagc agtttcttaa gacccatcag atgtttccag    2340
gctcccccaa ggacctgaaa tgaccctgcg ccttatttga attaaccaat cagcctgctt    2400
ctcgcttctg ttcgcgcgct tctgcttccc gagctctata aaagagctca caaccccctca   2460 ctcggcgcgc cagtcctccg acagactgag tcgcccgggg gatccgcgga attcgccgcc    2520
accatgtgcc atcagcaact cgtcatctcc tggttctccc ttgtgttcct cgcttcccct    2580
ctggtcgcca tttgggaact gaagaaggac gtctacgtgg tcgagctgga ttggtacccg    2640
gacgcccctg gagaaatggt cgtgctgact tgcgatacgc cagaagagga cggcataacc    2700
tggaccctgg atcagagctc cgaggtgctc ggaagcggaa agaccctgac cattcaagtc    2760
aaggagttcg gcgacgcggg ccagtacact tgccacaagg gtggcgaagt gctgtcccac    2820
tccctgctgc tgctgcacaa gaagaggat ggaatctggt ccactgacat cctcaaggac    2880
caaaaagaac cgaagaacaa gaccttcctc cgctgcgaag ccaagaacta cagcggtcgg    2940
ttcacctgtt ggtggctgac gacaatctcc accgacctga ctttctccgt gaagtcgtca    3000
cggggatcaa gcgatcctca gggcgtgacc tgtggagccg ccactctgtc cgccgagaga    3060 gtcagggag acaacaagga atatgagtac tccgtggaat gccaggagga cagcgcctgc    3120
cctgccgcgg aagagtccct gcctatcgag gtcatggtcg atgccgtgca taagctgaaa    3180
tacgagaact acacttcctc cttctttatc cgcgacatca tcaagcctga ccccccccaag    3240 aacttgcagc tgaagccact caagaactcc cgccaagtgg aagtgtcttg ggaatatcca    3300
gacacttgga gcacccgca ctcatacttc tcgctcactt tctgtgtgca agtgcaggga    3360
aagtccaaac gggagaagaa agaccgggtg ttcaccgaca aaacctccgc cactgtgatt    3420
tgtcggaaga acgcgtcaat cagcgtccgg gcgcaggata gatactactc gtcctcctgg    3480
agcgaatggg ccagcgtgcc ttgttccggt ggcggatcag gcggaggttc aggaggaggc    3540
tccgggagag gttcccggaa cctccctgtg gcaaccccg accctggaat gttcccgtgc    3600
ctacaccact cccaaaacct cctgagggct gtgtcgaaca tgttgcagaa ggcccgccag    3660
acccttgagt ctaccccctg cacctcggaa gaaattgatc acgaggacat caccaaggac    3720
aagacctcga ccgtggaagc ctgcctgccg ctggaactga ccaagaacga atcgtgtctg    3780
aactcccgcg agacaagctt tatcactaac ggcagctgcc tggcgtcgag aaagacctca    3840
ttcatgatgg cgctctgtct ttcctcgatc tacgaagatc tgaagatgta tcaggtcgag    3900
ttcaagacca tgaacgccaa gctgctcatg gacccgaagc ggcagatctt cctgaccag    3960 aatatgctcg ccgtgattga tgaactgatg caggccctga tttcaactc cgagactgtg    4020 cctcaaaagt ccagcctgga agaaccggac ttctacaaga ccaagatcaa gctgtgcatc    4080
ctgttgcacg ctttccgcat tcgagccgtg accattgacc gcgtgatgtc ctacctgaac    4140
gccagtagac ggaaacgcgg aagcggagag ggcagaggct cgctgcttac atgcggggac    4200
gtggaagaga ccccggtcc gatggaacgc attgtgatct gcctgatggt catcttcctg    4260
ggcaccttag tgcacaagtc gagcagccag ggacaggaca ggcacatgat tagaatgcgc    4320
cagctcatcg atatcgtgga ccagttgaag aactacgtga acgacctggt gcccgagttc    4380
ctgccggccc ccgaagatgt ggaaaccaat tgcgaatggt cggcattttc ctgctttcaa    4440
aaggcacagc tcaagtccgc taacaccggg aacaacgaac ggatcatcaa cgtgtccatc    4500
```

```
aaaaagctga agcggaagcc tccctccacc aacgccggac ggaggcagaa gcataggctg    4560
acttgcccgt catgcgactc ctacgagaag aagccgccga aggagttcct ggagcggttc    4620
aagtcgctcc tgcaaaagat gattcatcag cacctgtcct cccggactca tgggtctgag    4680
gattcatgag gttagtcgac aatcaacctc tggattacaa aatttgtgaa agattgactg    4740
gtattcttaa ctatgttgct cctttttacgc tatgtggata cgctgcttta atgcctttgt    4800
atcatgctat tgcttcccgt atggctttca ttttctcctc cttgtataaa tcctggttgc    4860
tgtctcttta tgaggagttg tggcccgttg tcaggcaacg tggcgtggtg tgcactgtgt    4920
ttgctgacgc aacccccact ggttggggca ttgccaccac ctgtcagctc ctttccggga    4980
cttttcgcttt ccccctccct attgccacgg cggaactcat cgccgcctgc cttgcccgct    5040
gctggacagg ggctcggctg ttgggcactg acaattccgt ggtgttgtcg ggaaatcat    5100
cgtcctttcc ttggctgctc gcctgtgttg ccacctggat tctgcgcggg acgtccttct    5160
gctacgtccc ttcggccctc aatccagcgg accttccttc ccgcggcctg ctgccggctc    5220
tgcggcctct tccgcgtctt cgccttcgcc ctcagacgag tcggatctcc ctttgggccg    5280
cctccccgct tagtactggt acctttaaga ccaatgactt acaaggcagc tgtagatctt    5340
agccactttt taaaagaaaa gggggggactg aagggctaa ttcactccca acgaagacaa    5400
gattccggaa tttatttgtg aaatttgtga tgctattgct ttatttgtaa accggtgcag    5460
ctgcttttg cctgtactgg gtctctctgg ttagaccaga tctgagcctg ggagctctct    5520
ggctaactag ggaacccact gcttaagcct caataaagct tgccttgagt gcttcaagta    5580
gtgtgtgccc gtctgttgtg tgactctggt aactagagat ccctcagacc cttttagtca    5640
gtgtggaaaa tctctagcat ctagagtatg caaagcatgc atctcaatta gtcagcaacc    5700
aggtgtggaa agtccccagg ctccccagca ggcagaagta tgcaaagcat gcatctcaat    5760
tagtcagcaa ccatagtccc gcccctaact ccgcccatcc cgcccctaac tccgcccagt    5820
tccgcccatt ctccgcccca tggctgacta atttttttta tttatgcaga ggccgaggcc    5880
gcctcggcct ctgagctatt ccagaagtag tgaggaggct ttttggagg cctaggctag    5940
agatcataat cagccatacc acatttgtag aggttttact tgctttaaaa aacctcccac    6000
acctcccct gaacctgaaa cataaaatga atgcaattgt tgttgttaac ttgtttattg    6060
cagcttataa tggttacaaa taagcaata gcatcacaaa tttcacaaat aaagcatttt    6120
tttcactgca ttctagttgt ggtttgtcca aactcatcaa tgtatcttat catgtctgct    6180
agccgggctt ttttttctta ggccttcttc cgcttcctcg ctcactgact cgctgcgctc    6240
ggtcgttcgg ctgcggcgag cggtatcagc tcactcaaag gcggtaatac ggttatccac    6300
agaatcaggg gataacgcag gaaagaacat gtgagcaaaa ggccagcaaa aggccaggaa    6360
ccgtaaaaag gccgcgttgc tggcgttttt ccataggctc cgcccccctg acgagcatca    6420
caaaatcga cgctcaagtc agaggtggcg aaacccgaca ggactataaa gataccaggc    6480
gtttccccct ggaagctccc tcgtgcgctc tcctgttccg accctgccgc ttaccggata    6540
cctgtccgcc tttctccctt cgggaagcgt ggcgctttct catagctcac gctgtaggta    6600
tctcagttcg gtgtaggtcg ttcgctccaa gctgggctgt gtgcacgaac cccccgttca    6660
gcccgaccgc tgcgccttat ccggtaacta tcgtcttgag tccaacccgg taagacacga    6720
cttatcgcca ctggcagcag ccactggtaa caggattagc agagcgaggt atgtaggcgg    6780
tgctacagag ttcttgaagt ggtggcctaa ctacggctac actagaagaa cagtatttgg    6840
tatctgcgct ctgctgaagc cagttacctt cggaaaaaga gttggtagct cttgatccgg    6900
```

-continued

```
caaacaaacc accgctggta gcggtggttt ttttgtttgc aagcagcaga ttacgcgcag   6960
aaaaaaagga tctcaagaag atcctttgat cttttctacg gggtctgacg ctcagtggaa   7020
cgaaaactca cgttaaggga ttttggtcat gagattatca aaaggatct tcacctagat    7080 cccttttaaat taaaaatgaa gttttaaatc aatctaaagt atatatgagt aaacttggtc  7140
tgacagttac caatgcttaa tcagtgaggc acctatctca gcgatctgtc tatttcgttc   7200
atccatagtt gcc                                                      7213
```

UNITED STATES PATENT AND TRADEMARK OFFICE
CERTIFICATE OF CORRECTION

| | |
|---|---|
| PATENT NO. | : 10,993,967 B2 |
| APPLICATION NO. | : 16/656452 |
| DATED | : May 4, 2021 |
| INVENTOR(S) | : Timothy Kuan-Ta Lu et al. |

It is certified that error appears in the above-identified patent and that said Letters Patent is hereby corrected as shown below:

In the Claims

In Column 287, Claim 2, Line 45, delete "MSC claim 1" and insert --MSC of claim 1--.

Signed and Sealed this
Fourteenth Day of February, 2023

Katherine Kelly Vidal
*Director of the United States Patent and Trademark Office*